US007668658B2

(12) United States Patent
Köster et al.

(10) Patent No.: US 7,668,658 B2
(45) Date of Patent: Feb. 23, 2010

(54) METHODS FOR GENERATING DATABASES AND DATABASES FOR IDENTIFYING POLYMORPHIC GENETIC MARKERS

(75) Inventors: Hubert Köster, La Jolla, CA (US); Andreas Braun, San Diego, CA (US); Dirk Van Den Boom, Hamburg (DE); Yip Ping, San Diego, CA (US); Charlie Rodi, Del Mar, CA (US); Liyan He, San Diego, CA (US); Norman Chiu, San Diego, CA (US); Christian Jurinke, Hamburg (DE)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 10/273,321

(22) Filed: Oct. 15, 2002

(65) Prior Publication Data

US 2003/0180749 A1 Sep. 25, 2003

Related U.S. Application Data

(60) Division of application No. 09/687,483, filed on Oct. 13, 2000, now abandoned, and a continuation-in-part of application No. 09/663,968, filed on Sep. 19, 2000.

(60) Provisional application No. 60/217,658, filed on Jul. 10, 2000, provisional application No. 60/159,176, filed on Oct. 13, 1999, provisional application No. 60/217,251, filed on Jul. 10, 2000.

(51) Int. Cl.
*G06F 19/00* (2006.01)
*C12Q 1/68* (2006.01)
*G01N 24/00* (2006.01)

(52) U.S. Cl. .............................. 702/19; 435/6; 436/173

(58) Field of Classification Search .................. 702/19, 702/32; 435/6, 183, 174; 530/300, 350; 536/24.3
See application file for complete search history.

(56) References Cited

U.S. PATENT DOCUMENTS

| | | | | |
|---|---|---|---|---|
| 3,645,090 | A | 2/1972 | Mochizuki et al. | |
| 3,687,808 | A | 8/1972 | Merigan, Jr. et al. | |
| 3,817,837 | A | 6/1974 | Rubenstein et al. | |
| 3,850,752 | A | 11/1974 | Schuurs et al. | |
| 3,939,350 | A | 2/1976 | Kronick et al. | |
| 3,940,475 | A | 2/1976 | Gross | |
| 3,996,345 | A | 12/1976 | Ullman et al. | |
| 4,076,982 | A | 2/1978 | Ritter et al. | |
| 4,179,337 | A | 12/1979 | Davis et al. | |
| 4,275,149 | A | 6/1981 | Litman et al. | |
| 4,277,437 | A | 7/1981 | Maggio | |
| 4,301,144 | A | 11/1981 | Iwashita et al. | |
| 4,366,241 | A | 12/1982 | Tom et al. | |
| 4,496,689 | A | 1/1985 | Mitra | |
| 4,511,503 | A | 4/1985 | Olson et al. | |
| 4,562,639 | A | 1/1986 | McElroy | |
| 4,568,649 | A | 2/1986 | Bertoglio-Matte | |
| 4,640,835 | A | 2/1987 | Shimizu et al. | |
| 4,656,127 | A | 4/1987 | Mundy | |
| 4,670,417 | A | 6/1987 | Iwasaki et al. | |
| 4,683,195 | A | 7/1987 | Mullis et al. | 435/6 |
| 4,683,202 | A | 7/1987 | Mullis | 435/91 |
| 4,722,848 | A | 2/1988 | Paoletti et al. | |
| 4,791,192 | A | 12/1988 | Nakagawa et al. | |
| 4,826,360 | A | 5/1989 | Iwasawa et al. | 406/51 |
| 4,851,018 | A | 7/1989 | Lazzari et al. | 55/356 |
| 4,981,957 | A | 1/1991 | Lebleu et al. | |
| 4,987,071 | A | 1/1991 | Cech et al. | |
| 4,988,617 | A | 1/1991 | Landegren et al. | |
| 4,998,617 | A | 3/1991 | Ladd, Jr. et al. | |
| 5,013,830 | A | 5/1991 | Ohtsuka et al. | |
| 5,024,939 | A | 6/1991 | Gorman | |
| 5,025,939 | A | 6/1991 | Bunn et al. | |
| 5,034,506 | A | 7/1991 | Summerton et al. | |
| 5,082,767 | A | 1/1992 | Hatfield et al. | |
| 5,118,800 | A | 6/1992 | Smith et al. | |
| 5,118,937 | A | 6/1992 | Hillenkamp et al. | 250/282 |
| 5,122,342 | A | 6/1992 | McCulloch et al. | |
| 5,128,448 | A | 7/1992 | Danho | |
| 5,149,797 | A | 9/1992 | Pederson et al. | |
| 5,166,315 | A | 11/1992 | Summerton et al. | |
| 5,175,430 | A | 12/1992 | Enke et al. | |
| 5,185,444 | A | 2/1993 | Summerton et al. | |
| 5,214,134 | A | 5/1993 | Weis et al. | |

(Continued)

FOREIGN PATENT DOCUMENTS

EP 0296781 A2 6/1988

(Continued)

OTHER PUBLICATIONS

Roses (Annals of the New York Academy of Sciences (1998) vol. 855, pp. 738-743.*
Eggertsen et al. (Clinical Chemistry (1993) vol. 30, No. 10, pp. 2125-2129).*
Arnheim et al. (PNAS (1985) vol. 82, pp. 6970-6974).*
Kirk et al. Nucleic Acids Research. 2002. vol. 30, No. 5, pp. 3295-3311.*
Journal of Bone and Mineral Research (1998) vol. 13, No. 10, pp. 1633-1639.*
Shaw et al. (Genome research (1998) vol. 8, pp. 111-123).*
Arrand et al., “Different Substrate Specificities of the Two DNA Ligases of Mammalian Cells”, *J. Biol. Chem.*, 261(20):9079-9082 (1986).

(Continued)

*Primary Examiner*—Lori A Clow
(74) *Attorney, Agent, or Firm*—Grant Anderson LLP

(57) ABSTRACT

Processes and methods for creating a database of genomic samples from healthy human donors, methods that use the database to identify and correlate polymorphic genetic markers and other markers with diseases and conditions are provided.

33 Claims, 51 Drawing Sheets

U.S. PATENT DOCUMENTS

| | | | |
|---|---|---|---|
| 5,216,141 | A | 6/1993 | Benner |
| 5,220,007 | A | 6/1993 | Pederson et al. |
| 5,235,033 | A | 8/1993 | Summerton et al. |
| 5,247,175 | A | 9/1993 | Schoen et al. |
| 5,256,775 | A | 10/1993 | Froehler |
| 5,259,044 | A | 11/1993 | Isono et al. |
| 5,264,562 | A | 11/1993 | Matteucci |
| 5,264,564 | A | 11/1993 | Matteucci |
| 5,270,170 | A | 12/1993 | Schatz et al. |
| 5,273,718 | A | 12/1993 | Sköld et al. |
| 5,283,173 | A | 2/1994 | Fields et al. |
| 5,319,080 | A | 6/1994 | Leumann |
| 5,338,665 | A | 8/1994 | Schatz et al. |
| 5,354,934 | A | 10/1994 | Pitt et al. |
| 5,363,885 | A | 11/1994 | McConnell et al. |
| 5,366,878 | A | 11/1994 | Pederson et al. |
| 5,393,878 | A | 2/1995 | Leumann |
| 5,403,711 | A | 4/1995 | Walder et al. |
| 5,405,938 | A | 4/1995 | Summerton et al. |
| 5,434,257 | A | 7/1995 | Matteucci et al. |
| 5,436,150 | A | 7/1995 | Chandrasegaran .......... 435/199 |
| 5,439,797 | A | 8/1995 | Tsien et al. |
| 5,440,119 | A | 8/1995 | Labowsky .................. 250/282 |
| 5,446,137 | A | 8/1995 | Maag et al. |
| 5,453,613 | A | 9/1995 | Gray et al. .................. 250/281 |
| 5,466,677 | A | 11/1995 | Baxter et al. |
| 5,466,786 | A | 11/1995 | Buhr et al. |
| 5,470,967 | A | 11/1995 | Huie et al. |
| 5,474,796 | A | 12/1995 | Brennan |
| 5,489,677 | A | 2/1996 | Sanghvi et al. |
| 5,491,133 | A | 2/1996 | Walder et al. |
| 5,492,806 | A | 2/1996 | Drmanac et al. |
| 5,498,545 | A | 3/1996 | Vestal ......................... 436/47 |
| 5,503,980 | A | 4/1996 | Cantor .......................... 435/6 |
| 5,506,137 | A | 4/1996 | Mathur et al. ............ 435/252.3 |
| 5,514,785 | A | 5/1996 | Van Ness et al. |
| 5,519,134 | A | 5/1996 | Acevedo et al. |
| 5,525,464 | A | 6/1996 | Drmanac et al. |
| 5,536,649 | A | 7/1996 | Fraiser et al. ............. 435/91.2 |
| 5,541,307 | A | 7/1996 | Cook et al. |
| 5,547,835 | A | 8/1996 | Köster et al. ................... 435/6 |
| 5,561,225 | A | 10/1996 | Maddry et al. |
| 5,565,350 | A | 10/1996 | Kmiec |
| 5,567,811 | A | 10/1996 | Misiura et al. |
| 5,571,676 | A | 11/1996 | Shuber |
| 5,576,427 | A | 11/1996 | Cook et al. |
| 5,580,732 | A | 12/1996 | Grossman et al. |
| 5,591,722 | A | 1/1997 | Montgomery et al. |
| 5,593,826 | A | 1/1997 | Fung et al. |
| 5,596,086 | A | 1/1997 | Matteucci et al. |
| 5,597,909 | A | 1/1997 | Urdea et al. |
| 5,602,240 | A | 2/1997 | De Mesmaeker et al. |
| 5,604,098 | A | 2/1997 | Mead et al. .................... 435/6 |
| 5,605,798 | A | 2/1997 | Köster et al. ................... 435/6 |
| 5,608,046 | A | 3/1997 | Cook et al. |
| 5,610,289 | A | 3/1997 | Cook et al. |
| 5,610,300 | A | 3/1997 | Altmann et al. |
| 5,618,704 | A | 4/1997 | Sanghvi et al. |
| 5,622,824 | A | 4/1997 | Köster et al. ................... 435/6 |
| 5,623,065 | A | 4/1997 | Cook et al. |
| 5,623,070 | A | 4/1997 | Cook et al. |
| 5,627,053 | A | 5/1997 | Usman et al. |
| 5,631,134 | A | 5/1997 | Cantor et al. .................. 435/6 |
| 5,633,360 | A | 5/1997 | Bischofberger et al. |
| 5,635,713 | A | 6/1997 | Labowsky .................. 250/282 |
| 5,639,873 | A | 6/1997 | Barascut et al. |
| 5,646,265 | A | 7/1997 | McGee |
| 5,652,355 | A | 7/1997 | Metelev et al. |
| 5,652,356 | A | 7/1997 | Agrawal |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,437 | A | 10/1997 | Teng et al. |
| 5,677,439 | A | 10/1997 | Weis et al. |
| 5,686,656 | A | 11/1997 | Amirav et al. ............. 73/23.41 |
| 5,691,141 | A | 11/1997 | Köster ........................... 435/6 |
| 5,695,940 | A | 12/1997 | Drmanac et al. |
| 5,700,672 | A | 12/1997 | Mathur et al. ............... 435/183 |
| 5,700,920 | A | 12/1997 | Altmann et al. |
| 5,714,330 | A | 2/1998 | Brenner et al. ................. 435/6 |
| 5,777,324 | A | 7/1998 | Hillenkamp ................ 250/288 |
| 5,786,146 | A | 7/1998 | Herman et al. ................. 436/6 |
| 5,786,464 | A | 7/1998 | Seed |
| 5,795,714 | A | 8/1998 | Cantor et al. .................. 435/6 |
| 5,807,693 | A | 9/1998 | Scott et al. |
| 5,834,189 | A | 11/1998 | Stevens et al. |
| 5,837,832 | A | 11/1998 | Chee et al. ................. 536/22.1 |
| 5,843,669 | A | 12/1998 | Kaiser et al. ................... 435/6 |
| 5,851,765 | A | 12/1998 | Köster ........................... 435/6 |
| 5,853,979 | A | 12/1998 | Green et al. ................... 435/5 |
| 5,856,092 | A | 1/1999 | Dale et al. |
| 5,858,659 | A | 1/1999 | Sapolsky et al. |
| 5,858,705 | A | 1/1999 | Wei et al. ................... 435/69.1 |
| 5,869,242 | A | 2/1999 | Kamb |
| 5,869,275 | A | 2/1999 | Huang |
| 5,871,911 | A | 2/1999 | Dahlberg et al. ............... 435/6 |
| 5,871,945 | A | 2/1999 | Lockerbie et al. |
| 5,872,003 | A | 2/1999 | Köster ..................... 435/283.1 |
| 5,874,283 | A | 2/1999 | Harrington et al. ....... 435/252.3 |
| 5,876,934 | A | 3/1999 | Duthie et al. |
| 5,885,841 | A | 3/1999 | Higgs, Jr. et al. .............. 436/89 |
| 5,888,795 | A | 3/1999 | Hamilton .................... 435/200 |
| 5,900,481 | A | 5/1999 | Lough et al. ............... 536/55.3 |
| 5,902,723 | A | 5/1999 | Dower et al. |
| 5,908,755 | A | 6/1999 | Kumar et al. |
| 5,912,118 | A | 6/1999 | Ansorge et al. |
| 5,925,525 | A | 7/1999 | Fodor et al. |
| 5,928,870 | A | 7/1999 | Lapidus et al. ................. 435/6 |
| 5,928,906 | A | 7/1999 | Köster et al. ............... 435/91.2 |
| 5,928,952 | A | 7/1999 | Hutchins et al. |
| 5,952,174 | A | 9/1999 | Nikiforov et al. |
| 5,952,176 | A | 9/1999 | McCarthy et al. .............. 435/6 |
| 5,975,492 | A | 11/1999 | Brenes ....................... 251/175 |
| 5,976,802 | A | 11/1999 | Ausorge et al. |
| 5,976,806 | A | 11/1999 | Mahajan et al. ................ 435/6 |
| 5,981,186 | A | 11/1999 | Gabe et al. |
| 5,985,214 | A | 11/1999 | Stylli et al. |
| 5,998,143 | A | 12/1999 | Ellis et al. |
| 6,004,744 | A | 12/1999 | Goelet et al. |
| 6,011,013 | A | 1/2000 | Carr et al. |
| 6,013,431 | A | 1/2000 | Söderlund et al. |
| 6,017,693 | A | 1/2000 | Yates, III et al. |
| 6,017,702 | A | 1/2000 | Lee et al. |
| 6,017,704 | A | 1/2000 | Herman et al. ................. 435/6 |
| 6,018,041 | A | 1/2000 | Drmanac et al. |
| 6,020,122 | A | 2/2000 | Okasinski et al. |
| 6,022,688 | A | 2/2000 | Jurinke et al. .................. 435/6 |
| 6,024,925 | A | 2/2000 | Little et al. ................. 422/100 |
| 6,025,136 | A | 2/2000 | Drmanac |
| 6,030,778 | A | 2/2000 | Acton et al. |
| 6,043,031 | A | 3/2000 | Köster et al. ................... 435/6 |
| 6,043,136 | A | 3/2000 | Jang et al. |
| 6,046,005 | A | 4/2000 | Ju et al. |
| 6,054,276 | A | 4/2000 | Macevicz ...................... 435/6 |
| 6,059,724 | A | 5/2000 | Campell et al. |
| 6,060,022 | A | 5/2000 | Pang et al. |
| 6,074,823 | A | 6/2000 | Köster et al. ................... 435/6 |
| 6,087,095 | A | 7/2000 | Rosenthal et al. |
| 6,090,558 | A | 7/2000 | Butler et al. |
| 6,090,606 | A | 7/2000 | Kaiser et al. ................ 435/199 |
| 6,099,553 | A | 8/2000 | Hart et al. ................... 606/232 |
| 6,107,104 | A | 8/2000 | Lockerbie et al. |
| 6,111,251 | A | 8/2000 | Hillenkamp ................ 250/288 |
| 6,114,148 | A | 9/2000 | Seed et al. |

| | | | | |
|---|---|---|---|---|
| 6,117,634 | A | 9/2000 | Langmore et al. | |
| 6,121,238 | A | 9/2000 | Dower et al. | |
| 6,132,685 | A | 10/2000 | Kercso et al. | |
| 6,133,436 | A | 10/2000 | Köster et al. | 536/24.3 |
| 6,133,502 | A | 10/2000 | Kasuga et al. | |
| 6,140,053 | A | 10/2000 | Köster et al. | 435/6 |
| 6,146,854 | A | 11/2000 | Köster et al. | 435/91.1 |
| 6,147,344 | A | 11/2000 | Annis et al. | |
| 6,156,501 | A | 12/2000 | McGall et al. | |
| 6,175,057 | B1 | 1/2001 | Mucke et al. | |
| 6,180,849 | B1 | 1/2001 | Streuli et al. | |
| 6,188,064 | B1 | 2/2001 | Köster | 250/282 |
| 6,197,498 | B1 | 3/2001 | Köster | |
| 6,200,756 | B1 | 3/2001 | Herman et al. | 435/6 |
| 6,207,370 | B1 | 3/2001 | Little et al. | 435/6 |
| 6,221,601 | B1 | 4/2001 | Köster et al. | |
| 6,221,605 | B1 | 4/2001 | Köster | |
| 6,225,450 | B1 | 5/2001 | Köster | 536/22.1 |
| 6,235,478 | B1 | 5/2001 | Köster | |
| 6,262,334 | B1 | 7/2001 | Endege et al. | |
| 6,265,171 | B1 | 7/2001 | Herman et al. | 435/6 |
| 6,268,131 | B1 | 7/2001 | Kang et al. | 435/6 |
| 6,270,835 | B1 | 8/2001 | Hunt et al. | 427/79 |
| 6,277,573 | B1 | 8/2001 | Köster et al. | 435/6 |
| 6,294,328 | B1 | 9/2001 | Fleischmann et al. | |
| 6,300,076 | B1 | 10/2001 | Köster | 435/6 |
| 6,322,970 | B1 | 11/2001 | Little et al. | 435/6 |
| 6,423,966 | B2 | 7/2002 | Hillenkamp et al. | 250/288 |
| 6,428,955 | B1 | 8/2002 | Köster et al. | 435/6 |
| 6,436,635 | B1 | 8/2002 | Fu et al. | 435/6 |
| 6,548,477 | B1 | 4/2003 | Olson et al. | |
| 6,566,055 | B1 | 5/2003 | Monforte et al. | 435/6 |
| 6,589,485 | B2 | 7/2003 | Köster | 422/104 |
| 6,602,662 | B1 * | 8/2003 | Koster et al. | 435/6 |
| 2002/0009394 | A1 | 1/2002 | Köster et al. | 422/65 |
| 2002/0040130 | A1 | 4/2002 | Braun | |
| 2002/0042112 | A1 | 4/2002 | Köster et al. | 435/174 |
| 2002/0151493 | A1 | 10/2002 | Olson et al. | |
| 2002/0155587 | A1 | 10/2002 | Opalsky et al. | 435/287.2 |
| 2003/0027169 | A1 | 2/2003 | Zhang et al. | |
| 2003/0180148 | A1 | 9/2003 | Weng | |
| 2003/0180149 | A1 | 9/2003 | Krugerke | |
| 2003/0190644 | A1 | 10/2003 | Braun et al. | |
| 2003/0207297 | A1 | 11/2003 | Koster et al. | |
| 2003/0193298 | A1 | 12/2003 | Olson et al. | |
| 2003/0232420 | A1 | 12/2003 | Braun et al. | |
| 2005/0079521 | A1 | 4/2005 | Beaulieu et al. | |

FOREIGN PATENT DOCUMENTS

| | | | |
|---|---|---|---|
| EP | 0299652 | A1 | 7/1988 |
| EP | 0395481 | A3 | 4/1990 |
| EP | 0596205 | | 5/1994 |
| EP | 0613683 | | 12/1999 |
| FR | 2650840 | A1 | 11/1989 |
| FR | 2749662 | | 12/1997 |
| GB | 2329475 | A | 8/1998 |
| WO | WO 9102087 | | 2/1991 |
| WO | WO 9113075 | | 9/1991 |
| WO | WO 91/16457 | | 10/1991 |
| WO | WO 9215712 | | 9/1992 |
| WO | 9315407 | | 8/1993 |
| WO | 9321592 | | 10/1993 |
| WO | WO 93/25221 | | 12/1993 |
| WO | WO 94/17784 | | 1/1994 |
| WO | 9415219 | | 7/1994 |
| WO | 9416101 | | 7/1994 |
| WO | 9421822 | | 9/1994 |
| WO | 9525281 | | 9/1995 |
| WO | WO 95/34326 | | 12/1995 |
| WO | 9629431 | | 9/1996 |
| WO | 9632504 | | 10/1996 |
| WO | 9703210 | | 1/1997 |
| WO | 9708306 | | 3/1997 |
| WO | 9737041 | | 10/1997 |
| WO | 9740462 | | 10/1997 |
| WO | 9742348 | | 11/1997 |
| WO | 9743617 | | 11/1997 |
| WO | WO 9747974 | | 12/1997 |
| WO | 9812734 | | 3/1998 |
| WO | WO 9812734 | | 3/1998 |
| WO | 9820019 | | 5/1998 |
| WO | 9820020 | | 5/1998 |
| WO | 9820166 | | 5/1998 |
| WO | WO 9822122 | | 5/1998 |
| WO | 9824935 | | 6/1998 |
| WO | WO 9830883 | | 7/1998 |
| WO | 9833808 | | 8/1998 |
| WO | 9835609 | | 8/1998 |
| WO | WO 98/48809 | | 11/1998 |
| WO | WO 9856954 | | 12/1998 |
| WO | 9905323 | | 2/1999 |
| WO | WO 9909218 | | 2/1999 |
| WO | 9912040 | | 3/1999 |
| WO | 9931278 | | 6/1999 |
| WO | 9950447 | | 10/1999 |
| WO | 9954501 | | 10/1999 |
| WO | 9957318 | | 11/1999 |
| WO | 0031300 | | 6/2000 |
| WO | 0051053 | | 8/2000 |
| WO | 0056446 | | 9/2000 |
| WO | WO 0058516 | | 10/2000 |
| WO | WO 0058519 | | 10/2000 |
| WO | 0060361 | | 11/2000 |
| WO | 0127857 | | 4/2001 |
| WO | WO 0204489 | | 1/2002 |
| WO | WO 03093296 | | 11/2003 |

OTHER PUBLICATIONS

Badger et al, "New features and enhancements in the X-PLOR computer program", *Proteins: Structure, Function, and Genetics*, 35(1):25-33 (1999).

Beck et al., "Chemiluminescent detection of DNA: application for DNA sequencing and hybridization", *Nucl. Acids Res.*, 17(13):5115-5123 (1989).

Bertina et al., "Mutation in blood coagulation factor V associated with resistance to activated protein C", *Nature*, 369:647 (1994).

Bessho et al., "Nucleotide excision repair 3' endonuclease XPG stimulates the activity of base excision repair enzyme thymine glycol DNA glycosylase", *Nucl. Acids Res.*, 27(4):79-83 (1999).

Bjelland et al., "Purification and characterization of 3-methyladenine DNA glycosylase I from *Escherichia coli", Nucl. Acids Res.*, 15(7):2787-2800 (1987).

Bleczinski et al., "Monitoring the Hybridization of the Components of Oligonucleotide Mixtures to Immobilized DNA via Matrix-assisted Laser Desorption/Ionization Time-of-flight Mass Spectrometry", *Rapid Communications in Mass Spectrometry*, 12:1737-1743 (1998).

Braun et al., "Detecting *CFTR* gene mutations by using primer oligo base extension and mass spectrometry", *Clinical Chemistry*, 43(7):1151-1158 (1997).

Braun et al., "Improved Analysis of Microsatellites Using Mass Spectrometry", *Genomics*, 46:18-23 (1997).

Bregman et al., "Molecular Characterization of Bovine Brain P75, a High Affinity Binding Protein for the Regulatory Subunit of cAMP-dependent Protein Kinase IIβ", *J. Biol. Chem.*, 266(11):7207-7213 (1991).

Buetow et al., "High-throughput development and characterization of a genomewide collection of gene-based single nucleotide polymorphism markers by chip-based matrix-assisted laser desorption/ionization time-of-flight mass spectrometry", *Proc. Natl. Acad. Sci. USA*, 98(2):581-584 (2001).

Burton et al., "Type II regulatory subunits are not required for the anchoring-dependent modulation of CA^2+ channel activity by cAMP-dependent protein kinase", *Proc. Natl. Acad. Sci. USA*, 94:11067-11072 (1997).
Carr et al., "Association of the Type II cAMP-dependent Protein Kinase with a Human Thyroid RII-anchoring Protein", *J. Biol. Chem.*, 267(19):13376-13382 (1992).
Carr et al., "Interaction of the Regulatory Subunit (RII) of cAMP-dependent Protein Kinase with RII-anchoring Protein Occurs through an Amphipathic Helix Binding Motif", *J. Biol. Chem.*, 266(22):14188-14192 (1991).
Chiu et al., "Mass Spectrometry of Nucleic Acids", *Clin. Chem.*, 45:1578 (1999).
Chiu et al., "Mass Spectrometry of single-stranded restriction fragments captured by an undigested complementary sequence", *Nucl. Acids. Res.*, 28(8):e31 (2000).
Clegg et al., "Genetic characterization of a brain-specific form of the type I regulatory subunit of cAMP-dependent protein kinase", *Proc. Natl. Acad. Sci. USA*, 85:3703-3707 (1988).
Coghlan et al., "Association of Protein Kinase A and Protein Phosphatase 2B with a Common Anchoring Protein", *Science*, 267:108-111 (1995).
Cohen et al., "Emerging Technologies for Sequencing Antisense Oligonucleotides: Capillary Electrophoresis and Mass Spectrometry", *Advanced Chromatography*, 36:127-162 (1996).
Colledge et al., "AKAPs: from structure to function", *Trends in Cell Biology*, 9:216-221 (1999).
Collins et al., "A DNA Polymorphism Discovery Resource for Research on Human Genetic Variation", *Genome Research*, 8:1229-1231 (1998).
Corder et al., "Gene Dose of Apolipoprotein E Type 4 Allele and the Risk of Alzheimer's Disease in Late Onset Families", *Science*, 261:921-923 (1993).
Eftedal et al., "Consensus sequences for good and poor removal or uracil from double stranded DNA by uracil-DNA glycosylase", *Nucl. Acids Res.*, 21(9):2095-2101 (1993).
Faux et al., "More on target with protein phosphorylation: conferring specificity by location", *Trends Biochem.*, 21:312-315 (1996).
Foster et al., "Naming Names in Human Genetic Variation Research", *Genome Research*, 8:755-757 (1998).
Fu et al., "Efficient preparation of short DNA sequence ladders potentially suitable for MALDI-TOF DNA sequencing", *Genetic Analysis: Biomolecular Engineering*, 12:137-142 (1996).
Fu et al., "Sequencing Exons 5 to 8 of the p53 Gene by MALDI-TOF Mass Spectrometry", *Nature Biotechnol.*, 16:381-384 (1998).
Fu et al., "A DNA sequencing strategy that requires only five bases of known terminal sequence for priming", *Proc. Natl. Acad. Sci. USA*, 92:10162-10166 (1995).
Fu et al., "Sequencing double-stranded DNA by strand displacement", *Nucl. Acids Res*. 25(3):677-679 (1997).
Gabbita et al., "Decrease in Peptide Methionine Sulfoxide Reductase in Alzheimer's Disease Brain", *J. Neurochemistry*, 73(4):1660-1666 (1999).
Glantz et al., "Characterization of Distinct Tethering and Intracellular Targeting Domains in AKAP75, a Protein That Links cAMP-dependent Protein Kinase IIβ to the Cytoskeleton", *J. Biol. Chem.*, 268(17):12796-12804 (1993).
Goldmacher et al., "Photoactivation of toxin conjugates", *Bioconj. Chem.*, 3:104-107 (1992).
Griffin et al., "Genetic analysis by peptide nucleic acid affinity MALDI-TOF mass spectrometry", *Nature Biotechnology*, 15:1368-1372 (1997).
Guatelli et al., "Isothermal, in vitro amplification of nucleic acids by a multienzyme reaction modeled after retroviral replication", *Proc. Natl. Acad. Sci. USA*, 87:1874-1878 (1990).
Hausken et al., "Mutational Analysis of the A-Kinase Anchoring Protein (AKAP)-binding Site on RII", *J. Biol. Chem.*, 271(46):29016-29022 (1996).
Hazum et al., "A photocleavable protecting group for the thiol function of cysteine", in *Pept., Proc. Eur. Pept. Symp.*, 16th, Brunfeldt, K., (Ed.), pp. 105-110 (1981).
Higgins et al., "Competitive Oligonucleotide Single-Base Extension Combined with Mass Spectrometric Detection for Mutation Screening", *BioTechniques*, 23(4):710-714 (1997).
Higgins et al., "DNA-Joining Enzymes: A Review", *Methods in Enzymology*, 68:50-71 (1979).
Higley et al., "Processivity of uracil DNA glycosylase", *Mutation Research, DNA Repair*, 294:109-116 (1993).
Hinton et al., "The application of robotics to fluorometric and isotopic analyses of uranium", Laboratory Automation & Information Management, NL, Elsevier Science publishers BV., Amsterdam, vol. 21 No. 2/03, pp. 223-227, Dec. 1, 1993.
Huang et al., "D-AKAP2, a novel protein kinase A anchoring protein with a putative RGS domain", *Proc. Natl. Acad. Sci. USA*, 94:11184-11189 (1997).
Hubbard et al., "On target with a new mechanism for the regulation of protein phosphorylation", *Trends Biochem. Sci.*, 18:172-177 (1993).
Instrumentation; "Multimek 96" automated pipettor; Beckman Coulter, Inc., located at http://www.coulter.com, Sep. 8, 1999.
International Search Report for International Application No. PCT/US00/08111, Date of Mailing Nov. 13, 2000.
Jahnsen et al., "Molecular Cloning, cDNA Structure, and Regulation of the Regulatory Subunit of Type II cAMP-dependent Protein Kinase from Rat Ovarian Granulosa Cells", *J. Biol. Chem.*, 261(26):12352-12361 (1986).
Jiang-Baucom et al., "DNA Typing of Human Leukocyte Antigen Sequence Polymorphisms Nucleic Acid Probes and MALDI-TOF Mass Spectrometry", *Analytical Chemistry*, 69:4894-4898 (1997).
Jurinke et al., "Detection of hepatitis B virus DNA in serum samples via nested PCR and MALDI-TOF mass spectrometry", *Genetic Analysis: Biomolecular Engineering*, 13:67-71 (1996).
Jurinke et al., "Recovery of Nucleic Acids from Immobilized Biotin-Streptavidin Complexes Using Ammonium Hydroxide and Applications in MALDI-TOF Mass Spectrometry", *Anal. Chem.*, 69:904-910 (1997).
Jurinke et al., "Analysis of Ligase Chain Reaction products via Matrix-Assisted Laser Desorption/Ionization Time-of-Flight-Mass Spectrometry", *Anal. Biochem.*, 237:174-181.
Jurinke et al., "Application of nested PCR and mass spectrometry for DNA-based virus detection: HBV-DNA detected in the majority of isolated anti-HBc positive sera", *Genetic Analysis: Biomolecular Engineering*, 14:97-102 (1998).
Kario et al., "Genetic Determinants of Plasma Factor VII Activity in the Japanese", *Thromb. Haemost.*, 73:617-22 (1995).
Klauck et al., "Coordination of Three Signaling Enzymes by AKAP79, a Mammalian Scaffold Protein", *Science*, 271:1589-1592 (1996).
Köster at al., "Oligonucleotide synthesis and multiples DNA sequencing using chemiluminescent detection", *Nucl. Acids Res.*, Symposium Series No. 24 (1991) 318-21.
Köster et al., "A strategy for rapid and efficient DNA sequencing by mass spectrometry", *Nature Biotechnology*, 14:1123-1128 (1996).
Kwoh et al., "Transcription-based amplification system and detection of amplified virus type 1 with a bead-based sandwich hybridization format", *Proc. Natl. Acad. Sci. USA*, 86:1173-1177 (1989).
Laken et al., "Familial colorectal cancer in Ashkenazim due to a hypermutable tract in APC", *Nature Genetics*, 17:79-83 (1995).
Lam et al., "Genetic influence of the R/Q353 genotype on factor VII activity is overwhelmed by environmental factors in Chinese patients with Type II (non-insulin-dependent) diabetes mellitus", *Diabetologia*, 41:760-766 (1998).
Lasko et al., "Eukaryotic DNA Ligases", *Mutation Research*, 236:277-287 (1990).
Lee et al., "Isolation of a CDNA clone for the type I regulatory subunit of bovine cAMP-dependent protein kinase", *Proc. Natl. Acad. Sci. USA*, 80:3608-3612 (1983).
Lehman, I.R., "DNA Ligase: Structure, Mechanism, and Function", *Science*, 186:790-797 (1974).
Li et al., "DNA ligase 1 is associated with the 21 S complex of enzymes for DNA synthesis in HeLa cells", *Nucl. Acids Res.*, 22(4):632-638 (1994).
Li et al., "High-Resolution MALDI Fourier Transform Mass Spectrometry of Oligonucleotides", *Anal. Chem.*, 68(13):2090-2096 (1996).

Lindahl et al., "Mammalian DNA Ligases", *Annu. Rev. Biochem.*, 61:251-281 (1992).
Little et al., "Detection of RET proto-oncogene codon 634 mutations using mass spectrometry", *J. Mol. Med.*, 75:745-750 (1997).
Little et al., "Direct detection of synthetic and biologically generated double-stranded DNA by MALDI-TOF MS", *International Journal of Mass Spectrometry and Ion Processes*, 169-170:323-330 (1997).
Little et al., "Mass spectrometry from miniaturized arrays for full comparative DNA analysis", *Nature Medicine*, 3:1413-1416 (1997).
Little et al., "Detection of *RET* proto-oncogene codon 634 mutations using mass spectrometry", *J. Mol. Med.*, 75:745-750 (1997).
Little et al., "Identification of apolipoprotein E polymorphisms using temperature cycled primer oligo base extension and mass spectrometry", *Eur. J. Clin. Chem. Clin. Biochem.*, 35(7):545-548 (1997).
Little et al., "MALDI on a chip: analysis of arrays of low-femtomole to subfemtomole quantities of synthetic oligonucleotides and DNA diagnostic products dispensed by a piezoelectric pipet", *Anal. Chem.*, 69:4540-4546 (1997).
Little et al., "Mass Spectrometry from miniaturized arrays for full comparative DNA analysis", *Nature Medicine*, 3(12):1413-1416 (1997).
Lizardi et al., "Exponential Amplification of Recombinant-RNA Hybridization Probes", *Bio/Technology*, 6:1197-1202 (1988).
Miki et al., "Single Amino Acids Determine Specificity of Binding Protein Kinase A Regulatory Subunits by Protein Kinase A Anchoring Proteins", *J. Biol. Chem.* 274(41):29057-29062 (1999).
Miki et al., "Identification of Tethering Domains for Protein Kinase A Type Iα Regulatory Subunits on Sperm Fibrous Sheath Protein FSC1", *J. Biol. Chem.*, 273(51):34384-34390 (1996).
Mochly-Rosen, D., "Localization of Protein Kinases by Anchoring Proteins: A Theme in Signal Transduction", *Science*, 268:247-251 (1995).
Moskovitz et al., "Overexpression of peptide-methionine sulfoxide reductase in *Saccharomyces cerevisiae* and human T cells provides them with high resistance to oxidative stress", *Proc. Natl. Acad. Sci. USA*, 95:14071-14075 (1998).
Nilges et al., "Automated NOESY interpretation with ambiguous distance restraints: the refined NMR solution structure of the pleckstrin homology domain from β-spectrin", *J. Mol. Biol.* , 269:408-422 (1997).
*Nucleases* 2nd ed., Linn, S.M. et al., (Eds.), Cold Spring Harbor Laboratory Press (1993).
Podhajska et al., "Conversion of the *Fok*I endonuclease to a universal restriction enzyme: cleavage of phage M13mp7 DNA at predetermined sites", *Gene*, 40:175-182 (1985).
Reymer et al., "A lipoprotein lipase mutation (Asn291Ser) is associated with reduced HDL cholesterol levels in premature atherosclerosis", *Nature Genetics*, 10:28-34 (1995).
Ross et al., "Analysis of Short Tandem Repeat Polymorphisms in Human DNA by Matrix-Assisted Laser Desorption/Ionization Mass Spectrometry", *Analytical Chemistry*, 69:3966-3972 (1997).
Ross et al., "Discrimination of Single-Nucleotide Polymorphisms in Human DNA Using Peptide Nucleic Acid Probes Detected by MALDI-TOF Mass Spectrometry", *Analytical Chemistry*, 69:4197-4202 (1997).
Ruppert et al., "A Filtration Method for Plasmid Isolation Using Microtiter Filter Plates", *Anal. Biochem.*, 230:130-134 (1995).
Samson et al., "Resistance to HIV-1 infection in caucasian individuals bearing mutant alleles of the CCR-5 chemokine receptor gene", *Nature*, 382:722-725 (1996).
Saparbaev et al., "*Escherichia coli, Saccharomyces cerevisiae*, rat and human 3-methyladenine DNA glycosylases repair 1, N^6-ethenoadenine when present in DNA", *Nucl. Acids Res.*, 23(18):3750-3755 (1995).
Sarkar et al., "Human Genetic Bi-allelic Sequences (HGBASE), a Databases of Intra-genic Polymorphisms", *Mem. Inst. Oswaldo Cruz*, 93(5):693-694 (1998).
Schachter et al., "Genetic associations with human longevity at the APOE and ACE loci", *Nature Genetics*, 6:29-32 (1994).
Scott et al., "Type II Regulatory Subunit Dimerization Determines the Subcellular Localization of the cAMP-dependent Protein Kinase", *J. Biol. Chem.*, 265(35):21561-21566 (1990).
Scott, J., "Cyclic Nucleotide-Dependent Protein Kinases", *Pharmac. Ther.*, 50:123-145 (1991).
Senko et al., "Automated Assignment of Charge States from Resolved Isotopic Peaks for Multiply Charged Ions", *J. Am. Soc. Mass Spectrom.*, 6:52-56 (1995).
Senter et al., "Novel photocleavable protein crosslinking reagents and their use in the preparation of antibody-toxin conjugates", *Photochem. Photobiol.*, 42:231-237 (1985).
Sequenom Advances the Industrial Genomics Revolution with the Launch of Its DNA MassArray™ Automated Process Line, Press Release: Sep. 28, 1998, http://www.sequenom.com/pressrelease.htm.
Sequenom Completes Design of More Than 400,000 SNP Assays; Mass EXTENDTM Assay Portfolio Covers Majority of SNPs in the Public Domain, Press Release; Oct. 10, 2000, http://www/sequenom.com/ir/ir_prs.asp.
Sequenom and Gemini Identify Genes Linked to Cardiovascular Disease, Press Release: Nov. 28, 2000, http://www/sequenom.com/ir/ir_prs.asp.
Sequenom Announces Publication of Results From Large-Scale SNP Study With the National Cancer Institute, Press Release: Jan. 16, 2001, http://www/sequenom.com/ir/ir_prs.asp.
Sequenom: Technologies and Tools, located at http://www.sequenom-san.com/tech/tools.html, dated Aug. 29, 1999.
Siegert et al., "Matrix-Assisted Laser desorption/Ionization Time-of-Flight Mass Spectrometry for the detection of Polymerase Chain Reaction Containing 7-Deazapurine Moieties", *Anal. Biochem.*, 243:55-65 (1996).
Smith, L.M., "Sequence from spectrometry: A realistic prospect", *Nature Biotechnology*, 14:1084-1085 (1996).
Srinivasan et al., "Matrix-assisted Laser Desorption/Ionization Time-of-flight Mass Spectrometry as a Rapid Screening Method to Detect Mutations Causing Tay-Sachs Disease", *Rapid Communications in Mass Spectrometry*, 11:1144-1150 (1997).
Sugisaki et al., "New restriction endonucleases from *Flavobacterium okeanokoites* (*Fok*I) and *Micrococcus luteus* (*Mlu*I)", *Gene*, 16:73-78 (1981).
Szybalski et al., "Class-IIS restriction enzymes—a review", *Gene*, 100:13-26 (1991).
Takio et al., "Primary structure of the regulatory subunit if type II cAMP dependent protein kinase from bovine cardiac muscle", *Proc. Natl. Acad. Sci. USA*, 79:2544-8 (1982).
Tammen et al., "Proteolytic cleavage of glucagon-like peptide-1 by pancreatic β cells and by fetal calf serum analyzed by mass spectrometry", *J. Cromatogr. A*, 852:285-295 (1999).
Tang et al., "Matrix-assisted laser desorption/ionization mass spectrometry of immobilized duplex DNA probes", *Nucl. Acids Res.*, 23(16):3126-3131 (1995).
Tang et al., "Chip-based genotyping by mass spectrometry", *Proc. Natl. Acad. Sci. USA*, 96:10016-10020 (1999).
Taranenko et al., "Laser desorption mass spectrometry for point mutation detection", *Genetic Analysis: Biomolecular Engineering*, 13:87-94 (1996).
Thompson, "Fitting robots with white coats", *Laboratory Automation and Information Management*, 31:173-193 (1996).
Uracil-DNA Glycosylase, product description. Roche Molecular Biochemicals Catalog Version 3, Nov. 1999 http:/biochem.roche.com/pack-insert/1269062a.pdf (Dec. 21, 2000).
Uracil-DNA Glycosylase (UDG), product description. New England Biolabs. http://circuit.neb.com/neb/products/mod_enzymes/280.html (Dec. 21, 2000).
van den Boom et al., "Forward and Reverse DNA Sequencing in a Single Reaction", *Anal. Biochem.*, 256:127-129 (1998).
van den Boom et al., "Combined amplification and sequencing in a single reaction using two DNA polymerase with differential incorporation rates for dideoxynucleotides", *J. Biochem. Biophys. Methods*, 35:69-79 (1997).
Vaughan et al., "Glycosylase mediated polymorphism detection (GMPD)—a novel process for genetic analysis", *Genetic Analysis: Biomolecular Engineering*, 14:169-175 (1999).
Wada et al., "Detection of Single-nucleotide Mutations Including Substitutions and Deletions by Matrix-assisted Laser Desorption/

Ionization Time-of-flight Mass Spectrometry", *Rapid Communications in Mass Spectrometry*, 11:1657-1660.
Waga et al., "Reconstitution of Complete SV40 DNA Replication with Purified Replication Factors", *J. Biol. Chem.*, 269(14):10923-10934 (1994).
Wang et al., "Allene $\gamma_9$ and $\gamma_{10}$: low-temperature measurements of line intensity", *J. Mol. Spectrosc.*, 194(20):256-268 (1999).
Weiler et al., "Hybridisation based DNA screening on peptide nucleic acid (PNA) oligomer arrays", *Nucleic Acids Res.*, 25:2792-2799 (1997).
Wilson et al., "Restriction and Modification Systems", *Annu. Rev. Genet.*, 25:585-627 (1991).
Yen et al., "Synthesis of water-soluble copolymers containing photocleavable bonds", *Makromol. Chem.*, 190:69-82 (1989).
Huang et al., "Identification of a Novel Protein Kinase A Anchoring Protein That Binds Both Type I and Type II regulatory Subunits", *Jounral of Biological Chemistry*, 272(12):8057-8064 (1997).
Laken et al., "Genotyping by mass spectrometric analysis fo short DNA fragments", *Nature Biotechnology*, 16:1352-1356 (1998).
Shriver et al., "Ethnic-Affilation Estimation by Use of Population-Specific DNA Markers", *Am. J. Hum. Genet.*, 60:957-964 (1997).
"Red Tape: It's in You to Give: Last year the Canadian Blood Services' security measures weeded out 200,000 would-be donors. Doug Fischer looks at the reasons behind the red tape." *Ottawa Citizen Saturday Final Edition* Oct. 5, 2002.
Cai et al., "Different Discrete Wavelet Transforms Applied to Denoising Analytical Data," *J. Chem. Inf. Comput. Sci.* 38: 1161-1170 (1998).
Cavalli-Sforza, L.I., "The DNA revolution in population genetics," *Trends in Genetics* 14(2): 60-65 (1998).
Dittmar, M., "Review of studies of polymorphic blood systems in the Aymara indigenous population from Bolivia, Peru, and Chile," *Anthropol. Anz.* 53(4): 289-315 (1995).
Dodgson et al., "DNA Marker Technology: A Revolution in Animal Genetics," *Poultry Science* 76: 1108-1114 (1997).
Hey, J., "Population genetics and human origins haplotypes are key," *Trends in Genetics* 14(8): 303-305 (1998) (with reply by L. Cavalli-Sforza).
Ikemoto, S., "Searching for Genetic Markers In the Fields of Forensic Medicine and Human Genetics," *Nippon Hoigaku Zasshi* 49(6): 419-431 (1995).
Li, J., "De-Noising ENMR Spectra by Wavelet Shrinkage, Abstract—Eleventh IEEE Symposium on Computer-Based Medical Systems," pp. 252-255 (1998).
Nagamura et al., "Rice molecular genetic map using RFLPs and its applications," *Plant Molecular Biology* 35: 79-87 (1997).
Nelson et al., "The Accuracy of Quantification from 1D NMR Spectra Using the PIQABLE Algorithm," *Journal of Magnetic Resonance* 84: 95-109 (1989).
Paterson, A.H., "Molecular Dissection of Quantitative Traits: Progress and Prospects," *Genome Research* 5(4): 321-333 (1995).
Pena et al., "DNA diagnosis of human genetic individuality," *J. Mol. Med.* 73: 555-564 (1995).
Polettini et al., "Fully-automated systematic toxicological analysis of drugs, poisons, and metabolites in whole blood, urine, and plasma by gas chromatography—full scan mass spectrometry," *Journal of Chromatography B* 713: 265-279 (1998).
Thompson, J.N., "Fitting robots with white coats," *Laboratory Automation and Information Management* 31: 173-193 (1996).
Yasuda et al., "Genetic Polymorphisms Detectable in Human Urine: Their Application to Forensic Individualization," *Japanese Journal of Legal Medicine* 51: 407-416 (1997).
Breen, G., et al., Determining SNP Allele Frequencies in DNA Pools, BioTechniques, (2000), 464-470, 28(3).
Buetow, Kenneth H. et al., High-throughput development and characterization of a genomewide collection of gene-based single nucleotide polymorphism markers by chip-based matrix-assisted laser desorption/ionization time-of-flight mass spectrometry, Proc. National Association of Science (2001), 581-584, 98(2) PNAS http://www.pnas.org.
Downes, Kate, et al., SNP allele frequency estimation in DNA pools and variance components analysis, BioTechniques, (2004), 840-845, 36(5), The Wellcome Trust Sanger Institute.
Germer, Soren, at al., High-Throughput SNP Allele-Frequency Determination in Pooled DNA Samples by Kinetic PCR, Methods, Genome Research, (2000), 258-266, 10, Cold Spring Harbor Laboratory Press.
Hoogendoorn, Bastiaan, et al., Cheap, accurate and rapid allele frequency estimation of single nucleotide polymorphisms by primer extension and DHPLC in DNA pools, Hum Genet (2000) 488-493, 107, Pringer-Verlag.
Le Hellard, Stephanie, et al., SNP genotyping on pooled DNA's: comparison of genotyping technologies and a semi automated method for data storage and analysis, Nucleic Acids Research, (2002) 1-10, 30(15), Oxford University Press.
Risch, Neil, et al., The Relative Power of Family-Based and Case-Control Designs for Linkage Disequilibrium Studies of Complex Human Diseases I. DNA Pooling, Genome Research, (1998), 1273-1288, 8, Cold Spring Harbor Laboratory Press.
Ross, Philip, et al., Quantitative Approach to Single-Nucleotide Polymorphism Analysis Using MALDI-TOF Mass Spectrometry, BioTechniques, (2000) 620-629, 29(3).
Sasaki, Tomonari, et al., Precise Estimation of Allele Frequencies of Single-Nucleotide Polymorphisms by a Quantitative SSCP Analysis of Pooled DNA, Am. J. Hum, Genet. (2001) 214-218, 68, The American Society of Human Genetics.
Zhou, Guo-Hua, et al., Quantitative detection of single nucleotide polymorphisms for a pooled sample by a bioluminometric assay coupled with modified primer extension reactions (BAMPER), Nucleic Acids Research, (2001) 1-11, 29(19 e93), Oxford University Press.
Herman et al., "Methylation-specific PCR: A Novel PCR Assay for Methylation Status of CpG Islands," *Proc. Natl. Acd. Sci.* 93:9821-26 (1996).
Clausen et al., J. Clinical Investigation, 98(5):1195-1209 (1996).
Dahl, et al., "DNA methylation analysis techniques," Biogerontology, 2003, vol. 4 pp. 233-250; especially pp. 242-245.
A Practical Guide to Molecular Cloning, Book: Perbal B., John Wiley & Sons, New York, 1984.
Aebersold and Mann, Nature 422:198-207 (2003).
Ali et al., "The A kinase anchoring protein is required for mediating the effect of protein kinase A on ROMK1 channels", Proc. Natl. Acad. Sci., 95:10274-10278 (1998).
Alto N.M., et al., "Bioinformatic design of A-kinase anchoring protein-in silico: A potent and selective peptide antagonist of type II protein kinase A anchoring," PNAS 100:8, Apr. 15, 2003 pp. 4445-4450.
Altschul et al., "Basic Local Alignment Search Tool", J. Mol. Biol., 215:403-410 (1990).
Amieux et al., "Compensatory Regulation of Rla Protein Levels in Protein Kinase A Mutant Mice", J. Biol. Chem., 272(7):3993-3998 (1997).
Angelo et al., "Molecular Characterization of an Anchor Protein (AKAPCE) That Binds the RI Subunit (RCE) of Type I Protein Kinase A from Caenorhabditis elegans", J. Biol. Chem., 273(23): 14633-14643 (1998).
Antibodies, Book: A Laboratory Manual, Harlow, E. and Lane D., Cold Spring Harbor Laboratory, 1988.
Antos et al., Circ. Res., 89:997-1004 (2001).
Araki et al., "Targeted integration of DNA using mutant lox sites in embryonic stem cells", Nucleic Acids Res., 25(4):868-872 (1997).
Baker et at., "A Scintillation Proximity Assay for UDP-GalNAc:Polypeptide, NAcetylgalactosaminyltransferase," Analytical Biochemistry 239: 20-24 (1996).
Banky et al. "Related protein-proteinn interaction modules present drastically different surface topographies despite a conserved helical platform," J. Mol. Biol. 330:1117-1129 (2003).
Banky et al., "Isoform-specific Differences between the Type Iα and IIα Cyclic AMPdependent Protein Kinase Anchoring Domains Revealed by Solution NMR", J. Biol. Chem., 275(45):35146-35152 (2000).
Banky et at., "Dimerizationl Docking Domain of the Type la Regulatory Subunit of cAMP dependent Protein Kinase", J. Biol. Chem., 273(52):35048-35055 (1998).

Bannwarth et al:, "Global Phosphorylation of Peptides Containing Oxidation-Sensitive Amino Acids," Bioorganic & Medicinal Chemistry Letters 6(17): 2141-2146 (1996).

Barradeau et al., "Musle-regulated expression and determinants for neuromuscular junctional localization of the mouse RIα regulatory subunit of CAMP-dependent protein kinase", Proc. Natl. Acad. Sci., 98(9):5037-5042 (2001).

Baum et al., "Development of a Scintillation Proximity Assay for Human Cytomegalovirus Protease Using 33Phosphorous," Analytical Biochemistry 237: 129-134 (1996).

Biernat et al., "The construction and cloning of synthetic genes coding for artificial proteins and expression studies to obtain fusion proteins", Protein Engineering, 1(4):345-351, (1997).

Biocomputing, "Informatics and Genome Projects", Smith, W.D. (Ed.), Academic Press, Inc. San Diego, California (1994).

Biological Techniques Series, Book: "Immunochemical Methods in Cell and Molecular Biology", Mayer, R.J. And Walker, J.H., Academic Press, San Diego, California, 1987.

Bolin et al., "Peptide and Peptide Mimetic Inhibitors of Antigen Presentation by HLA-DR Class II MHC Molecules. Design, Structure-Activity Relationships, and X-ray Crystal Structures", J. Med. Chem., 43:2135-2148 (2000).

Bosworth et al., "Scintillationproximity assay", Nature, 341:167-168 (1989).

Boudet et al., "UV-treated polystyrene microtitre plates for use in an ELISA to measure antibodies against synthetic peptides", J. Immunolog. Meth., 142:73-82 (1991).

Braunwalder et at., "Application of Scintillating Microtiter Plates to Measure Phosphopeptide'Interactions with the GRB2-SH2 Binding Domain," The Journal of Biomolecular Screening 1(1)1:23-26 (1996).

Bregman et al., "Molecular Characterization of Bovine Brain P75, a High Affinity Binding Protein for the Regulatory Subunit of CAMP-dependent", J. Biol. Chem., 266(11):7207-7213 (1991).

Brinstar et al., "Expression of a microinjected immunoglobulin gene in the spleen of transgenic mice", Nature, 306;332-336 (1983).

Burns-Hamuro et al., "Designing isoform-specific peptide disruptors of protein kinase A localization", Proc. Natl. Acad. Sci., 100(7):4072-4077 (2003).

Burns-Hamuro, L.L., "Using Peptide Arrays to Screen for Isoform-Selective Peptide Disruptors of Protein Kinase A Localization," Meeting Poster presented at the Keystone Symposia on Proteomics: Technologies and Applications (E21, Keystone, Colorado, Mar. 25-30, 2003.

Burton et al., "Type II regulatory subunits are not required for the anchoring-dependent modulation of Ca2+ channel activity by CAMP-dependent protein kinase", Proc. Natl. Acad. Sci. USA 94:11067-11072 (1997).

Carr et al,, "Interaction of the Regulatory Subunit (RII) of CAMP-dependent Protein Kinase with RII-anchoring Proteins occurs through an Amphipathic Helix Binding Motif", J. Biol. Chem., 266(22): 14188-14192 (1991).

Carr et al., "Association of the Type II CAMP-dependent Protein Kinase with a Human Thyroid RII-anchoring Protein", J. Biol. Chem., 267(19):13376-13382 (1992).

Carrillo et al., "The Multiple Sequence Alignment Problem in Biology", SIAM J. App. Math., 48(5): 1073-1082 (1988).

Casey et al., J. Clin. Invest. 106:R31-38 (2000).

Cech, T.R., "Between the 'RNA World' and the 'Protein World'," Structure 3:969 (1995).

Chaiken et al. , "Analysis of Macromolecular Interactions Using Immobilized Ligands," Analytical Biochemistry 201:197-210 (1992).

Chatterji et at., "Cowpea Mosaic Virus: From the Presentation of Antigenic Peptides to the Display of Active Biomaterials", intervirol., 45:362-370 (2002).

Chen et al., Interaction of Phosphorylated FceRig Irnunoglobulin Receptor Tyrosine Activation Motif-based Peptides with Dual and Single SH2 Domains of p72syk The Journal of Biological Chemistry 271(41):25308-25315 (1996).

Chen et al., "Organelle-specific Targeting of Protein Kinase All (PKAll)", J. Biol. Chem., 272(24):15247-15257 (1997).

Cho-Chung et al., "CAMP-dependent protein kinase: role in normal and malignant growth", Critical Reviews in Oncol./Hematol., 21:33-61 (1995).

Clegg et al., "Genetic characterization of a brain-specific form of the type I regulatory subunit of CAMP-dependent protein kinase", Proc. Natl. Acad. Sci USA, 85:3703-3707 (1988).

Coghlan et at., "Association of Protein Kinase A and Protein Phosphatase 2B with a Common Anchoring Protein", Science, 267: 108-111 (1995).

Colledge, M. and Scott, J.D., "AKAPs: from structure to function", Trends in Cell Biology, 9:216-221, (1999).

Computational Molecular Biology, Book: "Sources and Methods for Sequence Analysis", Lesk, A.M. (Ed.), Oxford University Press, New York (1988).

Cong, M. et al., J. Biol. Chem., 276(18):15192-15199 (2001).

Costantini, F. and Lacy, E., "Introduction of a rabbit β-globin gene into the mouse germ line", Nature, 294:92-94, (1981).

Cotton et al., "Reactivity of cytosine and thymine in single-base-pair mismatches with hydroxylamine and osmium tetroxide and its application to the study of mutations", Proc. Natl. Acad. Sci. USA, 85:4397-4401, (1988).

Cotton, R.G.H., "Current methods of mutation detection", Mutation Res., 285:125-144, (1993).

Cronin et al., "Cystic fibrosis mutation detection by hybridization to light-generated DNA probe arrays", Hum. Mutat., 7:244-255, (1996).

Culture of Animal Cells, A Manual of Basic Technique, Book: 2nd Edition, Freshney, R.I., Alan R. Liss, Inc., New York.

Cummings et al., "Genetically lean mice result from targeted disruption of the RIIb subunit of protein kinase A," Nature 382: 622-626 (1996).

Current Communications in Molecular Biology, Book: Gene Transfer Vectors for Mammalian Cells, Cold Spring Harbor Laboratory, New York, 1987.

Current Protocols In Immunology, Book: vol. 4, Coligan, J.E. et al. (Eds.), John Wiley & Sons, Inc. New York, 1994.

Cwirla et al., "Peptides on phage: A vast library of peptides for identifying ligands," Proc. Natl. Aced, Sci. USA 87: 6378-6382 (1990).

Devereux et al., "A comprehensive set of sequence analysis programs for the VAX," Nucleic Acids Research 12(1):387-395 (1984).

Diller et al., "Molecular Basis for Regulatory Subunit Diversity in CAMP-Dependent Protein Kinase: Crystal Structure of the Type IIb Regulatory Subunit"; Structure, 9:73-82 (2001).

Ding et al., PNAS, 100(6):3059-3064 (2003).

DNA cloning, a practical approach, Book: vol. II, Glover, D.M. (Ed.), IRL Press, Oxford, Washington DC (1985).

Dostmann et al., "Probing the Cyclic Nucleotide Binding Sites of CAMP-dependent Protein Kinases I and II with Analogs of Adenosine 3',5'-Cyclic Phosphorothioates", J. Biol. Chem., 265(181):10484-10491 (1990).

Dower et al., "Chapter 28. The Search for Molecular Diveristy (11): Recombinant and Synthetic Randomized Peptide Libraries," Annual Reports in Medicinal Chemistry 26:271-280 (1991).

Eck, M.J. and S.R. Sprang, "The Structure of Tumor Necrosis Factor-a at 2.6 A Resolution, Implications for Receptor Binding," The Journal of Biological Chemistry 264(29):17595-17605 (1989).

Edwards et. al., "A-kinase anchoring proteins: protein kinase A and beyond", Cur. Opin. Cell Biol., 12:217-221 (2000).

Edwards et al., PCR methods and Applications, 3(4):365-375 (1994).

Eichholtz et al., "A Myristoylated Pseudosubstrate Peptide, a Novel Protein Kinase C Inhibitor," J. Biol. Chem., 268:1982-1986 (1993).

Englisch, U. and Gauss, D.H., "Angewandte Chemie", Angew. Chem., 30(6):613-722, (1991).

Evans et al., "Design of Nonpeptidal Ligands for a Peptide Receptor: Cholecystokinin Antagonists," J. Med. Chem. 30:1229-1239 (1987).

Falcioni et al., "Peptidomimetic compounds that inhibit antigen presentation by antoimmune disease-associated class II major histocompatibility molecules", Nature Biotechnol., 17:562-567 (1999).

Fantozzi et al., "Effect of the Thermostable Protein Kinase Inhibitor on Intracellular Localization of the Catalytic Subunit of CAMP-dependent", J. Biol. Chem., 267(24): 16824-16828 (1992).

Fantozzi et al., "Thermostable Inhibitor of CAMP-dependent Protein Kinase Enhances the Rate of Export of the Kinase Catalytic Subunit from the Nucleus", J. Biol. Chem., 269(4):2676-2686 (1994).
Fauchere, J., "Elements for the Rational Design of Peptide Drugs," Advances in Drug Research 15:29-69 (1986).
Fayos, et al., "Induction of flexibility through protein-protein interactions," J. Biol. Chem. 278:18581-18587 (2003).
Fei et al., Rapid Comm. Mass. Spec., 14(11):950-959 (2000).
Felgner et al., "Lipofection: A highly efficient, lipid-mediated DNA-transfection procedure", Proc. Natl. Acad. Sci. USA, 84:7413-7417, (1987).
Feliciello et al., "The Biological Functions of A-Kinase Anchor Proteins", J. Mol. Biol., 308:99-114 (2001).
Fisher et al., "Surface plasmon resonance based methods for measuring the kinetics and binding affinities of biomolecular interactions", Cur, Opin. Biotechnol., 5:389-395 (1994).
Frank, R., "Spot-Synthesis: An Easy Technique for the Positionally Addressable, Parallel Chemical Synthesis on a Membrane Support," Tetrahedron, 48(42):9217-9232 (1992).
Gante, "Peptidomimetics—Tailored Enzyme Inhibitors," Angew. Chem. Int. Ed. Engl., 33:1699-1720 (1994).
Gasparini et al., "Restriction site generating-polymerase chain reaction (RG-PCR) for the probeless detection of hidden genetic variation: application to the study of some common cystic fibrosis mutations", Mol. Cell. Probes, 6:1-7, (1992).
Genbank Accession No. AF037439, Chatterjee et al. Dec. 1997.
Gibbs et al., "Detection of single DNA base differences by competitive oligonucleotide priming", Nucl. Acids Res., 17:2437-2448, (1989).
Gilman et al., "A Protein Binding Assay for Adenosine 3':5"-Cyclic Monophosphate", Proc. Natl, Acad. Sci. USA, 67(1):305-312 (1970).
Gonzalez, J.E. and R.Y. Tsien, "Voltage Sensing by Fluorescence Resonance Energy Transfer in Single Cells," Biophysical Journal 69:1272-1280 (1995).
Goueli et al., "A Novel and Simple Method to Assay the Activity of Individual Protein Kinases in a Crude Tissue Extract", Anal. Biochem., 255:10-17 (1995).
Gribskov, M. and Burgess, R.R., "Sigma factors from *E. coli, B. subtilis*, phage SP01, and T4 are homologous proteins", Nucl. Acids Res., 14(16):6745-6763 (1986).
Griffin, H.G. and Griffin, A.M., "DNA Sequencing. Recent Innovations and Future Trends", Appl. Biochem. Biotechnol., 38:147-159, (1993).
Guatelli et al., "Isothermal, in vitro amplification of nucleic acids by a multienzyme reaction modeled after retroviral replication", Proc. Natl. Acad. Sci. USA, 87:1874-1878, (1990).
Guerrier-Takada et al., "The RNA Moiety of Ribonuclease P Is the Catalytic Subunit of the Enzyme", Cell, 35:849-857, (1983).
Guide to Human Genome Computing, Book: Bishop, M.J. (Ed.), Academic Press, San Diego, California (1994).
Hampel et al., "'Hairpin' catalytic RNA model: evidence for helices and sequence requirement for substrate RNA", Nucl. Acids Res., 18(2):299-304, (1990.
Hampel, A. and Tritz, R., "RNA Catalytic Properties of the Minimum (−)s TRSV Sequence", Biochem., 28:4929-4933, (1989).
Hamuro et al., "Domain Organization of D-AKAP2 Revealed by Enhanced Deuterium Exchange-Mass Spectrometry (DXMS)", J. Mol. Biol., 321:703-714 (2002).
Hamuro et al., "Dynamics of cAPK Type II/3 Activation Revealed by Enhanced Amide H/2H Exchange Mass Spectrometry (DXMS)", J. Mol. Biol., 327: 1065-1076 (2003).
Handbook Of Experimental Immunology in Four Volumes, Book: vol. 1, "Immunochemistry", Weir, D.M., (and co-Eds), Fourth Edition, Blackwell Scientific Publications, Osney Mead, Oxford, 1986.
Harada et al., "Phosphorylation and Inactivation of BAD by Mitochondria-Anchored Protein Kinase A," Molecular Cell 3:413-422 (1999).
Harris et al., Cell Sci., 114:3219-3231 (2001).
Hasan et al., "Base-boronated dinucleotides: synthesis and effect of N7-cyanoborane substitution on the base protons", Nucl. Acids Res., 24(11):2150-2157 (1996).
Hauer et al., "Two well-defined motifs in the CAMP-dependent protein kinase inhibitor (PKIu) correlate with inhibitory and nuclear export function", Protein Sci, 8:545-553 (1999).
Hayashi, K., "PCR-SSCP: A Method for Detection of Mutations", Genet. Anal. Tech. Appl. (GATA), 9(3):73-79, (1992).
Heaton et al., "Estimation of DNA sequence diversity in bovine cytokine genes", Mammalian Genome, 12:32-37, (2001).
Herberg et al., "Physiological Inhibitors of the Catalytic Subunit of CAMP-Dependent Protein Kinase: Effect of MgATP on Protein-protein Interactions", Biochem., 32:14015-14022 (1993).
Herberg F.W., et al., "Analysis of A-kinase anchoring protein (AKAP) interaction with protein kinase A (PKA) regulatory subunits: PKA isoform specificity in AKAP binding," Journal of Molecular Biology 298:2, Apr. 28, 2000, pp. 329-339.
Herrgard et al., "Domain architecture of a Caenorhabditis elegans AKAP suggests a novel AKAP function", FEBS Lett., 486: 107-111 (2000).
Hruby et al., "Emerging appraches in the molecular design of receptor-selective peptide ligands: conformational, topographical and dynamic considerations," Biochem. J. 268: 249-262 (1990).
Hu, K. and Siddiqui, A., "Regulation of the Hepatitis B Birus Gene Expression by the Enhancer Element I", Virology, 181:721-726, (1991).
Huang et al., "Identification of a Novel Protein Kinase A Anchoring Protein That Binds Both Type I and Type II Regulatory Subunits", J. Biol. Chem., 272:8057-8064 (1997).
Huang et al., "NH2-Terminal Targeting Motifs Direct Dual Specificity A-Kinase anchoring Protein 1 (D-AKAPI) to Either Mitochondria or Endoplasmic Reticulum", J. Cell Biol., 145(5):951-959 (1999).
Huang Lily J-S et al., "D-AKAP2, a novel protein kinase A anchoring protein with a putative RGS domain," PNAS 94:21, Oct. 1997 pp. 11184-11189.
Hunenberger et al., "Determinants of Ligand Binding to CAMP-Dependent Protein Kinase", Biochem., 38:2358-2366 (1999).
Imaizumi-Scherrer et al., "Type I Protein Kinase A Is Localized to Interphase Microtubules and Strongly Associated with the Mitotic Spindle", Experimental Cell Res., 264:250-265 (2001).
Immobilised cells and enzymes, a practical approach, Woodward, J. (Ed.), IRL Press Limited, Oxford, Washington, DC, 1985.
IUPAC-IUB Commission on Biochemical Nomenclature: A One-Letter Notation for Amino Acid Sequences, The Journal of Biological Chemistry 243(13):3557-3559 (1968).
Jameson, D.M. and W.H. Sawyer, "[12] Fluorescence Anisotropy Applied to Biomolecular Interactions," Methods in Enzymology 246: 283-300 (1995).
Janin, J., "Surface and inside volumes in globular proteins", Nature, 277:491-492 (1979).
Jolley, M.E., "Fluorescence Polarization Assays for the Detection of Proteases and Their Inhibitors," Journal of Biomolecular Screening 1(1):33-38 (1996).
Jurinke et al., "Detection of RET proto-oncogene codon 634 mutations using mass spectrometry", J. Mol. Med., 75:745-750, (1997).
Kammerer et at., "Amino acid variant in the kinase binding domain of dual-specific A kinase-anchoring protein 2: A disease susceptibility polymorphism", Proc. Natl.Acad.Sci., 100(7):4066-4071(2000).
Kaufman et al., "Evolution of Chromosomal Regions Containing Transfected and Amplified Dihydrofolate Reductase Sequences," Molecular and Cellular Biology 3(4): 699-711 (1983).
Keen et al., "Rapid detection of single base mismatches as heteroduplexes on Hydrolink gels", Trends Genet., 7:5, (1991).
Keown et al., "Methods for Introducing DNA into Mammalian Cells", Meth. Enzynol., 185:527-537 (1990).
Kirschner et al., Nat. Genet., 26:89-92 (2000).
Komives, E.A., NIH Grant 5T32DK007233 "Hemoglobin and Blood Protein chemistry," funding period Jul. 1, 1976-Aug. 31, 2006, pp. 50-179.
Kornher, J.S. and Livak, K.J., "Mutation detection using nucleotide analogs that alter electrophoretic mobility", Nucl. Acids Res., 17:7779-7784, (1989).
Kozal et al., "Extensive polymorphisms observed in HIV-1 clade B protease gene using high-density oligonucleotide arrays", Nature, 2(7):753-759 (1996).

Kramer et al., "Combinatorial Cellulose-Bound Peptide Libraries: Screening Tools for the Identification of Peptides that Bind Ligands with Predefined Specificity," Methods: A Companion to Methods in Enzymology, 6:388-395 (1994).
Kramer et al., "Spot synthesis: observations and optimizations", J. Peptide Res., 54:319-327 (1999).
Kuppuswamy et al., "Single nucleotide primer extension to detect genetic diseases: Experimental application to hemophilia B (factor IX) and cystic fibrosis genes", Proc. Natl. Acad. Sci. USA, 88:1143-1147, (1991).
Kwok (NCBI SNP, ss266958, rs203462, Jun. 30, 2000.
Kyte, J. and Doolittle, R.F., "A Simple Method for Displaying the Hydropathic Character of a Protein", J. Mol. Biol., 157:105-132, (1982).
Lacy et al., "A Foreign β-Globin Gene in Transgenic Mice: Integration at Abnormal Chromosomal Positions and Expression in Inappropriate Tissues", Cell, 34:343-358, (1983).
Landegren et al., "A Ligase-Mediated Gene Detection Technique", Science, 241:1077-1080, (1988).
Lee et al., "Isolation of a cDNA clone for the type I regulatory subunit of bovine cAMP-dependent protein kinase", Proc. Natl. Acad. Sci. USA, 80:3608-3612, (1983).
Leon et al., "A Stable a-Helical Domain at the N Terminus of the Rla Subunits of CAMPdependent Protein Kinase Is a Novel Dimerization/Docking Motif", J. Biol. Chem., 272(45):28431-28437 (1997).
Leon et al., "Probing the Multidomain Structure of the Type I Regulatory Subunit of cAMP-Dependent Protein Kinase Using Mutational Analysis: Role and Environment of Endogenous Tryptophans", Biochem., 39:5662-5671 (2000).
Lerner et al., "High Throughput Screen for Inhibitors of Bacterial DNA Topoisomerase I Using the Scintillation Proximity Assay," Journal of Biomolecular Screening 1(3):135-143 (1996).
Li et al., "Boron-containing oligodeoxyribonucleotide 14mer duplexes: enzymatic synthesis and melting studies", Nucl. Acids Res., 23(21):4495-4501, (1995).
Li et al., "Consequences of CAMP and Catalytic-Subunit Binding on the Flexibility of the A-Kinase Regulatory Subunit", Biochem., 39:15626-15632 (2000).
Li et al., "Identification, Localization, and Function in Steroidogenesis of PAP7: A Peripheral-Type Benzodiazepine Receptor- and PKA (Rla- Associated Protein", Mol. Endocrinol., 15(12):2211-2228 (2001).
Liotta et al., "A Synthetic Tris-Sulfotyrosyl Dodecapeptide analogue of the Insulin Receptor 11 46-Kinase Domain Inhibits Tyrosine Dephosphorylation of the Insulin Receptor in Situ", J. Biol. Chem., 269(37):22996-23001 (1994).
Luthman, K. and U. Hacksell, "Peptides and Peptidornimetics," Chapter 14 in A Textbook of Drug Design and Development 2nd ed. Krogsgaard-Larsen et al. (Eds.) Australia: Harwood Academic Publishers pp. 386-406 (1996).
Lynch et al., "A Fluorescence Polarization Based Src-Sh2 Binding Assay", Anal. Biochem., 247:77-82 (1997).
Makarova et al., "Generation of Deletion and Point Mutations with One Primer in a Single Clonig Step", Biotech., 29:970-972 (2000).
Manipulating the Mouse Embryo, Book: A Laboratory Manual, Hogan et al., Cold Spring Harbor Laboratory (1986).
Marx et al., Science 295:496-499 (2002).
Maxam, A.M. and Gilbert, W., "A new method for sequencing DNA", Proc. Natl. Acad. Sci. USA, 74(2):560-564, (1977).
McCabe et al., Biochem Med. And Metabolic Bio., 44(3):294-295 (1990).
McDonald, T.P., "Thrombopoietin: Its Biology, Clinical Aspects, and Possibilities," The American Journal of Pediatric Hematology/ Oncology 14(1):8-21 (1992).
McKnight et al., "Expression of the Chicken Transferrin Gene in Transgenic Mice", Cell, 34:335-341 (1983).
Meinkoth et al., "Signal transduction through the CAMP- dependent protein kinase", Mol. Cell Biochem., 127-1 28:179-186 (1993).
Meinkoth et al., "Dynamics of the distribution of cyclic AMP-dependent protein kinase in living cells", Proc. Natl. Acad. Sci. USA, 87:9595-9599 (1990).
Merrifield et al., "Solid Phase Peptide Synthesis I. The Synthesis of a Tetrapeptide", J. Am. Chem. Soc., 85:2149-2154 (1998).
Methods in Enzymology, "Guide to Protein Purification", Book: vol. 182, Deutscher, M.P. (Ed.), Academic Press, Inc., New York (1990).
Methods in Enzymology, "Recombinant DNA", Book: vol. 154, Part E, Wu, R. and Grossman, L. (Eds.), Academic Press, Inc., New York (1987).
Methods in Enzymology, "Recombinant DNA", Book: vol. 155, Part F, Wu, R. (Ed.), Academic Press, Inc., New York (1987).
Methods in Molecular Biology. 24, "Computer Analysis of Sequence Data", Book: Part I, Griffin, A.M. and Griffin, H.G. (Eds.), Humana Press, Totowa, New Jersey (1994).
Molecular Biology Of The Gene, Book: "General Principles", vol. 1, Fourth Edition, Watson et al., The Benjamin/Cummings Publishing Company, Inc., 1987.
Molecular Cloning, a Laboratory Manual, Book: Second Edition, Sambrook, J. and Russell, D.W., Cold Spring Harbor Laboratory Press (1989).
Monfardini et al., "A Branched Monornethoxypoly(ethylene glycol) for Protein Modification," Bioconjugate Chemistry 6:62-69 (1995).
Monforte et al., "High-throughput DNA analysis by time-of-flight mass spectrometry," Nature Medicine, 3(3):360-362, (1997).
Moore et al. , "Structural Basis for Peptide Binding in Protein Kinase A", J. Biol. Chem., 278(12):10613-10618 (2003).
Morgan et al., "Chapter 26. Approaches to the Discovery of Non-Peptide Ligands for Peptide Receptors and Peptidases", Annual Reports in Medicinal Chemistry, 24:243-252 (1989).
Myers et al., "Detection of Single Base Substitutions by Ribonuclease Cleavage at Mismatches in RNA:DNA Duplexes", Science, 230:1242-1246, (1985).
Myers et al., "Detection of single base substitutions in total genomic DNA", Nature, 313:495-498, (1985).
Myszka et al., "Finetic analysis of macromolecular interations using surface plasmon resonance biosensors," Current Opinion in Biotechnology 8:50-57 (1997).
Naeve et al., "Accuracy of Automated DNA Sequencing: A Multi-Laboratory Comparison of Sequencing Results", Biotechniques, 19(3):448-453, (1995).
Nakamaye et al., "Direct sequencing of polymerase chain reaction amplified DNA fragments through the incorporation of deoxynucleoside a-thiotriphosphates", Nucl. Acids Res., 16:9947-9959, (1888).
Narayana et al., "A binary complex of the catalytic subunit of CAMP-dependent protein kinase and adenosine further defines conformational flexibility", Structure, 5(7):921-935 (1997).
Narayana et al., "Crystal Structure of a Polyhistdine-Tagged Recombinant Catalytic Subunit of CAMP-Dependent protein Kinase Complexed with the Peptide Inhibitor PKI(5-24) and Adenosine", Biochem., 36(15):4438-4448 (1997).
Needleman et al, "A General Method Applicable to the Search for Similarities in the Amino Acid Sequence of Two Proteins", J. Mol. Biol., 48:443-453 (1970).
Newlon et al, "The molecular basis for protein kinase A anchoring revealed by solution NMR," Nature Structural Biology 6(3):222-227 (1999).
Newlon et al., "A novel mechanism of PKA anchoring revealed by solution structures of anchoring complexes," The EMBO Journal 20(7):1651-1662 (2001).
Newton et al., "Analysis of any point mutation in DNA. The amplification refractory mutation system (ARMS)", Nucl. Acids Res., 17:2503-2516, (1989).
Ngai et al., "Protein A antibody-capture EIISA (PACE): and ELISA format to avoid denaturation of surface-adsorbed antigens," Journal of Immunological Methods 158:267-276 (1993).
Nickerson et al., "Automated DNA diagnostics using an ELISA-based ligonucleotides ligation assay", Proc. Natl. Acad. Sci. USA, 87:8923-8927, (1990).
Nollau et al. Clinical Chemistry, vol. 43, No. 7, pp. 1114-1128, 1997.
Nordhoff et al., "Matrix-assisted Laser Desorption/Ionization Mass Spectrometry of Nucleic Acids with Wavelengths in the Ultraviolet and Infrared", Rapid Comm. Mass Spectrom., 6:771-776, (1992).
Nucleic acid Hybridization, a practical approach, Book: Hames, B.D. and Higgins, S.J. (Eds.), IRL Press, Oxford, Washington DC (1985).

Nyrén et al., "Solid phase DNA minisequencing by an enzymatic luminometric inorganic pyrophosphate detection assay", Anal. Biochem., 208:171-175, (1993).
O'Brian et al., "N-MYRISTYL-Lys-Arg-Thr-Leu-Arg: A novel protein kinase C inhibitor", Biochem. Pharmacol., 39(1):49-57 (1990).
Oligonucleotides and Analogues, a practical approach, Book: Protocol 8. "Synthesis of 3'5'-O-(tetraisopropyldisiloxane-1,3-diyl)-N4-isobutyryl-2'-O-methylcytidine (compound 8); mol. Wt 569.85", Eckstein, F. (Ed.), Oxford University Press, New York, pp. 56-57; Chapter 6, "Synthesis of oligo-2'-deoxyribonucleoside methylphosphonates", pp. 137-139; and pp. 256-259, (1991).
Oligonucleotides synthesis, a practical approach, Book: Gait, M.J. (Ed.), IRL Press, Oxford, Washington DC (1984).
Olson et al., "Concepts and Progress in the Development of Peptide Mimetics", J, Med. Chem., 36(21):3039-3049 (1993).
Olson et al., "Peptide Mimetics of Thyrotropin-Releasing Hormone Based on a Cyclohexane Framework: Design, Synthesis, and Cognition-Enhancing Properties", J. Med. Chem., 3:2866-2879 (1995).
Orita et al., "Detection of polymorphisms of human DNA by gel electrophoresis as single-strand conformation polymorphisms", Proc. Natl. Acad Sci. USA, 86:2766-2770, (1989).
O'Shannessy et al., "Determination of kinetic rate and equilibrium binding constants for macromolecular interactions: a critique of the surface plasmon resonance literature," Current Opinion in Biotechnology 5:65-71 (1994).
Palmiter et al., "Differential Regulation of Metallothionein-Thymidine Kinase Fusion Genes in Transgenic Mice and Their Offspring", Cell, 29:701-710 (1982).
Palmiter et al., "Dramatic growth of mice that develop from eggs microinjected with metallothionein-growth hormone fusion genes", Nature 300:611-615 (1982).
Palmiter et al., "Matallothionein-human GH fusion genes stimulate growth of mice", Science, 222:809-814, (1983).
Pearson, R.B. and Kemp, B.E., "Protein Kinase Phosphorylation Site Sequences and Consensus Specificity Motifs: Tabulations", Meth. Enzymol., 200:62-81, (1991).
Pearson, W.R. and Lipman, D.J., "Improved toos for biological sequence comparison", Proc. Natl. Acad. Sci. USA, 85:2444-2448,(1988).
Perkins et al., "PKA, PKC, and AKAP localization in and around the neuromuscular junction", BMC Neurosci., 2:17 (2001).
Perrotta, A.T. and Been, M.D., "Cleavage of Oligoribonucleotides by a Ribozyme Derived from the Hepatitis d Virus RNA Sequence", Biochem., 31:16-21, (1992).
Porter et al., "N1-Cyanoborane_2'-Triphosphate Is a Good Substrate for DNA Polymerase", Biochem., 34:11963-11969, (1995).
Prezant, T.R. and Fischel-Ghodsian, N., "Trapped-Oligonucleotide Nucleotide Incorporation (TONI) Assay, a Simple Method for Screening Point Mutations", Human Mutation, 1:159-164, (1992).
Prosser, J., "Detecting single-base mutations", TIBTECH, 11:238-246, (1993).
Pruslin et al., "Caveats and ligonucleo for the ELISA," Journal of Immunoloigcal Methods 137:27-35 (1991).
Reinitz et al., Arch. Biochem. Biophys., 348:391-402 (1997).
Rizo, J and L.M. Gierasch, "Constrained Peptides: Models of Bioactive Peptides and Protein Substructures," Annu. Rev. Biochem. 61: 387-418 (1992).
Roberts, D.C. and F. Vellaccio, "Unusual Amino Acids in Peptide Synthesis," in The Peptides, 5(6):341-449 (1983).
Robinson et al., Arch. Biochem. Biophys., 330:181-187 (1996).
Roemer et al., "Knock-In And Knock-Out", New Biol., 3:331-335 (1991).
Rose et al., "Hydrophobicity of Amino Acid Residues in Globular Proteins", Science, 229:834-838, (1985).
Rosenbaum, V. and Riesner, D., "Temperature-gradient gel electrophoresis. Thermodynamic analysis of nucleic acids and proteins in purified form and in cellular extracts", Biophy. Chem., 26:235-246, (1987).
Rossi et al., "Ribozymes as Anti-HIV-1 Therapeutic Agents: Principles, Applications, and Problems", Aids Res. And Human Retroviruses, 8(2):183-189, (1992).
Saiki et al., "Analysis of enzymatically amplified β-globin and HLA-Dqa DNA with allele-specific ligonucleotides probes", Nature, 324:163-166, (1986).
Saleeba, J.A. and Cotton, R.G.H., "Chemical Cleavage of Mismatch to Detect Mutations", Meth. Enzymol., 217:286-295, (1993).
Sanger et al., "DNA sequencing with chain-terminating inhibitors", Proc. Natl. Acad. Sci. USA, 74(12):5463-5467, (1977).
Sanghvi, Y.S., Book: Antisense Research and Applications, Chapter 15, "Heterocyclic Base Modifications In Nucleic Acids and Their Applications In Antisense Oligonucleotides", S.T. Crooke et al. (Eds. ), CRC Press, Inc., Florida, 1993.
Sarabu et al., "Oxazole- and Imidazole- Based Ser-Leu Dipeptide Mimetics in Potent Inhibitors of Antigen Presentation by MHC Class II DR Molecules," Drug Design and Discovery, 18(1):3-7 (2002).
Sarin et al., "Inhibition of acquired immunodeficiency syndrome virus by oligodeoxy-nucleoside methylphosphonates", Proc. Natl. Acad. Sci. USA, 85:7448-7451, (1988).
Schillace et al., "Organization of kinases, phosphatases, and receptor signaling complexes", J. Clin. Invest., 103(61):761-765 (1999).
Schwartz, R.M. and M.O. Dayhoff, "23:Matrices for Detecting Distant Relationships," Atlas of Protein Science and Structure National Biomedical Research Foundation, pp. 353-358 (1979).
Scopes, R.K., Book: Protein Purification. Principles and Practice, Springer-Verlag, New York, (1982).
Scott et al., "Cyclic Nucleotide-Dependent Protein Kinases," Pharmac. Ther. 50:123-145 (1991).
Sequence Analysis in Molecular Biology, Book: Treasure Trove or Trivial Pursuit, von Heijne, G., Academic Press, Inc., New York, 1987.
Sequence Analysis Primer, Book: Gribskov M. and Devereux, J. (Eds.), W.H. Freeman and Company, New York, 1992.
Shih, M. et al., J. Biol. Chem., 274(3):1588-1595 (1999).
Silverman et al., "New assay technologies for high-throughput screening," Current Opinion in Chemical Biology 2:397-403 (1998).
Siow etal., "Effects of Vasoactive Intestinal Peptide on Human Sperm Motility", Archives of Andrology, 43(1):67-71 (1999).
Sittampalam et al., "High-throughput screening: advances in assay technologies," Current Opinion in Chemical Biology 1:384-391 (1997).
Skalhegg et al., "Location of CAMP-Dependent Protein Kinase Type I with the TCR-CD3 Complex," Science 263:84-87 (1994).
Smith et al., "Comparison of Biosequences," Advances in Applied Mathematics 2:482-489 (1981).
Smith, D.B. and Johnson, K.S., "Single-step purification of polypeptides expressed in *Escherichia coli* as fusions with glutathione S-transferase", Gene, 67:31-40, (1988).
Snapir, A. et al., Clin.Sci., 104:509-520 (2003).
Sokolov, B.P., "Primer extension technique for the detection of single nucleotide in genomic DNA", Nucl. Acids Res., 18(12):3671, (1989).
Sonatore et al., "The Utility of FK506-Binding Protein as a Fusion Partner in Scintillation Proximity Assays: Application to SH2 Domains," Analytical Biochemistry 240:289-297 (1996).
Stein et al., "Physicochemical properties of phosphorothioate oligodeoxynucleotides", Nucl. Acids Res., 16:3209-3221, (1988).
Stewart et al., "Human β-Globin Gene Sequence Injected into Mouse Eggs, Retained in Adults, and Transmitted to Progeny", Science, 217:1046-1048, (1982).
Stillman, B.W. and Gluzman, Y., "Replication and Supercoiling of Simian Virus 40 DNA in Cell Extracts from Human Cells", Mol. Cell. Biol., 5(8):2051-2060, (1985).
Storm, Methods Mol. Biol., 212:241-262 (2003).
Sullivan et al., "Development of a Scintillation Proximity Assay for Calcineurin Phosphate Activity," Journal of Biomolecular Screening 2(1):19-23 (1997).
Supplementary European Search Report EP-03-72-6581 (Completed Dec. 4, 2006).
Surface Plasmon Resonance- BIAcore, http://www.med.unc.edu/wrkunits/2depts/biochem/MACINFAC/biacore.html (accessed on Nov. 26, 2003).
Syvänen et al., "A Primer-Guided Nucleotide Incorporation Assay in the Genotyping of Apolipoprotein E", Genomics, 8:684-692, (1990).

Syvänen et al., "Identification of Individuals by analysis of Biallelic DNA markers, using PCR and Solid-Phase Minisequencing", Am. J. Hum. Genet., 52:46-59, (1993).
Szabo et al., "Surface plasmon resonance and its use in biomolecular interaction analysis," Current Opinion in Structural Biology, 5(5):699-705 (1995).
Tang et al., Int J. Mass Spec., 226(1):37-54 (2003).
Taylor, S.S., "Dynamics and Integration of Signaling by PKA," slides presented at at the $3^{rd}$ Annual WyethIDouglas College Lectureship held at Rutger's University on Mar. 4, 2003.
Taylor, S.S., NIH Grant 5P01DK54441-03 "PKA and PKC Targeting Mechanisims," funding period Dec. 5, 1998-Jun. 30, 2007, pp. 19-32.
Thiele et al., "High Ethanol Consumption and Low Sensitivity to Ethanol-Induced Sedation in Protein Kinase A-Mutant Mice," The Journal of Neuroscience 20:RC75:1-6 (2000).
Thompson, J.N., "Fitting robots with white coats", Laboratory Automation and Information Management, 31:173-193, (1996).
Tilley et al., "Structure activity of C-terminal modified analogs of AcCCK-7", Int. J. Pept. Protein Res., 3:322-336 (1992).
Tobe et al., "Single-well genotyping of diallelic sequence variations by a two-color ELISA-based ligonucleotides ligation assay", Nucl. Acids Res., 24:3728-3732, (1996).
Transscription and translation, a practical approach, Book: Hames, B.D. and Higgins, S.J. (Eds.), IRL Press Limited, Oxford, England (1984).
Udenfriend et al., "Scintillation Proximity Assay: A Sensitive and Continuous Isotopic Method for Monitoring Ligand/Receptor and Antigen/Antibody Interactions", Anal. Biochem., 161:494-500, (1987).
Udenfriend et al., "Scintillation proximity radioimmunoassay utilizing 125l-labeled ligands", Proc. Natl. Acad. Sci. USA, 82:8672-8676 (1985).
Ugozzoli, et al., "Detection of Specific Alleles by Using Allele-Specific Primer Extension Followed by Capture on Solid Support", Genet. Anal. Tech. Appl.(GATA), 9(4):107-112, (1992).
Urlaub, G. and Chasin, L.A., "Isolation of Chinese hamster cell mutants deficient in dihydrofolate reductase activity", Proc. Natl. Acad. Sci. USA, 77(7):4216-4220, (1980).
Veber et al., "The design of metabolically-stable peptide analogs," Trends in Neurosciences 8:392-396 ( 1985).
Vijayaraghavan et al. , "Protein Kinase A-anchoring Inhibitor Peptides Arrest Mammalian Sperm Motility", J. Biol, Chem., 272:4747-4752 (1997).
Vijayaraghavan S., et al., "Isolation and Molecular characterization of AKAP110, A Novel, Sperm-Specific Protein Kinase A-Anchoring Protein," Molecular Endocrinology, 13:5, May 1999, pp. 705-717.
Wagner et al., "The human β-globin gene and a functional viral thymidine kinase gene in developing mice", Proc. Natl. Acad. Sci. USA, 78:5016-5020, (1981).
Wallace et al., "Hybridization of synthetic oligodeoxyribonucleotides to phi chi 174 DNA: the effect of single base pair mismatch", Nucl. Acids Res., 6:3543-3557, (1979).
Wang Lin et al., "Cloning and mitochondrial localization of full-length D-AKAP2, a protein kinase A anchoring protein" PNAS 98:6, Mar. 13, 2001 pp. 3320-3225.
Watson et al. (Eds.) in Molecular Biology of the Gene $4^{th}$ Edition Menlo Park: The Benjamin/Cummings Publishing Company, Inc., pp. 224 (1987).
Weaner et al., "Tritium Labeling of N-Protected Amino Acids and Peptides Containing O-Alkyl- Tyrosyl residues," in Synthesis and Applications of Istopically Labelled Compounds J. Allen (Ed.) Chichester, New York: John Wiley & Sons Ltd, pp. 137-140 (1995).
Wen et al., "High Affinity Binding of the Heat-stable Protein Kinase Inhibitor to the Catalytic Subunit of cAMPA-dependent Protein Kinase Is Selectively Abolished by Mutation of Arg", J. Biol. Chem., 269(11):8423-8430 (1994).
Wenschuh et al., "Coherent Membrane Supports for Parallel Microsynthesis and Screening of Bioactive Peptides", Biopolymers, 55:188-206 (2000).
Westphal et al., "Transposon-generated 'knock-out' and 'knock-in' gene-targeting constructs for use in mice", Curr. Biol., 7:530-533 (1997).
Wigler et al., "DNA-mediated transfer of the adenine phosophoribosyltransferase locus into mammalian cells", Proc. Natl. Acad. Sci. USA, 76(3):1373-1376 (1979).
Wolfenden et al., "Affinities of Amino Acid Side Chains for Solvent Water," Biochemistry 20: 849-855 (1981).
Zalipsky et al., "Functionalized Poly(ethylene glycol) for Preparation of Biologically Relevant Conjugate," Bioconjugate Chemistry 6:150-165 (1995).
Zangenberg et al., PCR Applications: Protcols for Functional Genomics. Innis et al Eds. p. 73-94 (1999). Academic Press.
Zhang et at., "Long-Distance PCR-Based Strategy for Preparing Knock-In Vectors Directly from ES Cell Genomic DNA", Biotechniques, 25:784-786, 788 (1998).
Database WPI, Derwent publication # 011635345 (1988) citing International Patent Application WO 97/47974 (Dec. 18, 1997) of the parent French Patent Application FR 2,749,662 (Dec. 12, 1997).
Instrumentation; "Nano-Plotter" from GeSiM, Germany,(1999) located at http:/www.gesim.de/np-intro.htm.
Instrumentation: Model CRS A 255 Robot, "Digital Servo Gripper", "Plate Cube" system. "lid parking station", "shaker" Robocon Labor-und Industrueroboter Ges.mb.h. or Austria ("Robocon"), (Sep. 1999).
Instrumentation;"MJ Microseal" plate sealer; Thermal Cycler Accessories: Sealing Options, Sealing Products, MJ Research, (1999) located at http://www.mjresearch.com/html/consumables/ealing/sealing_products.html.
Instrumentation; "Genesis 200/8" (200 cm with including an 8-tip arm) liquid handling systems; Tecan AG of Switzerland ("Tecan"), Tecan Products for Diagnostics and Life Science (1999), located at http://www.tecan.ch/index.htm.
Instrumentation; Bar code systems, including one and two dimensional bar codes, readable and readable/writable codes and systems; Datalogic S.p. A. of Italy ("Datalogic")(1999) located at http://www.datalogic.com.
Instrumentation; DYNABEADS, streptavidin-coated magnetic beads; from Dynal, Inc. Great Neck, NY and Oslo Norway (1996).
Genebank Accession Number: AF037439 (Dec. 21, 1997).
Genebank Accession Number: NM007202 (Jan. 17, 2003).
Genebank Accession Number: AF021833 (Sep. 29, 1999).
Genebank Accession Number: AC005730 (Oct. 22, 1998).
Genebank Accession Number: AW195104 (Nov. 29, 1999).
Genebank Accession Number: AW874187 (May 22, 2000).
Genebank Accession Number: AF096289 (Mar. 22, 1999).
Genebank Accession Number: X86173 (Mar. 8, 1996).
Genebank Accession Number: AJ242973 (Oct. 26, 1999).
Xu et al., "Species-Specific Identification of Human Adenoviruses by a Multiplex PCR Assay," J. Clin. Microbiol., Nov. 2000; 38(11):4114-4120.
Yates, "Mass Spectrometry and the Age of the Proteome," J. Mass Spec. (1988) 33:1-19.
Genebank Accession Number: AC084019 (Oct. 16, 2001).
Genebank Accession Number: AL646042 (Jul, 9, 2007).
Genebank Accession Number: NM-019921 (Feb. 10, 2008).

* cited by examiner

Caucasians

| Number of Samples | 2801 |
|---|---|

Hispanics

| Number of Samples | 495 |
|---|---|

age- and sex-distribution of the 291S allele of the lipoprotein lipase gene. A total of 436 males and 586 females were investigated.

Age- related distribution of the 291S allele of the lipoprotein lipase gene within the male Caucasian population. A total of 436 males were tested.

Questionnaire for
Population-Based
Sample Banking

Data Collection Form

Collection Information

Consent Form Signed Yes No
Date of Collection (MM/DD/YY)__/__/98
Time of Sample Collection(nearest hour in 24 hour clock format)________
Initials of Data Collector________Collecting Agency____________________
(DO NOT COMPLETE: (For Date Entry Only)Sample_______intact______lost ______broken Affix Barcode Here Donor information Sex: ☐ Male ☐ Female Date of Birth (MM/YY)__/__
In which state do you live? ____________ How long have you lived there ? _________ Years
What is your highest grade you completed in school?
☐ less than 8th grade ☐ 8th,9th,10th or 11th grade ☐ high school graduate or equivalency
☐ some college 2 yr degree ☐ college graduate 4 yr degree ☐ post graduate education or degree To the best of your knowledge what is the Ethnic Origin of your:

| Father | Mother | |
|---|---|---|
| ☐ | ☐ | Caucasian (please check specific geographic area below if known) |
| ☐ | ☐ | Northern Europe (Austria,Denmark,Finland,France,Germany,Netherlands,Norway,Sweden,Switzerland,U.K.) |
| ☐ | ☐ | Southern Europe (Greece,Italy,Spain) |
| ☐ | ☐ | Eastern Europe (Czechoslovakia,Hungary,Poland,Russia,Yugoslavia) |
| ☐ | ☐ | Middle Eastern (Israel,Egypt,Iran,Iraq,Jordan,Syria, other Arab States) |
| ☐ | ☐ | African-American |
| ☐ | ☐ | Hispanic (please check specific geographic area below if known) |
| ☐ | ☐ | Mexico |
| ☐ | ☐ | Central America,South American |
| ☐ | ☐ | Cuba,Puerto Rico, other Caribbean |
| ☐ | ☐ | Asian (please check specific geographic area below if known) |
| ☐ | ☐ | Japanese |
| ☐ | ☐ | Chinese |
| ☐ | ☐ | Korean |
| ☐ | ☐ | Vietnamese |
| ☐ | ☐ | other Asian |
| ☐ | ☐ | Other ____________________ |
| ☐ | ☐ | Don't know |

Health information: Have you or has anyone in your immediate family(parents,brothers,sisters, or your children) had the following? Check all that apply

| Disease: | You | Mother | Father | Sister | Brother | Child |
|---|---|---|---|---|---|---|
| Heart Disease Stroke or Arteriosclerosis | | | | | | |
| Cancer (Specify type if known) | | | | | | |
| Alzheimer's Disease or Dementia | | | | | | |
| Chronic inflammatory or Autoimmune Disease | | | | | | |
| Nervous System Disease like Multiple Sclerosis | | | | | | |
| Other (please specify) | | | | | | |

Additional health information details you would like to provide:

African 4G 28.2% 5G 71.2%

Asian 4G 65.8% 5G 34.2%

Caucasian 4G 53.5% 5G 46.5%

Hispanic 4G 26.7% 5G 73.3%

African Ile 43.6% Val 56.4%

Asian Ile 60.7% Val 39.3%

Caucasian Ile 63.0% Val 37.0%

Hispanic Ile 70.1% Val 29.9%

African Arg>95% Glu<5%

Asian Arg>95% Glu<5%

Caucasian Arg 88.5% Glu 11.5%

Hispanic Arg 89.2% Glu 10.8%

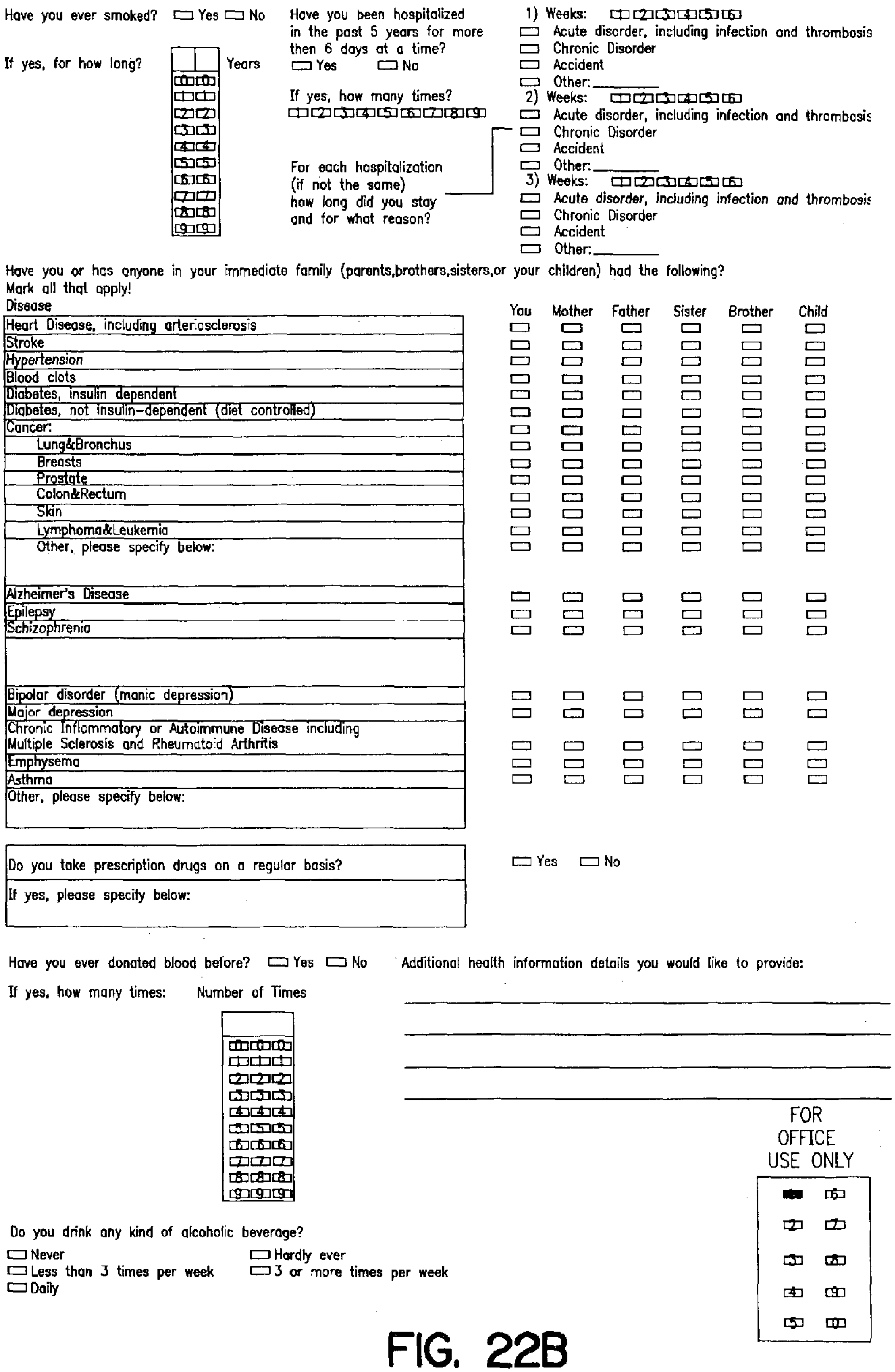

FIG. 22B

Have you ever smoked? ☐ Yes ☐ No    Have you been hospitalized    1) Weeks: ☐1 ☐2 ☐3 ☐4 ☐5 ☐6
                                    in the past 5 years for more     ☐ Acute disorder, including infection and thrombosis
If yes, for how long?         Years then 6 days at a time?           ☐ Chronic Disorder
                                    ☐ Yes      ☐ No                  ☐ Accident
                                                                     ☐ Other: _____
                                    If yes, how many times?       2) Weeks: ☐1 ☐2 ☐3 ☐4 ☐5 ☐6
                                    ☐1 ☐2 ☐3 ☐4 ☐5 ☐6 ☐7 ☐8 ☐9      ☐ Acute disorder, including infection and thrombosis
                                                                     ☐ Chronic Disorder
                                                                     ☐ Accident
                                    For each hospitalization         ☐ Other: _____
                                    (if not the same)             3) Weeks: ☐1 ☐2 ☐3 ☐4 ☐5 ☐6
                                    how long did you stay            ☐ Acute disorder, including infection and thrombosis
                                    and for what reason?             ☐ Chronic Disorder
                                                                     ☐ Accident
                                                                     ☐ Other: _____

Have you or has anyone in your immediate family (parents, brothers, sisters, or your children) had the following?
Mark all that apply!

| Disease | You | Mother | Father | Sister | Brother | Child |
|---|---|---|---|---|---|---|
| Heart Disease, including arteriosclerosis | ☐ | ☐ | ☐ | ☐ | ☐ | ☐ |
| Stroke | ☐ | ☐ | ☐ | ☐ | ☐ | ☐ |
| Hypertension | ☐ | ☐ | ☐ | ☐ | ☐ | ☐ |
| Blood clots | ☐ | ☐ | ☐ | ☐ | ☐ | ☐ |
| Diabetes, insulin dependent | ☐ | ☐ | ☐ | ☐ | ☐ | ☐ |
| Diabetes, not insulin-dependent (diet controlled) | ☐ | ☐ | ☐ | ☐ | ☐ | ☐ |
| Cancer: | ☐ | ☐ | ☐ | ☐ | ☐ | ☐ |
|     Lung&Bronchus | ☐ | ☐ | ☐ | ☐ | ☐ | ☐ |
|     Breasts | ☐ | ☐ | ☐ | ☐ | ☐ | ☐ |
|     Prostate | ☐ | ☐ | ☐ | ☐ | ☐ | ☐ |
|     Colon&Rectum | ☐ | ☐ | ☐ | ☐ | ☐ | ☐ |
|     Skin | ☐ | ☐ | ☐ | ☐ | ☐ | ☐ |
|     Lymphoma&Leukemia | ☐ | ☐ | ☐ | ☐ | ☐ | ☐ |
|     Other, please specify below: | ☐ | ☐ | ☐ | ☐ | ☐ | ☐ |
| Alzheimer's Disease | ☐ | ☐ | ☐ | ☐ | ☐ | ☐ |
| Epilepsy | ☐ | ☐ | ☐ | ☐ | ☐ | ☐ |
| Schizophrenia | ☐ | ☐ | ☐ | ☐ | ☐ | ☐ |
| Bipolar disorder (manic depression) | ☐ | ☐ | ☐ | ☐ | ☐ | ☐ |
| Major depression | ☐ | ☐ | ☐ | ☐ | ☐ | ☐ |
| Chronic Inflammatory or Autoimmune Disease including Multiple Sclerosis and Rheumatoid Arthritis | ☐ | ☐ | ☐ | ☐ | ☐ | ☐ |
| Emphysema | ☐ | ☐ | ☐ | ☐ | ☐ | ☐ |
| Asthma | ☐ | ☐ | ☐ | ☐ | ☐ | ☐ |
| Other, please specify below: | | | | | | |

Do you take prescription drugs on a regular basis?    ☐ Yes    ☐ No
If yes, please specify below:

Have you ever donated blood before? ☐ Yes ☐ No    Additional health information details you would like to provide:
If yes, how many times:    Number of Times

FOR OFFICE USE ONLY

Do you drink any kind of alcoholic beverage?
☐ Never              ☐ Hardly ever
☐ Less than 3 times per week    ☐ 3 or more times per week
☐ Daily

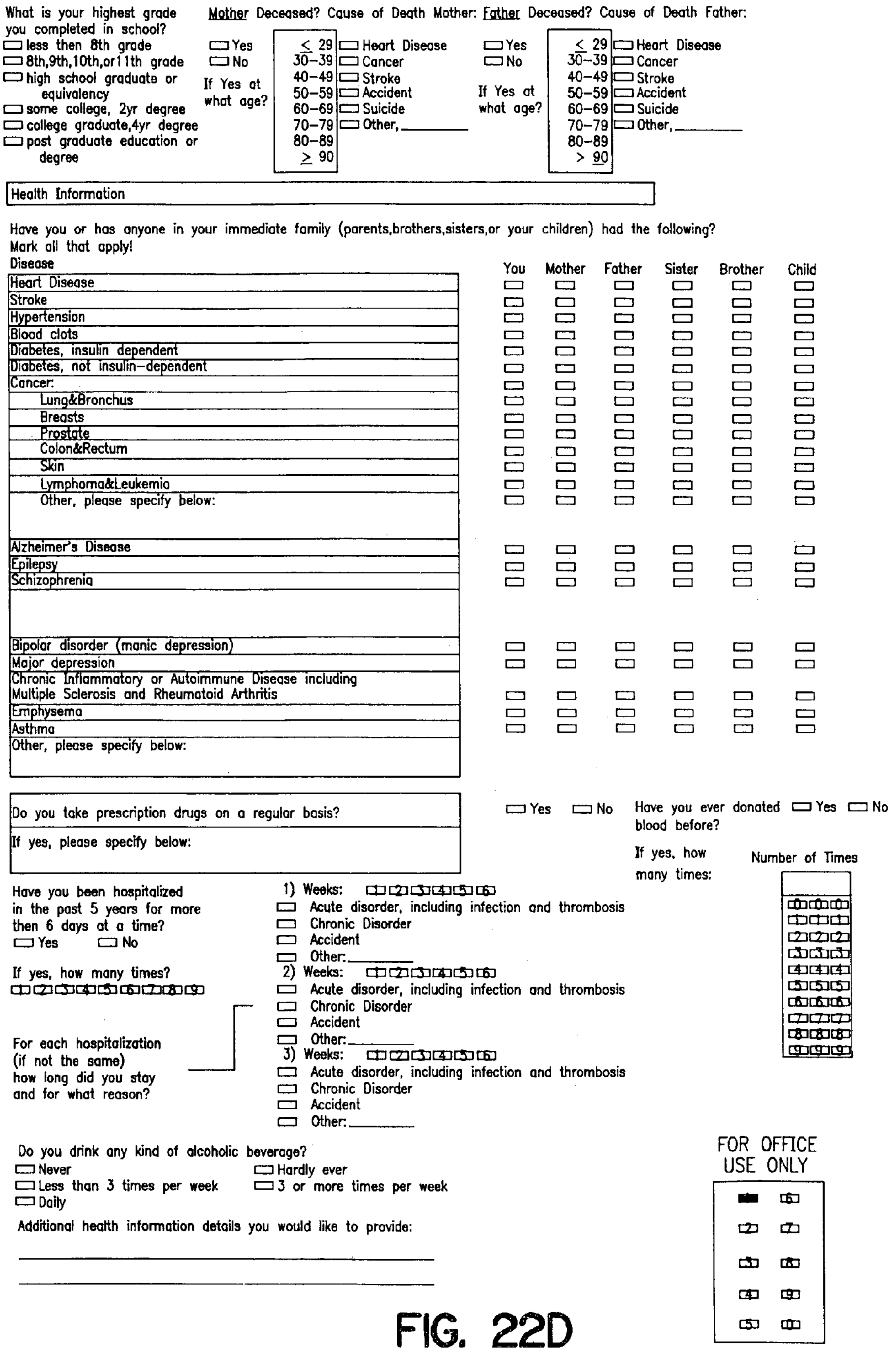

What is your highest grade you completed in school?
- less then 8th grade
- 8th,9th,10th,or11th grade
- high school graduate or equivalency
- some college, 2yr degree
- college graduate,4yr degree
- post graduate education or degree Mother Deceased? Yes / No. If Yes at what age? ≤ 29, 30–39, 40–49, 50–59, 60–69, 70–79, 80–89, ≥ 90

Cause of Death Mother: Heart Disease, Cancer, Stroke, Accident, Suicide, Other,________

Father Deceased? Yes / No. If Yes at what age? ≤ 29, 30–39, 40–49, 50–59, 60–69, 70–79, 80–89, > 90

Cause of Death Father: Heart Disease, Cancer, Stroke, Accident, Suicide, Other,________

Health Information

Have you or has anyone in your immediate family (parents,brothers,sisters,or your children) had the following? Mark all that apply!

| Disease | You | Mother | Father | Sister | Brother | Child |
|---|---|---|---|---|---|---|
| Heart Disease | ☐ | ☐ | ☐ | ☐ | ☐ | ☐ |
| Stroke | ☐ | ☐ | ☐ | ☐ | ☐ | ☐ |
| Hypertension | ☐ | ☐ | ☐ | ☐ | ☐ | ☐ |
| Blood clots | ☐ | ☐ | ☐ | ☐ | ☐ | ☐ |
| Diabetes, insulin dependent | ☐ | ☐ | ☐ | ☐ | ☐ | ☐ |
| Diabetes, not insulin–dependent | ☐ | ☐ | ☐ | ☐ | ☐ | ☐ |
| Cancer: | ☐ | ☐ | ☐ | ☐ | ☐ | ☐ |
| Lung&Bronchus | ☐ | ☐ | ☐ | ☐ | ☐ | ☐ |
| Breasts | ☐ | ☐ | ☐ | ☐ | ☐ | ☐ |
| Prostate | ☐ | ☐ | ☐ | ☐ | ☐ | ☐ |
| Colon&Rectum | ☐ | ☐ | ☐ | ☐ | ☐ | ☐ |
| Skin | ☐ | ☐ | ☐ | ☐ | ☐ | ☐ |
| Lymphoma&Leukemia | ☐ | ☐ | ☐ | ☐ | ☐ | ☐ |
| Other, please specify below: | ☐ | ☐ | ☐ | ☐ | ☐ | ☐ |
| Alzheimer's Disease | ☐ | ☐ | ☐ | ☐ | ☐ | ☐ |
| Epilepsy | ☐ | ☐ | ☐ | ☐ | ☐ | ☐ |
| Schizophrenia | ☐ | ☐ | ☐ | ☐ | ☐ | ☐ |
| Bipolar disorder (manic depression) | ☐ | ☐ | ☐ | ☐ | ☐ | ☐ |
| Major depression | ☐ | ☐ | ☐ | ☐ | ☐ | ☐ |
| Chronic Inflammatory or Autoimmune Disease including Multiple Sclerosis and Rheumatoid Arthritis | ☐ | ☐ | ☐ | ☐ | ☐ | ☐ |
| Emphysema | ☐ | ☐ | ☐ | ☐ | ☐ | ☐ |
| Asthma | ☐ | ☐ | ☐ | ☐ | ☐ | ☐ |
| Other, please specify below: | | | | | | |

Do you take prescription drugs on a regular basis? Yes / No

If yes, please specify below:

Have you ever donated blood before? Yes / No

If yes, how many times: Number of Times 0 1 2 3 4 5 6 7 8 9

Have you been hospitalized in the past 5 years for more then 6 days at a time? Yes / No If yes, how many times? 1 2 3 4 5 6 7 8 9

For each hospitalization (if not the same) how long did you stay and for what reason?

1) Weeks: 1 2 3 4 5 6
- Acute disorder, including infection and thrombosis
- Chronic Disorder
- Accident
- Other:________

2) Weeks: 1 2 3 4 5 6
- Acute disorder, including infection and thrombosis
- Chronic Disorder
- Accident
- Other:________

3) Weeks: 1 2 3 4 5 6
- Acute disorder, including infection and thrombosis
- Chronic Disorder
- Accident
- Other:________

Do you drink any kind of alcoholic beverage?
- Never
- Hardly ever
- Less than 3 times per week
- 3 or more times per week
- Daily Additional health information details you would like to provide:

FOR OFFICE USE ONLY
1 6
2 7
3 8
4 9
5 10

FIG. 22D

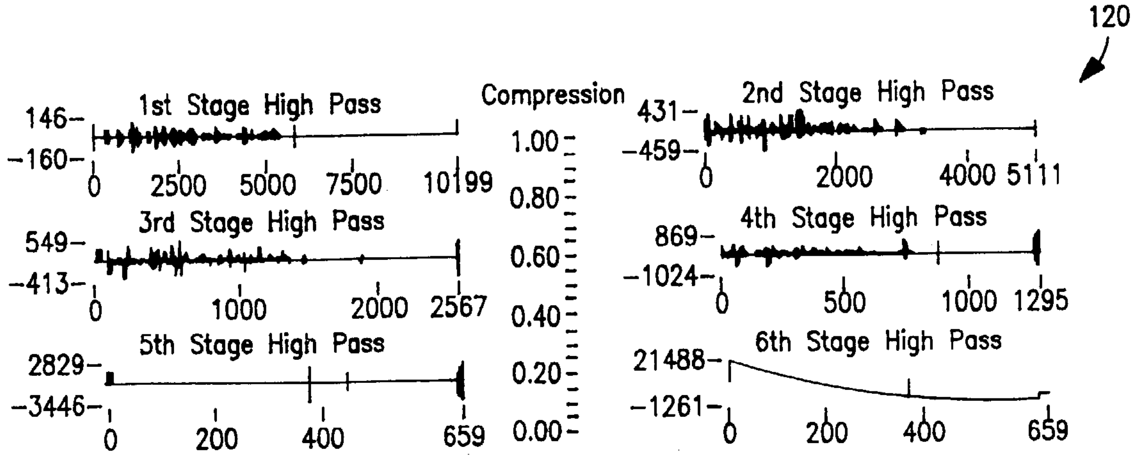
FIG. 32
$$\text{Signal}(t) = \frac{(\text{Start } 0(t) + \text{Start } 1(t) + \text{Start } 2(t)\ldots + \text{Start } 23\,(t))}{24}$$
SHIFT SIGNAL TO ACCOUNT FOR VARIATIONS DUE TO STARTING POINT
FIG. 33
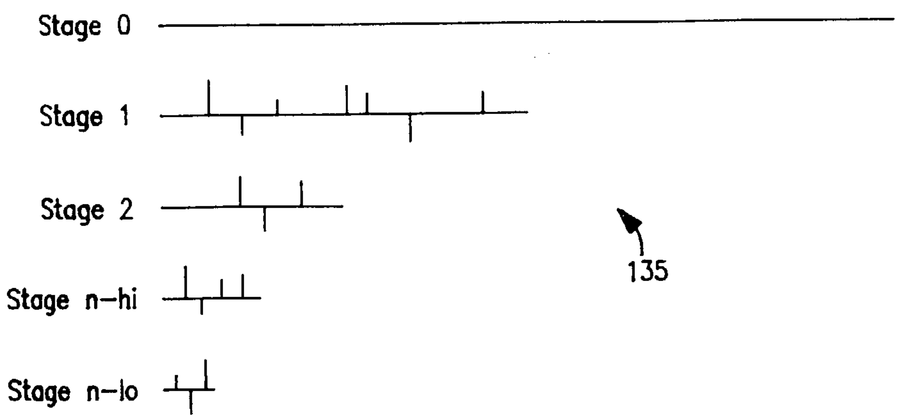
FIG. 34

FIND MINIMA IN REMAINING SIGNALS AND CONNECT TO FORM A PEAK FREE SIGNAL

GENRATE BASLELINE CORRECTION 180
182
183
184
186
188
190
195

| NON-0 COEFFICIENTS | COEFFICIENTS | INTERMEDIATE | RELATIVE |
|---|---|---|---|
| 100 | 25 | 100.025 | 100.025 |
| 150 | 220 | 150.220 | 50.220 |
| 500 | .1 | 500.0001 | 350.0001 |
| 10,050 | 800 | 10,050.8 | 9550.8 |
| 10,075 | 890 | 10,075.89 | 25.89 |
| 11,125 | 910 | 11,125.91 | 150.91 |
| 12,100 | 1000 (MAX) | 12,100.99999 | 975.99999 |
| 13,250 | 940 | 13,250.94 | 1150.94 |

METHODS FOR GENERATING DATABASES AND DATABASES FOR IDENTIFYING POLYMORPHIC GENETIC MARKERS

RELATED APPLICATIONS

This application is a divisional application of U.S. patent application Ser. No. 09/687,483, filed Oct. 13, 2000, now abandoned to Andreas Braun, Hubert Koster, Dirk Van den Boom, Ping Yip, Charles Rodi, Liyan He, Norman Chiu and Christian Jurinke entitled "METHODS FOR GENERATING DATABASES AND DATABASES FOR IDENTIFYING POLYMORPHIC GENETIC MARKERS."

Benefit of priority to the following provisional applications is claimed herein: U.S. provisional application Ser. No. 60/217,658 to Andreas Braun, Hubert Koster; Dirk Van den Boom, filed Jul. 10, 2000, entitled "METHODS FOR GENERATING DATABASES AND DATABASES FOR IDENTIFYING POLYMORPHIC GENETIC MARKERS"; U.S. provisional application Ser. No. 60/159,176 to Andreas Braun, Hubert Koster, Dirk Van den Boom, filed Oct. 13, 1999, entitled "METHODS FOR GENERATING DATABASES AND DATABASES FOR IDENTIFYING POLYMORPHIC GENETIC MARKERS"; U.S. provisional application Ser. No. 60/217,251, filed Jul. 10, 2000, to Andreas Braun, entitled "POLYMORPHIC KINASE ANCHOR PROTEIN GENE SEQUENCES, POLYMORPHIC KINASE ANCHOR PROTEINS AND METHODS OF DETECTING POLYMORPHIC KINASE ANCHOR PROTEINS AND NUCLEIC ACIDS ENCODING THE SAME". This application claims the benefit of priority to the above cited U.S. provisional application Ser. Nos. 60/217,658, 60/159,176, 60/217,251, as a divisional application of U.S. patent application Ser. No. 09/687,483 which claims the benefit of priority of U.S. provisional application Ser. Nos. 60/217,658, 60/159,176, 60/217,251. This application is also a continuation-in-part of U.S. application Ser. No. 09/663,968, to Ping Yip, filed Sep. 19, 2000, entitled "METHOD AND DEVICE FOR IDENTIFYING A BIOLOGICAL SAMPLE."

The above-noted applications and provisional applications are incorporated by reference in their entirety.

FIELD OF THE INVENTION

Process and methods for creating a database of genomic samples from healthy human donors. Methods that use the database to identify and correlate with polymorphic genetic markers and other markers with diseases and conditions are provided.

BACKGROUND

Diseases in all organisms have a genetic component, whether inherited or resulting from the body's response to environmental stresses, such as viruses and toxins. The ultimate goal of ongoing genomic research is to use this information to develop new ways to identify, treat and potentially cure these diseases. The first step has been to screen disease tissue and identify genomic changes at the level of individual samples. The identification of these "disease" markers has then fueled the development and commercialization of diagnostic tests that detect these errant genes or polymorphisms. With the increasing numbers of genetic markers, including single nucleotide polymorphisms (SNPs), microsatellites, tandem repeats, newly mapped introns and exons, the challenge to the medical and pharmaceutical communities is to identify genotypes which not only identify the disease but also follow the progression of the disease and are predictive of an organism's response to treatment.

Currently the pharmaceutical and biotechnology industries find a disease and then attempt to determine the genomic basis for the disease. This approach is time consuming and expensive and in many cases involves the investigator guessing as to what pathways might be involved in the disease.

Genomics

Presently the two main strategies employed in analyzing the available genomic information are the technology driven reverse genetics brute force strategy and the knowledge-based pathway oriented forward genetics strategy. The brute force approach yields large databases of sequence information but little information about the medical or other uses of the sequence information. Hence this strategy yields intangible products of questionable value. The knowledge-based strategy yields small databases that contain a lot of information about medical uses of particular DNA sequences and other products in the pathway and yield tangible products with a high value.

Polymorphisms

Polymorphisms have been known since 1901 with the identification of blood types. In the 1950's they were identified on the level of proteins using large population genetic studies. In the 1980's and 1990's many of the known protein polymorphisms were correlated with genetic loci on genomic DNA. For example, the gene dose of the apolipoprotein E type 4 allele was correlated with the risk of Alzheimer's disease in late onset families (see, e.g., Corder et al. (1993) *Science* 261: 921-923; mutation in blood coagulation factor V was associated with resistance to activated protein C (see, e.g., Bertina et al. (1994) *Nature* 369:64-67); resistance to HIV-1 infection has been shown in Caucasian individuals bearing mutant alleles of the CCR-5 chemokine receptor gene (see, e.g., Samson et al. (1996) *Nature* 382:722-725); and a hypermutable tract in antigen presenting cells (APC, such as macrophages), has been identified in familial colorectal cancer in individuals of Ashkenzi jewish background (see, e.g., Laken et al. (1997) *Nature Genet.* 17:79-83). There can be more than three million polymorphic sites in the human genome. Many have been identified, but not yet characterized or mapped or associated with a marker.

Single Nucleotide Polymorphisms (SNPs)

Much of the focus of genomics has been in the identification of SNPs, which are important for a variety of reasons. They allow indirect testing (association of haplotypes) and direct testing (functional variants). They are the most abundant and stable genetic markers. Common diseases are best explained by common genetic alterations, and the natural variation in the human population aids in understanding disease, therapy and environmental interactions.

Currently, the only available method to identify SNPs in DNA is by sequencing, which is expensive, difficult and laborious. Furthermore, once a SNP is discovered it must be validated to determine if it is a real polymorphism and not a sequencing error. Also, discovered SNPs must then be evaluated to determine if they are associated with a particular phenotype. Thus, there is a need to develop new paradigms for identifying the genomic basis for disease and markers thereof. Therefore, it is an object herein to provide methods for identifying the genomic basis of disease and markers thereof.

SUMMARY

Databases and methods using the databases are provided herein. The databases comprise sets of parameters associated with subjects in populations selected only on the basis of being healthy (i.e., where the subjects are mammals, such as humans, they are selected based upon apparent health and no detectable infections). The databases can be sorted based upon one or more of the selected parameters.

The databases, for example, can be relational databases, in which an index that represents each subject serves to relate parameters, which are the data, such as age, ethnicity, sex, medical history, etc. and ultimately genotypic information, that was inputted into and stored in the database. The database can then be sorted according to these parameters. Initially, the parameter information is obtained from a questionnaire answered by each subject from whom a body tissue or body fluid sample is obtained. As additional information about each sample is obtained, this information can be entered into the database and can serve as a sorting parameter.

The databases obtained from healthy individuals have numerous uses, such as correlating known polymorphisms with a phenotype or disease. The databases can be used to identify alleles that are deleterious, that are beneficial, and that are correlated with diseases.

For purposes herein, genotypic information can be obtained by any method known to those of skill in the art, but is generally obtained using mass spectrometry.

Also provided herein, is a new use for existing databases of subjects and genotypic and other parameters, such as age, ethnicity, race, and gender. Any database can be sorted according to the methods herein, and alleles that exhibit statistically significant correlations with any of the sorting parameters can be identified. It is noted, however, is noted, that the databases provided herein and randomly selected databases will perform better in these methods, since disease-based databases suffer numerous limitations, including their relatively small size, the homogeneity of the selected disease population, and the masking effect of the polymorphism associated with the markers for which the database was selected. Hence, the healthy database provided herein, provides advantages not heretofore recognized or exploited. The methods provided herein can be used with a selected database, including disease-based databases, with or without sorting for the discovery and correlation of polymorphisms. In addition, the databases provided herein represent a greater genetic diversity than the unselected databases typically utilized for the discovery of polymorphisms and thus allow for the enhanced discovery and correlation of polymorphisms.

The databases provided herein can be used for taking an identified polymorphism and ascertaining whether it changes in frequency when the data are sorted according to a selected parameter.

One use of these methods is correlating a selected marker with a particular parameter by following the occurrence of known genetic markers and then, having made this correlation, determining or identifying correlations with diseases. Examples of this use are p53 and Lipoprotein Lipase polymorphism. As exemplified herein, known markers are shown to have particular correlation with certain groups, such as a particular ethnicity or race or one sex. Such correlations will then permit development of better diagnostic tests and treatment regimens.

These methods are valuable for identifying one or more genetic markers whose frequency changes within the population as a function of age, ethnic group, sex or some other criteria. This can allow the identification of previously unknown polymorphisms and ultimately a gene or pathway involved in the onset and progression of disease.

The databases and methods provided herein permit, among other things, identification of components, particularly key components, of a disease process by understanding its genetic underpinnings and also permit an understanding of processes, such as individual drug responses. The databases and methods provided herein also can be used in methods involving elucidation of pathological pathways, in developing new diagnostic assays, identifying new potential drug targets, and in identifying new drug candidates.

The methods and databases can be used with experimental procedures, including, but are not limited to, in silico SNP identification, in vitro SNP identification/verification, genetic profiling of large populations, and in biostatistical analyses and interpretations.

Also provided herein, are combinations that contain a database provided herein and a biological sample from a subject in the database, and typically biological samples from all subjects or a plurality of subjects in the database. Collections of the tissue and body fluid samples are also provided.

Also, provided herein, are methods for determining a genetic marker that correlates with age, comprising identifying a polymorphism and determining the frequency of the polymorphism with increasing age in a healthy population.

Further provided herein are methods for determining whether a genetic marker correlates with susceptibility to morbidity, early mortality, or morbidity and early mortality, comprising identifying a polymorphism and determining the frequency of the polymorphism with increasing age in a healthy population.

Any of the methods herein described can be used out in a multiplex format.

Also provided are an apparatus and process for accurately identifying genetic information. It is another object herein that genetic information be extracted from genetic data in a highly automated manner. Therefore, to overcome the deficiencies in the known conventional systems, methods and apparatus for identifying a biological sample are provided.

Briefly, the method and system for identifying a biological sample generates a data set indicative of the composition of the biological sample. In a particular example, the data set is DNA spectrometry data received from a mass spectrometer. The data set is denoised, and a baseline is deleted. Since possible compositions of the biological sample can be known, expected peak areas can be determined. Using the expected peak areas, a residual baseline is generated to further correct the data set. Probable peaks are then identifiable in the corrected data set, which are used to identify the composition of the biological sample. In a disclosed example, statistical methods are employed to determine the probability that a probable peak is an actual peak, not an actual peak, or that the data too inconclusive to call.

Advantageously, the method and system for identifying a biological sample accurately makes composition calls in a highly automated manner. In such a manner, complete SNP profile information, for example, can be collected efficiently. More importantly, the collected data are analyzed with highly accurate results. For example, when a particular composition is called, the result can be relied upon with great confidence. Such confidence is provided by the robust computational process employed.

DESCRIPTION OF THE DRAWINGS

FIG. 3 is an exemplary questionnaire for population-based sample banking.

FIGS. 22A-D is a sample data collection questionnaire used for the healthy database.

FIG. 32 is a graphical representation of a sparse data set;

FIG. 33 is a formula for signal shifting;

FIG. 34 is a graphical representation of a wavelet transformation of a denoised and shifted signal;

DETAILED DESCRIPTION

Definitions

Figure 1A:
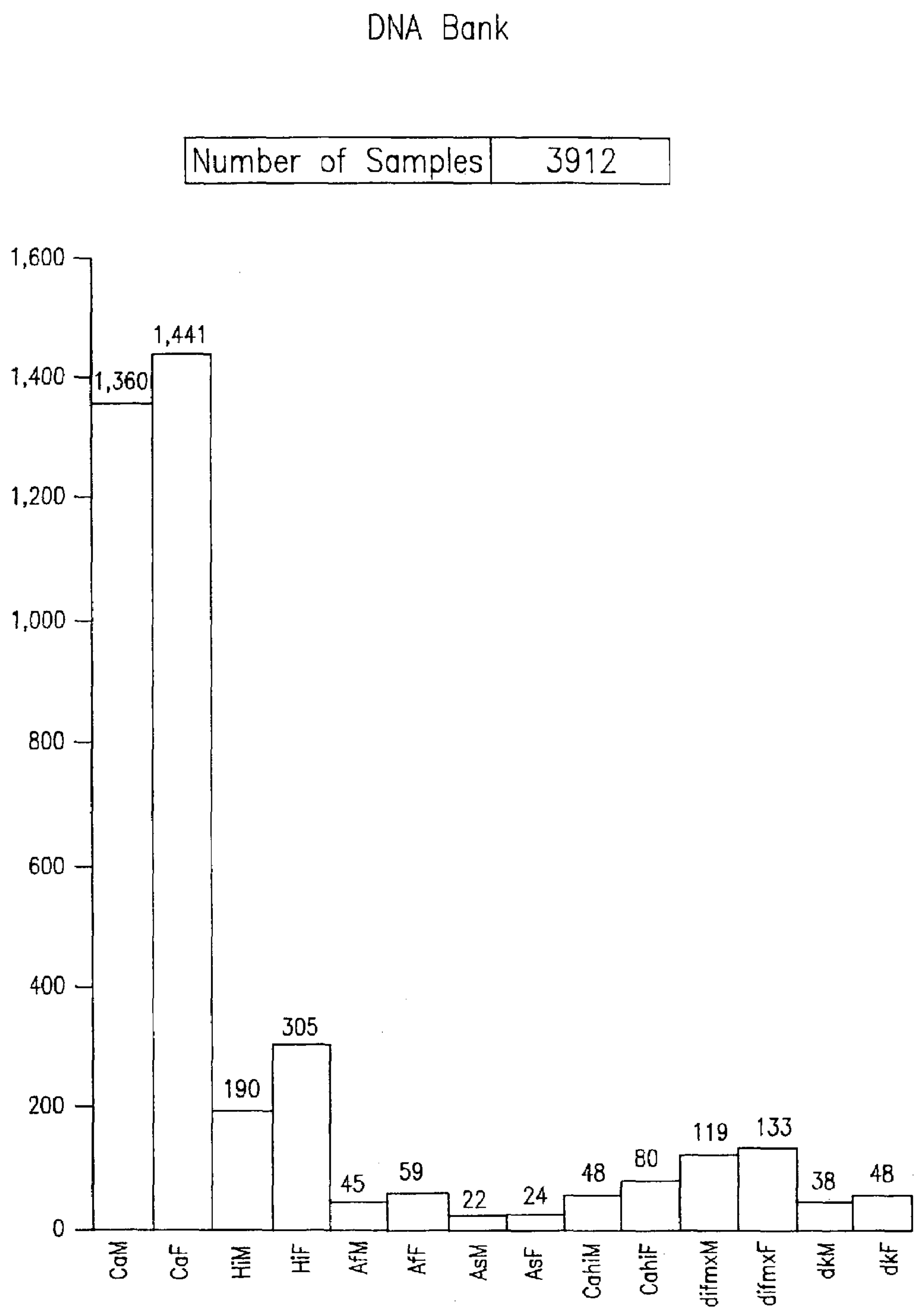
FIG. 1 depicts an exemplary sample bank. Panel 1 shows the samples as a function of sex and ethnicity. Panel 2 shows the Caucasians as a function of age. Panel 3 shows the Hispanics as a function of age.

Unless defined otherwise, all technical and scientific terms used herein have the same meaning as is commonly understood by one of ordinary skill in the art to which this invention belongs. All patents, applications, published applications and other publications and sequences from GenBank and other databases referred to herein throughout the disclosure are incorporated by reference in their entirety.

As used herein, a biopolymer includes, but is not limited to, nucleic acid, proteins, polysaccharides, lipids and other macromolecules. Nucleic acids include DNA, RNA, and fragments thereof. Nucleic acids can be derived from genomic DNA, RNA, mitochondrial nucleic acid, chloroplast nucleic acid and other organelles with separate genetic material.

As used herein, morbidity refers to conditions, such as diseases or disorders, that compromise the health and well-being of an organism, such as an animal. Morbidity susceptibility or morbidity-associated genes are genes that, when altered, for example, by a variation in nucleotide sequence, facilitate the expression of a specific disease clinical phenotype. Thus, morbidity susceptibility genes have the potential, upon alteration, of increasing the likelihood or general risk that an organism will develop a specific disease.

As used herein, mortality refers to the statistical likelihood that an organism, particularly an animal, will not survive a full predicted lifespan. Hence, a trait or a marker, such as a polymorphism, associated with increased mortality is observed at a lower frequency in older than younger segments of a population.

As used herein, a polymorphism, e.g. genetic variation, refers to a variation in the sequence of a gene in the genome amongst a population, such as allelic variations and other variations that arise or are observed. Thus, a polymorphism refers to the occurrence of two or more genetically determined alternative sequences or alleles in a population. These differences can occur in coding and non-coding portions of the genome, and can be manifested or detected as differences in nucleic acid sequences, gene expression, including, for example transcription, processing, translation, transport, protein processing, trafficking, DNA synthesis, expressed proteins, other gene products or products of biochemical pathways or in post-translational modifications and any other differences manifested amongst members of a population. A single nucleotide polymorphism (SNP) refers to a polymorphism that arises as the result of a single base change, such as an insertion, deletion or change in a base.

A polymorphic marker or site is the locus at which divergence occurs. Such site can be as small as one base pair (an SNP). Polymorphic markers include, but are not limited to, restriction fragment length polymorphisms, variable number of tandem repeats (VNTR's), hypervariable regions, minisatellites, dinucleotide repeats, trinucleotide repeats, tetranucleotide repeats and other repeating patterns, simple sequence repeats and insertional elements, such as Alu. Polymorphic forms also are manifested as different mendelian alleles for a gene. Polymorphisms can be observed by differences in proteins, protein modifications, RNA expression modification, DNA and RNA methylation, regulatory factors that alter gene expression and DNA replication, and any other manifestation of alterations in genomic nucleic acid or organelle nucleic acids.

As used herein, a healthy population refers to a population of organisms, including but are not limited to, animals, bacteria, viruses, parasites, plants, eubacteria, and others, that are disease free. The concept of disease-free is a function of the selected organism. For example, for mammals it refers to a subject not manifesting any disease state. Practically a healthy subject, when human, is defined as human donor who passes blood bank criteria to donate blood for eventual use in the general population. These criteria are as follows: free of detectable viral, bacterial, mycoplasma, and parasitic infections; not anemic; and then further selected based upon a questionnaire regarding history (see FIG. 3). Thus, a healthy population represents an unbiased population of sufficient health to donate blood according to blood bank criteria, and not further selected for any disease state. Typically such individuals are not taking any medications. For plants, for example, it is a plant population that does not manifest diseases pathology associated with plants. For bacteria it is a bacterial population replicating without environmental stress, such as selective agents, heat and other pathogens.

As used herein, a healthy database (or healthy patient database) refers to a database of profiles of subjects that have not been pre-selected for any particular disease. Hence, the subjects that serve as the source of data for the database are selected, according to predetermined criteria, to be healthy. In contrast to other such databases that have been pre-selected for subjects with a particular disease or other characteristic, the subjects for the database provided herein are not so-selected. Also, if the subjects do manifest a disease or other condition, any polymorphism discovered or characterized should be related to an independent disease or condition. In a one embodiment, where the subjects are human, a healthy subject manifests no disease symptoms and meets criteria, such as those set by blood banks for blood donors.

Thus, the subjects for the database are a population of any organism, including, but are not limited to, animals, plants, bacteria, viruses, parasites and any other organism or entity that has nucleic acid. Among subjects are mammals, such as, although not necessarily, humans. Such a database can capture the diversity of a population, thus providing for discovery of rare polymorphisms.

Figure 22A:
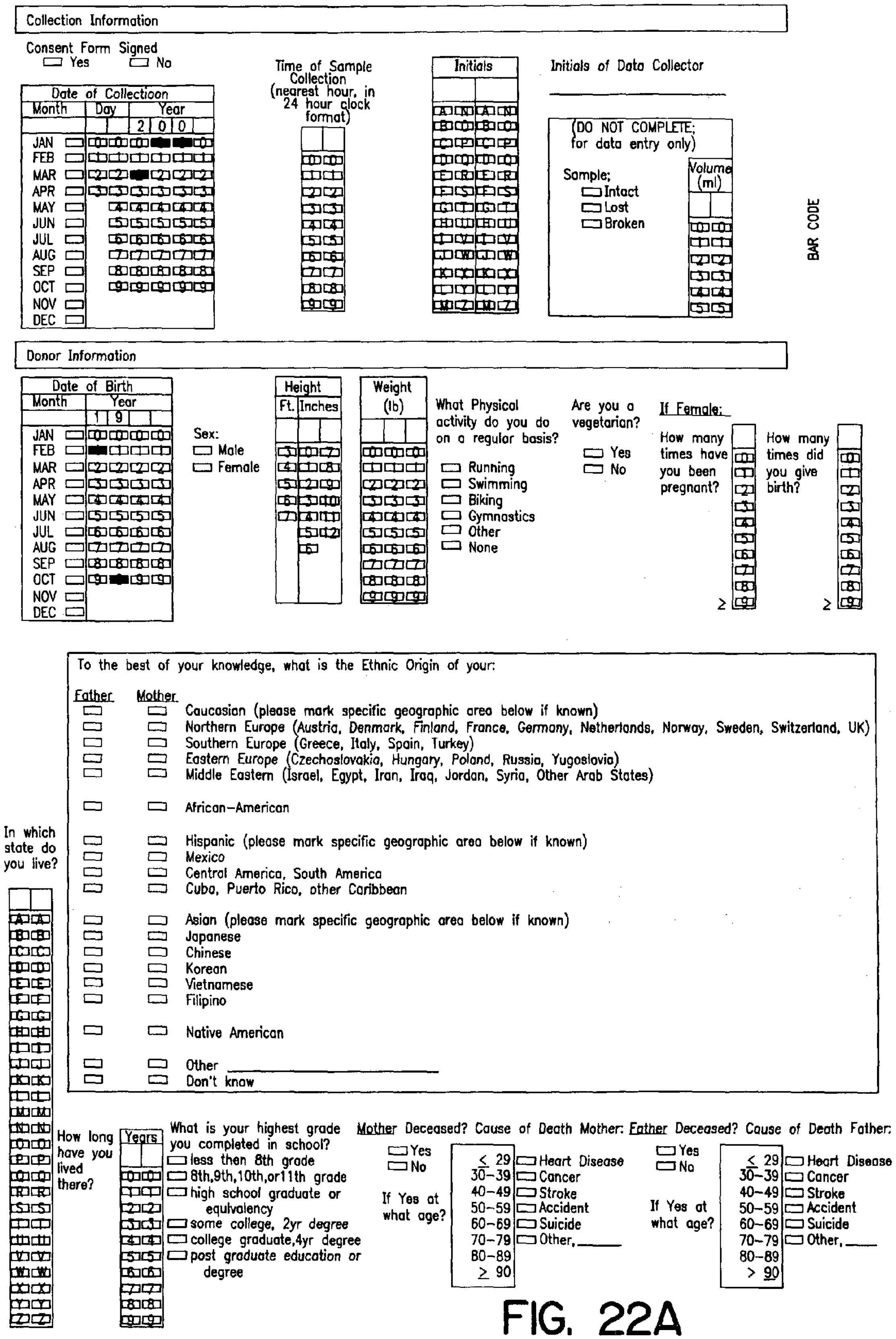
Figure 22C:
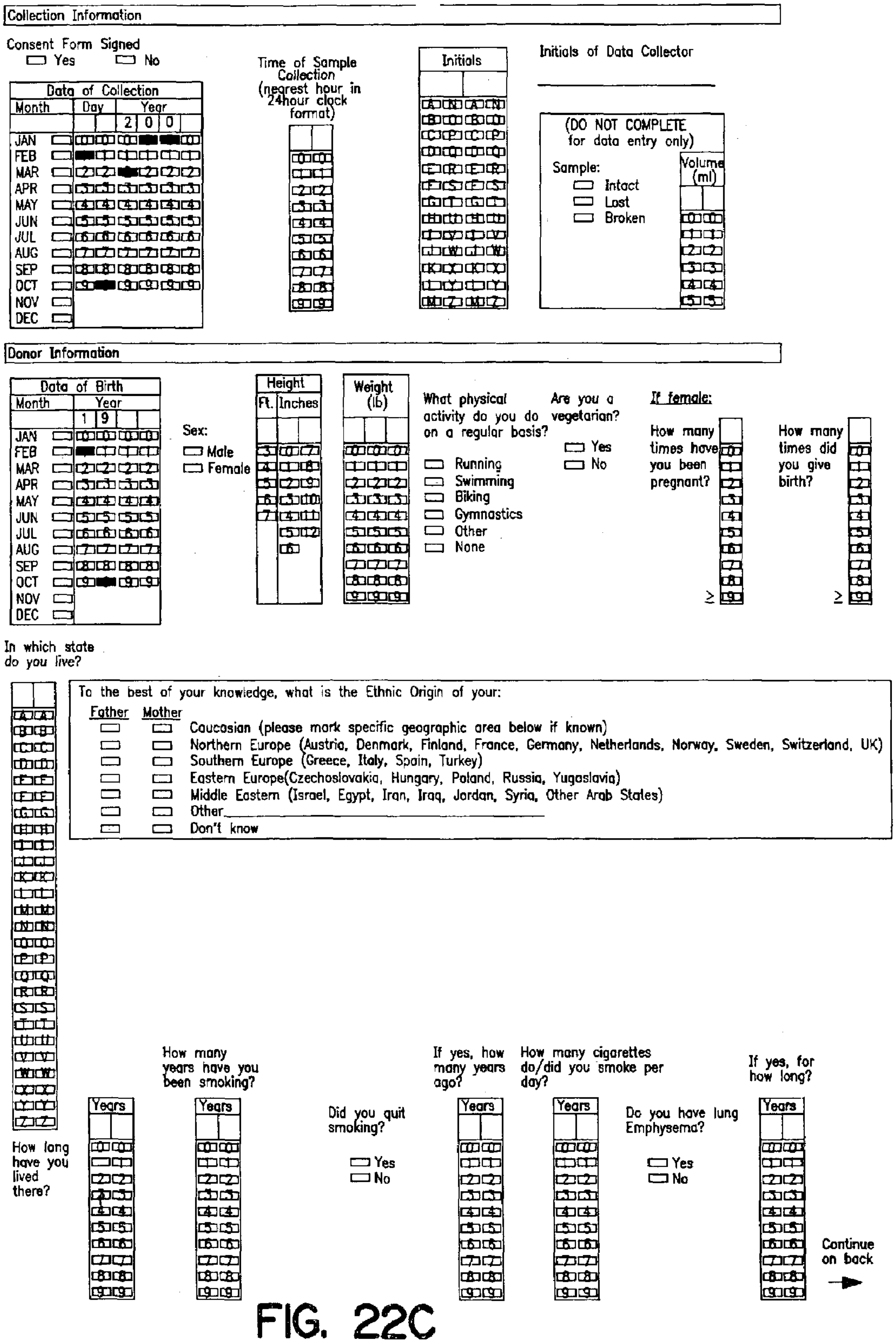

As used herein, a profile refers to information relating to, but not limited to and not necessarily including all of, age, sex, ethnicity, disease history, family history, phenotypic characteristics, such as height and weight and other relevant parameters. A sample collect information form is shown in FIG. 22, which illustrates profile intent.

As used herein, a disease state is a condition or abnormality or disorder that can be inherited or result from environmental stresses, such as toxins, bacterial, fungal and viral infections.

As used herein, set of non-selected subjects means that the subjects have not been pre-selected to share a common disease or other characteristic. They can be selected to be healthy as defined herein.

As used herein, a phenotype refers to a set of parameters that includes any distinguishable trait of an organism. A phenotype can be physical traits and can be, in instances in which the subject is an animal, a mental trait, such as emotional traits. Some phenotypes can be determined by observation elicited by questionnaires (see, e.g., FIGS. 3 and 22) or by referring to prior medical and other records. For purposes herein, a phenotype is a parameter around which the database can be sorted.

As used herein, a parameter is any input data that will serve as a basis for sorting the database. These parameters will include phenotypic traits, medical histories, family histories and any other such information elicited from a subject or observed about the subject. A parameter can describe the subject, some historical or current environmental or social influence experienced by the subject, or a condition or environmental influence on someone related to the subject. Paramaters include, but are not limited to, any of those described herein, and known to those of skill in the art.

As used herein, haplotype refers to two or polymorphism located on a single DNA strand. Hence, haplotyping refers to identification of two or more polymorphisms on a single DNA strand. Haplotypes can be indicative of a phenotype. For some disorders a single polymorphism can suffice to indicate a trait; for others a plurality (i.e., a haplotype) can be needed. Haplotyping can be performed by isolating nucleic acid and separating the strands. In addition, when using enzymes such a certain nucleases, that produce, different size fragments from each strand, strand separation is not needed for haplotyping.

As used herein, pattern with reference to a mass spectrum or mass spectrometric analyses, refers to a characteristic distribution and number of signals (such peaks or digital representations thereof).

As used herein, signal in the context of a mass spectrum and analysis thereof refers to the output data, which the number or relative number of moleucles having a particular mass. Signals include "peaks" and digital representations thereof.

As used herein, adaptor, when used with reference to haplotyping using Fen ligase, refers to a nucleic acid that specifically hybridizes to a polymorphism of interest. An adaptor can be partially double-stranded. An adaptor complex is formed when an adaptor hybridizes to its target.

As used herein, a target nucleic acid refers to any nucleic acid of interest in a sample. It can contain one or more nucleotides.

As used herein, standardless analysis refers to a determination based upon an internal standard. For example, the frequency of a polymorphism can be determined herein by comparing signals within a single mass spectrum.

As used herein, amplifying refers to methods for increasing the amount of a bipolymer, especially nucleic acids. Based on the 5' and 3' primers that are chosen, amplication also serves to restrict and define the region of the genome which is subject to analysis. Amplification can be performed by any method known to those skilled in the art, including use of the polymerase chain reaction (PCR) etc. Amplification, e.g., PCR must be done quantitatively when the frequency of polymorphism is required to be determined.

As used herein, cleaving refers to non-specific and specific fragmentation of a biopolymer.

As used herein, multiplexing refers to the simultaneous detection of more than one polymorphism. Methods for performing multiplexed reactions, particularly in conjunction with mass spectrometry are known (see, e.g., U.S. Pat. Nos. 6,043,031, 5,547,835 and International PCT application No. WO 97/37041).

As used herein, reference to mass spectrometry encompasses any suitable mass spectrometric format known to those of skill in the art. Such formats include, but are not limited to, Matrix-Assisted Laser Desorption/Ionization, Time-of-Flight (MALDI-TOF), Electrospray (ES), IR-MALDI (see, e.g., published International PCT application No. 99/57318 and U.S. Pat. No. 5,118,937), Ion Cyclotron Resonance (ICR), Fourier Transform and combinations thereof. MALDI, particular UV and IR, are among the formats contemplated.

As used herein, mass spectrum refers to the presentation of data obtained from analyzing a biopolymer or fragment thereof by mass spectrometry either graphically or encoded numerically.

As used herein, a blood component is a component that is separated from blood and includes, but is not limited to red blood cells and platelets, blood clotting factors, plasma, enzymes, plasminogen, immunoglobulins. A cellular blood component is a component of blood, such as a red blood cell, that is a cell. A blood protein is a protein that is normally found in blood. Examples of such proteins are blood factors VII and VIII. Such proteins and components are well-known to those of skill in the art.

As used herein, plasma can be prepared by any method known to those of skill in the art. For example, it can be prepared by centrifuging blood at a force that pellets the red cells and forms an interface between the red cells and the buffy coat, which contains leukocytes, above which is the plasma. For example, typical platelet concentrates contain at least about 10% plasma.

Blood can be separated into its components, including, but not limited to, plasma, platelets and red blood cells by any method known to those of skill in the art. For example, blood can be centrifuged for a sufficient time and at a sufficient acceleration to form a pellet containing the red blood cells. Leukocytes collect primarily at the interface of the pellet and supernatant in the buffy coat region. The supernatant, which contains plasma, platelets, and other blood components, can then be removed and centrifuged at a higher acceleration, whereby the platelets pellet.

As used herein, p53 is a cell cycle control protein that assesses DNA damage and acts as a transcription factor regulation gene which control cell growth, DNA repair and apoptosis. The p53 mutations have been found in a wide variety of different cancers, including all of the different types of leukemia, with varying frequency. The loss of normal p53 functions results in genomic instability and uncontrolled growth of the host cell.

As used herein, p21 is a cyclin-dependent kinase inhibitor, associated with G1 phase arrest of normal cells. Expression triggers apoptosis or programmed cell death and has been associated with Wilms' tumor, a pediatric kidney cancer.

As used herein, Factor VII is a serine protease involved the extrinsic blood coagulation cascade. This factor is activated by thrombin and works with tissue factor (Factor III) in the processing of Factor X to Factor Xa. Evidence has supported an association between polymorphisms in the gene and increase Factor VII activity which can result in an elevated risk of ischemic cardiovascular disease including myocardial infarction.

As used herein, a relational database stores information in a form representative of matrices, such as two-dimensional tables, including rows and columns of data, or higher dimensional matrices. For example, in one embodiment, the relational database has separate tables each with a parameter. The tables are linked with a record number, which also acts as an index. The database can be searched or sorted by using data in the tables and is stored in any suitable storage medium, such as floppy disk, CD rom disk, hard drive or other suitable medium.

As used herein, a bar codes refers any array of optically readable marks of any desired size and shape that are arranged in a reference context or frame of, typically, although not necessarily, one or more columns and one or more rows. For purposes herein, the bar code refers to any symbology, not necessary "bar" but can include dots, characters or any symbol or symbols.

As used herein, symbology refers to an identifier code or symbol, such as a bar code, that is linked to a sample. The index will reference each such symbology. The symbology is any code known or designed by the user. The symbols are associated with information stored in the database. For example, each sample can be uniquely identified with an encoded symbology. The parameters, such as the answers to the questions and subsequent genotypic and other information obtained upon analysis of the samples is included in the database and associated with the symbology. The database is stored on any suitable recording medium, such as a hard drive, a floppy disk, a tape, a CD ROM, a DVD disk and any other suitable medium.

DATABASES

Human genotyping is currently dependent on collaborations with hospitals, tissues banks and research institutions that provide samples of disease tissue. This approach is based on the concept that the onset and/or progression of diseases can be correlated with the presence of a polymorphisms or other genetic markers. This approach does not consider that disease correlated with the presence of specific markers and the absence of specific markers. It is shown herein that identification and scoring of the appearance and disappearance of markers is possible only if these markers are measured in the background of healthy subjects where the onset of disease does not mask the change in polymorphism occurrence. Databases of information from disease populations suffer from small sample size, selection bias and heterogeneity. The databases provided herein from healthy populations solve these problems by permitting large sample bands, simple selection methods and diluted heterogeneity.

Provided herein are first databases of parameters, associated with non-selected, particularly healthy, subjects. Also provided are combinations of the databases with indexed samples obtained from each of the subjects. Further provided are databases produced from the first databases. These contain, in addition to the original parameters, information, such as genotypic information, including, but are not limited to, genomic sequence information, derived from the samples.

The databases, which are herein designated healthy databases, are so-designated because they are not obtained from subjects pre-selected for a particular disease. Hence, although individual members can have a disease, the collection of individuals is not selected to have a particular disease.

The subjects from whom the parameters are obtained comprise either a set of subjects who are randomly selected across, typically, all populations, or are pre-selected to be disease-free or healthy. As a result, the database is not selected to be representative of any pre-selected phenotype, genotype, disease or other characteristic. Typically the number of subjects from which the database is prepared is selected to produce statistically significant results when used in the methods provided herein. Generally, the number of subjects will be greater than 100, 200, and typically than 1000. The precise number can be empirically determined based upon the frequency of the parameter(s) that can be used to sort the database. Generally the population can have at least 50, at least 100, at least 200, at least 500, at least 1000, at least 5000 or at least 10,000 or more subjects.

Upon identification of a collection of subjects, information about each subject is recorded and associated with each subject as a database. The information associated with each of the subjects, includes, but is not limited to, information related to historical characteristics of the subjects, phenotypic characteristics and also genotypic characteristics, medical characteristics and any other traits and characteristics about the subject that can be determined. This information will serve as the basis for sorting the database.

In an exemplary embodiment, the subjects are mammals, such as humans, and the information relates to one or more of parameters, such as age, sex, medical history, ethnicity and any other factor. Such information, when the animals are humans, for example, can be obtained by a questionnaire and by observations about the individual, such as hair color, eye color and other characteristics. Genotypic information can be obtained from tissue or other body and body fluid samples from the subject.

The healthy genomic database can include profiles and polymorphisms from healthy individuals from a library of blood samples where each sample in the library is an individual and separate blood or other tissue sample. Each sample in the database is profiled as to the sex, age, ethnic group, and disease history of the donor.

The databases are generated by first identifying healthy populations of subjects and obtaining information about each subject that will serve as the sorting parameters for the database. This information can be entered into a storage medium, such as the memory of a computer.

The information obtained about each subject in a population used for generating the database is stored in a computer memory or other suitable storage medium. The information is linked to an identifier associated with each subject. Hence the database will identify a subject, for example by a datapoint representative of a bar code, and then all information, such as the information from a questionnaire, regarding the individual is associated with the datapoint. As the information is collected the database is generated.

Thus, for example, profile information, such as subject histories obtained from questionnaires, is collected in the database. The resulting database can be sorted as desired, using standard software, such as by age, sex and/or ethnicity. An exemplary questionnaire for subjects from whom samples are to be obtained is shown in FIGS. 22A-D. Each questionnaire, for example, can be identified by a bar code, particularly a machine readable bar code for entry into the database. After a subject provides data and is deemed to be healthy (i.e., meets standards for blood donation), the data in the questionnaire is entered into the database and is associated with the bar code. A tissue, cell or blood sample is obtained from the subject.

Figure 4:
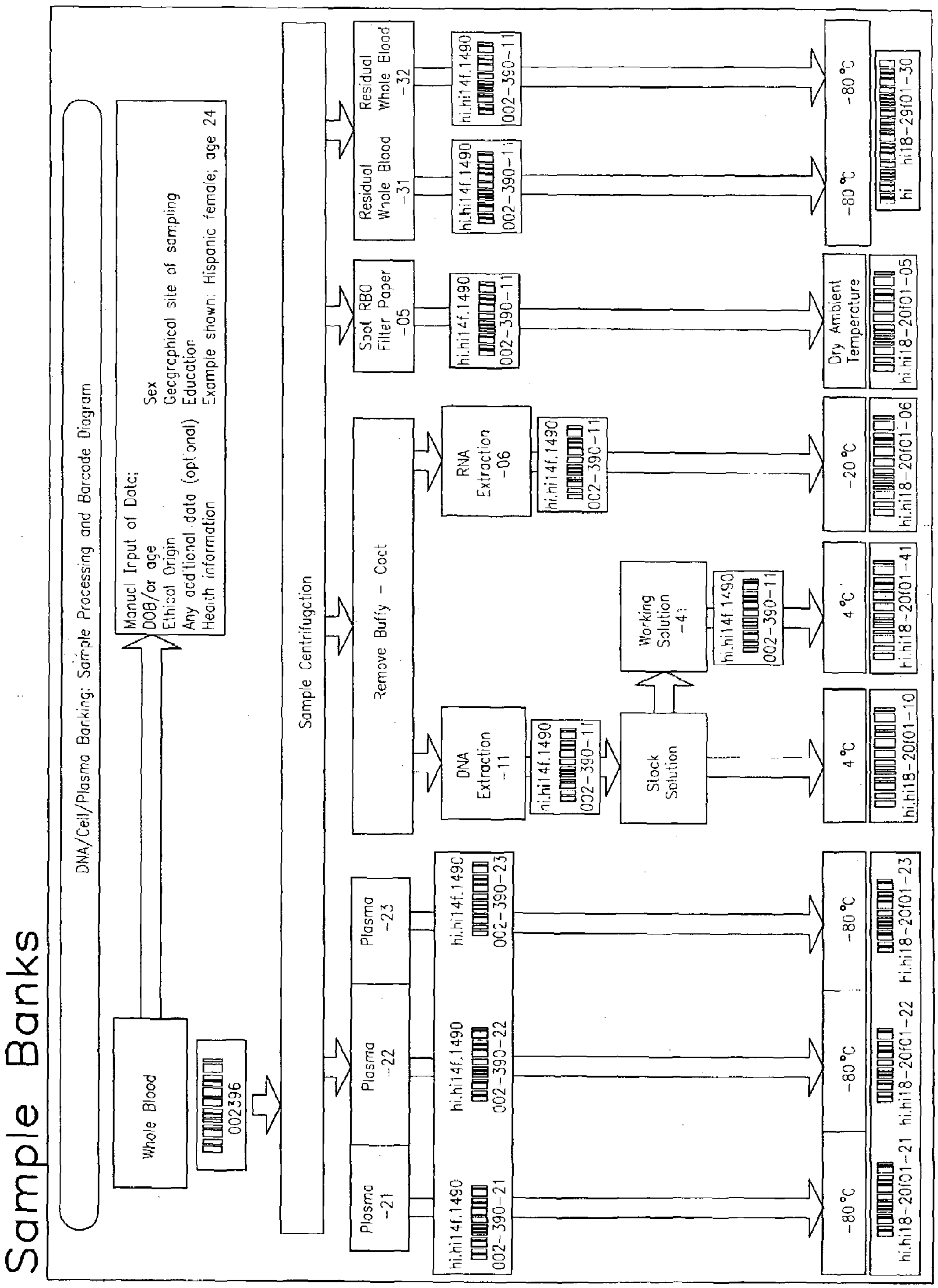
FIG. 4 depicts processing and tracking of blood sample components.
Figure 5:
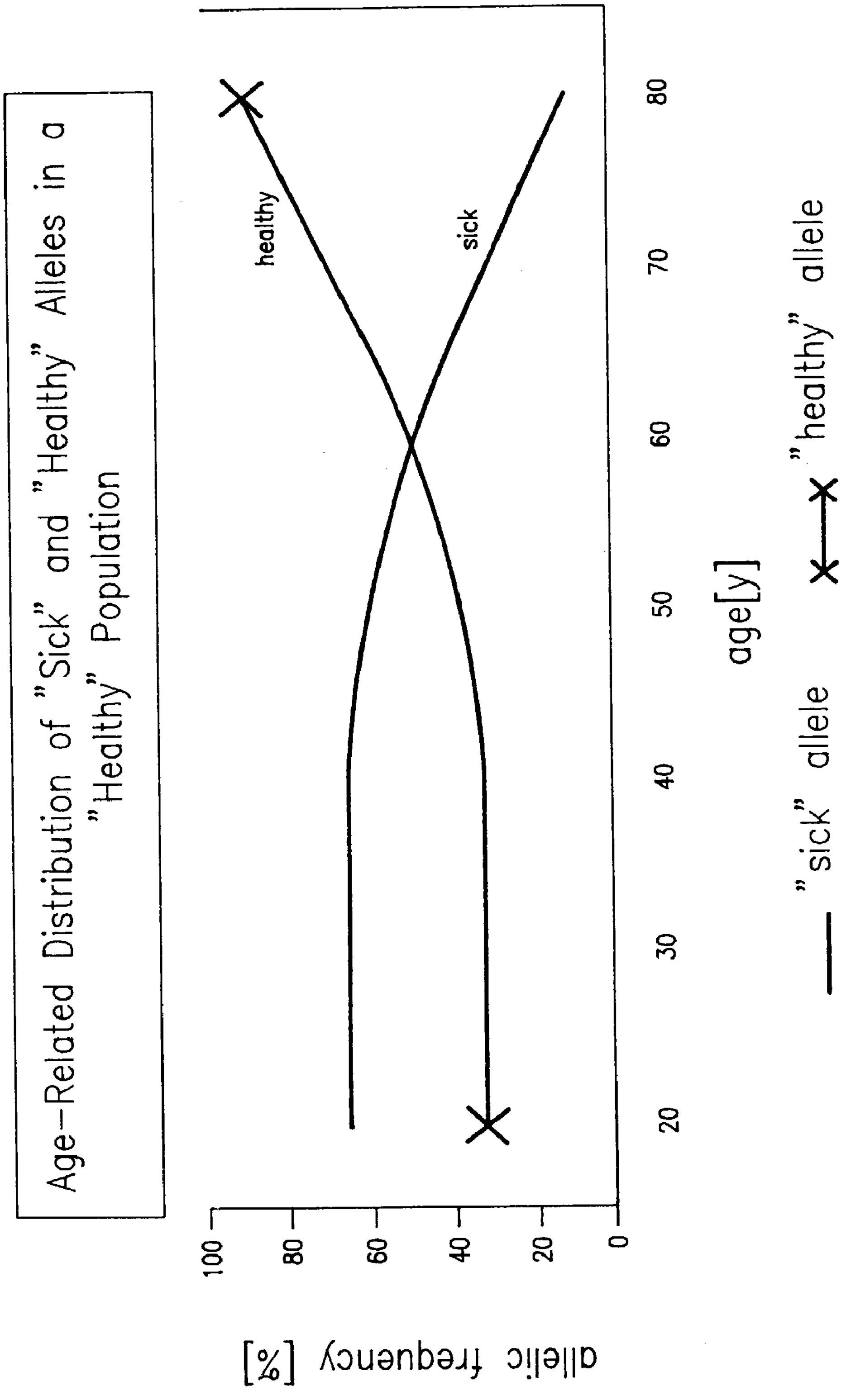
FIG. 5 depicts the allelic frequency of "sick" alleles and "healthy" alleles as a function of age. It is noted that the relative frequency of healthy alleles increases in a population with increasing age.
Figure 6:
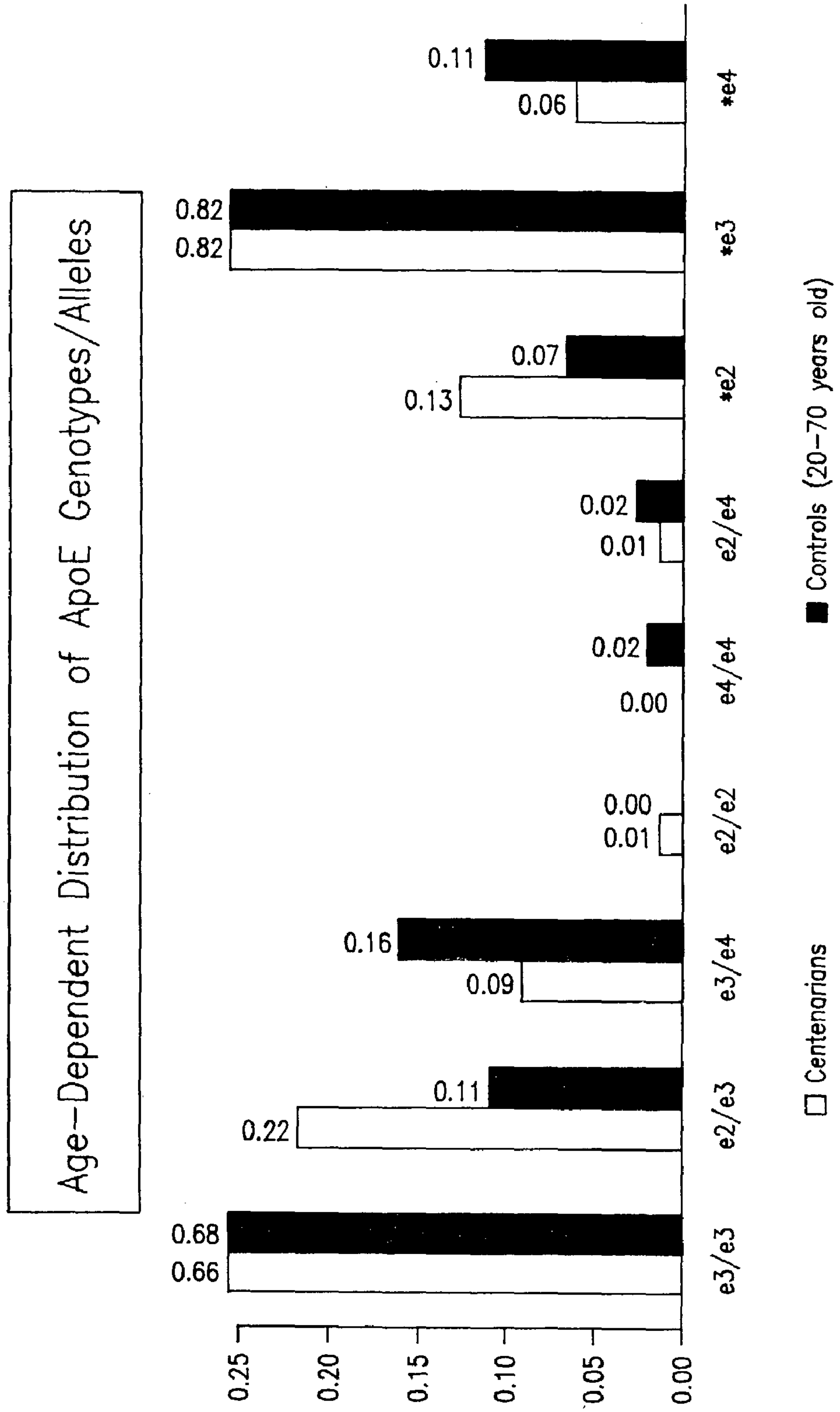
FIG. 6 depicts the age-dependent distribution of ApoE genotypes (see, Schächter et al. (1994) *Nature Genetics* 6:29-32).

FIG. 4 exemplifies processing and tracking of blood sample components. Each component is tracked with a bar code, dated, is entered into the database and associated with the subject and the profile of the subject. Typically, the whole blood is centrifuged to produce plasma, red blood cells (which pellet) and leukocytes found in the buffy coat which layers in between. Various samples are obtained and coded with a bar code and stored for use as needed.

Samples are collected from the subjects. The samples include, but are not limited to, tissues, cells, and fluids, such as nucleic acid, blood, plasma, amniotic fluid, synovial fluid, urine, saliva, aqueous humor, sweat, sperm samples and cerebral spinal fluid. It is understood that the particular set of samples depends upon the organisms in the population.

Once samples are obtained the collection can be stored and, in some embodiments, each sample is indexed with an identifier, particularly a machine readable code, such as a bar code. For analyses, the samples or components of the samples, particularly biopolymers and small molecules, such as nucleic acids and/or proteins and metabolites, are isolated.

After samples are analyzed, this information is entered into the database in the memory of the storage medium and associated with each subject. This information includes, but is not limited to, genotypic information. Particularly, nucleic acid sequence information and other information indicative of polymorphisms, such as masses of PCR fragments, peptide fragment sequences or masses, spectra of biopolymers and small molecules and other indicia of the structure or function of a gene, gene product or other marker from which the existence of a polymorphism within the population can be inferred.

Figure 1B:
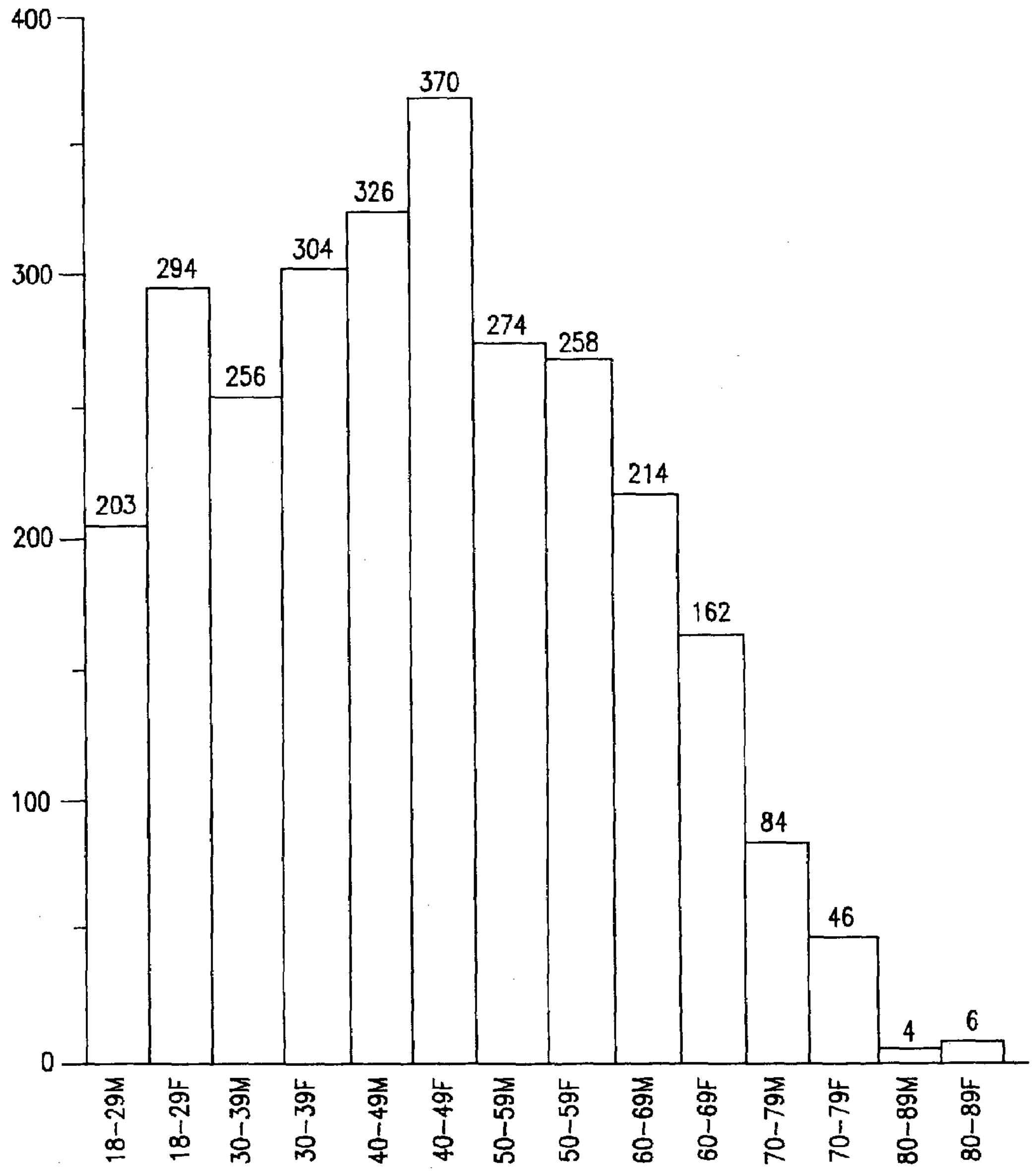
Figure 1C:
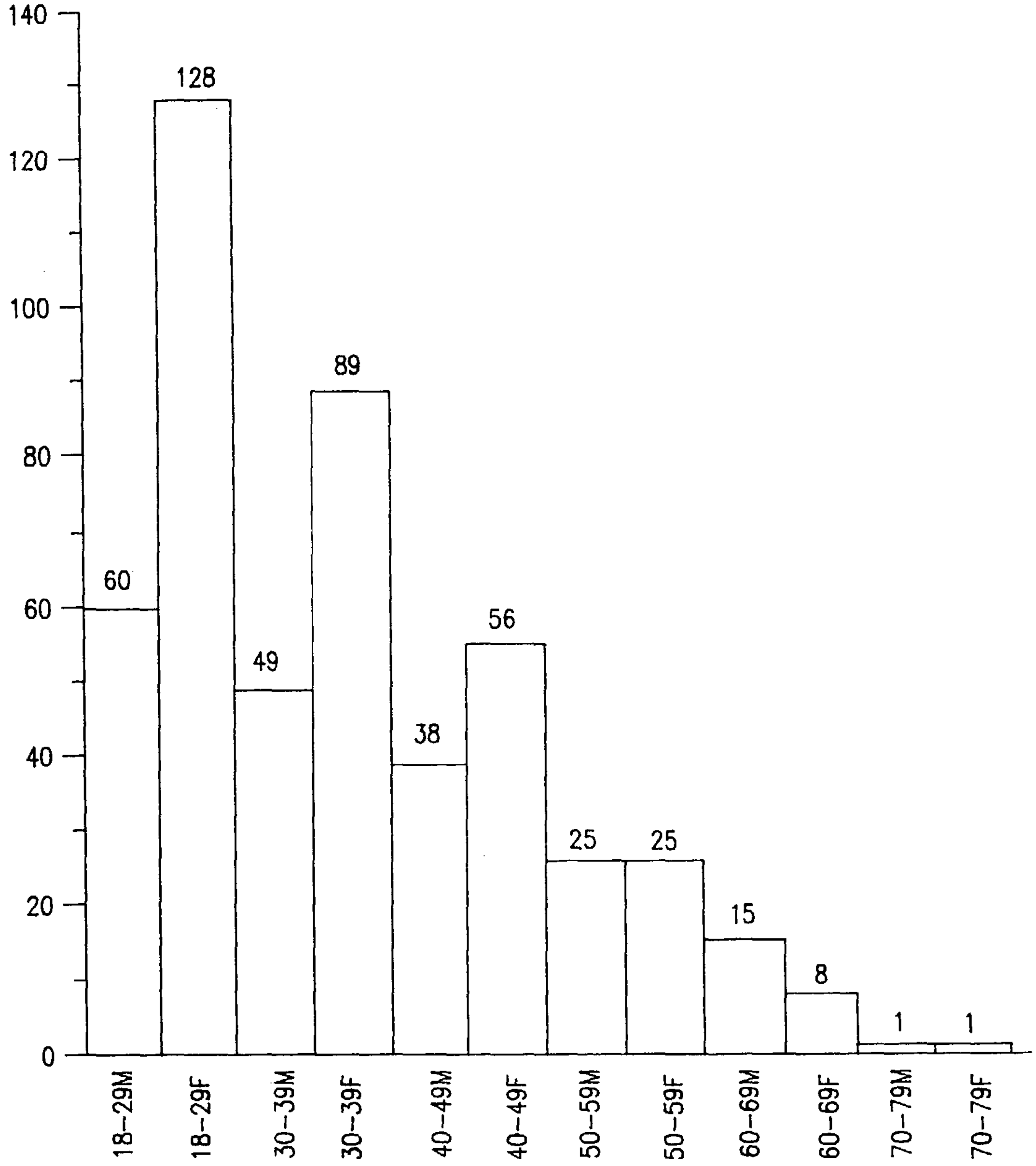

In an exemplary embodiment, a database can be derived from a collection of blood samples. For example, FIG. 1 (see, also FIG. 10) shows the status of a collection of over 5000 individual samples. The samples were processed in the laboratory following SOP (standard operating procedure) guidelines. Any standard blood processing protocol can be used.

For the exemplary database described herein, the following criteria were used to select subjects:

No testing is done for infectious agents.
Age: At least 17 years old
Weight: Minimum of 110 pounds Permanently Disqualified:
History of hepatitis (after age 11)
Leukemia Lymphoma
Human immunodeficiency virus (HIV),AIDS
Chronic kidney disease Temporarily Disqualified:
Pregnancy—until six weeks after delivery, miscarriage or abortion
Major surgery or transfusions—for one year
Mononucleosis—until complete recovery
Prior whole blood donation—for eight weeks
Antibiotics by injection for one week; by mouth, for forty-eight hours, except antibiotics for skin complexion;

5 year Deferment:
Internal cancer and skin cancer if it has been removed, is healed and there is no recurrence These correspond to blood bank criteria for donating blood and represent a healthy population as defined herein for a human healthy database.

Structure of the Database

Any suitable database structure and format known to those of skill in the art can be employed. For example, a relational database is a an exemplary format in which data are stored as matrices or tables of the parameters linked by an indexer that identifies each subject. Software for preparing and manipulating, including sorting the database, can be readily developed or adapted from commercially available software, such as Microsoft Access.

Quality Control

Quality control procedures can be implemented. For example, after collection of samples, the quality of the collection in the bank can be assessed. For example, mix-up of samples can be checked by testing for known markers, such as sex. After samples are separated by ethnicity, samples are randomly tested for a marker associated with a particular ethnicity, such as HLA DQA1 group specific component, to assess whether the samples have been properly sorted by ethnic group. An exemplary sample bank is depicted in FIG. 4.

Obtaining Genotypic Data and Other Parameters for the Database

After informational and historical parameters are entered into the database, material from samples obtained from each subject, is analyzed. Analyzed material include proteins, metabolites, nucleic acids, lipids and any other desired constituent of the material. For example, nucleic acids, such as genomic DNA, can be analyzed by sequencing.

Sequencing can be performed using any method known to those of skill in the art. For example, if a polymorphism is identified or known, and it is desired to assess its frequency or presence among the subjects in the database, the region of interest from each sample can be isolated, such as by PCR or restriction fragments, hybridization or other suitable method known to those of skill in the art and sequenced. For purposes herein, sequencing analysis can be effected using mass spectrometry (see, e.g., U.S. Pat. Nos. 5,547,835, 5,622,824, 5,851,765, and 5,928,906). Nucleic acids also can be sequenced by hybridization (see, e.g., U.S. Pat. Nos. 5,503, 980, 5,631,134, 5,795,714) and including analysis by mass spectrometry (see, U.S. application Ser. Nos. 08/419,994 and 09/395,409).

In other detection methods, it is necessary to first amplify prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA. In some embodiments, the primers are located between 150 and 350 base pairs apart.

Alternative amplification methods include: self sustained sequence replication (Guatelli, J. C. et al., 1990, Proc. Natl. Acad. Sci. U.S.A. 87:1874-1878), transcriptional amplification system (Kwoh, D. Y. et al., 1989, Proc. Natl. Acad. Sci. U.S.A. 86:1173-1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

Nucleic acids also can be analyzed by detection methods and protocols, particularly those that rely on mass spectrometry (see, e.g., U.S. Pat. No. 5,605,798, 6,043,031, allowed copending U.S. application Ser. No. 08/744,481, U.S. application Ser. No. 08/990,851 and International PCT application No. WO 99/31278, International PCT application No. WO 98/20019). These methods can be automated (see, e.g., copending U.S. application Ser. No. 09/285,481 and published International PCT application No. PCT/US00/08111, which describes an automated process line). Among the methods of analysis herein are those involving the primer oligo base extension (PROBE) reaction with mass spectrometry for detection (described herein and elsewhere, see e.g., U.S. Pat. No. 6,043,031; see, also U.S. application Ser. Nos. 09/287,681, 09/287,682, 09/287,141 and 09/287,679, allowed copending U.S. application Ser. No. 08/744,481, International PCT application No. PCT/US97/20444, published as International PCT application No. WO 98/20019, and based upon U.S. application Ser. Nos. 08/744,481, 08/744,590, 08/746,036, 08/746,055, 08/786,988, 08/787, 639, 08/933,792, 08/746,055, 08/786,988 and 08/787,639; see, also U.S. application Ser. No. 09/074,936, U.S. Pat. No. 6,024,925, and U.S. application Ser. Nos. 08/746,055 and 08/786,988, and published International PCT application No. WO 98/20020)

A chip based format in which the biopolymer is linked to a solid support, such as a silicon or silicon-coated substrate, such as in the form of an array, is among the formats for performing the analyses is. Generally, when analyses are performed using mass spectrometry, particularly MALDI, small nanoliter volumes of sample are loaded on, such that the resulting spot is about, or smaller than, the size of the laser spot. It has been found that when this is achieved, the results from the mass spectrometric analysis are quantitative. The area under the signals in the resulting mass spectra are proportional to concentration (when normalized and corrected for background). Methods for preparing and using such chips are described in U.S. Pat. No. 6,024,925, co-pending U.S. application Ser. Nos. 08/786,988, 09/364,774, 09/371,150 and 09/297,575; see, also U.S. application Ser. No. PCT/US97/20195, which published as WO 98/20020. Chips and kits for performing these analyses are commercially available from SEQUENOM under the trademark MassARRAY. MassArray relies on the fidelity of the enzymatic primer extension reactions combined with the miniaturized array and MALDI-TOF (Matrix-Assisted Laser Desorption Ionization-Time of Flight) mass spectrometry to deliver results rapidly. It accurately distinguishes single base changes in the size of DNA fragments associated with genetic variants without tags.

The methods provided herein permit quantitative determination of alleles. The areas under the signals in the mass spectra can be used for quantitative determinations. The frequency is determined from the ratio of the signal to the total area of all of the spectrum and corrected for background. This is possible because of the PROBE technology as described in the above applications incorporated by reference herein.

Additional methods of analyzing nucleic acids include amplification-based methods including polymerase chain reaction (PCR), ligase chain reaction (LCR), mini-PCR, rolling circle amplification, autocatalytic methods, such as those using Qβ replicase, TAS, 3SR, and any other suitable method known to those of skill in the art.

Other methods for analysis and identification and detection of polymorphisms, include but are not limited to, allele specific probes, Southern analyses, and other such analyses.

The methods described below provide ways to fragment given amplified or non-amplified nucleotide sequences thereby producing a set of mass signals when mass spectrometry is used to analyze the fragment mixtures.

Amplified fragments are yielded by standard polymerase chain methods (U.S. Pat. Nos. 4,683,195 and 4,683,202). The fragmentation method involves the use of enzymes that cleave single or double strands of DNA and enzymes that ligate DNA. The cleavage enzymes can be glycosylases, nickases, and site-specific and non site-specific nucleases, such as, but are not limited to, glycosylases, nickases and site-specific nucleases.

Glycosylase Fragmentation Method

DNA glycosylases specifically remove a certain type of nucleobase from a given DNA fragment. These enzymes can thereby produce abasic sites, which can be recognized either by another cleavage enzyme, cleaving the exposed phosphate backbone specifically at the abasic site and producing a set of nucleobase specific fragments indicative of the sequence, or by chemical means, such as alkaline solutions and or heat. The use of one combination of a DNA glycosylase and its targeted nucleotide would be sufficient to generate a base specific signature pattern of any given target region.

Numerous DNA glcosylases are known, For example, a DNA glycosylase can be uracil-DNA glycolsylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase (see, e.g.,, U.S. Pat. Nos. 5,536,649, 5,888,795, 5,952,176 and 6,099,553, International PCT application Nos. WO 97/03210, WO 99/54501; see, also, Eftedal et al. (1993) Nucleic Acids Res 21:2095-2101, Bjelland and Seeberg (1987) Nucleic Acids Res. 15:2787-2801, Saparbaev et al. (1995) Nucleic Acids Res. 23:3750-3755, Bessho (1999) Nucleic Acids Res. 27:979-983) corresponding to the enzyme's modified nucleotide or nucleotide analog target. uracil-DNA glycolsylase (UDG) is an exemplary glycosylase.

Uracil, for example, can be incorporated into an amplified DNA molecule by amplifying the DNA in the presence of normal DNA precursor nucleotides (e.g. dCTP, dATP, and dGTP) and dUTP. When the amplified product is treated with UDG, uracil residues are cleaved. Subsequent chemical treatment of the products from the UDG reaction results in the cleavage of the phosphate backbone and the generation of nucleobase specific fragments. Moreover, the separation of the complementary strands of the amplified product prior to glycosylase treatment allows complementary patterns of fragmentation to be generated. Thus, the use of dUTP and Uracil DNA glycosylase allows the generation of T specific fragments for the complementary strands, thus providing information on the T as well as the A positions within a given sequence. Similar to this, a C-specific reaction on both (complementary) strands (i.e. with a C-specific glycosylase) yields information on C as well as G positions within a given sequence if the fragmentation patterns of both amplification strands are analyzed separately. Thus, with the glycosylase method and mass spectrometry, a full series of A, C, G and T specific fragmentation patterns can be analyzed.

Nickase Fragmentation Method

A DNA nickase, or DNase, can be used to recognize and cleave one strand of a DNA duplex. Numerous nickases are known. Among these, for example, are nickase NY2A nickase and NYS1 nickase (Megabase) with the following cleavage sites:

NY2A:

5' . . . R AG . . . 3'

3' . . . Y TC . . . 5' where R=A or G and Y=C or T

NYS1:

5' . . . CC[A/G/T] . . . 3'

3' . . . GG[T/C/A] . . . 5'.

Fen-Ligase Fragmentation Method

The Fen-ligase method involves two enzymes: Fen-1 enzyme and a ligase. The Fen-1 enzyme is a site-specific nuclease known as a "flap" endonuclease (U.S. Pat. Nos. 5,843,669, 5,874,283, and 6,090,606). This enzyme recognizes and cleaves DNA "flaps" created by the overlap of two oligonucleotides hybridized to a target DNA strand. This cleavage is highly specific and can recognize single base pair mutations, permitting detection of a single homologue from an individual heterozygous at one SNP of interest and then genotyping that homologue at other SNPs occurring within the fragment. Fen-1 enzymes can be Fen-1 like nucleases e.g. human, murine, and Xenopus XPG enzymes and yeast RAD2 nucleases or Fen-1 endonucleases from, for example, *M. jannaschii, P. furiosus,* and *P. woesei.* Among such enzymes are the Fen-1 enzymes.

The ligase enzyme forms a phosphodiester bond between two double stranded nucleic acid fragments. The ligase can be DNA Ligase I or DNA Ligase III (see, e.g., U.S. Pat. Nos. U.S. 5,506,137, 5,700,672, 5,858,705 and 5,976,806; see, also, Waga, et al. (1994) J. Biol. Chem. 269:10923-10934, Li et al. (1994) Nucleic Acids Res. 22:632-638, Arrand et al. (1986) J. Biol. Chem. 261:9079-9082, Lehman (1974) Science 186:790-797, Higgins and Cozzarelli (1979) Methods Enzymol. 68:50-71, Lasko et al. (1990) Mutation Res. 236: 277-287, and Lindahl and Barnes (1992) Ann. Rev. Biochem. 61:251-281). Thermostable ligase (Epicenter Technologies), where "thermostable" denotes that the ligase retains activity even after exposure to temperatures necessary to separate two strands of DNA, are among the ligases for use herein.

Type IIS Enzyme Fragmentation Method

Restriction enzymes bind specifically to and cleave double-stranded DNA at specific sites within or adjacent to a particular recognition sequence. These enzymes have been classified into three groups (e.g. Types I, II, and III) as known to those of skill in the art. Because of the properties of type I and type III enzymes, they have not been widely used in molecular biological applications. Thus, for purposes herein type II enzymes are among those contemplated. Of the thousands of restriction enzymes known in the art, there are 179 different type II specificities. Of the 179 unique type II restriction endonucleases, 31 have a 4-base recognition sequence, 11 have a 5-base recognition sequence, 127 have a 6-base recognition sequence, and 10 have recognition sequences of greater than six bases (U.S. Pat. No. 5,604,098). Of category type II enzymes, type IIS is exemplified herein.

Type IIS enzymes can be Alw XI, Bbv I, Bce 83, Bpm I, Bsg I, Bsm AI, Bsm FI, Bsa I, Bcc I, Bcg I, Ear I, Eco 57I, Esp 3I, Fau I, Fok I, Gsu I, Hga I, Mme I, Mbo II, Sap I, and the otheres.

The Fok I enzyme endonuclease is an exemplary well characterized member of the Type IIS class (see, e.g., U.S. Pat. Nos. 5,714,330, 5,604,098, 5,436,150, 6,054,276 and 5,871,911; see, also, Szybalski et al. (1991) Gene 100:13-26, Wilson and Murray (1991) Ann. Rev. Genet. 25:585-627, Sugisaki et al. (1981) Gene 16:73-78, Podhajska and Szalski (1985) Gene 40:175-182. Fok I recognizes the sequence 5'GGATG-3' and cleaves DNA accordingly. Type IIS restriction sites can be introduced into DNA targets by incorporating the sites into primers used to amplify such targets. Fragments produced by digestion with Fok I are site specific and can be analyzed by mass spectrometry methods such as MALDI-TOF mass spectrometry, ESI-TOF mass spectrometry, and any other type of mass spectrometry well known to those of skill in the art.

Once a polymorphism has been found to correlate with a parameter such as age, age groups can be screened for polymorphisms. The possibility of false results due to allelic dropout is examined by doing comparative PCR in an adjacent region of the genome.

Analyses

In using the database, allelic frequencies can be determined across the population by analyzing each sample in the population individually, determining the presence or absence of allele or marker of interest in each individual sample, and then determining the frequency of the marker in the population. The database can then be sorted (stratified) to identify any correlations between the allele and a selected parameter using standard statistical analysis. If a correlation is observed, such as a decrease in a particular marker with age or correlation with sex or other parameter, then the marker is a candidate for further study, such as genetic mapping to identify a gene or pathway in which it is involved. The marker can then be correlated, for example, with a disease. Haplotying also can be carried out. Genetic mapping can be effected using standard methods and can also require use of databases of others, such as databases previously determined to be associated with a disorder.

Exemplary analyses have been performed and these are shown in the figures, and discussed herein.

Sample Pooling

It has been found that using the databases provided herein, or any other database of such information, substantially the same frequencies that were obtained by examining each sample separately can be obtained by pooling samples, such as in batches of 10, 20, 50, 100, 200, 500, 1000 or any other number. A precise number can be determined empirically if necessary, and can be as low as 3.

Figure 9:
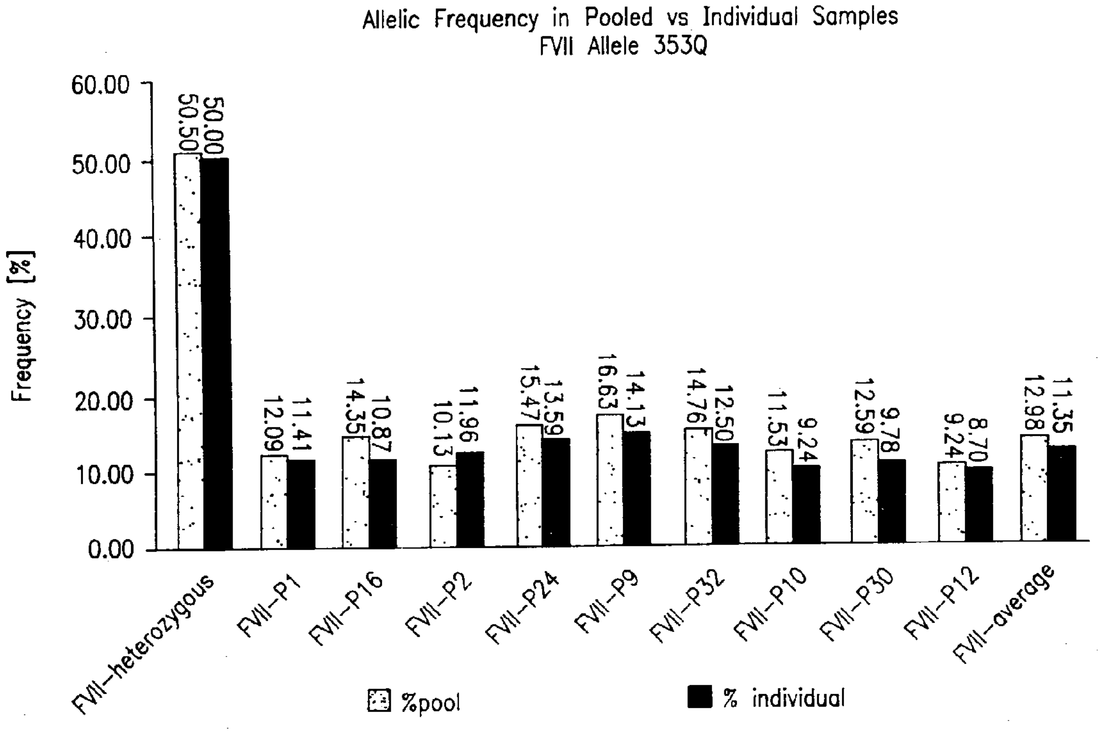
FIG. 9 depicts the frequency of the FVII Allele 353Q in pooled versus individual samples.
Figure 10:
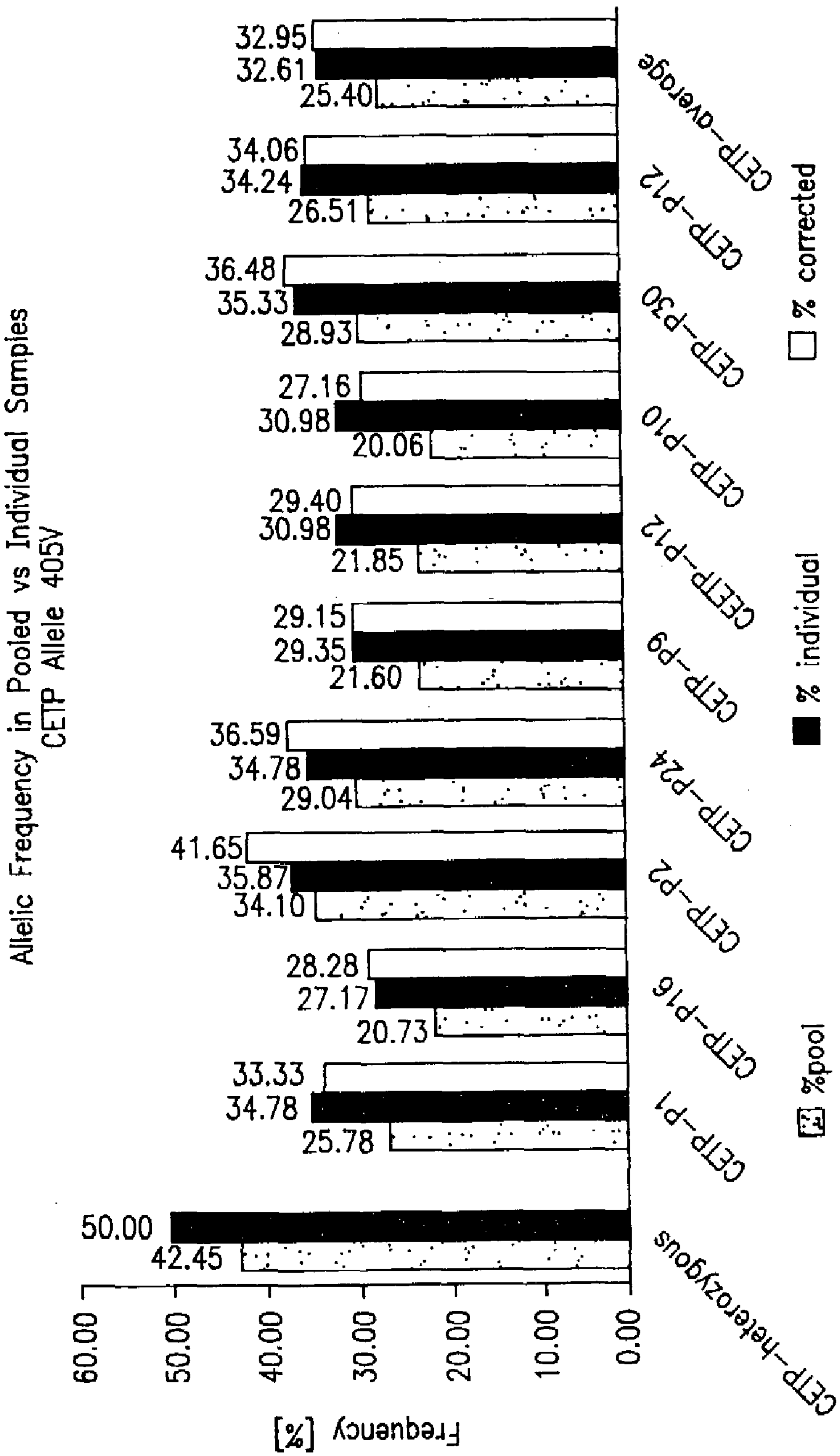
FIG. 10 depicts the frequency of the CETP (cholesterol ester transfer protein) allele in pooled versus individual samples.
Figure 11:
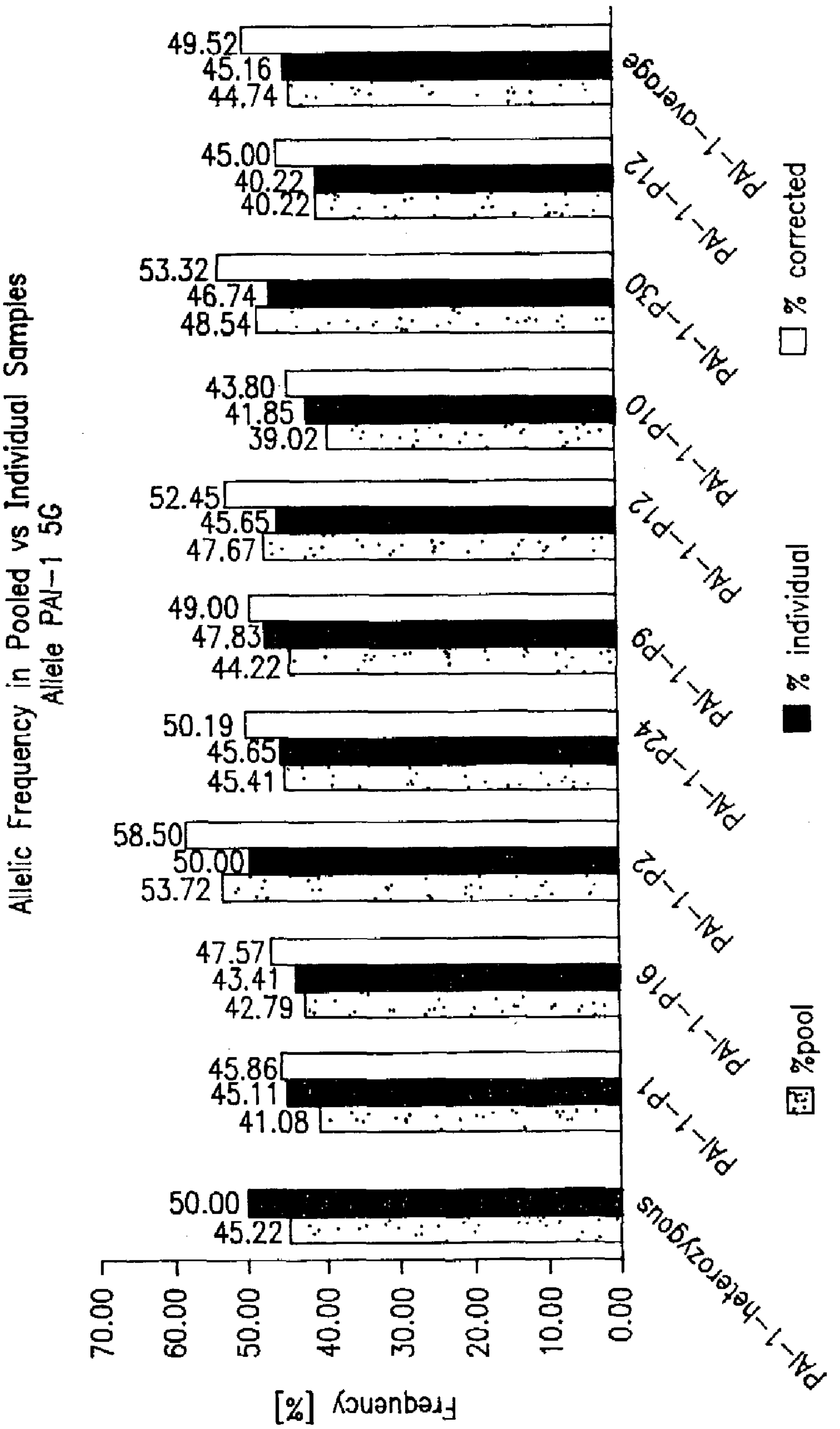
FIG. 11 depicts the frequency of the plasminogen activator inhibitor-1 (PAI-1) 5G in pooled versus individual samples.
Figure 12A:
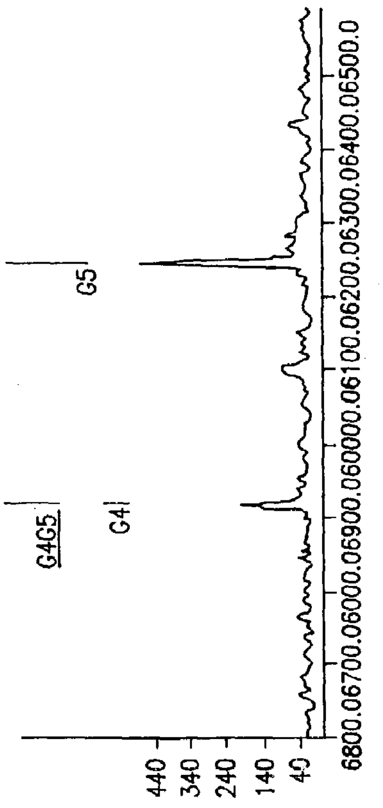
FIG. 12 shows mass spectra of the samples and the ethnic diversity of the PAI-1 alleles.
Figure 12B:
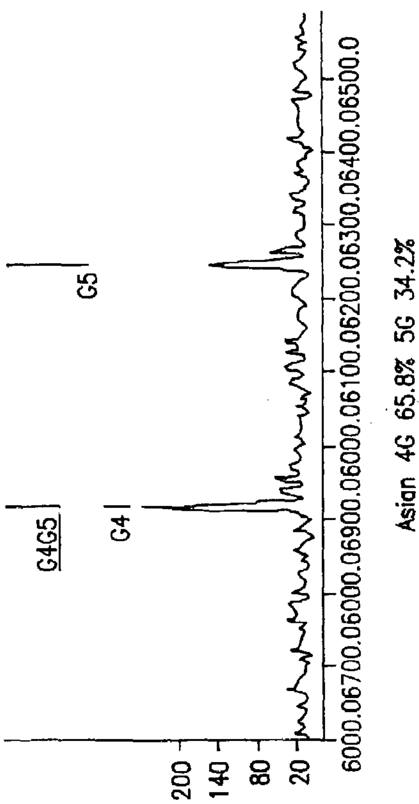
Figure 12C:
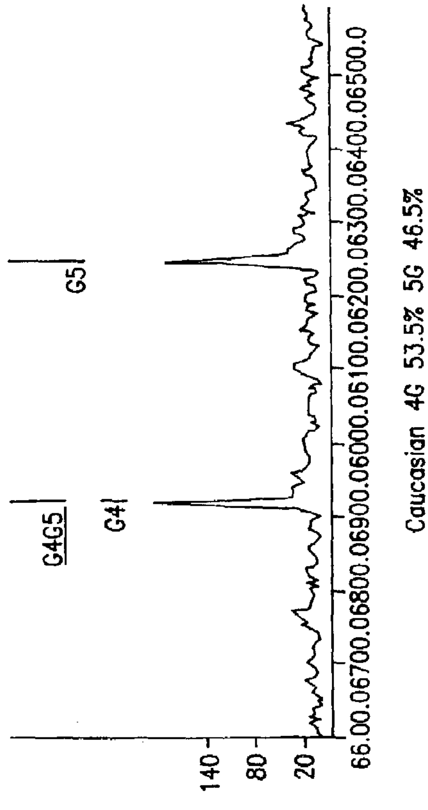
Figure 12D:
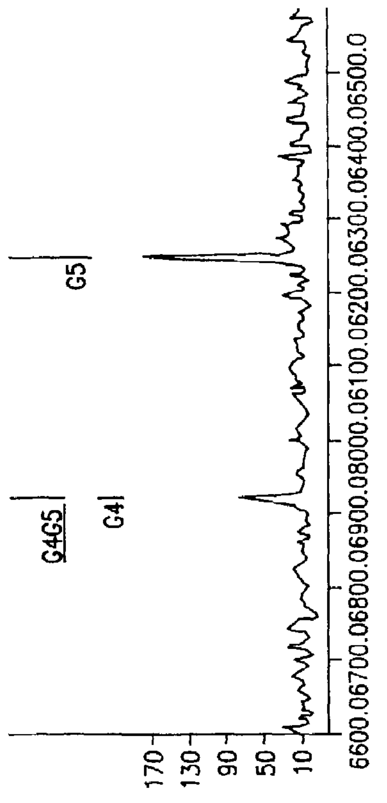
Figure 13A:
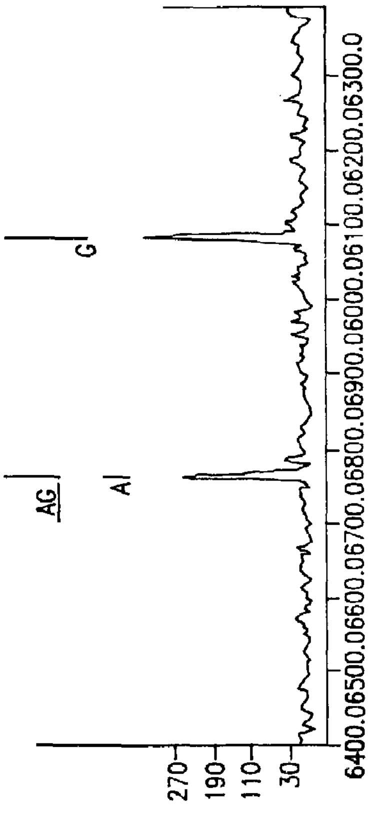
FIG. 13 shows mass spectra of the samples and the ethnic diversity of the CETP 405 alleles.
Figure 13B:
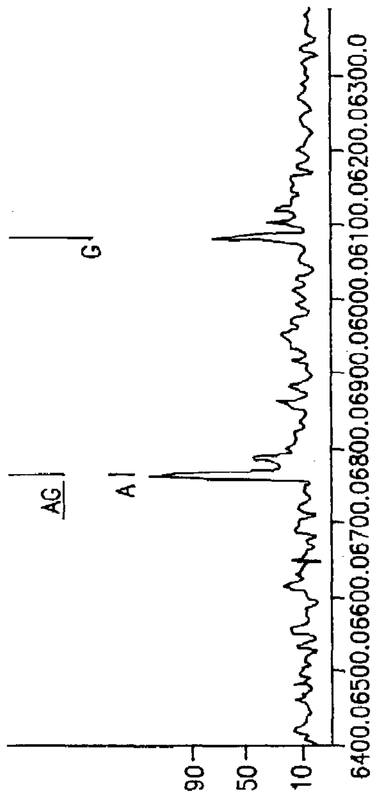
Figure 13C:
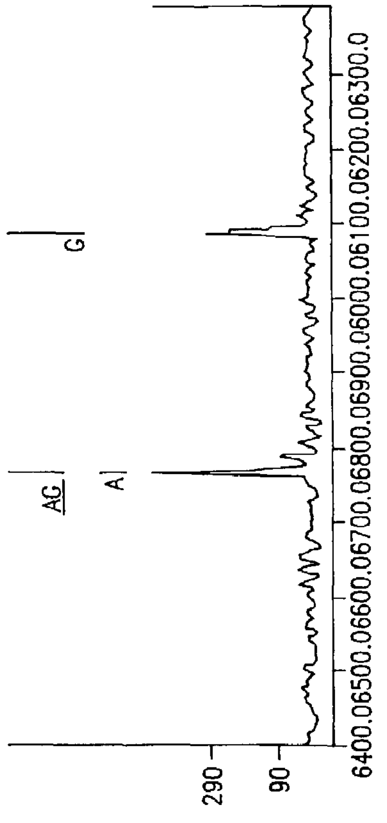
Figure 13D:
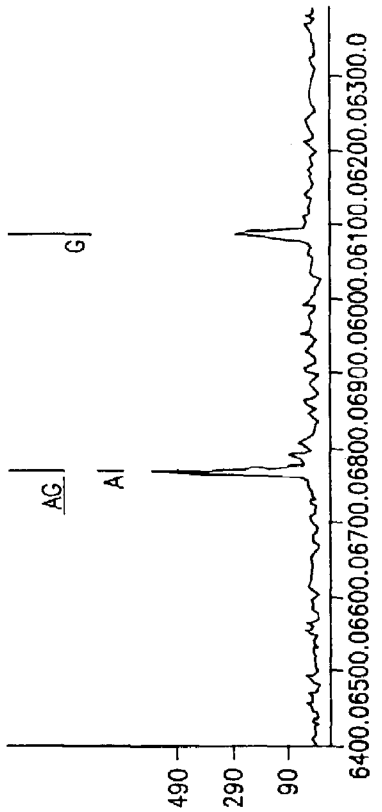
Figure 14A:
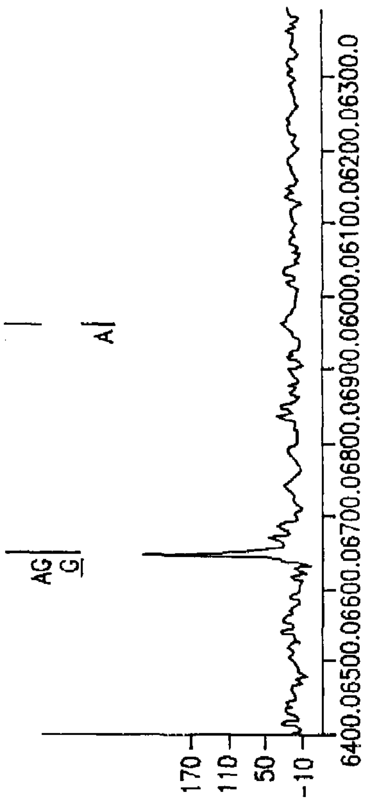
FIG. 14 shows mass spectra of the samples and the ethnic diversity of the Factor VII 353 alleles.
Figure 14B:
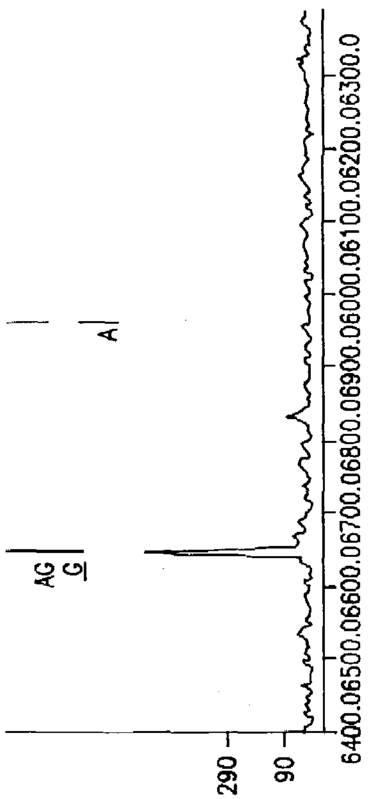
Figure 14C:
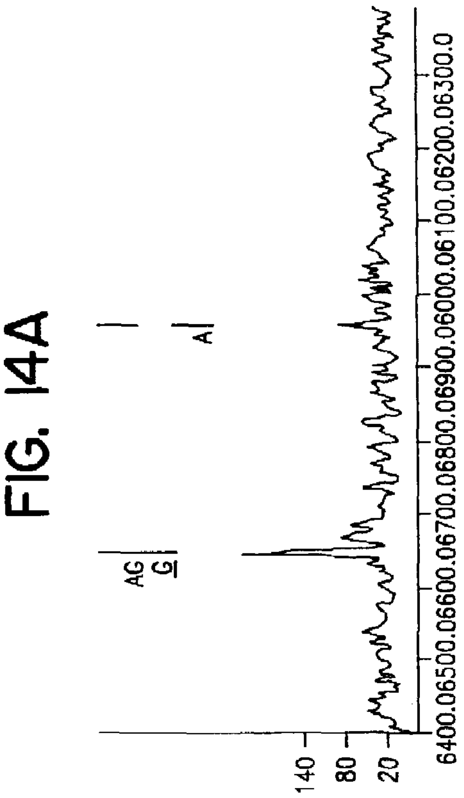
Figure 14D:
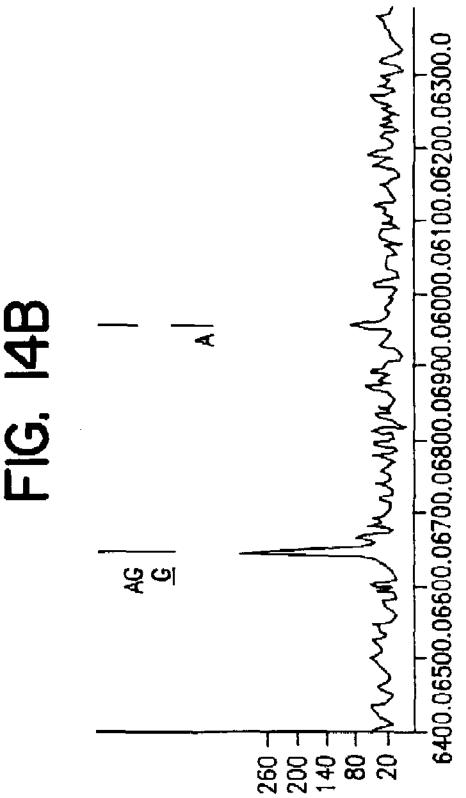
Figure 15:
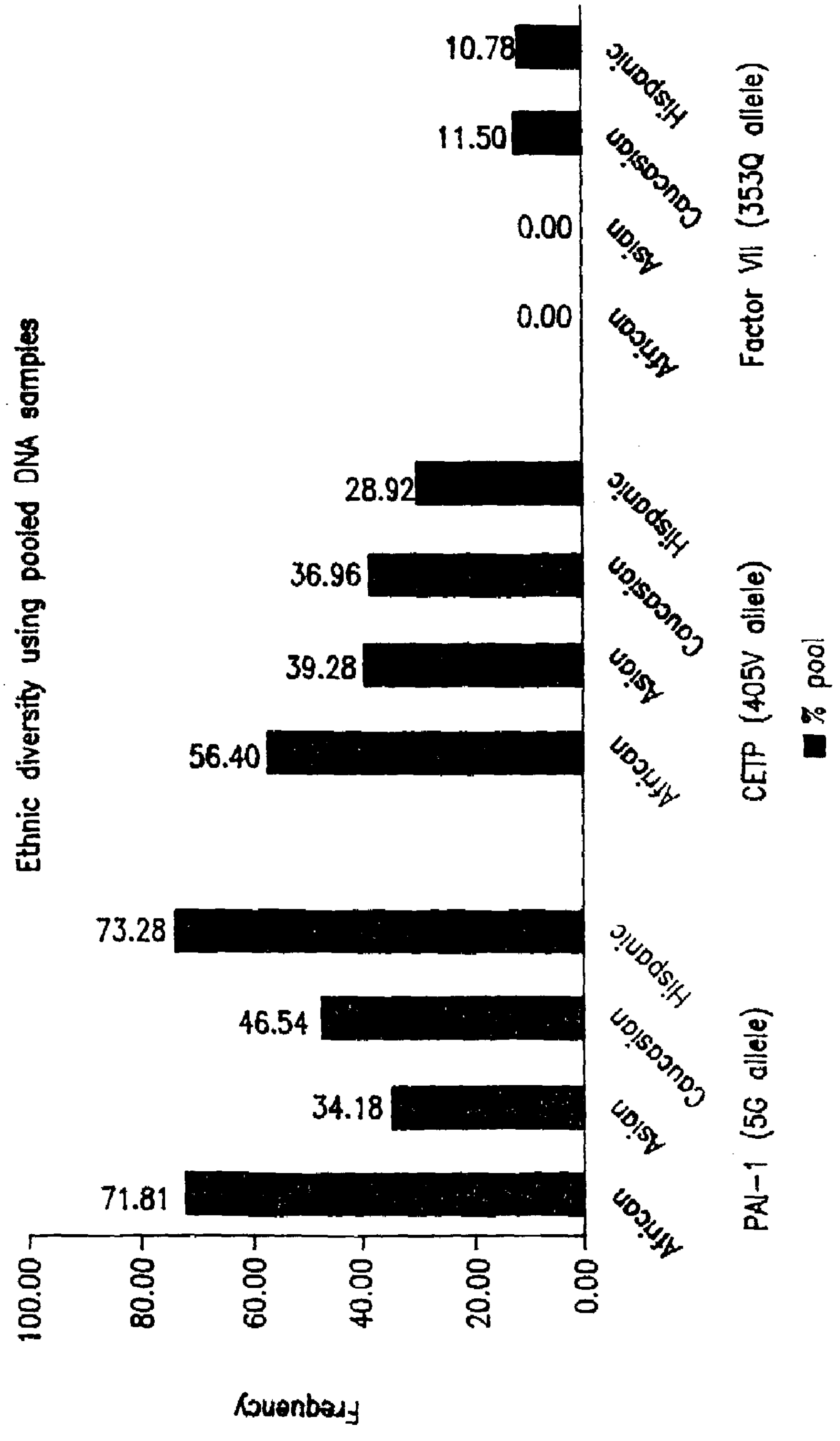
FIG. 15 shows ethnic diversity of PAI-1, CETP and Factor VII using the pooled DNA samples.
Figure 16:
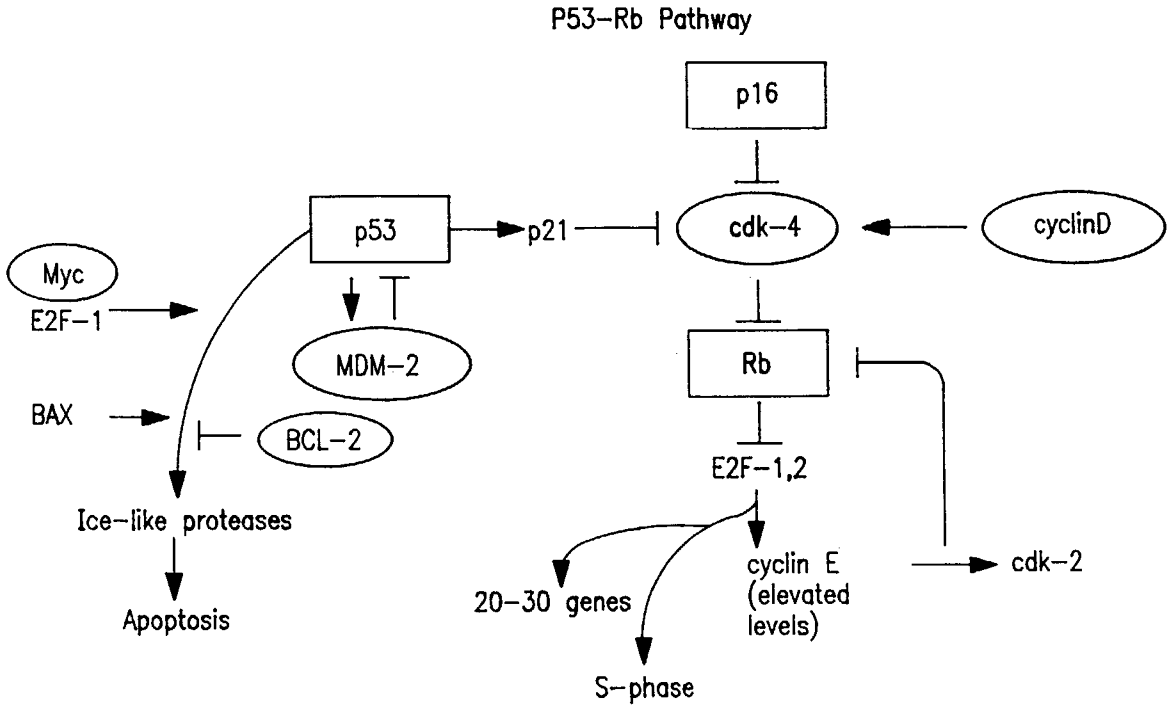
FIG. 16 shows the p53-Rb pathway and the relationships among the various factors in the pathway.

In one embodiment, the frequency of genotypic and other markers can be obtained by pooling samples. To do this a target population and a genetic variation to be assessed is selected, a plurality of samples of biopolymers are obtained from members of the population, and the biopolymer from which the marker or genotype can be inferred is determined or detected. A comparison of samples tested in pools and individually and the sorted results therefrom are shown in FIG. 9, which shows frequency of the factor VII Allele 353Q. FIG. 10 depicts the frequency of the CETP Allele in pooled versus individual samples. FIG. 15 shows ethnic diversity among various ethnic groups in the database using pooled DNA samples to obtain the data. FIGS. 12-14 show mass spectra for these samples.

Pooling of test samples has application not only to the healthy databases provided herein, but also to use in gathering data for entry into any database of subjects and genotypic information, including typical databases derived from diseased populations. What is demonstrated herein, is the finding that the results achieved are statistically the same as the results that would be achieved if each sample is analyzed separately. Analysis of pooled samples by a method, such as the mass spectrometric methods provided herein, permits resolution of such data and quantitation of the results.

For factor VII the R53Q acid polymorphism was assessed. In FIG. 9, the "individual" data represent allelic frequency observed in 92 individuals reactions. The pooled data represent the allelic frequency of the same 92 individuals pooled into a single probe reaction. The concentration of DNA in the samples of individual donors is 250 nanograms. The total concentration of DNA in the pooled samples is also 250 nanograms, where the concentration of any individual DNA is 2.7 nanograms.

It also was shown that it is possible to reduce the DNA concentration of individuals in a pooled samples from 2.7 nanograms to 0.27 nanograms without any change in the quality of the spectrum or the ability to quantitate the amount of sample detected. Hence low concentrations of sample can be used in the pooling methods.

Use of the Databases and Markers Identified Thereby

The successful use of genomics requires a scientific hypothesis (i.e., common genetic variation, such as a SNP), a study design (i.e., complex disorders), samples and technology, such as the chip-based mass spectrometric analyses (see, e.g., U.S. Pat. No. 5,605,798, U.S. Pat. No. 5,777,324, U.S. Pat. No. 6,043,031, allowed copending U.S. application Ser. No. 08/744,481, U.S. application Ser. No. 08/990,851, International PCT application No. WO 98/20019, copending U.S. application Ser. No. 09/285,481, which describes an automated process line for analyses; see, also, U.S. application Ser. Nos. 08/617,256, 09/287,681, 09/287,682, 09/287,141 and 09/287,679, allowed copending U.S. application Ser. No. 08/744,481, International PCT application No. PCT/US97/20444, published as International PCT application No. WO 98/20019, and based upon U.S. application Ser. Nos. 08/744,481, 08/744,590, 08/746,036, 08/746,055, 08/786,988, 08/787,639, 08/933,792, 08/746,055, 09/266,409, 08/786,988 and 08/787,639; see, also U.S. application Ser. No.

09/074,936). All of these aspects can be used in conjunction with the databases provided herein and samples in the collection.

The databases and markers identified thereby can be used, for example, for identification of previously unidentified or unknown genetic markers and to identify new uses for known markers. As markers are identified, these can be entered into the database to use as sorting parameters from which additional correlations can be determined.

Previously Unidentified or Unknown Genetic Markers

The samples in the healthy databases can be used to identify new polymorphisms and genetic markers, using any mapping, sequencing, amplification and other methodologies, and in looking for polymorphisms among the population in the database. The thus-identified polymorphism can then be entered into the database for each sample, and the database sorted (stratified) using that polymorphism as a sorting parameter to identify any patterns and correlations that emerge, such as age correlated changes in the frequency of the identified marker. If a correlation is identified, the locus of the marker can be mapped and its function or effect assessed or deduced.

Thus, the databases here provide means for:

identification of significantly different allelic frequencies of genetic factors by comparing the occurrence or disappearance of the markers with increasing age in population and then associating the markers with a disease or a biochemical pathway;

identification of significantly different allelic frequencies of disease causing genetic factors by comparing the male with the female population or comparing other selected stratified populations and associating the markers with a disease or a biochemical pathway;

identification of significantly different allelic frequencies of disease causing genetic factors by comparing different ethnic groups and associating the markers with a disease or a biochemical pathway that is known to occur in high frequency in the ethnic group;

profiling potentially functional variants of genes through the general panmixed population stratified according to age, sex, and ethnic origin and thereby demonstrating the contribution of the variant genes to the physical condition of the investigated population;

identification of functionally relevant gene variants by gene disequilibrium analysis performed within the general panmixed population stratified according to age, sex, and ethnic origin and thereby demonstrating their contribution to the physical condition of investigated population;

identification of potentially functional variants of chromosomes or parts of chromosomes by linkage disequilibrium analysis performed within the general panmixed population stratified according to age, sex, and ethnic origin and thereby demonstrating their contribution to the physical condition of investigated population.

Uses of the Identified Markers and Known Markers

The databases can also be used in conjunction with known markers and sorted to identify any correlations. For example, the databases can be used for:

determination and evaluation of the penetrance of medically relevant polymorphic markers;

determination and evaluation of the diagnostic specificity of medically relevant genetic factors;

determination and evaluation of the positive predictive value of medically relevant genetic factors;

determination and evaluation of the onset of complex diseases, such as, but are not limited to, diabetes, hypertension, autoimmune diseases, arteriosclerosis, cancer and other diseases within the general population with respect to their causative genetic factors;

delineation of the appropriate strategies for preventive disease treatment;

delineation of appropriate timelines for primary disease intervention;

validation of medically relevant genetic factors identified in isolated populations regarding their general applicability;

validation of disease pathways including all potential target structures identified in isolated populations regarding their general applicability; and validation of appropriate drug targets identified in isolated populations regarding their general applicability.

Among the diseases and disorders for which polymorphisms can be linked include, those linked to inborn errors of metabolism, acquired metabolic disorders, intermediary metabolism, oncogenesis pathways, blood clotting pathways, and DNA synthetic and repair pathways, DNA repair/replication/transcription factors and activities, e.g., such as genes related to oncogenesis, aging and genes involved in blood clotting and the related biochemical pathways that are related to thrombosis, embolism, stroke, myocardial infarction, angiogenesis and oncogenesis.

For example, a number of diseases are caused by or involve deficient or defective enzymes in intermediary metabolism (see, e.g., Tables 1 and 2, below) that result, upon ingestion of the enzyme substrates, in accumulation of harmful metabolites that damage organs and tissues, particularly an infant's developing brain and other organs, resulting in mental retardation and other developmental disorders.

Identification of Markers and Genes for such Disorders is of Great Interest.

Model Systems

Several gene systems, p21, p53 and Lipoprotein Lipase polymorphism (N291S), were selected. The p53 gene is a tumor suppressor gene that is mutated in diverse tumor types. One common allelic variant occurs at codon 72. A polymorphism that has been identified in the p53 gene, i.e., the R72P allele, results in an amino acid exchange, arginine to proline, at codon 72 of the gene.

Figure 7A:
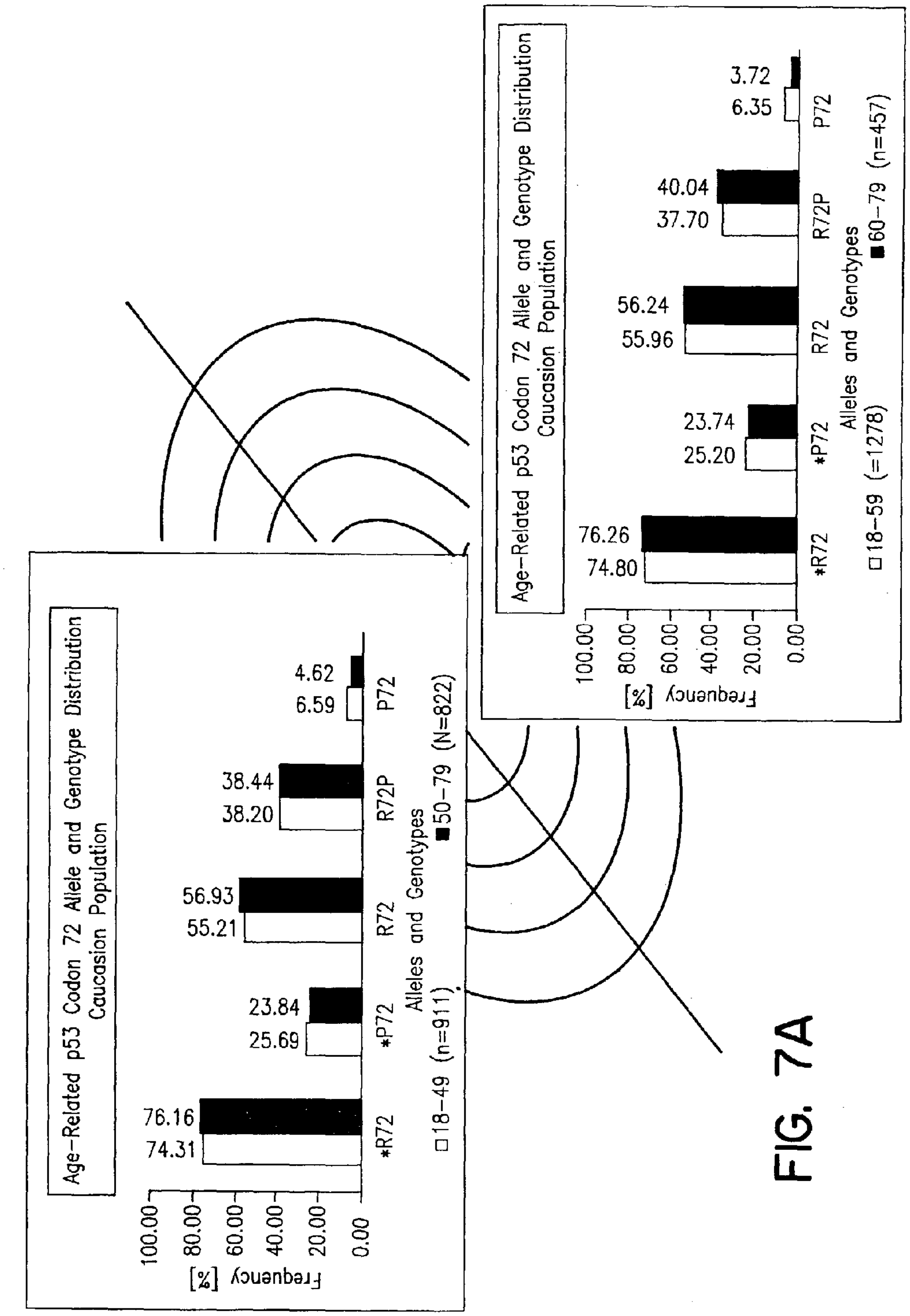
FIGS. 7A-D depicts age-related and genotype frequency of the p53 (tumor suppressor) codon 72 among the Caucasian population in the database. *R72 and *P72 represent the frequency of the allele in the database population. R72, R72P, and P72 represent the genotypes of the individuals in the population. The frequency of the homozygous P72 allele drops from 6.7% to 3.7% with age.
Figure 7B:
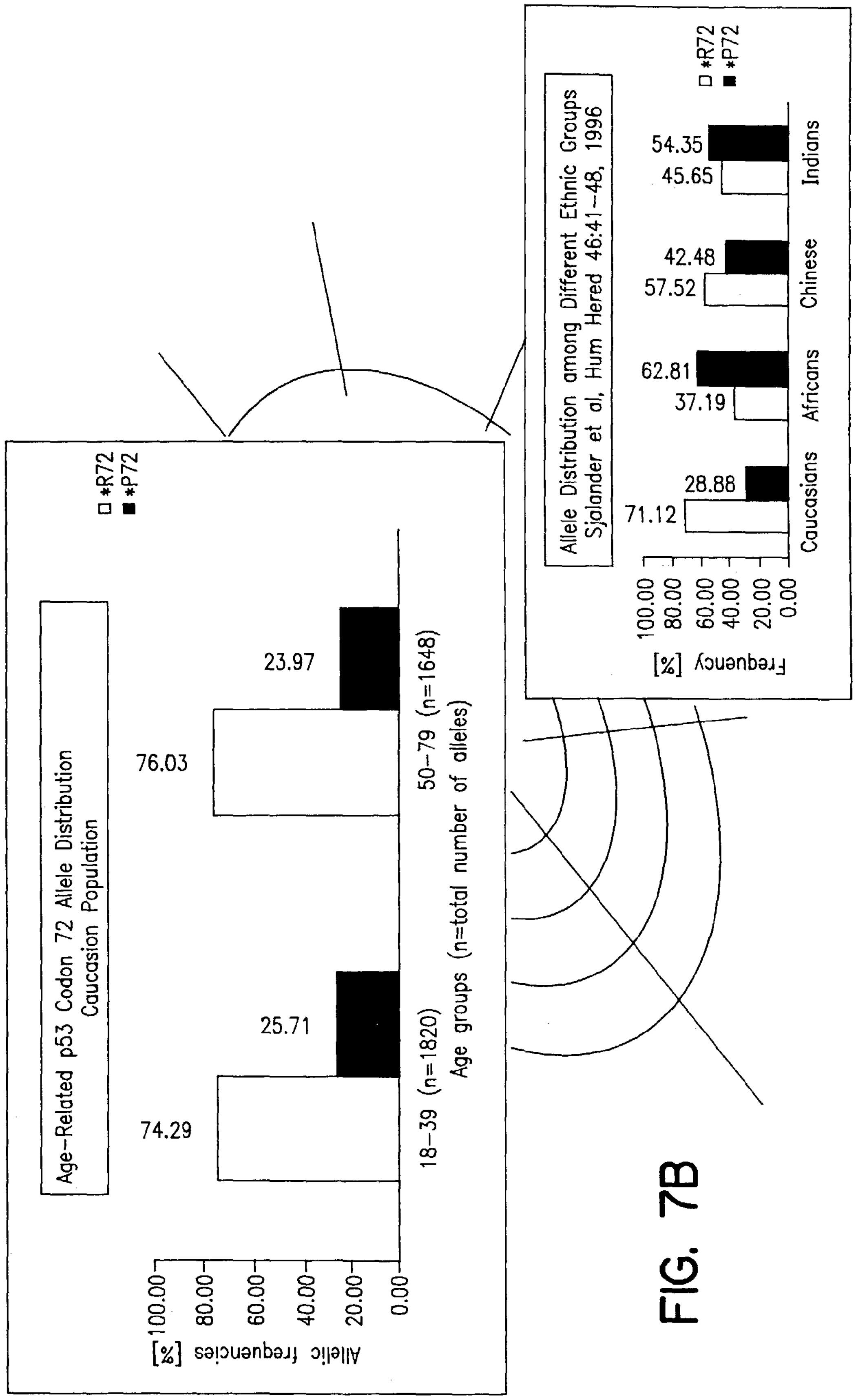

Using diseased populations, it has been shown that there are ethnic differences in the allelic distribution of these alleles among African-Americans and Caucasians in the U.S. The results here support this finding and also demonstrate that the results obtained with a healthy database are meaningful (see, FIG. 7B).

The 291S allele leads to reduced levels of high density lipoprotein cholesterol (HDL-C) that is associated with an increased risk of males for arteriosclerosis and in particular myocardial infarction (see, Reymer et al. (1995) *Nature Genetics* 10:28-34).

Both genetic polymorphisms were profiled within a part of the Caucasian population-based sample bank. For the polymorphism located in the lipoprotein lipase gene a total of 1025 unselected individuals (436 males and 589 females) were tested. Genomic DNA was isolated from blood samples obtained from the individuals.

Figure 2A:
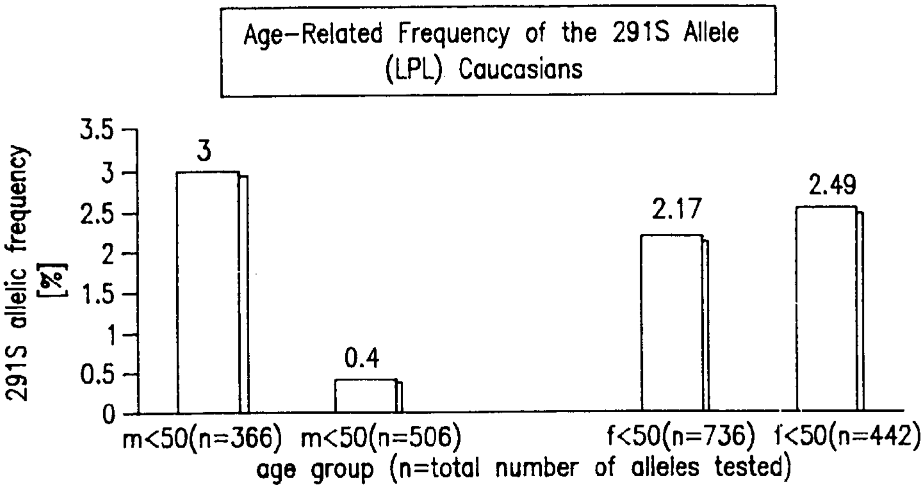
FIGS. 2A and 2C show an age- and sex-distribution of the 291S allele of the lipoprotein lipase gene in which a total of 436 males and 589 females were investigated.
Figure 2B:
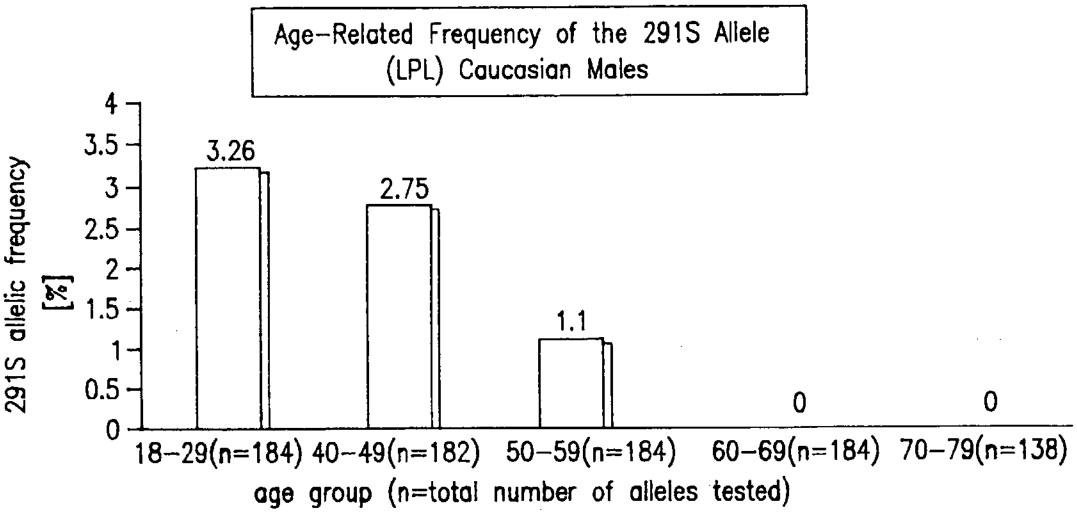
FIG. 2B shows an age distribution for the 436 males.
Figure 2C:
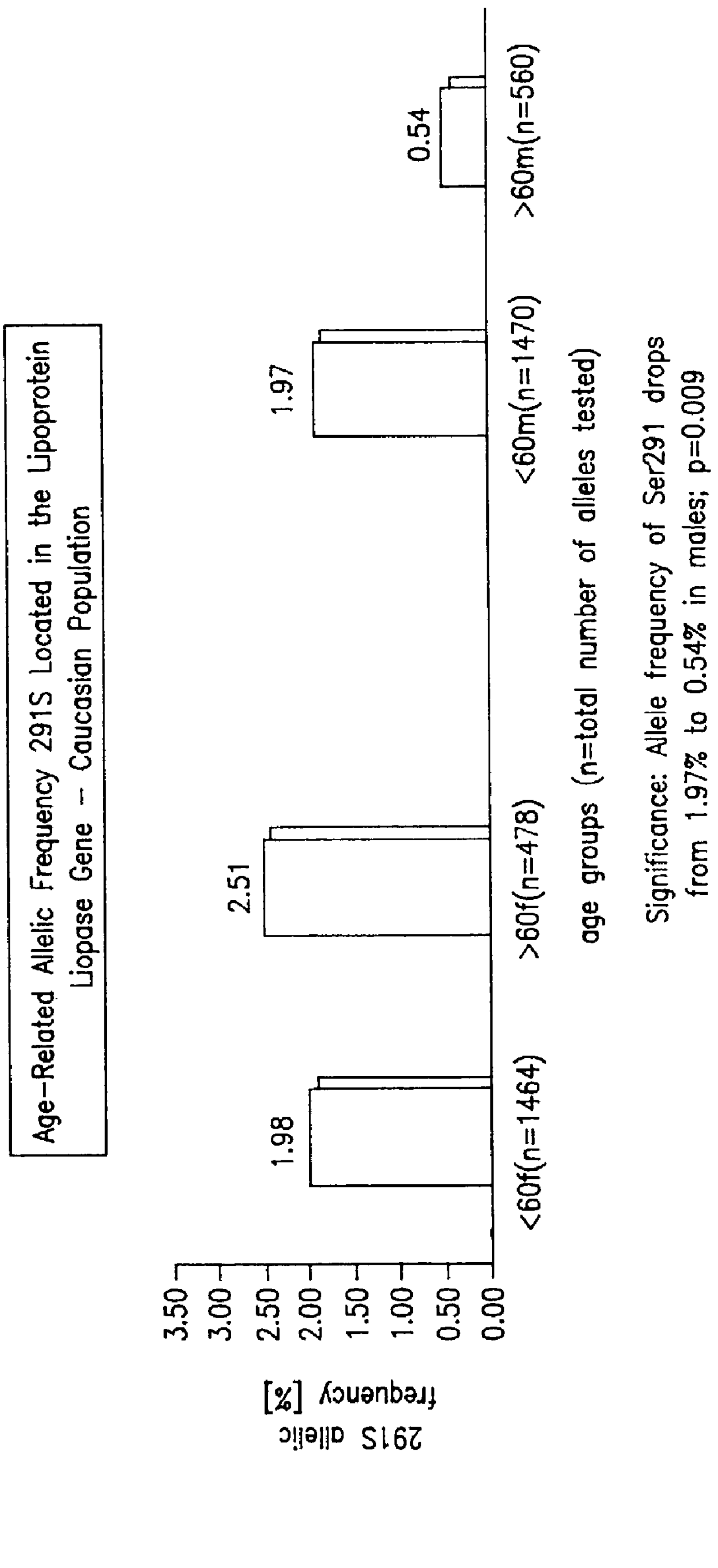

As shown in the Examples and figures, an exemplary database containing about 5000 subjects, answers to the questionnaire (see FIG. 3), and genotypic information has been stratified. A particular known allele has been selected, and the samples tested for the marker using mass spectrometric analyses, particularly PROBE (see the EXAMPLES) to identify polymorphisms in each sample. The population in the database has been sorted according to various parameters and correlations have been observed. For example, FIGS. 2A-C, show sorting of the data by age and sex for the Lipoprotein Lipase gene in the Caucasian population in the database. The results show a decrease in the frequency of the allele with age in males but no such decrease in females. Other alleles that have been tested against the database, include, alleles of p53, p21 and factor VII. Results when sorted by age are shown in the figures.

These examples demonstrate an effect of altered frequency of disease causing genetic factors within the general population. The scientific interpretation of those results allows prediction of medical relevance of polymorphic genetic alterations. In addition, conclusions can be drawn with regard to their penetrance, diagnostic specificity, positive predictive value, onset of disease, most appropriate onset of preventive strategies, and the general applicability of genetic alterations identified in isolated populations to panmixed populations.

Therefore, an age- and sex-stratified population-based sample bank that is ethnically homogenous is a suitable tool for rapid identification and validation of genetic factors regarding their potential medical utility.

Exemplary Computer System for Creating, Storing and Processing the Databases

Systems

Systems, including computers, containing the databases are provided herein. The computers and databases can be used in conjunction, for example, with the APL system (see, copending U.S. application Ser. No. 09/285,481), which is an automated system for analyzing biopolymers, particularly nucleic acids. Results from the APL system can be entered into the database.

Any suitable computer system can be used. The computer system can be integrated into systems for sample analysis, such as the automated process line described herein (see, e.g., copending U.S. application Ser. No. 09/285,481).

Figure 17:
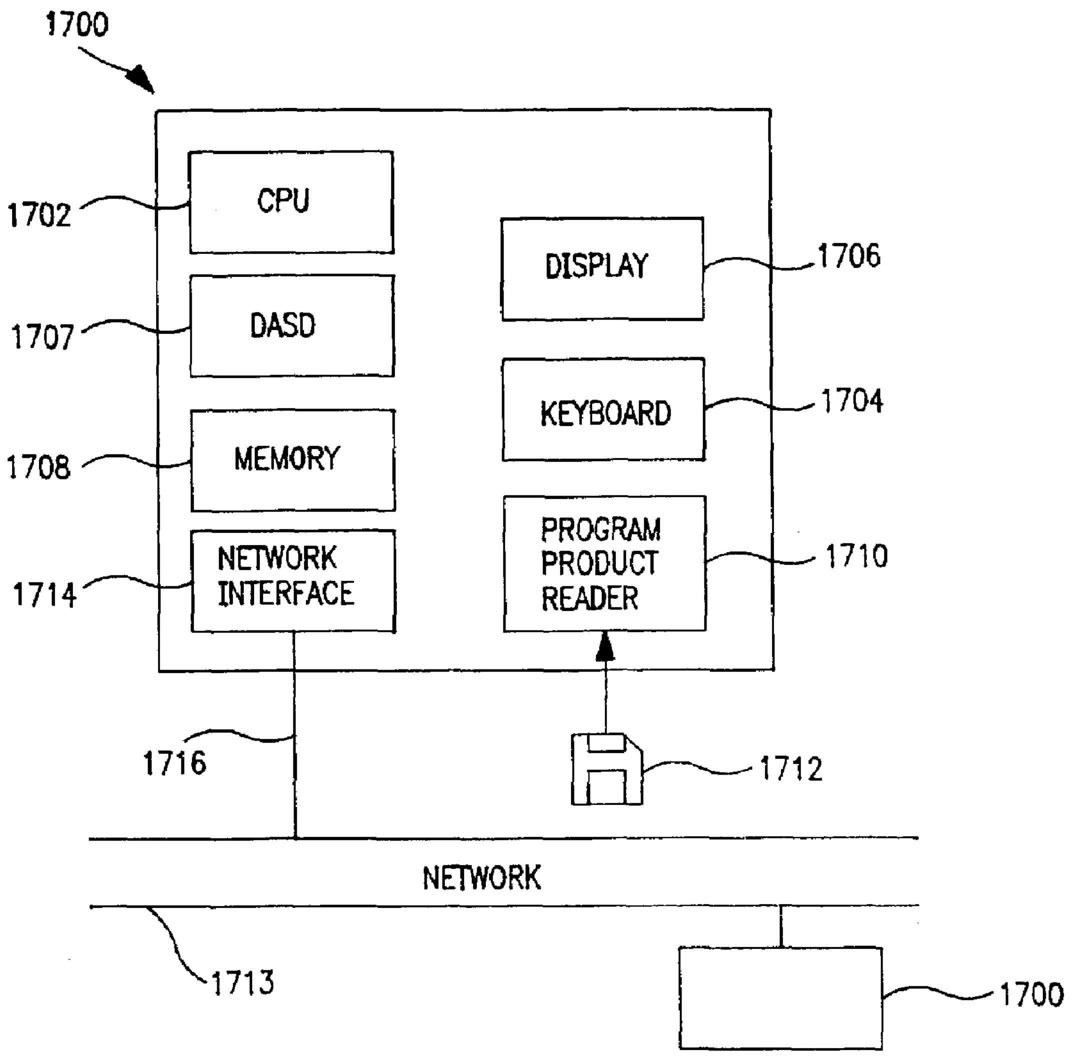
FIG. 17, which is a block diagram of a computer constructed to provide and process the databases described herein, depicts a typical computer system for storing and sorting the databases provided herein and practicing the methods provided herein.

FIG. 17 is a block diagram of a computer constructed to provide and process the databases described herein. The processing that maintains the database and performs the methods and procedures can be performed on multiple computers all having a similar construction, or can be performed by a single, integrated computer. For example, the computer through which data are added to the database can be separate from the computer through which the database is sorted, or can be integrated with it. In either arrangement, the computers performing the processing can have a construction as illustrated in FIG. 17.

FIG. 17 is a block diagram of an exemplary computer 1700 that maintains the database described above and performs the methods and procedures. Each computer 1700 operates under control of a central processor unit (CPU) 1702, such as a "Pentium" microprocessor and associated integrated circuit chips, available from Intel Corporation of Santa Clara, Calif., USA. A computer user can input commands and data from a keyboard and display mouse 1704 and can view inputs and computer output at a display 1706. The display is typically a video monitor or flat panel display device. The computer 1700 also includes a direct access storage device (DASD) 1707, such as a fixed hard disk drive. The memory 1708 typically comprises volatile semiconductor random access memory (RAM). Each computer can include a program product reader 1710 that accepts a program product storage device 1712, from which the program product reader can read data (and to which it can optionally write data). The program product reader can comprise, for example, a disk drive, and the program product storage device can comprise removable storage media such as a magnetic floppy disk, an optical CD-ROM disc, a CD-R disc, a CD-RW disc, or a DVD data disc. If desired, the computers can be connected so they can communicate with each other, and with other connected computers, over a network 1713. Each computer 1700 can communicate with the other connected computers over the network 1713 through a network interface 1714 that enables communication over a connection 1716 between the network and the computer.

The computer 1700 operates under control of programming steps that are temporarily stored in the memory 1708 in accordance with conventional computer construction. When the programming steps are executed by the CPU 1702, the pertinent system components perform their respective functions. Thus, the programming steps implement the functionality of the system as described above. The programming steps can be received from the DASD 1707, through the program product reader 1712, or through the network connection 1716. The storage drive 1710 can receive a program product, read programming steps recorded thereon and transfer the programming steps into the memory 1708 for execution by the CPU 1702. As noted above, the program product storage device 1710 can comprise any one of multiple removable media having recorded computer-readable instructions, including magnetic floppy disks and CD-ROM storage discs. Other suitable program product storage devices can include magnetic tape and semiconductor memory chips. In this way, the processing steps necessary for operation can be embodied on a program product.

Alternatively, the program steps can be received into the operating memory 1708 over the network 1713. In the network method, the computer receives data including program steps into the memory 1708 through the network interface 1714 after network communication has been established over the network connection 1716 by well-known methods that will be understood by those skilled in the art without further explanation. The program steps are then executed by the CPU 1702 to implement the processing of the Garment Database system.

It should be understood that all of the computers of the system and can have a construction similar to that shown in FIG. 17. Details described with respect to the FIG. 17 computer 1700 will be understood to apply to all computers of the system 1700. This is indicated by multiple computers 1700 shown connected to the network 1713. Any one of the computers 1700 can have an alternative construction, so long as they can communicate with the other computers and support the functionality described herein.

Figure 18:
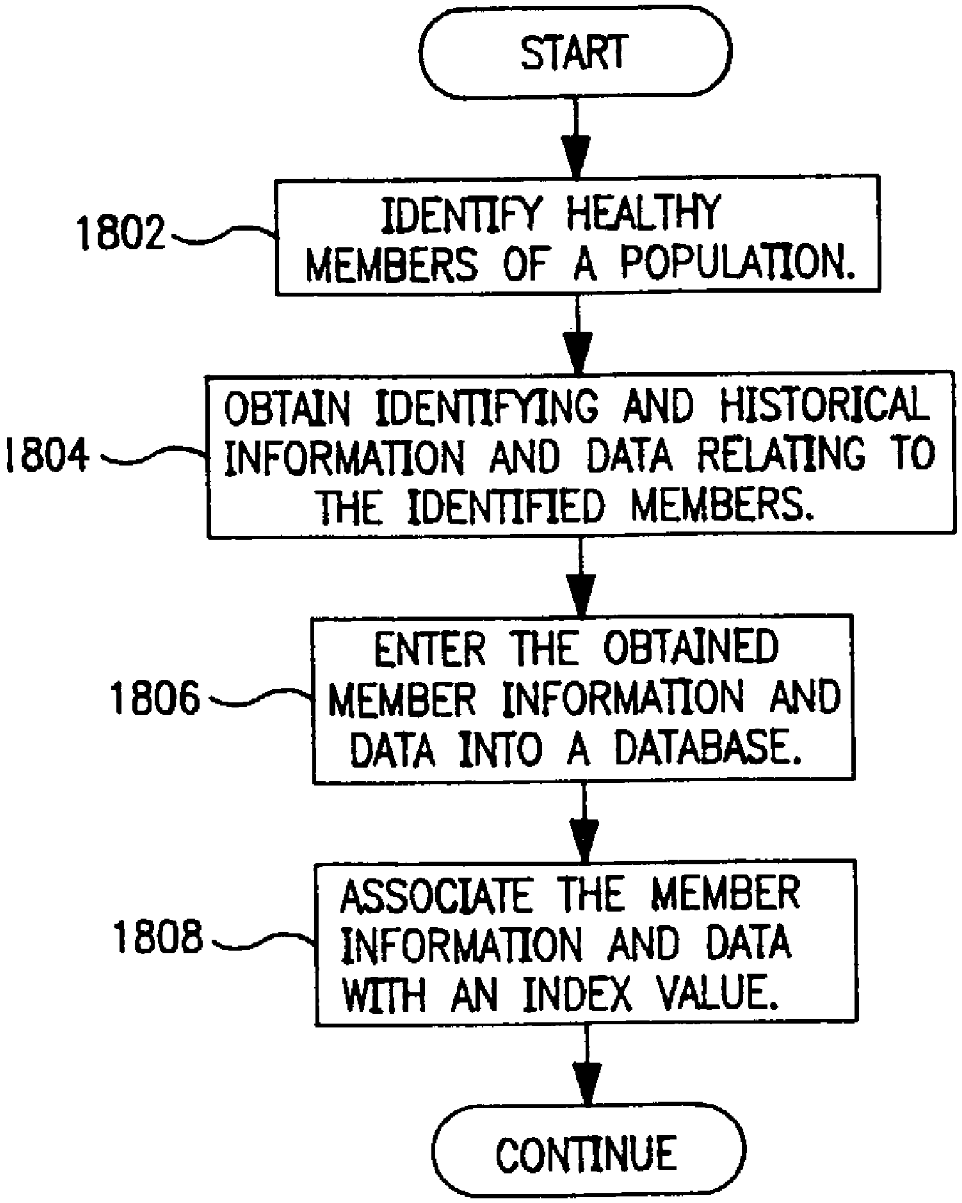
FIG. 18 is a flow diagram that illustrates the processing steps performed using the computer illustrated in FIG. 17, to maintain and provide access to the databases for identifying polymorphic genetic markers.

FIG. 18 is a flow diagram that illustrates the processing steps performed using the computer illustrated in FIG. 17, to maintain and provide access to the databases, such as for identifying polymorphic genetic markers. In particular, the information contained in the database is stored in computers having a construction similar to that illustrated in FIG. 17. The first step for maintaining the database, as indicated in FIG. 18, is to identify healthy members of a population. As noted above, the population members are subjects that are selected only on the basis of being healthy, and where the subjects are mammals, such as humans, they can be selected based upon apparent health and the absence of detectable infections. The step of identifying is represented by the flow diagram box numbered 1802.

The next step, represented by the flow diagram box numbered 1804, is to obtain identifying and historical information and data relating to the identified members of the population. The information and data comprise parameters for each of the population members, such as member age, ethnicity, sex, medical history, and ultimately genotypic information. Initially, the parameter information is obtained from a questionnaire answered by each member, from whom a body tissue or body fluid sample also is obtained. The step of entering and storing these parameters into the database of the computer is represented by the flow diagram box numbered 1806. As additional information about each population member and corresponding sample is obtained, this information can be inputted into the database and can serve as a sorting parameter.

In the next step, represented by the flow diagram box numbered 1808, the parameters of the members are associated with an indexer. This step can be executed as part of the database storage operation, such as when a new data record is stored according to the relational database structure and is automatically linked with other records according to that structure. The step 1806 also can be executed as part of a conventional data sorting or retrieval process, in which the database entries are searched according to an input search or indexing key value to determine attributes of the data. For example, such search and sort techniques can be used to follow the occurrence of known genetic markers and then determine if there is a correlation with diseases for which they have been implicated. Examples of this use are for assessing the frequencies of the p53 and Lipoprotein Lipase polymorphisms.

Such searching of the database also can be valuable for identifying one or more genetic markers whose frequency changes within the population as a function of age, ethnic group, sex, or some other criteria. This can allow the identification of previously unknown polymorphisms and, ultimately, identification of a gene or pathway involved in the onset and progression of disease.

In addition, the database can be used for taking an identified polymorphism and ascertaining whether it changes in frequency when the data are sorted according to a selected parameter.

In this way, the databases and methods provided herein permit, among other things, identification of components, particularly key components, of a disease process by understanding its genetic underpinnings, and also an understanding of processes, such as individual drug responses. The databases and methods provided herein also can be used in methods involving elucidation of pathological pathways, in developing new diagnostic assays, identifying new potential drug targets, and in identifying new drug candidates.

Morbidity and/or Early Mortality Associated Polymorphisms

A database containing information provided by a population of healthy blood donors who were not selected for any particular disease to can be used to identify polymorphisms and the alleles in which they are present, whose frequency decreases with age. These can represent morbidity susceptibility markers and genes.

Polymorphisms of the genome can lead to altered gene function, protein function or genome instability. To identify those polymorphisms which have a clinical relevance/utility is the goal of a world-wide scientific effort. It can be expected that the discovery of such polymorphisms will have a fundamental impact on the identification and development of novel drug compounds to cure diseases. The strategy to identify valuable polymorphisms is cumbersome and dependent upon the availability of many large patient and control cohorts to show disease association. In particular, genes that cause a general risk of the population to suffer from any disease (morbidity susceptibility genes) will escape these case/control studies entirely.

Here described is a screening strategy to identify morbidity susceptibility genes underlying a variety of different diseases. The definition of a morbidity susceptibility gene is a gene that is expressed in many different cell types or tissues (housekeeping gene) and its altered function can facilitate the expression of a clinical phenotype caused by disease-specific susceptibility genes that are involved in a pathway specific for this disorder. In other words, these morbidity susceptibility genes predispose people to develop a distinct disease according to their genetic make-up for this disease.

Candidates for morbidity susceptibility genes can be found at the bottom level of pathways involving transcription, translation, heat-shock proteins, protein trafficking, DNA repair, assembly systems for subcellular structures (e.g. mitochondria, peroxysomes and other cellular microbodies), receptor signaling cascades, immunology, etc. Those pathways control the quality of life at the cellular level as well as for the entire organism. Mutations/polymorphisms located in genes encoding proteins for those pathways can reduce the fitness of cells and make the organism more susceptible to express the clinical phenotype caused by the action of a disease-specific susceptibility gene. Therefore, these morbidity susceptibility genes can be potentially involved in a whole variety of different complex diseases if not in all. Disease-specific susceptibility genes are involved in pathways that can be considered as disease-specific pathways like glucose-, lipid, hormone metabolism, etc.

The exemplified method permit, among other things, identification of genes and/or gene products involved in a man's general susceptibility to morbidity and/or mortality; use of these genes and/or gene products in studies to elucidate the genetic underpinnings of human diseases; use of these genes and/or gene products in combinatorial statistical analyses without or together with disease-specific susceptibility genes; use of these genes and/or gene products to predict penetrance of disease susceptibility genes; use of these genes and/or gene products in predisposition and/or acute medical diagnostics and use of these genes and/or gene products to develop drugs to cure diseases and/or to extend the life span of humans.

SCREENING PROCESS

The healthy population stratified by age, gender and ethnicity, etc. is a very efficient and a universal screening tool for morbidity associated genes. Changes of allelic frequencies in the young compared to the old population are expected to indicate putative morbidity susceptibility genes. Individual samples of this healthy population base can be pooled to further increase the throughput. In an experiment, pools of young and old Caucasian females and males were applied to screen more than 400 randomly chosen single nucleotide polymorphisms located in many different genes. Candidate polymorphisms were identified if the allelic difference was greater than 8% between young and old for both or only one of the genders. The initial results were assayed again in at least one independent subsequent experiments. Repeated experiments are necessary to recognize unstable biochemical reactions, which occur with a frequency of about 2-3% and can mimic age-related allelic frequency differences. Average frequency differences and standard deviations are calculated after successful reproducibility of initial results. The final allelic frequency is then compared to a reference population of Caucasian CEPH sample pool. The result should show similar allelic frequencies in the young Caucasian population. Subsequently, the exact allele frequencies of candidates including genotype information were obtained by analyzing all individual samples. This procedure is straight forward with regard to time and cost. It enables the screening of an enormous number of SNPs. So far, several markers with a highly significant association to age were identified and described below.

In general at least 5 individuals in a stratified population should to be screened to produce statistically significant results. The frequency of the allele is determined for an age stratified population. Chi square analysis is then performed on the allelic frequencies to determine if the difference between age groups is statistically significant. A p value less than of 0.1 is considered to represent a statistically significant difference. Typically the p value should be less than 0.05.

Clinical Trials

The identification of markers whose frequency in a population decreases with age also allows for better designed and balanced clinical trials. Currently, if a clinical trial utilizes a marker as a significant endpoint in a study and the marker disappears with age, then the results of the study can be inaccurate. By using methods provided herein, it can be ascertained that if a marker decreases in frequency with age. This information can be considered and controlled when designing the study. For, example, an age independent marker could be substituted in its place.

The following examples are included for illustrative purposes only and are not intended to limit the scope of the invention.

EXAMPLE 1

This example describes the use of a database containing information provided by a population of healthy blood donors who were not selected for any particular disease to determine the distribution of allelic frequencies of known genetic markers with age and by sex in a Caucasian subpopulation of the database. The results described in this example demonstrate that a disease-related genetic marker or polymorphism can be identified by sorting a healthy database by a parameter or parameters, such as age, sex and ethnicity.

Generating a Database

Blood was obtained by venous puncture from human subjects who met blood bank criteria for donating blood. The blood samples were preserved with EDTA at pH 8.0 and labeled. Each donor provided information such as age, sex, ethnicity, medical history and family medical history. Each sample was labeled with a barcode representing identifying information. A database was generated by entering, for each donor, the subject identifier and information corresponding to that subject into the memory of a computer storage medium using commercially available software, e.g., Microsoft Access.

Model Genetic Markers

The frequencies of polymorphisms known to be associated at some level with disease were determined in a subpopulation of the subjects represented in the database. These known polymporphisms occur in the p21, p53 and Lipoprotein Lipase genes. Specifically, the N291S polymorphism (N291S) of the Lipoprotein Lipase gene, which results in a substitution of a serine for an asparagine at amino acid codon 291, leads to reduced levels of high density lipoprotein cholesterol (HDL-C) that is associated with an increased risk of males for arteriosclerosis and in particular myocardial infarction (see, Reymer et al. (1995) *Nature Genetics* 10:28-34).

The p53 gene encodes a cell cycle control protein that assesses DNA damage and acts as a transcription factor regulating genes that control cell growth, DNA repair and apoptosis (programmed cell death). Mutations in the p53 gene have been found in a wide variety of different cancers, including different types of leukemia, with varying frequency. The loss of normal p53 function results in genomic instability an uncontrolled cell growth. A polymorphism that has been identified in the p53 gene, i.e., the R72P allele, results in the substitution of a proline for an arginine at amino acid codon 72 of the gene.

The p21 gene encodes a cyclin-dependent kinase inhibitor associated with G1 phase arrest of normal cells. Expression of the p21 gene triggers apoptosis. Polymorphisms of the p21 gene have been associated with Wilms' tumor, a pediatric kidney cancer. One polymorphism of the p21 gene, the S31R polymorphism, results in a substitution of an arginine for a serine at amino acid codon 31.

Database Analysis

Sorting of Subjects According to Specific Parameters

The genetic polymorphisms were profiled within segments of the Caucasian subpopulation of the sample bank. For p53 profiling, the genomic DNA isolated from blood from a total of 1277 Caucasian subjects age 18-59 years and 457 Caucasian subjects age 60-79 years was analyzed. For p21 profiling, the genomic DNA isolated from blood from a total of 910 Caucasian subjects age 18-49 years and 824 Caucasian subjects age 50-79 years was analyzed. For lipoprotein lipase gene profiling, the genomic DNA from a total of 1464 Caucasian females and 1470 Caucasian males under 60 years of age and a total of 478 Caucasian females and 560 Caucasian males over 60 years of age was analyzed.

Isolation and Analysis of Genomic DNA

Genomic DNA was isolated from blood samples obtained from the individuals. Ten milliliters of whole blood from each individual was centrifuged at 2000×g. One milliliter of the buffy coat was added to 9 ml of 155 mM $NH_4Cl$, 10 mM $KHCO_3$, and 0.1 mM $Na_2EDTA$, incubated 10 min at room temperature and centrifuged for 10 min at 2000×g. The supernatant was removed, and the white cell pellet was washed in 155 mM $NH_4Cl$, 10 mM $KHCO_3$ and 0.1 mM $Na_2EDTA$ and resuspended in 4.5 ml of 50 mM Tris, 5 mM EDTA and 1% SDS. Proteins were precipitated from the cell lysate by 6 mM ammonium acetate, pH 7.3, and then separated from the nucleic acids by centrifugation at 3000×g. The nucleic acid was recovered from the supernatant by the addition of an equal volume of 100% isopropanol and centrifugation at 2000×g. The dried nucleic acid pellet was hydrated in 10 mM Tris, pH 7.6, and 1 mM $Na_2EDTA$ and stored at 4° C.

Assays of the genomic DNA to determine the presence or absence of the known genetic markers were developed using the BiomassPROBE™ detection method (primer oligo base extension) reaction. This method uses a single detection primer followed by an oligonucleotide extension step to give products, which can be readily resolved by mass spectrometry, and, in particular, MALDI-TOF mass spectrometry. The products differ in length depending on the presence or absence of a polymorphism. In this method, a detection primer anneals adjacent to the site of a variable nucleotide or sequence of nucleotides, and the primer is extended using a DNA polymerase in the presence of one or more dideoxyNTPs and, optionally, one or more deoxyNTPs. The resulting products are resolved by MALDI-TOF mass spectrometry. The mass of the products as measured by MALDI-TOF mass spectrometry makes possible the determination of the nucleotide(s) present at the variable site.

First, each of the Caucasian genomic DNA samples was subjected to nucleic acid amplification using primers corresponding to sites 5' and 3' of the polymorphic sites of the p21 (S31R allele), p53 (R72P allele) and Lipoprotein Lipase (N291S allele) genes. One primer in each primer pair was biotinylated to permit immobilization of the amplification product to a solid support. Specifically, the polymerase chain reaction primers used for amplification of the relevant segments of the p21, p53 and lipoprotein lipase genes are shown below: US4p21c31-2F (SEQ ID NO: 9) and US5p21-2R (SEQ ID NO: 10) for p21 gene amplification; US4-p53-ex4-F (also shown as p53-ex4US4 (SEQ ID NO: 2)) and US5-p53/2-4R (also shown as US5P53/4R (SEQ ID NO: 3)) for p53 gene amplification; and US4-LPL-F2 (SEQ ID NO: 16) and US5-LPL-R2 (SEQ ID NO: 17) for lipoprotein lipase gene amplification.

Amplification of the respective DNA sequences was conducted according to standard protocols. For example, primers can be used in a concentration of 8 pmol. The reaction mixture (e.g., total volume 50 μl) can contain Taq-polymerase including 10×buffer and dTNPs. Cycling conditions for polymerase chain reaction amplification can typically be initially 5 min. at 95° C., followed by 1 min. at 94° C., 45 sec at 53° C., and 30 sec at 72° C. for 40 cycles with a final extension time of 5 min at 72° C. Amplification products can be purified by using Qiagen's PCR purification kit (No. 28106) according to manufacturer's instructions. The elution of the purified products from the column can be done in 50 μl TE-buffer (10 mM Tris, 1 mM EDTA, pH 7.5).

The purified amplification products were immobilized via a biotin-avidin linkage to streptavidin-coated beads and the double-stranded DNA was denatured. A detection primer was then annealed to the immobilized DNA using conditions such as, for example, the following: 50 μl annealing buffer (20 mM Tris, 10 mM KCl, 10 mM $(NH_4)_2SO_4$, 2 mM $MgSO_2$, 1% Triton X-100, pH 8) at 50° C. for 10 min, followed by washing of the beads three times with 200 μl washing buffer (40 mM Tris, 1 mM EDTA, 50 mM NaCl, 0.1% Tween 20, pH 8.8) and once in 200 μl TE buffer.

The PROBE extension reaction was performed, for example, by, using some components of the DNA sequencing kit from USB (No. 70770) and dNTPs or ddNTPs from Pharmacia. An exemplary protocol could include a total reaction volume of 45 μl, containing of 21 μl water, 6 μl Sequenase-buffer, 3 μl 10 mM DTT solution, 4.5 μl, 0.5 mM of three dNTPs, 4.5 μl, 2 mM the missing one ddNTP, 5.5 μl glycerol enzyme dilution buffer, 0.25 μl Sequenase 2.0, and 0.25 pyrophosphatase. The reaction can then by pipetted on ice and incubated for 15 min at room temperature and for 5 min at 37° C. The beads can be washed three times with 200 μl washing buffer and once with 60 μl of a 70 mM $NH_4$-Citrate solution.

The DNA was denatured to release the extended primers from the immobilized template. Each of the resulting extension products was separately analyzed by MALDI-TOF mass spectrometry using 3-hydroxypicolinic acid (3-HPA) as matrix and a UV laser.

Specifically, the primers used in the PROBE reactions are as shown below: P21/31-3 (SEQ ID NO: 12) for PROBE analysis of the p21 polymorphic site; P53/72 (SEQ ID NO: 4) for PROBE analysis of the p53 polymorphic site; and LPL-2 for PROBE analysis of the lipoprotein lipase gene polymorphic site. In the PROBE analysis of the p21 polymorphic site, the extension reaction was performed using dideoxy-C. The products resulting from the reaction conducted on a "wild-type" allele template (wherein codon 31 encodes a serine) and from the reaction conducted on a polymorphic S31R allele template (wherein codon 31 encodes an arginine) are shown below and designated as P21/31-3 Ser (wt) (SEQ ID NO: 13) and P21/31-3 Arg (SEQ ID NO: 14), respectively. The masses for each product as can be measured by MALDI-TOF mass spectrometry are also provided (i.e., 4900.2 Da for the wild-type product and 5213.4 Da for the polymorphic product).

In the PROBE analysis of the p53 polymorphic site, the extension reaction was performed using dideoxy-C. The products resulting from the reaction conducted on a "wild-type" allele template (wherein codon 72 encodes an arginine) and from the reaction conducted on a polymorphic R72P allele template (wherein codon 72 encodes a proline) are shown below and designated as Cod72 G Arg (wt) and Cod72 C Pro, respectively. The masses for each product as can be measured by MALDI-TOF mass spectrometry are also provided (i.e., 5734.8 Da for the wild-type product and 5405.6 Da for the polymorphic product).

In the PROBE analysis of the lipoprotein lipase gene polymorphic site, the extension reaction was performed using a mixture of ddA and ddT. The products resulting from the reaction conducted on a "wild-type" allele template (wherein codon 291 encodes an asparagine) and from the reaction conducted on a polymorphic N291S allele template (wherein codon 291 encodes a serine) are shown below and designated as 291Asn and 291Ser, respectively. The masses for each product as can be measured by MALDI-TOF mass spectrometry are also provided (i.e., 6438.2 Da for the wild-type product and 6758.4 Da for the polymorphic product).

P53-1 (R72P)
PCR Product length: 407 bp

US4-p53-ex4-F (SEQ ID NO: 1)
ctg aggacctggt cctctgactg
ctcttttcac ccatctacagtcccccttgccgtcccaagc aat
ggatgatttgatgctgt ccccggacga tattgaacaa tggttcactg aagacccagg tccagatgaa gctc-
ccagaa
P53/72 72R
tgccagaggctgctccccgc gtggcccctg caccagcagc tcctacaccg gcggc-
ccctg c 72P
caccagcccc ctcctggccc ctgtcatctt ctgtcccttc ccagaaaacc tac-
cagggca

-continued

| P53-1 (R72P) PCR Product length: 407 bp |
|---|
| gctacggttt ccgtctgggc ttcttgcatt ctgggacagc caagtctgtg acttg-cacgg |
| tcagttgccc tgaggggct**g gcttccatga gacttcaa**<br>US5-p53/2-4R |

| Primers (SEQ ID NOs: 2-4) | |
|---|---|
| p53-ex4FUS4 | cccagtcacgacgttgtaaaacgc tga gga cct ggt cct ctg ac |
| US5P53/4R | agcggataacaatttcacacaggt tga agt ctc atg gaa gcc |
| P53/72 | gcc aga ggc tgc tcc cc |

Masses

| Allele | Product Termination: ddC | SEQ # | Length | Mass |
|---|---|---|---|---|
| P53/72 | gccagaggctgctcccc | 5 | 17 | 5132.4 |
| Cod72 G Arg (wt) | gccagaggctgctccccgc | 6 | 19 | 5734.8 |
| Cod72 C Pro | gccagaggctgctccccc | 7 | 18 | 5405.6 |

Biotinylated US5 primer is used in the PCR amplification.

LPL-1 (N291S)

Amino acid exchange asparagine to serine at codon 291 of the lipoprotein lipase gene.

Masses

| Allele | Product Termination: ddA, ddT | SEQ # | Length | Mass |
|---|---|---|---|---|
| LPL-2 | caatctgggctatgagatca | 19 | 20 | 6141 |
| 291 Asn | caatctgggctatgagatcaa | 20 | 21 | 6438.2 |
| 291 Ser | caatctgggctatgagatcagt | 21 | 22 | 6758.4 |

Biotinylated US5 primer is used in the PCR amplification.

P21-1 (S31R)

Amino acid exchange serine to arginine at codon 31 of the tumor suppressor gene p21.

| PCR Product length: 251 bp (SEQ ID NO: 15) |
|---|
| US4-LPL-F2 (SEQ ID NO: 16)<br>**gcgctccatt catctcttc**a tcgactctct gttgaatgaa gaaaatccaa gtaag-gccta |
| caggtgcagt tccaaggaag cctttgagaa agggctctgc ttgagttgta gaaa-gaaccg<br>LPL-2 291N |
| ctgcaacaatctgggctatgagatca**a**taa agtcagagcc aaaagaagca gcaaaat-gta<br>**g** 291S |
| cctgaa**gact cgttctcaga tgccc**<br>US4-LPL-R2 |

| Primers (SEQ ID NOs: 16-18): | |
|---|---|
| US4-LPL-F2 | cccagtcacgacgttgtaaaacgg cgc tcc att cat ctc ttc |
| US5-LPL-R2 | agcggataacaatttcacacaggg ggc atc tga gaa cga gtc |
| LPL-2 | caa tct ggg cta tga gat ca |

| Product length: 207 bp |
|---|
| US4p21c31-2F (SEQ ID NO: 8)<br>**gtcc gtcagaaccc atgcg-**<br>**g**cagc<br>p21/31-3 **31S**<br><br>aaggcctgcc gccgcctctt cggcccagtg gacagcgagcagctgagccg cgact-<br>gtgat<br>a 31R<br><br>gcgctaatgg cgggctgcat ccaggaggcc cgtgagcgat ggaacttcga<br>cttt**gtcacc**<br><br>**gagacaccac tggaggg**<br>USSp21-2R |

| Primers (SEQ ID NOs: 9-11) | |
|---|---|
| US4p21c31-2F | cccagtcacgacgttgtaaaacgg tcc gtc aga acc cat gcg g |
| US5p21-2R | agcggataacaatttcacacaggc tcc agt ggt gtc tcg gtg ac |
| P21/31-3 | cag cga gca gct gag |

| Masses | | | | |
|---|---|---|---|---|
| Allele | Product Termination: ddC | SEQ # | Length | Mass |
| p21/31-3 | cagcgagcagctgag | 12 | 15 | 4627 |
| P21/31-3 Ser (wt) | cagcgagcagctgagc | 13 | 16 | 4900.2 |
| P21/31-3 Arg | cagcgagcagctgagac | 14 | 17 | 5213.4 |

Biotinylated US5 primer is used in the PCR amplification.

Each of the Caucasian subject DNA samples was individually analyzed by MALDI-TOF mass spectrometry to determine the identity of the nucleotide at the polymorphic sites. The genotypic results of each assay can be entered into the database. The results were then sorted according to age and/or sex to determine the distribution of allelic frequencies by age and/or sex. As depicted in the Figures showing histograms of the results, in each case, there was a differential distribution of the allelic frequencies of the genetic markers for the p21, p53 and lipoprotein lipase gene polymorphisms.

Figure 8:
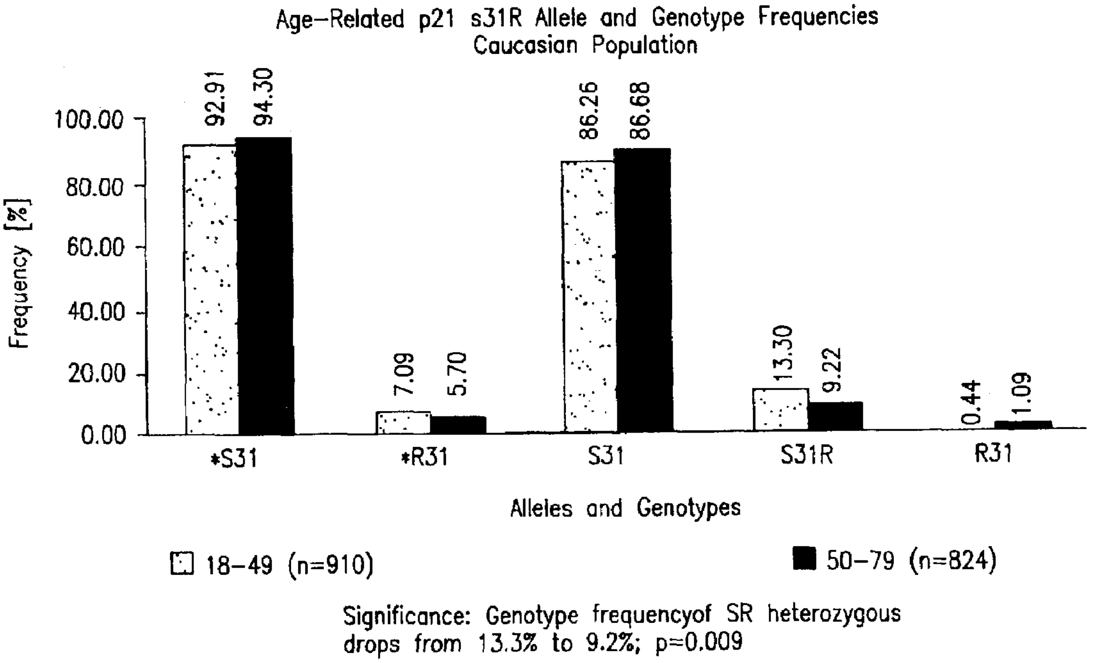
FIG. 8 depicts the allele and genotype frequencies of the p21 S31R allele as a function of age.

FIG. 8 shows the results of the p21 genetic marker assays and reveals a statistically significant decrease (from 13.3% to 9.2%) in the frequency of the heterozygous genotype (S31R) in Caucasians with age (18-49 years of age compared to 50-79 years of age). The frequencies of the homozygous (S31 and R31) genotypes for the two age groups are also shown, as are the overall frequencies of the S31 and R31 alleles in the two age groups (designated as *S31 and *R31, respectively in the Figure).

Figure 7C:
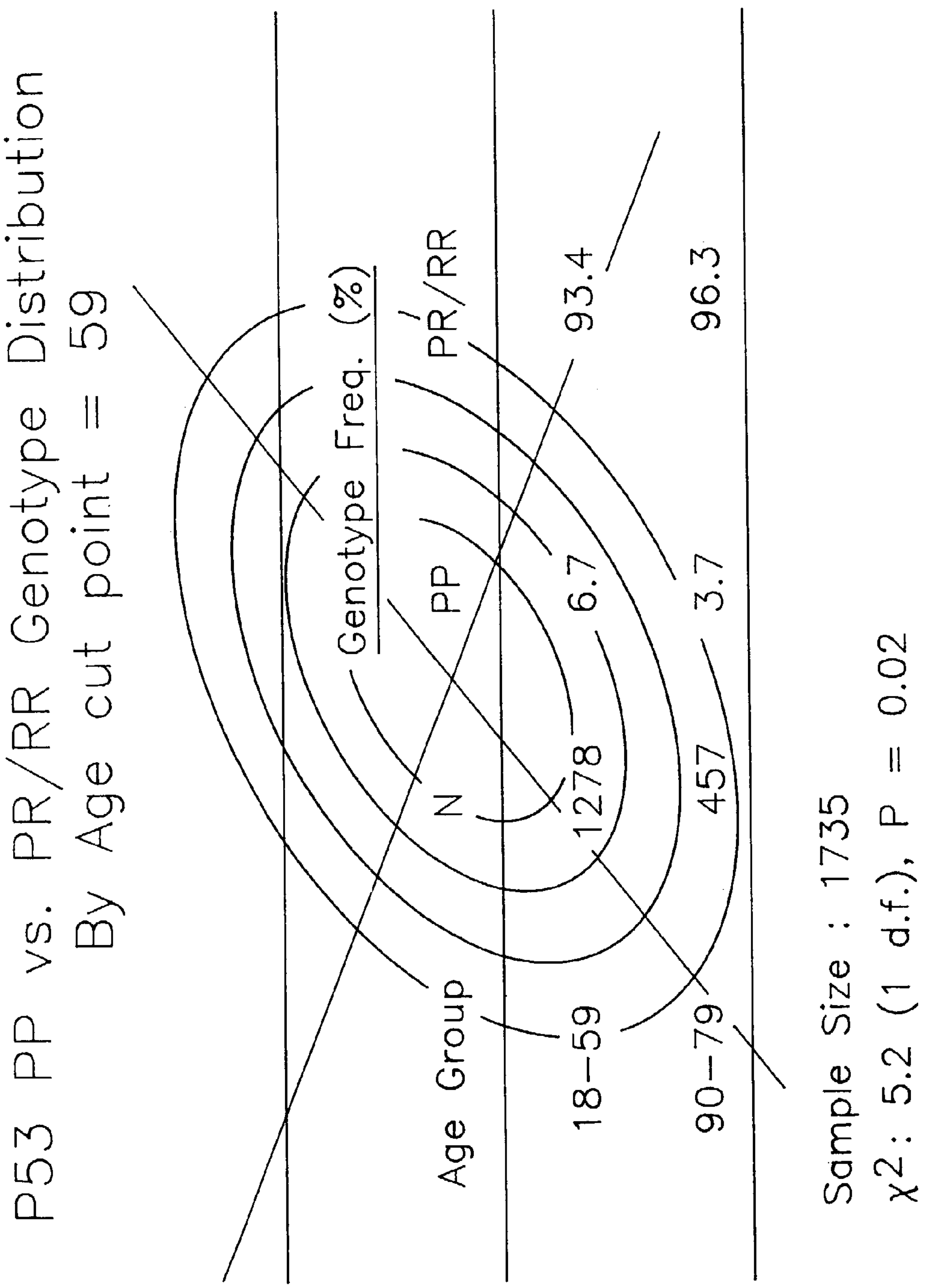
Figure 7D:
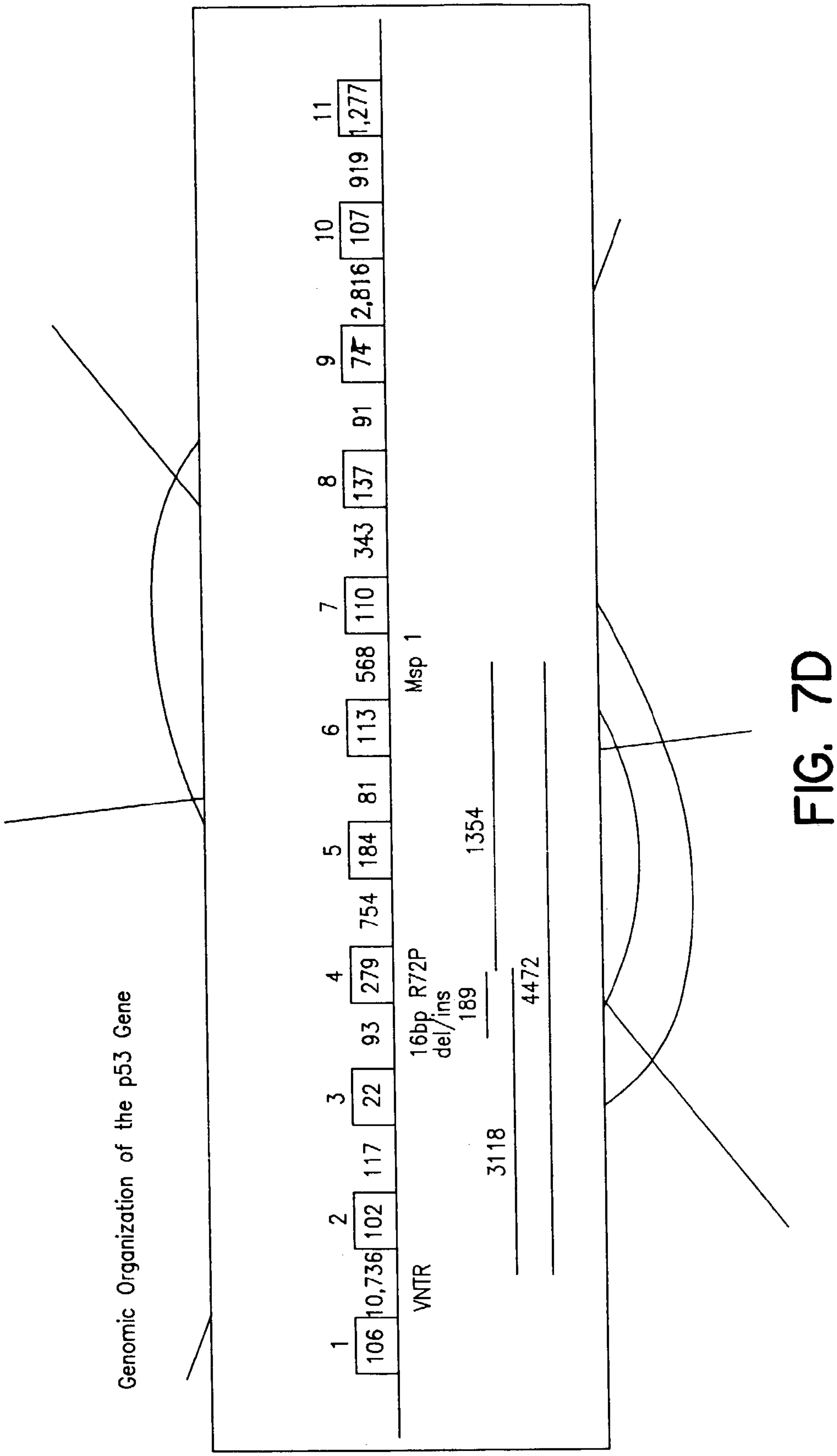

FIGS. 7A-C show the results of the p53 genetic marker assays and reveals a statistically significant decrease (from 6.7% to 3.7%) in the frequency of the homozygous polymorphic genotype (P72) in Caucasians with age (18-59 years of age compared to 60-79 years of age). The frequencies of the homozygous "wild-type" genotype (R72) and the heterozygous genotype (R72P) for the two age groups are also shown, as are the overall frequencies of the R72 and P72 alleles in the two age groups (designated as *R72 and *P72, respectively in the Figure). These results are consistent with the observation that allele is not benign, as p53 regulates expression of a second protein, p21, which inhibits cyclin-dependent kinases (CDKs) needed to drive cells through the cell-cycle (a mutation in either gene can disrupt the cell cycle leading to increased cell division).

FIG. 2C shows the results of the lipoprotein lipase gene genetic marker assays and reveals a statistically significant decrease (from 1.97% to 0.54%) in the frequency of the polymorphic allele (S291) in Caucasian males with age (see also Reymer et al. (1995) *Nature Genetics* 10:28-34). The frequencies of this allele in Caucasian females of different age groups are also shown.

EXAMPLE 2

This example describes the use of MALDI-TOF mass spectrometry to analyze DNA samples of a number of subjects as individual samples and as pooled samples of multiple subjects to assess the presence or absence of a polymorphic allele (the 353Q allele) of the Factor VII gene and determine the frequency of the allele in the group of subjects. The results of this study show that essentially the same allelic frequency can be obtained by analyzing pooled DNA samples as by analyzing each sample separately and thereby demonstrate the quantitative nature of MALDI-TOF mass spectrometry in the analysis of nucleic acids.

Factor VII

Factor VII is a serine protease involved in the extrinsic blood coagulation cascade. This factor is activated by thrombin and works with tissue factor (Factor III) in the processing of Factor X to Factor Xa. There is evidence that supports an association between polymorphisms in the Factor VII gene and increased Factor VII activity which can result in an elevated risk of ischemic cardiovascular disease, including myocardial infarction. The polymorphism investigated in this study is R353Q (i.e., a substitution of a glutamic acid residue for an arginine residue at codon 353 of the Factor VII gene) (see Table 5).

Analysis of DNA Samples for the Presence or Absence of the 353Q Allele of the Factor VII Gene Genomic DNA was isolated from separate blood samples obtained from a large number of subjects divided into multiple groups of 92 subjects per group. Each sample of genomic DNA was analyzed using the BiomassPROBE™ assay as described in Example 1 to determine the presence or absence of the 353Q polymorphism of the Factor VII gene.

First, DNA from each sample was amplified in a polymerase chain reaction using primers F7-353FUS4 (SEQ ID NO: 24) and F7-353RUS5 (SEQ ID NO: 26) as shown below and using standard conditions, for example, as described in Example 1. One of the primers was biotinylated to permit immobilization of the amplification product to a solid support. The purified amplification products were immobilized via a biotin-avidin linkage to streptavidin-coated beads and the double-stranded DNA was denatured. A detection primer was then annealed to the immobilized DNA using conditions such as, for example, described in Example 1. The detection primer is shown as F7-353-P (SEQ ID NO: 27) below. The PROBE extension reaction was carried out using conditions, for example, such as those described in Example 1. The reaction was performed using ddG.

The DNA was denatured to release the extended primers from the immobilized template. Each of the resulting extension products was separately analyzed by MALDI-TOF mass spectrometry. A matrix such as 3-hydroxypicolinic acid (3-HPA) and a UV laser could be used in the MALDI-TOF mass spectrometric analysis. The products resulting from the reaction conducted on a "wild-type" allele template (wherein codon 353 encodes an arginine) and from the reaction conducted on a polymorphic 353Q allele template (wherein codon 353 encodes a glutamic acid) are shown below and designated as 353 CGG and 353 CAG, respectively. The masses for each product as can be measured by MALDI-TOF mass spectrometry are also provided (i.e., 5646.8 Da for the wild-type product and 5960 Da for the polymorphic product).

The MALDI-TOF mass spectrometric analyses of the PROBE reactions of each DNA sample were first conducted separately on each sample (250 nanograms total concentration of DNA per analysis). The allelic frequency of the 353Q polymorphism in the group of 92 subjects was calculated based on the number of individual subjects in which it was detected.

Next, the samples from 92 subjects were pooled (250 nanograms total concentration of DNA in which the concentration of any individual DNA is 2.7 nanograms), and the pool of DNA was subjected to MALDI-TOF mass spectrometric analysis. The area under the signal corresponding to the mass of the 353Q polymorphism PROBE extension product in the resulting spectrum was integrated in order to quantitate the amount of DNA present. The ratio of this amount to total DNA was used to determine the allelic frequency of the 353Q polymorphism in the group of subjects. This type of individual sample vs. pooled sample analysis was repeated for numerous different groups of 92 different samples.

The frequencies calculated based on individual MALDI-TOF mass spectrometric analysis of the 92 separate samples of each group of 92 are compared to those calculated based on MALDI-TOF mass spectrometric analysis of pools of DNA from 92 samples in FIG. 9. These comparisons are shown as "pairs" of bar graphs in the Figure, each pair being labeled as a separate "pool" number, e.g., P1, P16, P2, etc. Thus, for example, for P1, the allelic frequency of the polymorphism calculated by separate analysis of each of the 92 samples was 11.41%, and the frequency calculated by analysis of a pool of all of the 92 DNA samples was 12.09%.

The similarity in frequencies calculated by analyzing separate DNA samples individually and by pooling the DNA samples demonstrates that it is possible, through the quantitative nature of MALDI-TOF mass spectrometry, to analyze pooled samples and obtain accurate frequency determinations. The ability to analyze pooled DNA samples significantly reduces the time and costs involved in the use of the non-selected, healthy databases as described herein. It has also been shown that it is possible to decrease the DNA concentration of the individual samples in a pooled mixture from 2.7 nanograms to 0.27 nanograms without any change in the quality of the spectrum or the ability to quantitate the amount of sample detected.

Factor VII R353Q PROBE Assay

PROBE Assay for cod353 CGG>CAG (Arg>Gln), Exon 9 G>A. Frequency of A allele: Europeans about 0.1, Japanese/Chinese about 0.03-0.05 (Thromb. Haemost. 1995, 73:617-22; Diabetologia 1998, 41:760-6):

PCR fragment: 134 bp (incl. US tags; SEQ ID Nos. 22 and 23)

F7-353FUS4>
1201 GTGCCGGCTA CTCGGATGGCAGCAAGGACTCCTGCAAGGG GGACAGTGGA

GGCCCACATG

F7-353-P> A <F7-353RUS5
1261 CCACCCACTACCGGGGCACG TGGTACCTGACGGGCATCGTCAGCTGGGGC

CAGGGCTGCG

| Primers | (SEQ ID NOs: 24-26) | $Tm^{gs}$ |
|---|---|---|
| F7-353FUS4 | **CCC AGT CAC GAC GTT GTA AAA CG**A TGG CAG CAA GGA CTC CTG | 64° C. |
| F7-353-P | CAC ATG CCA CCC ACT ACC | |
| F7-353RUS5 | **AGC GGA TAA CAA TTT CAC ACA GG**T GAC GAT GCC CGT CAG GTA C | 64° C. |

Masses

| Allele | Product Termination: ddG | SEQ # | Length | Mass |
|---|---|---|---|---|
| F7-353-P | atgccacccactacc | 27 | 18 | 5333.6 |
| 353 CGG | cacatgccacccactaccg | 28 | 19 | 5646.8 |
| 353 CAG | cacatgccacccactaccag | 29 | 20 | 5960 |
| US5-bio bio- | agcggataacaatttcacacagg | 30 | 23 | 7648.6 |

Conclusion

The above examples demonstrate an effect of altered frequency of disease causing genetic factors within the general population. Interpretation of those results allows prediction of the medical relevance of polymorphic genetic alterations. In addition, conclusions can be drawn with regard to their penetrance, diagnostic specificity, positive predictive value, onset of disease, most appropriate onset of preventive strategies, and the general applicability of genetic alterations identified in isolated populations to panmixed populations. Therefore, an age- and sex-stratified population-based sample bank that is ethnically homogenous is a suitable tool for rapid identification and validation of genetic factors regarding their potential medical utility.

EXAMPLE 3

Morbidity and Mortality Markers

Sample Band and Initial Screening

Healthy samples were obtained through the blood bank of San Bernardino, Calif.. Donors signed prior to the blood collection a consent form and agreed that their blood will be used in genetic studies with regard to human aging. All samples were anomymized. Tracking back of samples is not possible.

Isolation of DNA from Blood Samples of a Healthy Donor Population

Blood is obtained from a donor by venous puncture and preserved with 1 mM EDTA pH 8.0. Ten milliliters of whole blood from each donor was centrifuged at 2000×g. One milliliter of the buffy coat was added to 9 milliters of 155 mM NH$_4$Cl, 10 mM KHCO$_3$, and 0.1 mM Na$_2$EDTA, incubated 10 minutes at room temperature and centrifuged for 10 minutes at 2000×g. The supernatant was removed, and the white cell pellet was washed in 155 mM NH$_4$Cl, 10 mM KHCO$_3$, and 0.1 mM Na$_2$EDTA and resuspended in 4.5 milliliters of 50 mM Tris, 5 mM EDTA, and 1% SDS. Proteins were precipitated from the cell lysate by 6M Ammonium Acetate, pH 7.3, and separated from the nucleic acid by centrifugation 3000×g. The nucleic acid was recovered from the supernatant by the addition of an equal volume of 100% isopropanol and centrifugation at 2000×g. The dried nucleic acid pellet was hydrated in 10 mM Tris pH 7.6 and 1 mM Na2EDTA and stored at 4°C.

In this study, samples were pooled as shown in Table 1. Both parents of the blood donors were of Caucasian origin.

TABLE 1

| Pool ID | Sex | Age-range | # individuals |
|---|---|---|---|
| SP1 | Female | 18–39 years | 276 |
| SP2 | Males | 18–39 years | 276 |
| SP3 | Females | 60–69 years | 184 |
| SP4 | Males | 60–79 years | 368 |

More than 400 SNPs were tested using all four pools. After one test run 34 assays were selected to be re-assayed at least once. Finally, 10 assays showed repeatedly differences in allele frequencies of several percent and, therefore, fulfilled the criteria to be tested using the individual samples. Average allele frequency and standard deviation is tabulated in Table 2.

TABLE 2

| Assay ID | SP1 | SP1-STD | SP2 | SP2-STD | SP3 | SP3-STD | SP4 | SP4-STD |
|---|---|---|---|---|---|---|---|---|
| 47861 | 0.457 | 0.028 | 0.433 | 0.042 | 0.384 | 0.034 | 0.380 | 0.015 |
| 47751 | 0.276 | 0.007 | 0.403 | 0.006 | 0.428 | 0.052 | 0.400 | 0.097 |
| 48319 | 0.676 | 0.013 | 0.627 | 0.018 | 0.755 | 0.009 | 0.686 | 0.034 |
| 48070 | 0.581 | 0.034 | 0.617 | 0.045 | 0.561 | n.a. | 0.539 | 0.032 |
| 49807 | 0.504 | 0.034 | 0.422 | 0.020 | 0.477 | 0.030 | 0.556 | 0.005 |
| 49534 | 0.537 | 0.017 | 0.503 | n.a. | 0.623 | 0.023 | 0.535 | 0.009 |
| 49733 | 0.560 | 0.006 | 0.527 | 0.059 | 0.546 | 0.032 | 0.436 | 0.016 |
| 49947 | 0.754 | 0.008 | 0.763 | 0.047 | 0.736 | 0.052 | 0.689 | 0.025 |
| 50128 | 0.401 | 0.022 | 0.363 | 0.001 | 0.294 | 0.059 | 0.345 | 0.013 |
| 63306 | 0.697 | 0.012 | 0.674 | 0.013 | 0.712 | 0.017 | 0.719 | 0.005 |

So far, 7 out of the 10 potential morbidity markers were fully analyzed. Additional information about genes in which these SNPs are located was gathered through publicly available databases, including Genbank.

AKAPS

Candidate morbidity and mortality markers include housekeeping genes, such as genes involved in signal transduction. Among such genes are the A-kinase anchoring proteins (AKAPs) genes, which participate in signal transduction pathways involving protein phosphorylation. Protein phosphorylation is an important mechanism for enzyme regulation and the transduction of extracellular signals across the cell membrane in eukaryotic cells. A wide variety of cellular substrates, including enzymes, membrane receptors, ion channels and transcription factors, can be phosphorylated in response to extracellular signals that interact with cells. A key enzyme in the phosphorylation of cellular proteins in response to hormones and neurotransmitters is cyclic AMP (cAMP)-dependent protein kinase (PKA). Upon activation by cAMP, PKA thus mediates a variety of cellular responses to such extracellular signals. An array of PKA isozymes are expressed in mammalian cells. The PKAs usually exist as inactive tetramers containing a regulatory (R) subunit dimer and two catalytic (C) subunits. Genes encoding three C subunits (Cα, Cβ and Cγ) and four R subunits (RIα, RIβ, RIIα and RIIβ) have been identified [see Takio et al. (1982) *Proc. Natl. Acad. Sci. U.S. A.* 79:2544-2548; Lee et al. (1983) *Proc. Natl. Acad. Sci. U.S. A.* 80:3608-3612; Jahnsen et al. (1996) *J. Biol. Chem.* 261:12352-12361; Clegg et al. (1988) *Proc. Natl. Acad. Sci. U.S. A.* 85:3703-3707; and Scott (1991) *Pharmacol. Ther.* 50:123-145]. The type I (RI) α and type II (RII) α subunits are distributed ubiquitously, whereas RIβ and RIIβ are present mainly in brain [see. e.g., Miki and Eddy (1999) *J. Biol. Chem.* 274:29057-29062]. The type I PKA holoenzyme (RIα and RIβ) is predominantly cytoplasmic, whereas the majority of type II PKA (RIIα and RIIβ) associates with cellular structures and organelles [Scott (1991) *Pharmacol. Ther.* 50:123-145]. Many hormones and other signals act through receptors to generate cAMP which binds to the R subunits of PKA and releases and activates the C subunits to phosphorylate proteins. Because protein kinases and their substrates are widely distributed throughout cells, there are mechanisms in place in cells to localize protein kinase-mediated responses to different signals. One such mechanism involves subcellular targeting of PKAs through association with anchoring proteins, referred to as A-kinase anchoring proteins (AKAPs), that place PKAs in close proximity to specific organelles or cytoskeletal components and particular substrates thereby providing for more specific PKA interactions and localized responses [see, e.g., Scott et al. (1990) *J. Biol. Chem.* 265:21561-21566; Bregman et al. (1991) *J. Biol. Chem.* 266:7207-7213; and Miki and Eddy (1999) *J. Biol. Chem.* 274:29057-29062]. Anchoring not only places the kinase close to the substrates, but also positions the PKA holoenzyme at sites where it can optimally respond to fluctuations in the second messenger cAMP [Mochly-Rosen (1995) *Science* 268:247-251; Faux and Scott (1996) *Trends Biochem. Sci.* 21:312-315; Hubbard and Cohen (1993) *Trends Biochem. Sci.* 18:172-177].

Up to 75% of type II PKA is localized to various intracellular sites through association of the regulatory subunit (RII) with AKAPs [see, e.g., Hausken et al. (1996) *J. Biol. Chem.* 271:29016-29022]. RII subunits of PKA bind to AKAPs with nanomolar affinity [Carr et al. (1992) *J. Biol. Chem.* 267: 13376-13382], and many AKAP-RII complexes have been isolated from cell extracts. RI subunits of PKA bind to AKAPs with only micromolar affinity [Burton et al. (1997) *Proc. Natl. Acad. Sci. U.S.A.* 94:11067-11072]. Evidence of binding of a PKA RI subunit to an AKAP has been reported [Miki and Eddy (1998) *J. Biol. Chem* 273:34384-34390] in which RIα-specific and RIα/RIIα dual specificity PKA anchoring domains were identified on FSC1/AKAP82. Additional dual specific AKAPs, referred to as D-AKAP1 and D-AKAP2, which interact with the type I and type II regulatory subunits of PKA have also been reported [Huang et al. (1997) *J. Biol. Chem.* 272:8057-8064; Huang et al. (1997) *Proc. Natl. Acad. Sci. U.S.A.* 94:11184-11189].

More than 20 AKAPs have been reported in different tissues and species. Complementary DNAs (cDNAs) encoding AKAPs have been isolated from diverse species, ranging from *Caenorhabditis elegans* and Drosophilia to human [see, e.g., Colledge and Scott (1999) *Trends Cell Biol.* 9:216-221]. Regions within AKAPs that mediate association with RII subunits of PKA have been identified. These regions of approximately 10-18 amino acid residues vary substantially in primary sequence, but secondary structure predictions indicate that they are likely to form an amphipathic helix with hydrophobic residues aligned along one face of the helix and charged residues along the other [Carr et al. (1991) *J. Biol. Chem.* 266:14188-14192; Carr et al. (1992) *J. Biol. Chem.* 267:13376-13382]. Hydrophobic amino acids with a long aliphatic side chain, e.g., valine, leucine or isoleucine, can participate in binding to RII subunits [Glantz et al. (1 993) *J. Biol. Chem.* 268:12796-12804].

Many AKAPs also have the ability to bind to multiple proteins, including other signaling enzymes. For example, AKAP79 binds to PKA, protein kinase C (PKC) and the protein phosphatase calcineurin (PP2B) [Coghlan et al. (1995) *Science* 267:108-112 and Klauck et al. (1996) *Science* 271:1589-1592]. Therefore, the targeting of AKAP79 to neuronal postsynaptic membranes brings together enzymes with opposite catalytic activities in a single complex.

AKAPs thus serve as potential regulatory mechanisms that increase the selectivity and intensity of a cAMP-mediated response. There is a need, therefore, to identify and elucidate the structural and functional properties of AKAPs in order to gain a complete understanding of the important role these proteins play in the basic functioning of cells.

AKAP10

The sequence of a human AKAP10 cDNA (also referred to as D-AKAP2) is available in the GenBank database, at accession numbers AF037439 (SEQ ID NO: 31) and NM 007202. The AKAP10 gene is located on chromosome 17.

The sequence of a mouse D-AKAP2 cDNA is also available in the GenBank database (see accession number AF021833). The mouse D-AKAP2 protein contains an RGS domain near the amino terminus that is characteristic of proteins that interact with Gα subunits and possess GTPase activating protein-like activity [Huang et al. (1997) *Proc. Natl. Acad. Sci. U.S.A.* 94:11184-11189]. The human AKAP10 protein also has sequences homologous to RGS domains. The carboxy-terminal 40 residues of the mouse D-AKAP2 protein are responsible for the interaction with the regulatory subunits of PKA. This sequence is fairly well conserved between the mouse D-AKAP2 and human AKAP10 proteins.

Polymorphisms of the Human AKAP10 Gene and Polymorphic AKAP10 Proteins

Polymorphisms of AKAP genes that alter gene expression, regulation, protein structure and/or protein function are more likely to have a significant effect on the regulation of enzyme (particularly PKA) activity, cellular transduction of signals and responses thereto and on the basic functioning of cells than polymorphisms that do not alter gene and/or protein function. Included in the polymorphic AKAPs provided herein are human AKAP10 proteins containing differing amino acid residues at position number 646.

Amino acid 646 of the human AKAP10 protein is located in the carboxy-terminal region of the protein within a segment that participates in the binding of R-subunits of PKAs. This segment includes the carboxy-terminal 40 amino acids.

The amino acid residue reported for position 646 of the human AKAP10 protein is an isoleucine. Polymorphic human AKAP10 proteins provided herein have the amino acid sequence but contain residues other than isoleucine at amino acid position 646 of the protein. In particular embodiments of the polymorphic human AKAP10 proteins provided herein, the amino acid at position 646 is a valine, leucine or phenylalanine residue.

An A to G Transition at Nucleotide 2073 of the Human AKAP10 Coding Sequence

As described herein, an allele of the human AKAP10 gene that contains a specific polymorphism at position 2073 of the coding sequence and thereby encodes a valine at position 646 has been detected in varying frequencies in DNA samples from younger and older segments of the human population. In this allele, the A at position 2073 of the AKAP10 gene coding sequence is changed from an A to a G, giving rise to an altered sequence in which the codon for amino acid 646 changes from ATT, coding for isoleucine, to GTT, coding for valine.

Morbidity Marker 1: Human Protein Kinase A Anchoring Protein (AKAP10-1)

PCR Amplification and BiomassPROBE assay detection of AKAP10-1 in a healthy donor population PCR Amplification of Donor Population for AKAP 10

PCR primers were synthesized by OPERON using phosphoramidite chemistry. Amplification of the AKAP10 target sequence was carried out in single 50 μl PCR reaction with 100 ng-1 ug of pooled human genomic DNAs in a 50 μl PCR reaction. Individual DNA concentrations within the pooled samples were present in equal concentration with the final concentration ranging from 1-25 ng. Each reaction containing IX PCR buffer (Qiagen, Valencia, Calif.), 200 uM dNTPs, 1U Hotstar Taq polymerase (Qiagen, Valencia, Calif.), 4 mM $MgCl_2$, and 25 pmol of the forward primer containing the universal primer sequence and the target specific sequence 5'-TCTCAATCATGTGCATTGAGG-3'(SEQ ID NO: 45), 2 pmol of the reverse primer 5'-AGCGGATAACAATTTCACACAGGGATCACACAGCCATCAGCAG-3' (SEQ ID NO: 46), and I0 pmol of a biotinylated universal primer complementary to the 5' end of the PCR amplicon 5'-AGCGGATAACAATTTCACACAGG-3'(SEQ ID NO: 47). After an initial round of amplification with the target with the specific forward and reverse primer, the 5' biotinylated universal primer then hybridized and acted as a reverse primer thereby introducing a 3' biotin capture moiety into the molecule. The amplification protocol results in a 5'-biotinylated double stranded DNA amplicon and dramatically reduces the cost of high throughput genotyping by eliminating the need to 5' biotin label each forward primer used in a genotyping. Thermal cycling was performed in 0.2 mL tubes or 96 well plate using an MJ Research Thermal Cycler (calculated temperature) with the following cycling parameters: 94° C. for 5 min; 45 cycles: 94° C. for 20 sec, 56° C. for 30 sec, 72° C. for 60 sec; 72° C. 3 min.

Immobilization of DNA

The 50 μl PCR reaction was added to 25 ul of streptavidin coated magnetic bead (Dynal) prewashed three times and resuspended in 1M $NH_4Cl$, 0.06M $NH_4OH$. The PCR amplicons were allowed to bind to the beads for 15 minutes at room temperature. The beads were then collected with a magnet and the supernatant containing unbound DNA was removed. The unbound strand was released from the double stranded amplicons by incubation in 100 mM NaOH and washing of the beads three times with 10 mM Tris pH 8.0.

BiomassPROBE Assay Analysis of Donor Population for AKAP10-1 (Clone 48319)

Genotyping using the BiomassPROBE assay methods was carried out by resuspending the DNA coated magnetic beads in 26 mM Tris-HCl pH 9.5, 6.5 mM $MgCl_2$ and 50 mM each of dTTP and 50 mM each of ddCTP, ddATP, ddGTP, 2.5U of a thermostable DNA polymerase (Ambersham) and 20 pmol of a template specific oligonucleotide PROBE primer 5'-CTGGCGCCCACGTGGTCAA-3' (SEQ ID NO: 48) (Operon). Primer extension occurs with three cycles of oligonucleotide primer hybridization and extension. The extension products were analyzed after denaturation from the template with 50 mM $NH_4Cl$ and transfer of 150 nL each sample to a silicon chip preloaded with 150 nL of H3PA matrix material. The sample material was allowed to crystallize and was analyzed by MALDI-TOF (Bruker, PerSeptive). The SNP that is present in AKAP10-1 is a T to C transversion at nucleotide number 156277 of the sequence of a genomic clone of the AKAP10 gene (GenBank Accession No. AC005730) (SEQ ID NO: 36). SEQ ID NO: 35: represents the nucleotide sequence of human chromosome 17, which contains the genomic nucleotide sequence of the human AKAP10 gene, and SEQ ID NO: 36 represents the nucleotide sequence of human chromosome 17, which contains the genomic nucleotide sequence of the human AKAP10-1 allele. The mass of the primer used in the BioMass probe reaction was 5500.6 daltons. In the presence of the SNP, the primer is extended by the addition of ddC, which has a mass of 5773.8. The wildtype gene results in the addition of dT and ddG to the primer to produce an extension product having a mass of 6101 daltons.

The frequency of the SNP was measured in a population of age selected healthy individuals. Five hundred fifty-two (552) individuals between the ages of 18-39 years (276 females, 276 males) and 552 individuals between the ages of 60-79 (184 females between the ages of 60-69, 368 males between the age of 60-79) were tested for the presence of the polymorphism localized in the non-translated 3'region of AKAP 10. Differences in the frequency of this polymorphism with increasing age groups were observed among healthy individuals. Statistical analysis showed that the significance level for differences in the allelic frequency for alleles between the “younger” and the “older” populations was p=0.0009 and for genotypes was p=0.003. Differences between age groups are significant. For the total population allele significance is p=0.0009, and genotype significance is p=0.003.

Figure 19:
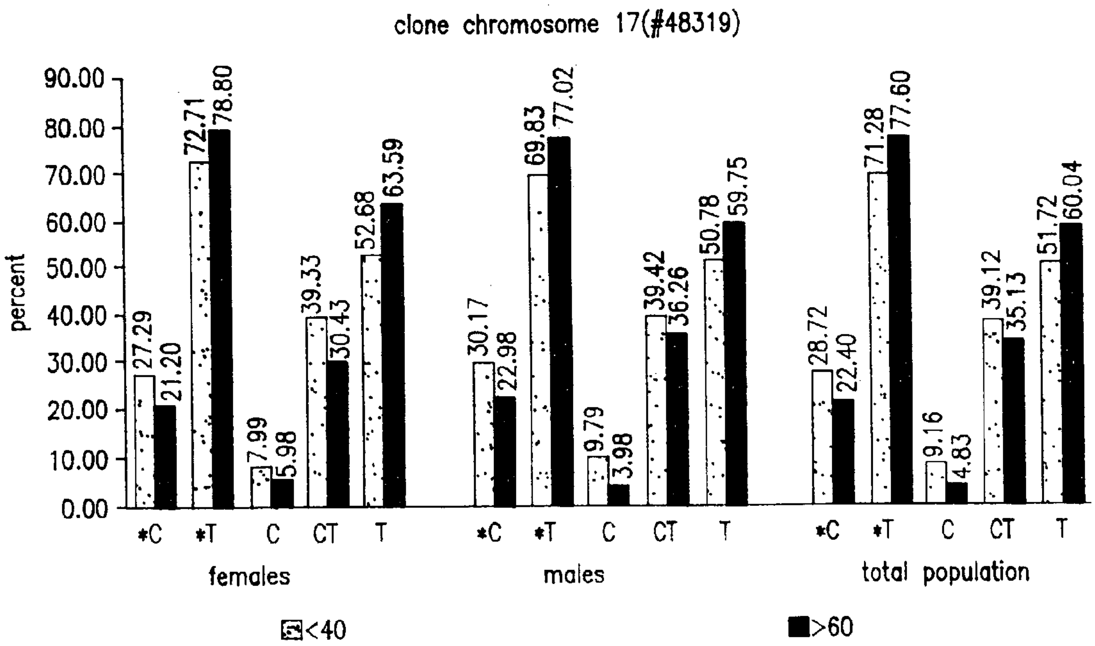
FIG. 19 is a histogram showing the allele and genotype distribution in the age and sex stratified Caucasian population for the AKAP10-1 locus. Bright green bars show frequencies in individuals younger than 40 years. Dark green bars show frequencies in individuals older than 60 years.

This marker led to the best significant result with regard to allele and genotype frequencies in the age-stratified population. FIG. 19 shows the allele and genotype frequency in both genders as well as in the entire population. For the latter, the significance for alleles was p=0.0009 and for genotypes was p=0.003. The young and old populations were in Hardy-Weinberg equilibrium. A preferential change of one particular genotype was not observed.

The polymorphism is localized in the non-translated 3'-region of the gene encoding the human protein kinase A anchoring protein (AKAP10). The gene is located on chromosome 17. Its structure includes 15 exons and 14 intervening sequences (introns). The encoded protein is responsible for the sub-cellular localization of the cAMP-dependent protein kinase and, therefore, plays a key role in the G-protein mediated receptor-signaling pathway (Huang et al. PNAS (1007) 94:11184-11189). Since its localization is outside the coding region, this polymorphism is most likely in linkage disequilibrium (LD) with other non-synonymous polymorphisms that could cause amino acid substitutions and subsequently alter the function of the protein. Sequence comparison of different Genbank database entries concerning this gene revealed further six potential polymorphisms of which two are supposed to change the respective amino acid (see Table 3).

TABLE 3

| Exon | Codon | Nucleotides | Amino acid |
|---|---|---|---|
| 3 | 100 | GCT > GCC | Ala > Ala |
| 4 | 177 | AGT > GTG | Met > Val |
| 8 | 424 | GGG > GGC | Gly > Gly |
| 10 | 524 | CCG > CTG | Pro > Leu |
| 12 | 591 | GTG > GTC | Val > Val |
| 12 | 599 | CGC > CGA | Arg > Arg |

Morbitity Marker 2: Human Protein Kinase A Anchoring Protein (AKAP10-5)

Discovery of AKAP10-5 Allele (SEQ ID NO: 33)

Genomic DNA was isolated from blood (as described above) of seventeen (17) individuals with a genotype CC at the AKAP10-1 gene locus and a single heterozygous individual (CT) (as described). A target sequence in the AKAP10-1 gene which encodes the C-terminal PKA binding domain was amplified using the polymerase chain reaction. PCR primers were synthesized by OPERON using phosphoramidite chemistry. Amplification of the AKAP10-1 target sequence was carried out in individual 50 μl PCR reaction with 25 ng of human genomic DNA templates. Each reaction containing I×PCR buffer (Qiagen, Valencia, Calif.), 200 μM dNTPs, IU Hotstar Taq polymerase (Qiagen, Valencia, Calif.), 4 mM $MgCl_2$, 25 pmol of the forward primer (Ex13F) containing the universal primer sequence and the target specific sequence 5'-TCC CAA AGT GCT GGA ATT AC-3' (SEQ ID NO: 53), and 2 pmol of the reverse primer (Ex14R) 5'-GTC CAA TAT ATG CAA ACA GTT G-3' (SEQ ID NO: 54). Thermal cycling was performed in 0.2 mL tubes or 96 well plate using an MJ Research Thermal Cycler (MJ Research, Waltham, Mass.) (calculated temperature) with the following cycling parameters: 94° C. for 5 min; 45 cycles; 94° C. for 20 sec, 56° C. for 30 sec, 72° C. for 60 sec; 72° C. 3 min. After amplification the amplicons were purified using a chromatography (Mo Bio Laboratories (Solana Beach, Calif.)).

The sequence of the 18 amplicons, representing the target region, was determined using a standard Sanger cycle sequencing method with 25 nmol of the PCR amplicon, 3.2 uM DNA sequencing primer 5'-CCC ACA GCA GTT AAT CCT TC-3'(SEQ ID NO: 55), and chain terminating dRhodamine labeled 2', 3' dideoxynucleotides (PE Biosystems, Foster City, Calif.) using the following cycling parameters: 96° C. for 15 seconds; 25 cycles: 55° C. for 15 seconds, 60° C. for 4 minutes. The sequencing products precipitated by 0.3M NaOAc and ethanol. The precipitate was centrifuged and dried. The pellets were resuspended in deionized formamide and separated on a 5% polyacrylimide gel. The sequence was determined using the "Sequencher" software (Gene Codes, Ann Arbor, Mich.).

The sequence of all 17 of the amplicons, which are homozygous for the AKAP10-1 SNP of the amplicons, revealed a polymorphism at nucleotide position 152171 (numbering for GenBank Accession No. AC005730 for AKAP10 genomic clone (SEQ ID NO: 35)) with A replaced by G. This SNP also can be designated as located at nucleotide 2073 of a cDNA clone of the wildtype AKAP10 (GenBank Accession No. AF037439) (SEQ ID NO: 31). The amino acid sequence of the human AKAP10 protein is provided as SEQ ID NO: 34. This single nucleotide polymorphism was designated as AKAP10-5 (SEQ ID NO: 33) and resulted in a substitution of a valine for an isoleucine residue at amino acid position 646 of the amino acid sequence of human AKAP10 (SEQ ID NO: 32).

PCR Amplification and BiomassPROBE Assay Detection of AKAP10-5 in a Healthy Donor Population The healthy population stratified by age is a very efficient and a universal screening tool for morbidity associated genes by allowing for the detection of changes of allelic frequencies in the young compared to the old population. Individual samples of this healthy population base can be pooled to further increase the throughput.

Healthy samples were obtained through the blood bank of San Bernardino, Calif. Both parents of the blood donors were of Caucasian origin. Practically a healthy subject, when human, is defined as human donor who passes blood bank criteria to donate blood for eventual use in the general population. These criteria are as follows: free of detectable viral, bacterial, mycoplasma, and parasitic infections; not anemic; and then further selected based upon a questionnaire regarding history (see FIG. 3). Thus, a healthy population represents an unbiased population of sufficient health to donate blood according to blood bank criteria, and not further selected for any disease state. Typically such individuals are not taking any medications.

PCR primers were synthesized by OPERON using phosphoramidite chemistry. Amplification of the AKAP10 target sequence was carried out in a single 50 μl PCR reaction with 100 ng-1 g of pooled human genomic DNAs in a 50 μl PCR reaction. Individual DNA concentrations within the pooled samples were present in equal concentration with the final concentration ranging from 1-25 ng. Each reaction contained 1×PCR buffer (Qiagen, Valencia, Calif.), 200 μM dNTPs, 1U Hotstar Taq polymerase (Qiagen, Valencia, Calif.), 4 mM $MgCl_2$, and 25 pmol of the forward primer containing the universal primer sequence and the target specific sequence 5'-AGCGGATAACAATTTCACACAGG-GAGCTAGCTTGGAAGAT TGC-3' (SEQ ID NO: 41), 2 pmol of the reverse primer 5'-GTCCAATATATGCAAA-CAGTTG-3' (SEQ ID NO: 54), and 10 pmol of a biotinylated universal primer complementary to the 5' end of the PCR amplicon BIO:5'-AGCGGATAACAATTTCACACAGG-3' (SEQ ID NO: 43). After an initial round of amplification with the target with the specific forward and reverse primer, the 5' biotinylated universal primer can then be hybridized and acted as a forward primer thereby introducing a 5' biotin capture moiety into the molecule. The amplification protocol resulted in a 5'-biotinylated double stranded DNA amplicon and dramatically reduced the cost of high throughput genotyping by eliminating the need to 5' biotin label every forward primer used in a genotyping.

Themal cycling was performed in 0.2 mL tubes or 96 well plate using an MJ Research Thermal Cycler (calculated temperature) with the following cycling parameters: 94° C. for 5 min; 45 cycles: 94° C. for 20 sec, 56° C. for 30 sec; 72° C. for 60 sec; 72° C. 3min.

Immobilization of DNA

The 50 μl PCR reaction was added to 25 μl of streptavidin coated magnetic beads (Dynal, Oslo, Norway), which were prewashed three times and resuspended in 1M $NH_4Cl$, 0.06M $NH_4OH$. The 5' end of one strand of the double stranded PCR amplicons were allowed to bind to the beads for 15 minutes at room temperature. The beads were then collected with a magnet, and the supernatant containing unbound DNA was removed. The hybridized but unbound strand was released from the double stranded amplicons by incubation in 100 mM NaOH and washing of the beads three times with 10 mM Tris pH 8.0.

Detection of AKAP10-5 using BiomassPROBE™ Assay

BiomassPROBE™ assay of primer extension analysis (see, U.S. Pat. No. 6,043,031) of donor population for AKAP 10-5 (SEQ ID NO: 33) was performed. Genotyping using these methods was carried out by resuspending the DNA coated magnetic beads in 26 mM Tris-HCL pH 9.5, 6.5 mM MgCl$_2$, 50 mM dTTP, 50 mM each of ddCTP, ddATP, ddGTP, 2.5U of a thermostable DNA polymerase (Ambersham), and 20 pmol of a template specific oligonucleotide PROBE primer 5'-ACTGAGCCTGCTGCATAA-3' (SEQ ID NO: 44) (Operon). Primer extension occurs with three cycles of oligonucleotide primer with hybridization and extension. The extension products were analyzed after denaturation from the template with 50 mM NH$_4$Cl and transfer of 150 nL of each sample to a silicon chip preloaded with 150 nl of H3PA matrix material. The sample material was allowed to crystallize and analyzed by MALDI-TOF (Bruker, PerSeptive). The primer has a mass of 5483.6 daltons. The SNP results in the addition of a ddC to the primer, giving a mass of 5756.8 daltons for the extended product. The wild type results in the addition a T and ddG to the primer giving a mass of 6101 daltons.

The frequency of the SNP was measured in a population of age selected healthy individuals. Seven hundred thirteen (713) individuals under 40 years of age (360 females, 353 males) and 703 individuals over 60 years of age (322 females, 381 males) were tested for the presence of the SNP, AKAP10-5 (SEQ ID NO: 33). Results are presented below in Table 4.

TABLE 4

AKAP10-5 (2073V) frequency comparison in 2 age groups

|   |   |   | <40 | >60 | delta G allele |
|---|---|---|---|---|---|
| Female | Alleles | *G | 38.6 | 34.6 | 4.0 |
|   |   | *A | 61.4 | 65.4 |   |
|   | Genotypes | G | 13.9 | 11.8 | 2.1 |
|   |   | GA | 49.4 | 45.7 |   |
|   |   | A | 36.7 | 42.5 |   |
| Male | Alleles | *G | 41.4 | 37.0 | 4.4 |
|   |   | *A | 58.6 | 63.0 |   |
|   | Genotypes | G | 18.4 | 10.8 | 7.7 |
|   |   | GA | 45.9 | 52.5 |   |
|   |   | A | 35.7 | 36.7 |   |
| Total | Alleles | *G | 40.0 | 35.9 | 4.1 |
|   |   | *A | 60.0 | 64.1 |   |
|   | Genotypes | G | 16.1 | 11.2 | 4.9 |
|   |   | GA | 47.7 | 49.4 |   |
|   |   | A | 36.2 | 39.4 |   |

Figure 20:
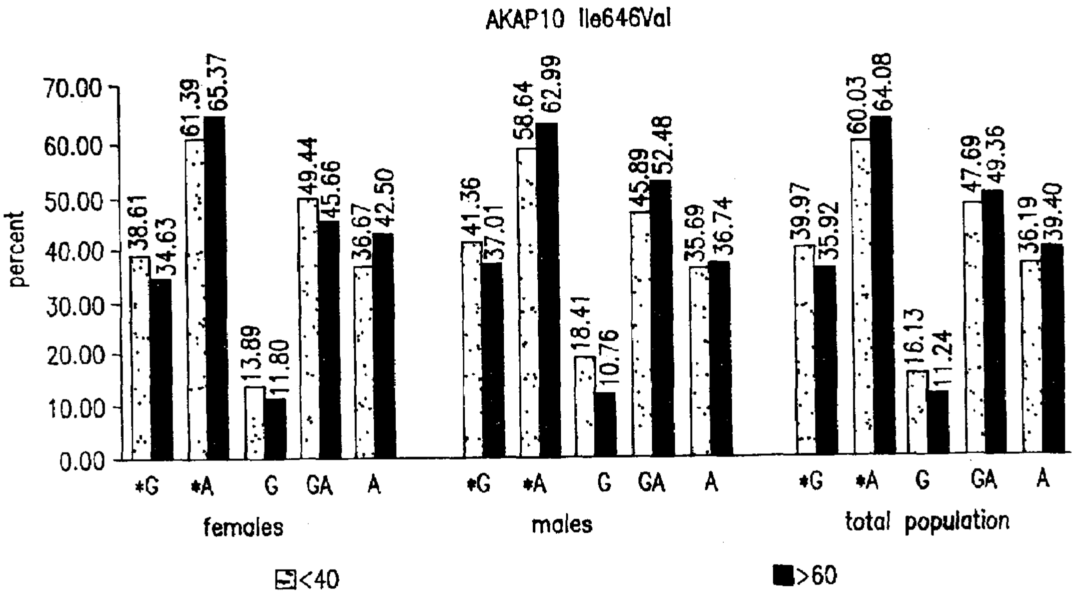
FIG. 20 is a histogram showing the allele and genotype distribution in the age and sex stratified Caucasian population for the AKAP10-5 locus. Bright green bars show frequencies in individuals younger than 40 years; dark green bars show frequencies in individuals older than 60 years.

FIG. 20 graphically shows these results of allele and genotype distribution in the age and sex stratified Caucasian population.

Morbidity Marker 3: Human Methionine Sulfoxide Reductase A (msrA)

Figure 21:
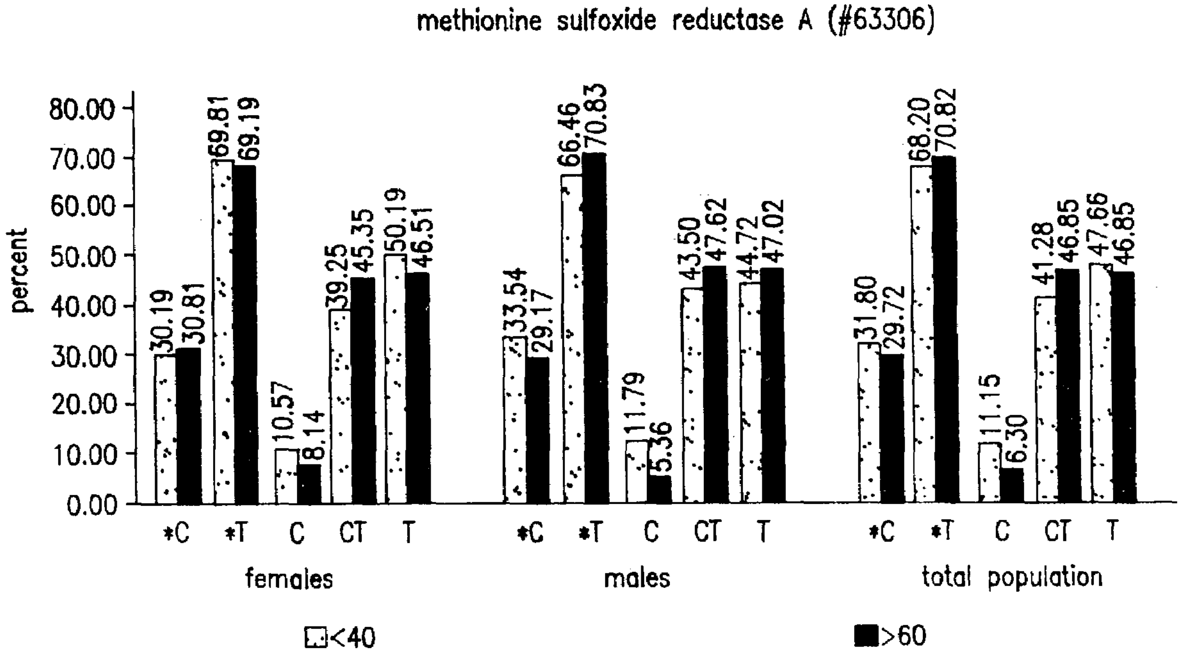
FIG. 21 is a histogram showing the allele and genotype distribution in the age and sex stratified Caucasian population for the h-msrA locus. Genotype difference between male age groups is significant. Bright green bars show frequencies in individuals younger than 40 years. Dark green bars show frequencies in individuals older than 60 years.

The age-related allele and genotype frequency of this marker in both genders and the entire population is shown in FIG. 21. The decrease of the homozygous CC genotype in the older male population is highly significant.

Methionine Sulfoxide Reductase A (#63306)

PCR Amplification and BiomassPROBE assay detection of the human methioine sulfoxide reductase A (h-msr-A) in a healthy donor population PCR Amplification of Donor Population for h-msr-A PCR primers were synthesized by OPERON using phosphoramidite chemistry. Amplification of the AKAP10 target sequence was carried out in single 50 µl PCR reaction with 100 ng-1 ug of pooled human genomic DNA templates in a 50 µl PCR reaction. Individual DNA concentrations within the pooled samples were present in an equal concentration with the final concentration ranging from 1-25 ng. Each reaction containing I X PCR buffer (Qiagen, Valencia, Calif.), 200 µM dNTPs, 1U Hotstar Taq polymerase (Qiagen, Valencia, Calif.), 4 mM MgCl$_2$, 25 pmol of the forward primer containing the universal primer sequence and the target specific sequence 5'-TTTCTCTGCACAGAGAGGC-3' (SEQ ID NO: 49), 2 pmol of the reverse primer 5'-AGCGGATAACAATTTCACACAGGGCTGAAATCCTTCGCTTTACC-3' (SEQ ID NO: 50), and 10 pmol of a biotinylated universal primer complementary to the 5' end of the PCR amplicon 5'-AGCGGATAACAATTTCACACAGG-3' (SEQ ID NO: 51). After an initial round of amplification of the target with the specific forward and reverse primers, the 5' biotinylated universal primer was then hybridized and acted as a reverse primer thereby introducing a 3' biotin capture moiety into the molecule. The amplification protocol results in a 5'-biotinylated double stranded DNA amplicon and dramatically reduces the cost of high throughput genotyping by eliminating the need to 5' biotin label each forward primer used in a genotyping. Thermal cycling was performed in 0.2 mL tubes or 96 well plate using an MJ Research Thermal Cycler (calculated temperature) with the following cycling parameters: 94° C. for, 5 min; 45 cycles: 94° C. for 20 sec, 56° C. for 30 sec, 72° C. for 60 sec; 72° C. 3 min.

Immobilization of DNA

The 50 µl PCR reaction was added to 25 ul of streptavidin coated magnetic bead (Dynal) prewashed three times and resuspended in 1M NH$_4$Cl, 0.06 M NH$_4$OH. The PCR amplicons were allowed to bind to the beads for 15 minutes at room temperature. The beads were then collected with a magnet and the supernatant containing unbound DNA was removed. The unbound strand was released from the double stranded amplicons by incubation in 100 mM NaOH and washing of the beads three times with 10 mM Tris pH 8.0.

BiomassPROBE Assay Analysis of Donor Population for h-msr A

Genotyping using the BiomassPROBE assay methods was carried out by resuspending the DNA coated magnetic beads in 26 mM Tris-HCl pH 9.5, 6.5 mM MgCl$_2$, 50 mM of dTTPs and 50 mM each of ddCTP, ddATP, ddGTP, 2.5 U of a thermostable DNA polymerase (Ambersham), and 20 pmol of a template specific oligonucleotide PROBE primer 5'-CTGAAAAGGGAGAGAAAG-3' (Operon) (SEQ ID NO: 52). Primer extension occurs with three cycles of oligonucleotide primer with hybridization and extension. The extension products were analyzed after denaturation from the template with 50 mM NH$_4$Cl and transfer of 150 nl each sample to a silicon chip preloaded with 150 nl of H3PA matrix material. The sample material was allowed to crystallize and analyzed by MALDI-TOF (Bruker, PerSeptive). The SNP is represented as a T to C tranversion in the sequence of two ESTs. The wild type is represented by having a T at position 128 of GenBank Accession No. AW 195104, which represents the nucleotide sequence of an EST which is a portion of the wild type human msrA gene (SEQ ID NO: 39). The SNP is presented as a C at position 129 of GenBank Accession No. AW 874187, which represents the nucleotide sequence of an EST which is a portion of an allele of the human msrA gene (SEQ ID NO: 40).

In a genomic sequence the SNP is represented as an A to G transversion. The primer utilized in the BioMass probe reaction had a mass of 5654.8 daltons. In the presence of the SNP the primer is extended by the incorporation of a ddC and has a mass of 5928. In the presence of the wildtype the primer is extended by adding a dT and a DDC to produce a mass of 6232.1 daltons.

The frequency of the SNP was measured in a population of age selected healthy individuals. Five hundred fifty-two (552) individuals between the ages of 18-39 years (276 females, 276 males and 552 individuals between the age of 60-79 (184 females between the ages of 60-69, 368 males between the age of 60-79) were tested for the presence of the polymorphism localized in the nontranslated 3'region of h-msr-A.

Genotype difference between male age group among healthy individuals is significant. For the male population allele significance is p=0.0009 and genotype significance is p=0.003. The age-related allele and genotype frequency of this marker in both genders and the entire population is shown in FIG. 21. The decrease of the homozygous CC genotype in the older male population is highly significant.

The polymorphism is localized in the non-translated 3'-region of the gene encoding the human methionine sulfoxide reductase (h-msrA). The exact localization is 451 base pairs downstream the stop codon (TAA). It is likely that this SNP is in linkage disequilibrium (LD) with another polymorphism more upstream in the coding or promoter region; thus, it does not directly cause morbidity. The enzyme methionine sulfoxide reductase has been proposed to exhibit multiple biological functions. It can serve to repair oxidative protein damage but also play an important role in the regulation of proteins by activation or inactivation of their biological functions (Moskovitz et al. (1990) PNAS 95:14071-14075). It has also been shown that its activity is significantly reduced in brain tissues of Alzheimer patients (Gabbita et al., (1999) J. Neurochem 73:1660-1666). It is scientifically conceivable that proteins involved in the metabolism of reactive oxygen species are associated to disease.

CONCLUSION

The use of the healthy population provides for the identification of morbidity markers. The identification of proteins involved in the G-protein coupled signaling transduction pathway or in the detoxification of oxidative stress can be considered as convincing results. Further confirmation and validation of other potential polymorphisms already identified in silico in the gene encoding the human protein kinase A anchoring protein could even provide stronger association to morbidity and demonstrate that this gene product is a suitable pharmaceutical or diagnostic target.

EXAMPLE 4

MALDI-TOF Mass Spectrometry Analysis

All of the products of the enzyme assays listed below were analyzed by MALDI-TOF mass spectrometry. A diluted matrix solution (0.15 μL) containing of 10:1 3-hydroxypicolinic acid:ammonium citrate in 1:1 water:acetonitrile diluted 2.5-fold with water was pipetted onto a SpectroChip (Sequenom, Inc.) and was allowed to crystallize. Then, 0.15 μL of sample was added. A linear PerSeptive Voyager DE mass spectrometer or Bruker Biflex MALDI-TOF mass spectrometer, operating in positive ion mode, was used for the measurements. The sample plates were kept at 18.2 kV for 400 nm after each UV laser shot (approximate 250 laser shots total), and then the target voltage was raised to 20 kV. The original spectra were digitized at 500 MHz.

EXAMPLE 5

Sample Conditioning

Where indicated in the examples below, the products of the enzymatic digestions were purified with ZipTips (Millipore, Bedford, Mass.). The ZipTips were pre-wetted with 10 μL 50% acetonitrile and equilibrated 4 times with 10 μl 0.1 M TEAAc. The oligonucleotide fragments were bound to the C18 in the ZipTip material by continuous aspiration and dispension of each sample into the ZipTip. Each digested oligonucleotide was conditioned by washing with 10 μL 0.1 M TEAAc, followed by 4 washing steps with 10 μL $H_2O$. DNA fragments were eluted from the Ziptip with 7 μL 50% acetonitrile.

Any method for condition the samples can be employed. Methods for conditioning, which generally is used to increase peak resolution, are well known (see, e.g., International PCT application No. WO 98/20019).

EXAMPLE 6

DNA Glycosylase-Mediated Sequence Analysis

DNA Glycosylases modifies DNA at each position that a specific nucleobase resides in the DNA, thereby producing abasic sites. In a subsequent reaction with another enzyme, a chemical, or heat, the phosphate backbone at each abasic site can be cleaved.

The glycosylase utilized in the following procedures was uracil-DNA glycosylase (UDG). Uracil bases were incorporated into DNA fragments in each position that a thymine base would normally occupy by amplifying a DNA target sequence in the presence of uracil. Each uracil substituted DNA amplicon was incubated with UDG, which cleaved each uracil base in the amplicon, and was then subjected to conditions that effected backbone cleavage at each abasic site, which produced DNA fragments. DNA fragments were subjected to MALDI-TOF mass spectrometry analysis. Genetic variability in the target DNA was then assessed by analyzing mass spectra.

Glycosylases specific for nucleotide analogs or modified nucleotides, as described herein, can be substituted for UDG in the following procedures. The glycosylase methods described hereafter, in conjunction with phosphate backbone cleavage and MALDI, can be used to analyze DNA fragments for the purposes of SNP scanning, bacteria typing, methylation analysis, microsatellite analysis, genotyping, and nucleotide sequencing and re-sequencing.

A. Genotyping

A glycosylase procedure was used to genotype the DNA sequence encoding UCP-2 (Uncoupling Protein 2). The sequence for UCP-2 is deposited in GenBank under accession number AF096289. The sequence variation genotyped in the following procedure was a cytosine (C-allele) to thymine (T-allele) variation at nucleotide position 4790, which results in a alanine to valine mutation at position 55 in the UCP-2 polypeptide.

DNA was amplified using a PCR procedure with a 50 μL reaction volume containing of 5 pmol biotinylated primer having the sequence 5'-TGCTTATCCCTGTAGCTACCCTGTCTTGGCCTTGCAGATCCAA-3' (SEQ ID NO: 91), 15 pmol non-biotinylated primer having the sequence 5'-AGCG- GATAACAATTTCACACAGGCCATCACAC-CGCGGTACTG-3' (SEQ ID NO: 92), 200 μM dATP, 200 μM dCTP, 200 μM dGTP, 600 μM dUTP (to fully replace dTTP), 1.5 mM to 3 mM $MgCl_2$, 1 U of HotStarTaq polymerase, and 25 ng of CEPH DNA. Amplification was effected with 45 cycles at an annealing temperature of 56° C.

The amplification product was then immobilized onto a solid support by incubating 50 μL of the amplification reaction with 5 μL of prewashed Dynabeads for 20 minutes at room temperature. The supernatant was removed, and the beads were incubated with 50 μL of 0.1 M NaOH for 5 minutes at room temperature to denature the double-stranded PCR product in such a fashion that single-stranded DNA was linked to the beads. The beads were then neutralized by three washes with 50 μL 10 mM TrisHCl (pH 8). The beads were resuspended in 10 μL of a 60 mM TrisHCl/1 mM EDTA (pH 7.9) solution, and 1 U uracil DNA glycosylase was added to the solution for 45 minutes at 37° C. to remove uracil nucleotides present in the single-stranded DNA linked to the beads. The beads were then washed two times with 25 μL of 10 mM TrisHCl (pH 8) and once with 10 μL of water. The biotinylated strands were then eluted from the beads with 12 μL of 2 M $NH_4OH$ at 60° C. for 10 minutes. The backbone of the DNA was cleaved by incubating the samples for 10 min at 95° C. (with a closed lid), and ammonia was evaporated from the samples by incubating the samples for 11 min at 80° C.

The cleavage fragments were then analyzed by MALDI-TOF mass spectrometry as described in Example 4. The T-allele generated a unique fragment of 3254 Daltons. The C-allele generated a unique fragment of 4788 Daltons. These fragements were distinguishable in mass spectra. Thus, the above-identified procedure was successfully utilized to genotype individuals heterozygous for the C-allele and T-allele in UCP-2.

B. Glycosylase Analysis Utilizing Pooled DNA Samples

The glycosylase assay was conducted using pooled samples to detect genetic variability at the UCP-2 locus. DNA of known genotype was pooled from eleven individuals and was diluted to a fixed concentration of 5 ng/μL. The procedure provided in Example 3A was followed using 2 pmol of forward primer having a sequence of 5'-CCCAGTCACGACGT-TGTAAAACGTCTTGGCCTTGCAGATCCAAG-3' (SEQ ID NO: 93) and 15 pmol of reverse primer having the sequence 5'-AGCGGATAACAATTTCACACAGGCCAT-CACACCGCGGTACTG-3' (SEQ ID NO: 94). In addition, 5 pmol of biotinylated primer having the sequence 5'bioC-CCAGTCACGACGTTGTAAAACG 3' (SEQ ID NO: 97) can be introduced to the PCR reaction after about two cycles. The fragments were analyzed via MALDI-TOF mass spectroscopy (Example 4). As determined in Example 3A, the T-allele, which generated a unique fragment of 3254 Daltons, could be distinguished in mass spectra from the C-allele, which generated a unique fragment of 4788 Daltons. Allelic frequency in the pooled samples was quantified by integrating the area under each signal corresponding to an allelic fragment. Integration was accomplished by hand calculations using equations well known to those skilled in the art. In the pool of eleven samples, this procedure suggested that 40.9% of the individuals harbored the T allele and 59.09% of the individuals harbored the C allele.

C. Glycosylase-Mediated Microsatellite Analysis

A glycosylase procedure was utilized to identify microsatellites of the Bradykinin Receptor 2 (BKR-2) sequence. The sequence for BKR-2 is deposited in GenBank under accession number X86173. BKR-2 includes a SNP in the promoter region, which is a C to T variation, as well as a SNP in a repeated unit, which is a G to T variation. The procedure provided in Example 3A was utilized to identify the SNP in the promotor region, the SNP in the microsattelite repeat region, and the number of repeated units in the microsattelite region of BKR-2. Specifically, a forward PCR primer having the sequence 5'-CTCCAGCTGGGCAGGAGTGC-3' (SEQ ID NO: 95) and a reverse primer having the sequence 5'-CACTTCAGTCGCTCCCT-3' (SEQ ID NO: 96) were utilized to amplify BKR-2 DNA in the presence of uracil. The amplicon was fragmented by UDG followed by backbone cleavage. The cleavage fragments were analyzed by MALDI-TOF mass spectrometry as described in Example 4.

With regard to the SNP in the BKR-2 promotor region having a C to T variation, the C-allele generated a unique fragment having a mass of 7342.4 Daltons, and the T-allele generated a unique fragment having a mass of 7053.2 Daltons. These fragments were distinguishable in mass spectra. Thus, the above-identified procedure was successfully utilized to genotype individuals heterozygous for the C-allele and T-allele in the promotor region of BKR-2.

With regard to the SNP in the BKR-2 repeat region having a G to T variation, the T-allele generated a unique fragment having a mass of 1784 Daltons, which was readily detected in a mass spectrum. Hence, the presence of the T-allele was indicative of the G to T sequence variation in the repeat region of BKR-2.

In addition, the number of repeat regions was distinguished between individuals having two repeat sequences and individuals having three repeat sequences in BKR-2. The DNA of these individuals did not harbor the G to T sequence variation in the repeat sequence as each repeat sequence contained a G at the SNP locus. The number of repeat regions was determined in individual samples by calculating the area under a signal corresponding to a unique DNA fragment having a mass of 2771.6 Daltons. This signal in spectra generated from individuals having two repeat regions had an area that was thirty-three percent less than the area under the same signal in spectra generated from individuals having three repeat regions. Thus, the procedures discussed above can be utilized to genotype individuals for the number of repeat sequences present in BKR-2.

D. Bisulfite Treatment Coupled with Glycosylase Digestion

Bisulfite treatment of genomic DNA can be utilized to analyze positions of methylated cytosine residues within the DNA. Treating nucleic acids with bisulfite deaminates cytosine residues to uracil residues, while methylated cytosine remains unmodified. Thus, by comparing the sequence of a PCR product generated from genomic DNA that is not treated with bisulfite with the sequence of a PCR product generated from genomic DNA that is treated with bisulfite, the degree of methylation in a nucleic acid as well as the positions where cytosine is methylated can be deduced.

Genomic DNA (2 μg) was digested by incubation with 1 μL of a restriction enzyme at 37° C. for 2 hours. An aliquot of 3 M NaOH was added to yield a final concentration of 0.3M NaOH in the digestion solution. The reaction was incubated at 37° C. for 15 minutes followed by treatment with 5.35M urea, 4.44M bisulfite, and 10 mM hydroquinone, where the final concentration of hydroquinone is 0.5 mM.

The sample that was treated with bisulfite (sample A) was compared to the same digestion sample that had not undergone bisulfite treatment (sample B). After sample A was treated with bisulfite as described above, sample A and sample B were amplified by a standard PCR procedure. The PCR procedure included the step of overlaying each sample with mineral oil and then subjecting the sample to thermocycling (20 cycles of 15 minutes at 55° C. followed by 30 seconds at 95° C.). The PCR reaction contained four nucleotide bases, C, A, G, and U. The mineral oil was removed from each sample, and the PCR products were purified with glassmilk. Sodium iodide (3 volumes) and glassmilk (5 μL) were added to samples A and B. The samples were then placed on ice for 8 minutes, washed with 420 μL cold buffer, centrifuged for 10 seconds, and the supernatant fractions were removed. This process was repeated twice and then 25 μL of water was added. Samples were incubated for 5 minutes at 37° C., were centrifuged for 20 seconds, and the supernatant fraction was collected, and then this incubation/centrifugation/supernatant fraction collection procedure was repeated. 50 μL 0.1 M NaOH was then added to the samples to denature the DNA. The samples were incubated at room temperature for 5 minutes, washed three times with 50 μL of 10 mM TrisHCl (pH 8), and resuspended in 10 μL 60 mM TrisHCl/1 mM EDTA, pH 7.9.

The sequence of PCR products from sample A and sample B were then treated with 2U of UDG (MBI Fermentas) and then subjected to backbone cleavage, as described herein. The resulting fragments from each of sample A and sample B were analyzed by MALDI-TOF mass spectroscopy as described in Example 4. Sample A gave rise to a greater number of fragments than the number of fragments arising from sample B, indicative that the nucleic acid harbored at least one methylated cytosine moiety.

EXAMPLE 7

Fen-Ligase-Mediated Haplotyping

Haplotyping procedures permit the selection of a fragment from one of an individual's two homologous chromosomes and to genotype linked SNPs on that fragment. The direct resolution of haplotypes can yield increased information content, improving the diagnosis of any linked disease genes or identifying linkages associated with those diseases. In previous studies, haplotypes were typically reconstructed indirectly through pedigree analysis (in cases where pedigrees were available) through laborious and unreliable allele-specific PCR or through single-molecule dilution methods well known in the art.

A haplotyping procedure was used to determine the presence of two SNPs, referred to as SNP1 and SNP2, located on one strand in a DNA sample. The haplotyping procedure used in this assay utilized Fen-1, a site-specific "flap" endonuclease that cleaves DNA "flaps" created by the overlap of two oligonucleotides hybridized to a target DNA strand. The two overlapping oligonucleotides in this example were short arm and long arm allele-specific adaptors. The target DNA was an amplified nucleic acid that had been denatured and contained SNP1 and SNP2.

The short arm adaptor included a unique sequence not found in the target DNA. The 3' distal nucleotide of the short arm adaptor was identical to one of the SNP1 alleles. Moreover, the long arm adaptor included two regions: a 3' region complementary to the short arm and a 5'gene-specific region complementary to the fragment of interest adjacent to the SNP. If there was a match between the adaptor and one of the homologues, the Fen enzyme recognized and cleaved the overlapping flap. The short arm of the adaptor was then ligated to the remainder of the target fragment (minus the SNP site). This ligated fragment was used as the forward primer for a second PCR reaction in which only the ligated homologue was amplified. The second PCR product (PCR2) was then analyzed by mass spectrometry. If there was no match between the adaptors and the target DNA, there was no overlap, no cleavage by Fen-1, and thus no PCR2 product of interest.

If there was more than one SNP in the sequence of interest, the second SNP (SNP2) was found by using an adaptor that was specific for SNP2 and hybridizing the adaptor to the PCR2 product containing the first SNP. The Fen-ligase and amplification procedures were repeated for the PCR2 product containing the first SNP. If the amplified product yielded a second SNP, then SNP1 and SNP2 were on the same fragment.

If the SNP is unknown, then four allele-specific adaptors (e.g. C, G, A, and T) can be used to hybridize with the target DNA. The substrates are then treated with the Fen-ligase protocol, including amplification. The PCR2 products can be analyzed by PROBE, as described herein, to determine which adaptors were hybridized to the DNA target and thus identify the SNPs in the sequence.

A Fen-ligase assay was used to detect two SNPs present in Factor VII. These SNPs are located 814 base pairs apart from each other. SNP1 was located at position 8401 (C to T), and SNP2 was located at 9215 (G to A).

A. First Amplification Step

A PCR product (PCR1) was generated for a known heterozygous individual at SNP1, a short distance from the 5' end of the SNP. Specifically, a 10 μL PCR reaction was performed by mixing 1.5 mM $MgCl_2$, 200 μM of each dNTP, 0.5 U HotStar polymerase, 0.1 μM of a forward primer having the sequence 5'-GCG CTC CTG TCG GTG CCA (SEQ ID NO: 56), 0.1 μM of a reverse primer having the sequence 5'-GCC TGA CTG GTG GGG CCC (SEQ ID NO: 57), and 1 ng of genomic DNA. The annealing temperature was 58° C., and the amplification process yielded fragments that were 861 bp in length.

The PCR1 reaction mixture was divided in half and was treated with an exonuclease 1/SAP mixture (0.22 μL mixture/5 μL PCR1 reaction) which contained 1.0 μL SAP and 0.1 μL exon1. The exonuclease treatment was done for 30 minutes at 37° C. and then 20 minutes at 85° C. to denature the DNA.

B. Adaptor Oligonucleotides

A solution of allele-specific adaptors (C and T), containing of one long and one short oligonucleotide per adaptor, was prepared. The long arm and short arm oligonucleotides of each adaptor (10 μM) were mixed in a 1:1 ratio and heated for 30 seconds at 95° C. The temperature was reduced in 2° C. increments to 37° C. for annealing. The C-adaptor had a short arm sequence of 5'-CAT GCA TGC ACG GTC (SEQ ID NO: 58) and a long arm sequence of 5'-CAG AGA GTA CCC CTC GAC CGT GCA TGC ATG (SEQ ID NO: 59). Hence, the long arm of the adaptor was 30 bp (15 bp gene-specific), and the short arm was 15 bp. The T-adaptor had a short arm sequence of 5'-CAT GCA TGC ACG GTT (SEQ ID NO: 60) and a long arm sequence of 5'-GTA CGT ACG TGC CAA CTC CCC ATG AGA GAC (SEQ ID NO: 61). The adaptor could also have a hairpin structure in which the short and long arm are separated by a loop containing of 3 to 10 nucleotides (SEQ ID NO: 118).

C. FEN-Ligase Reaction

In two tubes (one tube for each allele-specific adaptor per sample) was placed a solution (Solution A) containing of 3.5 μl 10 mM 16%PEG/50 mM MOPS, 1.2 μl 25 mM $MgCl_2$, 1.5 μl 10×Ampligase Buffer, and 2.5 μl PCR1. Each tube containing Solution A was incubated at 95° C. for 5 minutes to denature the PCR1 product. A second solution (Solution B)

containing of 1.65 μl Ampligase (Thermostable ligase, Epicentre Technologies), 1.65 μl 200 ng/μl MFEN (from *Methanocuccus jannaschii*), and 3.0 μl of an allele specific adaptor (C or T) was prepared. Thus, different variations of Solution B, each variation containing of different allele-specific adaptors, were made. Solution B was added to Solution A at 95° C. and incubated at 55° C. for 3 hours. The total reaction volume was 15.0 μl per adaptor-specific reaction. For a bi-allelic system, 2×15.0 μl reactions were required.

The Fen-ligase reaction in each tube was then deactivated by adding 8.0 μl 10 mM EDTA. Then, 1.0 μl exoIII/Buffer (70%/30%) solution was added to each sample and incubated 30 minutes at 37° C., 20 minutes at 70° C. (to deactivate exoIII), and 5 minutes at 95° C. (to denature the sample and dissociate unused adaptor from template). The samples were cooled in an ice slurry and purified on UltraClean PCR Clean-up (MoBio) spin columns which removed all fragments less than 100 base pairs in length. The fragments were eluted with 50 μl $H_2O$.

D. Second Amplification Step

A second amplification reaction (PCR2) was conducted in each sample tube using the short arm adaptor (C or T) sequence as the forward primer (minus the SNP1 site). Only the ligated homologue was amplified. A standard PCR reaction was conducted with a total volume of 10.0 μl containing of 1×Buffer (final concentration), 1.5 mM final concentration $MgCl_2$, 200 μM final concentration dNTPs, 0.5 U HotStar polymerase, 0.1 μM final concentration forward primer 5'-CAT GCA TGC ACG GT (SEQ ID NO: 62), 0.1 μM final concentration reverse primer 5'-GCC TGA CTG GTG GGG CCC (SEQ ID NO: 63), and 1.0 μl of the purified FEN-ligase reaction solution. The annealing temperature was 58° C. The PCR2 product was analyzed by MALDI TOF mass spectroscopy as described in Example 4. The mass spectrum of Fen SNP1 showed a mass of 6084.08 Daltons, representing the C allele.

E. Genotyping Additional SNPs

The second SNP (SNP2) can be found by using an adaptor that is specific for SNP2 and hybridizing that adaptor to the PCR2 product containing the first SNP. The Fen-ligase and amplification procedures are repeated for the PCR2 product containing the first SNP. If the amplified product yields a second SNP, then SN1 and SN2 are on the same fragment. The mass spectrum of SNP2, representing the T allele, showed a mass of 6359.88 Daltons.

This assay also can be performed upon pooled DNA to yield haplotype frequencies as described herein. The Fen-ligase assay can be used to analyze multiplexes as described herein.

EXAMPLE 8

Nickase-Mediated Sequence Analysis

A DNA nickase, or DNase, was used to recognize and cleave one strand of a DNA duplex. NY2A nickase and NYS1 nickase (Megabase), which cleave DNA at the following sites:

NY2A:

5' . . . R AG . . . 3'

3' . . . Y↓TC . . . 5' where R=A or G and Y=C or T

NYS1:

5' . . . ↓CC[A/G/T] . . . 3'

3' . . . GG[T/C/A] . . . 5' were used.

A. Nickase Digestion

Tris-HCl (10 mM), KCl (10 mM, pH 8.3), magnesium acetate (25 mM), BSA (1 mg/mL), and 6 U of Cvi NY2A or Cvi NYS1 Nickase (Megabase Research) were added to 25 pmol of double-stranded oligonucleotide template having a sequence of 5'-CGC AGG GTT TCC TCG TCG CAC TGG GCA TGT G-3' (SEQ ID NO: 90, Operon, Alameda, Calif.) synthesized using standard phosphoramidite chemistry. With a total volume of 20 μL, the reaction mixture was incubated at 37° C. for 5 hours, and the digestion products were purified using ZipTips (Millipore, Bedford, Mass.) as described in Example 5. The samples were analyzed by MALDI-TOF mass spectroscopy as described in Example 1. The nickase, Cvi NY2A yielded three fragments with masses 4049.76 Daltons, 5473.14 Daltons, and 9540.71 Daltons. The Cvi NYS1 nickase yielded fragments with masses 2063.18 Daltons, 3056.48 Daltons, 6492.81 Daltons, and 7450.14 Daltons.

B. Nickase Digestion of Pooled Samples

DQA (HLA ClassII-DQ Alpha, expected fragment size=225 bp) was amplified from the genomic DNA of 100 healthy individuals. DQA was amplified using standard PCR chemistry in a reaction having a total volume of 50 μL containing of 10 mM Tris-HCl, 10 mM KCl (pH 8.3), 2.5 mM $MgCl_2$, 200 μM of each dNTP, 10 pmol of a forward primer having the sequence 5'-GTG CTG CAG GTG TAA ACT TGT ACC AG-3'(SEQ ID NO: 64), 10 pmol of a reverse primer having the sequence 5'-CAC GGA TCC GGT AGC AGC GGT AGA GTT G-3'(SEQ ID NO: 65), 1 U DNA polymerase (Stuffed fragment, Perkin Elmer), and 200 ng human genomic DNA (2 ng DNA/individual). The template was denatured at 94° C. for 5 minutes. Thermal cycling was continued with a touch-down program that included 45 cycles of 20 seconds at 94° C., 30 seconds at 56° C., 1 minute at 72° C., and a final extension of 3 minutes at 72° C. The crude PCR product was used in the subsequent nickase reaction.

The unpurified PCR product was subjected to nickase digestion. Tris-HCl (10 mM), KCl (10 mM, pH 8.3), magnesium acetate (25 mM), BSA (1 mg/mL), and 5 U of Cvi NY2A or Cvi NYS1 Nickase (Megabase Research) were added to 25 pmol of the amplified template with a total reaction volume of 20 μL. The mixture was then incubated at 37° C. for 5 hours. The digestion products were purified with either ZipTips (Millipore, Bedford, Mass.) as described in Example 5. The samples were analyzed by MALDI-TOF mass spectroscopy as described in Example 4. This assay also can be used to do multiplexing and standardless genotyping as described herein.

To simplify the nickase mass spectrum, the two complementary strands can be separated after digestion by using a single-stranded undigested PCR product as a capture probe. This probe (preparation shown below in Example 8C) can be hybridized to the nickase fragments in hybridization buffer containing 200 mM sodium citrate and 1% blocking reagent (Bushranger Mannheim). The reaction is heated to 95° C. for 5 minutes and cooled to room temperature over 30 minutes by using a thermal cycler (PT-200 DNA engine, MJ Research, Waltham, Mass.). The capture probe-nickase fragment is immobilized on 140 μg of streptavidin-coated magnetic beads. The beads are subsequently washed three times with 70 mM ammonium citrate. The captured single-stranded nickase fragments are eluted by heating to 80° C. for 5 minutes in 5 μL of 50 mM ammonium hydroxide.

C. Preparation of Capture Probe

The capture probe is prepared by amplifying the human β-globins gene (3' end of intone 1 to 5' end of axon 2) via PCR methods in a total volume of 50 μL containing of Gene Amp 1×PCR Buffer II, 10 mM Tris-HCl, pH 8.3, 50 mM KCl, 2 mM $MgCl_2$, 0.2 mM dNTP mix, 10 pmol of each primer (forward primer 5'-ACTGGGCATGTGGAGACAG-3'(SEQ ID NO: 66) and biotinylated reverse primer bio5'-GCACTTTCTTGCCATGAG-3'(SEQ ID: 67), 2 U of AmpliTaq Gold, and 200 ng of human genomic DNA. The template is denatured at 94° C. for 8 minutes. Thermal cycling is continued with a touch-down program that included 11 cycles of 20 seconds at 94° C., 30 seconds at 64° C., 1 minute at 72° C.; and a final extension of 5 minutes at 72° C. The amplicon is purified using UltraClean™ PCR clean-up kit (MO Bio Laboratories, Solano Beach, Calif.).

EXAMPLE 9

Multiplex Type IIS SNP Assay

A Type IIS assay was used to identify human gene sequences with known SNPs. The Type IIS enzyme used in this assay was Fok I which effected double-stranded cleavage of the target DNA. The assay involved the steps of amplification and Fok I treatment of the amplicon. In the amplification step, the primers were designed so that each PCR product of a designated gene target was less than 100 bases such that a Fok I recognition sequence was incorporated at the 5' and 3' end of the amplicon. Therefore, the fragments that were cleaved by Fok I included a center fragment containing the SNP of interest.

Ten human gene targets with known SNPs were analyzed by this assay. Sequences of the ten gene targets, as well as the primers used to amplify the target regions, are found in Table 5. The ten targets were lipoprotein lipase, prothrombin, factor V, cholesterol ester transfer protein (CETP), factor VII, factor XIII, HLA-H exon 2, HLA-H exon 4, methylenetetrahydrofolate reductase (MTHR), and P53 exon 4 codon 72.

Amplification of the ten human gene sequences were carried out in a single 50 μL volume PCR reaction with 20 ng of human genomic DNA template in 5 PCR reaction tubes. Each reaction vial contained 1×PCR buffer (Qiagen), 200 μM dNTPs, 1U Hotstar Taq polymerase (Qiagen), 4 mM $MgCl_2$, and 10 pmol of each primer. US8, having sequence of 5'TCAGTCACGACGTT3'(SEQ ID NO: 68), and US9, having sequence of 5'CGGATAACAATTTC3'(SEQ ID NO: 69), were used for the forward and reverse primers respectively. Moreover, the primers were designed such that a Fok I recognition site was incorporated at the 5' and 3' ends of the amplicon. Thermal cycling was performed in 0.2 mL tubes or a 96 well plate using a MJ Research Thermal Cycler (calculated temperature) with the following cycling parameters: 94° C. for 5 minutes; 45 cycles: 94° C. for 20 seconds, 56° C. for 20 seconds, 72° C. for 60 seconds; and 72° C. for 3 minutes.

Following PCR, the sample was treated with 0.2 U Exonuclease I (Amersham Pharmacia) and S Alkaline Phosphotase (Amersham Pharmacia) to remove the unincorporated primers and dNTPs. Typically, 0.2 U of exonuclease I and SAP were added to 5 μL of the PCR sample. The sample was then incubated at 37° C. for 15 minutes. Exonuclease I and SAP were then inactivated by heating the sample up to 85° C. for 15 minutes. Fok I digestion was performed by adding 2 U of Fok I (New England Biolab) to the 5 uL PCR sample and incubating at 37° C. for 30 minutes. Since the Fok I restriction sites are located on both sides of the amplicon, the 5' and 3' cutoff fragments have higher masses than the center fragment containing the SNP. The sample was then purified by anion exchange and analyzed by MALDI-TOF mass spectrometry as described in Example 4. The masses of the gene fragments from this multiplexing experiment are listed in Table 6. These gene fragments were resolved in mass spectra thereby allowing multiplex analysis of sequence variability in these genes.

TABLE 5

Genes for Multiplex Type IIS Assay

| Gene | Sequence | Seq. ID No. | Primers | Seq. ID No. |
|---|---|---|---|---|
| Lipoprotein Lipase (Asn291Ser) | cctttgagaa agggctctgc ttgagttgta gaaagaaccg ctgcaacaat **ctgggctatg** agatca[a▶g]taa agtcagagcc **aaaagaagca** gcaaaatgta | 98-99 | 5' caatttcatcgctggatgcaatct gggctatgagatc 3'<br>5' caatttcacacagcggatgcttct tttggctctgact3' | 70<br>71 |
| Prothrombin | 26731 gaattatttttgtgtttctaaaactatggt tc**ccaataaaagtgactctc**<br>26781 agc[g▶a]agcctc aatgctccca gtgctattca tgggcagctc tctgggctca | 100-101 | 5' tcagtcacgacgttggat**gccaa taaaagtgactctcagc**3'<br>5' cggataacaatttcggat**gcact gggagcattgaggc**3' | 72<br>73 |
| Factor V (Arg506Gln) | taataggact acttctaatc tgtaagagca **gatccctgga caggc[g▶a]agga**<br>**atacaggtat** tttgtccttg aagtaacctt tcag | 102-103 | 5' tcagtcacgacgttggat**gagca gatccctggacaggc**3'<br>5' cggataacaatttcggat**ggaca aaatacctgtattcc**3' | 74<br>75 |
| Cholesterol ester transfer protein (CETP) (I405V) | 1261 ctcaccatgg gcatt**tgatt** gcagagcage **tccgagtcc[g▶a]** tccagagctt<br>1311 **cctgcagtca** atgatcaccg ctgtgggcat ccctgaggtc atgtctcgta | 104-105 | 5' tcagtcacgacgttggat**gcaga gcagctccgagtc** 3'<br>5' **cagcggtgatcatt**ggatgcagg **aagctctgg** 3' | 76<br>77 |

TABLE 5-continued

Genes for Multiplex Type IIS Assay

| Gene | Sequence | Seq. ID No. | Primers | Seq. ID No. |
|---|---|---|---|---|
| Factor VII<br>(R353Q) | 1221 agcaaggact cctgcaaggg ggacagtgga ggcccacatg ccacccacta<br>1271 cc[a▸g]gggcacg tggtacctga cgggcatcgt cagctggggc cagggctgcg | 106-<br>107 | 5' tcagtcacgacgttggatgccca catgccacccactac 3'<br>5' cggataacaatttcggatgcccg tcaggtaccacg 3' | 78<br>79 |
| Factor XIII<br>(V34L) | 111 caataactct aatgcagcgg aagatgacct gcccacagtg gagcttcagg<br>161 gc[g▸t]tggtgcc ccggggcgtc aacctgcaag gtatgagcat acccccccttc | 108-<br>109 | 5' tcagtcacgacgttggatgccca cagtggagcttcag 3'<br>5' gctcataccttgcaggatgacg | 80<br>81 |
| HLA-H exon 2<br>(His63Asp) | 361 ttgaagcttt gggctacgtg gatgaccagc tgttcgtgtt ctatgat[c▸g]at<br>411 gagagtcgcc gtgtggagcc ccgaactcca tgggtttcca gtagaatttc | 110-<br>111 | 5' tcagtcacgacgttggatgacca gctgttcgtgttc 3'<br>5' tacatggagttcggggatgcaca cggcgactctc 3' | 82<br>83 |
| HLA-H exon 4<br>(Cys282Tyr) | 1021 ggataacctt ggctgtaccc cctggggaag agcagagata tacgt[g▸a]ccag<br>1071 gtggagcacc caggcctgga tcagcccctc attgtgatct gggagccctc | 112-<br>113 | 5' tcagtcacgacgttggatggggga agagcagagatatacgt 3'<br>5' gaggggctgatccaggatgggt gctccac 3' | 84<br>85 |
| Methylentetrahy drofolateredctase (MTHR)<br>(Ala222Val) | 761 tgaagcactt gaagga gaag gtgtctgcgg114- gag[c▸t]cgattt catcatcacg<br>811 cagcttttct ttgaggctga cacattcttc | 5'<br>115 | 86 tcagtcacgacgttggatggggga agagcagagatatacgt 3'<br>5' gaggggctgatccaggatgggt gctccac 3' | <br>87 |
| P53 Exon4 Codon 72<br>(Arg72Pro) | 12101 tccagatgaa gctcccagaa tgccagaggc tgctcccc[g▸c]c gtggcccctg<br>12151 caccagcagc tcctacaccg gcggcccctg | 116-<br>117 | 5' gatgaagctcccaggatgccag aggc 3'<br>5' gccgccggtgtaggatgctgctg gtgc 3' | 88<br>89 |

TABLE 6

The mass of Center Fragments for Ten Different SNP Typing by IIS Assay

| Gene | LPL($^{Asn}291^{Ser}$) | | Prothrombin | | FV($^{Arg}506^{Gln}$) | | CETP($^{I}405^{V}$) | | FVII($^{R}353^{Q}$) | | FXIII($^{V}34$) | |
|---|---|---|---|---|---|---|---|---|---|---|---|---|
| Genotype | A | G | G | A | G | A | G | A | G | A | G | T |
| + strand mass (Da) | 6213 | 6229 | 5845 | 5829 | 5677 | 5661 | 3388 | 3372 | 6128 | 6112 | 5058 | 5033 |
| − strand mass (Da) | 6129 | 6114 | 5949 | 5964 | 5472 | 5487 | 3437 | 3452 | 6174 | 6189 | 4916 | 4940 |

| Gene | Hlah2 | | Hlah4 | | MTHR($^{Ala}222^{Val}$) | | P53exon4($^{Arg}72^{Pro}$) | |
|---|---|---|---|---|---|---|---|---|
| Genotype | C | G | G | A | C | T | G | C |
| + strand mass (Da) | 5889 | 5929 | 4392 | 4376 | 4400 | 4415 | 4586 | 4546 |
| − strand mass − (Da) | 5836 | 5796 | 4319 | 4334 | 4368 | 4352 | 4724 | 4764 |

EXAMPLE 10

Exemplary Use of Parental Medical History Parameter for Stratification of Healthy Datebase A healthy database can be used to associate a disease state with a specific allele (SNP) that has been found to show a strong association between age and the allele, in particular the homozygous genotype. The method involves using the same healthy database used to identify the age dependent association, however stratification is by information given by the donors about common disorders from which their parents suffered (the donor's familial history of disease). There are three possible answers a donor could give about the health status of their parents: neither were affected, one was affected or both were affected. Only donors above a certain minimum age, depending on the disease, are utilized, as the donors parents must be old enough to have exhibited clinical disease phenotypes. The genotype frequency in each of these groups is determined and compared with each other. If there is an association of the marker in the donor to a disease the frequency of the heterozyous genotype will be increased. The frequency of the homozygous genotype should not increase, as it should be significantly underrepresented in the healthy population.

EXAMPLE 11

Method and Device for Identifying a Biological Sample Description

Figure 24:
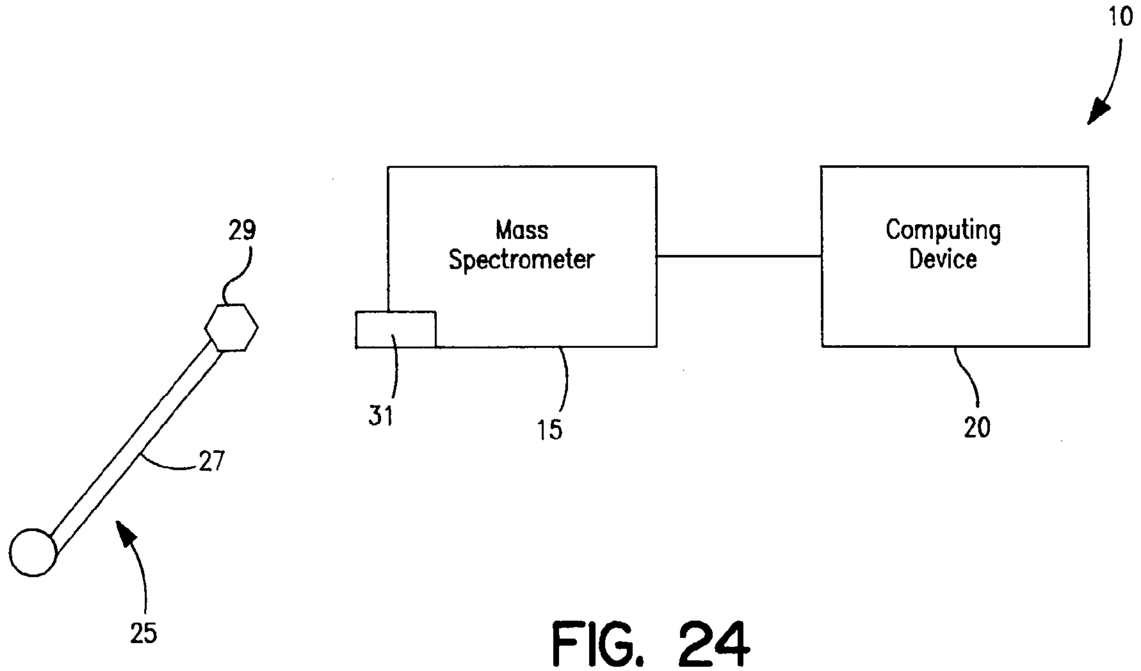
FIG. 24 is a block diagram showing a system provided herein.

A method and device for identifying a biological sample is provided. Referring now to FIG. 24, an apparatus 10 for identifying a biological sample is disclosed. The apparatus 10 for identifying a biological sample generally comprises a mass spectrometer 15 communicating with a computing device 20. In an embodiment, the mass spectrometer can be a MALDI-TOF mass spectrometer manufactured by Bruker-Franzen Analytik GmbH; however, it will be appreciated that other mass spectrometers can be substituted. The computing device 20 is typically a general purpose computing device. It will be appreciated that the computing device could be alternatively configured, for example, it can be integrated with the mass spectrometer or could be part of a computer in a larger network system.

The apparatus 10 for identifying a biological sample can operate as an automated identification system having a robot 25 with a robotic arm 27 configured to deliver a sample plate 29 into a receiving area 31 of the mass spectrometer 15. In such a manner, the sample to be identified can be placed on the plate 29 and automatically received into the mass spectrometer 15. The biological sample is then processed in the mass spectrometer to generate data indicative of the mass of DNA fragments in the biological sample. This data can be sent directly to computing device 20, or can have some preprocessing or filtering performed within the mass spectrometer. In an embodiment, the mass spectrometer 15 transmits unprocessed and unfiltered mass spectrometry data to the computing device 20. It will be appreciated that the analysis in the computing device can be adjusted to accommodate preprocessing or filtering performed within the mass spectrometer.

Figure 25:
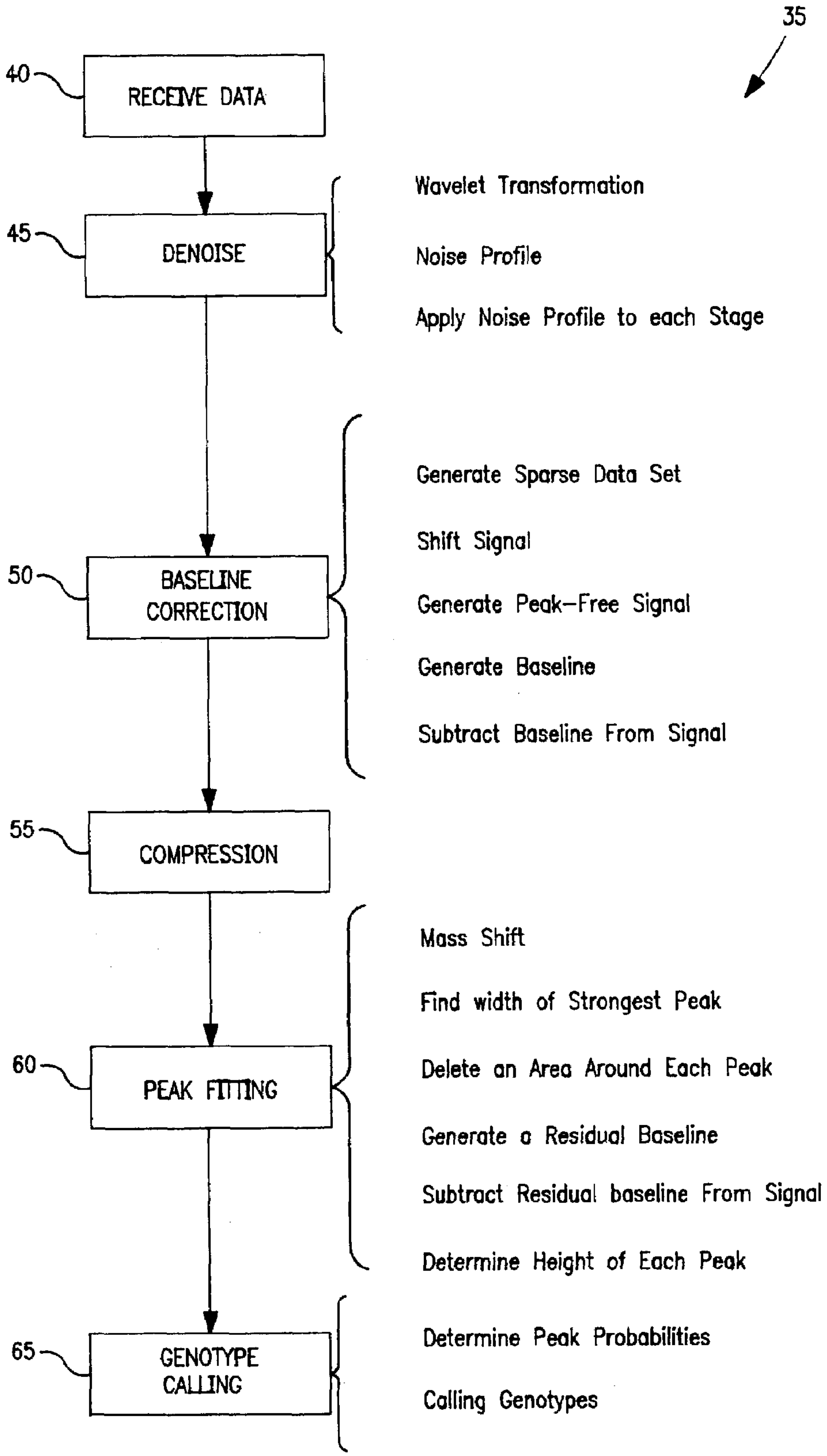
FIG. 25 is a flowchart of a method of identifying a biological sample provided herein.

Referring now to FIG. 25, a general method 35 for identifying a biological sample is shown. In method 35, data are received into a computing device from a test instrument in block 40. Generally the data are received in a raw, unprocessed and unfiltered form, but alternatively can have some form of filtering or processing applied. The test instrument of an exemplary embodiment is a mass spectrometer as described above. It will be appreciated that other test instruments could be substituted for the mass spectrometer.

The data generated by the test instrument, and in particular the mass spectrometer, includes information indicative of the identification of the biological sample. More specifically, the data are indicative of the DNA composition of the biological sample. Typically, mass spectrometry data gathered from DNA samples obtained from DNA amplification techniques are noisier than, for example, those from typical protein samples. This is due in part because protein samples are more readily prepared in more abundance, and protein samples are more easily ionizable as compared to DNA samples. Accordingly, conventional mass spectrometer data analysis techniques are generally ineffective for DNA analysis of a biological sample. To improve the analysis capability so that DNA composition data can be more readily discerned, an embodiment uses wavelet technology for analyzing the DNA mass spectrometry data. Wavelets are an analytical tool for signal processing, numerical analysis, and mathematical modeling. Wavelet technology provides a basic expansion function which is applied to a data set. Using wavelet decomposition, the data set can be simultaneously analyzed in the time and frequency domains. Wavelet transformation is the technique of choice in the analysis of data that exhibit complicated time (mass) and frequency domain information, such as MALDI-TOF DNA data. Wavelet transforms as described herein have superior denoising properties as compared to conventional Fourier analysis techniques. Wavelet transformation has proven to be particularly effective in interpreting the inherently noisy MALDI-TOF spectra of DNA samples. In using wavelets, a "small wave" or "scaling function" is used to transform a data set into stages, with each stage representing a frequency component in the data set. Using wavelet transformation, mass spectrometry data can be processed, filtered, and analyzed with sufficient discrimination to be useful for identification of the DNA composition for a biological sample.

Referring again to FIG. 25, the data received in block 40 is denoised in block 45. The denoised data then has a baseline correction applied in block 50. A baseline correction is generally necessary as data coming from the test instrument, in particular a mass spectrometer instrument, has data arranged in a generally exponentially decaying manner. This generally exponential decaying arrangement is not due to the composition of the biological sample, but is a result of the physical properties and characteristics of the test instrument, and other chemicals involved in DNA sample preparation. Accordingly, baseline correction substantially corrects the data to remove a component of the data attributable to the test system, and sample preparation characteristics.

After denoising in block 45 and the baseline correction in block 50, a signal remains which is generally indicative of the composition of the biological sample. Due to the extraordinary discrimination required for analyzing the DNA composition of the biological sample, the composition is not readily apparent from the denoised and corrected signal. For example, although the signal can include peak areas, it is not yet clear whether these "putative" peaks actually represent a DNA composition, or whether the putative peaks are the result of a systemic or chemical aberration. Further, any call of the composition of the biological sample would have a probability of error which would be unacceptable for clinical or therapeutic purposes. In such critical situations, there needs to be a high degree of certainty that any call or identification of the sample is accurate. Therefore, additional data processing and interpretation is necessary before the sample can be accurately and confidently identified.

Since the quantity of data resulting from each mass spectrometry test is typically thousands of data points, and an automated system can be set to perform hundreds or even thousands of tests per hour, the quantity of mass spectrometry data generated is enormous. To facilitate efficient transmission and storage of the mass spectrometry data, block 55 shows that the denoised and baseline corrected data are compressed.

In one embodiment, the biological sample is selected and processed to have only a limited range of possible compositions. Accordingly, it is therefore known where peaks indicating composition should be located, if present. Taking advantage of knowing the location of these expected peaks, in block 60 the method 35 matches putative peaks in the processed signal to the location of the expected peaks. In such a manner, the probability of each putative peak in the data being an actual peak indicative of the composition of the biological sample can be determined. Once the probability of each peak is determined in block 60, then in block 65 the method 35 statistically determines the composition of the biological sample, and determines if confidence is high enough to calling a genotype.

Figure 26:
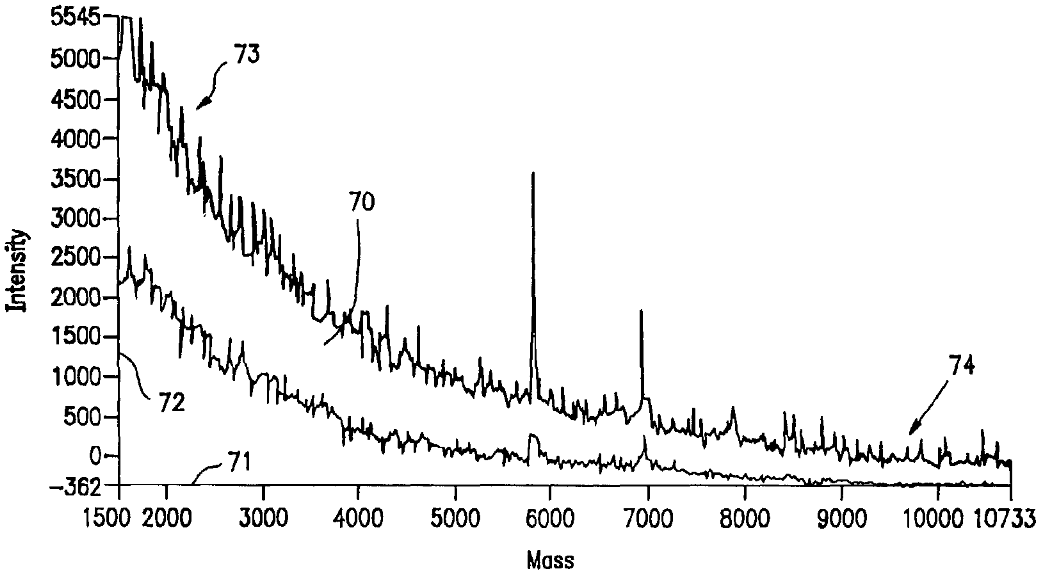
FIG. 26 is a graphical representation of data from a mass spectrometer.

Referring again to block 40, data are received from the test instrument, which can be a mass spectrometer. In a specific illustration, FIG. 26 shows an example of data from a mass spectrometer. The mass spectrometer data 70 generally comprises data points distributed along an x-axis 71 and a y-axis 72. The x-axis 71 represents the mass of particles detected, while the y-axis 72 represents a numerical concentration of the particles. As can be seen in FIG. 26, the mass spectrometry data 70 is generally exponentially decaying with data at the left end of the x-axis 73 generally decaying in an exponential manner toward data at the heavier end 74 of the x-axis 71. The general exponential presentation of the data is not indicative of the composition of the biological sample, but is more reflective of systematic error and characteristics. Further, as described above and illustrated in FIG. 26, considerable noise exists in the mass spectrometry DNA data 70.

Referring again to block 45, where the raw data received in block 40 is denoised, the denoising process will be described in more detail. As illustrated in FIG. 25, the denoising process generally entails 1) performing a wavelet transformation on the raw data to decompose the raw data into wavelet stage coefficients; 2) generating a noise profile from the highest stage of wavelet coefficients; and 3) applying a scaled noise profile to other stages in the wavelet transformation. Each step of the denoising process is further described below.

Figure 27:
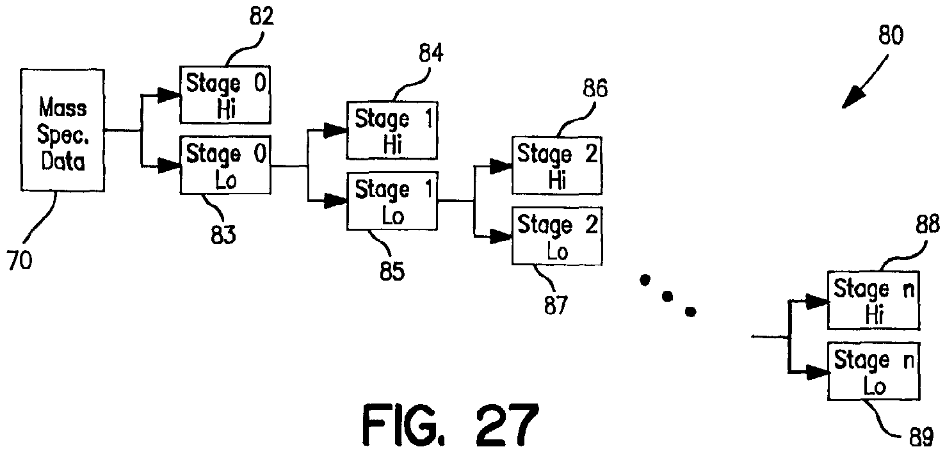
FIG. 27 is a diagram of wavelet transformation of mass spectrometry data.

Referring now to FIG. 27, the wavelet transformation of the raw mass spectrometry data is generally diagramed. Using wavelet transformation techniques, the mass spectrometry data 70 is sequentially transformed into stages. In each stage, the data are represented in a high stage and a low stage, with the low stage acting as the input to the next sequential stage. For example, the mass spectrometry data 70 is transformed into stage 0 high data 82 and stage 0 low data 83. The stage 0 low data 83 is then used as an input to the next level transformation to generate stage 1 high data 84 and stage 1 low data 85. In a similar manner, the stage 1 low data 85 is used as an input to be transformed into stage 2 high data 86 and stage 2 low data 87. The transformation is continued until no more useful information can be derived by further wavelet transformation. For example, in the one embodiment a 24-point wavelet is used. More particularly a wavelet commonly referred to as the Daubechies 24 is used to decompose the raw data. It will be appreciated that other wavelets can be used for the wavelet transformation. Since each stage in a wavelet transformation has one-half the data points of the previous stage, the wavelet transformation can be continued until the stage n low data 89 has around 50 points. Accordingly, the stage n high 88 would contain about 100 data points. Since the exemplary wavelet is 24 points long, little data or information can be derived by continuing the wavelet transformation on a data set of around 50 points.

Figure 28:
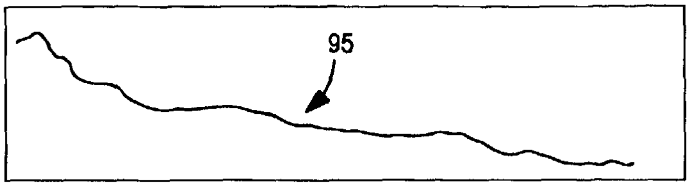
FIG. 28 is a graphical representation of wavelet stage 0 hi data.
Figure 29:
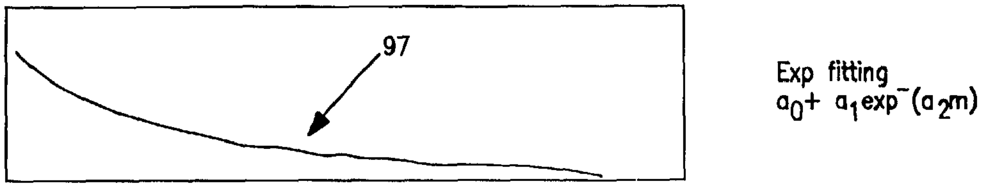
FIG. 29 is a graphical representation of stage 0 noise profile.

FIG. 28 shows an example of stage 0 high data 95. Since stage 0 high data 95 is generally indicative of the highest frequencies in the mass spectrometry data, stage 0 high data 95 will closely relate to the quantity of high frequency noise in the mass spectrometry data. In FIG. 29, an exponential fitting formula has been applied to the stage 0 high data 95 to generate a stage 0 noise profile 97. In particular, the exponential fitting formula is in the format $A_0+A_1$ EXP $(-A_2\ m)$. It will be appreciated that other exponential fitting formulae or other types of curve fits can be used.

Figure 30:
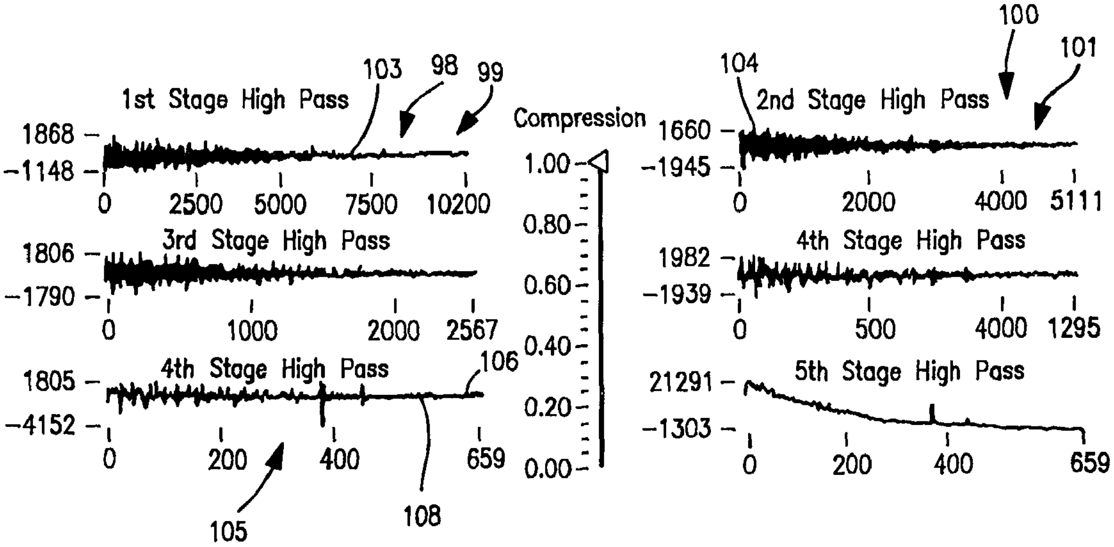
FIG. 30 is a graphical representation of generating stage noise standard deviations.

Referring now to FIG. 30, noise profiles for the other high stages are determined. Since the later data points in each stage will likely be representative of the level of noise in each stage, only the later data points in each stage are used to generate a standard deviation figure that is representative of the noise content in that particular stage. More particularly, in generating the noise profile for each remaining stage, only the last five percent of the data points in each stage are analyzed to determined a standard deviation number. It will be appreciated that other numbers of points, or alternative methods could be used to generate such a standard deviation figure.

The standard deviation number for each stage is used with the stage 0 noise profile (the exponential curve) 97 to generate a scaled noise profile for each stage. For example, FIG. 30 shows that stage 1 high data 98 has stage 1 high data 103 with the last five percent of the data points represented by area 99. The points in area 99 are evaluated to determine a standard deviation number indicative of the noise content in stage 1 high data 103. The standard deviation number is then used with the stage 0 noise profile 97 to generate a stage 1 noise profile.

In a similar manner, stage 2 high 100 has stage 2 high data 104 with the last five percent of points represented by area 101. The data points in area 101 are then used to calculate a standard deviation number which is then used to scale the stage 0 noise profile 97 to generate a noise profile for stage 2 data. This same process is continued for each of the stage high data as shown by the stage n high 105. For stage n high 105, stage n high data 108 has the last five percent of data points indicated in area 106. The data points in area 106 are used to determine a standard deviation number for stage n. The stage n standard deviation number is then used with the stage 0 noise profile 97 to generate a noise profile for stage n. Accordingly, each of the high data stages has a noise profile.

Figure 31:
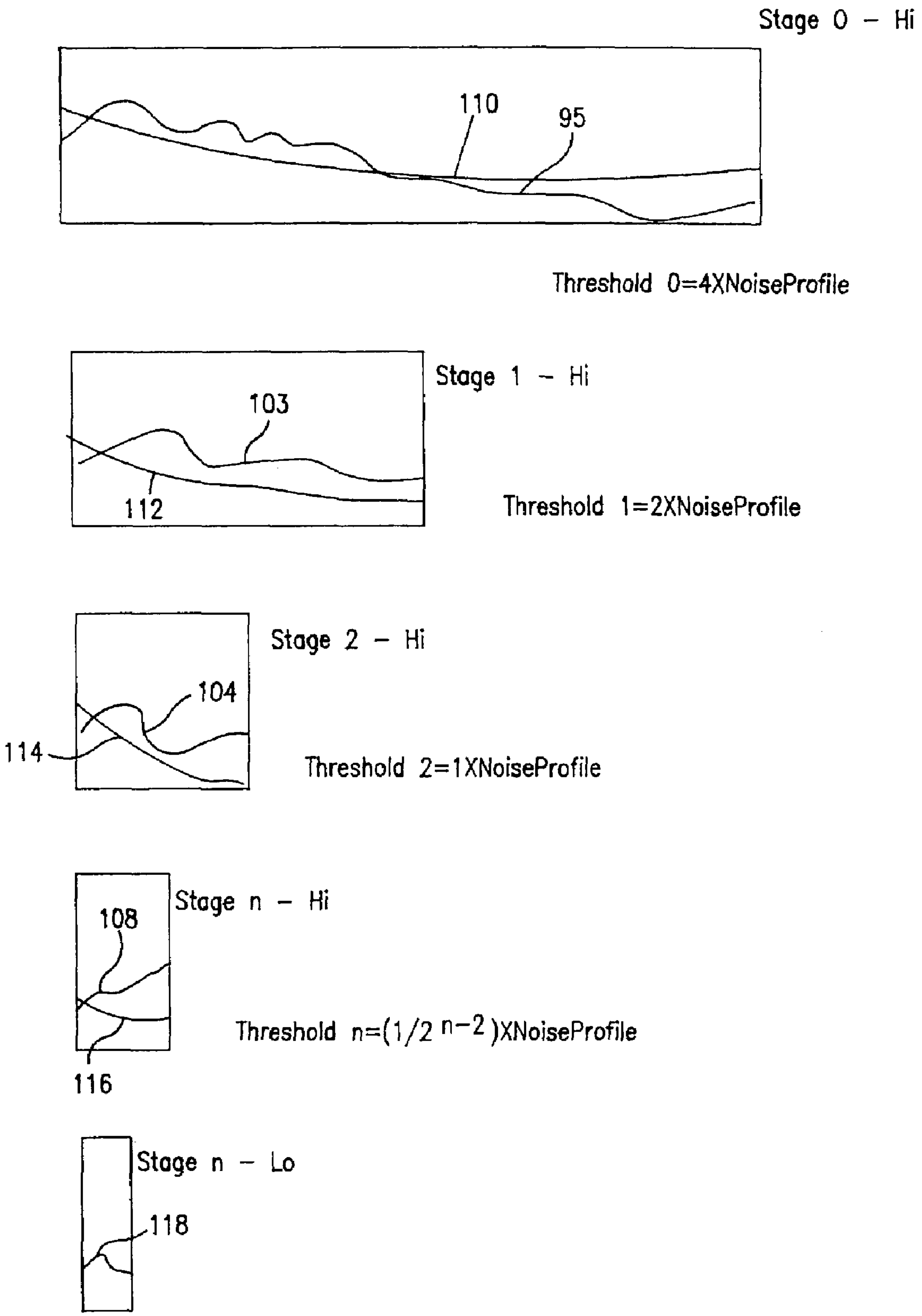
FIG. 31 is a graphical representation of applying a threshold to data stages.
Figure 35:
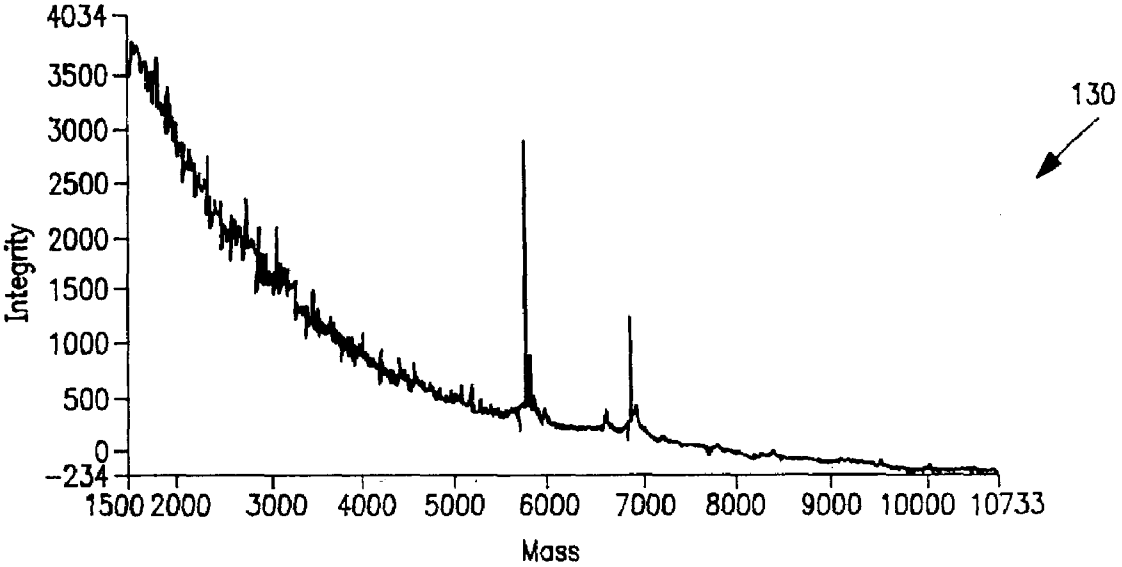
FIG. 35 is a graphical representation of a denoised and shifted signal.

FIG. 31 shows how the noise profile is applied to the data in each stage.

Generally, the noise profile is used to generate a threshold which is applied to the data in each stage. Since the noise profile is already scaled to adjust for the noise content of each stage, calculating a threshold permits further adjustment to tune the quantity of noise removed. Wavelet coefficients below the threshold are ignored while those above the threshold are retained. Accordingly, the remaining data have a substantial portion of the noise content removed.

Due to the characteristics of wavelet transformation, the lower stages, such as stage 0 and 1, will have more noise content than the later stages such as stage 2 or stage n. Indeed, stage n low data are likely to have little noise at all. Therefore, in an embodiment, the noise profiles are applied more aggressively in the lower stages and less aggressively in the later stages. For example, FIG. 31 shows that stage 0 high threshold is determined by multiplying the stage 0 noise profile by a factor of four. In such a manner, significant numbers of data points in stage 0 high data 95 will be below the threshold and therefore eliminated. Stage 1 high threshold 112 is set at two times the noise profile for the stage 1 high data, and stage 2 high threshold 114 is set equal to the noise profile for stage 2 high. Following this geometric progression, stage n high threshold 116 is therefore determined by scaling the noise profile for each respective stage n high by a factor equal to ($\frac{1}{2}^{n-2}$). It will be appreciated that other factors can be applied to scale the noise profile for each stage. For example, the noise profile can be scaled more or less aggressively to accommodate specific systemic characteristics or sample compositions. As indicated above, stage n low data does not have a noise profile applied as stage n low data 118 is assumed to have little or no noise content. After the scaled noise profiles have been applied to each high data stage, the mass spectrometry data 70 has been denoised and is ready for further processing. A wavelet transformation of the denoised signal results in the sparse data set 120 as shown in FIG. 31.

Referring again to FIG. 25, the mass spectrometry data received in block 40 has been denoised in block 45 and is now passed to block 50 for baseline correction. Before performing baseline correction, the artifacts introduced by the wavelet transformation procedure can be removed. Wavelet transformation results vary slightly depending upon which point of the wavelet is used as a starting point. For example, an exemplary embodiment uses the 24-point Daubechies-24 wavelet. By starting the transformation at the 0 point of the wavelet, a slightly different result will be obtained than if starting at points 1 or 2 of the wavelet. Therefore, the denoised data are transformed using every available possible starting point, with the results averaged to determine a final denoised and shifted signal. For example, FIG. 33 shows that the wavelet coefficient is applied 24 different times and then the results averaged to generate the final data set. It will be appreciated that other techniques can be used to accommodate the slight error introduced due to wavelet shifting.

Figure 58:
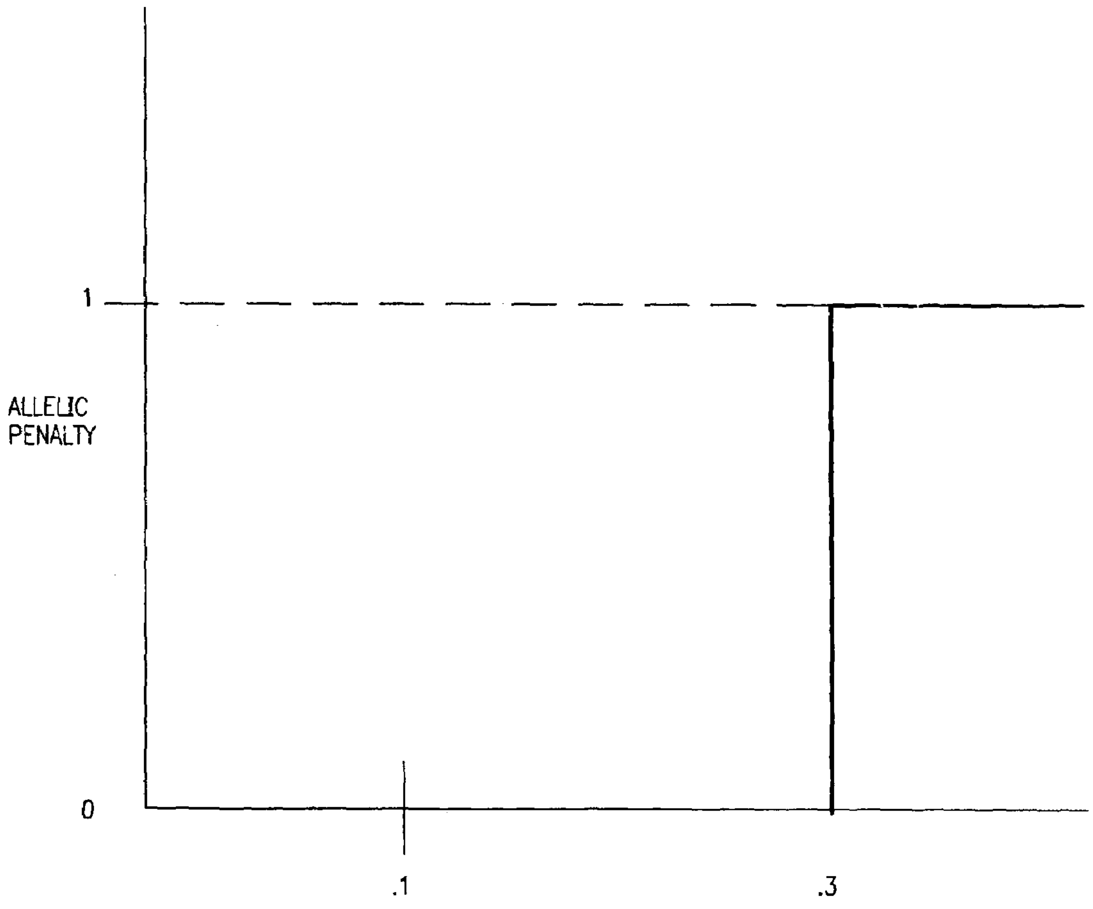
FIG. 58 is graphical representation of applying an allelic ratio to peak probability for standardless genotype processing.

The formula 125 is generally indicated in FIG. 33. Once the signal has been denoised and shifted, a denoised and shifted signal 130 is generated as shown in FIG. 58. FIG. 34 shows an example of the wavelet coefficient 135 data set from the denoised and shifted signal 130.

Figure 36:
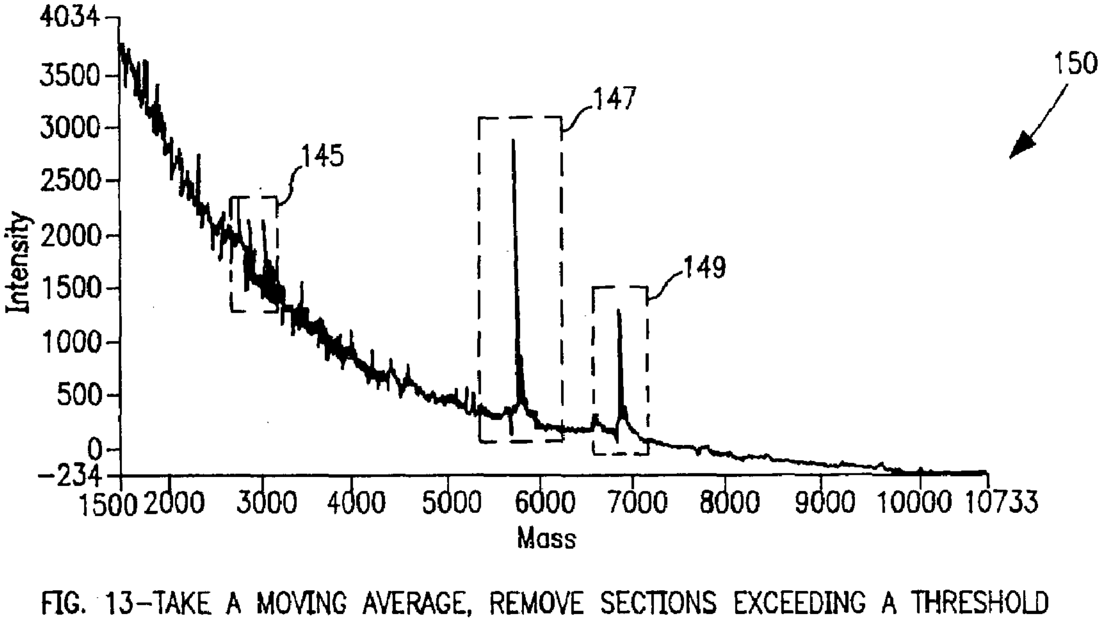
FIG. 36 is a graphical representation of removing peak sections.

FIG. 36 shows that putative peak areas 145, 147, and 149 are located in the denoised and shifted signal 150. The putative peak areas are systematically identified by taking a moving average along the signal 150 and identifying sections of the signal 150 which exceed a threshold related to the moving average. It will be appreciated that other methods can be used to identify putative peak areas in the signal 150.

Figure 37:
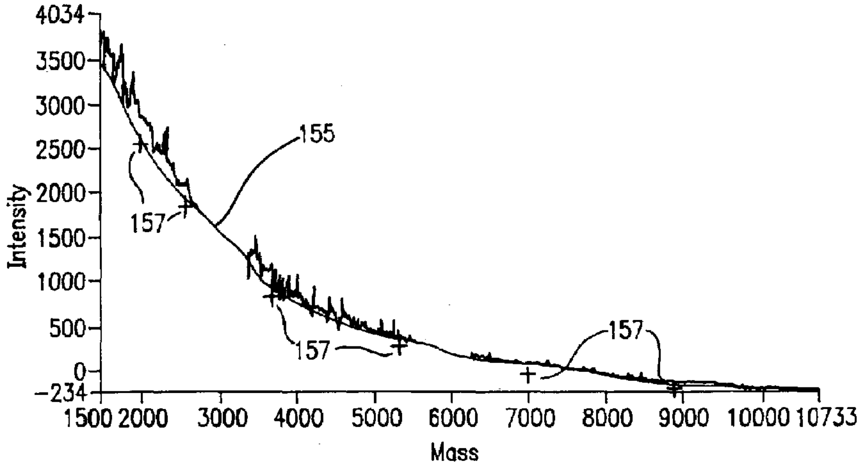
FIG. 37 is a graphical representation of generating a peak free signal.

Putative peak areas 145, 147 and 149 are removed from the signal 150 to create a peak-free signal 155 as shown in FIG. 37. The peak-free signal 155 is further analyzed to identify remaining minimum values 157, and the remaining minimum values 157 are connected to generate the peak-free signal 155.

Figure 38:
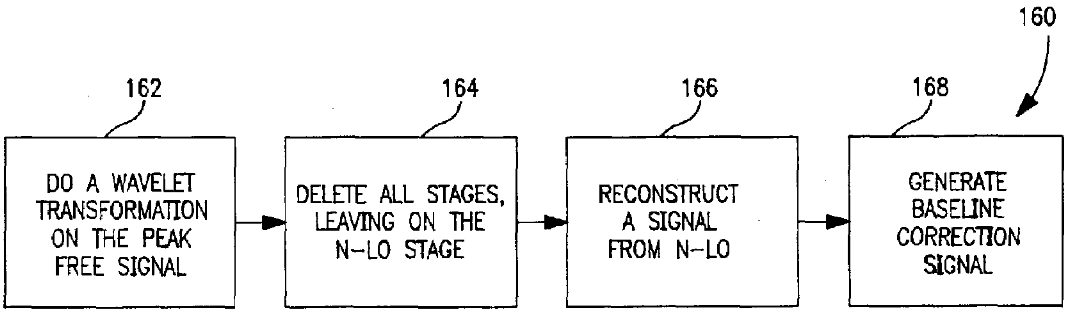
FIG. 38 is a block diagram of a method of generating a baseline correction.
Figure 39:
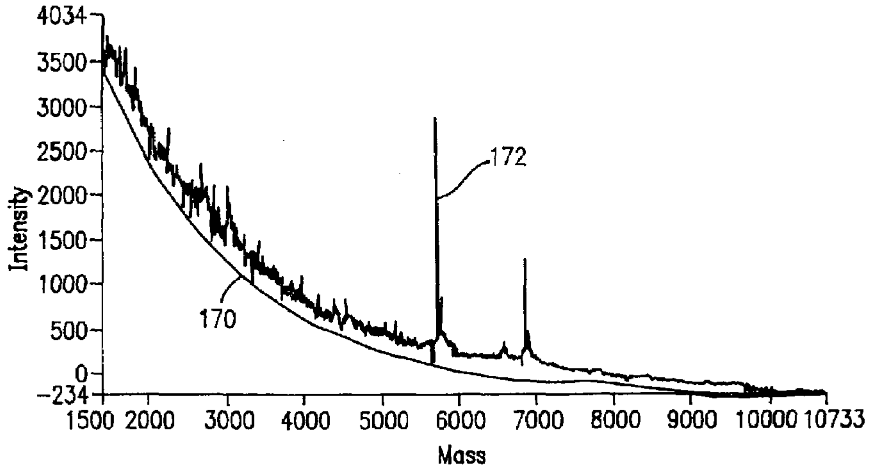
FIG. 39 is a graphical representation of a baseline and signal.

FIG. 38 shows a process of using the peak-free signal 155 to generate a baseline 170 as shown in FIG. 39. As shown in block 162, a wavelet transformation is performed on the peak-free signal 155. All the stages from the wavelet transformation are eliminated in block 164 except for the n low stage. The n low stage will generally indicate the lowest frequency component of the peak-free signal 155 and therefore will generally indicate the system exponential characteristics. Block 166 shows that a signal is reconstructed from the n low coefficients and the baseline signal 170 is generated in block 168.

Figures 40, 41:
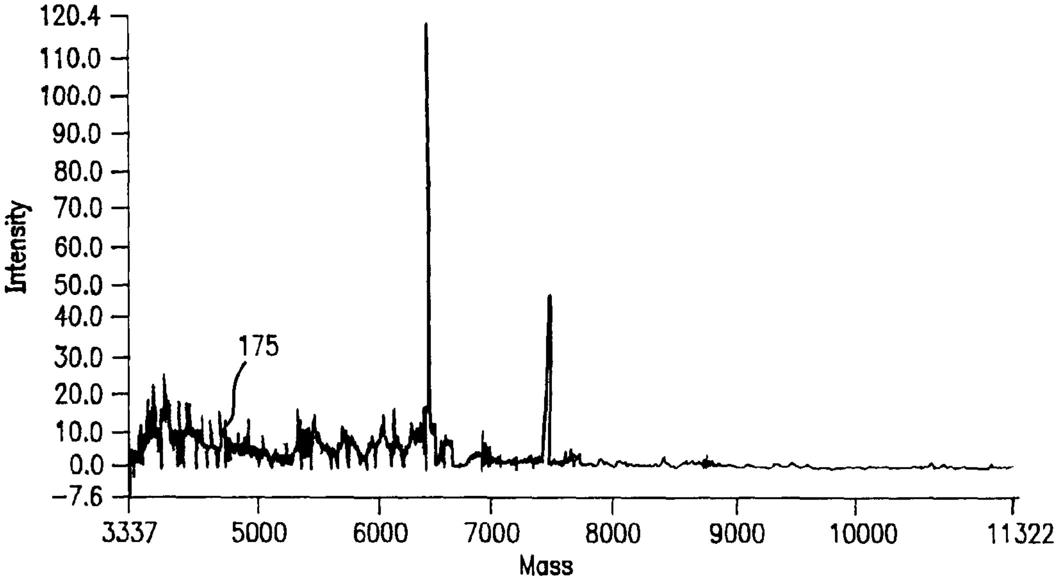
FIG. 40 is a graphical representation of a signal with baseline removed.
FIG. 41 is a table showing compressed data.

FIG. 39 shows a denoised and shifted data signal 172 positioned adjacent a correction baseline 170. The baseline correction 170 is subtracted from the denoised and shifted signal 172 to generate a signal 175 having a baseline correction applied as shown in FIG. 40. Although such a denoised, shifted, and corrected signal is sufficient for most identification purposes, the putative peaks in signal 175 are not identifiable with sufficient accuracy or confidence to call the DNA composition of a biological sample.

Referring again to FIG. 25, the data from the baseline correction 50 is now compressed in block 55; the compression technique used in an exemplary embodiment is detailed in FIG. 41. In FIG. 41 the data in the baseline corrected data are presented in an array format 182 with x-axis points 183 having an associated data value 184. The x-axis is indexed by the non-zero wavelet coefficients, and the associated value is the value of the wavelet coefficient. In the illustrated data example in table 182, the maximum value 184 is indicated to be 1000. Although a particularly advantageous compression technique for mass spectrometry data is shown, it will be appreciated that other compression techniques can be used. The data also can be stored without compression.

In compressing the data according to one embodiment, an intermediate format 186 is generated. The intermediate format 186 generally comprises a real number having a whole number portion 188 and a decimal portion 190. The whole number portion is the x-axis point 183 while the decimal portion is the value data 184 divided by the maximum data value. For example, in the data 182 a data value "25" is indicated at x-axis point "100". The intermediate value for this data point would be "100.025".

From the intermediate compressed data 186 the final compressed data 195 is generated. The first point of the intermediate data file becomes the starting point for the compressed data. Thereafter each data point in the compressed data 195 is calculated as follows: the whole number portion (left of the decimal) is replaced by the difference between the current and the last whole number. The remainder (right of the decimal) remains intact. For example, the starting point of the compressed data 195 is shown to be the same as the intermediate data point which is "100.025". The comparison between the first intermediate data point "100.025" and the second intermediate data point "150.220" is "50.220". Therefore, "50.220" becomes the second point of the compressed data 195. In a similar manner, the second intermediate point is "150.220" and the third intermediate data point is "500.0001". Therefore, the third compressed data becomes "350.000". The calculation for determining compressed data points is continued until the entire array of data points is converted to a single array of real numbers.

Figure 42:
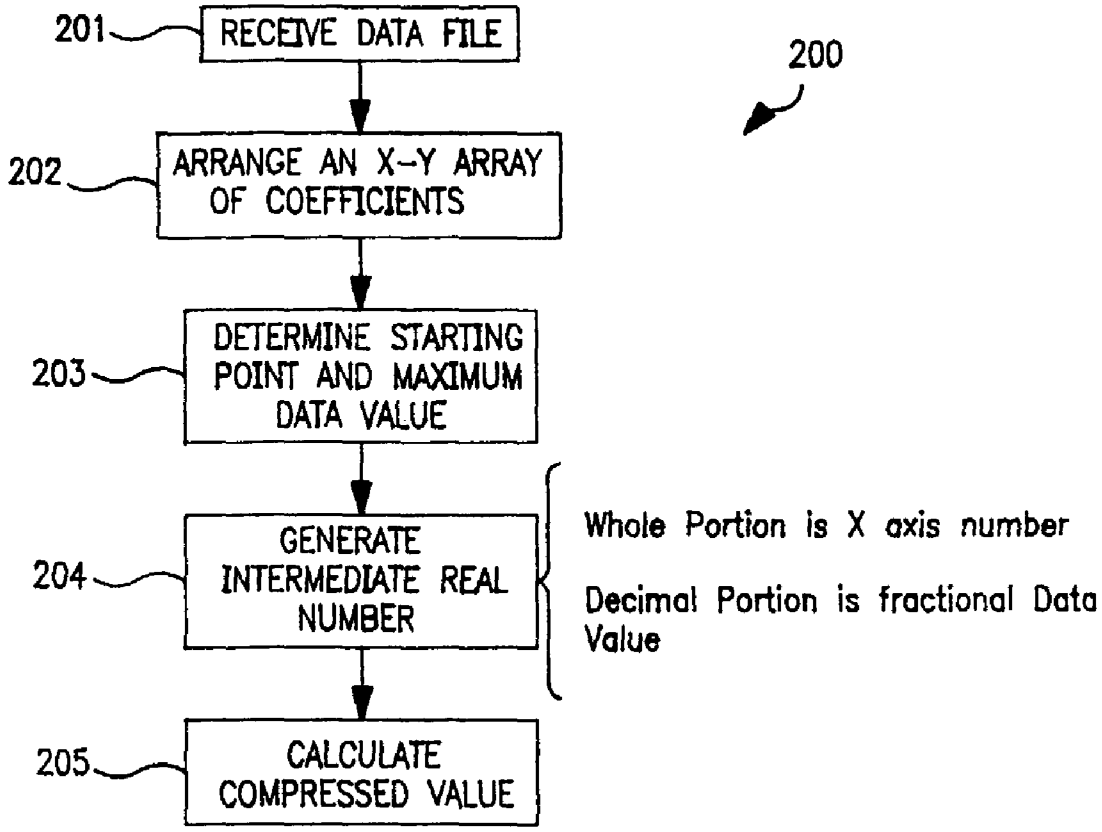
FIG. 42 is a flowchart of method for compressing data.

FIG. 42 generally describes the method of compressing mass spectrometry data, showing that the data file in block 201 is presented as an array of coefficients in block 202. The data starting point and maximum is determined as shown in block 203, and the intermediate real numbers are calculated in block 204 as described above. With the intermediate data points generated, the compressed data are generated in block 205. The described compression method is highly advantageous and efficient for compressing data sets such as a processed data set from a mass spectrometry instrument. The method is particularly useful for data, such as mass spectrometry data, that uses large numbers and has been processed to have occasional lengthy gaps in x-axis data. Accordingly, an x-y data array for processed mass spectrometry data can be stored with an effective compression rate of 10×or more. Although the compression technique is applied to mass spectrometry data, it will be appreciated that the method can also advantageously be applied to other data sets.

Figure 43:
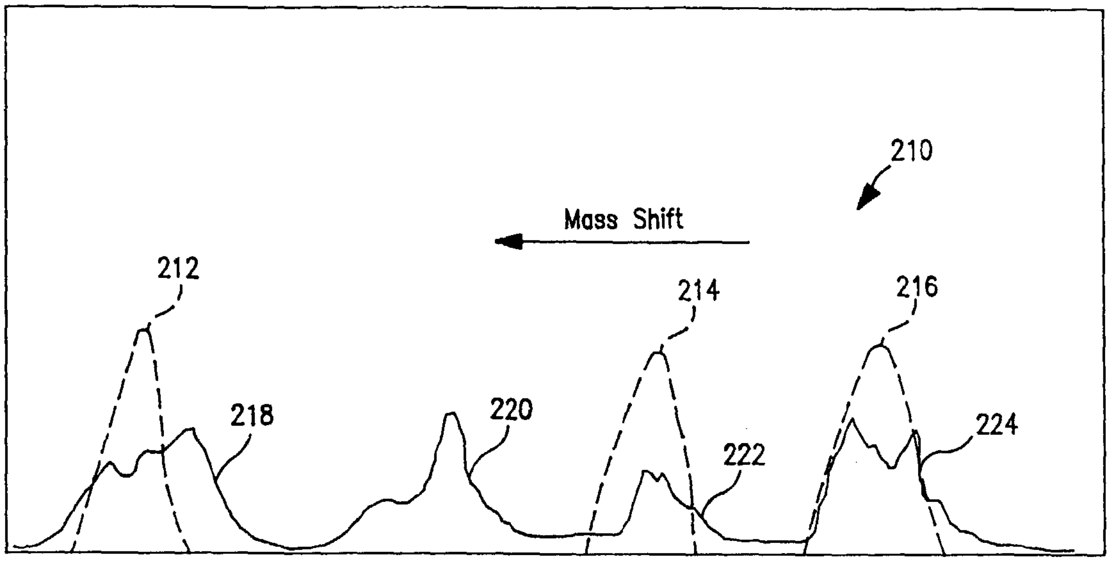
FIG. 43 is a graphical representation of mass shifting.

Referring again to FIG. 25, peak heights are now determined in block 60. The first step in determining peak height is illustrated in FIG. 43 where the signal 210 is shifted left or right to correspond with the position of expected peaks. As the set of possible compositions in the biological sample is known before the mass spectrometry data are generated, the possible positioning of expected peaks is already known. These possible peaks are referred to as expected peaks, such as expected peaks 212, 214, and 216. Due to calibration or other errors in the test instrument data, the entire signal can be shifted left or right from its actual position, therefore, putative peaks located in the signal, such as putative peaks 218, 222, and 224 can be compared to the expected peaks 212, 214, and 216, respectively. The entire signal is then shifted such that the putative peaks align more closely with the expected peaks.

Figure 44:
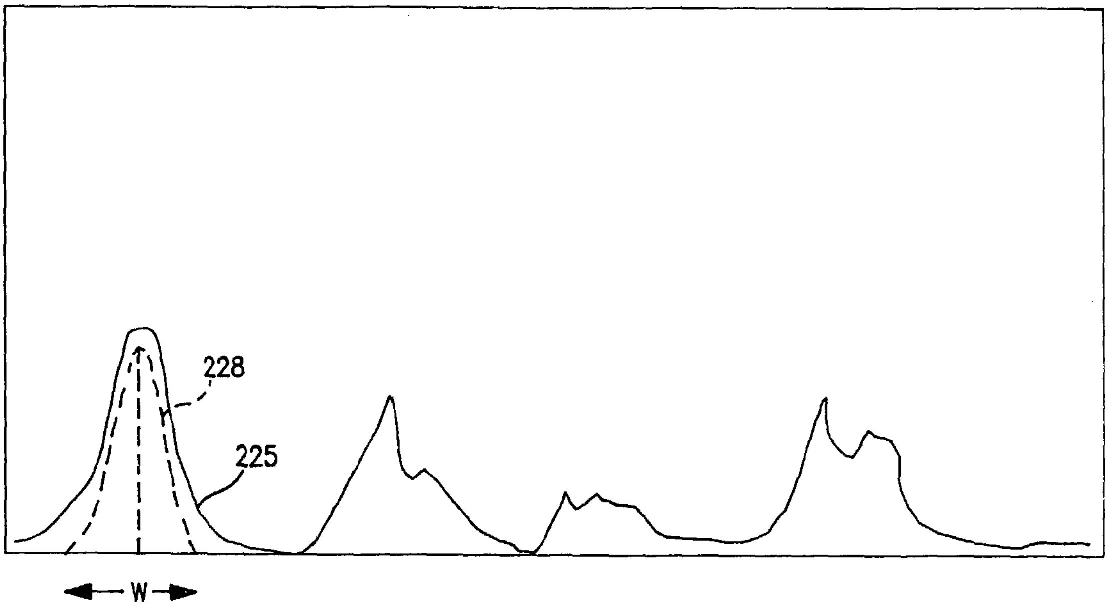
FIG. 44 is a graphical representation of determining peak width.

Once the putative peaks have been shifted to match expected peaks, the strongest putative peak is identified in FIG. 44. In one embodiment, the strongest peak is calculated as a combination of analyzing the overall peak height and area beneath the peak. For example, a moderately high but wide peak would be stronger than a very high peak that is extremely narrow. With the strongest putative peak identified, such as putative peak 225, a Gaussian 228 curve is fit to the peak 225. Once the Gaussian is fit, the width (W) of the Gaussian is determined and will be used as the peak width for future calculations.

As generally addressed above, the denoised, shifted, and baseline-corrected signal is not sufficiently processed for confidently calling the DNA composition of the biological sample. For example, although the baseline has generally been removed, there are still residual baseline effects present. These residual baseline effects are therefore removed to increase the accuracy and confidence in making identifications.

Figure 45:
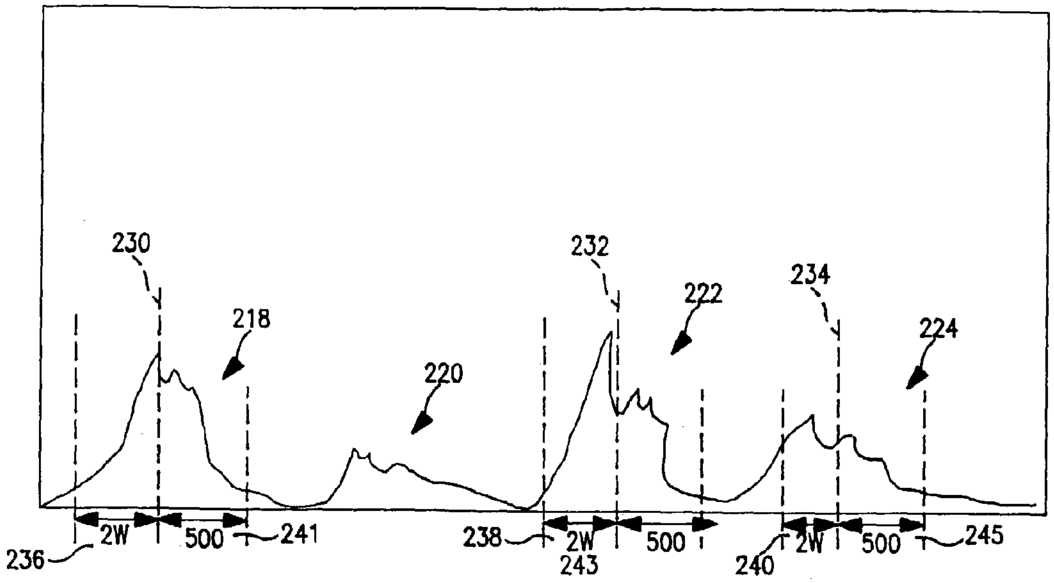
FIG. 45 is a graphical representation of removing peaks.

To remove the residual baseline effects, FIG. 45 shows that the putative peaks 218, 222, and 224 are removed from the baseline corrected signal. The peaks are removed by identifying a center line 230, 232, and 234 of the putative peaks 218, 222, and 224, respectively and removing an area to the left and to the right of the identified center line. For each putative peak, an area equal to twice the width (W) of the Gaussian is removed from the left of the center line, while an area equivalent to 50 daltons is removed from the right of the center line. It has been found that the area representing 50 daltons is adequate to sufficiently remove the effect of salt adducts which can be associated with an actual peak. Such adducts appear to the right of an actual peak and are a natural effect from the chemistry involved in acquiring a mass spectrum. Although a 50 Dalton buffer has been selected, it will be appreciated that other ranges or methods can be used to reduce or eliminate adduct effects.

Figure 46:
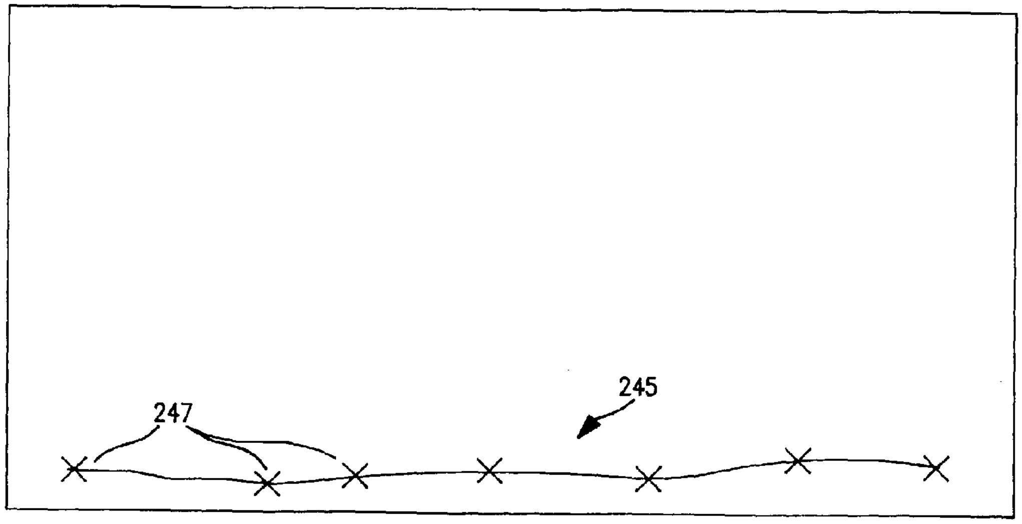
FIG. 46 is a graphical representation of a signal with peaks removed.
Figure 47:
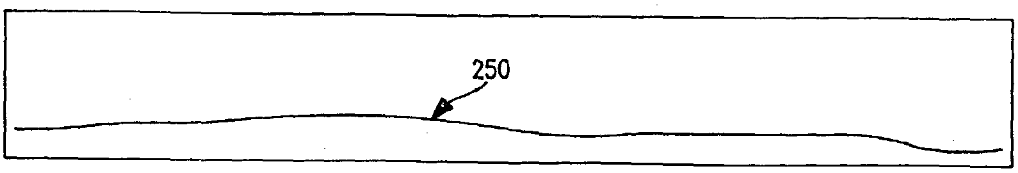
FIG. 47 is a graphical representation of a residual baseline.
Figure 48:
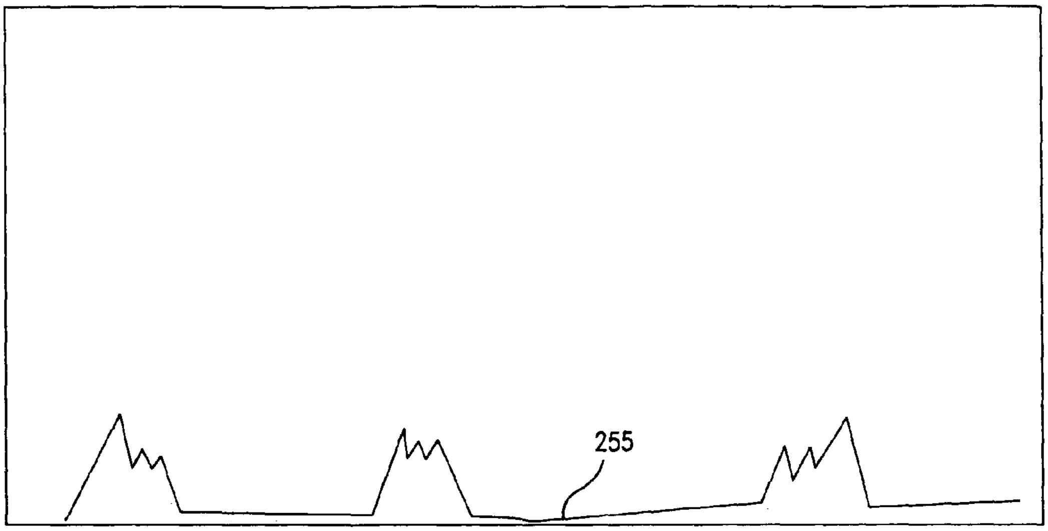
FIG. 48 is a graphical representation of a signal with residual baseline removed.

The peaks are removed and remaining minima 247 located as shown in FIG. 46 with the minima 247 connected to create signal 245. A quartic polynomial is applied to signal 245 to generate a residual baseline 250 as shown in FIG. 47. The residual baseline 250 is subtracted from the signal 225 to generate the final signal 255 as indicated in FIG. 48. Although the residual baseline is the result of a quartic fit to signal 245, it will be appreciated that other techniques can be used to smooth or fit the residual baseline.

Figure 49:
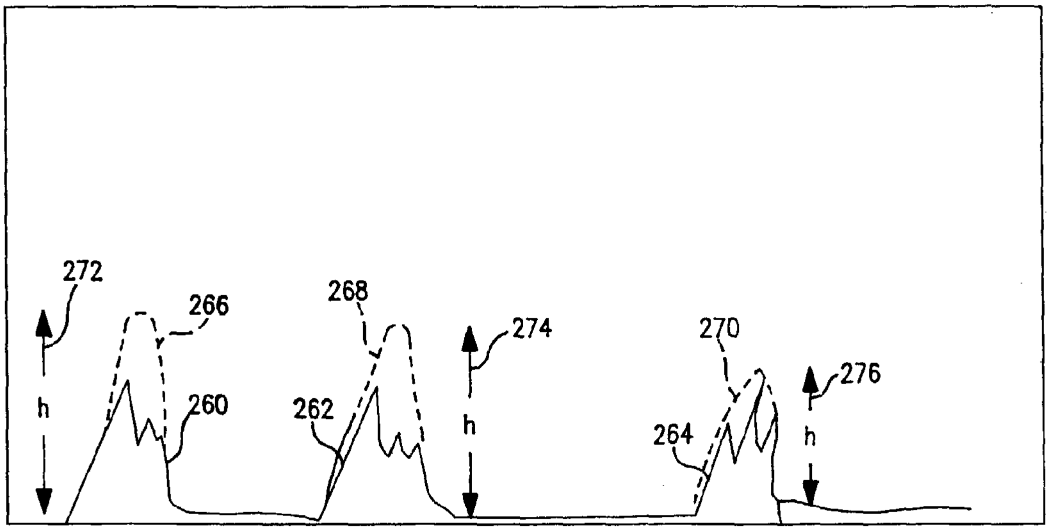
FIG. 49 is a graphical representation of determining peak height.

To determine peak height, as shown in FIG. 49, a Gaussian such as Gaussian 266, 268, and 270 is fit to each of the peaks, such as peaks 260, 262, and 264, respectively. Accordingly, the height of the Gaussian is determined as height 272, 274, and 276. Once the height of each Gaussian peak is determined, then the method of identifying a biological compound 35 can move into the genotyping phase 65 as shown in FIG. 25.

Figure 50:
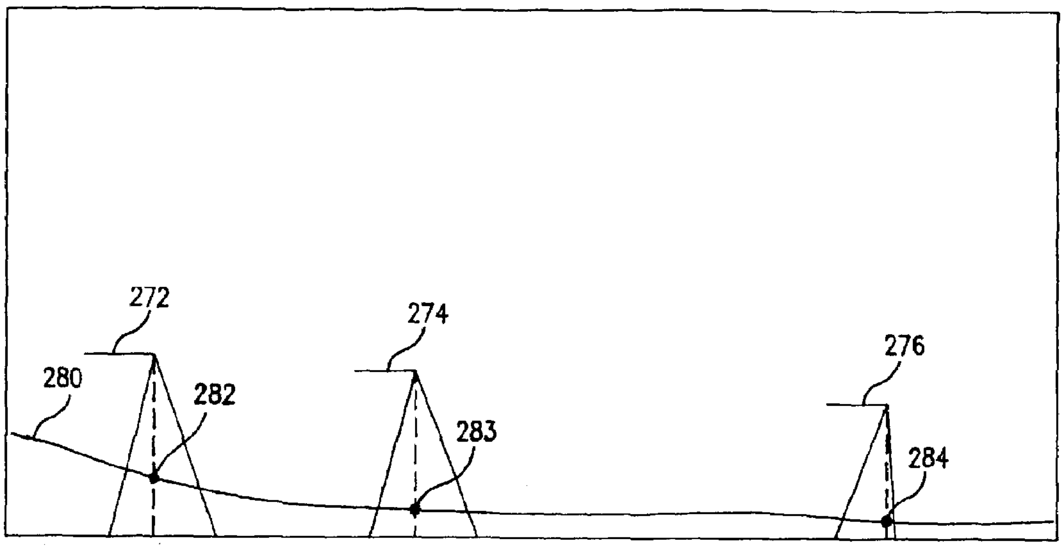
FIG. 50 is a graphical representation of determining signal-to-noise for each peak.

An indication of the confidence that each putative peak is an actual peak can be discerned by calculating a signal-to-noise ratio for each putative peak. Accordingly, putative peaks with a strong signal-to-noise ratio are generally more likely to be an actual peak than a putative peak with a lower signal-to-noise ratio. As described above and shown in FIG. 50, the height of each peak, such as height 272, 274, and 276, is determined for each peak, with the height being an indicator of signal strength for each peak. The noise profile, such as noise profile 97, is extrapolated into noise profile 280 across the identified peaks. At the center line of each of the peaks, a noise value is determined, such as noise value 282, 283, and 284. With a signal values and a noise values generated, signal-to-noise ratios can be calculated for each peak. For example, the signal-to-noise ratio for the first peak in FIG. 50 would be calculated as signal value 272 divided by noise value 282, and in a similar manner the signal-to-noise ratio of the middle peak in FIG. 50 would be determined as signal 274 divided by noise value 283.

Although the signal-to-noise ratio is generally a useful indicator of the presence of an actual peak, further processing has been found to increase the confidence by which a sample can be identified. For example, the signal-to-noise ratio for each peak in the exemplarly embodiment can be adjusted by the goodness of fit between a Gaussian and each putative peak. It is a characteristic of a mass spectrometer that sample material is detected in a manner that generally complies with a normal distribution. Accordingly, greater confidence will be associated with a putative signal having a Gaussian shape than a signal that has a less normal distribution. The error resulting from having a non-Gaussian shape can be referred to as a "residual error".

Figure 51:
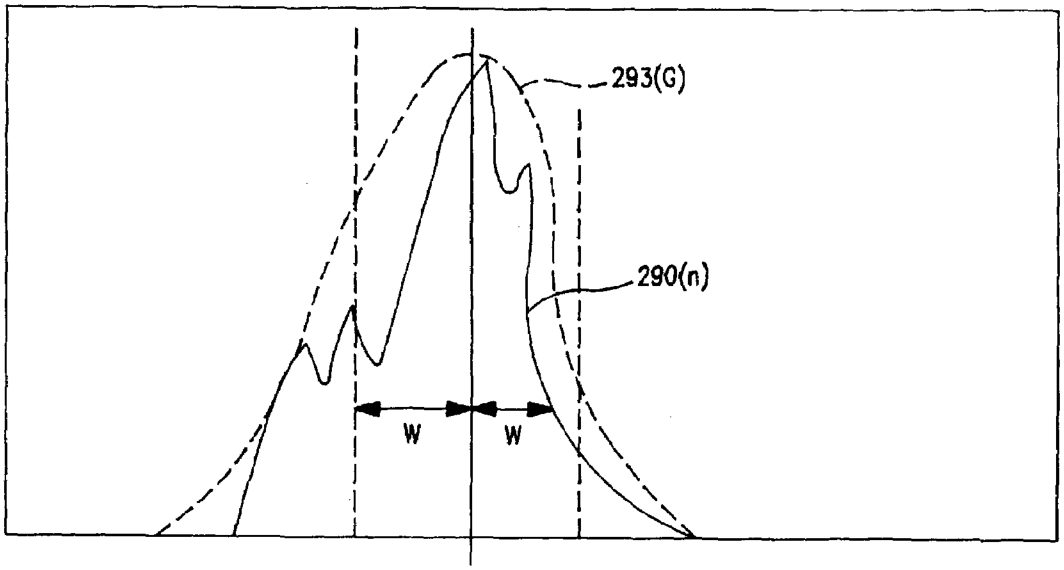
FIG. 51 is a graphical representation of determining a residual error for each peak.

Referring to FIG. 51, a residual error is calculated by taking a root mean square calculation between the Gaussian 293 and the putative peak 290 in the data signal. The calculation is performed on data within one width on either side of a center line of the Gaussian. The residual error is calculated as:

$$\sqrt{[(G-R)^2/N]},$$

where G is the Gaussian signal value, R is the putative peak value, and N is the number of points from −W to +W. The calculated residual error is used to generate an adjusted signal-to-noise ratio, as described below.

An adjusted signal noise ratio is calculated for each putative peak using the formula (S/N) * $EXP^{(-0.1 * R)}$, where S/N is the signal-to-noise ratio, and R is the residual error determined above. Although the exemplary embodiment calculates an adjusted signal-to-noise ratio using a residual error for each peak, it will be appreciated that other techniques can be used to account for the goodness of fit between the Gaussian and the actual signal.

Figure 52:
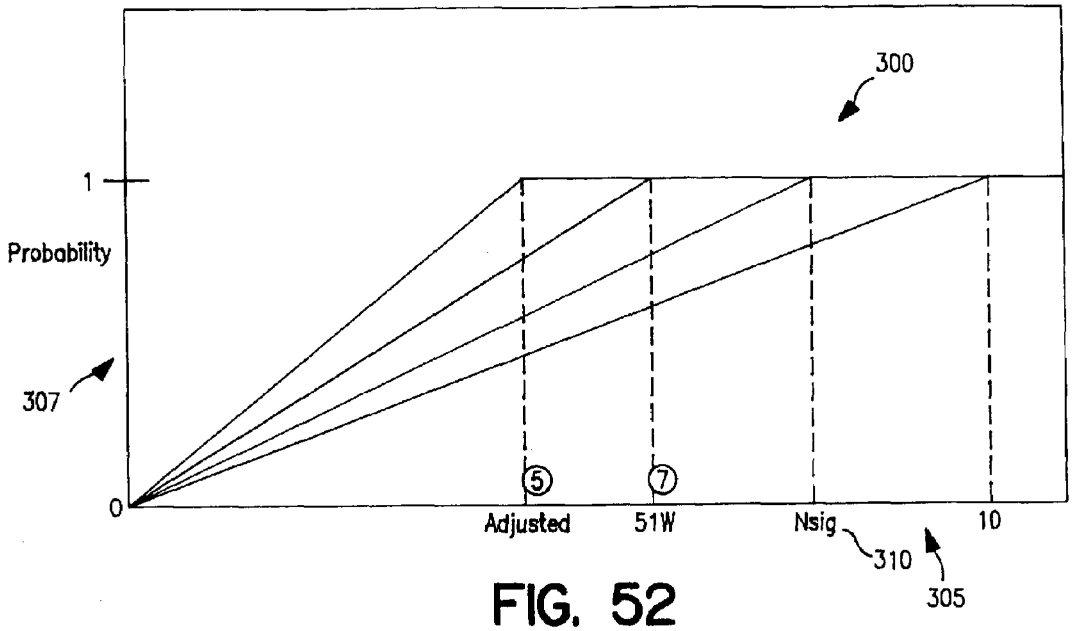
FIG. 52 is a graphical representation of peak probabilities.

Referring now to FIG. 52, a probability is determined that a putative peak is an actual peak. In making the determination of peak probability, a probability profile 300 is generated where the adjusted signal-to-noise ratio is the x-axis and the probability is the y-axis. Probability is necessarily in the range between a 0% probability and a 100% probability, which is indicated as 1. Generally, the higher the adjusted signal-to-noise ratio, the greater the confidence that a putative peak is an actual peak.

At some target value for the adjusted signal-to-noise, it has been found that the probability is 100% that the putative peak is an actual peak and can confidently be used to identify the DNA composition of a biological sample. The target value of adjusted signal-to-noise ratio where the probability is assumed to be 100% is a variable parameter which is to be set according to application specific criteria. For example, the target signal-to-noise ratio will be adjusted depending upon trial experience, sample characteristics, and the acceptable error tolerance in the overall system. More specifically, for situations requiring a conservative approach where error cannot be tolerated, the target adjusted signal-to-noise ratio can be set to, for example, 10 and higher. Accordingly, 100% probability will not be assigned to a peak unless the adjusted signal-to-noise ratio is 10 or over.

In other situations, a more aggressive approach can be taken as sample data is more pronounced or the risk of error can be reduced. In such a situation, the system can be set to assume a 100% probability with a 5 or greater target signal-to-noise ratio. Of course, an intermediate signal-to-noise ratio target figure can be selected, such as 7, when a moderate risk of error can be assumed. Once the target adjusted signal-to-noise ratio is set for the method, then for any adjusted signal-to-noise ratio a probability can be determined that a putative peak is an actual peak.

Figure 53:
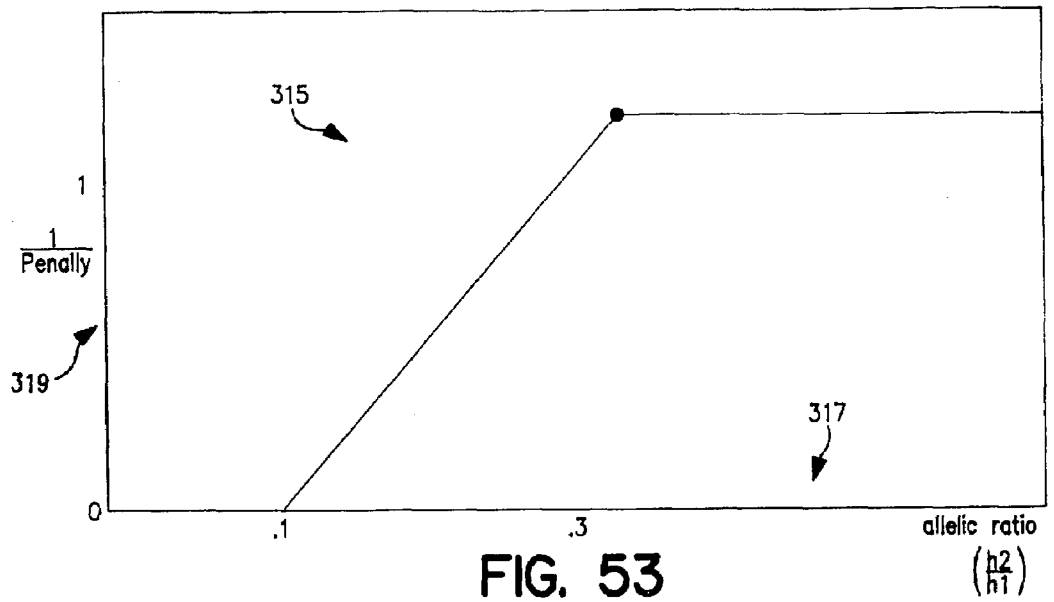
FIG. 53 is a graphical representation of applying an allelic ratio to peak probability.

Due to the chemistry involved in performing an identification test, especially a mass spectrometry test of a sample prepared by DNA amplifications, the allelic ratio between the signal strength of the highest peak and the signal strength of the second (or third and so on) highest peak should fall within an expected ratio. If the allelic ratio falls outside of normal guidelines, the exemplary embodiment imposes an allelic ratio penalty to the probability. For example, FIG. 53 shows an allelic penalty 315 which has an x-axis 317 that is the ratio between the signal strength of the second highest peak divided by signal strength of the highest peak. The y-axis 319 assigns a penalty between 0 and 1 depending on the determined allelic ratio. In the exemplary embodiment, it is assumed that allelic ratios over 30% are within the expected range and therefore no penalty is applied. Between a ratio of 10% and 30%, the penalty is linearly increased until at allelic ratios below 10% it is assumed the second-highest peak is not real. For allelic ratios between 10% and 30%, the allelic penalty chart 315 is used to determine a penalty 319, which is multiplied by the peak probability determined in FIG. 52 to determine a final peak probability. Although the exemplary embodiment incorporates an allelic ratio penalty to account for a possible chemistry error, it will be appreciated that other techniques can be used. Similar treatment will be applied to the other peaks.

Figure 54:
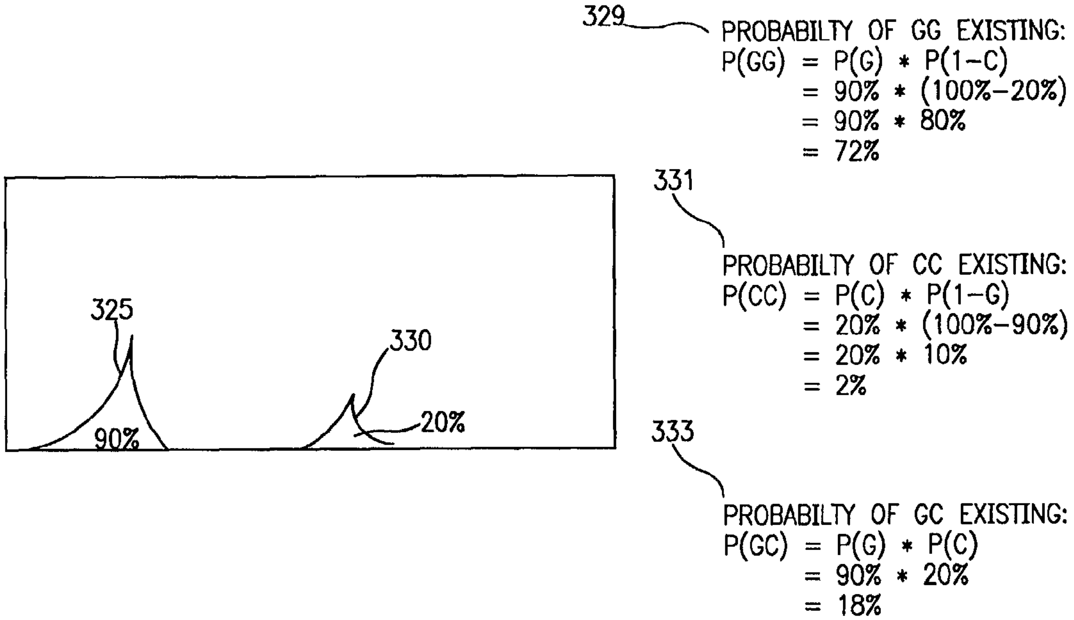
FIG. 54 is a graphical representation of determining peak probability.

With the peak probability of each peak determined, the statistical probability for various composition components can be determined, as an example, in order to determine the probability of each of three possible combinations of two peaks,—peak G, peak C and combinations GG, CC and GC. FIG. 54 shows an example where a most probable peak 325 is determined to have a final peak probability of 90%. Peak 325 is positioned such that it represents a G component in the biological sample. Accordingly, it can be maintained that there is a 90% probability that G exists in the biological sample. Also in the example shown in FIG. 54, the second highest probability is peak 330 which has a peak probability of 20%. Peak 330 is at a position associated with a C composition. Accordingly, it can be maintained that there is a 20% probability that C exists in the biological sample.

With the probability of G existing (90%) and the probability of C existing (20%) as a starting point, the probability of combinations of G and C existing can be calculated. For example, FIG. 54 indicates that the probability of GG existing 329 is calculated as 72%. This is calculated as the probability of GG is equal to the probability of G existing (90%) multiplied by the probability of C not existing (100%−20%). So if the probability of G existing is 90% and the probability of C not existing is 80%, the probability of GG is 72%.

In a similar manner, the probability of CC existing is equivalent to the probability of C existing (20%) multiplied by the probability of G not existing (100%−90%). As shown in FIG. 54, the probability of C existing is 20% while the probability of G not existing is 10%, so therefore the probability of CC is only 2%. Finally, the probability of GC existing is equal to the probability of G existing (90%) multiplied by the probability of C existing (20%). So if the probability of G existing is 90% and the probability of C existing is 20%, the probability of GC existing is 18%. In summary form, then, the probability of the composition of the biological sample is:

probability of GG: 72%;
probability of GC: 18%; and
probability of CC: 2%.

Figure 55:
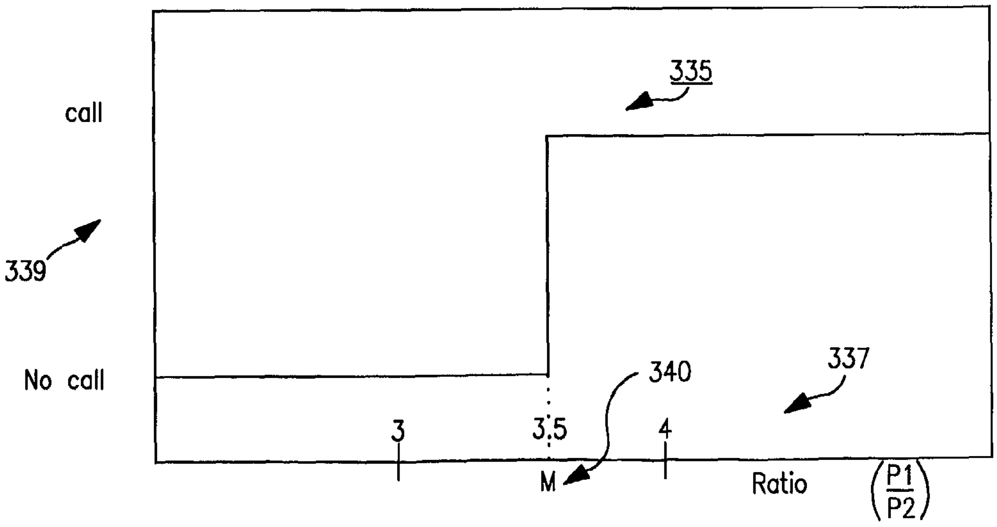
FIG. 55 is a graphical representation of calling a genotype.

Once the probabilities of each of the possible combinations has been determined, FIG. 55 is used to decide whether or not sufficient confidence exists to call the genotype. FIG. 55 shows a call chart 335 which has an x-axis 337 which is the ratio of the highest combination probability to the second highest combination probability. The y-axis 339 simply indicates whether the ratio is sufficiently high to justify calling the genotype. The value of the ratio can be indicated by M 340. The value of M is set depending upon trial data, sample composition, and the ability to accept error. For example, the value M can be set relatively high, such as to a value 4 so that the highest probability must be at least four times greater than the second highest probability before confidence is established to call a genotype. If a certain level of error can be acceptable, the value of M can be set to a more aggressive value, such as to 3, so that the ratio between the highest and second highest probabilities needs to be only a ratio of 3 or higher. Of course, moderate value can be selected for M when a moderate risk can be accepted. Using the example of FIG. 54, where the probability of GG was 72% and the probability of GC was 18%, the ratio between 72% and 18% is 4.0, therefore, whether M is set to 3, 3.5, or 4, the system would call the genotype as GG. Although the exemplary embodiment uses a ratio between the two highest peak probabilities to determine if a genotype confidently can be called, it will be appreciated that other methods can be substituted. It will also be appreciated that the above techniques can be used for calculating probabilities and choosing genotypes (or more general DNA patterns) containing of combinations of more than two peaks.

Figure 56:
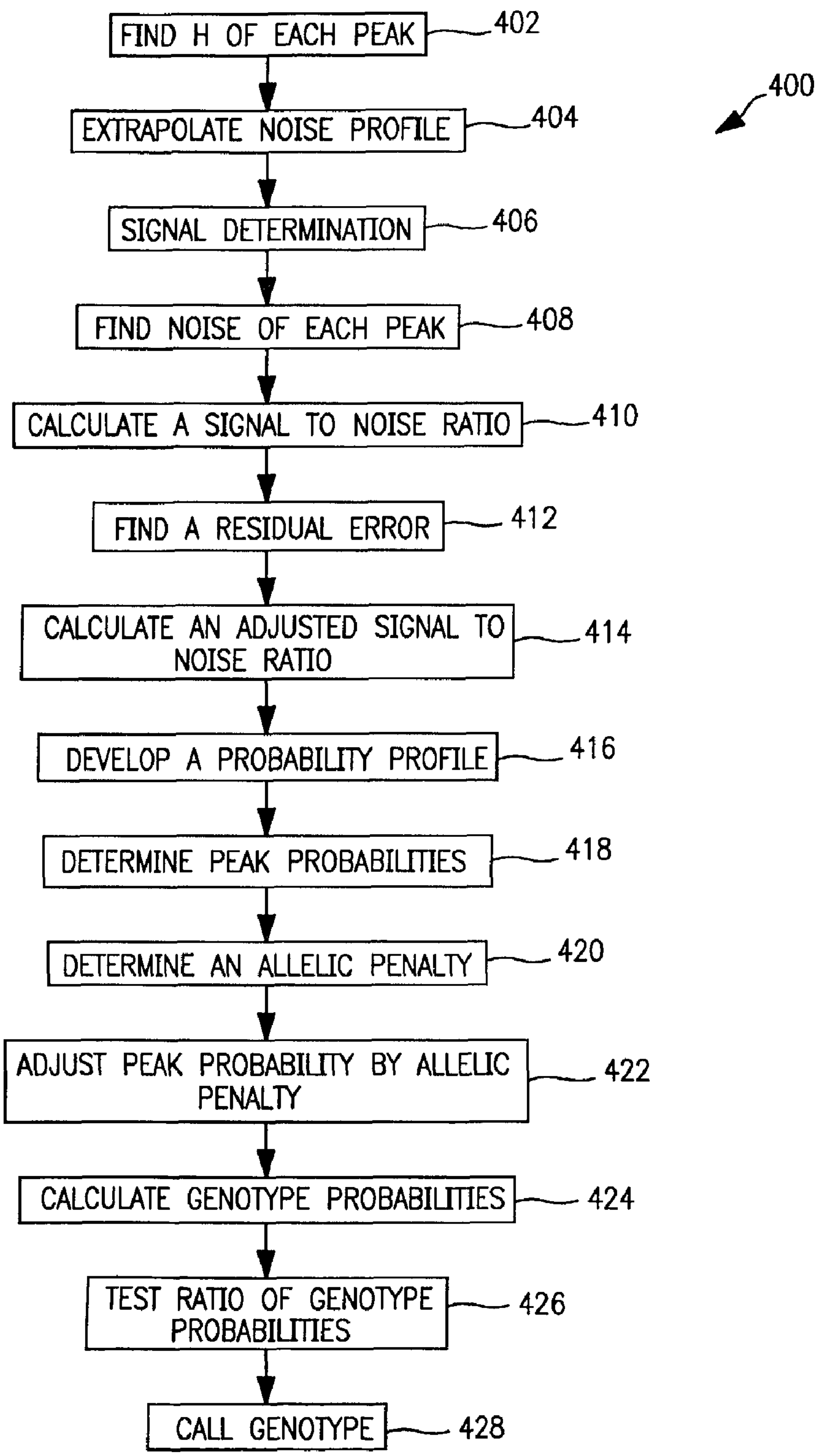
FIG. 56 is a flowchart showing a statistical procedure for calling a genotype.

Referring now to FIG. 56, a flow chart is shown generally defining the process of statistically calling genotype described above. In FIG. 56 block 402 shows that the height of each peak is determined and that in block 404 a noise profile is extrapolated for each peak. The signal is determined from the height of each peak in block 406 and the noise for each peak is determined using the noise profile in block 408. In block 410, the signal-to-noise ratio is calculated for each peak. To account for a non-Gaussian peak shape, a residual error is determined in block 412 and an adjusted signal-to-noise ratio is calculated in block 414. Block 416 shows that a probability profile is developed, with the probability of each peak existing found in block 418. An allelic penalty can be applied in block 420, with the allelic penalty applied to the adjusted peak probability in block 422. The probability of each combination of components is calculated in block 424 with the ratio between the two highest probabilities being determined in block 426. If the ratio of probabilities exceeds a threshold value then the genotype is called in block 428.

In another embodiment, the computing device 20 (FIG. 24) supports "standardless" genotyping by identifying data peaks that contain putative SNPs. Standardless genotyping is used, for example, where insufficient information is known about the samples to determine a distribution of expected peak locations, against which an allelic penalty as described above can be reliably calculated. This permits the computing device to be used for identification of peaks that contain putative SNPs from data generated by any assay that fragments a targeted DNA molecule. For such standardless genotyping, peaks that are associated with an area under the data curve that deviates significantly from the typical area of other peaks in the data spectrum are identified and their corresponding mass (location along the x-axis) is determined.

More particularly, peaks that deviate significantly from the average area of other peaks in the data are identified, and the expected allelic ratio between data peaks is defined in terms of the ratio of the area under the data peaks. Theoretically, where each genetic loci has the same molar concentration of analyte, the area under each corresponding peak should be the same, thus producing a 1.0 ratio of the peak area between any two peaks. In accordance with the methods provided herein, peaks having a smaller ratio relative to the other peaks in the data will not be recognized as peaks. More particularly, peaks having an area ratio smaller than 30% relative to a nominal value for peak area will be assigned an allelic penalty. The mass of the remaining peaks (their location along the x-axis of the data) will be determined based on oligonucleotide standards.

Figure 57:
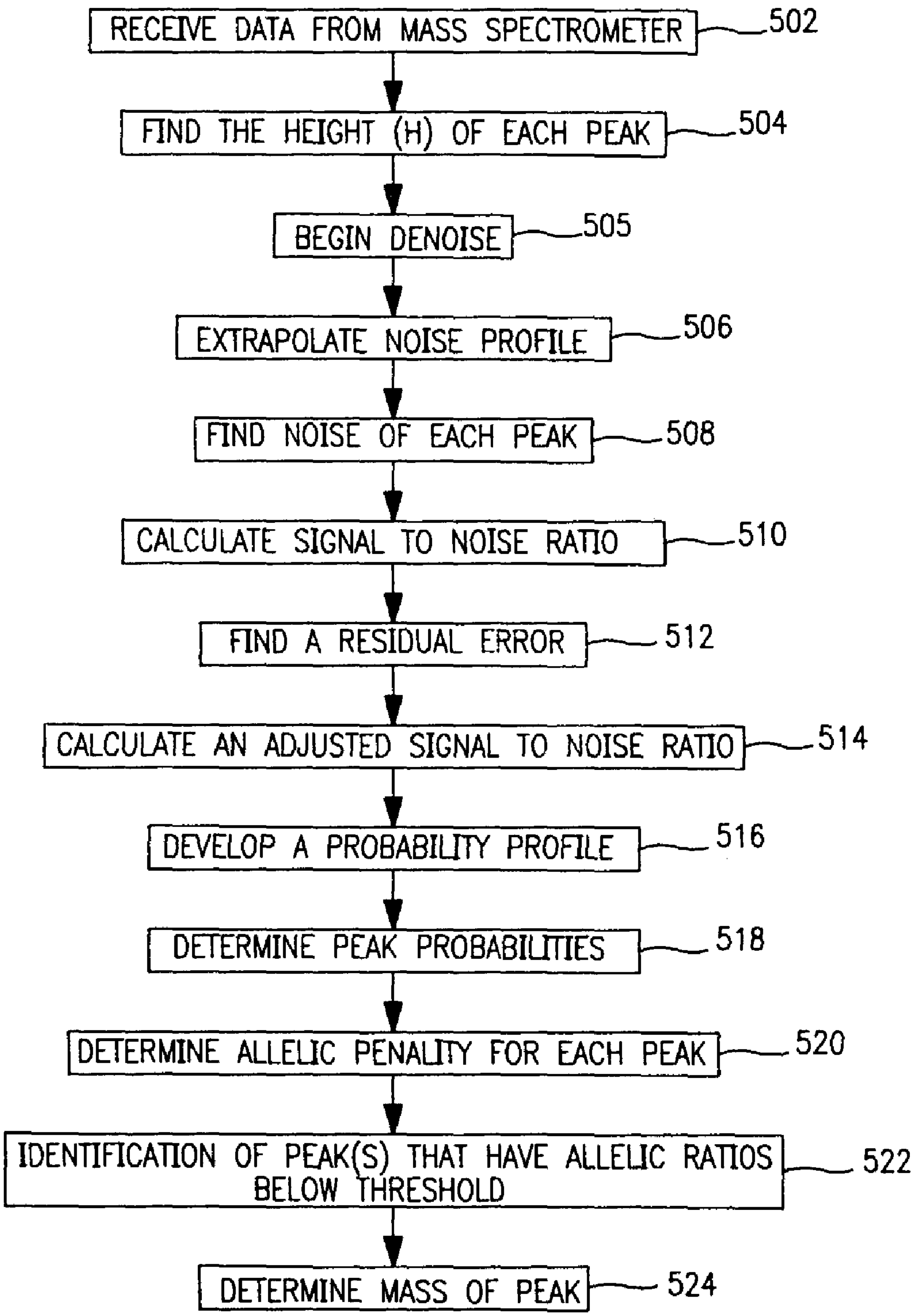
FIG. 57 is a flowchart showing processing performed by the computing device of FIG. 1 when performing standardless genotyping.

FIG. 57 shows a flow diagram representation of the processing by the computing device 20 (FIG. 24) when performing standardless genotyping. In the first operation, represented by the flow diagram box numbered 502, the computing device receives data from the mass spectrometer. Next, the height of each putative peak in the data sample is determined, as indicated by the block 504. After the height of each peak in the mass spectrometer data is determined, a de-noise process 505 is performed, beginning with an extrapolation of the noise profile (block 506), followed by finding the noise of each peak (block 508) and calculating the signal to noise ratio for each data sample (block 510). Each of these operations can be performed in accordance with the description above for denoise operations 45 of FIG. 25. Other suitable denoise operations will occur to those skilled in the art.

The next operation is to find the residual error associated with each data point. This is represented by the block 512 in FIG. 57. The next step, block 514, involves calculating an adjusted signal to noise ratio for each identified peak. A probability profile is developed next (block 516), followed by a determination of the peak probabilities at block 518. In an exemplary embodiment, the denoise operations of FIG. 57, comprising block 502 to block 518, comprise the corresponding operations described above in conjunction with FIG. 56 for block 402 through block 418, respectively.

The next action for the standardless genotype processing is to determine an allelic penalty for each peak, indicated by the block 524. As noted above, the standardless genotype processing of FIG. 57 determines an allelic penalty by comparing area under the peaks. Therefore, rather than compare signal strength ratios to determine an allelic penalty, such as described above for FIG. 53, the standardless processing determines the area under each of the identified peaks and compares the ratio of those areas. Determining the area under each peak can be computed using conventional numerical analysis techniques for calculating the area under a curve for experimental data.

Thus, the allelic penalty is assigned in accordance with FIG. 58, which shows that no penalty is assigned to peaks having a peak area relative to an expected average area value that is greater than 0.30 (30%). The allelic penalty is applied to the peak probability value, which can be determined according to the process such as described in FIG. 52. It should be apparent from FIG. 58 that the allelic penalty imposed for peaks below a ratio of 30% is that such peaks will be removed from further measurement and processing. Other penalty schemes, however, can be imposed in accordance with knowledge about the data being processed, as determined by those skilled in the art.

After the allelic penalty has been determined and applied, the standardless genotype processing compares the location of the remaining putative peaks to oligonucleotide standards to determine corresponding masses in the processing for block 524. For standardless genotype data, the processing of the block 524 is performed to determine mass and genotype, rather than performing the operations corresponding to block 424, 426, and 428 of FIG. 33. Techniques for performing such comparisons and determining mass will be known to those skilled in the art.

In another embodiment, the computing device 20 (FIG. 24) permits the detection and determination of the mass (location along the x-axis of the data) of the sense and antisense strand of fragments generated in the assay. If desired, the computing device can also detect and determine the quantity (area under each peak) of the respective sense and antisense strands, using a similar technique to that described above for standardless genotype processing. The data generated for each type of strand can then be combined to achieve a data redundancy and to thereby increase the confidence level of the determined genotype. This technique obviates primer peaks that are often observed in data from other diagnostic methods, thereby permitting a higher level of multiplexing. In addition, when quantitation is used in pooling experiments, the ratio of the measured peak areas is more reliably calculated than the peak identifying technique, due to data redundancy.

Figure 23:
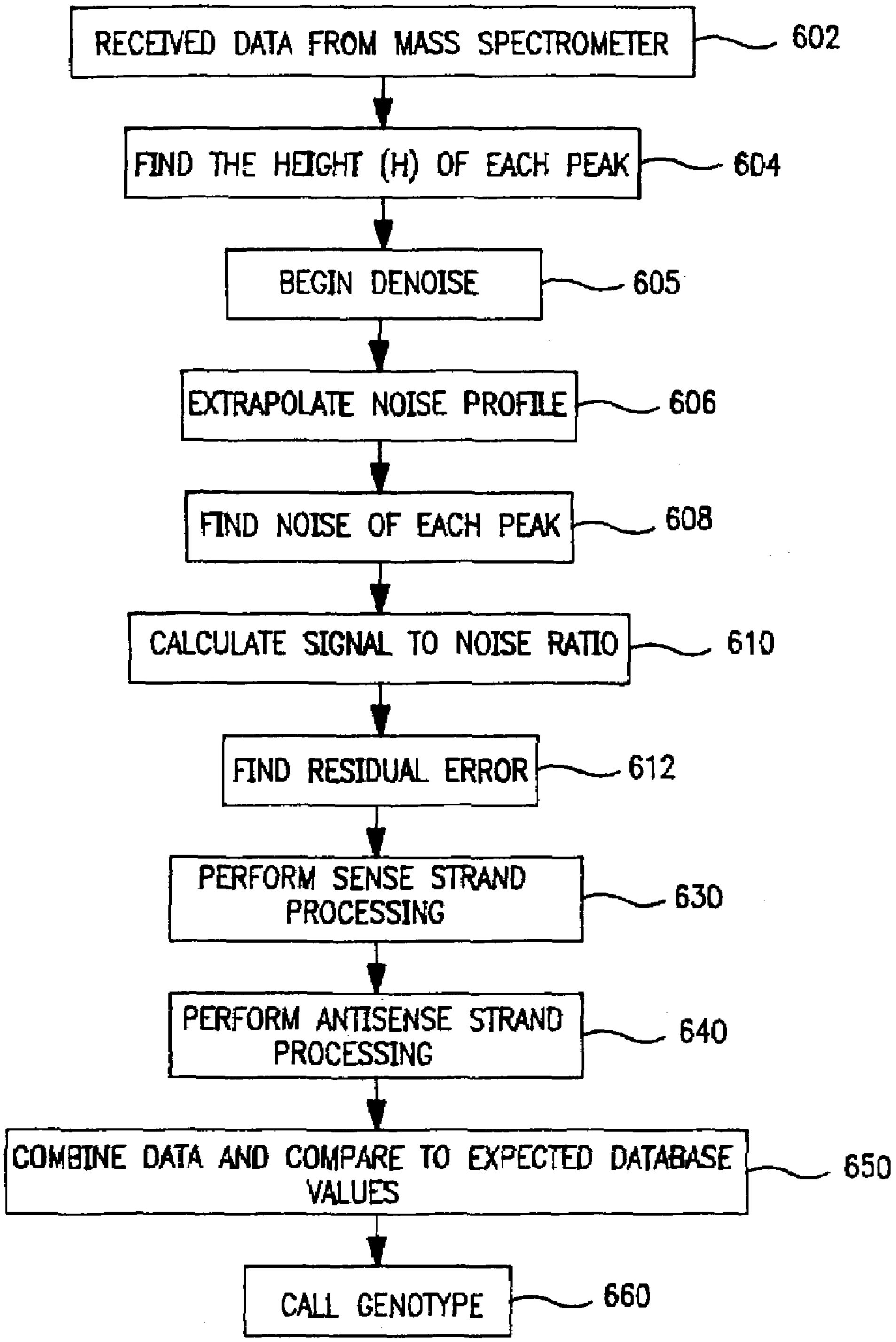
FIG. 23 is a flowchart showing processing performed by the computing device of FIG. 24 when performing genotyping of sense strands and antisense strands from assay fragments.

FIG. 23 is a flow diagram that illustrates the processing implemented by the computing device 20 to perform sense and antisense processing. In the first operation, represented by the flow diagram box numbered 602, the computing device receives data from the mass spectrometer. This data will include data for the sense strand and antisense strand of assay fragments. Next, the height of each putative peak in the data sample is determined, as indicated by the block 604. After the height of each peak in the mass spectrometer data is determined, a de-noise process 605 is performed, beginning with an operation that extrapolates the noise profile (block 606), followed by finding the noise of each peak (block 608) and calculating the signal to noise ratio for each data sample (block 610). Each of these operations can be performed in accordance with the description above for the denoise operations 45 of FIG. 25. Other suitable denoise operations will occur to those skilled in the art. The next operation is to find the residual error associated with each data point. This is represented by the block 612 in FIG. 36.

After the residual error for the data of the sense strand and antisense strand has been performed, processing to identify the genotypes will be performed for the sense strand and also for the antisense strand. Therefore, FIG. 23 shows that processing includes sense strand processing (block 630) and antisense strand processing (block 640). Each block 630, 640 includes processing that corresponds to adjusting the signal to noise ratio, developing a probability profile, determining an allelic penalty, adjusting the peak probability by the allelic penalty, calculating genotype probabilities, and testing genotype probability ratios, such as described above in conjunction with blocks 414 through 426 of FIG. 56. The processing of each block 630, 640 can, if desired, include standardless processing operations such as described above in conjunction with FIG. 57. The standardless processing can be included in place of or in addition to the processing operations of FIG. 56.

After the genotype probability processing is completed, the data from the sense strand and antisense strand processing is combined and compared to expected database values to obtain the benefits of data redundancy as between the sense strand and antisense strand. Those skilled in the art will understand techniques to take advantage of known data redundancies between a sense strand and antisense strand of assay fragments. This processing is represented by the block 650. After the data from the two strands is combined for processing, the genotype processing is performed (block 660) and the genotype is identified.

Since modifications will be apparent to those of skill in this art, it is intended that this invention be limited only by the scope of the appended claims.

What is claimed is:

1. A method for correlating a change in the frequency of a polymorphism in a gene or a non-coding portion of a genome with increasing age, comprising;

obtaining samples from healthy individuals within an age range;

pooling the samples from healthy individuals within the age range;

determining the frequency of a polymorphism in said samples, wherein said polymorphism or said gene have not been correlated with susceptibility to morbidity, early mortality, or morbidity and early mortality; and correlating a change in frequency of the polymorphism with increasing age in a healthy population.

2. The method of claim 1, wherein the frequency of said polymorphism in said samples is in a database, and said database is sorted to identify correlations between the frequency of said allele and age.

3. The method of claim 1, wherein said polymorphism comprises a SNP.

4. The method of claim 1, further comprising correlating said polymorphism with a gene or pathway in which said polymorphism is involved.

5. The method of claim 4, comprising using a database to correlate said polymorphism with said gene or pathway.

6. The method of claim 1, further comprising identifying the locus of said polymorphism and assessing or deducing the function of a gene at said locus.

7. The method of claim 6, comprising using a database to assess or deduce the function of said gene.

8. The method of claim 1, wherein the frequency of said polymorphism decreases with increasing age.

9. The method of claim 1, wherein the frequency of said polymorphism increases with increasing age.

10. The method of claim 1, wherein said sample comprises body tissue or fluid from said organism.

11. The method of claim 1, wherein the frequency of the polymorphism is determined using mass spectrometry.

12. The method of claim 11, wherein the mass spectrometric format is selected from among Matrix-Assisted Laser Desorption/Ionization, Time-of-Flight (MALDI-TOF), Electrospray (ES), IR-MALDI, Ion Cyclotron Resonance (ICR), Fourier Transform, and combinations thereof.

13. The method of claim 11, wherein samples are presented to the mass spectrometer as arrays on chips.

14. The method of claim 1, wherein said method comprises obtaining genomic nucleic acid from a sample from a healthy organism.

15. The method of claim 14, further comprising amplifying a portion of the genomic nucleic acid to produce amplified fragments thereof.

16. The method of claim 1, wherein the presence of the polymorphism is identified by a method comprising primer oligo base extension.

17. The method of claim 16, wherein primer oligo base extension comprises hybridizing a nucleic acid molecule from a sample from a healthy organism with a primer oligonucleotide that is complementary to the nucleic acid molecule at a site adjacent to the polymorphic marker.

18. The method of claim 17, further comprising:

a) optionally immobilizing the nucleic acid molecule onto a solid support, to produce an immobilized nucleic acid molecule;

b) contacting the optionally-immobilized nucleic acid molecule with a composition comprising a dideoxynucleoside triphosphate or a 3'-deoxynucleoside triphosphate and a polymerase, so that only a dideoxynucleoside or 3'-deoxynucleoside triphosphate that is complementary to the polymorphic marker is extended onto the primer; and c) detecting the extended primer, thereby identifying the presence of the polymorphism.

19. The method of claim 18, wherein detection of the extended primer is effected by mass spectrometry, comprising:

ionizing and volatizing the product of step c); and detecting the extended primer by mass spectrometry, thereby identifying the target nucleotide.

20. The method of claim 1, wherein the presence of the polymorphism is identified by a method comprising:

identifying samples by sorting a database comprising datapoints representative of a plurality of healthy organisms from whom biological samples are obtained, wherein each datapoint is associated with data representative of the organism type and other identifying information, wherein said database is sorted according to a selected parameter to identify samples that match the selected parameter;

isolating a nucleic acid molecule from each identified sample;

pooling each isolated nucleic acid molecule; and identifying the presence of a polymorphism in the nucleic acid molecule by a method comprising primer oligo base extension.

21. The method of claim 1, wherein the presence of the polymorphism is identified by a method comprising:

identifying samples by sorting a database comprising datapoints representative of a plurality of healthy organisms from whom biological samples are obtained, wherein each datapoint is associated with data representative of the organism type and other identifying information, wherein said database is sorted according to a selected parameter to identify samples that match the selected parameter;

isolating a biopolymer from each identified sample;

pooling each isolated biopolymer;

cleaving the pooled biopolymers to produce fragments thereof;

obtaining a mass spectrum of the resulting fragments and comparing the mass spectrum with a control mass spectrum to identify differences between the spectra and thereby identifying any polymorphisms; wherein:

the control mass spectrum is obtained from either a) samples represented by datapoints in said database that were not selected by sorting said database; or b) samples identified by sorting said database according to a different selected parameter.

22. The method of claim 1, wherein the presence of the polymorphism is identified by a method comprising:

isolating a biopolymer from samples of body tissue or fluid from a plurality of organisms;

pooling each isolated biopolymer;

cleaving the pooled biopolymers to produce fragments thereof;

obtaining a mass spectrum of the resulting fragments;

determining a frequency of each fragment, whereby an average frequency is calculated; and comparing the frequency of each fragment to identify fragments present in amounts lower than the average frequency, thereby identifying the presence of any polymorphism.

23. The method of claim 1, further comprising using genetic mapping to identify a gene or pathway that correlates with said polymorphism.

24. The method of claim 1, further comprising identifying the locus of the polymorphism and assessing or deducing its function.

25. A method for identifying a gene or gene product comprising a polymorphism whose frequency decreases with increasing age, comprising:

determining the frequency of a polymorphism in pooled samples from healthy individuals within an age range, wherein said polymorphism has not been correlated with susceptibility to morbidity, early mortality, or morbidity and early mortality;

correlating a change in frequency of the polymorphism with increasing age in a healthy population; and identifying the gene that comprises said polymorphism.

26. A method for determining whether a polymorphism correlates with age, ethnicity or gender, comprising:

identifying the presence of a polymorphism, wherein said polymorphism has not been correlated with susceptibility to morbidity, early mortality, or morbidity and early mortality;

obtaining samples from individuals of a given age range, ethnicity, or gender;

pooling samples from individuals of a given age range, ethnicity, or gender;

determining the frequency of the polymorphism in said samples; and correlating a change in frequency of the polymorphism with increasing age, with ethnicity or with gender in a healthy population.

27. The method of claim 26, wherein said biopolymers comprise genomic nucleic acid molecules.

28. The method of claim 26, wherein the frequency of the polymorphism is determined using mass spectrometry.

29. The method of claim 26, wherein the presence of the polymorphism is identified by a method comprising primer oligo base extension.

30. A method for identifying a genetic marker in a gene or a non-coding portion of a genome that correlates with age, comprising a. identifying a previously unknown genetic marker using mapping, sequencing, or amplification, of pooled samples, wherein the gene has not been correlated with susceptibility to morbidity, early mortality, or morbidity and early mortality;

b. analyzing the presence of the genetic marker among a population;

c. entering the analysis of the presence of the genetic marker into a database;

d. determining whether the frequency of the presence of the genetic marker correlates with age; and e. determining the locus of the genetic marker.

31. The method of claim 30, wherein the database is sorted by age.

32. The method of claim 30, further comprising assessing the function or the effect of the genetic marker.

33. The method of claim 30, wherein the frequency of the genetic marker decreases with age.

* * * * *

UNITED STATES PATENT AND TRADEMARK OFFICE

CERTIFICATE OF CORRECTION

PATENT NO. : 7,668,658 B2
APPLICATION NO. : 10/273321
DATED : February 23, 2010
INVENTOR(S) : Braun et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 126 days.

Signed and Sealed this

Seventh Day of December, 2010

David J. Kappos
*Director of the United States Patent and Trademark Office*

SEQUENCE LISTING

```
<160> NUMBER OF SEQ ID NOS: 118

<210> SEQ ID NO 1
<211> LENGTH: 361
<212> TYPE: DNA
<213> ORGANISM: Homo Sapien

<400> SEQUENCE: 1

ctgaggacct ggtcctctga ctgctctttt cacccatcta cagtccccct tgccgtccca     60

agcaatggat gatttgatgc tgtccccgga cgatattgaa caatggttca ctgaagaccc    120

aggtccagat gaagctccca gaatgccaga ggctgctccc cgcgtggccc ctgcaccagc    180

agctcctaca ccggcggccc ctgcaccagc cccctcctgg cccctgtcat cttctgtccc    240

ttcccagaaa acctaccagg gcagctacgg tttccgtctg ggcttcttgc attctgggac    300

agccaagtct gtgacttgca cggtcagttg ccctgagggg ctggcttcca tgagacttca    360

a                                                                    361


<210> SEQ ID NO 2
<211> LENGTH: 44
<212> TYPE: DNA
<213> ORGANISM: Artificial Sequence
<220> FEATURE:
<223> OTHER INFORMATION: Oligonucleotide Primer

<400> SEQUENCE: 2

cccagtcacg acgttgtaaa acgctgagga cctggtcctc tgac                       44


<210> SEQ ID NO 3
<211> LENGTH: 42
<212> TYPE: DNA
<213> ORGANISM: Artificial Sequence
<220> FEATURE:
<223> OTHER INFORMATION: Oligonucleotide Primer

<400> SEQUENCE: 3

agcggataac aatttcacac aggttgaagt ctcatggaag cc                         42


<210> SEQ ID NO 4
<211> LENGTH: 17
<212> TYPE: DNA
<213> ORGANISM: Artificial Sequence
<220> FEATURE:
<223> OTHER INFORMATION: Probe

<400> SEQUENCE: 4

gccagaggct gctcccc                                                     17
```

-continued

<210> SEQ ID NO 5
<211> LENGTH: 17
<212> TYPE: DNA
<213> ORGANISM: Artificial Sequence
<220> FEATURE:
<223> OTHER INFORMATION: Probe

<400> SEQUENCE: 5
gccagaggct gctcccc 17

<210> SEQ ID NO 6
<211> LENGTH: 19
<212> TYPE: DNA
<213> ORGANISM: Artificial Sequence
<220> FEATURE:
<223> OTHER INFORMATION: Probe

<400> SEQUENCE: 6
gccagaggct gctccccgc 19

<210> SEQ ID NO 7
<211> LENGTH: 18
<212> TYPE: DNA
<213> ORGANISM: Artificial Sequence
<220> FEATURE:
<223> OTHER INFORMATION: Probe

<400> SEQUENCE: 7
gccagaggct gctccccc 18

<210> SEQ ID NO 8
<211> LENGTH: 161
<212> TYPE: DNA
<213> ORGANISM: Homo Sapien

<400> SEQUENCE: 8
gtccgtcaga acccatgcgg cagcaaggcc tgccgccgcc tcttcggccc agtggacagc 60
gagcagctga gccgcgactg tgatgcgcta atggcgggct gcatccagga ggcccgtgag 120
cgatggaact tcgactttgt caccgagaca ccactggagg g 161

<210> SEQ ID NO 9
<211> LENGTH: 43
<212> TYPE: DNA
<213> ORGANISM: Artificial Sequence
<220> FEATURE:
<223> OTHER INFORMATION: Oligonucleotide Primer

<400> SEQUENCE: 9
cccagtcacg acgttgtaaa acggtccgtc agaacccatg cgg 43

<210> SEQ ID NO 10
<211> LENGTH: 44
<212> TYPE: DNA
<213> ORGANISM: Artificial Sequence
<220> FEATURE:
<223> OTHER INFORMATION: Oligonucleotide Primer

<400> SEQUENCE: 10
agcggataac aatttcacac aggctccagt ggtgtctcgg tgac 44

<210> SEQ ID NO 11
<211> LENGTH: 15
<212> TYPE: DNA
<213> ORGANISM: Artificial Sequence
<220> FEATURE:

-continued

<223> OTHER INFORMATION: Oligonucleotide Primer

<400> SEQUENCE: 11
cagcgagcag ctgag 15

<210> SEQ ID NO 12
<211> LENGTH: 15
<212> TYPE: DNA
<213> ORGANISM: Artificial Sequence
<220> FEATURE:
<223> OTHER INFORMATION: Probe

<400> SEQUENCE: 12
cagcgagcag ctgag 15

<210> SEQ ID NO 13
<211> LENGTH: 16
<212> TYPE: DNA
<213> ORGANISM: Artificial Sequence
<220> FEATURE:
<223> OTHER INFORMATION: Probe

<400> SEQUENCE: 13
cagcgagcag ctgagc 16

<210> SEQ ID NO 14
<211> LENGTH: 17
<212> TYPE: DNA
<213> ORGANISM: Artificial Sequence
<220> FEATURE:
<223> OTHER INFORMATION: Probe

<400> SEQUENCE: 14
cagcgagcag ctgagac 17

<210> SEQ ID NO 15
<211> LENGTH: 205
<212> TYPE: DNA
<213> ORGANISM: Homo Sapien

<400> SEQUENCE: 15
gcgctccatt catctcttca tcgactctct gttgaatgaa gaaaatccaa gtaaggccta 60
caggtgcagt tccaaggaag cctttgagaa agggctctgc ttgagttgta gaaagaaccg 120
ctgcaacaat ctgggctatg agatcaataa agtcagagcc aaaagaagca gcaaaatgta 180
cctgaagact cgttctcaga tgccc 205

<210> SEQ ID NO 16
<211> LENGTH: 42
<212> TYPE: DNA
<213> ORGANISM: Artificial Sequence
<220> FEATURE:
<223> OTHER INFORMATION: Oligonucleotide Primers

<400> SEQUENCE: 16
cccagtcacg acgttgtaaa acggcgctcc attcatctct tc 42

<210> SEQ ID NO 17
<211> LENGTH: 42
<212> TYPE: DNA
<213> ORGANISM: Artificial Sequence
<220> FEATURE:
<223> OTHER INFORMATION: Oligonucleotide Primer

<400> SEQUENCE: 17

-continued agcggataac aatttcacac agggggcatc tgagaacgag tc 42

<210> SEQ ID NO 18
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 18
caatctgggc tatgagatca 20

<210> SEQ ID NO 19
<211> LENGTH: 20
<212> TYPE: DNA
<213> ORGANISM: Artificial Sequence
<220> FEATURE:
<223> OTHER INFORMATION: Probe

<400> SEQUENCE: 19
caatctgggc tatgagatca 20

<210> SEQ ID NO 20
<211> LENGTH: 21
<212> TYPE: DNA
<213> ORGANISM: Artificial Sequence
<220> FEATURE:
<223> OTHER INFORMATION: Probe

<400> SEQUENCE: 20
caatctgggc tatgagatca a 21

<210> SEQ ID NO 21
<211> LENGTH: 22
<212> TYPE: DNA
<213> ORGANISM: Artificial Sequence
<220> FEATURE:
<223> OTHER INFORMATION: Probe

<400> SEQUENCE: 21
caatctgggc tatgagatca gt 22

<210> SEQ ID NO 22
<211> LENGTH: 60
<212> TYPE: DNA
<213> ORGANISM: Homo Sapien
<220> FEATURE:
<223> OTHER INFORMATION: Probe

<400> SEQUENCE: 22
gtgccggcta ctcggatggc agcaaggact cctgcaaggg ggacagtgga ggcccacatg 60

<210> SEQ ID NO 23
<211> LENGTH: 60
<212> TYPE: DNA
<213> ORGANISM: Homo sapien

<400> SEQUENCE: 23
ccacccacta ccggggcacg tggtacctga cgggcatcgt cagctggggc cagggctgcg 60

<210> SEQ ID NO 24
<211> LENGTH: 42
<212> TYPE: DNA
<213> ORGANISM: Artificial Sequence
<220> FEATURE:

-continued

<223> OTHER INFORMATION: Oligonucleotide primer

<400> SEQUENCE: 24
cccagtcacg acgttgtaaa acgatggcag caaggactcc tg 42

<210> SEQ ID NO 25
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 25
cacatgccac ccactacc 18

<210> SEQ ID NO 26
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 26
agcggataac aatttcacac aggtgacgat gcccgtcagg tac 43

<210> SEQ ID NO 27
<211> LENGTH: 15
<212> TYPE: DNA
<213> ORGANISM: Artificial Sequence
<220> FEATURE:
<223> OTHER INFORMATION: Probe

<400> SEQUENCE: 27
atgccaccca ctacc 15

<210> SEQ ID NO 28
<211> LENGTH: 19
<212> TYPE: DNA
<213> ORGANISM: Artificial Sequence
<220> FEATURE:
<223> OTHER INFORMATION: Probe

<400> SEQUENCE: 28
cacatgccac ccactaccg 19

<210> SEQ ID NO 29
<211> LENGTH: 20
<212> TYPE: DNA
<213> ORGANISM: Artificial Sequence
<220> FEATURE:
<223> OTHER INFORMATION: Probe

<400> SEQUENCE: 29
cacatgccac ccactaccag 20

<210> SEQ ID NO 30
<211> LENGTH: 23
<212> TYPE: DNA
<213> ORGANISM: Artificial Sequence
<220> FEATURE:
<223> OTHER INFORMATION: Probe

<400> SEQUENCE: 30
agcggataac aatttcacac agg 23

-continued

```
<210> SEQ ID NO 31
<211> LENGTH: 2363
<212> TYPE: DNA
<213> ORGANISM: Homo Sapien
<220> FEATURE:
<221> NAME/KEY: CDS
<222> LOCATION: (138)...(2126)
<223> OTHER INFORMATION: AKAP-10
<300> PUBLICATION INFORMATION:
<308> DATABASE ACCESSION NUMBER: GenBank AF037439
<309> DATABASE ENTRY DATE: 1997-12-21

<400> SEQUENCE: 31

gcggcttgtt gataatatgg cggctggagc tgcctgggca tcccgaggag gcggtggggc      60

ccactcccgg aagaagggtc ccttttcgcg ctagtgcagc ggcccctctg gacccggaag     120

tccgggccgg ttgctga atg agg gga gcc ggg ccc tcc ccg cgc cag tcc        170
                   Met Arg Gly Ala Gly Pro Ser Pro Arg Gln Ser
                    1               5                  10

ccc cgc acc ctc cgt ccc gac ccg ggc ccc gcc atg tcc ttc ttc cgg       218
Pro Arg Thr Leu Arg Pro Asp Pro Gly Pro Ala Met Ser Phe Phe Arg
            15                  20                  25

cgg aaa gtg aaa ggc aaa gaa caa gag aag acc tca gat gtg aag tcc       266
Arg Lys Val Lys Gly Lys Glu Gln Glu Lys Thr Ser Asp Val Lys Ser
        30                  35                  40

att aaa gct tca ata tcc gta cat tcc cca caa aaa agc act aaa aat       314
Ile Lys Ala Ser Ile Ser Val His Ser Pro Gln Lys Ser Thr Lys Asn
    45                  50                  55

cat gcc ttg ctg gag gct gca gga cca agt cat gtt gca atc aat gcc       362
His Ala Leu Leu Glu Ala Ala Gly Pro Ser His Val Ala Ile Asn Ala
 60                  65                  70                  75

att tct gcc aac atg gac tcc ttt tca agt agc agg aca gcc aca ctt       410
Ile Ser Ala Asn Met Asp Ser Phe Ser Ser Ser Arg Thr Ala Thr Leu
                 80                  85                  90

aag aag cag cca agc cac atg gag gct gct cat ttt ggt gac ctg ggc       458
Lys Lys Gln Pro Ser His Met Glu Ala Ala His Phe Gly Asp Leu Gly
            95                 100                 105

aga tct tgt ctg gac tac cag act caa gag acc aaa tca agc ctt tct       506
Arg Ser Cys Leu Asp Tyr Gln Thr Gln Glu Thr Lys Ser Ser Leu Ser
        110                 115                 120

aag acc ctt gaa caa gtc ttg cac gac act att gtc ctc cct tac ttc       554
Lys Thr Leu Glu Gln Val Leu His Asp Thr Ile Val Leu Pro Tyr Phe
    125                 130                 135

att caa ttc atg gaa ctt cgg cga atg gag cat ttg gtg aaa ttt tgg       602
Ile Gln Phe Met Glu Leu Arg Arg Met Glu His Leu Val Lys Phe Trp
140                 145                 150                 155

tta gag gct gaa agt ttt cat tca aca act tgg tcg cga ata aga gca       650
Leu Glu Ala Glu Ser Phe His Ser Thr Thr Trp Ser Arg Ile Arg Ala
                160                 165                 170

cac agt cta aac aca atg aag cag agc tca ctg gct gag cct gtc tct       698
His Ser Leu Asn Thr Met Lys Gln Ser Ser Leu Ala Glu Pro Val Ser
            175                 180                 185

cca tct aaa aag cat gaa act aca gcg tct ttt tta act gat tct ctt       746
Pro Ser Lys Lys His Glu Thr Thr Ala Ser Phe Leu Thr Asp Ser Leu
        190                 195                 200

gat aag aga ttg gag gat tct ggc tca gca cag ttg ttt atg act cat       794
Asp Lys Arg Leu Glu Asp Ser Gly Ser Ala Gln Leu Phe Met Thr His
    205                 210                 215

tca gaa gga att gac ctg aat aat aga act aac agc act cag aat cac       842
Ser Glu Gly Ile Asp Leu Asn Asn Arg Thr Asn Ser Thr Gln Asn His
220                 225                 230                 235

ttg ctg ctt tcc cag gaa tgt gac agt gcc cat tct ctc cgt ctt gaa       890
```

-continued

```
Leu Leu Leu Ser Gln Glu Cys Asp Ser Ala His Ser Leu Arg Leu Glu
                240                 245                 250

atg gcc aga gca gga act cac caa gtt tcc atg gaa acc caa gaa tct      938
Met Ala Arg Ala Gly Thr His Gln Val Ser Met Glu Thr Gln Glu Ser
            255                 260                 265

tcc tct aca ctt aca gta gcc agt aga aat agt ccc gct tct cca cta      986
Ser Ser Thr Leu Thr Val Ala Ser Arg Asn Ser Pro Ala Ser Pro Leu
        270                 275                 280

aaa gaa ttg tca gga aaa cta atg aaa agt ata gaa caa gat gca gtg     1034
Lys Glu Leu Ser Gly Lys Leu Met Lys Ser Ile Glu Gln Asp Ala Val
    285                 290                 295

aat act ttt acc aaa tat ata tct cca gat gct gct aaa cca ata cca     1082
Asn Thr Phe Thr Lys Tyr Ile Ser Pro Asp Ala Ala Lys Pro Ile Pro
300                 305                 310                 315

att aca gaa gca atg aga aat gac atc ata gca agg att tgt gga gaa     1130
Ile Thr Glu Ala Met Arg Asn Asp Ile Ile Ala Arg Ile Cys Gly Glu
                320                 325                 330

gat gga cag gtg gat ccc aac tgt ttc gtt ttg gca cag tcc ata gtc     1178
Asp Gly Gln Val Asp Pro Asn Cys Phe Val Leu Ala Gln Ser Ile Val
            335                 340                 345

ttt agt gca atg gag caa gag cac ttt agt gag ttt ctg cga agt cac     1226
Phe Ser Ala Met Glu Gln Glu His Phe Ser Glu Phe Leu Arg Ser His
        350                 355                 360

cat ttc tgt aaa tac cag att gaa gtg ctg acc agt gga act gtt tac     1274
His Phe Cys Lys Tyr Gln Ile Glu Val Leu Thr Ser Gly Thr Val Tyr
    365                 370                 375

ctg gct gac att ctc ttc tgt gag tca gcc ctc ttt tat ttc tct gag     1322
Leu Ala Asp Ile Leu Phe Cys Glu Ser Ala Leu Phe Tyr Phe Ser Glu
380                 385                 390                 395

tac atg gaa aaa gag gat gca gtg aat atc tta caa ttc tgg ttg gca     1370
Tyr Met Glu Lys Glu Asp Ala Val Asn Ile Leu Gln Phe Trp Leu Ala
                400                 405                 410

gca gat aac ttc cag tct cag ctt gct gcc aaa aag ggg caa tat gat     1418
Ala Asp Asn Phe Gln Ser Gln Leu Ala Ala Lys Lys Gly Gln Tyr Asp
            415                 420                 425

gga cag gag gca cag aat gat gcc atg att tta tat gac aag tac ttc     1466
Gly Gln Glu Ala Gln Asn Asp Ala Met Ile Leu Tyr Asp Lys Tyr Phe
        430                 435                 440

tcc ctc caa gcc aca cat cct ctt gga ttt gat gat gtt gta cga tta     1514
Ser Leu Gln Ala Thr His Pro Leu Gly Phe Asp Asp Val Val Arg Leu
    445                 450                 455

gaa att gaa tcc aat atc tgc agg gaa ggt ggg cca ctc ccc aac tgt     1562
Glu Ile Glu Ser Asn Ile Cys Arg Glu Gly Gly Pro Leu Pro Asn Cys
460                 465                 470                 475

ttc aca act cca tta cgt cag gcc tgg aca acc atg gag aag gtc ttt     1610
Phe Thr Thr Pro Leu Arg Gln Ala Trp Thr Thr Met Glu Lys Val Phe
                480                 485                 490

ttg cct ggc ttt ctg tcc agc aat ctt tat tat aaa tat ttg aat gat     1658
Leu Pro Gly Phe Leu Ser Ser Asn Leu Tyr Tyr Lys Tyr Leu Asn Asp
            495                 500                 505

ctc atc cat tcg gtt cga gga gat gaa ttt ctg ggc ggg aac gtg tcg     1706
Leu Ile His Ser Val Arg Gly Asp Glu Phe Leu Gly Gly Asn Val Ser
        510                 515                 520

ccg act gct cct ggc tct gtt ggc cct cct gat gag tct cac cca ggg     1754
Pro Thr Ala Pro Gly Ser Val Gly Pro Pro Asp Glu Ser His Pro Gly
    525                 530                 535

agt tct gac agc tct gcg tct cag tcc agt gtg aaa aaa gcc agt att     1802
Ser Ser Asp Ser Ser Ala Ser Gln Ser Ser Val Lys Lys Ala Ser Ile
540                 545                 550                 555
```

-continued

```
aaa ata ctg aaa aat ttt gat gaa gcg ata att gtg gat gcg gca agt      1850
Lys Ile Leu Lys Asn Phe Asp Glu Ala Ile Ile Val Asp Ala Ala Ser
                560                 565                 570

ctg gat cca gaa tct tta tat caa cgg aca tat gcc ggg aag atg aca      1898
Leu Asp Pro Glu Ser Leu Tyr Gln Arg Thr Tyr Ala Gly Lys Met Thr
            575                 580                 585

ttt gga aga gtg agt gac ttg ggg caa ttc atc cgg gaa tct gag cct      1946
Phe Gly Arg Val Ser Asp Leu Gly Gln Phe Ile Arg Glu Ser Glu Pro
        590                 595                 600

gaa cct gat gta agg aaa tca aaa gga tcc atg ttc tca caa gct atg      1994
Glu Pro Asp Val Arg Lys Ser Lys Gly Ser Met Phe Ser Gln Ala Met
    605                 610                 615

aag aaa tgg gtg caa gga aat act gat gag gcc cag gaa gag cta gct      2042
Lys Lys Trp Val Gln Gly Asn Thr Asp Glu Ala Gln Glu Glu Leu Ala
620                 625                 630                 635

tgg aag att gct aaa atg ata gtc agt gac att atg cag cag gct cag      2090
Trp Lys Ile Ala Lys Met Ile Val Ser Asp Ile Met Gln Gln Ala Gln
                640                 645                 650

tat gat caa ccg tta gag aaa tct aca aag tta tga ctcaaaactt           2136
Tyr Asp Gln Pro Leu Glu Lys Ser Thr Lys Leu  *
            655                 660

gagataaagg aaatctgctt gtgaaaaata agagaacttt tttcccttgg ttggattctt   2196

caacacagcc aatgaaaaca gcactatatt tctgatctgt cactgttgtt tccagggaga   2256

gaatggggag acaatcctag gacttccacc ctaatgcagt tacctgtagg gcataattgg   2316

atggcacatg atgtttcaca cagtgaggag tctttaaagg ttaccaa                 2363


<210> SEQ ID NO 32
<211> LENGTH: 662
<212> TYPE: PRT
<213> ORGANISM: Homo Sapien

<400> SEQUENCE: 32

Met Arg Gly Ala Gly Pro Ser Pro Arg Gln Ser Pro Arg Thr Leu Arg
 1               5                  10                  15

Pro Asp Pro Gly Pro Ala Met Ser Phe Phe Arg Arg Lys Val Lys Gly
            20                  25                  30

Lys Glu Gln Glu Lys Thr Ser Asp Val Lys Ser Ile Lys Ala Ser Ile
        35                  40                  45

Ser Val His Ser Pro Gln Lys Ser Thr Lys Asn His Ala Leu Leu Glu
    50                  55                  60

Ala Ala Gly Pro Ser His Val Ala Ile Asn Ala Ile Ser Ala Asn Met
65                  70                  75                  80

Asp Ser Phe Ser Ser Ser Arg Thr Ala Thr Leu Lys Lys Gln Pro Ser
                85                  90                  95

His Met Glu Ala Ala His Phe Gly Asp Leu Gly Arg Ser Cys Leu Asp
            100                 105                 110

Tyr Gln Thr Gln Glu Thr Lys Ser Ser Leu Ser Lys Thr Leu Glu Gln
        115                 120                 125

Val Leu His Asp Thr Ile Val Leu Pro Tyr Phe Ile Gln Phe Met Glu
    130                 135                 140

Leu Arg Arg Met Glu His Leu Val Lys Phe Trp Leu Glu Ala Glu Ser
145                 150                 155                 160

Phe His Ser Thr Thr Trp Ser Arg Ile Arg Ala His Ser Leu Asn Thr
                165                 170                 175

Met Lys Gln Ser Ser Leu Ala Glu Pro Val Ser Pro Ser Lys Lys His
            180                 185                 190
```

-continued

```
Glu Thr Thr Ala Ser Phe Leu Thr Asp Ser Leu Asp Lys Arg Leu Glu
        195                 200                 205

Asp Ser Gly Ser Ala Gln Leu Phe Met Thr His Ser Glu Gly Ile Asp
    210                 215                 220

Leu Asn Asn Arg Thr Asn Ser Thr Gln Asn His Leu Leu Leu Ser Gln
225                 230                 235                 240

Glu Cys Asp Ser Ala His Ser Leu Arg Leu Glu Met Ala Arg Ala Gly
                245                 250                 255

Thr His Gln Val Ser Met Glu Thr Gln Glu Ser Ser Ser Thr Leu Thr
            260                 265                 270

Val Ala Ser Arg Asn Ser Pro Ala Ser Pro Leu Lys Glu Leu Ser Gly
        275                 280                 285

Lys Leu Met Lys Ser Ile Glu Gln Asp Ala Val Asn Thr Phe Thr Lys
    290                 295                 300

Tyr Ile Ser Pro Asp Ala Ala Lys Pro Ile Pro Ile Thr Glu Ala Met
305                 310                 315                 320

Arg Asn Asp Ile Ile Ala Arg Ile Cys Gly Glu Asp Gly Gln Val Asp
                325                 330                 335

Pro Asn Cys Phe Val Leu Ala Gln Ser Ile Val Phe Ser Ala Met Glu
            340                 345                 350

Gln Glu His Phe Ser Glu Phe Leu Arg Ser His His Phe Cys Lys Tyr
        355                 360                 365

Gln Ile Glu Val Leu Thr Ser Gly Thr Val Tyr Leu Ala Asp Ile Leu
    370                 375                 380

Phe Cys Glu Ser Ala Leu Phe Tyr Phe Ser Glu Tyr Met Glu Lys Glu
385                 390                 395                 400

Asp Ala Val Asn Ile Leu Gln Phe Trp Leu Ala Ala Asp Asn Phe Gln
                405                 410                 415

Ser Gln Leu Ala Ala Lys Lys Gly Gln Tyr Asp Gly Gln Glu Ala Gln
            420                 425                 430

Asn Asp Ala Met Ile Leu Tyr Asp Lys Tyr Phe Ser Leu Gln Ala Thr
        435                 440                 445

His Pro Leu Gly Phe Asp Asp Val Val Arg Leu Glu Ile Glu Ser Asn
    450                 455                 460

Ile Cys Arg Glu Gly Gly Pro Leu Pro Asn Cys Phe Thr Thr Pro Leu
465                 470                 475                 480

Arg Gln Ala Trp Thr Thr Met Glu Lys Val Phe Leu Pro Gly Phe Leu
                485                 490                 495

Ser Ser Asn Leu Tyr Tyr Lys Tyr Leu Asn Asp Leu Ile His Ser Val
            500                 505                 510

Arg Gly Asp Glu Phe Leu Gly Gly Asn Val Ser Pro Thr Ala Pro Gly
        515                 520                 525

Ser Val Gly Pro Pro Asp Glu Ser His Pro Gly Ser Ser Asp Ser Ser
    530                 535                 540

Ala Ser Gln Ser Ser Val Lys Lys Ala Ser Ile Lys Ile Leu Lys Asn
545                 550                 555                 560

Phe Asp Glu Ala Ile Ile Val Asp Ala Ala Ser Leu Asp Pro Glu Ser
                565                 570                 575

Leu Tyr Gln Arg Thr Tyr Ala Gly Lys Met Thr Phe Gly Arg Val Ser
            580                 585                 590

Asp Leu Gly Gln Phe Ile Arg Glu Ser Glu Pro Glu Pro Asp Val Arg
        595                 600                 605
```

-continued

```
Lys Ser Lys Gly Ser Met Phe Ser Gln Ala Met Lys Lys Trp Val Gln
    610                 615                 620

Gly Asn Thr Asp Glu Ala Gln Glu Glu Leu Ala Trp Lys Ile Ala Lys
625                 630                 635                 640

Met Ile Val Ser Asp Ile Met Gln Gln Ala Gln Tyr Asp Gln Pro Leu
                645                 650                 655

Glu Lys Ser Thr Lys Leu
            660


<210> SEQ ID NO 33
<211> LENGTH: 2363
<212> TYPE: DNA
<213> ORGANISM: Homo Sapien
<220> FEATURE:
<221> NAME/KEY: CDS
<222> LOCATION: (138)...(2126)
<223> OTHER INFORMATION: AKAP-10-5
<220> FEATURE:
<221> NAME/KEY: allele
<222> LOCATION: 2073
<223> OTHER INFORMATION: Single Nucleotide Polymorphism: A to G

<400> SEQUENCE: 33

gcggcttgtt gataatatgg cggctggagc tgcctgggca tcccgaggag gcggtggggc      60

ccactcccgg aagaagggtc ccttttcgcg ctagtgcagc ggcccctctg gacccggaag     120

tccgggccgg ttgctga atg agg gga gcc ggg ccc tcc ccg cgc cag tcc        170
                   Met Arg Gly Ala Gly Pro Ser Pro Arg Gln Ser
                     1               5                  10

ccc cgc acc ctc cgt ccc gac ccg ggc ccc gcc atg tcc ttc ttc cgg       218
Pro Arg Thr Leu Arg Pro Asp Pro Gly Pro Ala Met Ser Phe Phe Arg
            15                  20                  25

cgg aaa gtg aaa ggc aaa gaa caa gag aag acc tca gat gtg aag tcc       266
Arg Lys Val Lys Gly Lys Glu Gln Glu Lys Thr Ser Asp Val Lys Ser
        30                  35                  40

att aaa gct tca ata tcc gta cat tcc cca caa aaa agc act aaa aat       314
Ile Lys Ala Ser Ile Ser Val His Ser Pro Gln Lys Ser Thr Lys Asn
    45                  50                  55

cat gcc ttg ctg gag gct gca gga cca agt cat gtt gca atc aat gcc       362
His Ala Leu Leu Glu Ala Ala Gly Pro Ser His Val Ala Ile Asn Ala
 60                  65                  70                  75

att tct gcc aac atg gac tcc ttt tca agt agc agg aca gcc aca ctt       410
Ile Ser Ala Asn Met Asp Ser Phe Ser Ser Ser Arg Thr Ala Thr Leu
                80                  85                  90

aag aag cag cca agc cac atg gag gct gct cat ttt ggt gac ctg ggc       458
Lys Lys Gln Pro Ser His Met Glu Ala Ala His Phe Gly Asp Leu Gly
            95                  100                 105

aga tct tgt ctg gac tac cag act caa gag acc aaa tca agc ctt tct       506
Arg Ser Cys Leu Asp Tyr Gln Thr Gln Glu Thr Lys Ser Ser Leu Ser
        110                 115                 120

aag acc ctt gaa caa gtc ttg cac gac act att gtc ctc cct tac ttc       554
Lys Thr Leu Glu Gln Val Leu His Asp Thr Ile Val Leu Pro Tyr Phe
    125                 130                 135

att caa ttc atg gaa ctt cgg cga atg gag cat ttg gtg aaa ttt tgg       602
Ile Gln Phe Met Glu Leu Arg Arg Met Glu His Leu Val Lys Phe Trp
140                 145                 150                 155

tta gag gct gaa agt ttt cat tca aca act tgg tcg cga ata aga gca       650
Leu Glu Ala Glu Ser Phe His Ser Thr Thr Trp Ser Arg Ile Arg Ala
                160                 165                 170

cac agt cta aac aca atg aag cag agc tca ctg gct gag cct gtc tct       698
His Ser Leu Asn Thr Met Lys Gln Ser Ser Leu Ala Glu Pro Val Ser
            175                 180                 185
```

-continued

```
cca tct aaa aag cat gaa act aca gcg tct ttt tta act gat tct ctt      746
Pro Ser Lys Lys His Glu Thr Thr Ala Ser Phe Leu Thr Asp Ser Leu
        190                 195                 200

gat aag aga ttg gag gat tct ggc tca gca cag ttg ttt atg act cat      794
Asp Lys Arg Leu Glu Asp Ser Gly Ser Ala Gln Leu Phe Met Thr His
    205                 210                 215

tca gaa gga att gac ctg aat aat aga act aac agc act cag aat cac      842
Ser Glu Gly Ile Asp Leu Asn Asn Arg Thr Asn Ser Thr Gln Asn His
220                 225                 230                 235

ttg ctg ctt tcc cag gaa tgt gac agt gcc cat tct ctc cgt ctt gaa      890
Leu Leu Leu Ser Gln Glu Cys Asp Ser Ala His Ser Leu Arg Leu Glu
                240                 245                 250

atg gcc aga gca gga act cac caa gtt tcc atg gaa acc caa gaa tct      938
Met Ala Arg Ala Gly Thr His Gln Val Ser Met Glu Thr Gln Glu Ser
            255                 260                 265

tcc tct aca ctt aca gta gcc agt aga aat agt ccc gct tct cca cta      986
Ser Ser Thr Leu Thr Val Ala Ser Arg Asn Ser Pro Ala Ser Pro Leu
        270                 275                 280

aaa gaa ttg tca gga aaa cta atg aaa agt ata gaa caa gat gca gtg     1034
Lys Glu Leu Ser Gly Lys Leu Met Lys Ser Ile Glu Gln Asp Ala Val
    285                 290                 295

aat act ttt acc aaa tat ata tct cca gat gct gct aaa cca ata cca     1082
Asn Thr Phe Thr Lys Tyr Ile Ser Pro Asp Ala Ala Lys Pro Ile Pro
300                 305                 310                 315

att aca gaa gca atg aga aat gac atc ata gca agg att tgt gga gaa     1130
Ile Thr Glu Ala Met Arg Asn Asp Ile Ile Ala Arg Ile Cys Gly Glu
                320                 325                 330

gat gga cag gtg gat ccc aac tgt ttc gtt ttg gca cag tcc ata gtc     1178
Asp Gly Gln Val Asp Pro Asn Cys Phe Val Leu Ala Gln Ser Ile Val
            335                 340                 345

ttt agt gca atg gag caa gag cac ttt agt gag ttt ctg cga agt cac     1226
Phe Ser Ala Met Glu Gln Glu His Phe Ser Glu Phe Leu Arg Ser His
        350                 355                 360

cat ttc tgt aaa tac cag att gaa gtg ctg acc agt gga act gtt tac     1274
His Phe Cys Lys Tyr Gln Ile Glu Val Leu Thr Ser Gly Thr Val Tyr
    365                 370                 375

ctg gct gac att ctc ttc tgt gag tca gcc ctc ttt tat ttc tct gag     1322
Leu Ala Asp Ile Leu Phe Cys Glu Ser Ala Leu Phe Tyr Phe Ser Glu
380                 385                 390                 395

tac atg gaa aaa gag gat gca gtg aat atc tta caa ttc tgg ttg gca     1370
Tyr Met Glu Lys Glu Asp Ala Val Asn Ile Leu Gln Phe Trp Leu Ala
                400                 405                 410

gca gat aac ttc cag tct cag ctt gct gcc aaa aag ggg caa tat gat     1418
Ala Asp Asn Phe Gln Ser Gln Leu Ala Ala Lys Lys Gly Gln Tyr Asp
            415                 420                 425

gga cag gag gca cag aat gat gcc atg att tta tat gac aag tac ttc     1466
Gly Gln Glu Ala Gln Asn Asp Ala Met Ile Leu Tyr Asp Lys Tyr Phe
        430                 435                 440

tcc ctc caa gcc aca cat cct ctt gga ttt gat gat gtt gta cga tta     1514
Ser Leu Gln Ala Thr His Pro Leu Gly Phe Asp Asp Val Val Arg Leu
    445                 450                 455

gaa att gaa tcc aat atc tgc agg gaa ggt ggg cca ctc ccc aac tgt     1562
Glu Ile Glu Ser Asn Ile Cys Arg Glu Gly Gly Pro Leu Pro Asn Cys
460                 465                 470                 475

ttc aca act cca tta cgt cag gcc tgg aca acc atg gag aag gtc ttt     1610
Phe Thr Thr Pro Leu Arg Gln Ala Trp Thr Thr Met Glu Lys Val Phe
                480                 485                 490

ttg cct ggc ttt ctg tcc agc aat ctt tat tat aaa tat ttg aat gat     1658
Leu Pro Gly Phe Leu Ser Ser Asn Leu Tyr Tyr Lys Tyr Leu Asn Asp
```

-continued

```
            495                 500                 505

ctc atc cat tcg gtt cga gga gat gaa ttt ctg ggc ggg aac gtg tcg      1706
Leu Ile His Ser Val Arg Gly Asp Glu Phe Leu Gly Gly Asn Val Ser
        510                 515                 520

ccg act gct cct ggc tct gtt ggc cct cct gat gag tct cac cca ggg      1754
Pro Thr Ala Pro Gly Ser Val Gly Pro Pro Asp Glu Ser His Pro Gly
    525                 530                 535

agt tct gac agc tct gcg tct cag tcc agt gtg aaa aaa gcc agt att      1802
Ser Ser Asp Ser Ser Ala Ser Gln Ser Ser Val Lys Lys Ala Ser Ile
540                 545                 550                 555

aaa ata ctg aaa aat ttt gat gaa gcg ata att gtg gat gcg gca agt      1850
Lys Ile Leu Lys Asn Phe Asp Glu Ala Ile Ile Val Asp Ala Ala Ser
                560                 565                 570

ctg gat cca gaa tct tta tat caa cgg aca tat gcc ggg aag atg aca      1898
Leu Asp Pro Glu Ser Leu Tyr Gln Arg Thr Tyr Ala Gly Lys Met Thr
            575                 580                 585

ttt gga aga gtg agt gac ttg ggg caa ttc atc cgg gaa tct gag cct      1946
Phe Gly Arg Val Ser Asp Leu Gly Gln Phe Ile Arg Glu Ser Glu Pro
        590                 595                 600

gaa cct gat gta agg aaa tca aaa gga tcc atg ttc tca caa gct atg      1994
Glu Pro Asp Val Arg Lys Ser Lys Gly Ser Met Phe Ser Gln Ala Met
    605                 610                 615

aag aaa tgg gtg caa gga aat act gat gag gcc cag gaa gag cta gct      2042
Lys Lys Trp Val Gln Gly Asn Thr Asp Glu Ala Gln Glu Glu Leu Ala
620                 625                 630                 635

tgg aag att gct aaa atg ata gtc agt gac gtt atg cag cag gct cag      2090
Trp Lys Ile Ala Lys Met Ile Val Ser Asp Val Met Gln Gln Ala Gln
                640                 645                 650

tat gat caa ccg tta gag aaa tct aca aag tta tga ctcaaaactt           2136
Tyr Asp Gln Pro Leu Glu Lys Ser Thr Lys Leu  *
            655                 660

gagataaagg aaatctgctt gtgaaaaata agagaacttt tttcccttgg ttggattctt   2196

caacacagcc aatgaaaaca gcactatatt tctgatctgt cactgttgtt tccagggaga   2256

gaatggggag acaatcctag gacttccacc ctaatgcagt tacctgtagg gcataattgg   2316

atggcacatg atgtttcaca cagtgaggag tctttaaagg ttaccaa                 2363


<210> SEQ ID NO 34
<211> LENGTH: 662
<212> TYPE: PRT
<213> ORGANISM: Homo Sapien

<400> SEQUENCE: 34

Met Arg Gly Ala Gly Pro Ser Pro Arg Gln Ser Pro Arg Thr Leu Arg
 1               5                  10                  15

Pro Asp Pro Gly Pro Ala Met Ser Phe Phe Arg Arg Lys Val Lys Gly
            20                  25                  30

Lys Glu Gln Glu Lys Thr Ser Asp Val Lys Ser Ile Lys Ala Ser Ile
        35                  40                  45

Ser Val His Ser Pro Gln Lys Ser Thr Lys Asn His Ala Leu Leu Glu
    50                  55                  60

Ala Ala Gly Pro Ser His Val Ala Ile Asn Ala Ile Ser Ala Asn Met
65                  70                  75                  80

Asp Ser Phe Ser Ser Ser Arg Thr Ala Thr Leu Lys Lys Gln Pro Ser
                85                  90                  95

His Met Glu Ala Ala His Phe Gly Asp Leu Gly Arg Ser Cys Leu Asp
            100                 105                 110
```

-continued

```
Tyr Gln Thr Gln Glu Thr Lys Ser Ser Leu Ser Lys Thr Leu Glu Gln
        115                 120                 125

Val Leu His Asp Thr Ile Val Leu Pro Tyr Phe Ile Gln Phe Met Glu
    130                 135                 140

Leu Arg Arg Met Glu His Leu Val Lys Phe Trp Leu Glu Ala Glu Ser
145                 150                 155                 160

Phe His Ser Thr Thr Trp Ser Arg Ile Arg Ala His Ser Leu Asn Thr
                165                 170                 175

Met Lys Gln Ser Ser Leu Ala Glu Pro Val Ser Pro Ser Lys Lys His
            180                 185                 190

Glu Thr Thr Ala Ser Phe Leu Thr Asp Ser Leu Asp Lys Arg Leu Glu
        195                 200                 205

Asp Ser Gly Ser Ala Gln Leu Phe Met Thr His Ser Glu Gly Ile Asp
    210                 215                 220

Leu Asn Asn Arg Thr Asn Ser Thr Gln Asn His Leu Leu Leu Ser Gln
225                 230                 235                 240

Glu Cys Asp Ser Ala His Ser Leu Arg Leu Glu Met Ala Arg Ala Gly
                245                 250                 255

Thr His Gln Val Ser Met Glu Thr Gln Glu Ser Ser Ser Thr Leu Thr
            260                 265                 270

Val Ala Ser Arg Asn Ser Pro Ala Ser Pro Leu Lys Glu Leu Ser Gly
        275                 280                 285

Lys Leu Met Lys Ser Ile Glu Gln Asp Ala Val Asn Thr Phe Thr Lys
    290                 295                 300

Tyr Ile Ser Pro Asp Ala Ala Lys Pro Ile Pro Ile Thr Glu Ala Met
305                 310                 315                 320

Arg Asn Asp Ile Ile Ala Arg Ile Cys Gly Glu Asp Gly Gln Val Asp
                325                 330                 335

Pro Asn Cys Phe Val Leu Ala Gln Ser Ile Val Phe Ser Ala Met Glu
            340                 345                 350

Gln Glu His Phe Ser Glu Phe Leu Arg Ser His His Phe Cys Lys Tyr
        355                 360                 365

Gln Ile Glu Val Leu Thr Ser Gly Thr Val Tyr Leu Ala Asp Ile Leu
    370                 375                 380

Phe Cys Glu Ser Ala Leu Phe Tyr Phe Ser Glu Tyr Met Glu Lys Glu
385                 390                 395                 400

Asp Ala Val Asn Ile Leu Gln Phe Trp Leu Ala Ala Asp Asn Phe Gln
                405                 410                 415

Ser Gln Leu Ala Ala Lys Lys Gly Gln Tyr Asp Gly Gln Glu Ala Gln
            420                 425                 430

Asn Asp Ala Met Ile Leu Tyr Asp Lys Tyr Phe Ser Leu Gln Ala Thr
        435                 440                 445

His Pro Leu Gly Phe Asp Asp Val Val Arg Leu Glu Ile Glu Ser Asn
    450                 455                 460

Ile Cys Arg Glu Gly Gly Pro Leu Pro Asn Cys Phe Thr Thr Pro Leu
465                 470                 475                 480

Arg Gln Ala Trp Thr Thr Met Glu Lys Val Phe Leu Pro Gly Phe Leu
                485                 490                 495

Ser Ser Asn Leu Tyr Tyr Lys Tyr Leu Asn Asp Leu Ile His Ser Val
            500                 505                 510

Arg Gly Asp Glu Phe Leu Gly Gly Asn Val Ser Pro Thr Ala Pro Gly
        515                 520                 525

Ser Val Gly Pro Pro Asp Glu Ser His Pro Gly Ser Ser Asp Ser Ser
```

-continued

```
    530                 535                 540

Ala Ser Gln Ser Ser Val Lys Lys Ala Ser Ile Lys Ile Leu Lys Asn
545                 550                 555                 560

Phe Asp Glu Ala Ile Ile Val Asp Ala Ala Ser Leu Asp Pro Glu Ser
                565                 570                 575

Leu Tyr Gln Arg Thr Tyr Ala Gly Lys Met Thr Phe Gly Arg Val Ser
            580                 585                 590

Asp Leu Gly Gln Phe Ile Arg Glu Ser Glu Pro Glu Pro Asp Val Arg
        595                 600                 605

Lys Ser Lys Gly Ser Met Phe Ser Gln Ala Met Lys Lys Trp Val Gln
    610                 615                 620

Gly Asn Thr Asp Glu Ala Gln Glu Glu Leu Ala Trp Lys Ile Ala Lys
625                 630                 635                 640

Met Ile Val Ser Asp Val Met Gln Gln Ala Gln Tyr Asp Gln Pro Leu
                645                 650                 655

Glu Lys Ser Thr Lys Leu
            660
```

<210> SEQ ID NO 35
<211> LENGTH: 162025
<212> TYPE: DNA
<213> ORGANISM: Homo Sapien
<300> PUBLICATION INFORMATION:
<308> DATABASE ACCESSION NUMBER: GenBank AC005730
<309> DATABASE ENTRY DATE: 1998-10-22

<400> SEQUENCE: 35

```
gaattcctat ttcaaaagaa acaaatgggc caagtatggt ggctcatacc tgtaatccca     60

gcactttggg aggccgaggt gagtgggtca cttgaggtca ggagttccag gccagtctgg    120

ccaacatggt gaaacactgt ctctactaaa aatacaaaaa ttagccgggc gtggtggcgg    180

gcacctgtaa tcccagctac tcaggaggct gaggcaggag aattgcttga acctgggaga    240

tggaggttgc agtgagccga gatcgcgcca ctgctctcca gcctgggtgg cagagtgaga    300

ctctgtctca aaaagaaaca aagaaataaa tgaaacaatt ttgttcacat atatttcaca    360

aatttgaaat gttaaaggta ttatggtcac tgatatcctg tttcattctt tatataatca    420

ttaagtttga aatgtatact tgcactacta acacagtagt taatcttagt cctacaagtt    480

actgctttta cacaatatat tttcgtaata tgtatgcact ggtgtttatg tacgtgttta    540

tgtttatatc tgttaaaatt agcagtttcc atctttttct attttgtacc atcacatcag    600

ttcagaagga ttgacagagc aaaatgattt gatgaagtat aaaagtcaca tggtgagtgg    660

cataaataca actctgaaca attaggaggc tcactattga ctggaactaa actgcaagcc    720

agaaagacac atatcctata tgtcaagaga tgtaccaccc aggcagttaa agaagggaag    780

tacacataga aagcacaatg gtgaataatt aaaaaattgg aatttatcag acactggatt    840

catttgctcc taaagtcaga gtcctctatt gttttttttgt ttttgtgggt ttcttttttaa    900

atttttttat tttttgtaga gtcggagtct cactgtgtta cccgggctgg tctagaactc    960

ctggcctcaa acaaacctcc tgcctcagct tcccaaagca ttgggattac agacatgagc   1020

cactgagccc agcccagacg ctttagcatt tatgaagctt ctgaaatagt tgtagaaacc   1080

gcataagctt tccatgtcac tttcaaagtt tgatggtctc tttagtaaac caaccaagtt   1140

attcctcaag ggcaaaataa catttctcag tgcaaaactg atgcacttca ttaccaaaag   1200

gaaaagacca caactataga ggcgtcattg aaagctgcac tcttcagagg ccaaaaaaaa   1260
```

-continued

```
aggtacaaac acatactaat ggaacattct ttagaagagc cccaaagtta atgataaaca   1320
ttttcatcaa agagaaaaga gaacaaggtg ttagcaaatt cctctatcaa ataacactaa   1380
acatcaagga acatcaatgg catgccatgt ggaagaggaa gtgctagctc atgtacaaac   1440
cagtagataa tttcaacttg ctgccgaatg aaacctcttt gcaaggtatg aatcagcact   1500
tctcatgttt gttttgcttt gttttgtttt gtttttagag acaggccctt gctctgtcac   1560
acaggctgga gtgcagtggc acgatcagag ctcactgcaa cctgaaactc ctgggctcaa   1620
gggatcctcc tgccttagcc tcccaagtag ctgggactac aggcccacca tgcccagcta   1680
attttttaaa ttttctatag agatgggatc tcactagcac ctttcatgtt tgatgttcat   1740
atacaacgac caaggtacaa tgtggaaaag ggtctcaggg atctaaagtg aaggaggacc   1800
agaaagaaaa ggggttgcta catagagtag aagaagttgc acttcatgcc agtctacaac   1860
actgctgttt tcctcagagc agagttgatg atctaaatca ggggtcccca acccccagtt   1920
catagcctgt taggaaccgg gccacacagc aggaggtgag caataggcaa gcgagcatta   1980
ccacctgggc ttcacctccc gtcagatcag tgatgtcatt agattctcat aggaccatga   2040
accctattgt gaactgagca tgcaagggat gtaggttttc cgctctttat gagactctaa   2100
tgccggaaga tctgtcactg tcttccatca ccctgagatg ggaacatcta gttgcaggaa   2160
aacaacctca gggctcccat tgattctata ttacagtgag ttgtatcatt atttcattct   2220
atattacaat gtaataataa tagaaataaa ggcacaatag gccaggcgtg gtggctcaca   2280
cctgtaatcc cagcacttcg ggaggccaag gcaggcggat cacgaggtca ggagatcgag   2340
accatcctgg ctaaaacggt gaaaccccgt ctactaaaaa ttcaaaaaaa aattagccgg   2400
gtgtggtggt gggcacctgt agtcccagct actcgagagg ctgaggcagg agaatggtgt   2460
gaacctggga ggcagagctt gaggtaagcc gagatcacgc cactgcactc cagcctgggc   2520
gacagagcga tactctgtct caaaaaaaaa aaaaaaaaaa aaagaaataa agtgaacaat   2580
aaatgtaatg tggctgaatc attccaaaac aatcccccca ccccagttca cggaaaaatt   2640
ctcccacaaa accagtccct ggtgccaaaa aggttgggga ccgctaatct aaataatcta   2700
atcttcattc aatgctaaaa aatgaataaa ctttttttta aatacacggt ctcactttgt   2760
tgcccaggct ggagtacggt ggcatgatca cagctcactg tagcctcaat cacccaggcc   2820
ccagcgatcc tcccacctaa acttcctgag tagctgggac tacaggcacg caccaccatg   2880
cccagctaat ttttaaattt tttatagaga tgggggtctc accatgttgc ccagactggt   2940
ctcaaaccct gggctcaagt gatcctccct caaactcctg gactcaagtg atcctccttc   3000
cttggcctcc caaagtgctg ggattacaag catgagccac tgtacccagc tggataaaca   3060
ttttaagtcg cactacagtc atggacaatc aggcttttca acatgcagta tggacagtga   3120
gtcccagggt ctgcttttcc atactgaaat acatgtgata ctaaggagaa aggtgctcgc   3180
aaggatattt aaaatgaaga atatttaaaa tgaggaaaaa actgtttctt catgactttg   3240
ataaggctga taaagaccat ttctgtgatc tcaggtgatt cactcaagta gtatatttca   3300
gtaatcatta tctggaacag cctgaatctt aaccaaaata ccatgatttt ttaatgctgt   3360
tatgatacct tgatgatatg accaaactgc aatgtaggca gctaaatctc cacgagtttg   3420
acttccccga gagttgacag ttttcttcac aaattaaaga aatatatttt ttgatacatg   3480
attggcatat ttaaaaacta cactgaaatg ctgcaaaatg atataaagaa acattttcca   3540
gaatcaaatg caatcaaaga gtggattagg aatctactca ccattatcaa ctaaatagaa   3600
acacttggac tgggtgtggt ggctcacatc tgtaatctca gcactttggg aggccaaggc   3660
```

-continued

```
aggtggattg cttgaggcca ggagctcaag accagcctga gcaacatagc aaaactctgt   3720
ctctacaaaa aaaaaaaaaa attaaccagg catggtggca gatgcttgta atcccagcta   3780
ctctggaagc tgaagtagga ggactgcttg agcccaggag atcaagactg cagtgagccg   3840
tggtcatgct gcgccacagc ctgagtgaca gagagagacc ctgtctcaaa aacaaaaaca   3900
aacaaaaaac acttaacctt cctgtttttt gctgttgttg ttgttgtttg tttgttttga   3960
gatggagtct cactctgttg cccaggctgg agtgcagtgg cgtgatcttg gctcactgca   4020
agctctgcct cccgggttca cgccattctc ctgcctcagc ctcccgagta gctgggacta   4080
taggcgcccg ccaccacgcc cggctacttt tttgcatttt tagtagagat ggggtttcac   4140
cgtgttagcc aggatggtct tgatctcctg acctcgtgat ccacctgcct cggcctccca   4200
aagtgctggg attacaggca tgagccaccg cacccggcca acctttctgt tttttagttt   4260
gatatgcttg ttaactcagc agctgaaaga atgctgaaag tggccttcag taaaaaaatt   4320
tcactagaat ctctacatcc atatttaatc tgaatgcata tccagattga tcagttagag   4380
caaaaacact catcatcatt cctgatgacc tctaattctg gtttcggctt tctatttcaa   4440
tggaaacaga ataaggaaag aaatggaagg gctctggaaa tttgtcctgg gctatagata   4500
ctatcaaaga tcaccaacaa taagatctct cctataaata taaaacaagt ataattaatt   4560
ttttaattat ttttttctct tcagaggatt ttatttcaag ataaaacata acttctaccc   4620
atactattga ttccaaaggt tagaaaaagt gtttttcctc atcttatcct tcaaagaggt   4680
cacagcaatg caaacatcta taaaatgcct ctgcataatt gtcagaagct atagtccaga   4740
aatcattgaa aatgcttttc cattttaagc ttaggtgagg tgtcttagga aacctctatg   4800
acaacttact ctatttattg ggaggtaaac tcccagactc tcccagggtc tcctgtattg   4860
atctcatttt ttaggcttcc taatcccttg aagcacaatc gaaaaagccc tggatctctt   4920
ttctgcacat atcatcgcgg aattcattcg gcttccagca agctgacact ccatgataca   4980
agcggcctcg cccttctccg gacgccagtc cttgctgcgg ttagctagga tgaggggttt   5040
gctgggcttc agtgcaggct tctgcgggtt cccaagccgc accaggtggc ctcacaggct   5100
ggatgtcacc attgcacact gagctcctgg caggctgtac caattttttta attatttaat   5160
atttattttt aaaattatgg tgaatatttt ggtattctgc tctaaaatag gcccataaat   5220
gcacagcaga tatctcttgg aacccacagc tttccactgg aagaactaag tatttttctt   5280
ttaaagatgc tactaagtct ctgaaaagtc cagatcctct acctctttcc atcccaaact   5340
aagacttgga atttatgaga gatctagcta acagaaatcc cagacacatc attggttctt   5400
cccagagtgc agtcctccta aagaggctca gccctaagca ggcccctgca ccaggagggt   5460
gggtctgaga cccacatagc acttcccaag gtgcatgctc cagagaggca ctgaaacagc   5520
tgagcacaag cctgcaagcc tggagaactc tcacagtcag aacggagggg gcccagtggg   5580
actaacataa agagaaaagg gaacacagag aaatggatgg caccaacaac cagcaaagcc   5640
ttcatggcca atgaaagcat cagtgacggg gccagaaccc tcatccccaa agactcttca   5700
ctgcctttag tgaaaaacaa tggctagaga gtgaagttat gatcatgtat agagaggtaa   5760
agttacattt ttatattctg actctgctaa tgtgaaattc cctatctgct agactaaaag   5820
tttcagacac cctgttcaaa tatcccatta gttgctagag acttaaaatg aacagaacgc   5880
acattgtcag gatgactatt accaaaaaat caaaagacag caagtattgg tgaggatgta   5940
gagaaactgg aacttttgtg cactgtttat gagaatgtaa aatggagcag ctgctgtgga   6000
```

-continued

```
aaagagtatg caggttcctc aaagagtaaa accaagatgt ggaaacaact aaatgcccat   6060
cagtggatga aggggtagac aatatgtggt atatacatac catggagtac tattcagcct   6120
ctaaaaaaaa aaaaggaaat tctataacat gcaacagcat ggatgaatct tgaggacatt   6180
ttgctaatga aataaggcag tcatagaaag acaaatactg cacgactcca cttatatgag   6240
ataccaaaaa tagacaaatt catagaatca aagagtacaa tggaggttac ctggagctgc   6300
agggcgggaa acgaggagtt actaatcaac gaacataacg ttgcagttaa gtaagatgaa   6360
taagctctca agatcagctg tacaacactg tacctagagt caacaataat gtattgtaca   6420
cttaaaaatt tgttaagggt agattaacaa atgtagtaga tccacaaatg tggttaagtg   6480
ttcttaccac agtaaaataa aaaaagaata tcaagcccag gagttcgaga ctagcctggg   6540
taacatggtg aaaccctgtc tctacagaaa atacaaaaat tagccagctg tggaggtgca   6600
ctcctaggga ggctgaggtg ggaggcttgc ttgagcccag gaggtcaagg ctgcagtgag   6660
ccatgattgc accactgtac tccagcccag atgacagagc aagacaccac cccccccaaa   6720
aaaagaaaaa gaatatcaaa cattttaaaa gatcagatac gcaagaacaa caacaaaaaa   6780
gagatgaaca gagcatcgac cctcatctag tgggattctt ggtctaactg aaaaacagac   6840
attgagagac aaacaatgac agtgatgtga tcacagcaat tacacaggta tcccctgggg   6900
actgcagaag aaaggaggaa tgcctaactt tcagaaaata gagaaagcgt caaacagttg   6960
gtgaaagcct tccaaaacta gagagaactg cacacaccaa atcacagaaa gaagaaaagc   7020
cgtgggagat tctgggaccc accggctatt tttgatggct gaacaccctg ctgcaggaga   7080
gacaggagct ggaaagcatg gtgggatgaa acctcaaaca gctttgcctg cattgcttaa   7140
gatgactggg cttgattaac tctagtcaat ggggacaatt caatcaaaga agaaagatgc   7200
tcaaattcac attttagaat gattttttat ggcagtatgg ggaatagatt aaaagagagt   7260
gaagctggag gcaagaaact tgttaagagg caactgaaac agtctagatg ataaataata   7320
aactgacaga gtgactagaa aaatcagaac aggctgaatc aacagatacc tagatgaaaa   7380
taacaggact tgatcaccag ttgtatcttg gagaggaagg agttgtttcc ttgctttccc   7440
tacgactggg aatacggaag gtttgccgtg tgtattggtt atatactggt gtgtagccaa   7500
tcactgacaa ccatttagca gcttaaaaca caaaggctta tctcccagtt tctgtgggcc   7560
aggaatctaa gataggctta gctggctggt tctggctcag agtttctcaa gaggttgcaa   7620
tcaagatgtc agctggggtt gcatcatctg aaggctcaac tggggccgga gggtccactt   7680
ccaaggagtt cactcacctg cctgacaagg cagtgctggt tgttggcagg agatctcaat   7740
tcattgccaa gtgagcctct ctatagcatt gctggaacat cctccccatc tggcagttgg   7800
cttctctcag catgagtgat ctgagagaga gagcaaggag gaagccacag tgttcttcct   7860
actcctactc ctaacactat ggacctactc ctaacactct cacttctgcc ttattccatt   7920
agttagaaag ggaactaagc tccacctctt gaaataagaa gtgtcaaaga atttgtggat   7980
atatttaaaa atcatcacac tgtggaagtg gatagggggt tcaattaatg ctgaacttga   8040
aatgcctgag acattcaaat gtccaacagg caatgaacat acccatagat ggtcatgact   8100
ttagcaagaa tagaggaaga tcacagaatt aaggaggaat tgaaaggtaa aagaagtgga   8160
gtcagattcc ccctgaaaag tgagccatga aaggaacttt aactattgag ttagaggtca   8220
gagtaggaaa tttcggtgga attctttttt aaagaaagga accatataag catgttttga   8280
ggtagaggga gaataaatca gtagacaggg agaggtaaaa aacataaatg ataggggata   8340
gttgacaaag gtcttggcag aatcccttac ccattgactt ggggccaaga gagggacact   8400
```

-continued

```
tctttgtttg agggataagg aaaataagaa agaatgggtg ctatttagtg tggtcctgtc   8460
tctagggcaa acgcataggt aacaaactgt gtgtgttagg aatatagatg tgacctcaca   8520
ttgagattct cacctcaaat ccattttgtt gttacctgta ccttcctacc ttctcttttt   8580
gctacatgca gactgctgtt ttgtcttcct ggcctgttcc aggtttcagc attctggcat   8640
atctgctacc ctgttcccaa acctctctag agtccatgct ccttccttgg atagtgtttg   8700
attgggccac gtatctaaga agtgatgcct tcagttaggc ctgagaacct cctctatgga   8760
aatctccatc agtgaccctg acagacttgg tatcttggag atgtcactgc tcccagcctg   8820
tggtctagga gaatctcagc ctgggcctct agtagtatgg ataaggcgtt aaggtatctt   8880
tgaaccagag tctgtcatat tcctcaatgt gggacagata aaacagtggt agtgctggtg   8940
tttctgagct agaactctgg tttttggtct agattctttg atgtatgacc tttcagaggt   9000
attaaaattt gttctaatac aatgttcaat acaaatgtag ttccttttct gttaggacct   9060
caacaaaaca tgaccaactg tagatgaaca ttaaactatg acaattcatg gaaatgaata   9120
cagtaatacc tgcggttccc ccattttagc agtcactatg gtgacatttg gcacaaatgg   9180
ctatttaagg gtgcttttgt taaaacctac catcttacta ggcacatgat attgaaacta   9240
atgaaataat ggagaaactt cttaaaaact tttaatgaat aaagtgatga agtgataata   9300
ttttagctgc tatttataaa gtgactatta caggtcaaac attcttctag ggtttttttg   9360
ttgaagttgt cacatttaat ccttaataac ccactatgag tcaggtattc ttctctcccc   9420
tttggacagt tggggaaatg ggggtcagag aggttaggta atttgctcag ggccacacaa   9480
cctgcatgta gaaaatctga gatttgtaca ggaacgtatc aaactctgaa gtccatgctt   9540
ctattttccc atgctgcctt tctaataaaa ggtaactaat gctactggat gctgccccca   9600
aagtgagtca ctttcacccc accctacttg attttctcca taaaactaat cacatcctga   9660
caacttattt attgctgatc tcccccacta gattataaac tcaataaaag caagatcctt   9720
gtctgctgaa tatcagtacc taaaacgctg tctagcacag agcaagtaat taatatttgt   9780
tgaatgaaca aataaaggaa aaaaattcaa aggaagaaaa agccctaaaa cagatgttta   9840
cctaaacata cattttaaaa gaaagcatat aacaaattca ggacagaatt taaatttgat   9900
tttttaaaga aataaccaag tgctagctgg gcacagtggc tcacacctgt aatcctagca   9960
ctctgggagg ccgaggcagg cagatcactt gaggtcaaga gttcaagacc agcctggcca  10020
acatggtgaa acctgtctct actaaaaata cagaaattat ccaggcatgg tggcaggtcc  10080
ctgtaacccc agctactcag gaggctgagt caggagaatt gcttgaaccc aggaggcaga  10140
ggttgcagtg ggccaagatt gcaccactgc actccagcct gagtaacaaa gcaagactct  10200
gtctgaagga gaaggaaaga aagaaggaaa gaaggaaaga aggaaagaag gaaagaagga  10260
aagaaagaaa gaaagaaaga aagaaagaaa gaaagaaaga aagaaagaaa gaaagaaaga  10320
aagaaagaaa aagaaagaaa gaaagaaaga accaagtgct tatttgggac ctactatgct  10380
atgtttttcc atgcacgcta ttttcagtaa agcagttagc aaacttgcaa gatcataaca  10440
acaaatatat gcttctataa ctctaaaatt gtgctttaag aagttcctct ttaccagctc  10500
atgtatgcat tagttttcta agagttacta gtaacttttt ccctggagaa tatccacagc  10560
cagtttattt aaccaaagga ggatgcttac taacatgaag ttatcaaatg tgagcctaag  10620
ttgggccagt tcatgttaat atactccaga acaaaaacca tcctactgtc ctctgacaat  10680
tttacctgaa aattcatttt ccacattacc aaggagccag ggtaggagaa tatagaaaga  10740
```

-continued

```
ccacccaaga atccttactt ctttcagcaa aatcaattca aagtaggtaa ctaaacacat  10800
gccctaacaa tgaatagcag attgtgctca gaagaatgat ctacaacatc ttactgtgaa  10860
ggaactactg aaatattcca ataagacttc tctccaaaat gattttattg aatttgcatt  10920
ttaaaaaata ttttaagcct aaattttaaa aggtttgata ttggtacatg aatagacaaa  10980
cagacatgga ctagaccaag aattaggttc aaacatatac aggaatttaa tatacgataa  11040
atctagtatt ccaaaggaac caacaaatgg tgttcagaca gcaggatagg catcaggaaa  11100
aacacagttg ggcaccctac cttactccta acaccaggag taactgaagg agcaccaaat  11160
atttatttat tttaattata gttttaagtt ctagggtacg tgtgcacaac atgcaggttt  11220
attacatagg tatacatgtg ccatgttggt gaggagcacc aaatatttaa aagaaaaaaa  11280
ttggccaggg gcggtggctc acacctgtaa tcccagcact ttgggaggcc aaggtgggca  11340
gatcacctga ggtcgggagt tcgagaccag cctgagcaac atggagaaac cccatctcta  11400
ctaaaaatac aaaattagcc aggcatggtg gcacatgcct gtaatcccag ctacttggga  11460
ggctgaggca ggagaatagc tttaatctgg gaggcacagg ttgcggtgag ctgagatatt  11520
gcactccagc ctgggcaaca agagcaaaac ttcaactcaa aaaaattaat aaataaataa  11580
aaataaagaa agaaaagaaa aaaatgaaaa tagtataatt agcagaagaa aacaccgtag  11640
aatcctcgga ctcttaggat ggggaatgcc tataatataa aaaccctgaa gttataaaag  11700
agaaaatcac ctacatacaa accaaatctt tctacatgcc taaaacatag cacaaacaca  11760
gctaaataat catagctgaa tgaactggga aaacaaaact tgactcatat ccagacagag  11820
ttaattttcc tacacataaa gagtacctat ataaacccaa caaaaaaacc accactaacc  11880
caaaataaaa atgtgacagg taatgaacag gtagttcaca gagaatacaa atggctcttc  11940
ggcacataag atgctcagac tgacttttac ttatttattt tttgagagac agggtctcac  12000
gatgttgccc aggttaggct caaactcctg ggctcaaatg atagtaccag gactacaggt  12060
gtgccccacc gcacctggct cctcaaccac ctgtattaac aggaaatgca aaataaaact  12120
ttcaaatcta ttttacctat tagaatggca aaaatttgaa aaacttcaaa catcatcatg  12180
ttggtgagaa tgtgaggaga ctggcactct catttttttgc tgatagcata tatatactga  12240
tggcttctat ggaaagcaat ctggcagcgt ctatcaaatg tacaagtgca tatatccttt  12300
gacaaagcaa ttccactcta ggaatgtgtt ctatatggtt gtgcttcctg gggctgggaa  12360
ctgggagcta agggacaggg gcagaagata atcttctttt ccctccttcc ccgttaaaca  12420
tgttgaattt tatatactgt aatatattat ttttcacaaa agataatttt taagcgatat  12480
gtctgggaat tttttttttt cttttctgag acagggtctc actctgtcat ccaggctgga  12540
atgccatggt atgatctcag ctgactgcag cctcgacctc ctgggttcaa gcaatcctcc  12600
cacctcagcc tcctgagtag ctgggactac aggcacgtgc catcatgcta atttttgtat  12660
atacagggtc tcactatgtt gcccaggcta atgtcaaact cctaggctca agcaatccac  12720
ccacctcagg ctccaaagtg ctgggattac aggcgtgagc caccgcgcct ggccctggga  12780
attcttacaa aagaaaaaat atctactctc cccttctatt aaagtcaaaa cagagaagga  12840
aattcaacct ataatgaaag tagagaaggg cctcaaccct gagcaacaaa cacaaaggct  12900
atttctgaga caggaatttg ctgaacaaaa tcgagggaag atgacaagaa tcaagactca  12960
cttctcggct gggcgcagtg gctcacacct gtaatcccag cactttggga ggccgaggcg  13020
gacagatcac gaggtcagga gattgagacc atactggcta acacagtgaa acccagtctc  13080
tactaaaaat acaaaaaatt agccgggcgt ggtggcaggt gcctgtagtc ccagctactt  13140
```

-continued

```
gggaagctga ggcaggagaa tggcgtgaac ccaggaagcg gagcttgcag tgagccgaga  13200
tcacgccact gcactccagc ctgggtgaca gagcaagact ctgtctcaaa aaaaaaaaaa  13260
aagactcatt tctctagatc ttgagccgta ttcaaattta tctcagctta gtgagaggtt  13320
aaagcaagga atatccttcc ctgtgggccc tgctccttac tgaaggaagg taacggatga  13380
gtcaaggaca ccaatggaga aaagcactaa caccattatc tgatgaacat tacgtgaaga  13440
agggtaagaa gtgaagtgga attgctgaag aagtcagtga aagcggacat tcatttgggg  13500
aaatggaata taggaaatcc ataaaagtga ttaaaaagat gttagaggct gaggcggggg  13560
gaccacaggg tcaggagatc gagaccatcc tggctaacac ggtgaaaccc catctctact  13620
aaaaatacaa aaaattagcc aggcgtggtg gcaggcacct gtagtcccaa ctactcggga  13680
gactgaggca ggagaatggc atgaacctgg gagacggagc ttgcagtgag ccgagatcac  13740
gccactgcac tccagcctgg gtgacagagt gagactccat ctcaaaaaaa aaagttagat  13800
acgagagata aagatccaac agacacacaa ctgctaattc tgaacagaac aaaacaaatg  13860
gcacaggaaa agaaaattta agatataaca ccggaaaact ttcctgaaat tgagtaactg  13920
aatctatagc ttgaaagggt ttagcatatg ccaagaaaaa tcagtagagt ccaaccagca  13980
caagacacat ctagcaaggc tggtgattct accaacacag agaaagaagt gggtgaccca  14040
taatgcggaa aaaggcagac catctgcagt cttctccaga acactggagt ctgaagacaa  14100
aagaatgctg cctactgagc cagaagggag agaaagtgac ccaacacatc tttaccaagt  14160
tagaatgtca cgcattattt aaaggctgca aaagccatga aagacatgaa agaacacaag  14220
catttacaac atgaaagaac acaagcattc tcatactcaa gaatccttaa gaaaaatgta  14280
gtcctaatcc agcccactga aagttaaatg tacttaatgt gctcattaat gggaacttca  14340
tagcttcaaa tcagtctggt cccatctacc aacatctctc gcccggcttt cctgcaatag  14400
tcagcacctt tccctcctcc cagtcttgtc ccctggagtc tgctctcagc atagcagagt  14460
gaccacatca acacccaagt cagagccctc cagtgcgcac tggtctacaa agcccttccc  14520
accccccacc ccacgtgccc tccggatcct tgtgacgtgt ctcctgcata ccctagcagc  14580
cctggcctcc tcactgcccc tcctgtacat caggaaggcg actccttgag tcttggctct  14640
ggccgcctcc tccacctgca gtgagttaac tcccttacct actctaggtc attgctcaaa  14700
tgtcagcatc tcaatggggc cctccctgac taccctattt aaattctaca tactcccctt  14760
gaccccatgg acctcactca ccctattcca cttttattct tacaatttag cacttgttct  14820
cttctaacgt attctaagac ttactcattt attacattgt ttgccacccc ctctagtaca  14880
taaactccag aggggcaggg atttctgtct atttattcat ttctttatcc ctaggacata  14940
gaacagggca tagttcagag tattcaatgt tatcaatgaa tgaactagca gtagtaccag  15000
ttccagttag gcacagaatt aaatctaaat agaattaaat ctcatggtct gggttaacta  15060
tggatagaaa attagatata attttaagaa gcctagaaag aaaaaattaa taatgtaaaa  15120
ataatattaa tttgataata ataacaaaaa ctctgccagg cactgtggct caaatctgca  15180
atcccagcta ctcaggaggc tgaggtggaa ggatcacttg agaccagagt tcaagactca  15240
gcctaggcaa cacggcaaga aactgtctct aaaaaaatta aaacttaaat ttttaaaaaa  15300
gaattctcaa agcgtcacaa aaactggaga ttaaggtaca ggaagtgtga agtaatatta  15360
ctatgctaat ggtttttttt ttttttagaa aggtataacc aaaagatttc tttctcaagt  15420
cgataaactg agaaagataa gcatatcttc caattaacag agggggagga aaagccagat  15480
```

-continued

```
acaacaaaat aagatataaa ttagtttcca gttgaaaaca agagtaggag ttattttgca  15540
tcacctcacc tgtgacctcc cccagcccaa aaaacactac tgataaacag ggtagaaaag  15600
catcatctca gataaagcag gaaaaactgc cacagtctca aaccacaaac tataagcaca  15660
cacctggcca accctgccaa gtctgggctc agtaggagga acgtgctgag agctaggatg  15720
taccaactta gacattctgt gggatacaga tgtccctgga agggtcacac catctcaaag  15780
gcacctgtaa tgcccactga ttacagccac catatgtgag agagaaactc agggcactta  15840
gagagtataa caagaacctt atgtcatctg agatgaggaa tcctcagccc tgcaaattaa  15900
ccaactcttt agaacaactg gcaaaacata aatatccaca acttttgttt cagtaattcc  15960
actcttagat atcaatccaa agtacatgag acagcagata cacacacaaa atggtattta  16020
ctgcagcatt gtttataata gcaaaaaaca agaaataatc catatgtctc aataggatac  16080
tgggtacatg agggtatgta cccatcattc aaccatcaaa aagagtgata tggatgtcca  16140
cagatggaca taaaaagctg tgtgttacgt gaaaacaaac tcaagcagca gcaggatggg  16200
cttatgatag tcagtatgag ctaatttctg gaaaaaaaaa tctagtgtgt gcacagaaaa  16260
catctgaaag aacagaaaca aaactatcag cagaatattg agatgtttta ctaagttgta  16320
tatctatact gcttgtaatt tttaccccaa gcaagaatta ctttttggaa aaagaaaatt  16380
caggaaataa agcatttctt taaacttcat gtttaaacaa atggtgatgg aataaaagag  16440
ttcttattca tcataaacac acacagcaca catgcacgca tgtgcgtgag cacacccttt  16500
acttgataaa taccatgttg aatattttag tctttccttt taggttctat cccttcactc  16560
aaaatgcggt tataaataaa tgtacttttc atgtgccttc tgcctaaacc cactttaata  16620
taactttaca gtcccattat cattatagtc tcaaagctag actcagcctg aaactaccct  16680
ttcatttgga acccttatta aaatgccaca tacagctcct tcaaataaaa acaaacccta  16740
ggacctgaca ctaggcttcc tttgttgcta ctcataatgg ccaagttctg tgcttataat  16800
acatcttctt tcattttatt gctacatatc caagggtttt atatgttttt cttattatat  16860
cttaattcaa aacaccatca cgctcttttc cagatgaaaa taaggaaaag aaattgagca  16920
actgactgac ttaaaggtca taaaactata tagtagcaga gtcagcaaaa gaagaaacac  16980
acatctccca agtagaggct gaaaaccagt accattcacc tccagggtga gctatataca  17040
gattacaaag tcaccttctc taaatgttca aactgaatcc catacccata ctttaccact  17100
acctcgtaag aacagcctca gatcttgtta tagccttttt tttagcatgc tgaagccaat  17160
aaaatgcttc ccattcagca agagaaacaa gttctgaaac actgaataat ctgcccaggg  17220
cctatgaaca tttccactgt gagaaatgtt ctccactgtg tggagaagat ccttactctt  17280
ctccacacag gcagaacatt agaaaaattc ttggattcta tgatgcacag cttaggagtc  17340
tgtttagcac aatttaagtc caaatagtta ttaaatcctc ctctgttcca gaaacagtgc  17400
taaatactgt gaatataaaa attgaaaaga tactctcctg gctcccaaga aagtcagcca  17460
gatagaggag acacaggcac acaaatcact gtcacatgaa gctctacctc cctaacttca  17520
aacgagggcc taagtcacca agaatacagt agcagttgtg actacgagta actactataa  17580
ttcaatactt tatcttccct tagaaaactc ttctcccttg gaaatttatt tgcatttcta  17640
aataccattc cttactaaaa ggaagcaggg ctccttgggg aaatagctga ttctaggtgt  17700
ggactatgaa atgaaaatgg tgagtctggg acatcccatg ttgcccagaa atcaaggaac  17760
tgcccaaaga ttaacagagt catgttaaat ggacctaaga gtgaaccaga aggagctcac  17820
tttgccccgc gtggaacaat ttcaagaaaa acatgacagt aatgaattat aaaacatgaa  17880
```

-continued

```
ttaaaataca tattggtact aaaaagagaa caaaaggatg tggctttgga taaagctctt  17940
cttcatggaa gaataccagc taataaatgt aaaggaaatg agagaattag aaaaattatc  18000
attttgtaaa ccttaatata ttcacctaga catgctaaaa ccactgagta aaaggctgct  18060
tgggaagagg atgctcacat gatctcagag tttcacacca cagataattt attagataca  18120
ggaaggaaga tgtgatcaag cttcctgtga cccccagcca ggccccacaa cactatgtgc  18180
ctccttgtga tgtgggagct acacagcatc gcccacacag cttctcgcca aaactgtttg  18240
aagctaatca caagggaaga actggacagc ttctgaccat gagacgctcc accagacaac  18300
ttgcttggcc tctccaaaga aacttgcttg gcctctccaa agaaaactca gtttcattta  18360
aaaacaaaac taattattta aaaacaaacg aaaagcaagt tgtggacttg agctccaggg  18420
acagagcaga catacttttc cctgttcttc ccagtaagtg gtaataaaaa ccctcaacac  18480
tagatataaa acaaatataa gaaggttctg gaaggggaag aggaggcaga ctatccaggt  18540
gccttgaggc ccacagaaca acccagtgat gggttcactg ggtcttcttt ttgcttcatt  18600
atctcagact tggagctgaa gcagcaggca acttcaaaac accaaggggc acagattgaa  18660
aagccccaag aaaagcctgc cctctctagc caaaggacca ggaaggagac agtctaatga  18720
gatggaacac atttagacag taactgccca tttaccagca ataactgagc agggagccta  18780
gacttccagt cttgtgagga cgtaccaagg tacccaacac ccccaccaag gctgagtaag  18840
gactgcgact tttatccctg catggcagta gtaaggagcc catccctcac ccgccagcag  18900
tgtcagggga acctggactt ccactcccac ccaggagtga tgaggccctc cctgctgggg  18960
tcatgtcaga ggaggcctag tggagattca gtgacttaac cttttcccag agataatgag  19020
gccacctttc ctccctcttc ccccatggtg acagtgaaag cactgtggca agcagtaggc  19080
actcctaccc ctcctagcca gggaggtatc agggaggcca agtagggaac cagaataccc  19140
acaaccaccc agcagcaaca ggggtccccc accccattgg gtgtcaatgg aagcagagcg  19200
gaaagcctgg atatttaccc ccatctagaa gtaacaagct gatgtccccc ttcttctact  19260
acaatggtgt tcaaaacagg tttaaataag gtctagagtc tgataacgta atacccaaat  19320
cgttgaagtt ttcattgagg atcatttata ccaagagtca ggaagatccc aaactgaaag  19380
agagaaaaga caattgacag acactagcac taagagagca cagatattag aactacctga  19440
aaggatgtta aagcacatat cataagcctc aacaggctgg gcgcggtggc tcacgcctgt  19500
aaccccagca ctttgggagg ccgaggcagg tggatcacaa gatcaggaga tcgagaccat  19560
cctggctaac acggtgaaac cccgtctcta ctaaaaatac aaaaaaaaat agcaaggcat  19620
ggtggtgggc acctgtagtc ccagctactc gggagcctga ggcaggagaa tggcatgaac  19680
ctgggaagag gagcagtgag ccgagatcgc accaccgcac tccagcctgg gcaacagagc  19740
aagacttcgt cccaaaaaaa aaaaaaaaaa aaaaaaaagc ctcaacaaac aactacaaac  19800
gtgcttgaaa caaatgaaaa aaaaatcttg gcaaagaaat aaaagatata tattttggcc  19860
aggtgcagtg gctcacagcc tgtaatccct gcactttggg aggctgaggc aggcggatca  19920
cctgaggtca ggagtttgag accagcctga ccaacatgga gaaaccccgt ctctactaaa  19980
aatacaaaat tagccagtca tggtggcaca tgcctgtaat cctagctact caggaggccg  20040
aggcaggaga atcgcttgaa ctcaggaggt ggaggttgcg gtgagccgag atcccgccat  20100
tgcacattgc actccagcct gggcaacaag agcaaaactc catctcaaaa aaatagatac  20160
atattttaat ggaaatttta gaattgaaaa atacagtaac caaattgaat ggaaagacaa  20220
```

-continued

```
catagaatgg agggggcaga caaaataatc agtgaacttc aacagaaaat aatagaaatt  20280
acccaatatg aagaacagaa agaaaataga ctggccaaaa aataaagaag aaaaaagagg  20340
agcagcagga ggaatgatgg aaaaagagaa aggaaggaag gaagggaagg agggagggaa  20400
ggagtgaggg agaaagtctc aaagacctct gagactaaaa taaaagatct aacacttgtc  20460
atcagggtcc aggaaagaga caaagatggc acagctggaa acgtattcaa aaaataatag  20520
ctgaaaactt cccaaatttg gcaagagaca taaacctata gattcgaaat gctgaacccc  20580
aaataaaaag cccaataaaa tccacaccaa aatacatcat agtcaaactt ctgaaaagac  20640
gaaaagagaa aacgtcttga aagcagtgag tgaaacaaca cttcatgtat aagggaaaaa  20700
caattcaagt aacagatttc ttacagaaat taaggaagcc agaaggaaat gacacaatgg  20760
ttttcaagtg ctgaaagaaa agaagtgtca acacaaaatt ctagattcag taaaaatatc  20820
cttcaagaat caatgggaaa tcaagacagt ctcagataaa gcaaaataag agaatatgtt  20880
gccagcagat ctcccctaaa ggaatggcaa aaggaagatc atgcaacaga ccaaaaaatg  20940
atgaaagaag gaatccagaa acatcaagaa gaaagaaata acatagtaag caaaaataca  21000
tgtaattaca ataaaatttc tatctcctct taagacttct aaattatatt gatggttgaa  21060
gcaaaaatta taaccctgtc tgaagtgctt ctactaaatg tatgcagaga attataaatg  21120
gggaaagtat aggtttctat acctcattga agtggtaaaa tgacaacact gtgaaaagtt  21180
acatacacac acacacgtaa gtatatataa atatatgtgt gtatatgtgt gtgtatatat  21240
atatatacat ataatgtaat acagcaacca ctaacaacac tatacaaaga gataataacc  21300
aaaaacaatt tagataaatt gaaatggaat tctaaaaaat attcaaatac tctacaggaa  21360
gacaagacaa aaagagaaaa aaagaggagg acaaactaaa tttttaaaa acataaataa  21420
aatggtagac ttaagcccta acttatcaat aattacataa atgtaaatga tctaattata  21480
tcaattaaaa gacagagata gcagagttaa tttaaaaaca tagctataag aaacctgctt  21540
tgggctgagt gcagtgactc acacttgtaa tcccagcact tcgggaggcc aaggcgggtg  21600
gatcacctga ggtcaggagt tccagaccag cctggacaac atggtaatac cccatctcta  21660
ctaaaaatac aaaaaaatta gccaggcatg gtggcacacg cctgtagtcc caactactca  21720
ggaggctgcg acacaagaac tgcttgaacc cgggcagcag aggtagcagt gggccaagat  21780
tgcgccactc cagcctgaac gacagagtga gactccacct cagttgaaaa acaaaaaaga  21840
aacctgcttt aaatatacca acatatgttg gttgaaatta aaagaataaa atatatcatg  21900
aaaacattaa tcaaaagaaa ggagtggcta tattaataac ataaaataga cttcagagaa  21960
aagaaaattt caagagacag gaataaaagg atcaagaaaa gatcctgaaa gaaaagcagg  22020
caaatcaatc attctgcttg gagattcaac accctctctt aacaactgat agaacaacta  22080
gacaaaaaaa tcagcatgga gttgagaaga acttaacacc actgaacaac aggatctaat  22140
agacatttac ggaacactct acccaacaat agcaaaataa acattctttt caagtattca  22200
ctgaacatat ccttagaccc taccctgggc cataaaacaa agctcactag tgattgccga  22260
aggcttggat ggacagtgga agagctgcat ggggagggag aaggtgacag ttaaagagtg  22320
taggatttct ttttgggata atgaaaatgt tccaaaattg attgtggtga tgttggcgca  22380
actctacaaa tataaaaaag gccattgaat tgtacgtttt aagtgggtga aacatatggt  22440
atgtggatta tatctaacgc tttttaaaaa cttaacacat ttcaaagaat agaagtcata  22500
cagagtgtgc tctactggaa tcaaactaga aagaggtaac tggaggataa cgagaaaagc  22560
ctccaaatac ttgaaaactg gacagcacat ttctaaaatc atccgtgggt caaagatatt  22620
```

-continued

```
catttctgat attcattttt attgtttaat gtatttttaa aaatttctta agggaaataa  22680
actgactaaa aatgaatatg gctgggtgcg gtggctcacg cctgtgatcc cagcactttg  22740
ggaggccgag gctggtggat cacaagatca ggagttcgag accagcctgg ccaagatggt  22800
gaaaccccgt ctcaactaaa aaactacaaa aagtagccaa gcgcagtggc gggagcctgt  22860
ggtcccagct acttgggagg ctgaggtagg agaatcgctt gaacacaggc agcagaggtt  22920
gcagtgagcc aagattgtgc cactgcacgc cagcctgggc gacagagact gcctcaaaaa  22980
aaaaaaaaaa aaaaagaata tcaaaatttg tgggacatag ttaaagcaat gctgagaggg  23040
aaatttataa cactaaatgt ttacattaga aaagagaaaa agtttcaaat caatagtctc  23100
cactcccatc tcaagaacac agaagatgaa gagcaaaata aacccaaagc aagcaaaaga  23160
aagaaaatat aaaaataaat cagtaaaatt gaaaacagaa acacaataaa gaaaatcagt  23220
gaaacaaagt actgattctt cgaaagatta ataaaattga caaacctcta gcaaggctaa  23280
caaacaaaaa agaaagaaga cacggattac cagttattag aatgaaagca taattagaaa  23340
caactctaca cattataaat ttgacaatgt agatgaaatg gactaattac tgaaaaaaca  23400
caaattacca caactcaccc aatatgaaat agataattgg gatagcctga taactactga  23460
gaaaattgaa tttgtaattt taacactctt aaaacagaaa cattaaactt aatattttat  23520
aaatattaga taaggtaatt atacccttcc ttaacaaata aaaacgacaa attattttgc  23580
agctaaagag atgtatgtac tgtgaaaaat atcttcagaa aaatagaact ttgtttgaag  23640
aataaggatt taaaaaatgt ttttaactct caagaagcaa atatctgggc ccagatggtt  23700
tcactgaaga attctaccaa atgtttaatg aagaattacc accaactcta catagcatct  23760
ttgagaaaac tgaagagaag ggaacatctc ccagttcatt ttatgaagtg ggtgttactc  23820
tgatactaga actgtataag gacagctact cttgacacac tgcctatggg tagctctgct  23880
ctgcaggaac agtcagaaaa aaaaaaaaaa gaagcactgg acaagggcag tataaaaaaa  23940
gaaaactggg ccaggtgcag tggctcacac ctgtaatctc agcactttgg gaggctgacg  24000
ctggtggatc acctgaggtc aggagtttga gactagcctg gccaacatgg taaaaccctg  24060
tctctactaa aatacaaaaa ttagccaggc agggtggtgg ggaaaataaa aaggaaaaaa  24120
aaacaaaaat aaactgcaga ccaatatcct tcatgagtat agacacaaaa ctccttaaac  24180
tccttaacaa aatattagca agtagaagca atatataaaa ataattatac accatgatca  24240
agtgggactt attccagaaa cgcaagtctg gttcaacatt tgaaaacaag gtaacccact  24300
atatgaacgt actaaagagg aaaactacat aatcacatca atcaatgcag aaaaaagcat  24360
ttgccaaaat ccaatatcca ttcatgatac tctaataaga aaaataagaa taaaggggaa  24420
attccttgac ttgataaagc ttacaaaaga ctacaaaagc ttacagctaa cctatactta  24480
atggtgaaaa actaaatgct ttcccctacg atcaggaaca aagcaaggat gttcactctc  24540
attgctctta tttaacatag ccctgaagtt ctaacttgtg caaaacgata agaaagggaa  24600
atgaaagacc tgcagattgg caaagaagaa ataaaactgt tcctgtttgc agatgacatg  24660
attgtctcat agaaaatgta aagcaactag gggtaggggg gcagtggaga cacgctggtc  24720
aaaggatacc aaatttcagt taggaggagt aagttcaaga tacctattgc acaacatggt  24780
aactatactt aatatattgt attcttgaaa atactaaaag agtgggtgtt aagcgttctc  24840
accacaaaaa tgataactat gtgaagtaat gcatacgtta attagcacaa cgtatattac  24900
tccaaaacat catgttgtac atgataaata cacacaattt tatctgtcag tttaaaaaca  24960
```

-continued

```
catgattttg gccaggcaca gtggctcata cctgtaatcc cagcatttta ggaggctgag  25020
gcgagcagaa aacttgaggt cgggagtttg agaccagaat ggtcaacata gtgaaatccc  25080
gtctccacta ataatacaaa aattagcagg atgtggtggc gtgcacctgt agacccagct  25140
acttgggagg ctgaggcacg agaattgctt gaacaaggga ggcagaggtt gcagtgagct  25200
gggtgccact gcattccagc ctggtgacag agtgagactc catctcaaaa aaaataaaat  25260
aaagcatgac ttttcttaaa tgcaaagcag ccaagcgcag tggctcatgc ctgtaatccc  25320
accactttgg gaggccgagg caggcagatc acaaggtcag gagtttgaga ccagcctgac  25380
caacatggtg aaaccccatc tctactaaaa aatatataaa ttagccaggc atgtgtagtc  25440
tcagctactc aggaggctga ggcaggagaa tcacttgaac ccggaggcag aggttgcagt  25500
gttgagccac cgcactccag cctgggtgag agaacgagac tccgtctcaa aaaaaaaaag  25560
caaaataacc taattttaaa aacactaaaa ctactaagtg aattcagtaa gtctttagga  25620
ttcaggatat atgatgaaca tacaaaaatc aattgagctg gacaaaggag gattgtttta  25680
ggtcagtagt ttgaggctgt aatgcacaat gattgtgcct gtgaatagct gctgtgctcc  25740
agcctgagca gcataatgag accacatctc tatttaaaaa aaaaaaaatt gtatctctat  25800
gtactagcaa taagcacatg ggtactaaaa ttaaaaacat aataaatact gtttttaatt  25860
gcctgaaaaa aatgaaatac ttacatataa atctaacaaa atgtgcagga cttgtgtgct  25920
gaaaactaca aaacgctgat aaaagaaatc aaagaagact taaatagcgt gaaatatacc  25980
atgcttatag gttggaaaac ttaatatagt aaagatgcca attttatcca aattattaca  26040
caggataaca ttattactac caaaatccca gaaaaatttt acatagatat agacaagatc  26100
atacaaaaat gtatacggaa atatgcaaag gaactagagt agctaaaaca aatttgaaaa  26160
agaaaaataa agtgggaaga atcagtctat ccagtttcaa gacttacata gctacagtaa  26220
tcaagactgt gatattgaca gagggacagc tatagatcaa tgcaaccaaa tagagaacta  26280
agaaagaagc acacacaaat atgcccaaat gatttctgac aaaggtgtta aaacacttca  26340
acgggggaag atatgtctct cattaaaggg tgtagagtca ttgcacatct ataggcaaaa  26400
agatgaacct gaacctcaca ccctacagaa aaattaactc aaaatgactc aaggactaaa  26460
cataagatat acatctataa aacatttaga aaaaggccac gcacggtggc tcacgctcgt  26520
aatcccagca ctttgggagg ccaaggcagg tggatcacct aaggtcagga gtttgagacc  26580
agccggatca acatggagaa gccccatctc tactaaaaat acaaaattag ctggacgtgg  26640
tggcacatgc ctgtaatccc agctacttgg gaggctgagg catgagaatc gcttgaaccc  26700
ggggggcaga ggttgcggtg agccaagatc acaccattgc actccagcct gggcaacaag  26760
agcaaaactc caactcaaaa aaaaaaaaaa aaaggaaaaa tagaaaatct ttgggatgta  26820
aggcgaggta aagaattctt acacttgatg ccaaactaag atctataagg ccagtcgtgg  26880
tggctcatgc ctgtaattcc agcactttgg tcaactagat gaaaggtata tgggaattca  26940
ctgtattatt ctttcaactt ttctgtaggt ttgacatttt tttagtaaaa aattggggga  27000
aagacctgac gcagtggctc acacctgtaa tcccagcact ttgggaggcc ggggcaggtg  27060
gatcacacgg tcaggagttc gagaccagcc tggccaacat ggtgaaaccc cgtctctacc  27120
aaaaatataa aaaattagcc gggtgtcatg gtgcatgcct gtaatcccag ctactgagga  27180
ggctgaggca ggagaatcac ttgaacctgg gaggtggaag ttgcagtgag ccgagattgt  27240
gccactgcac tccagccttg ggtgacagag cgagactccg tctcaaaaga aaaaaaaaaa  27300
aaagaatatc aaacgcttac tttagaaact atttaaagga gccagaattt aattgtatta  27360
```

-continued

```
gtatttagag caatttttat gctccatggc attgttaaat agagcaacca gctaacaatt  27420
agtggagttc aacagctgtt aaatttgcta actgtttagg aagagagccc tatcaatatc  27480
actgtcattt gaggctgaca ataagcacac ccaaagctgt acctccttga ggagcaacat  27540
aaggggttta accctgttag ggtgttaatg gtttggatat ggtttgtttg gccccaccga  27600
gtctcatgtt gaaatttgtt ccccagtact ggaggtgggg ccttattgga aggtgtctga  27660
gtcatggggg tggcatatcc ctcctgaatg gtttggtgcc attcttgcag gaatgagtga  27720
gttcttactc ttagttccca caacaactgg ttattaaaaa cagcctggca ctttccccca  27780
tctctcgctt cctctctcac catgtgatct cactggttcc ccttcccttt atgcaatgag  27840
tggaagcagc ctgaagccct cgccagaagc agatagtgat gccatgcttc ttgtacagcc  27900
tacaaaacca tgagcccaat aaaccttttt tctttataaa ttatccagcc tcaggtattc  27960
ctttatagca agacaaatga accaagacag gggggaaatca acttcattaa aataatctat  28020
gcagtcacta aacaaataag aacaagaggc tccagaagtg ggaagccaat acccagagtt  28080
cctacaatac agtatctgaa aagtccagtt tccaaccaaa aaatatatat atacaggccg  28140
gacatggtag cttatgtctg taatcccagc actttgggat gctgaggcgg gcagatcacc  28200
ctaggtcagg agttcgagac cagcctggcc aatatggcaa aaccccgtct ctactaaaaa  28260
tacaaaaatt agccaggcat ggtggtggat gcctgtaatc ccagctactc gggaggctga  28320
ggcagggaat cacttgaacc caggaggcag aggttgcagt gagccgagat cacgccactg  28380
aactccagcc tgggcaacaa agtgagactc cacctcaaaa aaaaaaaaaa tatacatata  28440
tatatgtgtg tgtgtgtgtg tgcgcgcgtg tgtgtatata cacatacaca tatatacata  28500
tatacagaca cacatatata tatgaagcat gaaaagaaac aaggaagtat gaaccatact  28560
ttctgtggtt atgataggat ggggtatcac gggggaagta gacaagggaa actgcaagtg  28620
agagcaaaca gttatcagat ttaacagaaa aagactttgg agtaaccatt ataaatatgt  28680
ccacagaatt aaagaaaagc gtgattaaaa aaggaaagga aagtatcata acaatattac  28740
tccaaataga gaatatcaat aaaggcatag aaattataaa atataataca atggaaattc  28800
cggagttgaa aggtagaata actaaaattt aaaattcact agagaaggtt caacactata  28860
tttgaactgg cagaagaaaa atttagtgag acaaatatac ttcaatagac attattcaaa  28920
tgaaaaataa aaagaaaaaa gaatgaagaa aaataaacag aatctcagca aaatgtggca  28980
caccattaat cacattaaca tatgcatact gagagtaccg gaagcagatg agaaagagga  29040
agaaaaaata ttcaaatgat ggccagtaac ttcctagatt tttgttttaa agcaataacc  29100
tatacaatca agaaactcaa tgaattccaa gtaggataaa tacaaaaaga accacaaaca  29160
gatacaccat ggtaaaaatg ctgtaagtca aaaacagaga aaatattgaa agcagctaga  29220
ggaaaactta taagagaacc tcacttacaa aagaacatca cttataaaag aaccacaata  29280
atagaaacag ttgacctctc atcagaaaca atgaatgata acatatttga agtgctcaaa  29340
gaaaaaaaat aaagattcct atatacgaca aagctgtctt tcaaaaatat acatccaaaa  29400
ggattgaaac cagggtcttg aagagttatt tgtacatcca tgttcatagc agcattattc  29460
acaatagcca aaaggtagaa gcaacccaag ggtccatcga caaataaata aaatgtggta  29520
tatgtataca caatggaatt tattcagtat taaaaaggaa tgaaattctg acacatgcta  29580
caacatggct aaaccttgag aacactatgc taagtgaaat aagccagcca caaaaggaca  29640
aataccatat tacttcactt gtatgaaata cctagggtag tcaaattcag agatagaaag  29700
```

-continued

```
taaaacagtg gttgccaagg gctgagggag ggagtaacgt ggagttattg ttgaatgggt  29760
acagaatttc agttttgcaa gataaaaaga gttctggaga cagatggtgg tgagggtggt  29820
acaacaatac aaatatactt tatactactg aacagtatac ttaaaaatga ttaacatggt  29880
gaaaccccgt ctctactaaa aatacaaaaa aattagctgg gtgtggtggc gggcacctgt  29940
aatcccagct acttgggagg ctgaggcagc agaattgctt gaaaccagaa ggcggaggtt  30000
gcagtgagct gagattgcgc caccgcactc tagcctgggc aataagagca aaactccgtc  30060
tcaaaaaata aaaaataaaa aaaatttaaa aatgattaag caggaggcca ggcacggtgg  30120
ctcacaccta taatgccagc actttgggag gccgaggcag gcgatcactt gagaccagga  30180
gtttgagacc agcctggcca acatggcaaa accctgtctc tgctaaaaat acaaaaatta  30240
gccaggcatg gtggcatata cttataatcc cagctactgg tgagactgag acacgagaat  30300
tgcttgaacc caggaggcag agattgcagt gagtcgagat cgcgccactg aattccagcc  30360
tgggcgacag agcaagattc tgtctcgaaa aaacaaaaac aaaaacaaaa agcaaaacca  30420
aaaaataatt aagcaggaaa cgagattgct gctgaggagg agaaagatgt gcaggaccaa  30480
ggctcatgag agcacaaaac ttttcaaaaa atgtttaatg attaaaatgg taaattttat  30540
atgtatctta ccacaaaaaa aagggctggg gggcaggaaa tgaaggtgaa ataaagacat  30600
cccagagaaa caaaagtaga gaatttgttg ccttagaaga aacaccacag gaagttcttc  30660
aggctgaaaa caagtgaccc cagagggtaa tctgaattct cacagaaaat tgaagcatag  30720
cagtaaaggt tattctgtaa ctatgacact aacaatgcat attttttcct ttcttctctg  30780
aaatgattta aaaagcaatt gcataaaata ttatatataa agcctattgt tgaacctata  30840
acatatatag aaatatactt gtaatatatt tgcaaataac tgcacaaaag agagttggaa  30900
caaagctgtt actaggctaa agaaattact acagatagta aagtaatata acagggaact  30960
taaaaataaa attttaaaaa atttaaaaat aataattaca acaataatat ggttgggttt  31020
gtaatattaa tagacataat acaaaaatac cacaaaaagg gaagaagaca atagaactac  31080
ataggaataa cattttggta tctaactaga attaaattat aaatatgaag tatattctgg  31140
taagttaaga cacacatgtt aaaccctaga tactaaaaag taactcacat aaatacagta  31200
aaaaaataaa taaaataatt aaaatgtttg tattagtttc ctcagggtac agtaacaaac  31260
taccacaaat tgagtggctt aacacaactt aaatgtattt tctcccagtt ctggaggcta  31320
aacacctgca atcaaggtga gtacagggcc atgctccctg tgaaggctct aggaaagaat  31380
cctcccttgt ctcttccagc ttccagtggt tctcagtaac cctaagtgct ccttggcttg  31440
tagctatatc attcctagca accagaaaga agaaaataat aaagattatg gcaaaaaata  31500
atgaaatcaa aaggagaaaa atggaaaaaa ataaataaaa ccaaaagcta gttctttgaa  31560
aagatcaacc aagttaacaa accttttaac tagactgaca aaaaggaggt aagactcaaa  31620
ttactagaat cagaaataaa agaggggaca ttactaatga gggattagaa aagaatacta  31680
cgaacaaatg tgtgccaaca aattagaaaa cttagatgaa atggacaggt tcctaggaca  31740
acatcaacta ccaaaattta ctcaagaaga aagagacaat ttgaatgagc tataacaagg  31800
gaagagactg aattgacaac caagaaacta tccacaaaga aaatcccagg cccagaagat  31860
ttcactgtga aattctttca aacttataaa tataaattaa catcagttct tcacaaactc  31920
ctccaaaaaa aagaacagat ctctatttac aggcgatacg atctttagaa aatcctaagg  31980
gaactactaa gacactatga taactgataa acaagttcag caaggctgca ggatagaaaa  32040
ccaatataca aaaatctatt atatttctat acacttgcag tgaacaaccc aaaaatgaga  32100
```

-continued

```
ttaagaaaat aattcaattt acaataacat caaaaagaat aaaaacactc aaaaataaat  32160
ttattcaagt aagtgcaaaa cttatactct agaagctaca aaacactgtt aaaagaaatt  32220
aaaggtttac ataaatgaaa aactatccca tgttcatgga tcaaaagact tattactggc  32280
aatgctctcc aaattgatct ataaattcaa caaaatcctt atcaaaatcc cagatgaggc  32340
tgggggtggc ggttcatgcc tgtaatccca gcactttggg aggctgaggc acgcagatta  32400
cctgaggtcg ggagctcgag atcagcctga ccaacatgga gaaaccctat ctcttctaaa  32460
aatacaaaat tagtcaggcg tggtggcaca tgcctataat cccagctact cgggaagctg  32520
aggcaggaga atcgcttgaa cccaggaggc agaggttgca gtgagccaag atcgtgccat  32580
tgcactccag cctgggcaac aagagcaaaa ttccatctca aaaaaaaaaa aaaaaaaatc  32640
ccagatgact tcactgttga aattgaaaag attattctaa aattcacatg gaattgcaag  32700
accttgagaa tagccaaaac aaacttgaaa aacacgaaca aaatatagga tgactcactt  32760
gccaattgca aatgttacga cacagcaaca gtaatcaaga ctgtgtggta ctggcaaaag  32820
acacatacat acatacatat caatggaata taattgagag tacagaaaca agcctaaaca  32880
tctatggtaa gtgcttttct atttttttct tttttttttt cttttttgta gagatagaat  32940
ctcaccatgt tgcccaggct ggtcttcaac ttctgggctc aagcaatcct cccactgtgg  33000
cctcccaaag tgctgggata actggcatga gccaccacat ccagcccaga tgattttcaa  33060
aaaagtcaac aagaccattc ttttcaacaa ataggtctgg gatgatcaga tagtcacatg  33120
aaaaaaaaaa tgaagttgga ccctccatca cactaaagtg ctgcgattat aggcatcagc  33180
caccacatcc agcccaaatg attttcaaaa aggtcaacaa gaccattctt ttcaacaaat  33240
aggtctggga taatcagata gtcacatgaa aaaaaaaatg aagttggacc ctccatcaca  33300
ccatatgcaa aaattaattc aaaaatgaat tgatgactta aacgtaagag ttacgactgt  33360
aaaactctta gaaggaaaca tacgggtaaa tcttaaagac gttaggtttg acaaagaatt  33420
cttagacatg acaccaaaag catgaccaac taaggtaaaa tagggtaaat tgtacctacc  33480
aaaatgaaaa acctttgtgc tggaaaggac accatcaaga aatggaaagc caaaatagcc  33540
aaggcaatat taagcaaaaa gaacaaagct ggaggcatca tactacctga cttcaaagca  33600
acagtaacca aaacagcatg gtactagtag aaaaacagac acatagacca atggaacaga  33660
ataaagaacc caaaaataaa tccacatatt tatagtcaac tgatttttga caatgacacc  33720
ccttcaataa atgatactag gaaaactgga tatcgatatg cagaagaata aaactagacc  33780
cctatctctc accatataga aaaatcaact cagactgaat taaagacttg aatgtaagac  33840
ccaaaactat aaaactactg gtagaaaaca taaggaaaaa cgcttcagga cattggtcca  33900
ggcaaagatc ttatggctaa aacctcaaaa acacaggcaa caaaaacaaa aatggaaaaa  33960
tagcacttta ttaaactaaa aagctcctgc acagcaaagg aaacaacaga atgaaaagac  34020
aacctgtaga atgggagaaa atatttgcaa actatccatc catcaaggga ctagtatcca  34080
gaacacacaa gtgactaaaa caactcaaca gcaaaaaagc aaataatctg gtttttatat  34140
gggcaaaaga tctgaataaa cattctcaaa ggaagacata caaatgtcac tatcattctg  34200
ccagtaccac actgtcttga ttacttgtta gtgtataaat ttttaaattg ggaagtgtga  34260
gtcatcctac actttgttct tgtttttcaa gtttgttttg gctattctgg gagccttgca  34320
agtataaaat agccaacaag tatgaaaaaa tgctcaccat cactaatcat cagagaaata  34380
aaaatcaaga ccactatgag atatcctctc actccagtta gaatggctac tatcaaaaag  34440
```

-continued

```
acaaaatata atggatgctg gcaaagattt ggagaaaggg gaactcctat acactgtggg  34500
tagggatgca aattggtaat ggccattatg gaaaataata ctgaggtttt tcaaaaaact  34560
gaaaatagaa ctaccatatg atccagcaac cctactactg ggtatttatc caaaggaaag  34620
aagtcagtat actgaagaaa tatatgcact ctcatgttaa ttgcaacact gttcacaaca  34680
gccaagacag ggaataaatc taaatgtgca tcaacagatg aatggataaa gaaaatgtgg  34740
catatacact caatagaata ctattcagcc attaaagaag aatgaaatcc tgtcatccca  34800
gcaacatgga tgaacctgga ggacattata tttaatgaaa taagtaaagc acaaaaagat  34860
aaacagtaca tgttctcact cagacatggg tgctaaaaag aaaatggggt cacagaatta  34920
gaaggggagg cttgggaaaa gttaatggat aaaaatttac agctatgtaa gaagaataag  34980
ttttagtgtt ctatagaact gtagggcgag tatagttacc aataacttat tgtacatgtt  35040
caaaaagcta gaagagattt tggatgttcc cagcacaaag gaatgataaa tgtttgtgat  35100
gatggatatc ctaattaccc tgattcaatc attacacatt gcatacatgt atcaaattat  35160
cactctgtac ctcataaata tgtataatta ttacgtcaac aaaaaaagga aaaaaaagaa  35220
aattaagaca acccacataa tggaagaaat aaaatatctg caaattatat atatctgata  35280
aatatttaat atttataata tataaagaac tcctacaact caagaacaac aacaaaacaa  35340
cccaattcaa aaatgggtaa aagccttgaa tatacactta tctaaagact atatacaatt  35400
ggccaataaa gacacgaaaa gatgctcaac atcactagtc atcagggaaa tataaatcaa  35460
aaccacaatg tagaatgtag acaccacttc atatgcacta ggatggctag aataaaaagg  35520
taataacaaa tgttggtaag gatgtgaaaa aatcagaaac ctcattcgct gctgttggga  35580
atgtaaagtg atgcagccac tttggaaaac agtctggcag ctcctcaaat tattaaatac  35640
agagttaccg tatgacccag gaatattcct cctgggtcta taaccaaaaa aatgaaaaca  35700
tatatccaca taaaaacttg tacatgggca tttatagcaa cattattcat aacagcaaag  35760
gtggtaagaa cccatatgcc catcatctga tgaacaggta aataacatgc ggtattatcc  35820
atacactaga atattatctg cccatacaag gagtgacatc cagctacatg ctacaaggat  35880
gaatctcgga aaccttatgc taagtgaaag aagccagtca caaatgacca cagattatga  35940
ttccatgcat cggaaatgac cagaataggg aaatctatag agacagaaag tagattagtg  36000
gttgggtggg gctgggagga caggtagtac actactttcc cagaactact ggaacaaagt  36060
accacaaact ggggagctta aacatagaaa ttgatttcct cacagttctg gagactagga  36120
ctctgagatc aaggtgtcag cagagctggt tctttctgag ggccctgagg caaggctctg  36180
tcccaggcct ctctccttgg ctggcaggtg gccatcttct ccctgcgtct tcacatcatc  36240
ttttctctgt gtgtgcccat gtccaaattt tgattggctc attctgggtc atggccaatt  36300
gctatgcaca aagtgaagtc tacttccaaa agaagggaag agggaacact gactaggcta  36360
aacttatagt cattttaatg tccgcttttc ctatgagatt gtgaacacac agaagtaggg  36420
tttttatcta cattgtgcaa agtttaataa gaaaaataga attcaagaga agcagttcaa  36480
tagcaggaat ttaatatggg aactaattac aaggtttagg gcaggactaa aaagccagtt  36540
gggatggtga gccaacccag agattagcaa cagtgggacc ccatctacct accacccatg  36600
aagctggaag gataaaggag gggctattat cagagtccac aagccagtgt cagagtcctt  36660
ggctggagct gggaccaccc tagagacact gtgcaaagca gaaaacaagg gggaaaaacc  36720
ctgacttctc ccttcctccc acctttcaat ctcccactag tgcttcctac tagccatact  36780
tggccagaga cagtgacaag gaacactgca aaatgaagtt tgtaggaatc atctccctct  36840
```

-continued gagacagaga aatatggaag ggtagaaaat gaatcagagg ataaagagaa aaaaccctga 36900
gtactatctt atttatcttt gtatctccag tgcctaatct gtctctcaaa aaaggaaagc 36960
aattgagaga aactgaaaac tccaattgaa atgaaagaat ggagaattac tggactagaa 37020
gagaagagaa aaatttattc cgcatagagt aaacaagaat ggattcacaa aggacgtgat 37080
gaatgaaaag ctataatcag caaagatttg ccagagaaat taaaaagtgg taaactcagc 37140
cacgctgtac aacctgaagg cacaatgcat gaaaacgttt caagaaatga caagatttga 37200
agtcaaattc taagtgcttt tccagaatct ctcaagacga ttatatagct accccatttt 37260
attaaataaa atggaaactt actaaacttt ccccttgtat taaactaaca tatgtcctaa 37320
tagcaaacga ttctggaatt cctagagtaa aatatatttc gtcaaagtgt attgctcttt 37380
taatattctg ctgacctcct tttgctattt aggatatttg tatacacatc acacgtaaat 37440
ttggtctata gtttacatct acgggcttat actgttcttt ttttcatttt tttaaaattt 37500
ccaacccccca gtatccatat actgctctct atcagggtta ttttaacttt gtaaaatcag 37560
ctgagatgct ttccatgttt ttttttttta ttttctgcca catttgaata gcataggagt 37620
taccaccatc aaccttggat tatttaagca ttcacgattc cacgtgtgga tttttttattc 37680
agagtctttc ttgtcattcc tgctatcagc acagaaccca atctcagctt tccagctata 37740
ctctcacccc atggaatttg cagatgaagt tcaaaaggac ctttgcatta tcctgcctcg 37800
ccctcttccc ccttcattta gacatcacct tcttctagaa cgtcttacct gacatgccct 37860
gctcccaacc cctgctgccc aattgtgtgc tctcccgtgt cctggcctgc catcctcttt 37920
agtaattgcc tgctccctca tctgtctccc cacccagaca ttaagctgaa tagactggat 37980
ttgtgtcttg tccatcacta taatctcagc acctagtacc tagtaggtac ttaccatgta 38040
ttcattagca aaatgttatg tataaccttg caccttaaaa acaagagaag gaagacaaaa 38100
ttaagtctta agactatggt ttagaacatg gatcagaaac tacagtctgc agcccaaatc 38160
cagaccaaat gaagagacca tgttcattta catacaacct atagcagctt tcacactaca 38220
ggagcagagc taagtagttc caagggaaca cacggccctg caaagcctaa aatatttact 38280
ctatagctct tcacagaaaa agttttcaga tccctcgttt agaactcttg ttcatatgca 38340
atttcactaa accatagttt tttgggtttg tttggttttt tttggcaaaa aggaatgagc 38400
cgatccagaa aaggttgaaa agaatgaatc attactgctg aaagaatgtg cacacagtcc 38460
gtcagtattc tgctgccatg ctgacaccca tccaatagtg tcatgagatg cagcagctac 38520
tactgtgttc tcaatgccga gtccacccac tccataacca tgtccaagca atcttgggaa 38580
catcatcacc atgcttgttt atccttaagg tattgcctca catacagcag tggctggtca 38640
taaagtcaaa tgacactagt ggccaggagg tcaagagaat gagtgaggac aggtgggtag 38700
gcagcccagg ccctagcaac agcaggagct cacccctcag tcactctagc caggactgaa 38760
atacttttca ccctttcaag agagactagg aatctggatt tttatgtgaa atatcttgat 38820
tactaaatgt tgtcaacaga catgtcaaaa ggtaaaacta agtaagttca tggggcagat 38880
tgactattca ggttatagaa ttaaggattc ttatccaaca cagataccaa ccaaaaagct 38940
gacgtataac atattaggag aaactatgtg cactgtcgaa acatcaacaa ggggctaatg 39000
tctaaaatag tctatattgg attccagttg aaacatgggg aaaggacatg aacaggcaac 39060
ttatgtcaat ggaaactcaa aaagataaca agcatatata aaagcattct caaattcagt 39120
agtaaacaga cagatgcaaa taaaaagagg gaaactgctg ccgggcacag tggctcacac 39180

-continued

```
ctgtaatccc agcactttgg gaggccgagg cgggcggatc atgaagtcag gagatcgaga  39240
ccatcctggc taacatggtg aaaccccgtc tctactgaaa acacaaaaaa ttagccaggc  39300
gtagtggtgg gcaccagtag tcccagctac tcaggaggtt gaggcaggag aatggcatga  39360
acccaggagg cggagattgc agtgagccga gaccatgcca ctgcactcca gcctgggcga  39420
ctgagtgaaa ctccatctca aaaaatataa taataattat aattataata ataataaata  39480
gtaaataaat aaaaagagag agactgctaa agtctagaaa gttgaatgat gccaagcgca  39540
tgcaaagatc agggccttgg gatggccggg tgcagtggct cacgcctgta atcccaccac  39600
tttgggaggc caaggcgggc ggatcatgag gtcaagagat caagaccatc ctggccgaca  39660
cagtgaaacc cggtctctac taaaagtaca aaaaaatata tatatatata tatattatta  39720
tattatatat atatatatca gagccttggg aatccttgtg tgctgctggg gaaggtagtg  39780
gtgcagccac ccttgacagc aatctggcag tacttggtta tattaagtat aggcacacac  39840
cacgaccagg cagtcctact cctgggtcta aatcccaaag aattctcaca caagtccata  39900
aggagacatg tacgaggctc attcagcatt actgggagtg ggaatcaacc tgggtgtcca  39960
tctacaggag acgagatgga caaaatgtgg tggatattaa gaccagaatc accaagtaac  40020
agagatgggt ggtgagtgac aatcctaaga tacagaataa aggctagaac atgatgccat  40080
tcatgtaaat taaaaataga tgcacacaaa gcagtatacg cgtgaccctt gaatagcaca  40140
ggtttgaact gcctgtgtcc acttacatgt ggattttctt ccacttctgc tacccccaag  40200
acagcaagac caacccctct tcttcctcct ccccctcagc ctactcaaca tgaagatgac  40260
aaggatgaag acttttatga taatccaatt ccaaggaact aatgaaaagt atattttctc  40320
ttccttatga ttttctttat ctctagctta cattattcta agaatatggt acataataca  40380
catcacacgc aaaataaatg ttaattgact gtttatatta tgggtaaggc ttccactcaa  40440
cagtaggctg tcagtagtta agttttggga gtcaaaagtt atacacagat tttcaactgt  40500
gcaggcaatc agttcccctg accccctcat tgttcacggg tcaactgtat atacacaaaa  40560
gtattatatg aacctcatta gaatagctgt ctatagggag aagagaatga gagtgggata  40620
aaacggaatg aacaaataaa ccaacaaatg cattaacaag caaaacaaca gaggggcttg  40680
catgggccag tgatgataaa gggctaagaa tgagaatata attaattcaa ttcctcacac  40740
ctgaggtcta aaaccaagga aagggagggc caggcgtgga ggctcacgcc tgtaatccca  40800
gcactttggg aggctgaggc gggcggatca caagattagg agtttgagat cagcctggcc  40860
aacacagtga aagcccatct ctacaaaaaa tacaagaatt acccaggtgt ggtggcacat  40920
gcctgtagtt agctactctg gaggctgagg caggagaatc acttgaaccc aggaggcgga  40980
ggttgcaggg agccgagatc acaccattgc actccagcct gggtgacaga gtaagactct  41040
gtctcaaaaa aataaaaaaa ataaaaaaac agagaaaggg aggaaactag atccaggctg  41100
actagataca gcctttagag ttagaaaaga tgatttgaca atctaagccc acactcagat  41160
tgaatgaaat tgaaaagcct ttcaaactaa aacatttaat tacaccatct gctgcagaca  41220
gaactcagac aactcaaaca ggtaatgtca gcgtggtgtt ttatatcacc accctcaaca  41280
cagaataaaa atcagctgca tgtgaagcag tgactagaat gaagaaaagg ctgcttctta  41340
cttccttcta gtggttcttt ccgaaaacat taataggcac cagctctatg catgtcaccc  41400
tgcagggaga catggggtat ataactatga cttactgttc attcctcaag gaattcccaa  41460
tcttgtggaa gattatacac aatgaggcaa caaaaactat ccaataaaac cacggaaaag  41520
aagccagtga caaagaagcc agtgatgaaa ggccctgtga gcagagctga tggccatttg  41580
```

-continued

```
gggaagaaag accaacatgg atgggggtga tcagggtggc tccgtgggaa agctggaaga  41640
gaagtggcag atctctgagc tggatgatgg gccactacca tctgtatatg gctaattaaa  41700
gaccatgtgt ggattttta ttcagctctt tcgtgtcatt cctgctatca gcacagaacc  41760
caatctcaac tttccagcta tattgagcta aacttctcac ctcatggaat ttgcagataa  41820
agttcaaaag gatccttgcc ttttcaaaat aattttgaat ggttgagtag tccctctgtg  41880
ctctctcact gacaccctct caaggctgct gagcacgtgc catgctatgg ctttctccaa  41940
catcaggaaa tgttctccac tcagtttcac cttaatacaa atgtgttctc tcttcagaga  42000
aggcaaaaaa attcatgacc atctgactgg gagaagtcat ttctaggtaa agtgtccatc  42060
tttttctgag gaacacagga ggaaaatctt acagaaaaga gttaacacag caggcctaag  42120
actgcttttt aaaataaata aataaataaa taaataaata aataaataaa taaataaata  42180
aataaatgaa tgatagggtc ttctgtattg gccaggctag tctcaaattc ctggcttcaa  42240
gagatcctcc caccttggtc tcccacagtg ttgggattat agacatgagc cattgtgctt  42300
ggcccaagac tgttattctt aaaaagtctc ataaaaagca tggttaatcc ttggctggca  42360
cctgggaact tagatttcag aagggttccc accatccaac ctggaaagag ggactcactg  42420
tgcctaaatt attgtgtggt ttatgctgaa ctcctgcttt tcttcaggta gcgtggaatg  42480
tggtatgtgc tgggcaaagg gggcctgcat gaccagcccc caataaaaac cctgggtgtt  42540
gggtctctag tgagtttccc tggtagacag catttcacat gcgttgtcac agctccttcc  42600
tcggggagtt aagcacatac atcctgtgtg actgcactgg gagaggatgc ttggaagctt  42660
gtgcctggct tcctttggac ttggccccat gcacctttcc ctttgctgat tgtgctttgt  42720
atcctttcac tgtaataaat tacagccgtg agtacaccac atgctgagtc ttccaagtga  42780
accaccagat ctgagcatgg tcctgggggc ccccaacaca gaaataaatt ataaaagacc  42840
aaggactggg catggtggcc catgccggta atctcagcgc tttgggaggc cgaggcagga  42900
ggaccagtta agcccaaaag ttcaaagtta cagtgaccta tgactgcgcc aatgcactct  42960
aacctgggag acagagcaag accctgtccc caaaacaata aactaaacac atacttctgc  43020
cttccaagtg tcttaaaatt caatggaatg gtagaaacat ttttaaaaca ctaaatcaaa  43080
agaaacctgg aaaacaagag tgccgatggc caactaaaat gtctaggaaa tttctgaaaa  43140
gtaaaaagta ctcagaacca gattacctga gcaaaccata gcccaataca agcttgggag  43200
gaggctgtta tgcagaagga aatggtaaca ggtttccagg aacagacttg taacagcaga  43260
tagaacagca gaggtagaac ctgacaaggt gattacctgg ggaactgcag tctgaatgac  43320
caggactgtt ggacccttcc cctcacatgg aatacacacg ccactcagca gcacaccaca  43380
gctcttcaac aatcacagga ggcacgctac gcctagtaag acaggaaaaa aggaattctc  43440
aaacttcgaa gatgaacaca taaagaatca ccaagttttt attcagtatg atgaaacagg  43500
gacactgaat caacagaaca caaacccaag caaagataat tactagagca catagaagaa  43560
attattagat attcttggga agacctaagg ggacattata aagagcaagc agttggtatg  43620
tgacgatctt tgtgatatac caagaaataa aaacacagga tgaagaccag atagagaata  43680
atgctactat ttgtgcaaaa aaggagaaat ggagaatctg attcatattt gcttgtattt  43740
gcatgaagaa actttggaag gtacataagt aactaacaac aatggttacc tacttgtaag  43800
gcgagagaag taagaggaca ggaatggtgg gaacaccttt tgtgtccgga attggtgggt  43860
tcttggtctg acttggagaa tgaagccgtg gaccctcgcg gtgagcgtaa cagttcttaa  43920
```

-continued

```
aggcggtgtg tctggagttt gttccttctg atgtttggat gtgttcggag tttcttcctt  43980
ctggtgggtt cgtagtctcg ctgactcagg agtgaagctg cagaccttcg cggcgagtgt  44040
tacagctctt aagggggcgc atctagagtt gttcgttcct cctggtgagt tcgtggtctc  44100
gctagcttca ggagtgaagc tgcagacctt cgaggtgtgt gttgcagctc atatagacag  44160
tgcagaccca aagagtgagc agtaataaga acgcattcca aacatcaaaa ggacaaacct  44220
tcagcagcgc ggaatgcgac cgcagcacgt taccactctt ggctcgggca gcctgctttt  44280
attctcttat ctggccacac ccatatcctg ctgattggtc cattttacag agagccgact  44340
gctccatttt acagagaacc gattggtcca tttttcagag agctgattgg tccattttga  44400
cagagtgctg attggtgcgt ttacaatccc tgagctagac acagggtgct gactggtgta  44460
tttacaatcc cttagctaga cataaaggtt ctcaagtccc caccagactc aggagcccag  44520
ctggcttcac ccagtggatc cggcatcagt gccacaggtg gagctgcctg ccagtcccgc  44580
gccctgcgcc cgcactcctc agccctctgg tggtcgatgg gactgggcgc cgtggagcag  44640
ggggtggtgc tgtcagggag gctcgggccg cacaggagcc caggaggtgg gggtggctca  44700
ggcatggcgg gccgcaggtc atgagcgctg ccccgcaggg aggcagctaa ggcccagcga  44760
gaaatcgggc acagcagctg ctggcccagg tgctaagccc ctcactgcct ggggccgttg  44820
gggccggctg gccggccgct cccagtgcgg ggcccgccaa gcccacgccc accgggaact  44880
cacgctggcc cgcaagcacc gcgtacagcc ccggttcccg cccgcgcctc tccctccaca  44940
cctccctgca aagctgaggg agctggctcc agccttggcc agcccagaaa ggggctccca  45000
cagtgcagcg gtgggctgaa gggctcctca agcgcggcca gagtgggcac taaggctgag  45060
gaggcaccga gagcgagcga ggactgccag cacgctgtca cctctcactt tcatttatgc  45120
ctttttaata cagtctggtt ttgaacactg attatcttac ctattttttt tttttttttt  45180
tgagatggag tcgctctctg tcgcccagac tggagtgcag tggtgccatc ctggctcact  45240
gcaagctccg cctcccgggt tcacaccatt ctcctgcctc aacctcctga gtagctggga  45300
ctacaggcaa tcgccaccac gcccagctaa tttttttattt tattttttttt ttagtagaag  45360
cggagtttca ccatgttagc cagatggtct caatctcctg acctcgtgat ccatccgcct  45420
cggcctccca aagtgctggg attacagacg tgagccactg cgccctgcct atcttaccta  45480
tttcaaaagt taaactttaa gaagtagaaa cccgtggcca ggcgtggtgg ctcacgcctg  45540
taaccccagc actttgggag gccgaggcgg gcggatcacg aggtcaggag atcgagatca  45600
tcctggttaa cacagtgaaa ccccgtcgct actaaaaata caaaaaatta gccgggcgtg  45660
gtggtgggca ccggcagtcc tcgctactgg ggaggctgag gcaggagaat ggcgtgaacc  45720
tgggaggcag agcttgcagt gagccgagat agtgccattg ccttccagcc tgggcgacag  45780
agcgagactc cacctcaaaa aaaaaaaaaa aaaatagaga cccggaaagt taaaaatatg  45840
ataatcaata tttaaaaaca ctcaagagat gggctaaaga gttgacggaa caaatctaaa  45900
tattagattg gtgacctgca aaaccagccc aaggaacatc ccagaatgca gcccataaag  45960
ataaagagag catttccgct gggcacagtg gtatggcagg ggaattgcct gagtccaaga  46020
gttgcaggtc acattgaacc acaccattgc actccaggcc tgggcaacac agcaatactc  46080
tgtctcaaaa aaaaaaaaaa ttaaattaaa aaagacagaa tatttgagag aaaaaaatgc  46140
ttatttcaag aaacatgaaa gataaatcaa gatattctaa ttcccaagta agaataattc  46200
cagaagcaga aaatagaata gaggcaagga aacactcaaa acttctccag tgccatagaa  46260
atgtgtatta atctttagaa tgaaacggac taccaaatgc tgagcaggaa gaacaaaaga  46320
```

-continued gatccactct taagccagtg tggtgcccaa gcgcagtggc tcatgcctgt aatcccagca 46380
ctttgggagg ccgaggcagg tggatcacct gaggtcagga gtttgagatc agtcaggcca 46440
acatggtgaa accctgtctg tactaaaaat acaaacatta gctgggtatg gtggtgcaca 46500
tctgtaatcc caactacttg ggaggctaag gcaggagaat cacttgaaac caggaggtgg 46560
aggttgtagt gagccgagat catgccacac tcccagcctg ggtgacagag caagattcca 46620
tctcaaaaaa aaaatccact cctagacaaa taatagttaa attttagaac accaaggaga 46680
aagaaaaaaa attgtaaagc ttcagagaaa ataaacatta actacaaaga aacgagagtc 46740
agacgcgtgc acttcttcct agataccagc agataaagca atatctccaa aattcagaag 46800
gttttaacgt agaatcctat acccagtcaa gaatattcac atggaaaagt gaaataaaaa 46860
acattgttta aacatgcaag ggttcagaaa gtttaccatt cacagaatcc ctgaaaacaa 46920
aaccaaataa tcacttaagg actcattaag aaaacaaatg aaataaaagc accaatgatg 46980
agtaaataat cagaaaaatt tacagtttac ctaaataact gtttatgcat aatgtatgaa 47040
aacccaaaaa tttaatatgg gacagaatta aaatcatgat aagattcttt tttgctttac 47100
tcatggagag ttcacataaa cagattatct tttaatagca agagaaaaaa atgtttagat 47160
atgtgtgaaa aactaagggt accaaaacag tgcaaattca tttatcatca ggaaaatcca 47220
aattaaaacc acagtatcca ccagaataac taaaaggtaa aagacagaaa ttaccaagag 47280
ttggcaagaa tgtggagcaa ccacatatac ttctggggta aataagttgg tgcaaccggt 47340
actgaaaact gtttgctagt atctactaaa accgagcaca tgcacagact acaaccaagc 47400
agttccactc ccagatacac actcaacaga aatgcacaca ctcactcaac aaaagacgtg 47460
tactagagtg ttcatgtact tactattcat aatagtccaa aaatgcaaac aaccaactgc 47520
caatcaaagt caaatgtata tctatattag ggatatatac aatggcatat acacagcaat 47580
gagaatgaaa tgaaccagct cggcacagtg gttcatgcct gtaatctcag cactttgggc 47640
gggtaaggca ggcagatcac ttgaggtcag aaatttgaga ctagcctggc caacacggtt 47700
aaaacctgtc cccactaaaa acacaaaaat tagccgggca tagtggttgc aggcctgtaa 47760
ttccagctac tcgggaggct gggttgggag aatcgtttga acccgaaagc cggaggtcgc 47820
agtgagcgga gatcgtgcca ctgcactcca gcctggacga tagagcaaga ctccgtctca 47880
aaaaaggaaa tcaaaaatat aaaataagat gacaggaata atccgcaaaa gatcagtaat 47940
caaaataaat ataaatgggc taaagctacc tattaaaaga caaagatttc acacccataa 48000
ggatagctac tatcaaaaaa agagagagaa taacagatgt tagcaaggat gtatggaaac 48060
tgaaattctc acgcattgct ggtgagaata taaaatggtt cagcctctgc ggaaaacact 48120
atgctgggtc atcaaaaaat taaaaataga agtactactt gatccaacaa ttctacttct 48180
gggtatatac ccaaataact gaaagcaggg tcttgaagag atatttgtac acccatgatc 48240
atggcagcat tattcataat agctatgatg tggaaccaac ataaatatcc tttgataaat 48300
atatggataa gcaaaatgtg gtgtatacat tcaatggaat attaattagc aataaaaatg 48360
aagaaaattc tgacacatgc tacaacatgg atgaaccttg agggcattac attaaatgaa 48420
ataagccagt tataaaaaga caaatactat atgaggtact atattagata ctcatgcaag 48480
gtacctaaaa taggcaaatt catagagaca aaaagcagaa tggtggttgc caggggctgc 48540
ggtaatggat acagagcttc aattttgtaa gatgaaaaaa ttctggagat tggttgcata 48600
acaatgtgca cacacttaac actggggaac tgtaaactta aaagtagtaa atggtaaaaa 48660

-continued

```
taaaaataat aaataataaa ttttatgtta ttttaccaca atatttatta aaagacaaag  48720
attaactaat taaacaaaat ccagccataa gctaatggta agagtaacaa ttaaagaaga  48780
cacagaaaat tgaaaatcag tgactagaaa aagatattcc atataaatgc taacaaaaag  48840
caagtacagc aatataaaga gaatgaacaa aaaaaaaatt aaataagatg gctcgtttat  48900
tcccaaaagg tacaattcac caagaagata caagaattgt gaacctttaa gcacataaaa  48960
cagcttcaaa aatacaacat ttaaagaaaa atatatatta aacatagaaa tagtacaaaa  49020
acccctacaa gaatcataat gggagtcttc aatacaactc tccatatcaa caggtcaaac  49080
agagaaaaaa aataagttaa ggatgcagaa aacctgaatt accatcaata aacttgagat  49140
taatatagaa ctgtataccc aatatactaa gagttcaggg aacagtcgtg actgacagtg  49200
gactgcaaat taatctgttc ttaatctttg tttttcttc agcactgtgg cagaatagag  49260
atcctaaaaa ccttccagct acaaaacatc tttttaaaaa tataaaaaaa tacaaaaata  49320
actctgaaat caatagaaga cacatggtga aaccaaaatt ctagaataca gggagaataa  49380
aggcattttc agatattaca aaaacagaaa attgatcatt gctgaagtaa tttctaaaga  49440
atgtacttga gggagaagaa aaatgttcca aagaaaagta tctgtgatac aagaaggaat  49500
ggaaagtgaa gaaatggtaa acaggtagat aaagctaata aatgttgacc tagaaaataa  49560
caaaaacaat agcaataatg tctcgttgga agggttgaag taaaaataca attaaggcca  49620
aatgtgaggt aagtggaatg aaagaattag aagtccttgc cttgttcaca ggactgatta  49680
aataaatgag ccaggttttc cattcaaaca gttaaaactt gaacaaaata aactcaaatt  49740
aagtagaaag ataaaaaaca gaaattaatg tcatagaaaa ataaaaaatc aatagaatta  49800
atcaataaat cctggttaat aaaagctggt tctttgaaag gattaataaa ataatcatta  49860
agcaagtctg atcaaaaaaa aagagaaaag gtaccaaaaa aagtactgta tcagaaagag  49920
aacatacaga tacatacaga tatgtaagag tctgttttct tacaccagaa tactatatac  49980
aacattatgc tagcatatat taaatttcaa taatgttaat gattttctag gaaaacagaa  50040
aatattaaat ttactttgaa gaaacagaaa aactgagaaa aataaatgat catgaaaaaa  50100
atgaaaaggt aattaaatac tgatattaac tgcctaaaca acaccagcag cagcccaggc  50160
agtctgcagt caagttctgc caaacttgag ggaacagata attcttctat tccagagcat  50220
agaaaatgat ggaaagtttc ccaatttaat cagagaggac agcctgatcc ttgttatgaa  50280
cacagataaa aatggggtaa actatatgcc aaactcagat accaaaaccc taaataagat  50340
gctagcttat tgatgtgaac aatccaaaag tgcattttaa attagcccag ggttttagag  50400
aaagaaaatc tagcaatgtg accaccactt atgttaacaa ttttaagacg aaaatctaca  50460
tgatcatatc aatgcatgct acacaaaagc atttgggcaa aaaacccaac acccacccct  50520
gactttttaa actcttagta attaggcata aacagaaatg tacttaatgt gatagaatac  50580
actcggtgaa gatacagagg gaatgctccc taaaaccaag cccaagacaa agattcctat  50640
ttaacctcaa tagtcaacac tgcagcgaga gtaatctatg gaagacaagg aaaaaagtaa  50700
aaacatgaga gacatctgtt gtttaacaga caataagatc acctacttgg aagaggcaaa  50760
cgaatcaagc gaaaaactat taaaactgag acaggcttta gtatggaggc tcagcttcag  50820
ctgtagtttg ggctaccaaa ttcaactcgc ttgcttggag agttaatcct gcaaagctaa  50880
tttctgttga ggtattagga ttgacaagcc tgtgctcctc cctcctcccc catcttcaac  50940
actgaaataa cacggtgttt ggaactggat aacagaatct tccaaaaaca aaaattgtcc  51000
tgaagggctg acttgtgccc ttactcaaaa aacactttat ctgctgcctg cagctcctac  51060
```

-continued

```
agttgctggt ggataagcct gccaaccagc tcggcgtaat tcttcctgca gagggcaagg  51120
aagagcactt tcacaggaaa attttttttcc gaactgtatg ccgcttatta cataaactta  51180
cgtgctggca aatggagctc cagcaaaata agatattcag agtcaaactt ccttaggaaa  51240
aaaaaaaaaa aaaagcaagc acataacact aatttccttg catgggcact ggggaaggag  51300
gtcgttactt ccgcacgccc gcaggtccgc accaccggga aacccacggg caccgcgcgc  51360
tgcccccggg ccttccaggt gcactgcgcc gcggcgcccc agctgacccg ggatgcgcag  51420
ccctagccct tcccctgtca ccccggccag gaaggggcgg gagcgcggcg gacgccgagg  51480
gcgaagggct tctcggtcct ctgcaccacg cagcaccccc aaggcacaac agggagggtg  51540
cgggaggctc ccgagaccca ggagccgggg ccgggcgtgc ccgcgcacct gtcccactgc  51600
ggcgagggct ggggtcgcct ccagggccgc agctgtcggg agccacctgg ctctcagtcc  51660
cgggtccctg cgacaaccct cgggcccgga ggggaggagg cggccacctg ccgctgccac  51720
ctgcggcacc ggtcccaccg ctccgggccg ggcaggacag gccaggacgt ccctcctggg  51780
ctggggacag gacacgcgac gaggggaccg gggcccccgc ggcgaagacg cagcacgcct  51840
tcccagaaag gcagtcccgt gcccccacga cggactgccg gacccccgcg ctcgcccgcc  51900
catcccttca gaccacgcgg ctgaggcgca aagagccggc cggcgggcgg gctggcggcg  51960
cggctagtac tcaccggccc cgctggctca gcgccgccgc aacccccagc ggccacggct  52020
ccgggcgctc actgatgctc aggagaggga cccgcgctcc gccggcgcct ccagccatcg  52080
ccgccagggg gcgagcgcga gccgcgcggg gctcgctggg agatgtagta cccggaccgc  52140
cgcctgcgcc gtcctccttc agccggcggc cgggggcccc ctctctccca gctctcagtg  52200
tctcatctcc ctatctgctc atcctctggt cgcacataat cgatgtttgg gcgtcccaag  52260
ccagatgtgg accccatttc cgcactctac actggaggtt ttctaagggt ggtgcccgga  52320
ccagcagctt cagcctcatc tgggaacttg agaaaatgca gattctccgt cccacccagc  52380
ctattcggtt tttcctgcac taaaaccatg aaggtggggc ccagcagtcc acattctcgc  52440
aagcccgtca agtgattctg aggcgccctc cagtttgaga gctatgctca cggcctcacc  52500
tccgccccgc aaggagcccg gtcttgcctg tggcgctagc cgcacacgga cacctcatcc  52560
tgcggggccc gcccccccgc tgcaccctca ccgcccaacg cctcctccgg gatgcagcgg  52620
aggcgcctgg aagtcggcaa ggtcaacatc cccctcagca tcttccctac cctcacggct  52680
cctcctccag gggtgcctca tggccagggg ttagaaagag ccactgtgtt tcttgacatg  52740
gaagtggcct aagaccttaa tgaaaactgc aggagtggaa tgacagaacc tttggtcata  52800
cttgagggcg tgaagctcaa atgaggagga aggaaaggat ccagggagaa taaccaaccc  52860
tggcaagttg tggcgcccag gtagaggggc gagcctaggc tagcggttct cgaccagggc  52920
cggtgttgcc cctcctcgcc gccccgcgta catttgggga ggtctggaga catttttggt  52980
tgtcatgatg cgggagttgc tactgttgcc taagtgggta gacacgaggg tgctcctcaa  53040
catcctacct gaaggacagg actgccccac aaggaagaat gatccggccc caaataagaa  53100
accctgggct ggtcagcaac aacccctttg ttctgagaag agaggaggaa agaataaaag  53160
aagtggggtg aagttttggt ttggtagagg aaacttgaag acattttcac tggaaaggaa  53220
gagaggaaga ggagggagat gtctgtaagg acgagcaaac cgggtgacag ctgatttcct  53280
catattgaag taatgagtcc tagttataat aaattcctaa taaaaaccca gtttatccct  53340
gcaataaact tgtctttttt ttttaaatat actgcttgat tctgtttgct aatattttat  53400
```

-continued

```
ttacaggctt tgcattgata tgcaaaaatg agatgggcaa taattttctt tttgaatgtc  53460
taatgttgtt tggtttcaga atcaatgtta tgctcacatc ataaaaaatt tggaaccgag  53520
gcaggaggag tgcttgaggc cagaagttcg agaccagtct aggaaacaca gtgagacccc  53580
cccatctcta caaaaaaaaa aaaagaaaaa aaaatgggca tgtttgcttt ttcctttttac  53640
tctgaacaat ttaaggagca ttaaaattat ctattctttg aggtttgatc atttcccagt  53700
taaaaatgtt cctcccagcc tgatgctttc tttggggagg gtaaatcttt taaggctaga  53760
aaagtttctt ctgtggcaat tttattattt acattttaaa aattattcta gagttaattt  53820
tgataaagca tgtatttctt aaaacaaatt atcctttttt tccagatgtt caagtgtatt  53880
tgcataaagt tgaggaaagt agtcttttgt gaatctttta acttctccca aatatcttat  53940
tttgtgtatt tttgcttctt tattttgtta acttttaaaa gtgtattttt ttttcaaaga  54000
atcagctctt aggtttatgt ttttggttat actggagctt ttttcttctt ctttttaaaa  54060
tatttttttct cctttatttt ttagacgtat tttgatctaa cgtaatcgga agaaggtaaa  54120
ttagaatctt ttgttactat tgtgttttta tttctcctta tttctctgaa gtcctgcttt  54180
ataaatagta ccatgttatt tgtgcataaa tattcatttg tcttatattc ttgggaattt  54240
tcccacttca tcataaaatg accttccttg tctcatttaa tgtgttcaaa ctttgccctg  54300
aatttaactt tgtctgatat tttaccatcc tgctgaattt tgtttgttac cccaaacaac  54360
ctttgctgtt ttcgtctttt ctgaaccctt tattttaggt aatcccttga attagagcac  54420
taagttttgc tttgtgatta aatctgaaaa tctttatctt gccatagatg agttgagccc  54480
tattcatgtg acagctatat tatgctgttt catagccctt ttggtccttt tttcactctt  54540
gcattgcata ttttgtgttt attgtgtttt gtgtttcttc tgataatttg gaaggtttgt  54600
atttttattc agggagttgc cttataatca tactccgcaa tacacatcgt cctcagtttc  54660
ttcagactgt ctgttaactc cctattctga ataaaaatga cattgtaatt tccctctttt  54720
ttctttaccc cttttcttct cctcacctaa tgtaaatgat tttatccttc tttagtattt  54780
gctttttttaa ttaactacat ttataaatat ctttatcact tgatttttaa atcagctttg  54840
aatgagatat ttggattcct agatataaaa gatgttaatt ataccatttc cacgttagta  54900
ggtttataaa atcatacatt ctgctgtgta accataatcc cacgtttgtt ttagttccac  54960
tcctacagtt aaaagattca gaagtattat taacagttat tttgccatag tttttttcccc  55020
aacccatttt gtggtaagtt atgatcctgc tttagtttct taagaataat ttatagagca  55080
gagtgtggtg gctcacgttt gtaatcccag cactttggga gacaagaggt agaaggatcg  55140
cttgaagcca gcagttcaag accaccctga gcaacatagt gagaccttgt ctctacaaaa  55200
aattttaaaa tttagccaga cgtagtggcg tgtgcctata gtcccagcta ctcaggaggc  55260
tgaggcaaga ggattgctag agcccagaag tttgaggctg cagtgacctc tgattgtgcc  55320
actgcacccc agtctgggca agaaagtgag aacctatctc tttaaaataa caataataac  55380
ttatgaaaat tatattccct gagtttttca tgtttaaaaa tatttgttgc ctttatcctg  55440
taaaagtttg agtataaatt cttgggttat actttattta ttgaagaatg tataagtatt  55500
gtcttctaga attgagtgtt gctgtaatga aaccagaagt cagcctggtt tatttttcct  55560
cagaaatgag gtaattgccg gccggacacc gtggctcatg cctgtaatcc caacactttg  55620
ggaggccgag acaggtggat cacgaggtca ggagattgag accatcctgg ctaacatggt  55680
gaaaccccgg ctctactaaa agtacaaaaa gttagctggg catggtggtg gacgcctgta  55740
atcccagcta cccgggaggc tgaggcagga gaatggcgtg aacctgggag gaggagcttg  55800
```

-continued

```
cagagagctg agatcgcgcc actgcactcc agcctgggcg acagagtgag actccgtctc  55860
aaaaaaacaa aaaaaaaaca aagaagtgaa gtaattgcca tgatgctcca agaattatct  55920
ctttgtctat gaaatccaga aatctcactg ttatacattt tggaattatt attctgggcc  55980
aatatttcct gggacacaat agattgactc tatagattta attttttttt tttttttgag  56040
acagagtctc actgcaatct cagcttactg caacctctgc ctcacgggtt caagcaattc  56100
tcctgcctca gcctcccaag tagctgggac tacaggcgcg tggcaccatg cctggctaat  56160
ttttgtcttt ttagtagaga cagggtttca ccatgttggc caggctggtc ttgaacgcct  56220
aacctcaagt gatccacctg cctcagcctc ccaaagtgct gggattacag gcgtgagcca  56280
ccatgcccag cctcaattcc tctttctatc tggtaatttt tctgaagttg aaaacatttg  56340
ttctaatacg ttatttcagt gttcttctaa gatgtgtaaa gcaccctatt cccaggtcag  56400
cccccatctt gctagtgagc tcggctggtt cttcacaaga gctctggttt tctcctgctt  56460
aatctcaagt acctctgtca gcctccacct ggtttatgat ttggagtttt ttggtttttg  56520
ttttttgttt ttgacagagt cttactctgt cacccaggct ggagagcagt ggcataatct  56580
cagctcactg caacctctgt ctcccaggtt tgagcgattc tcctgcctca gcctactgag  56640
tagctgggat tacaggcgcg tgccaccaca cccggctaat ttttgtattt ttagtagaga  56700
tggggtttca ccatgttggc cagggtggtc ttgaactcct gacctcaggt aatccacctg  56760
cctcagcctc ccaaagtgct gagattacag gcgtgagcca ccgcgcctgg catggtttgg  56820
agttttaatc tgtagtttta ataaagatag tgcttatgtt tgtgtttctt atatttcttg  56880
gtactcttgg gtaatttgta agatccccat atctacacaa gaagtccatt ttcaattctt  56940
ttcttcagac tgtttatttt attttatttt attttatttt tatgtttgag atggagtctc  57000
gctgtgtcac ttctggaggc tggagtgcag tggcgcgatc tcaggtcact gcaacctccg  57060
tctcccgggt tcaagcaatt ctcctgcctc agcctcccga gtagctggga ttacaggcac  57120
ctgccacttt ttaatttttt tagagacaga gtctcgcttt gttgaccagg ctggagtgcg  57180
gtggtgcaat catggctgac tataacctcc aaatcctggg ctcaagtgat cctcctgcct  57240
cagcctcctg agtagctggg actacaggca catgccacca tgcccagtta attttaattt  57300
ttttgtagag acagggtctc catatgttgc ccaggctggc ctcctactcc tggcctcaag  57360
taatcctcct acctcagcct cccaaattac taggattata agcatgagcc accatgccca  57420
gccttgttct actactttaa tttcatatgt taggtgacca tgtaattgat catccaaacc  57480
aggatactgt aagaatgaaa gaggctgaca gtagtatgat gctgggacta gcattgtgca  57540
ctgagattat ttctgggaaa gcaggagata cggtcaccct acttatagtg tgcttgtctt  57600
tggattgttg aatttggagt ttctatttgc aggcttattt caactgggca gccttgatcc  57660
gccctgccca gcaatgctac cgttctctcc accgggtctc tgggacccct tcagtcacta  57720
tacttagctc agttccccac cctcccactc cctaaaagcg taaccaggaa tcctgcctca  57780
ggtctactgc cgtcttccgt gggctgtttc agttcctatt acccagagtc aaactcccag  57840
cattccctac ctgattccag acttggagtc cagagcttta acctcttcag gccaactccc  57900
cactttgcat ttctgtccct atatcttagt ccatggagat acatttcatg tctttgagtc  57960
tacttacaaa gtaaattttg ctgtttttta attttttttt tgagatggag tcttgccctg  58020
tcacccaggc tgtggtgcaa tgacgccatc tcggctcact gcaacctccg cctcctgggt  58080
tcaagcgatt catctgcctc agcctcccaa gtagctgtga ttacagacag gcaccaccac  58140
```

-continued

```
gcccagctaa ttttttttat cttttagtag agacagggtt tcaccatgtt ggccaggctg  58200
gtcttgaatt cctgacctcg tgatctgccc atctcggcct cccaaagtgc tgagattaca  58260
ggcgtgagcc actgtgccca gccaattttg cttttttat atttcattgc tatatgttta  58320
gaggataagt ttacagtgct atatgcattc ccaaatatta gaccaaaaaa atctccaaaa  58380
aattagaaag aaaatccaaa aaatctcaaa aaataccaaa aagcaacaat ctcacagacc  58440
atactcactg acccccaata aaataaaatt agaaattaac cacaacttaa caaaataaag  58500
tactcaagtc agagaggaaa gaggaaataa acatcaaaat tacaaagtct aggcggtggc  58560
tcacgcctgt aatcccagca ctttgggagg ccaaggcggg cagatcacaa ggtcaggaat  58620
tcgagaccag cctggccaat atggtgaaac cccgtttcca ctaaaaatac aaaaattagc  58680
caggcatagt gatgtgtgcc tgtaatccag ccacttggga ggctgaggca ggagaatcac  58740
tgaacccagg gagacgaaga ttgcagtgag ccaaaatcgt gccactgcac ttcggcctgg  58800
gtgacaaagc gagactccat ctcaaaaaaa aaaaaattac aaactcttta gatagaaatt  58860
ttggtgtttt tttttgagac ggagtctcac tctgtcgcag aggctggagt gcagtgggac  58920
tatgtcagct caccgcaacc tccatctcct ggattcaagc aattctcctg tctcagcctc  58980
ccaagtagct aggattacag gcgcccacca ccagacccag ctagttttta tatttttagt  59040
agagatggtg tttcaccatg ttggccaggc tggtctcaaa ctcctgacct caagtgatcc  59100
acctgcttca gcctcccaaa gtgctcagat tacaggcgtg agccaccgca ccccacctag  59160
atagaaattt caacatgagg ccgggcacaa tggctcacgc ctgtaatctc agcacttcag  59220
gaggctgagg cgtgggagga tcacttgggc ccaggagttc aggaccagca tgggtgacag  59280
agacagaccc tgtctctatt tatttgaaaa aaaaaaaaaa aaagagagag agaaagaaat  59340
ttcaacatga aaagtatctc tcaaaccctt cgagatgttg gcaaaaagcg actcaaagga  59400
aaatgtatta ctgtgtgtga atttgcttga aaataagaaa gaggccgggt gtggtggcta  59460
acacctgtaa tcccaacact ctgggagtcc gaatcaagtg gatcatgagg tcaggagatc  59520
gagaccatcc tggctaacat ggtgaaaccc tgtctctact aaaaatacaa aaaattagct  59580
aggcgcggtg gctcatgcct gtaatcccag cactttggga ggctgaggca ggtggatcac  59640
ctgaggtcag ggtttgaga ccagcctggc ctacatggtg aaacctcgtc tcttctacaa  59700
atacaaaaat tagctgggcg tggtggtggg tgcctgtaat cccagctact cagaggctga  59760
ggcaggagaa tcgcttgaac ccgggaggcg gaggttgcgg tgagccgaga tcgcaccact  59820
acactccagc ctgggcaaca gcctgggtga cacagtgaga ctccatctca aaaaatacaa  59880
aaaattagct gggtgtggtg gcctgcgcct gtagtcccag ctacccggga ggctgaggca  59940
ggagaatgga gtgaacctgg gaggaggagc ttgcagtgag ccgagatccc accactgcac  60000
tccagcctgg gcgacagagc aagactcttg tctcaaaaaa aagaaaaaaa aaggaaaaaa  60060
gaaccctgat aataaagaaa ccaaatgttc aactctcaaa gctcggacac tttaaagaaa  60120
taattaataa aggcagaagt taaagggagg atgataaagc aattttttt gttggttttt  60180
ttgagatgga gtcttgctct gtcacccagg ctggagtgca gtgatgcgat cttggctcac  60240
tgcaacctct gcctcccggg ttcaagcaat tctcctgcct cagcctcctg agtagctggt  60300
actacaggtg cgcgccacct ggcccagcta atttttgtat ttttattaga gacggggttt  60360
caccatattt gttaggctgg tctcaaactc ctgatctcag gtaatctgcc cacctcggcc  60420
tctcaaagtg ctgggattac aggcaggcgc caccgcgcct ggcctaaagc aaaatattgg  60480
ttctgtgcaa aaggtcaata aaaagagcaa acgtttacaa actggagcca gcacccattc  60540
```

-continued

```
agctcagtgt gtctggagaa aaaacaatct cgcttcagaa ttcatgatta cgcagccctt  60600
tttgcttcct aaaaatccta ctatgttgct gttgaccatt ctctctcttt ctctctctct  60660
tgctttctct ccagaaaagc tattcagaca ttctcctctt tcctcaaacc tccaacactt  60720
cctcctccat ccttagcctc agctgctgac ctcacttcta atcattgaga aaccaggaga  60780
agcatttaag agtgaacctc cgcctccccg cacgggcaaa accacccacc cacagaattg  60840
tgccccaatt ctgcgtcctc tcctctcacc atggatggac ggtccaggct ccgagccaaa  60900
gccaggcctc ccctggagct ctggatccac cacctgcagc ttctcaggca gggccccagc  60960
agctcccctg ctcccttgta ccatcaatcc ctcccctcac tgggtcactc ccaacaatat  61020
atatatttag tgatgtttct cccatgtggt aaaatcactt agcctctctc ctcccccagc  61080
tactatccta tttgtttctt tccattctct gcaaaacttc tcaaagcatt gtgtctatgt  61140
gctgactcca tttatcttct cccgttctct gctgagtcct tcccacagac tctcacccca  61200
gttactccat gaaatgacct ctgcactgcc acatccaatg gtgaatgttc agttcttaat  61260
tttattcagt ctttcagcag catttgacct ggccgatcac tccctcttct taaaaatact  61320
tttctcagcc aggcgtgatg gctcacacct gtaatcccaa cactttggga ggccaaggcg  61380
ggaggatcat gagagcccag gagttcaaga tcagcctggg caacatggca agaccctatc  61440
tctacaaaaa ctaaaaagta gccagtgtga tggcatgcac ctgtagtccc atctacttag  61500
gaggctgagg cagtaggatg acttgagcct gggaaatcaa ggctgcagtg agccatgatt  61560
gcaccactgc actccagcct gagtgacagc gagaccctgt ctcaaaaaga caaaatagga  61620
aactttctc agcatattcc tctgattctc ctgctgcttc tgtctgcaca gattcagtct  61680
cctttgccgg ttcttcctca tcctcctgat ctcttgacct tgaagtgccc cagagtacag  61740
tctttttttt tttttttgag acgcagtctc gtctgtcacc caagctggag tgcaatggcg  61800
aggtctcagc tcatgcaacc tctgcctcct gggttcaagc gattctcctg cctcagcctc  61860
ccaagtagcc aggactacag gcacatgcca ccatgcccag caaattgttg tatttttagt  61920
agagacaggg ttttactata ttggccacgc tggtctcaaa ctcctgaact cgtgaaccac  61980
ccgcctcggc ctcccaaagt gctgagatta caggcatgag ccaccacacc cggcccagag  62040
tacagtcttt agacggcctc tctacctata cttgctcccc tcataaactc ctcctgcctc  62100
atggctttaa ataccatcgg tagactgatg actcccatat ttctcttttt tttttggaga  62160
cggagtctcg ctcagtcccc caggctggag tgcagtggcg cgatctcggc tcactgcaag  62220
ctccacctgc caagttcaca ccattctcct acctcagcct ctccagtagc tgggactaca  62280
ggcacccgcc accacgcctg gctaattttt ttgtattttt agtagagatg gggtttcacc  62340
atgttagcca ggatggtctc gatctcctga cctcgtgatc cgcccatctc ggcctcccaa  62400
agtgctggga ttataggtgt gagccaccgt gcccagccga tgactcccat atttctatct  62460
cttgctgtgt gggagttctc ctcagaactc catactcata aatccaactc tcataaatag  62520
tatctcaaat gggcaatatg ctcaaaagtc aattcctact tttctcccta aacttgcttt  62580
cctgcagtct ccaccatctt aatgtccaat ctaacattag gaggcaaaaa ctttgaagtc  62640
attcttgact cttctctatt acacacccta tccaatcttt ctgcagatcc agtcgacccc  62700
caaatccagt tagctctcat catctcccct gttacccccct ggtccaggcc atcttcctct  62760
ctcacctgaa tcactgcagc attctcctca ctggtctctt tggttctgtt ttcactccac  62820
cttagcatag tctccacaga gcagtcagag ggatcctttt aaagtgtaat tcccatcctg  62880
```

-continued

```
tccctgctct gctcaaaacc ctgtcgtgat tcccgtttta atctgtcaga ttaaaagcca  62940
gagtctttcc agtgacctac atgatctgcc tattatcacc tcccacttct ttccccttgc  63000
tcactccact ccagctctgc agctgtcctt tctgtttcct gaacagccca gattttgctt  63060
ctttagaacc tttgtatttg ctgtcccctc tgtctggaat gtttttccag gaagtcacct  63120
ggctctctcc tgcacttcct tcctgaccac catgtttaaa aatcactcaa acacacttca  63180
ggccggacat ggtggctcac gcctgtaatc ccagcacttt gggaggccaa ggtgggtgga  63240
tcacctgagg tcaggagttc gagaccagcc tggccaacat ggtgaaactt cgtctctact  63300
acaaatacaa atagtagcca ggtgtagtgg cacacacctg taatctcagc tactcaggag  63360
gctgaggcag gagaatcgct tgaacccaga aggcagagga ggtgcagtga gccaagatca  63420
cgccacaaca ccccagcctg ggtgacagag caagacccca tctcaaaaaa aaaaaaagaa  63480
aaaaaaatca cacaaacaca cttctcttca tattcctttt ccaagtttta tttttctcca  63540
gaatacttta cattgtttta atggaagttc tccgtttccc cccaactaga atggatactt  63600
cctgcaggta ggcactctag tcctcccatc caagtactaa ccaggctcaa ccctgcttag  63660
cttctgagag caggggagat caggcctgtt cagggtggta tggcccagga attttgattc  63720
tgttttattc attgctgttc tgttgattct cttttgttcc tcctcctagt gctgagaaca  63780
ctacttgtac ataataagca ttcaataaat atttgttgaa tgaatgactt gttgaatgaa  63840
ttaatctcag aaatgcagga ctggttctac attagaaaat ttttcaaggt cattctctgt  63900
tgtcgtaaca cattaagaga ggaaaatttt gtactctaaa tcatttgata aaatacatac  63960
tgatttctgt tttcaaaaac tcttagtggc tgggcgaggt ggctcacatc tataatccca  64020
gcattttggg aggacgaggt gggcggatca cttgaggtca ggagtttgag accagcctgg  64080
ccatcatggt gaaaccctat ctctactgaa aatagaaaaa ttagccgggt gtggtggcgc  64140
atgcctgtag tcccagctac ctgggaggct gaggcaggag aatggcttga acccgggagg  64200
cggaggttgc agtgagccaa gatcatgcca ttgcactcca gcctgggtaa cagagtgaga  64260
ctccatctca aaagaaaact cttagtgagt ttaggaatcc aaggaagacc ctcaaactaa  64320
atagataatc tagctaccag aagccttcag taaaccttaa cactccatgg tgaaacatta  64380
gaaacattcc tactaaaaga caggctaaga atgcctgcaa tcttcacggc tagtccaaga  64440
agtcaaaaag aagaaatgag cgctgattta aaaaaataaa caaacaaaaa actaccgatg  64500
cagaggctgg cagcaaggac tgaaggactg tacagtactt gcctggagca ggcggatggc  64560
cacaccccctg cgaagcctgc tcagctggct gggggacgct ccagtgtgtg agtggcagga  64620
tgcagggtac ttcctctgcc agggagttgc actggggaga tcctccccca ctcacacttt  64680
ggcagctggg gctttggaat gtgacttagc ttctgtcaaa gggtcaatcc accctttgat  64740
atatgatgca aaggcgaaca tatgatgcaa aggtgagaga acagcccaaa ttaggacttt  64800
taccacagct gtggaggtgg acagcgacag tggtgggccc tggccagact tttcatgctc  64860
aaaggtggtg gttgttcttc ctacttcttg tccctccagg gcttcctttg cctgtgtgct  64920
gaacctgctt cttttaattt tttttaactt ttttaaattt ttaattgttt taattaaaac  64980
aaattttgaa aactgtctga acctgctttt gaaccctgct atgatttgaa tgtttgtccc  65040
ctgccaaact gattttgaaa cttaatctcc aaagtggcaa tattgagatg gggctttaag  65100
cagtgactgg atcatgagag ctctgacctc atgagtggat taatggatta atgagttgtc  65160
atgggagtgg catcagtggc tttataagag gaagaattaa gacctgagct agcatggtcg  65220
ccccttcacc atttgatatc ttacactgcc taggggctct gcagagagtc cccaccaaca  65280
```

-continued agaaggctct caccagatac agctcctcaa ccttgtactt ctcagcctct gtaactgtaa 65340
gaaataaatg ccttttcttt atgaattacc cagtttcaga tattctgtta taaacaatag 65400
aaaacgaact aaggcaaact ctcatgattc tactgccatg ccattccaat aaactccctt 65460
tatgcttaag agagccagag ttggccaggc gtggtgactc acgcctgtaa ttccagcact 65520
ttgggaggcc gaggcaggtg gatcacaagg tcaggagatc gagaccatcc tggctaacac 65580
ggtgaaaccc cgtctctact aaaaatacaa aaaaattagc tgggcgtggt agtgggtgcc 65640
tgtagtccca gctactcggg aggctgaagc aggaggagaa tggcgtggac ccaggaggcg 65700
gagcttgcag tgagtcgaga tcgtgccact gcactccagc ctgggtgaca gaatgagact 65760
ccgtctcaaa aaaaaagaga gccagagttt atttctgttg cttgcaacca agaaatctgg 65820
ctggtgcact gaagtttcca taaataatag caatttaaag actctttcca agccaggcaa 65880
tgcctagcct tgtgtagtcc ttgtggtaat acattcattc attcatttgt tcaaccaact 65940
gtgctccaga gactaagaat acaaaaatgg gggccgggtg tggtggctca cacctataat 66000
cctagcactt tgggaggccg aggcaggtag atcacctgag gtcaggagtt cgagaccaac 66060
ctggccaaaa tggtgaaacc cctactctac taaaaataca aaaaattagc tgggggtggt 66120
ggcggacacc tgtaatccca gctactcgtg agactgaggc aggagaatca cttgaacccg 66180
ggaggcagag gttgcagtga gccgagatcg caccactgca ctccagcctg ggcaacaaga 66240
gcgaaactcc acctcgaaaa aaaaaaaaaa aaaaaaagag ggccggggct gggcgcagtg 66300
gctcacgcct gtaatcccag cactctggga ggccaaggca ggagaattac gaggtcagca 66360
gatcgagacc agcctgacca acatggtgaa accccatctc tactaaaaat acaaaaatta 66420
tccgggcgtg gtggcgcaca cctctagtcc cagctacttg ggaggctgag gcaggagaat 66480
cgcttgaacc cgggaggcag aggttgcagt gagccgaaat catgccactg cactccagcc 66540
tgggtgacag agtgagactc cgtctcaaaa aaaaaataaa aaaaaaaaaa gaattcaaaa 66600
attgtagagt tatagtgtgc ttctagttta gttgagagga catctgtcct tcaaggaagg 66660
ctagaatcta taccctgagt ccttactgaa atcaatccag cagtcaaaac atgggaccaa 66720
cgatcacagc agtaagatag gaagagcacc tttgtacatt tagctcatgt tgagataagc 66780
cactgacaga gctgaaggaa gctcacagtt ctgggttcca tcctttggca tttaaaaaga 66840
aaagtgctaa gaaaattcgg ttggtcacgg tggctcacgc ctgtaatccc aacactttga 66900
gaggccaagg caggcagatc acgaggtcag gagttcgaaa ccagcctggc caacatggtg 66960
aaaccccgtc tctactaaaa acagaaaaat tagccgggca tggtggcgca tgcctataat 67020
cccagctact caggaggctg aggcaggaga attgcttgaa cccgggaggg ggaggttgca 67080
gcgagtgaga gcaggccact gcactccagc ctgggagaca gagcaagact ctgtctcaaa 67140
aaaaaaaaag aaaaaaagaa agaaaggaaa aaaagaaaga aaaaaaaaga aaaaagaaaa 67200
ttcaggccag gccaggcctg gtggctcaca cctgtaatcc caacactttg ggaggctgaa 67260
gcgagacggt gccttagccc aggagtttga gaccagcctg agcaacatag cgagaccctg 67320
tctctataaa aaaaaatttt tttttggcca gacgcagtgg ctcacgcctg taatcccagc 67380
actttgggag gccgaggcag gtggatcacg aggtcaggag atggagacca tcctggctaa 67440
cacggtgaaa ccccatctct actaaaaaat acaaaaaatt aaccgggcgt ggtggcgggc 67500
gcctgtagtc ccagctactc gggaggctga ggcaggagaa tggcgtgaac ccgggaggcg 67560
gagcttgcag tgagccgaga ttgcgccact gcactccaga ctgggagaga gtgagactcc 67620

-continued

```
gtctcaaaaa aaaaaaaaaa aaaaaaaaat taattgtcag gtgtgctggc atgcagctgt  67680
agtcctagct actcgggagg ctgaggtaag aagatcgctt gagcccagga gttcaaggct  67740
gcagtaatag tgcctctcac tctaccctgg gtgacaatga gaccctctct caaaaagaaa  67800
gaaaaaaggg aaagaagaaa agaaagaaag aaagagaaga aaggaaggaa gaaagaaaga  67860
aaaagaaaag gaaggaagga agaagaaaaa aaaagaaaga aagaaaagag agagaagttc  67920
aaagaccaaa gggtcaggat cccaaaatag tttttatgtt ttatttattt atttacttat  67980
ttatttttga gacagtatgg ctctgtcgcc caggctggag tgcagtgatg cgattgcggc  68040
tcactgcagc ctccaaactg ggctcaggtg gccctcccac ctcagcctcc cgagtagctg  68100
ggaccacagg cgcgtgccac catgcccagc taattttta attctttgta gagatgaggt  68160
ctctatatgc tgcccaggct ggtctcgagc tcctgggctt aagccatcca cccgcctggg  68220
cctcccaaag tgctgggatt acagaagtga gccaccgcgc ctaatcgggt ggtttgtttg  68280
tttattgacg gggtctcgct gctgcccagg ctggagtgcc agtggctgtt cacaggtgca  68340
gtcctggagc attgcatcag ctcttgggct ctagcgatcc tccagagtag ctgcagctgg  68400
gattccaggc gcgccaccgc gcggggctca gaatgggttt ttatattgag ggttatgctg  68460
ccacctagag gatatatgta gtaccgaact gtgtgcgcag ggaggctgag gttgcagtga  68520
gccaagatga tgccagggca ctccagcgtg ggtgacagag caagatttca tctcaaaaaa  68580
aaaaaaaaaa aaaaaaaaaa aagaattgaa agtaaggtct tgaagagata tttgtgcctg  68640
tatggtcata gcagtattaa ctttgaccca ctagctaaaa cacaaaagca acatgtgtct  68700
gtcagcaggt gaacggataa acaaaatgtg gtatatatgt acaattgaat attattcagc  68760
ctttaaaaag gaataaaagg ctggatgcgg gggctcacgc ctgtaatcct aacactttgg  68820
gagactgagg tgggtggatc acccgaggtt aggagtttga gaacagcctg gccaacatgg  68880
tgaaacttca tctctactaa aaatactaaa attagccggg catggtggca cttgtctgta  68940
atccaagcta ctggggaggc taaggcagga gaattgcttg aactcaggag ccggaggttg  69000
cagtgagcta agatggcacc actgcactcc agcctgggca acagagtgag actccatctc  69060
aaaacaaaca aacaaaaaat tattatttcc aaagaaacaa gaccctgggt ccatttccca  69120
gcccacacct gatgttgact cacaacacac agcctggttt gctatgagcc tgcttcattt  69180
aattgtcacc ttaacttcac atcaccctca agtcctggaa taactctttg ctgacctttg  69240
tgtgctgagc catctccatg tcgctcaacg tgcagtccct ctcactgcac tgagtcaata  69300
gccagacgtg gtctgactgc agggtcatcc ttggtggctt aggctgactc gggcatagca  69360
gggtgctctg agacctcacc gcatataggc tttgccccca ataaactcta tataatattc  69420
atattatgtg gtctgggtgt gtgtagcttt gcactgtctt ctcgtgacag tgccctcaac  69480
ctctttccca ggatttcctc ctctacctcc tcaagtccca ctgctctgca aagaccaaaa  69540
gctgcagagt cccagctccc tcctttacac ccccacgacgc agcctcctct ctcagaaccc  69600
tttaaacaga gtcttttact gcagatccca agaacagcca cacccctctc tcccacccac  69660
tccagacaca cccaggtaat tatagcaccc agggtaacta tgtagatgga gtccctggaa  69720
catgtggata gtgccccctg ggagtatgca aaagcaacat tgctggcacc tgcagagaac  69780
agggtgacat ccaggaatca gagcatgggc ctctgggagg tagggatgtg gccaggcagg  69840
ctgccaaaaa ttggtagagc aaggccacag gatctttctg accttccttc caaacagagg  69900
ctcctgtact ggtgatccct gtgttgattg accactccct tcctgggggt cgtggtctct  69960
gtcccagttg cccggacttc tgtgagtgtc ctactgaggt ccttttcatg agaagcatgc  70020
```

-continued

```
tgtccttcca cctgctggga gcaagagtga caacttcaat actataatag cagtggcata  70080
cagagaagaa gaaagatgaa gtggcaagaa aaacaggctt ccaagcagga gtttttctat  70140
aaaaacaaaa acgtttacaa gcaaactttt tataaagggc tagatagtaa atattttagg  70200
ctttgagagc cacatagact tgtttgcagg gactcaatgt cgctattgta gtttgaaagc  70260
agccatcagg gttatgtaaa tgagtgagtc tgattttgtt tcagcaaaat tttatttacc  70320
aaaacagaca atgagtgggc tggatttggc ccatgatcct tagtttgcca actcctgctt  70380
tgggctcacc cagatctgat tttgaattct ggctctgcta ctggttagct gcaggagctt  70440
ggaaggctct ctgagcctgt ttcctcatct gtaaaattaa agcaataatt tctaacactc  70500
aagagtgtta cctcacgcct gtaatcccag cactttggag gctgaggcag gcggatcacc  70560
tgaggtcaga agttcaagac cagcgtggcc aacgtggcaa aaccctgtct ctactaaaaa  70620
atacaaaaag tagccgggca tggtggcgcg catctgtaat cccagctact tgggaggctg  70680
aggcagggat actgctagaa cctgggaggt ggagcgtgca gtgagtggag atcacacctc  70740
cacactccag cctggccgac agagcgagac tccatctcaa aaaaaaaaaa aaaaagagtg  70800
ttagaaggtt ttgagataat gaataaaaga tgccttgtgt atactaagta ttcaacaact  70860
gatagctgca ttggtctaat tataacagtt tagaagcgat tgagtcaaca aatgctggat  70920
ttgtcaggga ggacttccta tcaggaggta gatcttgggc tgagtcctga agcaaagata  70980
ggcattggat agaggagttg agagaacacc ctaggactgt tattattatt attcgacacg  71040
gagtctcttg ctctgtcacc caggctggag tgcagtggcg cgatctcggc tcactgcaac  71100
ctctgcctcc caggttcaag cgattctcct gcctcctaag tagctgagac tacaggtgtg  71160
tgccaccaca cccggctaat ttttatattt ttagtagaga cagagtttca ccatgttggc  71220
catgctggtc tcgaactcct gacttcaggt gatccacccg cctcagcctc ccaaagtgct  71280
ggaataacag atgtgagcca ccgcacccag cccagaacca tttttcaatc cttggctctg  71340
ccttttatta gctgcaagat ctcaggcaat ttatttaacc tctccaaaga ctcattttct  71400
cattcacaaa atgaggcaaa taataatatc tactatccca ggttgtcatg agaattaaat  71460
gcaacatgac atttaatgaa atgagaagtc ccttggacat taactggcta aagtatgtgc  71520
tcgacaagga tatcatttta ggtggatact tagcatctca gaactgatgc tcacaatgga  71580
atatcattga aacgcattaa aattcatttt aaatgattgt aggtagtgag gcaattgaaa  71640
gaagaagaca agaggactga ttataatgct tcaggctcac tagtctcctt ttaggaggga  71700
aaaacaattt caagttaaat tttaggctct agatttttac ccctgctgct cattagaatc  71760
acccagattg atgaaatcag agcccatctg aggctgtgtt tttcatctcc agaatgagag  71820
ctgttgtggg gattaagttt ttgaaaaagt acatctaaca ggtgatcgaa aatgatagtg  71880
atattattgc agtgatggtc attattgttg ttattattat actgaaagag gcttcagttt  71940
tctgatccat aaagtgaggg aattgcatga gaccattgct aagattcctt ctagctctgt  72000
tttttgtttt ttgtttttta gacagagtct ctgtcgccca ggctggagtg caatggcatg  72060
atcttggctc actgcaacct ccgcctcccg ggttcaaatg atcctcctgt ctcagcctcc  72120
gaagtagctg ggactacagg cacacaccac catgcccagc taacttttat atttttaata  72180
gaggtggggt ttcaccatat tggtcaggct ggtctcaaac tcctgacctc aggtgatcca  72240
cccgcctcgg cctcccaaca tgctgggatt acaggcatga gccactgtgc ccaacccctt  72300
ctagctttct tgatcactga ttctagggtt ctctgctgaa atatatttga gacatcctgg  72360
```

-continued

```
ataaaagatc atgcaagagc tcccaatatg gtattaataa ttgattctgg aggcttagct  72420
actcctgatg gattagacat gactcaactg cctctcttat gtgtacaaca caacaacaca  72480
accaagaaag gttattctgg cattccattt attcagttta tttacagccc ttacttccag  72540
cagcacgtta aagatatggc cagggccggg tgcagtggct caagtctgta atcccaggac  72600
tttgggaggc caaggtgggc ggatcacaag gtcaggagtt tgagaatctg gcaattcttc  72660
agacttagaa gcaaccagct cgataacaca gtcttgtgtg ggctctccct ctgtccctcc  72720
ctcgcttccc tcatttctca tccctgcccc tgagactgtg caccttcaca tagccctgcc  72780
atgagacctt catctcaggc tttgctttct ggggtaactg aggctaaaca ctgagtggcc  72840
ctaaaagagg attgggattt ggaagttaga ttattcacca gagaacagac tttgctgatg  72900
atcaggccca ggttgtaatt gttgaaaaaa agagaggatg catagtctta tctcatctcc  72960
tagtcaaagt caacaccatg ataaataaga gtcaaatcct gagatgtgaa ttggggacat  73020
ttgagtggtt aaccctgaga agcttgcacc ttcagacccc tcaatacccc tgctccccag  73080
agaaggctgg acattgacct cagcacaggc aggagccctg caagatgcca tttgtcctac  73140
taaagatgga cccctccact ctgtttctag gtaaataacc aaagtcaagt ctccacacag  73200
cctgagcaag aaagtcagag cctgctacag gagaaaatac cacactggcc aaaggattca  73260
ctagccctgg ccactgtgtg tgggaggaac cagggaatca tgtgtgggag tcaatgttga  73320
agctgttgga ctgggggtgg ggtggaatat aagcctggcc ctggggagtt tttcccgttt  73380
gagggccttt acccacaact caagatccag tgctatagca ggagatccca gagctagtcc  73440
taacagatgg tcaggattga acttggccta gagtaaaatg aggaggatag tgccagaact  73500
ttctcaacat actattgagg aagaggtcag aaggcttaag gaggtagtgt aactggaaag  73560
gggtcctgat ccagacccca ggagagggtt cttggacctt gcataagaaa gagttcgaga  73620
cgagtccacc cagtaaagtg aaagcaattt tattaaagaa gaaacagaaa aatggctact  73680
ccatagagca gcgacatggg ctgcttaact gagtgttctt atgattattt cttgattcta  73740
tgctaaacaa agggtggatt atttgtgagg tttccaggaa aggggcaggg atttcccaga  73800
actgatggat ccccccactt ttagaccata tagagtaact tcctgacgtt gccatggcgt  73860
ttgtaaactg tcatggccct ggagggaatg tcttttagca tgttaatgta ttataatgtg  73920
tataatgagc agtgaggacg gccagaggtc gctttcatca ccatcttggt tttggtgggt  73980
tttggccggc ttctttatca catcctgttt tatgagcagg gtctttatga cctataactt  74040
ctcctgccga cctcctatct cctcctgtga ctaagaatgc agcctagcag gtctcagcct  74100
cattttacca tggagtcgct ctgattccaa tgcctctgac agcaggaatg ttggaattga  74160
attactatgc aagacctgag aagccattgg aggacacagc cttcattagg acactggcat  74220
ctgtgacagg ctgggtggtg gtaattgtct gttggccagt gtggactgtg ggagatgcta  74280
ctactgtaag atatgacaag gtttctcttc aaacaggctg atccgcttct tattctctaa  74340
ttccaagtac cacccccgc ctttcttctc cttttccttc tttctgattt tactacatgc  74400
ccaggcatgc tacggcccca gctcacattc ctttccttat ttaaaaatgg actggggctg  74460
ggcgcggtgg ctcatgcctg taatcccagc actttgggag gccgaggcgg gcggatcatg  74520
aggtcaggag atcgagacca tcctggctaa cacggtgaaa ccccgtctct actaaaaatg  74580
caaaaacatt agccaggcgt ggttgcaggt gcctgcagtc ccagcggctc aggaggctga  74640
ggcaggagaa tggcgtgaac ctgggaggtg gaggttgcaa tgagccgaga ttgtgccact  74700
gcactccagc ctgggtgaca gagcgagact ccgtctcaaa aaaaaaaaaa aaaaaaaaaa  74760
```

-continued

```
tagctgggca tggtggcgcg tgcctgtaat accagctact ctggaggctg aggcaagaga  74820
atcgcttgaa cccagtaggc ggaagttgca gtgagccgag atcttgacac tgcactccag  74880
cctggtgaca gagtgagact ctgtctcaaa aaaaaaaaaa agaaaaaaaa agacagaaag  74940
aaagagcaca gacagagtca caggtatttg cagtaggaag ctgtcaggtt agagtgcacg  75000
gaaatagaaa gtatatttta cacttacagc acatcttcgt ttgattagcc acatttaaaa  75060
tactgaatag caacgtgtgg ctatttagta ttcactaaaa tcttggacag tgcaagtcta  75120
aagaatcctt gatccgtccg gcatggtggc tcacgccttt aatcccagca ctttgggagg  75180
ccaaggtgga aggatcactt aaggtcagga gttcgagacc agcctggcca acatggtgaa  75240
acctcgtctc tactaataat acaaaaaaaa ttagccgggc atggtggtgc atgcctgtaa  75300
tcccaggtac ttgggaggct gaggcaggag aatagcttga atccaggagg cgctgcagtg  75360
agccgagatc atgccatgcc actactgcac tccagcctgg gcaacagagt gagactgtct  75420
caaaaaaaaa aaaaaaattg ttgggcgtgg tggctcacgc ctgtaatccc agcactttgg  75480
gaggctgagg ggggtggatc acctgggttc tggagttcga gaccagcctg gccaacatgg  75540
tgaaacccca tctctactaa aaatacaaaa attagctggg cgtggtggtg ggcacctgaa  75600
atctcagcta ctcaggaggc tgaggcagga gaatttcttg aacccaggag gcagaggttg  75660
cagtgagcca agatcgcgcc tctgcactcc atcctgggtg gcagagcaag actatgtctc  75720
aaaaaaaaaa aaaaaaatac ttgattgtct ggacattctg cagaacatca tatggagaca  75780
ctatgttgac gacatcatgc tgattgtaag caagaaatgg caagtgttcc agaaacacag  75840
tcaagacaca tacatgccag aaggtgagat ataaactcta ctaagattca gtggcctgcc  75900
acactggtga catttttaaa cctgctagat gtttgtgtag aaaaggattt aaccttgccc  75960
aaagaggggt ctggcctttg tccccagcta ctggacataa tctctttaaa ctcttgaaat  76020
atcattcctg atagaagtat ttttgttttg actaggggcc ttgggccagc cagatagcaa  76080
caatgtgatc tgggttgggg gctttggatc aggtggcatc agtgtgacct cctgagtggc  76140
tagagactag aatcaaccac atgggcagac aacccagctt acatgatgga attccaataa  76200
agactttgga cacaagggct tgggtaagct ttcctggttg gcaatgctct atactgggaa  76260
acccattctg actccatagg gagaggacaa ctggatattc tcatttggta cctccctggg  76320
ctttgcccta tgcatttttc ccttgtctga ttattattat tattatgaga tggaatctcg  76380
ctctgtcacc caggctggag tgcagtggaa tgatctcaac tcactgcaac ctctgcctcc  76440
ccggttcaag cgattttcct gtctcggcct cccgagtagc tgggactaca gatgcatacc  76500
accacacccg gctaattttt ttgtattttt agtagagacg gggtttcacg ttagccagga  76560
tggtctcgat ctcctgacct catgttccgc ctgcctcggc ctctcaaagt gctaggaata  76620
catgtgtgag ccaccgcgcc cagccccctt ggctgattat taaagtgtat ccttgagctg  76680
tagtaaatta taaccgtgaa tataacagct tttagtgagt tttgtgagca cttctagcaa  76740
attatcaaac ctaaggatag ccttggggac ccctgaactt gcagttggtg tcagaaataa  76800
gggtgctcat gtgtgtacca tgccctctaa ttttgtagtt aattaacttt cacaacttta  76860
ttattaccgc ttacactcaa tgtttattca catttatcca cataccactt attctagtgc  76920
cttgcatcaa agactttcta tctcatgtac tttattctgc ttgaagtaaa tcctttagga  76980
tattcttttt ttttttaaa ctttgcacat acatactttt atttttttatt tatttttaat  77040
tttgttattt ttgtgggtac gtagtagata tatgtattta tggagtacat gagatgtttt  77100
```

-continued

```
gatacaggca tgcaatgtga aataagcaca tcatggagaa tggggtatcc atcctctcaa  77160
gcaatttatc cttcaagtta caaacaatcc aattacactc tttaagttat tttaaaatgt  77220
acatttaatt ttgtattgac tagagtcact ctgttgtgct atcaaatata attttttttt  77280
tttttgagac agagtctcac tcagtggccc agactgaaag tgcagtggca caagctcggc  77340
tcacttcaat ctctgcctcc ctggttcaag cgaatctcct gcctcagcct cccacatagc  77400
tgggattaca ggcacacacc accatgccca gctaattttt atattttttt agtagagacg  77460
ggttttcgcc atgttggcca ggctggtctt gaactcctgg cctcaaatga tctgaccacc  77520
tcagcctccc aaagtgctag gattacaggc atgagccacc acacctggcc aaaatagaat  77580
attctttagt gaggtctgct ggtgacaatt tttttctttt ttttgagact gagtctcgct  77640
gttgtcagct tgggctggag tgcaatagca cgatctcagc tcactgcaac ctccacctcc  77700
cggattccag caattctcct gcctcagcct cccaagtagc tgagagatta caggcaccca  77760
ccaccacacg cggctaattt ttgtattttt agtagaaatg ggggttcacc gtgttggcca  77820
ggctggtctc gaactcctga cctcaggtga tccacccacc ttggcctccc aaagtgctgg  77880
gattacaagc atgagccacc acgcacagcc aatttttttcc gtttttgtct gaaatcttat  77940
tttgtgtcat ctttgaaata tatttttgat ggatataaaa ttgttggttg atagttatta  78000
tcattattat tattattttg agacagggtc tcactctgtt gcctatgctg gggtgtagta  78060
atgtgatctc ggttcactgc agacttgacc tcctagggct caggtgatct tcccacctca  78120
gcctccctag tagctgggac tacagatgca tgccaccata cccaactaat ttttctattt  78180
tttgtagaga tgaggctttg ccacatttcc caggctggtc tctaactcct gagctctagc  78240
aatccaccca ccttggcctt acaaagtgct gggccatgac tagccagcag ttacttttta  78300
tagcatattg aatatttaat atgaatcttc tggcatccac tgtaactgtt taaaaaatca  78360
gctgtttact tggcactctt tttttttttt ttttttttga gacagagtct tgccctgtcg  78420
cccaggctgg agtgcagtgg cgtgatcttg gctcactgca agctctgcct cccgggttca  78480
cgccattctc ctgcctcagc ctccggagta gctgggacta aaggcgcccg ccaccacgcc  78540
cggctgattt ttttgtattt ttcgtagagt tggggtttca ccgtgttagc caggatggtc  78600
tcgatctcct gacctcgtga tctgtccgcc tcggcctccc aaagtgctgg gattataggc  78660
gtgagccacc gcgcccagcc tctttttttt tttttttttag acggagtctt actctgtcat  78720
ctaggctggt gtacagtggc gtgatctcag ctcagtgcaa cctccacctc ctgcctcagc  78780
ctgccaaata gctgggatta caggtgcgta ccatcacgcc cggctaattt ttgtattttc  78840
agtagagatg gggtttcacc atgttagaca ggctggtctc gaactcctgg cctcaagtga  78900
tctgcctgcc ccagcctccc aaagattaca ggcatgagcc accgcacccg gccaagtagc  78960
actcctttga aggtaatctg cttcccctac ccctagcaat ttttaacaat ttttcttcat  79020
ttttatttcc tgaagttttg ttattaataa tctgtgtgca gatttctttg tatttctttt  79080
gtttgcagtt catagtgatt cttgaattag tgtgttggtt tctgttatca ccacaggaaa  79140
attgtcagcc gttagctttt caaatatttc cttgctaaat tctctcttct cccctttcgg  79200
tacaattgat ttgattaaaa ctaaaaccag ggccgggtgc agtgactcat gcctgtaatc  79260
ccaacacttt gagaggctga ggcaggtgga tcacctaagc tcaggagttc aagaccagcc  79320
tggccaatat ggtgaaaccc cgtctctact aaaaatacaa aaattaccag gcatggtggc  79380
acacatttgt agtcaggagg ctgaggcagg agaattgctt gaatccagga ggtggaggtt  79440
gcagtgagct gagatcccac cactgcagtc tggcctgggc gacagagtga gatgagaatc  79500
```

-continued

```
tgtctcgaaa aaaaaagtta tgaatgtttg ataaactata tttgttagaa tgtttgttgt  79560
agaatactat tcattgattt ttaaacaatg ttagattaaa ccattcactg gatttgtgat  79620
aattaactta ctgattttac ctcactgatt tgttgtaatt aatacaactg gtataaaaag  79680
actgtgacga ggccgggcat ggtggctccc gcctataatc ccagcacttt gggaggctga  79740
ggcaggcgga tcacctgagg tcaggagttc aagaccagcc tgaccaacat ggtgaaaccc  79800
catctttact aaaaatacaa aattagccgg tcgtggtggt gcatgcctgt aatcccagct  79860
cttcgggagg ctgtggcagg agaatcactt gaacccggga ggtggaggtt gcagtgagcc  79920
gatatcgcgc cattgcactc cagcctgggc aacaagagcg aaactccgtc taaaaaaaaa  79980
aaagaaaaaa aacacataaa acaaaacaac actgtgacgg ttcccaaaaa ttaggagcat  80040
aattaaagga actcctgata aaaattaatt ttatcttaca tgtaaactaa aatgacttta  80100
tgaagttaat tcagaaatac aatgcagggt attagtttgc cacagctgcg tattcagcct  80160
aatgtaatat tcttgttatt tttaaattct tcttttaact ttactcatat gtggatcatc  80220
aaatttcaaa agattaaatg acaatactct tagcagcaag cttccctaag catataaaca  80280
ttttaatggg tgatgattca gaaggtaccc gaagaatatg tactgccaga tatcattcac  80340
ccccatatac ctgcccgaca gacatcccat tttgggaccc tggataaatg tgtgggtgga  80400
gagaaagata ggagaaagtg gtataagcaa atggctttgg agtctgattg acagcgattg  80460
aaatcctgtc tctacctctt aacagcctca tgatcctaca taagttaccc cgatcctcag  80520
ggccacatct gtaaattggg ggttgcgatg gcagccatct cacagggtct cttttcgggg  80580
aagggcagga attatggatt aagtgagcta gtaattgtaa agcacttaat acaaggaggg  80640
cgcataataa gtacttcata aataatgacg gccattatca tgactgaggt gtatgcagct  80700
gtcggggatt acggcgactt cagaatttct ggtgggcagg gctcaaaggc agcaaatcac  80760
actggaagtc gaggtgaggc actgcttctg cacagactgc ttagctggag agaatgagga  80820
aggcttagag gagatttaga ggaacttaga gtcctccgcc tccaactctg tgggatctgc  80880
tcccgtgcca gagacattca ggggatttct cgcactctcc cctcccctac gtccctcccg  80940
ccccatccaa ctaaccacac aacacataca aaatagcccc tgcgaggttc tgcacgctgg  81000
aagggaacag gagaagggcg ctgcgctttc ttgctgatgc cctgtacttg ggcccctggt  81060
agacacagcc acttgtcccc tcagcctgca gagaaatccc acgtagaccg cgcccgggtc  81120
cttggcttca gccaatctcc ctttggtggg ggtgggatgc acgatccaag gttttattgg  81180
ctacagacag cggggtgtgg tccgccaaga acacagattg gctcccgagg gcatctcgga  81240
tccctggtgg ggcgccgctc agcctcccgg tgcaggcccg gccgaggcca ggaggaagcg  81300
gccagaccgc gtccattcgg cgccagctca ctccggacgt ccggagcctc tgccagcgct  81360
gcttccgtcc agtgcgcctg gacgcgctgt ccttaactgg agaaaggctt caccttgaaa  81420
tccaggcttc atccctagtt agcgtgtgac cttgagcagt tgactttatt tttcagtgcc  81480
tagttttcca gataccagga ctgactccaa ggactattac tcatctggag ggtttagcac  81540
agtaccgtcg catagtaaat ttccatgtca gttttggtta cctttcatgc acttgcaaac  81600
atgccatgct ctgaaacgaa ataggcacat cttttttttt ttttttttta aggagtcttc  81660
ctctcgccca ggctggagtg cagtggcgcg atcttggctc actgcaacct ccacctcccg  81720
tgttcgagat tctcctgcct cagcctcctg attagctggg actacaggca tgccacgacg  81780
cccagttaat ttttgtattt ttagtagaga cggggtttcg ccatcttggc caggctggtc  81840
```

-continued

```
taactcctga cctcaggtga tctgactgcc tcagcctctc aaagtgttgg gattacaggc  81900
ataagccact gcatctggcc agaaatgaaa taagtaaatc ttttaacctg ctctaacaat  81960
atagtgaaaa gaccatatta ttattagagc aggttaaggg atttgcctat ttcgggttct  82020
agttatagtc ttaaacttgg acattcttgt agaaagtaaa aagtttcctc ttcaaagttc  82080
cccttcttgt taaagaatac atcataagtg ttagaagtaa tagtttattt taaagactaa  82140
ctttcttcaa gcctccttgc tttgtgctaa taactctttg ttaagcccta tcctatgtaa  82200
ctgttggaca tgctcacagg cacgttccag ttcacagcct atgccccttc cttatttgga  82260
aatgttattg cttccttaaa cctttcggta agcaacttcc tctccttctt cgttcttcct  82320
tgcacttacc tatttagaaa gttttaggct attagcaaat cggctatcag tttaagagtg  82380
tgaggtcccg ctccagccaa tggatgcagg acatagcagt gaggacgacc caaatgcgta  82440
agggataaat atgtttgctt ttcctttgtt caggtgtgct ctcgacatcg ttccatctgc  82500
gattgagcac cctttctgca gaaagtaaag attgccttgc tggagatctt ttgtctccgt  82560
gctgactttt cttcgtggca ccgattatct atttctaaca attttggtat ttctaacatt  82620
ctgaacaatc ttgggctagt tgtctcttct gggcctgttt ccccatccgt cacatgataa  82680
acttcattgg tttaaaaacc ccagcgaaca tttattgagt tactattacc ttcctgccct  82740
ccccaacccc aaccccaggg agcagttaca acctcagccg ctgagcgcac tcgccgggtg  82800
ttaagaagca ccaaagacag ggaggcttga ttgattttgc tttgggagta gagggtcaga  82860
agattcacag gaaaatggca tttgagcaag gatgattcac tggagctagc ttttaaatac  82920
tggcgaggct tttatgttgc agtcccttac aaagttgagc attcgcaggg actgcactcc  82980
gaaataagcc cgcttcccct tttcattcgc taatgatcca gggagctgct ggttccgcat  83040
gcggcaggtt gtgccttttc ctaatcaggg ttctgcatcg cctcgaaccc gcaggccgtg  83100
gcgggttctc ctgaggaagc agggactggg gtgcagggtg aagctgctcg tgccggccag  83160
cgcctgtgag caaaactcaa acggaggagc aggaggggtc gagctggagc gtggcagggt  83220
tgaccctgcc ttttagaagg gcacaatttg aagggtaccc aggggccgga agccggggac  83280
ctaaggcccg ccccgttcca gctgctggga gggctcccgc cccagggagt tagttttgca  83340
gagactgggt ctgcagcgct ccaccggggg ccggcgacag acgccacaaa acagctgcag  83400
gaacggtggc tcgctccagg cacccagggc ccgggaaaga ggcgcgggta gcacgcgcgg  83460
gtcacgtggg cgatgcgggc gtgcgcccct gcacccgcgg gagggggatg gggaaaaggg  83520
gcggggccgg cgcttgacct cccgtgaagc ctagcgcggg gaaggaccgg aactccgggc  83580
gggcggcttg ttgataatat ggcggctgga gctgcctggg catcccgagg aggcggtggg  83640
gcccactccc ggaagaaggg tcccttttcg cgctagtgca gcggcccctc tggacccgga  83700
agtccgggcc ggttgctgaa tgaggggagc cgggccctcc ccgcgccagt ccccccgcac  83760
cctccgtccc gacccgggcc ccgccatgtc cttcttccgg cggaaaggta gctgaggggg  83820
cgccggcggg gagtcaggcc gggcctcagg ggcggcggtg gggcaggtgg gcctgcgagg  83880
gctttcccca aggcggcagc aaggccttca gcgagcctcg acctcggcgc agatgccccc  83940
tgagtgcctt gctctgctcc gggactcttc tgggagggag aaggtggcct tcttgcgcga  84000
ggtcagagga gtattgtcgc gctggttcag aagcgattgc taaagcccat agaagttcct  84060
gcctgtttgg ttaagaacag ttcttaggtg ggggttagtt tttttgtgtt tctttgagga  84120
ccgtggatca agatcaagga aatctcttta gaaccttatt atggaagtct gaagtttcca  84180
aatgttgagg gttttatgtc taaaagcaac acgtgaaaaa attgttttct tcacccagtg  84240
```

-continued

```
ctgtcttcca atttcctctt tggggggagg ggtagttact gctgttacta aaataaaatt  84300
acttattgct aaagttcccc aacaggaaga ccactacttt tgatgacttt ggcaagtttg  84360
ctaactactg gaaccctaac ttacaaacga actacttaca tttttgattt ccagttgtat  84420
tacctgccca atgtttacgt agaaacagct taattttgat tctgggtaac gttgttgcac  84480
ttcattaaaa atacatatcc gaagtgagca agtatgggtc tgtggacagc agtgattttt  84540
cctgtcaatt cctgttgctt cagataaaat gtaccagaca gaggccgggc gcggtggctc  84600
acgcctgtaa tcccagcact ttgggaggct tggcgggtgg atcacctgag atcgggagtt  84660
caagaccagc ctgaccaaca tggagaaacc ccgtgtctac taaaaataca aaattagcca  84720
gggtggtggc gcatgcctgt aatgccagct acttgggagg ctgaagcagg agaatcgctt  84780
gaacctggga ggcggaggtt gcggtgagcc gagatagcac cattgcactc cagcctgggc  84840
aaaaagagcg aaactccgtc tcaaaaaaaa agtaccagac agaaatgggt tttgttttct  84900
ttttttgttt tgagacggag tttcgctctt gttgcccagg ctcgagtgca atggcgcgat  84960
ctcagtctcg gctcactgca acctctgtct cccaggttta atcgattctc ctgcctcagc  85020
ctcccaagta gctgggatta cccatgcccc accatgcccg gctaattttt gtatttttag  85080
tagaaacggg gcttcaccat gttaggctgg tcttgaaccc ctgacctcaa gtgggcctcc  85140
cacctcggcc tcccaaagtg ccaggattac aggcatgagc caccgcggcc agccagaaat  85200
gggttttgga aaaagcacta aacaaaatcg aacttggttt catatgacag ctctgctgct  85260
aactgtaaca ggggcagacc agttaaccta cttttctgtc ttctgtcagc tgagaattag  85320
atgattccca aaggcccatt gaactctgaa tgactttaaa tacttcttct taagtgggta  85380
cacggttttg gtaactgatg ccaggtgatg aatgcatgaa agtgcttaat gaatgaaacc  85440
ggtaaaatag taggaggaag ctttattggt aaggcagggg tatacctaat agctctctaa  85500
tttattggta ttgaagtggt taacttttgt ttttttaagg ggggaaaaca ttctaagaat  85560
aatgaggcaa actgcatatt gcacaagaga ctgttgtctc tattcaacaa ataccttttg  85620
agtgtccaga gtctgccagg tgctgtgcta ggccctcacg attgagtagt gaaccagaga  85680
atgtccctgc acccatggag cttattgtct actggggtag acagataata aataagcaaa  85740
caaatcttct ctcttctccc tttcgctcca tgtaagtgtg tgtgtatagg tgtatactta  85800
caagttgagt aaagtgttat gaaagattaa gaggagaaat gcattttggt tagatgttag  85860
aggactcagc aggtgacctt gaaacttaga gctgaaggat cagtaggagg taactagaga  85920
ggccagggaa tcgcatgttc aaaggccagg aggcaagaaa gagcatggtg cccttcaaga  85980
gaggaaagaa ggctactgtg actggagcat agatgtaggc aagtgttggg tgattgagag  86040
ctctacgggc catggttagg ttttattcct aatgccgaga tgccaaacat ggtggttcat  86100
atctgtaatc ccagtatttt aggaggccga ggcaggaata tagcttgaac ccaggagttc  86160
aagaccagcc tgagcaacat gagacctgta caaaacattt aaaaaattgc tgggtatgat  86220
ggtgcacacc tgtggtccca gctactcagg aggctgaggc agaaggatca cttgagccta  86280
ggaggtggag gctacaatga gccatatttg agtcactaca ctccagcctg gatgacaaag  86340
tgagaccatg tgtcaaacaa aatacagaaa gaatattaat ttaaaatttt gaaagaggag  86400
tgatctgaac ttatatctta aaaagatcat tctagggcat ggtggctcat gcctgtaatc  86460
aagggctttg ggaggctgag acaggaggat cacctgaggc cagttcgaga tcaacctgta  86520
cagcatagag agactccatc tctacaaaaa gaaaaaataa atagctgggt gttgtgagtt  86580
```

-continued

```
attcaggagg ctgaagcaga aagatcactt gagcccagga gtttgaggct gcagtaagct  86640
atgatcccac cactgcaaca cagtgagatc ttgtctcaaa aaaaaaaaaa aatcattcta  86700
ggtgcttttt ggaggctgga tgtggtaaga gtagaagctg gagatggtcc tgttagggat  86760
tcgattcaga ctttaaatac catcaatgca ttgagtccca aatttacatc actacgttgg  86820
atccttgccc ctgaatccag actggtatat ccaactttag gttcagtttg tatctctacc  86880
tgaccaatat agaggtgtcc agtcttttgg cttccctagg ccacattgga agaagaattg  86940
tcttgagcca cacatagagt acactaacgc taacaatagc agatgagcta aaaaaaaatc  87000
gcaaaactta taatgtttta agaaagttta cgaatttgtg ttgggcacat tcagagccat  87060
cctgggccgc gggatggaca agcttaatcc agtagatacc ttcaacttac aatatctaaa  87120
attttatgcc agatttagtc attttaaacc tgctcatcag tttttctcaa gaagtagtat  87180
tttggctttt tttcttttct ttttttgag atggagtttc gctcttatcg ttcaagctgg  87240
agtgcagtgg cggatcttgg ctcactgcaa cctccgcctc ctgggttcaa gtgattctcc  87300
tgcctcagcc tcgcaagtag ctggaattac aggcatgcgc caccatgacc agctaatttt  87360
tggagacagg gtttcaccat gttggtcagg ctggttttgt actcctgacc tcaggtgatc  87420
tgcctgcctc ggcctcccaa aggctgggat tacaggcatg agccaccgct cccggctgca  87480
tttttggatt tttagttgct cagcccaaaa ctttagtaca tctttgaacc tcttctttcc  87540
tcctactcta tatctgatcc atcagcaaat ctgttaggtc tacctcacac atatcgaaat  87600
cctaccacgt ctcaccatct gtgacaatta acaccctggt ctaggcagtc atctctgtta  87660
agattgagtg gttaaggatg tcctctaagg agatgacatt caaatcttag cttaaatgtc  87720
aagagggagc tggttttata aagattgagg aggcagcatt attttgccat aggcttccat  87780
ttggtttcca ttccattctt gatacttatg gtatatattc aaaacaaatg cacagaaaca  87840
gacccaggta tattgggaat ttcggatata gagttcctag ttgggaaaag atagactgat  87900
ctgtaaatga tgctagttat ccatcatctg gcaaaaaata atttcctgcc tcctctcata  87960
tatctcagat caacagactt tttctgttaa gggccaaatc ataaatattt taggctttcc  88020
agaccatatg gtttctgtca cactctcctt tatccttgaa gccatagaca atatgtaaac  88080
aaatgggcat ggctgtgcta cgataaaact ttacttacaa aaactggtag tgggccagtt  88140
taggcatggc cagcactttg ggaggctaag gcagatggat cacttggggt caggagtttg  88200
agaccagcct ggccaacatg gtgaaaccct gtctctacta aaaatacaaa aaatagctgg  88260
gcatggtggt gggtgtctat aattccagct actctggagg ctaagacaca agaatcactt  88320
gaacccagga ggcagaggtt gcagtgagct gagatagcac cactgcactc cagccagggt  88380
gacggagtct taaagcaaaa caaaacaaaa ggtagtgggt tgtatttggc ccatgggctg  88440
tagtttgcca atccctgatg cagaaacaaa ttccaggtaa ataagagcct ggaatgttaa  88500
aaaaacaaaa cttgaagtca tgtagaagaa caggtagggg gaacaatcct gatctcagga  88560
taggaaggga tattgcttaa aataagacac aggaaaatat aatccatgtt gtgtaaattt  88620
gactacgtta aaacttaaaa ctttcgccaa gcgcggtggc tcacgcctgt aataccagta  88680
ctttgggagg ccgaggtgag cagatcacca ggtcaggaga ttgagaccat cctggctaac  88740
acggtgaaac cccgtctcta ctaaaaatac aaaacattag ccgggcgtgg tggcgggcgc  88800
ctgtagtccc agctacttgg gaggctgagg caggagaatg gcctgaaccc gggaggcgaa  88860
gcttgcagtg agctgagatc gcgccactgc actccagcct gggcgacaga gtgagattcc  88920
gtctcaaaaa aacaaaacaa aacaaagcaa aaaacctaaa actttcatac aataaagtat  88980
```

-continued

```
acctaagata cttctagaag agaagattta catccaggac gtgtatggaa tttctgcaag  89040
taataagtaa aagacaaggg acatgaagag gcagttcaca aaagaggaag ccaaaatgac  89100
caataaacat gaaaggatgt ttaacctcaa aggaaacaag gaaatgaatt aaaaacatca  89160
aatgccattt caaaactagt aagttggcaa aattaaaaat accaaggatg agaatatgaa  89220
gcatggctat atgagtgcat ggaatggtac agtcactttc attaaaaatg cacataattt  89280
gtttttattt tattttttg agacagtcta tgtcgcccag gctagaatgc agtggcatga  89340
tctcggctca ccacaatctc tgcctcctgg gttcaagcaa ttctcctgcc tcagcctcct  89400
gagtagctgg gattacaggc acatgccaca acgcccggtt aagttttgta tttttagtag  89460
agacagggtt ttgccatgtt ggccaggctg gtctcgaact cctgacctca ggtgagctgc  89520
ttcccaaagt gctgggatta gaggcgtgag ccaatgctcc tggctgaaaa aaatgcacat  89580
aatttgttac ctagcaattc catgtctaga ggcttatcct agagaaattc ttgcttatat  89640
gcataggaag acgtgtacta gaatgttcac tagttgaatg tttaagtgaa aattaggaaa  89700
taaagtaaat gttcattaac aggaaaatga gtaaaggtat atttataaaa caattaagta  89760
gctaaaatga ataaactaga gctgcgtgaa tgaactagaa ctggttcaat agtcatgtca  89820
gattattgaa tgaatacagg tcagatatgt atagagtgtc atttgtgtaa ttaatttttt  89880
tttttttttt gagatggagt ctcactctgt tgcccaggct ggagtgcagt ggcgtgatct  89940
cagctcactg caacctccac ctcctgggtt aaagtgattc tcctgcctca gcctcccgag  90000
tagttgggat tacaggcatg caccaccatg cccagctcat tttcctattt ttagtggcca  90060
cagggtttca ccatgttggc caggctggtc ttgaactcct gacctcaagt gttccaccca  90120
acttggcctc ccaaagtgct aggattacag gcgtgagcca ccgtgctcag ccatttgcgt  90180
gatttttaaa gatgtgcaga ataatgccat taaaaaaaat acacatacat gtatatatat  90240
acacgtttgg ctgggtgtgg tggctcacac ctgtaatccc agcactttgg gaggctgagg  90300
caggaggatc acttgagccc aggtgtacaa gactagcctg ggcgagatag caagacccca  90360
tctcaacaac agaaaggata attaggtatg gtggcatgag aggatcactt gagcccagga  90420
gttcgagtgt tatcaggcca ctgcactcta gcctggacaa caaagcaaga ccgtgtctca  90480
aaaaaataaa aataaaaagt atttgtatgt ggtcatagtc aaaaaacgta catggaagga  90540
aaatgtcttt atttatttat ttattttttt tttttaaga cagagtcttg ctctgtcacc  90600
caggctgggg tacagtggtg taatctcagc tcaccgcaat ctcggcctcc cgggttcaag  90660
cgattcttct gcctcagcct tctaagtagc tgggactaca ggtacccgcc accacaccct  90720
gctaattctt gtgttttcag tagagacagg gtttcaccat gttggcaagg ctggtctcga  90780
actcctgacc ttaagtgagc cacccgcctt ggcctcccaa agtcctggga ttacaggtgt  90840
gagccactgc gcttggccag gaaatatcta atttagtaag tatttatatc tgggaaagga  90900
agggtcaggt ggtgattcat aggaactcta aagtctatgt ataatactta gggggacaga  90960
aggaaataaa gcaaaatgct gatatttgat tgttgagttg tgtatatgtt agaagtataa  91020
cataggagat ctgattgata gtaggagaat gtttttaggt ggtaaaagtg gaaccgtggt  91080
ggtttgtttt ggcagtagaa tcagttggtc atagtttgta tgtggaaggt aataaacaga  91140
ccatgttaag gatgacttcc ggaattttgg tctgagtagt gggtggatga cagtgtcatt  91200
catgagggaa gatgaagact gaggtaggaa caggtttggg agaagatgac atgttccctt  91260
ttagacaagt ggaattatgg aagatggcag gtaggtggtt agctatatga atttgagata  91320
```

-continued

```
aaagatttag gatggagata taaatttagg agtaacagcg tatctatggt attgtaagcc  91380
ttaagaatgg gtaggatcag ccaggaaata cagatgtata tgcagaagag aggagtcaag  91440
gaagccaaga caagttaatg tttaaagtga gtgatgtagt ccatgggcag atgctgctga  91500
gagggctgca aacaccagtg accctacaac atttttaaat gtcgtcttcc tgacagcagt  91560
gatcagtacc tgcaacgatc ttatttattt ttttcatgtt agtctccaca cacttgaatg  91620
tagacttttt gaaggcaaaa tcattgcctt ttctgagctg ggagcatgtc tggcacatac  91680
caagcactca acagttgatg tattgacttc atccagatac tctgagggcg agttatttcc  91740
tgctactagc ctttcacctt tcaatgttta agagcacaaa tacagagatg ggcacgtttt  91800
ggcatttctt attttgataa ccttttcctg gtaagatttt ttaatgttga aaaaaaaaaa  91860
caagaaaaga gggttaaaaa tagtcttatg tcagatcctg tgatagaatt cacacttggc  91920
ttaagctgct gggcaccttc ctatcttgga tgtcatatta gcttatctac agcagaattt  91980
ttactgtttt atgtagtaag gaagcaatta tatgattatt ttacagacaa attattcttt  92040
atcttttatt tttttagacg gagtctctct ttgtctccca ggctggagta cagtgtcgcg  92100
atctcggctc actgcaacct ccgcctcctg ggttcaagca attctctgcc tcagcctccc  92160
aagtagctgg gcttacaggt gtccgccacc acacccagct cattgttttg tatttttagt  92220
agagatgggg tttcaccatg ttggccaggc tggtcttgag ctactgacct caggtgatcc  92280
acccgccttg gcatcccaaa gtgctggaat tacaggcgtg agccaccgtg cctggcccag  92340
acaaattatt atactctgag tgttagaggc ttaggatgtt ttcacttgat gctatgggag  92400
gaataagtaa taagatatga tacacaacca aagacctttc ttcactatgc ttctagtagc  92460
tagtactatg gatgacacat ggtaataata ttggttagca tttgtcctca atttactgtg  92520
ctagttactc ttctaagccc cttacaggta tatatttttt ttcatcaata atcctctaag  92580
gtagttttta ttattgacct aattttataa atcaagaaaa ttaagaccca gagaagtaag  92640
taacttgtcc aagatcacat ggcttataag tggtagagcc agaatttgac cccagatgtt  92700
gtgactacat tgtctctcca taagcaggtt caactctttt gactggatgc tgttccaagg  92760
tcacttcctt agagaagcct ttgctgacaa ctaccctcct gtgccctcct ccaaggctgt  92820
ccattgttct agaactttga atactcatct tagaataaag ctggtctaat ttttacagtg  92880
ttatagaatg gatctctgac tgcaaaagtt ggtcataatt atctttttat gttctagtga  92940
aaggcaaaga acaagagaag acctcagatg tgaagtccat taaaggtaag ttctgccctt  93000
ggcagtccac tgcattaaaa agtgatgtgc tttgcatttg tgagttcttt aatcctgtta  93060
tactctctct tttggcatta atcatttctg ccttatttta taattactta tgattttgat  93120
ttatttccct ctttaacctg tataatgctt taacatctag catataataa gtaggctttt  93180
tttttttttt tttttttgga gacggagtct tgctctgtta cccaggctgg agtgcagtgg  93240
cgcgatcttg gctcactgca agctctgtct cccgggttca caccattctc ctgcctcagc  93300
ctccccagca gctgggacta caggtgcacg gcgccacgcc tggctaattt tttgtatttt  93360
ttagtagaga cagagtttca ccatgttagc cagtatggtc tcgatctcct gaccttgtga  93420
tccgcccgcc tcggcctccc aaagtgctgg gattacaagc gtgagccacc gcacccggcc  93480
gtaagtaggc tttttttacc ttaattttat tttttgaga tggagtcttg ctcttatccc  93540
caggctggag tgcagtggtg ccatctcggc tcactgcagc atccacctcc cgggttcaag  93600
cgattctcct gcctcagcct cccgagtagc tgggattaca ggtggccgcc accatgccca  93660
gctaattttt gtatttttag tagagacagg gtttcaccgt gttggccagg ccagtctcaa  93720
```

-continued

```
actcctgacc tcaagtgatc cactcgcctt ggcctcccaa agtcctggga ttacaggcgt  93780
gagccaccat gcctggccat aagtaggctt ttactgagcc ttgtgtgtat tggctatcct  93840
agtgattaca gtgaaccagt gcccttctta ttaatcacac atttaattgt tccctaaaag  93900
tgattagttc actttattta tttagtaaga caaaaaatga agaatactct taactgagca  93960
gtctgttaac tgtaggaaag cactgacact tataaggctt agttttctgt catttatcca  94020
gaagtatggt tgattacagt ttttactttt ttatttgaat gaacaacctt aatttaaaat  94080
atattttgtt tattttttgt tgggatcgat acattgtcct tgtttataga ttagagcatg  94140
ctttttaaag atgctgtatt actcactgat tttatttgtc cagtgtacag agattgaagt  94200
gggaaaatta taatggaaat tgtttccata gtcattacat attaatttca tcaatttatt  94260
tccataaaat ctgtagattg ctacttattt agatttttcc ttcaaatgtt tttatgttgt  94320
attgcttgca ctgagtattt attctatatg ctcaatttgc tggagaagaa gactaattat  94380
aacttaggca agttgtaaaa ttagggaaaa aagtaaggta ccttacagcc tagtttactt  94440
atttcttatg taaagccagt tagattccac attagttcaa actgccttct ttgagcaaaa  94500
cttgattggc agtgataaag gcttaaagcc cttctcaagc agagacctgt aaagactaga  94560
tctgactgta gtagaaggaa ggaacttaga tgtttcaggc agtgagaaca ccagtcttcc  94620
actctaaact ttgccactaa cagtatgacc ttgggaagtt gtaactttct tcagattctt  94680
catttgttga atggggggat tggcctagct aatttctaaa tctctactgg gctaaaaaat  94740
tctgtgctta tactctgatt atgaagtaca taatctgtgc ttaacattca ctgacttatc  94800
cttaggataa tacagaagca gtacaagaaa cagcccctca agatgtttgc agtctggtta  94860
gaaagacaaa cttatacaca gaacagtagc aaatagacca aaataataat agctgccatt  94920
tatagaacac ttcttctgtt ctgggcatta gacaaaaact gactataacg gtgaacaaaa  94980
aagacttagg tcctgccctc attgaactta cagattagta ggggagagga acattaatca  95040
agtaattcca cagatggctt agcctagatt ggtagtgatg gaagtaaaga gatgtgaacg  95100
gacttgaaaa aaaattcgga ggcaaaatgg atagaagttt attattgatt aaatatgagg  95160
tgtgagagag agggatattt aagattgata cctaccttct ggcttgccta acagaaccaa  95220
aacaggaaat tatatgttca gttttgttat gttgggtggg aggtgctttt gagtcattca  95280
tttatatatg ttatatatgt tattttatat gcatagtaat tttaaggtct gagttttaaa  95340
ccaaaggtta gagagtgatt ttttagagtc tagcaaacct aagttgaaat cctgcctgtt  95400
gaaatggctg tttactagct cattaaccta gggcaaagta ttcaacttgt tttcattttt  95460
gtcttcatct ctaaaatgag gaaaatatgg tcttacaaga ttgtcctgag agatagatga  95520
aataatatcc aaaaaaaaaa aaggtacata gagaaactcg tatagtgcct ggtatatagt  95580
aggtcctcca ttggtagcta tcattatcta gttttaacat agccttcagt ttgttgaatt  95640
agtcaaactg agtgaagcac tgcaaggaat tcagaggaat ttgagatcaa caaatgattt  95700
ctgaagttta gggaagactt catggcaatg acacttacct tgtataaaag ttgaagaata  95760
agaaagattt gaatgagaga ttctttctct tctccctacc agcccagctt cttatttgag  95820
gatatattgg gcaaaggggc cttcagacaa gtagagggag atttttacag aaagattgag  95880
atgaaggtat agaaggctgt aaagaccaga aaagagaatt gagacagagg aagcaggaag  95940
ccactgtagg tttttgagca agatattgat gctgtaagta tggtgtttat gaaaggttag  96000
tctggaagag atttgcagga tggagacccc ggaagttttt ttgttataat acagaaagac  96060
```

-continued

```
ttgcactgag ggtgaggtgt taaaaataaa caggtaagta aatgtttaaa catcttgaag  96120
gaaaagtcaa caaatcttgg caagtaaaca gataacagtg aaaaagaatg ggaccaagat  96180
tttgagtttt ggagactggt ggattgaaca gacagggaaa ttgagaggag aatcagatga  96240
tgatgtttta agttgatatt tagacagatt gtgcttgaga tggtaaagtc aatgtgggtg  96300
ggaatgctta gtagcgagta atcagtgata caagaccaaa gcccaggtca aagacaagtc  96360
acagatacag atcagggctt tttcatctgc tccacagagg tgtaccctag gagctgttgc  96420
aaacagtcca tgtggagggt gtgagtaaga tgtttccctt gaatttgcca gaattacttt  96480
tttgttgttg ttgttgtttt ttctgagaca gattctcgct ctgttgccca ggctggaggg  96540
cagtggcgag atcgcgcagc tcactgcaac ctctgcctct cgggttcgag tgattctcct  96600
gcctcagcct cccaagtagc tgggattaca ggcttgtgcc accaagccca gctaatttct  96660
tttgtatttt tagtagagat ggggtttcac catgttggcc agactggtct cgaactcctg  96720
gcctcgtgat ctgcctgcct cagcctccaa aagttctggg attacaggcg tgaaccactg  96780
cacccggtcc cttgttaagt ttattttggt gggaagcaaa ggaggtttca gcttttaaaa  96840
agtttgaaaa ttattgctct ggtaataatt aaagatttga gagtaaatat gctttctagc  96900
agaaagaata aaagaagaac agatagcctc aagaagggga gccaaagaag caggctatat  96960
ctgacacact gggtgttgat aaatgggtat taaaagaatg agagcaatga gcagatagaa  97020
gaggaaatta ggagagtata ataccatgga gaccaagaaa gatagactat caggaaggag  97080
tggtaaaaat aagttactag ttctaagaga gatgttaaga gggaccgggg aaagccttgt  97140
acaaatgagt tagtagcatt ttacattata tacatctaat taagaaacaa tgcgagagtc  97200
tcaccattcc tatagactct tacttgtact tgtctgaaca cgaaaactgg cttttgttta  97260
taaataagct aaaaattatt ttgctccaat ttctcatgaa aataaaaata aaccttcttt  97320
taacattgaa aaaatagttt gaagacagtc actcttcatt ttgtaattcc cacaactatt  97380
attgaatgac tgaaattatc tttattctga agccaaaggg gtgatactga tatttcttca  97440
gactactaaa aatatatttt atgaattttt agtgtgcttt atcttttttt gttttttttt  97500
ttgagatgga gtttcactcc cgttgctcag gctggagggc agtggtgcaa tctcagctca  97560
ctgcaacctt cgcctcccag attcaagcaa ttctcctgcc tcggtctccc aagtagctgg  97620
gattacaggc acctgccccc acacccagct aatttttttgt atttttagta gagacagggt  97680
ttcaccatgt tggtcaggct ggtcttgaac tcctgacctc aggtgatcca cccaccttgg  97740
cctcccaaag tactgcgatt gcaggcatga gccaccatgc ctggcctgag gaatattttt  97800
ctaggttccc cccaccccaa gcatttattc tgcaatttta gttttgttcc taaagcaagc  97860
aaggtttaag gatttaaaaa taatccgtat tttagaatgc tttctggctt tgttactttt  97920
tatccacagt agaagttctc agagaatgat ctccctcttt taatttaact ttttggcaca  97980
gtattttgag aattataaat aatattagaa tgttttctgg ctgggtgtgg tggctcatgc  98040
ctgtaatcct ggctacttgg gaggctgagg caggagaatc acttgaacat gggaggcaga  98100
ggttgcagtg agccgaggtc atgccactgc actccagcct gggtgacaga gcaagactct  98160
gtctgggaaa aaaaaaaaaa aaaaaaagag tgttttcttt cctattttcc accacttgat  98220
taagttactt ttcctcttaa gtatttttttg ctgagtatgc tgacttaaga gtaatgttac  98280
aaaatttaat ttttaaagtt ctctgaaagc ccctttatga gagttttagg ctatcaaatt  98340
gtgtttaatt cttaacaatt ttttgaaaaa ttatagcttc aatatccgta cattccccac  98400
aaaaaagcac taaaaatcat gccttgctgg aggctgcagg accaagtcat gttgcaatca  98460
```

-continued atgccatttc tgccaacatg gactcctttt caagtagcag gacagccaca cttaagaagc 98520
agccaagcca catggaggcc gctcattttg gtgacctggg taagtaacta tcatttttta 98580
ttaacttgta ttagaaggat ttgagtacaa tatgtgaaac ttctgtcata ggatacagaa 98640
ctatataatt ggaaagtgct ttggaaaaaa tgtatttaaa ataacagcta caagtataat 98700
gggtagctgt gttgtgttcc tgtaaatata gaatataaag catgcccagt agaaaaacaa 98760
gcatttccag aagaaatata tctgatcact aaatataaat atatgaaaaa gatgtctcac 98820
tttattactg agggaagtgc aaattaaaat aatcagttaa tgttctccta acacattagc 98880
atatttttta aagtttgaca atttgaatgt cagtgaagat gcagggaaat acccctccta 98940
tttagtgata atataatctg gtgaagactc tttggaaagc aatttggaaa tcagtataaa 99000
atatgcatgt catttaggcc actctttcta agacctagcc ctcagatatg ctcattcata 99060
tgtgcaggtg tgtatgtgtg tgtgtgtgtg tgtgtgtgtg tgtatatgta tgtatgtatg 99120
tatgtatgta tgtatgttga aggctattca ttatagtatt gtttgtgata gcaaaaaatt 99180
atggacaaca tataaatatc tgttataggg aaataaccaa attgtggtat acgcatgctc 99240
tggagtataa tatagccatt tgtttctatt tatttatttt cttgagacag ggttttactc 99300
tgttgcccag gctggagtgc agtggtatga tcatggttca ctgcagcctt cacctcctgg 99360
gcacaagcca ttctctcgcc tcagcctcca gagttactag gactgcaggc atgtgtcacc 99420
acacccagat aattttttaa ttttttgtag agacagggtc tcactatgtt gcctaagctg 99480
gtctcaaact cctggcctca agcaattctc ccacacaggc ctcccaaagt gctgggatta 99540
ccaacgtgaa ccaccacacc tggttcagtg tagccattta gaaatctaaa aaagacgtgg 99600
gaaaatgtct aaggcatgtt taaatgtgag aaaagcaagt cacagtatgc atggtaaaat 99660
ccgttatatt aaaataagtt cttccaaaac aaaaacatat gcaggagacc tttattttgt 99720
cagtatttct tacccaaatt tctgcactta gaaaattgca tgtcatgttg tcataagttg 99780
aaaaaaagat ccatgaacca atggacttct aataaaatca gtcctgcttt tgacatctct 99840
ctctactttt gtgtatattc aaaccagagt gtcaatgtgt ttgtggggca cacttagcaa 99900
taatacatag cagacaaaat gcatatagct cagagagtaa aattgtaagt tttgctagat 99960
cactcataaa ttgctgatga gaatttaaaa tggtgcagat gctctggaaa acaggcagtt 100020
tctttctttc tttttttttt tctttttgag acagggtctc actctgttgc gcaggctgga 100080
gtacagtggc gtgattacaa ctcactgcag cctcaccctc ctcaggttca ggtgatcctc 100140
cctcagtctc ctgagtagct gggactatag gcatgcacca ccacgcctgg ctaatttttg 100200
tatttttttt tttttttttt gtagagacgg ggtttcgcca tgtttcccag gctggtctca 100260
aactcctgga atcaagcgat ccacttgcgt aggcctccca aagtgctggg attacgggcg 100320
tgagctactg tgcctggcct aggcagtttg tttgtttgtt tgtttgtttg tttatttatt 100380
tgtagacgga gtctcacagg ctggagtgca gtggcccaat ttttggctca ctgcaacctc 100440
cgcctcccag gttcaagcta ttctcctgcc tcagcctcct gagtagctgg gatgacaggt 100500
gcctgccata atgcctggct gatttttgta tatttagtag atatggggtt tcaccatgtt 100560
ggtcaggctg gttttgaact cctgacctca ggtgatcagc ccgcctcggc ctcccaaagt 100620
gctgggatta caggcatgag ccgtcatccc tggctggtgg tttcttatga cgtgaaacat 100680
gcaattacca tatgacctag cagttgcact ctgtatttat cccagataaa tgaaaactta 100740
ccttccaata aaaacctgtg cacaaatgtt catagcagct taatattgaa aaactggatg 100800

-continued ttcttcagca ggtgaatgaa ctggttcatt cataccatgg aataccattc agcaataaaa 100860
aggaacaaac tgttgataca tttaaccacc tggatgaata tcaagggaat tatgctgtca 100920
gacaaaaacc agtccctaaa gactacatat agtatgattc cgtttggata atattcttga 100980
aatagagaaa ttaagagaaa tgaaaagatt agtgtttgcc agatgttaga gacagggagg 101040
tgagaggggt aagtgggtgt agttataaaa gtgcaacatg agggatcttt gtgatgttga 101100
agttgtatct tggcagtgga tgcagaaatc tcaatgtgat aaaattacaa agaactaaaa 101160
acaagaatga gtatagataa aactggggaa atctgaacaa gttagagtgt tgtatcactg 101220
tcagtatctt agagtgatat tgtactatag ctttgcaaga tgttaccatg ggagaaacta 101280
aagtgtacaa gggatctcta ggtattatta ttttttaga gatggggttt cactatgttc 101340
cccaggccgg tcttgaactc ctgggctcta gtgatccgcc tgccccagcc tcctaaagta 101400
ctggaattac aggcgtgagc gaccatgcct ggccctttca gtattgtatc ttagaacttc 101460
atgtgaatct agcattatct catagaattt aattaaaaga aattgtaaac ctcacagaag 101520
atcagaattt cctcaagttt gtgatgttga caaagatgaa ctagttgaca ctgacagtaa 101580
gactgaggat gaagacacga cgtgcttcaa aaaaatgatt tgaatatcaa tggattaaga 101640
agaactcttt tgacaaattg atgaaaccct cagtcagttt tataagaatg cccatcttta 101700
tgatcatgct atgaaagcca atttttaaaa aaatttttg tctttcctaa caattagctt 101760
gtggttataa tttaaattta gttaaatata agataaatga tttttatta agtttagttt 101820 catttttcaa ggtacgatct caaagctact ctttaaccta ctatgaatga ataatgctga 101880
gttcataaca tctttgtaga tatatccaca attttccctc aggataagtg cctacaagtg 101940
gaattactgg actgaaaata atgcagtttg ctaagacttt gctatctgtt cctgaatgct 102000
cctccaaaaa ggttttgcca gtttacatcc tcatgaccag cgaatgagag tgttgcctat 102060
tttcctgtgc ccttgttact gcttaataat ttttgaaaaa aatctaattt gacagacaaa 102120
aatgcatttt atgttaattt gcttttctgg gatttttaat gaggttgagt atagttttta 102180
atatttttat tggcccttt ggaactagta tcataagttt tttttcttaa gaatttatgt 102240
agtctgggct gggcgcagtg gctcacgcct gcaatcccag cactttggga ggccgaggtg 102300
ggtggattgc cgaaggtcag gagtttgaga ccatcctgac caacatggtg aaaccgaatc 102360
tctactaaaa gtacaaaaac tagctcagcg tggtggcggg tgcctgtaat cccagctact 102420
taggaggctg agtcaagaga atcgcttgaa cccgggaggt ggaggttggt tgcattgagc 102480
cgagatcgcg ccattgctct ccagcctagg caacaagagt gaaaagtctc aaaaaaaaaa 102540
aaaaaaaaaa aaaaaagaat ttacatggtc tgaattgcca ttaaaagaga tatgagaatt 102600
attgagtaac aaataacttt ttaataattt aggcaagttt tggacgattg tactttgttt 102660
agaaaccaaa agcatagtat ttgtagtttt tttatttact ttagttgcta ggaagtaaac 102720
tttattcaag gtctctggta ccagttgttg ctaaaagtga ttgactaatc tgtcaatctg 102780
aaattatttg ttgctgaact gctaattctt ttgcttctat cttttaggca gatcttgtct 102840
ggactaccag actcaagaga ccaaatcaag cctttctaag acccttgaac aagtcttgca 102900
cgacactatt gtcctccctt acttcattca attcatggaa cttcggcgaa tggagcattt 102960
ggtgaaattt tggttagagg ctgaaagttt tcattcaaca acttggtcgc gaataagagc 103020
acacagtcta aacacagtga agcagagctc actggctgag cctgtctctc catctaaaaa 103080
gcatgaaact acagcgtctt ttttaactga ttctcttgat aagagattgg aggattctgg 103140
ctcagcacag ttgtttatga ctcattcaga aggaattgac ctgaataata gaactaacag 103200

-continued cactcagaat cacttgctgc tttcccagga atgtgacagt gcccattctc tccgtcttga 103260
aatggccaga gcaggaactc accaagtttc catggaaacc caagaatctt cctctacact 103320
tacagtagcc agtagaaata gtcccgcttc tccactaaaa gaattgtcag gaaaactaat 103380
gaaaagtgag tatgtgattt tcttgtgtgt acatatgtgt ctcactttct ttttttaatt 103440
tactaagcag aacttcagat gaggaataaa atgattggaa tatttttttt ctcctctaac 103500
tacttgtaaa tttgggagaa tttggagagt gtagtagagt cagatcagtg tatggaaaag 103560
gagcaggagt gactggacct tctaagaagt gtgttatcag aattagtaaa tgaagggtca 103620
aatgtcctac ttttcccctc cactgatttt gacatcaaac cattatccac atagccttat 103680
ttcctccctc ggtcttaatt ttattaatat tttactgcac tttgcagata aaatttttaa 103740
aaaattttta aaaattgcca ataagtgaca tttattaagt tcagtgctta gtgtatattt 103800
ggattttatt tattagtcac aagacctttg tgcaggtagt aggcatgatt atcttttttt 103860
ttttgagatg gagtcttgct ctgtcgccca ggctggagtg caatggcgcg gtctcggctc 103920
actgcaacct ccgggttcat gccattctcc tgcctcagcc tcccaaatag ctgggactac 103980
aggcgcctgc caccacaccc ggctaatttt tttgtatttt tagtagagac ggggtttcac 104040
catgttcgcc aggatggtct cgatctcctg actttgtgat ccgcctgcct cggcctccca 104100
aagtgctggg attacaggca tgagccaccg cgcccggact gattatctta tttacacatg 104160
agaaaaccag ggcttagaaa ggttaggtaa cttcctctag gttgtacagt aaatgtggac 104220
ctagaagcat tttgacaaga gcacctgttt ttttttcttc tctattagtt tagaaattat 104280
atactcttaa ttatcacctg ggattttgat tagacagcct tcatgttctt tttcatctta 104340
aatgttcttt gtgtcttaaa gggctaagtg atttcttcag atcttttagt tcactcattc 104400
tcagtgaact aaaatgaggt ctaatctgct actgaatcaa gttttcagca tgttatttcc 104460
ttcctccctc cctccctcct tccttccctc aaccaggctc ccgaggagct gggattacag 104520
gcgcccgcca ccactcctgg ctaattttta tattttagta gagacggggt ttcaccatgt 104580
tggtcaggct gatcttgaac tcctgacctc aagtgaccca cctgcctcgg cctcccaaag 104640
tgctgggatt acaggcatga atcaccacac ctgacggcat gttattttca tcgcaaagtt 104700
actgtaagct gggagaagtg gcacacactt gtactcccag ctactcagga agcttaaggt 104760
gagaagattg cttgagccca ggagttttga gaccaacctg ggcaacacag caagacccca 104820
gctcaaacaa agaaaaaaag ttattgaatt ttttatttct atggatcatt ttttgtagtt 104880
tcttattcct ttcacccttc attcccactt ttgatcccat cttttattta tttagtttta 104940
ttaaatgtat atttgtctga taattctgct atctacagtt ttttgtggac ctgactcagc 105000
atttctttgt ttcttcggat tcagactgtt ggtggcttgt gattttagtg atttttggcc 105060
gtgaacatgt ttcttggact tttgtctgtg ggaattctct gtgtactctg tataaattaa 105120
gttacttcag gtgttttgca ttttcttttg ccatgcacct ggggcctggg tcactaccct 105180
tctggtacca cttaaaactg aatttttgtc ttgggtgctc gtactgatcc tgtatgagta 105240
caggtttata cttactgtag aaatatggtg tttgattatg gggtattgtc ccagatggtg 105300
ctggagtatt aatatgctct ctgttaaact taatgtgttg tccctgtaaa actccaaaat 105360
tctgaattcc agaatactac tggccccaaa tgtttaagat aagggcactg cctgtatttg 105420
tttctgcctc ccactatttt ccttagttta acacaaactc acctttttaa aaaacatttt 105480
gagagaattc agtattggga agagtttcta acctgtttct ggaaatggaa gtccaaagtc 105540

-continued tgtttctgta attgtttttt ttttgagatg gagtctcact ctgtcaccca ggctggagtg 105600
caatgacgta ctctcagctc actgcaacct ccacctcccg ggttcaagcg attctcttgc 105660
ctcagccccc tgagtagctg ggattacagg tgcccaccac catgcctggc tgatttttgt 105720
atttttagaa gagatggggt ttcgccatgt tggccaggct ggtcttgaac tcctgacttt 105780
gtgatctgcc cacctcagcc tcccaaagtg ctaggattat gtttctgtaa ttgtaataca 105840
tttattgttt ttagaaactg tctttgcttt agtggtaatt ttcaataaaa atagaaatag 105900
cagtggagtt attaaaagag cattagttac atttttccct ttttcattat cttcaaatat 105960
tatatatagt aagtttgacc tttttaaaat gtatacttgt atcagtttta acacatacat 106020
agattcctgt aactgtcacc actataaggg taaagaacag ttagttcctt cacctttgaa 106080
gtcaagcccc acctctatcc caacacttgg caaccgctga tctttctccg tctcaatagc 106140
tttgcctttt ctcttttttt ttcttatttt ttttttgag acagcgtctt gctctgtcgc 106200
ccgagctgga gtgcagtgag gcaatctcgg ctcactgcaa cctccgcctc ctgggttcaa 106260
gcagttctcc tgccttagcc tccctagtag ctgggattat aggcacgcac caccacaccc 106320
ggctgatttt tttgtatttt tagtagaaat ggggtttcac catgttggcc aggctggtct 106380
caaactcttg acctcaagtg atccacctgc ctcggcctcc caaagtgctg ggattacagg 106440
cgtgagccac tgtgcccaat caggactttt ttttttaaa tttacattca acttgtcatt 106500
tttttcttgt atggattgtg ccttcagagt cacacctaag agccctttgc ctaagcaaag 106560
gtcatgaaga ttttctcata tgtttccttt taaaagtatt gtggttggcc aggtgccatg 106620
gcttatgcct gtaatctcag cactttgaga agctgaggtg ggcagattac gaggtcagga 106680
gatcgagacc atcctggcta atgcggtgaa accccatctc tactaaaaat acaaaaaaaa 106740
aaaaaaatta gccgggcgtg gtggcgggca cctgtagtcc cagctacttg agaggttgag 106800
gcaggagaat agtgtgaacc cgggaggtgg agcttgcagt gagccgagat cgcgccactg 106860
cactccagcc tgggcaacac agtgagactc catctcaaaa aaaaaaaaaa agtattatgg 106920
ttttacactt tacgtttaga tatatatctt ttttgagtta atgtcgtata agtatgaggg 106980
ttacgtcaga ttttttgttt tttgtttatt tttacatatg gatgtctagt tgttctaata 107040
ccatttgttg aaaagacaac ctttactcca ttgaattgcc tttgtacttt tgccatattt 107100
gtctaggcct gtttttggac tccttttct gtttcatgat gtgtgtgtct attcctttgt 107160
taataccaca tggtcttaat tactgtatag taagtcttaa aattgggtaa tgctggcctt 107220
ataaaacgaa ttgggaagtt tttattttta ctcttatttc cattttctag aagagattgt 107280
gtagaattgg tgtcatttct tctttagata tttggttgaa ttgggaagtg atgccatctg 107340
ggcctagggt tttgtttttt gtgtgtgaga cagagtctca cttctgtcac ccaggttgga 107400
gtgcagtggt gagatcttgg cttactgcaa cctctgcctc ccaggttcaa gttatcctcc 107460
tgcctcagcc tcccaaatag ctgggattac aagcgtgtgc caccatgccc gactaatttt 107520
tgtattttta atgcagacag ggtttcacca tgttagccaa gctggtctcg aacttgtgac 107580
ctcaagtgat tagcccacct tggcctccca aagtgttagg attatagatg tgagccaccg 107640
tgcctggcag gggcctaggg ttttcttttt cagagtattt taaactatga attcagatta 107700
tttaatagat ataggactat ttaagttatc tgtttcttct tgagtgaatt tttactgtag 107760
tttatggcct ttgagtaatt aattgtattg aattgtcaaa tttatgagcg tgtaattatt 107820
tatagcattt cgggtttgta gtggtatccc tcttttattc ctggtgttgg caattgtgtc 107880
ttgtttttct ttgtcagatt gtatagggat ttattagtct tttcaaagaa ctagcttttg 107940

-continued ttttgatttt tctgttgttt tgttttcaat tttattgatt ttctgctctt tattatttct 108000
tttctattat ttctgcttgc tttgggttta ttttactctt ttttttttct ccaagttgct 108060
taaagtagaa acttagattt ctggtttgag acctttcttt tctaagataa gcatttaata 108120
ctgtaaattt ccttctaacc actgctttag ttacaccccc acaaattctg gtattttgaa 108180
ctgagcacaa atgaaatgtt ctaatttccc ttgaatctta ttcttttacc aatgaattat 108240
ttagaaatat gttatttagt ttgcaagcaa ttggagactt ttttcctgtt atttttctac 108300
catttatttc tcatttcatt atattatggt cagagaatat attttgaatg atttcattta 108360
ttaattttta aaaataacat taaaaaattt tttaaaatgt gaatatacca catacagtat 108420
aaagattgta cattctgttt ttggacagtt ttctataaat gtcaagttga tttagttggt 108480
taatgatggt gttcagtttt tctttattct tgctgatact ttgtatgcag ttatatcact 108540
ttattactca gaagagtgtt gaactttcca actacaattt ttttttccaa ttttactttc 108600
agctctatct ggttttgctt catgtatttt gaggctctgt tgttaggtgt gtacacattc 108660
aggatgatat cttctgggtg aattgcctgt tttatcatta tgtaattccc tctttatggt 108720
aattttcctt gttctaagat cagaaatatc tgttgtccaa tttatataga cactgcagct 108780
ttcatttgat tagtgcttgc atggcatatc tttttccatt tttttacttt tgatctacct 108840
ttataattct atttaaaggg ggcttcttgt aggcagcata tagttgggta gtgttattta 108900
tttatttatt tatttattta tttatttatt tattgagaca gagttttgct cttgttgccc 108960
aagctggagt gcagtggtgc aatcctggct taccacaacc tccacctcct gggttgcagt 109020
gattctcctg cctcagcctc ccaagtagct gggattacag gcacgcgcac catgcctggc 109080
tgattttttg tatttttagt agaaacggat tttcaccatg ttagccaggc tcgtcttgaa 109140
ctcctgacct caggtgatcc acctgctttg gcctcccaaa gtgctgggat tacaggcgtg 109200
agccactgca cccggctgag tcatgttatt tttaatcttt tctcacaata cagggttttt 109260
gttggtaaat ttaattattt taatataaat tttagtataa ttatttacat taaatgtaac 109320
tgttgcactg ggtatttat aatgtgtaaa tataattatt ggtattaata taattatatt 109380
actcataata atattaatat ctttggattt agattaccag tttagtatat gtttttctgt 109440
ttctccctct ttgatttccc cttttttgct tttttttttt ttttaattct tatttttttt 109500
tagtatttgt tgatcattct tgggtgtttc ttggagaggg ggatttggca gggtcatagg 109560
acaatagttg agggaaggtc agcagataaa catgtgaaca aggtctctgg ttttcctaga 109620
cagaggaccc tgcggccttc tgcagtgttt gtgtccctgg gtacttgaga ttagggagtg 109680
gtgatgactc ttaacgagca tgctgccttc aagcatctgt ttaacaaagc acatcttgca 109740
ccacccttaa tccatttaac cctgagtggt aatagcacat gtttcagaga gcagggggtt 109800
gggggtaagg ttatagatta acagcatccc aaggcagaag aatttttctt agtacagaac 109860
aaaatggagt ctcccatgtc tacttctttc tacacagaca cagtaacaat ctgatctctc 109920
tttcttttcc ccacatttcc ccctttttcta ttcgacaaaa ctgccatcgt catcatggcc 109980
cgttctcaat gagctgttgg gtacacctcc cagacggggt ggcagctggg cagaggggct 110040
cctcacttcc cagatggggc agccgggcag aggcgccccc cacctcccag acggggcagt 110100
ggccgggcgg aggcgccccc cacctccctc ccggatgggg cggctggccg ggcgggggct 110160
gaccccccac ctccctcccg gacggggcgg ctggccgggc gggggctgac cccccacctc 110220
cctcccagat ggggcggctg gccgggcggg ggctgccccc cacctccctc ccggacgggg 110280

-continued cggctgccgg gctgaggggc tcctcacttc gcagaccggg cggctgccgg gcggaggggc 110340
tcctcacttc tcagacgggg cggccgggca gagacgctcc tcacctccca gatggggtgg 110400
cggtcgggca gagacactcc tcagttccca gacggggtcg cggccgggca gaggcgctcc 110460
tcccatccca gacggggcgg cggggcagag gtggtcccca catctcagac gatgggctgc 110520
cgggcagaga cactcctcac ttcctagacg ggatggcagc cgggaagagg tgctcctcac 110580
ttcccagacg gggcggccgg tcagaggggc tcctcacatc ccagacgatg ggcggctagg 110640
cagagacgct cctcacttcc cggacggggt ggcggccggg cagaggctgc aatctcggca 110700
ctttgggagg ccaaggcagg cggctgggaa gtggaggttg tagggagctg agatcacgcc 110760
actgcactcc agcctgggca acattgagca ttgagtgagc gagactccgt ctgcaatcct 110820
ggcacctcgg gaggccgagg caggcagatc actcgcggtc aggagctgga gaccagcccg 110880
gccaacacag cgaaaccccg tctccaccaa aaaatgcaaa aaccagtcag gtgtggcggc 110940
gtgcgcctgc aatcccaggc actctgcagg ctgaggcagg agaatcaggc agggaggttg 111000
cagtgagccg agatggcggc agtacagtcc agcctcggct ttcacaactt tggtggcatc 111060
agagggagac cggggagagg gagagggaga cgagggagag cccctttttt gctttctttt 111120
ggattatttg aatttttcct taaatttatt tatcttactt atttatttat ttttttgagt 111180
gattctcctg ccacagctcc caagtagctg ggactgcagg catgtgccac tacacccagc 111240
taattttttt gtatttttag tagagacagg gtttcaccat attggccagg ctggtcttga 111300
actcttgacc tcaagtgatc cacctgcctc ggcctcccaa agtgctggga ttacaggcgt 111360
gagccaccat gccctgcctt tttctagaat ttatatattg agttcttgat tgtatctttt 111420
tatgtaggct ttttagtggc ttctctagga attacaatat acatactttt cacagtgtac 111480
tcacatttaa tattttgtaa cttcaagtgg aatgtagaaa acttaaccac cataaaaata 111540
gaactaggga tgaggttaaa aaagagagag aaaagaaatg taataaagat ttaataacac 111600
cgtttttttt tttttttctc tttttttttt gagacagagt ctctctttct gttaccaggc 111660
tggagtgcag tggcgtgatc ttggctcact gcaacctccg cctcctgggt tcaagtgttt 111720
ctcctgcctc agcctactga gtagctggga ttacaggtgc gcgccaccat gcccagctaa 111780
tttttgtatt tttagtagag acggtttcac tgtgttggcc aggatggtct cgatttcttg 111840
accttgtgat tcgctctcct cagcctccca aagtgctggg attacaggcg tgagccaccg 111900
cgcccggcta agtctttaaa tattttttttg acattgcact ttttctcttt tccttctagg 111960
attttagtaa cccaaatgtt agttttgtta ttgtttggca ggttcctgag gctttcctta 112020
cttctttaaa tttttttttc ctgttgttca gcttcgaaaa tttctattca tctgtcttca 112080
aattcactgg ttctttcccg ttatttccat tctgttattg agtctttgta gtgaatttta 112140
aattttgttt attatgtttt ttagttctaa aattttcttt ttttgtgtat gtcttatact 112200
ttgctcctga aactcttatt tgtttcagga gtgatcttat ttcttagagc atggttttag 112260
tagctactta aaatttgttt tatcatccca gcatatgtgt cctcttgatt gtcttttctc 112320
ttgtgagata atgggatttt ctggttcttt atatgacaat taattttgga ttgtatcttg 112380
gacagtttga cttacgttac atgattctga atcttgttta aatcctgtgg aaaatattga 112440
agtttttgct ttaacaagca gttgacctag ttaggttcag tccacaaatt ctaagcagca 112500
ttctgtcggc tctggttcca tcatcagttc agttttgtat cttatctgct tatgtgcctt 112560
tctgtgtcca gtctgggacc tggccaatgg tcaggtccca aagcctttgt acacttttag 112620
aagcagggcc atgcacaccc agctcacgag tggccccggg agtgcacata caactcgacg 112680

-continued ttttcatggg ctccttcttt tctgtgatgt ccctgacacg ttctgccttc taagaacctc 112740
cctttatccc tttcctgttg tctggctaga aagtcagggc tttagattcc ctatacttca 112800
gcacacttcc tgtagctatg tcaacctctg tggccacgac ttcttcttct tgggactgca 112860
gtttctcttg tcagaaagta ggattcttgg agctgctgtc attgctgctg tggctgctct 112920
gatgctgcct gggagtcgaa ggagagaaag gaacaaaaca aaacaaccca ggggatttcc 112980
tccactctct ttgatccgtg agagccccct ttcctgttcc tcagaccaga aatagagggc 113040
ctgtcttgga acttcttctt tgtgcatctg gtgtgcagtt tcagcttttg agtccaggcc 113100
aggaggtgct ggacaaactt gtcaggagta cggaggtact gcaagttctg attacttttc 113160
tcagtccacc tgcttccaag tccttggatg catttgtcca ttgttttgag ttgcattcca 113220
tgggagagac agaagagtgt gcttatttca tcttgacata cttattagga tttcatatca 113280
aatcaacgga tgatattctc tatattaatt tgctgttttc cctttagcaa gcacattagg 113340
aaaataacac tttaacaccc gcctttggtg gtttctgtca taattattaa tacttgactt 113400
ttttttttt tttgagacgg agtctcactc tgtcctttga ggcattgtcc ccataaactt 113460
ttggtaaagc atcaataatt ttatctttca tccacacaag cttcaccata aatttgatgt 113520
ttattcttcc attttagcag aattcatgtt gctccaatag gggctgtctt caaactgatg 113580
ttttctcctt cttagtgcct cagagtagat cctgttcaga tacgttataa caggttaata 113640
tgagtttatt ttggtgtaaa agtactttga aattcatgca tagtttttttc atcatatgca 113700
ttttccatag ctttgaacac cccatgtaa ctctcctctt ccacaaacca aacaatgaaa 113760
aagcaccttt gtgatggaag tttattttgc aataggaact cacagtgatc taagccctgc 113820
tattcatgaa tataattcat tactggagtc caagttgctt tttggttttt gaagttctct 113880
tcttcccttg caggtataga acaagatgca gtgaatactt ttaccaaata tatatctcca 113940
gatgctgcta aaccaatacc aattacagaa gcaatgagaa atgacatcat aggtaagcag 114000
tgcttgaaac tatggcaaaa aaaaaatgac aaaaaatgca cagaactgac aattttcgtt 114060
attgactaag ataatttttt cttaacatgg aatttagcag ttcccttcct aatttgtttt 114120
ctgagtattt tttatatcgg attatagctc actttaaaag tttctcggct gcattcggtg 114180
cgagggtctt tgcctgggcc agatgggctg cagtgtagcg ggtgctcagg cctgcccgct 114240
gctgagcagc cgggccggcg ggcggctacg ctaaccggca cagaccaccg gatggactgg 114300
ccggcagccc cgcaccagtg cacgaagtgg gcgggacaga aacttctggg gttggaagtc 114360
cagtgaggct aaaagccggt accaaagtct ctaggcatca gggctgcagc ccaagagtct 114420
cacgaccagt gggcaactgg atggccagac aggtgtctca gtggtggcct ctccgtctca 114480
gggcttcatc ccacttctca gtgggcctga cgtccctggg caccctggat gtctacctgc 114540
attagccaga gccatcacat ggcctgtgac ttgccttttt ttgccagttg attgtgccac 114600
acacagtgtc atttctgtgt catttggcac agctggaggt gcaaggagga gggcagcctc 114660
atgtccagtc ccagtttcac gtaactttat tcttctgaat aaagacaatt tgctaacctt 114720
aaaaaaaaaa aaaaaaaaaa agtttttctt atatgttgga cccaaattct taggctttaa 114780
cctgaataac aatgacagca agatcaataa atagtacaca tttattaaac actcactgtg 114840
tcccagacaa tattccaagc actttttatg gatagactca ttttaacttc taaagaactt 114900
tgtgggataa atacagttat tttatagatg aagaaactga agcacagaga agttaagtgc 114960
tttgtccagg gtaacagctc agatatggca gagtcaggat ttgaaactag accctcacat 115020

-continued accttaactg ctgtgctgtg gcagtgtttt tcatactgta ggttgggacc agccttctct 115080
tatgccctca ccccctgcca aaaaaaaaaa aaaaaaaaaa aaatatatat atatatatat 115140
atatatatat atatatatat aatatatata tatataaaat atatatatat ataaaatata 115200
tgtattagta tatatgcata tatagtatat attatatatt agtatatata ctaatatata 115260
atatacatat tagtgtgtgt atatatatat atactagaat aaaaaaatca aagtatctca 115320
gagtagtaag gacaaacatt tcagaaaaat gttttcatta tatatacatg tatgtatgtg 115380
tatgctgatt caacaaatat atttcttata ggttatagca aaatagtttg aaagctttta 115440
ctgtgtttta tcaggaagac cttaggtgaa cgtatattca cagataaaag aggttattta 115500
ttcattcaat aaatattaca ttctcataag tcctaatatt atgtattttt attcttcaaa 115560
aaagttagta tttgtgattt atgaaataag acatgttctt gcacttttag cagatctgtc 115620
ccgatgttgg gcttctttaa tccttagtgt gggtgctttg cactcactca ctgctgggga 115680
cagcaagacc cctgttagtc tcagctgtgt ttcttaaatt ggcccactgt accttccagt 115740
tagctattct ggggtccatg tcatgttggc tccattttcc ttttctttct cccacacaga 115800
tacctataac ggctataaca taggcctggt ggctgttggt ggcttatccc tatctgcttg 115860
tatttaaggg gtactgtttc actgagtttt gctgacagat gttgtcatga gatttgaggt 115920
tttctgtgtt gttgctctat ttttatgtgg gaatttgcta ctatcatcat ccctagacca 115980
gcttttccta gtaatacaac agggatgttc tgactgatta gagtttgcct gtttgaagaa 116040
ttggttggct agtgattttt ttttgagggg agtctgtacc agttaatagc ctgactggcg 116100
tgtggataaa aaggaagcag tttcaagtca aataaaacac ttaaaatgaa accacactgc 116160
aactctcttt cttttactta agcttaatca aattaatgat gatgtaatcc catgaaggaa 116220
aagtcttctg aaggatcaag ttgataacat tttgtgatca aagaatttga gaaaacctct 116280
atcccagtgt ctatcattat atattttagg atgttaatta cctgtgtggc tttaggcaag 116340
tcatttttcc tccttgagcc ccattcttaa tcctgtccaa attatttgtc tcctcttgca 116400
gttggactat tttaatatag ctgtccttca agtgagtttt gttcaaagga gccttcactt 116460
tagctcttac tgtgtaccca ctttgcatag tcttgtttta aatgtaatcc ttggattttt 116520
ggtgttgcta actaattact gtttttatgt gaggatttag agtgatccag aatctatact 116580
tgcactacct ccttcatctt ccacaaatgt ttgaagtggt agaattttta aaaactttga 116640
aggtacagct gacagaattt gctgatggtt tggaagtgag tggtatgaga gggaaaaaaa 116700
ggaataaagc atgactgcat tttttgtttg tttgtttgtt tgtttttgag acggagtctc 116760
actctcgcca ggctggagtg cagtggcgtg atcttggctc acggcaacct ccgcctcctg 116820
ggttcaagcg attcccctgc ctcagcctcc caagtagctg ggactacagg cgctcgccac 116880
cacgcctggc taattttttt ttttgtattt tagtagaaac ggggtttcac cgtgttggcc 116940
aggatggtct ccatctcctg acctcatgat ctactcacct tggcctccca aagtgctgag 117000
gttacaggca tatatataag catataaagt gtgttatagc atacaaacag gtatatatat 117060
aaacatgcag tccacacagc tgataggaat gaggcagtag tgaaggagaa gttgatgtag 117120
gagaggggac agttgttaca ggaaagaagt ctggaggcag aagggatgaa ttccagtgct 117180
cacatagaag attgcttaga tgggagcaag gacaatttat ctagagtcac aggaaagaat 117240
gcagtacacg ggtagagatg caggtgagtt gaaagatgtg agagatgatg gaaataattt 117300
tctgattgct tctatattct caaggaagca ggaagcaaag tcctcagcaa agagaataga 117360
agaggtgtta aatatttgag aaaggagatg tactgtagaa aaaaaaaaaa ctcagtttct 117420

-continued ccttctgaac tctcacaaaa cagaaccctt ccatgactct agttgtgtgg ggttttttcc 117480
ctgtcagcta ccaattctgc agatgattgt tcagtgaaca ccaactgggt gtcctctaag 117540
tcagttcagt tctcacactg tttacctgga gatagcatca gatcccacag attgaggact 117600
ctgtcccaca agactgcctc cacttcagat gccagtctca agtacaagtt gtggcctgtg 117660
cttctgactg accttctata aattggagtt cccacagtcc cctccttggg ttcaataaat 117720
ttgctagagc agctctcaga actcagggaa atgctttaca tatatttacc catttattat 117780
aaaggatatt acaaaggata cagattgaac aggcagatgg aagagatgca tgggcaaggt 117840
atgggagagg ggcacagagc ttccatgcac tctccaggtc atgccaccct ccaagaacct 117900
ctacagattt agctattcag aagccccccct ccccattctg tccttttggg tttttgtgg 117960
agacttcatt atataggcat gattgatcat tggctattgg tgatcagctc aaccttcagc 118020
cccctcatcc cgggaggttg gtgggtaggg ctgaaagtcc caaacgtgta attctgcctt 118080
ggtctttctg gtgattagcc ctcatcctaa agctctttag aggccacagc cacaagtcat 118140
ctcattagcc ttcaaaagaa tccagagatt ccatgaattt taggcgctgt atgctaagaa 118200
actggctaaa ggccagttgc aatgtctcag gcctgtaatc ccagcacttt gggaggctga 118260
ggcaggagga tcgtttcagg ccatgagatc aaaaccagcc tggtcaacat agtgagaccc 118320
ccttacaaaa aatttaaaaa ttggccaggc gtaatagctc ttgtctgtag tctcagctac 118380
tcagaaggct gaggatcact gagccctgga gttgaaggca gcagtgagcc atgatcgtgc 118440
cactgactcc ggcttgggtg acaaagtgag accttgtctc agaagaaaaa ggaaaaaaaa 118500
aaaactgggc aaagactaaa taacatattt cacagtatca cagatttgta ttgtctagga 118560
aagtgaatgt aaacagacca ggacactagt atgatccctt ggtttcatga aggtcccact 118620
aaagtcatga acacaaagtg agactaggca tcatgttata tggtttttcc agccatgttt 118680
aacagctagc taaatagcta attgtttcgc tgcagtttat tttagcagtt ccttatttta 118740
gcacatttca tgttttaaaa tttctaccaa taacatttta ataaactttt ttacagataa 118800
cttcacaaat ccataatttt ttaagttaca atcccagaaa tagaattgct cattgaaagg 118860
gtatgttcat ttttaaagtt atgctagaaa ctgccaaatt gccttcagaa aaaggtgttt 118920
gtatccccac taacactagt gttagttttc ttgtgccctt gctcaagtat acatattatt 118980
aaaaacaatg ttgggccagt ttactagata aaaggtgtag tgcctcctta ttctaatcta 119040
tttgattact agtgagtatg tatgtctttt cacgttggtc attttatgtt tgttcctttg 119100
tggattgtca tgtcctttgc tcatttttct tttggaacat ttcttagtag tttataagag 119160
ctcttggtat tttaatgata gtaacctttt aactgtcatg catgctgcaa atcttttttc 119220
tgtttgtttg cctttgtatt ttgtttttgg agggtttcta tgtataggaa ttaaatttta 119280
tgttgttaaa tcttttgatt tctgcttttg catatgtact tcaaaagact ttctatttta 119340
agatcaagtg ttacctgtat tttcttttag ttctatttaa aacctcttaa tttatatgcc 119400
tgtgctgtta actcccaagt tgattcacaa gtgtgtatac atagtttgaa tttagtggca 119460
atttaattat ttacaacttc ttttgcagca aggatttgtg gagaagatgg acaggtggat 119520
cccaactgtt tcgttttggc acagtccata gtctttagtg caatggagca agagtaagtt 119580
agttcatatt ttcacattgt gcatcctagg gaatttgggt tcattgttag gaatgggctt 119640
cactcagcta aaaacaaagt atttttgaga atttaaatat tttggatatt tacaagatca 119700
tataaagcat actctatctt ggttaacagt ttcttttaaa tataaattat gtgaactctt 119760

-continued aaaattttca ttttcatttt caatgttaat atttcctaag ttaaaataat ttgtttttag 119820
ttctgaaata atttggggag tgattgagtc tgtagtgatt atgactatta gaattggttt 119880
atttatttaa ataatgcatg tcttcagatg gctctcctaa tttgttagtt aggctttaag 119940
ctaaatggat gctatataac taaatccaca tagatttgtt gaaatggctc cagaggtttt 120000
ttagatttat tactgctatg tgcccttaaa aaaaatctat tcattctttc acttaacatt 120060
tatcagaaga gtgctctgtg taagacgtgg ttaggcatag tgccagtctt gaaggaagtt 120120
acagcctaat aaaagacata gggcatgttg tttggttact gtaatatgaa gtggcatgtg 120180
ttaaatgtca ggggagaact acaaagtcat aaaaaggtgg gagagattac atacaggtaa 120240
aggaatcagg aatgacacca tggggagtaa ggtagtgttg acctaggcct ttaagataca 120300
atagggacag tatggaaaga gtatattttt cccacttaaa ctctttcctt ggtcgttccc 120360
tcaaatttc ccttttgtcc atgtgcaggc actttagtga gtttctgcga agtcaccatt 120420
tctgtaaata ccagattgaa gtgctgacca gtggaactgt ttacctggct gacattctct 120480
tctgtgagtc agccctcttt tatttctctg aggtaaagtc tgcatttctt ttcacactct 120540
attcgagcat tccagcctct aactatcaat gctggggccc tgtctatagg aaataacaca 120600
gaagagccaa gtcatttcca aaaagatgta tcattgtttc aagttgtttc tgatggcaag 120660
agtaatttaa taatatatta gagagaacat gaaaattcaa tgtattaaat aactctaatt 120720
ttgagaaacc taattaaact actgcatgta agagagtgca tgtttttaat tatttggagc 120780
tattttaaaa ccacagaatt tgaaacttgc ttccagtgca taaattgcag accagacttc 120840
agaagagaaa aaaagtagta aatttttttct tatgctcatc atttttactt tagtcacttg 120900
ataggattgc ccagtgaaga agcatttgca acagacaatg agtatattaa tctttttgag 120960
gcatacagtt tagtataatg ctctttgtta ggcttcaaca agtgaaatta ttttgttgga 121020
aagcaaatga ctattaagta gaaagaggat tcccagtctc acaaagcagt aatttagaca 121080
ctcgattctg cctctttaca agaatacagg tactcagttg atttgttttc tcactccctt 121140
tctttgctat aagtttaaat caacaatttg tttaggttaa tatgtcctca tggaatggtg 121200
gaaatgatca gatataaaat atttggtttg gttagtttac tctttatatg tttgctggca 121260
aggaaccaca aatccagttt agtataattt ttactctagt tcactaaaag tttgcatcca 121320
gctgtgtagg tagtgtttgt ttcttgttaa cttttttttc gtctaaaaga atactttaaa 121380
acttttcaat ctcaaatgac tgtaacttgc tgacaggtgt taacagaaga agtagatctt 121440
tttgtttttt gcttatgacc tgtattttaa tatttgagct tatagattag agattgtgag 121500
agaaatctgt ttatagtctt attttccctt gtgtattttt tcttcctagt acatggaaaa 121560
agaggatgca gtgaatatct tacaattctg gttggcagca gataacttcc agtctcagct 121620
tgctgccaaa aagggccaat atgatggaca ggaggcacag aatgatgcca tgattttata 121680
tgacaagtga gttatattga tagatggatt cagcagatac ttattgaaca tttgatatgt 121740
tttgtggaaa taaagatgaa taaactcagt ctctgttgtc aaggagctca caggaggcag 121800
cataaaagct gcttttatat ggtgtttgta aagctttggg ggttcttaga acaaaagttt 121860
ctgctgggaa aggggaggtg tatgtggggt aaacaggatg gcaatggtgg tgttcaagga 121920
gtgtttccca gaagagagat tttgtttgga tcccaaagaa agaagggaat tttgctaccc 121980
agagaaggca gaaaacaaca ttctaggcaa aggcattggc ccagaagcca tggaaacgta 122040
ggggaaagtg gcactttcaa gaaacttgag tttagataat caaaggagtg gggaataaat 122100
atgaggatgc tggtactaat tggaatagat tgtaagggac cttgaatgcc tatttatggg 122160

-continued tatattatac tttctgtata aatctgctca ggcacgttgt taattagttt tttattagtt 122220
ttcactgaaa atgagaggat ggaaacatca tacagtaaac aaaattgaaa atatctggtc 122280
aggcagatga tgagcttgtg gccagctctg taacgtatgg tattcttttc atttaacttt 122340
tcttactctg taaaaaaagt aattcgtggt cgggcacggt ggctcactcc tgtaatcaca 122400
acactttgag aggcagaggc aggtgaatcg cttgagccca ggaatttgag accagcctgg 122460
gcaacatggc aaaacccgcc tttactaaaa atacaaaaat tagctgagcg tgatggcgtg 122520
cgcctgttgt cctagctact taggggcctg aggcagaagg atcacctgag ccttgggagg 122580
tcgaggctgc agtgagctgt gatccactgt actccaccct gggcagggca gtagagtgag 122640
accctgtctc caaaaaaaaa aaaaacaaca aaggtaattt gttatttgta tccttaagca 122700
aatgctaaag gggtaacttg gggatagaga aaagtccaca gatgttaggg tttgaagaca 122760
ctaatagtat ctaggccagt ggttcctgaa cattagtctg tgggctcttg ctgggctgtc 122820
tgcataggaa tcacctgaga gcttattaaa aataggtttt caggctggtt gcggtggctc 122880
acgcctataa tcccagcact ttgggaggct gaggcaggcg gattacttga ggtcaggcgt 122940
tcaagaccag cctggccaac atggtaaaac cccgtctcta ctaaaaatac aagaattagc 123000
caggcatgat ggcacacacc tgtaatccca gctactcagg aggctgagga aggagaattg 123060
ctcgagcccg ggaggtggag gttgcagtga gcggagatca tgccactgca ctccaggctg 123120
gctgacagag ggagactctg tctcagaaaa aaaaaaaaaa ataggttttc agtctgggta 123180
ccggtggctc acacctgtaa tcccagcact ttgggaggcc aaggcaggca gatcacttga 123240
ggtcaggagt ttgagaactg cctggccaac atagtgaaac cttgtctcta ctagaaacta 123300
caaaaaatta actgggcatt ttgacgggtg cctataatcc cagctactag ggaggctgag 123360
gcaggagaat tgcttgaacc cgggaggcag aggactgcat ctcaaaaaaa aaaaaaaaaa 123420
aaaggtttcc agtccccctg tctcagaaat tctgattctg caggtttgag gtgtgaccag 123480
gaatctttat ttttagaaga cataccagat aattctgata aatagccagt ttagggatgt 123540
agtctaattt tcctattttg caagtaagga aaataaggcc cagagaggta atgattttct 123600
caaagtcaca gaacaagtta gtggcagaat ttggactgga atgcagttct taatgttctg 123660
tccagtgttt attctggtac agtatgtttg tagaaggtat tacgtaagaa acattgttat 123720
atagatgttg agataggaag agtttacatt tagaaatttg gtctaaaatg cctgaacatt 123780
caagtcgtgg aggagtattg accaacttac tcaatacaac ataggagatt cacattttgt 123840
tacaaaaatg ctgatttaaa aggagagttt tctttttttt cttctttttt atttttttgag 123900
atggagtctt gctctgtcac ccaggctaga gtgcagtgac acgatctcag ctcactgcaa 123960
cctccacctc ctgggttcaa gcggttctcc tgcctcagcc tcctgagtag ctgggattac 124020
aggtgggggc caccacgccc agctaatttt tgtattttta gtagagacag ggtttcacca 124080
tgttggccag gccggtcttg aactcctgac ctcaagtgat ccacccacca ctgcctccca 124140
aagtgctggg attataggcg tgagccactg tgcccagcct gcttgttttt gtatcatata 124200
tatgcatcat cataatcatg cattatcaac ctttgtattt ctgtcaggac atagaaacca 124260
ttagagtgct tggaagagag ccttttttttt tttctcgcat ttaatgcttt ttttggtatt 124320
catttcataa tcagcttacc aaaacattac ctgcattata ccccatcaag gtagaaatct 124380
ttgtgttatc aatattggtt actccctttc cacaccgagt catcagtaag tcctgttcta 124440
tccaaatagg tcatatgcat ctagctcacc cctcagtgct gttttgtttt gaatttgtac 124500

-continued atgtttactc ctgatgcctt gtagttatga tgatgtgttc ttattttatt ctgtgcatac 124560
aagttctcag ctcgcttttt agggaaaatg accatgtctt cctttcctat aaattccttt 124620
ctatctatca agtcctcaac agagaatagg tacccataaa tatgtgattg ttagtttctt 124680
tgcctcagtt gtagtctgat ccttacagct tttaaacaac agtagagttc accgtcaaga 124740
actaaggatg gttggcaggc agatagaaag gtagcaagtt gacccaacta tctctgggga 124800
agtgggaaca aagaaaggtt acatcagcac tgtcatcaca tagctctata gttctaggcc 124860
tgcaggctca atcaagtagc cttgtataag attctctgga ggaggtgctg aaagttgctt 124920
atacttgcta tggaatttga ttttacttcg gatatctttt taccataggt acttctccct 124980
ccaagccaca catcctcttg gatttgatga tgttgtacga ttagaaattg aatccaatat 125040
ctgcagggaa ggtgggccac tccccaactg tttcacaact ccattacgtc aggcctggac 125100
aaccatggag aaggtaaccc agaacttcaa acgtatcaaa ctacaagaag ttttattggt 125160
agaactcata aaatataagg tgggaaaacc aagcagaata gcacagtgga aattgaagca 125220
gtccagcaaa gtgattaaga gcagaggcct tgagtctggc ctggtatgta cagtcacgtg 125280
ccacataaca ttttagtcaa cagtggactg cgtgtacgat ggtcctgtac gattataatg 125340
gatcaaagct ggtagtgcaa taataacaaa agttagaaaa aataaatttt aataagtaaa 125400
aaagaaaaaa gaaaaactaa aaagataaaa gaataaccaa gaacaaaaca aaaaaaatta 125460
taatggagct gaaaaatctc tgttgcctca tatttactgt actatacttt taatcattat 125520
tttagagtgc tccttctact tactaagaaa acagttaact gtaaaacagc ttcagacagg 125580
tccttcagga ggtttccaga aggaggcatt gttatcaaag gagatgacgg ctccatgcgt 125640
gttactgccc ctgaagacct tccagtggga caagatgtgg aggtgaaaga aagtgttatt 125700
gatgatcctg accctgtgta ggcttaggct aatgtgggtg tttgtcttag tttttaacaa 125760
acaaatttaa aaagaaaaaa aaaattaaaa atagaaaaaa gcttataaaa taaggatata 125820
atgaaaatat ttttgtacag ctgtatatgt ttgtgtttta agctgttatg acaacagagt 125880
caaaaagcta aaaaaagtaa aacagttaaa aagttacagt aagctaattt attattaaag 125940
aaaaaaattt taaataaatt tagtgtagcc taagtgtaca gtgtaagtct acagtagtgt 126000
acaataatgt gctaggcctt cacattcact taccactcac tcgctgactc acccagagca 126060
acttccagtc ttgcaagctc cattcatggt aagtgcccta tacagatgta ccattttttta 126120 tcttttatac tgtattttta ctgtgccttt tctgtatttg tgtttaaata cacaaattct 126180
taccattgca atagtggcct acgatattca ttatagtaac atgtgataca ggtttgtagc 126240
ccaaaagcaa taggttgtac catatagcca aggggtgtag taggccatac catctaggtt 126300
tgtataagta cactctgtga tgttagcaca atggcaagca gcctaacgga aattctgttt 126360
attgattgat tgattgattg attgattgag acagagtttc actccattgt ccaggctgga 126420
gtgcagttgc acagtcttgg cacactgcaa cttctgcctc ccaggttcaa ccaattatcc 126480
tgcctcatcc tcccaagtag ctgggattac aggcaggcac caccatacct ggctaatttt 126540
tgtattttag tagagacagg gtttcaccat tttggccagg ctgttctcga actcctgacc 126600
ttaagtgatc tgcctgcttt ggcctccgaa agtgctggga ttacaggcat gagctaccat 126660
gcctgggcag taactgaaat tctctaatgc cattttcctt atctgtaaag tgacgataat 126720
atgcacgttt acctcaaagt tactttgatg attaaagtaa ggtaatgtat ataaaataca 126780
tattaacata gtacctgaca catggtaagc atcaaaaaat gttaactact tttattacta 126840
ttattattac gtatttttaa ataattagag agcagtatca aaaattagct gggcgtagtg 126900

-continued gcatgcacct atagttccag ctactcagga ggctgaagct ggaggattgc atgagcctgg 126960
gaattaaagg ctgcagtgag ccgtgttcat gcccctgcac tccagccttg gtgacagagc 127020
aagaccctgt cttgaacaat taaagaaggc attatgccgc aacgttagct tagaaatgat 127080
ccacatatat caccagtaac tgtcaacagg attggaaccc tagttttggg tattatgatc 127140
acaaggtatt attaatagct tattaataat aaagcgttgg ctaggcacgg cgactcacat 127200
ctgtaatccc agcactttgg gaggccgagg tgggtggatc acctgaggtc aggagtttga 127260
gaccagcctg accaacatgg agaaacccca tctctactaa aaatacaaaa ttagccgggc 127320
gtggtggtgc atgcctgtaa tcccagctac ttaggaggct gaggcaggaa aatctcttga 127380
acccgggagg cagaggttgc agtgagctga gatcgcacca ttgcactcca gcctgggcaa 127440
caagagcaaa actccgtctc aaaaatataa ttataataaa taaataaaag taaagtattg 127500
atgtttgtga atgatttatt cttctaatga actagaggag atttttccag gaatttcaga 127560
gccagtgagg ttatgttgct tgtatgtgtc atgtgtatcc aggtgaaaaa acttaattaa 127620
acgctattat ataataccat acataaaaac tgaattttag gaatactgaa gaatgacata 127680
tagaagtcaa atcattaaat agctagtagt aaacagaata gagtgtcagc tgttacccaa 127740
tgatgataat attttcacga ttaaaattaa accttttctg attttaaagg aaaagttcag 127800
atctgtatca tataaagaat gtaaattttc agggtaataa aattaaaatg cagagagaaa 127860
aatgcaaaaa tagttcttac tagatgtgtg tatgtaagga acttagacta attttaagaa 127920
cactgtcaag accctggtag ttaggtagga aaaaagacat gaatgattca ttcaacaaaa 127980
actttgagta tttctgtgct agatggtagt gttacagtgg taaacaaaat aaatgtgttt 128040
ctgctatcct ggagcttagt ctacaaaaaa ggtacatatt ggccgggcac ggtggctcac 128100
gcctgtaatc ctagcacttt ggaagatcga ggcgggtgga tcacctgagg tcaggagttc 128160
aagaccagct tggccaacat ggcgaaaccc cgtctctact aaaaatacaa aaattaactg 128220
ggtgtggtgg cggacacctg taatcccagc tactcgggag gctgaggcag gagaatcact 128280
tgaacctggg agacagaggt tccagtgagt cgagatcatg ccactgcatt ccagcccggg 128340
ggacaaaagc gaaaatacgt ctcaaaaaaa caaaaacaaa caacaaaggc acgtattaaa 128400
tacgaacata aatatttaca aattatactg aataagttct catgtttatt atttgcttgt 128460
ccagttacaa acttttcctt cgtagaatta gaaatataaa taataaacat gagaactcat 128520
tcagtataat taataattat taaatgtaaa taaaaacatc tatgtacaat taggcattta 128580
tttaagaatt atttgaaaaa aaaacaatgt ggaaacagat attttgatat attgctagtg 128640
attgaaattg ataatgttct tttgaagagt aaagtgacca tatatattaa agttaaaatt 128700
taactcagca atcacacgcc tggtgagtta tcttaaggaa atcagtttga aagtaaaatc 128760
aatatatgca caaagacttt aacatttatc ataaaccaga aaaatcgagt ttcaaattat 128820
atcctatgga ctattttctg ctaaaaagta ttaatatcaa ctttatgtaa tactttcgtg 128880
acaaatattt tgggggagaa aacccaacaa aattacatgc attgtaattt tttttttttt 128940
ttttttttta gacagtcttg ctccagcgtc caggctggag tgcagtggtg caatctcggc 129000
tcactgcaac ctccatctcc caggttcaag caattctcct gcctcaggcc tcccgagtag 129060
ctgggattac aggcgctcac caccatgcct agctaatttt tatagttttt agtagagatg 129120
gggtttcatc atgttggcca ggctggtctt gaactcctgg tctcaagtga tccgtctgcc 129180
tcggcctcct agagtgctga gattacaggt gtaagccact gcacccagcc ttatgcatta 129240

-continued

```
taattttaat ttgtaaactg tacaaaggga taatacttgt agtacaacaa gaagtaaaaa 129300
catttgttat aggtagttaa catttgtaac cagtagaatt ataggtaaaa tttatttatt 129360
taaaacagtt ttagttggat ttgatttcaa ctttaaaata atgcttttca tctctatcag 129420
gtctttttgc ctggcttttt gtccagcaat ctttattata aatatttgaa tgatctcatc 129480
cattcggttc gaggagatga atttctgggc gggaacgtgt cgctgactgc tcctggctct 129540
gttggccctc ctgatgagtc tcacccaggg agttctgaca gctctgcgtc tcaggtattg 129600
actgattgcg tctgccatta gggagaaaag catacacatc ctttccttca catcccagta 129660
acagatccta ttatttgtaa attttaagtt gtggaaaaaa aagataaaag ccaggcacag 129720
tggcctgtgc ctgtaatccc agcactttgg gaggctgcgg tgggcggatc acacgaggtc 129780
aggaattcga gaccagcctg gccgacatgg tgaaacccca tctctactaa aaatacaaaa 129840
attagccggg catggtggca ggcacctgta atcctagcta cttgggaggc tgaggcagga 129900
gaatcgcttg aacccaggag gcagaggttg caatgaacca aaatcacgcc actgcactcc 129960
agcctgggtg acaaagtgag actgtgtctc aaaaaaaaaa aaaaaagaga gaaataaaat 130020
tagcctactt actatcttct aatcaaagca tttgtggtaa cttaaaatat actgtattgt 130080
aaagtatcat gctgtttcat ttaggccatt attctatttg aatctgtggc tgtttctctt 130140
aataaatcaa gtaatatgga atatattcat agcctctgaa gagctcttta tgtaagtatt 130200
tatttaggat actttttgta aaataagtga atgaattctt aggtctcctt ttttttttctt 130260
ttcttgagac agggtctcct cgctgcaacc tggaaattct gggctcaaat aatccaccca 130320
ccacagcctc ctgaatagct gggactagag gcatgcacca ccacgcctgg ctaatttgaa 130380
attttttttt ggccaggcat gatggttcac gcctgtaatc ccagcacttt gggagaccga 130440
ggcaggcaga tcacgaggtc gggagatgga gaccagcctg gccaacgtgg tgaaaccccg 130500
tctctactaa aaatacaaaa attagctggt tatggtggct catgcctgta atcccagcta 130560
cttgggaggc tgaggcagga gaatggcttc aaccagggag tcggaggttg cagtgagccg 130620
agatcacgcc actgcactcc tgcatggtga cagagtgaga ctccatctca aaaaaaattt 130680
ttttttaaa tgatggagtc ttgctgtgtt gctcaggctg gtcttgaacc cctgacctca 130740
aatgccgcct gcttcagcct aagtttcttt tttttttgta aagagacagg gtcttgctat 130800
gttggccagg gtagtctcaa actcctggct tcaagcagtc ctcccacctt ggcctctcaa 130860
agtgctggga ttacaggcgt gaaccactac ctataatgtt gtgtttcact caaggccttt 130920
tgatttcgtt ttgcattacc gtgccacatt gtgcatttcc ttgacctttt ttgggttttt 130980
tggagtgctt tcatatgtta aaccatacct gattctcctc aaaatcacac aaagtagaat 131040
atcctaagac aagaaatcta aggaggcata aagaagttaa ctggttttat taaactcaca 131100
cagtaaatga tagagccaga aatattcccc ttctagtgtt cttcaccatc agcttaatgt 131160
agcataataa ttttctaatt actgttgaca aataaataac cctttgaatt ttcaatactg 131220
ggccttggat aaattttcct aatttgtaag agagtattat cgtattgcca tttacaaagc 131280
tctcctgagt atctttttct tctgttaagt ttacctagga gataaactgc tgagtatggt 131340
tgccattttg gtttttttgat ataggttaga atgtcttggt tttttttttt tttttttttg 131400
gtttttgttg ttgtcattgt ttgagacagc atcttgctct gtcgcccagg ctggagtgca 131460
atggcacgat cgtggctcac tgcaacctcc acctcccggg ttcaagcaat tctcctgcct 131520
cagcttcctg agtagctggg attacaggca tgtgcaacca cacctggcta atttttgtgt 131580
ttttagtaga gaaggggttt caccatgttg gtcaggctgg tattgaactg ctgacctcat 131640
```

-continued gatccacctg cctcggcctc ccaaagtgct gggattgcag gcatgagcca ctgcacctgg 131700
ctgaatgtct tgtttttgat taggcactta agaaaggcct aggtactaac cataaaatat 131760
atttttatac cttttgttga tactatatat atagaaaact gcacttatca taaccttaga 131820
caccttgaag aatgttcaca agcagaacta acccatgtga cccagcatcc agatcaaaaa 131880
cagcattatc agcccctcta gaagccctct tgggcccctt ccattcactg tccttcttgt 131940
caccagggta gctactatcc tgacttttga tggcatagat tagcattacc tgttcttgtc 132000
attttataaa taaaaccata ctgtgtattc ttttcttgta cagctttatt gtgctaattc 132060
acatttacat catacaattc agtggttttt atatggtcac agagttaggt aaccattacc 132120
acatcgattt tagaacattt ttttcactcc agatagaaac cccctttact taaactccaa 132180
atcccccact ccaccagccc taggcagcca ctagtctact ttttatctct atagagacaa 132240
tagatttgct tattctggac atttcataaa catggaaccg tatattatgt ggtcttttgt 132300
tgccaactgt ctttcactta gcatcatgtg ttcaaaagag catcatgtta tccatgtttg 132360
gcatgtatca gaattttatt cctcattatg gccaaatatc ccattgcaag gatttatgac 132420
attttatttg aattgtaccc tcctttctgc catttatcaa taatgctact gtgaccattt 132480
gtgtacaagt ttttgtgtgg atacaggttt tctttttgtt tttaaatttg aggtggagtc 132540
ttgctctgtc gcccaggctg gagtgcagtg gcacaatctc ggctcactgc aacctctgtc 132600
tcctgggttc aagcagttct cctgcctcag cctcccgagt atctgggact ataggcacgc 132660
accaccacgc ccagctaatt ttttagtaga gatggggttt caccatgttg gccagtctgg 132720
tctcgaactc ttgacctcaa gtgatccacc catctcggcc tcccaaagtg ctgggattac 132780
aggggtgagc cactatgccc ggctgtggtt ttcatttctt ttgttgtata tacataggag 132840
tagaattgct gagtcaagag gtaactctta aacttattga aaaactgcca gattgttttc 132900
cgaaaaggct gcaccatttt gcaatcccac cagcagtgta tgagttttac agcttctcca 132960
catttcattg gaacttatta tctgtttggc tgtttttaaa aatgatagtc attccaataa 133020
gttctacttc agtgtggttt ttgcacttct ctgatgagta atgatgttga gcatcttttc 133080
atttgcttat tggcctttgt tctagctttg gaaaaatgtt tattcaaatc ctttggccat 133140
ttttattttt atttttattt atttattttt ttttgagacc aagtctcact ctgtcagcca 133200
ggctggagta caatggtgtg gtctcagctc actgcaacct ccgcctcctg tgttcaagtg 133260
attctcctgc ctcagcctcc cgagtagctg ggattacatt tcaggcacct gccagcatgc 133320
cgggctgatt tttgtatttt tactagtgac agggtttcac catgttagcc aggctggtca 133380
caaactcctg acctcaggtg atctgcctgc ctaggcttcc caaagtgctg ggattacagg 133440
cgtgagccat tgggcccagc ctagattttc ttttttcttt ttttttttga gaaggagtct 133500
tgctcttgtt gcccaggctg gagtgcaatg gcacaatctt ggctcactgc aacctctgcc 133560
tcctgggttc aagcgatttt cctgcctcag cctccccagt agctgggatt acaggtgcct 133620
accaccacac ccagctaact tttgtatttt ttttagagac agggtttcac catgttggcc 133680
aggctggtct caactcctga cctcaggtga tccacctgcc ttggcctccc gaagtgctgg 133740
gattaccggc atgagctacc aggcccagcc aattttctca ttatattgcc caggctggtc 133800
tcaaactcct gggttcaagt gatcctcctg ccttggcctc ccaaagtgtg gggagtacag 133860
gcgtgagcca ccttgctcag ccccttttgcc catttttaaa ttagattgcc tttttatatt 133920
gagtttcagg agtcctttat atattctaga taaatgtccc ttatcaaatt atattatttc 133980

-continued caggtatttt cttcattctg tgagttgtct ttcctctacc ttttaaaaaa ggtgggtttt 134040
tgtttgtttg tttgtttgtt tttttaagat aaggtctcat tctgctgccc aggctggagt 134100
gcagtggcac aatcacagct cactgccacc tcaacttcct gggccgaagt gatcctctta 134160
cttcagcctc ctgaatagct agggccatag atacacacta tcacacccag cttttttttt 134220
ctgtttgtag agacagatct tactgtgttg cccaagttgg tctcaaactc taggctcaaa 134280
gtgattctcc cacctctgcc tcccagagtg ctgggattac aggtgtgagc cacacgcaac 134340
ctgtcttttc actattaata gtgtcttcct gcttcagcct cccgagtagc tgggattaca 134400
ggcacccacc accatgcctg gctaattttt ttgcattttt agtagagaca gtgtttcacc 134460
atgttcaccc ggctggtctt gaactcctga cctcaggtga ttcacctgcc atggcctccc 134520
aaagtgctgg gattacaggc gtgagccact gcacccggcc aaaatattgc cttcttaaca 134580
gtattgtctt ctaatttgtg aacatggatg tatcttcatg tatttatgtg ttctttcatt 134640
tcagcagaat tttgtagttt tcagagtaga agcctttcac ctccttgggt catttattcc 134700
tatgttttaa gttcttttcg attccattat aaatagaatt gttttcttaa tttcattttc 134760
agattgtttg atgagagagc atagaaatac aagtgatttt tacatgttga tcttgcaact 134820
tcaactttga taaatctgat tgttagctct aatagttttc ttgtggattc tttaggattt 134880
tcaatatata agatcatgtc atttatggat agagatagtt ttttttctgg ctagaactta 134940
cagagcaatg atgagtagaa gtggcagaag caaaaatctt tgtcttgttt cctatctgac 135000
agggaaagct ttcagtttca tcatttaata tgatgttagg tgtgggtttt caataaatgc 135060
ctttttttcag attcaggaat ttccctatca ttcctgattt tttaaggctt tttttttttt 135120
ttaaatcatg aaagggtgtt gaatattgtc atgttctttc tgtatcagta taaatgatcc 135180
tatggatttt gggttttatt ctgttgatgt gaaatattaa ttgattttca gatgttaaac 135240
caaccttgca tacctgagat gaatctcact tggtcatggt gtataatctt ttcaatatgc 135300
tgctggattc catttactgg tattttgttg aagattttgt atctgaacgc ttaagataac 135360
atttacactc tatcagaaat gaattgacca taaatgtgag agtgtatttg tgggttcttg 135420
attctcttcc attccaaaga tagacataca tccgtctgta tgtctgtctt tatgccagta 135480
ccatactctc ttgattacta ttgctttgta ataagttttg aaatcagaaa gtataaatga 135540
gattttggta tctgagtaac agtcctcata gaattagttg ggaaatattc cctctttatt 135600
ctggtccctc tttcttttt gtttaactgt gtatcttgga gattgttcct tctcaacaca 135660
tgagagccgc tttccctacc ctcccacccc tgctatagag aggtctataa gtgtctgttc 135720
aattatttta tttacttaac ctattactta gtcggggaca ttaagcttgt ttatgtcttt 135780
tattttaaac aatgctgcag tgaataatct tgtatataag tcattttcca tcaatataag 135840
tctctctgta actgaatttt tagaagtgga atttctaggt caacctatgg ctctgtattt 135900
cacaaaaata ccaattctgg tttttcttgt ggaggtgggg agtaggaggt agaatgctgg 135960
aggagaactt gctgtactca gctggctagt cattttagaa aggtttcctt agcttctttt 136020
tgtcatatgg cctcaccaag aatcaaaaac attcctattt accctgtaaa catggggctt 136080
tactacccaa gatacatatt tctggatgta tgacagcttt tcatattgaa gaaataatgc 136140
tgtgagtaca gcacatttgt tggaacttag gtcgttaaga atgtcttata aattcataca 136200
ttatacattt tattttattt tattttttag tttttgatac agagtcttcc tctgtcgccc 136260
aggccagcgt gcagtggtac aatcttggct cactgcgacc tccatctcct gggctcaagt 136320
gattctcatg tctcagcctc cagagtagct atggttacag gcatgcacca ccatgcccgg 136380
ctaatttttt tatttttagt agaaactggg tttcaccata ttgaccatgc tggcctcgaa 136440
ctcttggcct caagtgatcg gcctgcctca gcctcccaaa gtgctgggat ccttgtattg 136500
ggtaaaagat gaatattgag ggctgcatgg tggctcatac ctgtaatccc agcactttct 136560
gagactgagg tgggaggagt cctggagccc aggagggtga ggctgcagtg agttgtgatc 136620
gcgccattgc acttcaacct aggaattata ggcttcagtc actgtgcccg gcatgtacat 136680
tttaatattg tgctttcctc ttttagctat agtatgaggt tacatttcag agtcattgtt 136740
gttaagcatc ttaatagtga tgaggttgag tgaaagttac ttctatttca aacactgaag 136800 aaaatttgt acaaatctgt cacattccaa gcccaggact gattgtttca tatacttcta 136860
attttacaat ttctattgta gtccagtgtg aaaaaagcca gtattaaaat actgaaaaat 136920
tttgatgaag cgataattgt ggatgcggca agtctggatc cagaatcttt atatcaacgg 136980
acatatgccg ggtaagctta gctcatgcct agaattttta caagtgtaaa taactttgca 137040
tcttttaaat tttttaatta aattttacat ttttttctaa tctattatta tatgcccaga 137100
actttcactt agagtgtgca gtataatgtg gtggttaagt ataaaggctc tggagtgact 137160
tcctgggttt taatcttggc tctgccattt attggcagcc gctaacctct tggtatctca 137220
gtttcttcat ctgtaaaatg agaataataa agtgaaaaga tgccaacatc atttactctg 137280
ggctgcataa ctgatacttg gaaaaagtat tcctttgagt ttaagaatta agttggttat 137340
tcattttagc ttgtaataaa aagatagtga ttcataggat atgccactta ctgaaattta 137400
ccacagatcc aatcataaaa tcactttctc ttccctaaag atagcttgat taacatgtaa 137460
aggtgtgtaa aggcttgatt acactaccct gatccgtacc ccagttccca gcagcaccat 137520
gaaaaaggga tttcaacata tttaattact ttcagtagaa agtaacagtg gtaggccagg 137580
cgcagtggct cacacctgta atcccagcac tttgggaggc cgaggtgggc ggatcacgag 137640
gtcaggagat tgagaccatc ctggctaaca cgatgaaacc ccgtctctac taaaaataca 137700
aaaaattagc cgggcatggt ggcaggcacc tgtagtccca gctacttggg aggctgagac 137760
aggagaatgg cgtgagcccg ggaggcggag cttgcagtga gcttagattg tgccactgca 137820
ctccagcctg cgcagtggag cgagactctt gtctcaaaaa aaaagaaagt aacagtggta 137880
ttgggagact gaggagccta gaaagtactt gaaggaagta aaaggtttgt ttgaccacat 137940
tgtatttgga aagccagctt tttcagctgt gtcagctttg tgtagtgatt tttagttctt 138000
cttttagaaa ataacggaca aggccgggca cggtggctca cgcctgtaat cccaccactt 138060
tgggaggccg agacgggcgg attacctgat ctcaggagtt cgagaccagc ctgggcaaca 138120
tggtgaaacc ccgtctctac taaaatacaa aaagttagcc gggcgtggtg gcgtgtgcct 138180
gtagtcccag ctactccgga ggctgaggca ggagaattgc ttgaacccgg gaggcggagg 138240
ttgcagtgag ccaagatcac accattgcac tgcagcctgc gcgacagagt aagactctgt 138300
ctcaaaaaat aataataaaa taaaaaagaa tggacagtaa acctaaatga gttcattccc 138360
aaagatgatg ttattcttaa gggatggttc atttatttaa gaccttacat aaagtctatc 138420
aattgcgtga tttttcactt ctgtaattgt gtgtatgtat aatgtaaata tatatgtttt 138480
tgttttgttt tggtttttttg agacggagtc tcgctctgtt gctcaggctg gaatgcagtg 138540
gtgcaatctc agctctctgc aacctctgtc tcccaggttc aagcgtttct tctgcctcat 138600
cctcccaagt agctgggact acaggcacgt gccaccacgc ccggctaatt ttttgtattt 138660
ttagtagaga tggggtttca ccgtgttagc caggatggtc tcaatctcct gacctcgtga 138720

-continued tccacccgcc ttggcttccc aaagtgttgc tattacaggc atgagccacc acacccagca 138780
tgtatttttt aaatgtataa aatgaagcag aaaagagaaa tgataatttt tcttcatctt 138840
gaaagattat cttcaccagg cgcagtggct cacacttgta atcccagcac tttgggaggc 138900
ctcggcaggc ggctcacttg agttcgaaac cagcctggcc gacatggtga aactccgtct 138960
ctactaaaaa taaataaata aagatggttt taatatatgt tttagtttta tgattttagc 139020
atctttctga aatttttctc aaggcaagta aatttgtatc agttggtata ttggtaccca 139080
tctatgaaat aacttattag gaagatatct ctaaaataag atcactttgc ctaaaataaa 139140
ctgatatatt gatgttcaca gaatttttct tttaaccgac ttgataaatg cattattctt 139200
gacgtcaagt gatccacctt cctcagcctc ccaaagtgct gggattacac acatgagcca 139260
ccgcacctgg cattattctt ataaaaggtt aaatttctag ttaagtttaa tgtcctcttt 139320
gttcatgtac cattgcttat tttcttccct tcctactcac agtaatcatt cttatggtat 139380
gcacttttgt ttgcttattt ttatgtaatt gatattacgc tccattctgt acgttgtact 139440
ttcattcaca gtgagttttg gacattccta tgttcatcta tacagactta cttcatttta 139500
actacactgt agtattccgt atgtaatatt tactataact catcactgta gcagagcatc 139560
tcatagtgta tgtattactg ttttgccatt ttggtatcaa tgagtattta agtcatttgc 139620
agtttttccc tcttataccc agtattacag aggatctctt tttatatgct tctttgtacc 139680
aagaggcaga ttaaaaaatt tttttttgaa aaaatttttg aaaaaaaatg aaatgaagtc 139740
tcactatgtt gcccaggctg gtctcaaact cctaggctca agcaatcctt ccatcttggc 139800
ctcccaaagt gctggggtta caggcatgag ccaccatgcc tggcctacat tttaaatttt 139860
gatagctctt acaatttact ttgtaaagta tctgcatcat tttatgttct caccagtctt 139920
taataagaat acttcatact tttggctgga cacagtggct cacgcctgta atcccagcac 139980
tttgggaggc cgaggcgggc agatcaagag atcgagacca ccctggccaa tatggtgaaa 140040
ccctgtctct actaaaaata caaaaattag ctgggcgtgg tggcgcaccc gtagtcccag 140100
ctactcgaga ggctgagaca ggagaatcac ttgaacccgg gaggtggagg ttgcagtgaa 140160
cttagatcac accactgcac tccagcctag caacagagtg agactctgtc tcaaaaaaaa 140220
aaaagaatac ttcagactta atttttttc cagtcttaag tgtttgctaa tgagattgag 140280
tttcttttgg tatgtctctt gattgttcag gtttttttctt ttatgaattg actgttcatc 140340
tctttttcac attatttctg ttgggtgatt ttattagtga cttgttaaaa ttctgtatat 140400
tttttcagca tgacacttca ttattcaaaa aaaaaaaaag attctctatg tttctcgata 140460
ctaatcattg gttggtaata ccttaaaaat aagaccctta ctgtattttt tgcttttttt 140520
tttttttttt tttttttttt tttgagatag agtcttgctc tgttgcccag gctggagtgc 140580
aatggtatga tctcggctct cagctcactg caactgcaac ctctacctcc ctgtttcaag 140640
caattctcct gccttagcct cccaagtagc tgggattaca ggcatccacc accacaccca 140700
gctaattttt gtatttttag tagagacagg gtttcaccat gttggccagg ctggtctcaa 140760
actactggcc tcaagtgatc cgcctgcctc ggcatcccaa agtactggga ttacaggcat 140820
gagccacagt gcctagccac tttttgcttt ttaactttgt tttatagtac tatagtttta 140880
gtataaacag atgtatgtat acacacaact atggctttat aatatgtttc agtcattgtt 140940
agagcaaggc ctacctttttg ggtgcttctt ttacaaaatt gtcttggcta ttcttgtgcc 141000
tttttcttta tttgtgaatt ttagaattgt gaattacctg ttgactcacc atgttttgta 141060
aactgaggat tttgaatgga attgcactca attaaagatt atcttgcttt ctgtgcagca 141120

-continued atgttttatt tcaaataatc cctactttaa attacttagg atagctataa attgtgtttc 141180
tggctttcta gatttagatg aaacgcttta aattgattgt tttctcctaa atttaaaact 141240
gattgttaga agttaaagtc ttctgttcat tcttatttag gaagatgaca tttggaagag 141300
tcagtgactt ggggcaattc atccgagaat ctgagcctga acctgatgta aggaaatcaa 141360
aaggtttgtg gtgtttttat acttcatatt aagcctttac tcacattagt gattgactgt 141420
aagtcaaaga ccacttaagg tttaaactgt ttattttgta aagtaaccac tgtatctttc 141480
accttgtgtt tatagtcaga agtaagtaca agggcttcct gtagtcacat ctttatgcaa 141540
tctcctctga atcaaaagtt agtgaacttg ctttgccact ccagaaggca catgaatatg 141600
aaaaagcatt gtctattttc ttatttaatg gcaaaatacc cgacctaagt tggacttaat 141660
gtttgagacc gtttatttta ttaaattata ttttttctct tttctttttt tttttgaga 141720 cagttcttgc tctgtcaccc agaccggagt gcagtggtct gaccgcacct cactgcaacc 141780
tctgcttcct aggttcaagc gattttcctg cctcatcctc ctgagtagct gggactacaa 141840
gtgcgcacca ccacacctgg ctaattttg tatttttagc agagatgagg tttcaccacg 141900
ttggctaggc tggtctcata ctcctgacct caagcaatcc atccgccttg gcttcccaaa 141960
gtgctgggat tacaagtgtg agccaccatg cctggcctta ttaaattatt tttattaaat 142020
ttcctcaaga ttgatgaaag taatgaaata taaaagtaat gaaatatatg tggaaaatag 142080
actggattaa gaaaatgtgg cacatataca ccatggatac tatgcagcca taaaaaagga 142140
tgagttcatg tcctttgtag ggacatggat gaagctggaa accatcattc tgagcaaact 142200
gtctcaagga tagaaaacca aacaccgcat gctctcactc ataggtggga attgaacaat 142260
gagaacactt ggacacaggg tggggaacat cacacgctgg ggcctgtcgt ggggtggggg 142320
gctgggggag gaatagcatt aggagatata cctaatataa atgacgagtt aatgggtgca 142380
gcacaccaac atggtacatg tatacatatg taacaaagct gcacgttgtg cacatgtacc 142440
ctagaactta aagtataata aatttaaaaa aaataaatat atgtggaaaa tattaatagg 142500
tcaaaattca aattgttcat ttaatcagaa gagtagttta gtcaaatcca agggttagac 142560
aacagaaatc tttttgtca agtgcattct ttgtgactga tttcattttc ttcctggttt 142620
acacaggaag atttcagaaa caaatgtgga tccgtgacag atggtatcta gaagttttta 142680
gtttggttga attgacagta ttttattgag taaaagatac taatttttgt aagaagaaaa 142740
attcaatttt gataagtatg tttaagatta agagctattg gccaggcgct gtggctcatg 142800
cctgtaatcc tagcactttg ggaagctgga gcaggtgggt cacgaggtca agagattgag 142860
accatcctgg ccaacatggt gaaaccctgt ctctactaaa ttagccaggc gtggtggcac 142920
atgcctgtgc acccgcctcc gggtttaagc gatcctactg cctcaggctc ctgagtagct 142980
gggattacag gcgccatggc taatttttgc atttttagta gagacagggt ttcactacat 143040
tggccaggct ggtctggtct caaactcctg acctcaggtg atctgcccgc cttagcctcc 143100
caaagtgctg ggattacagg catgattcac catgtctggc catttatctt attttctttt 143160
tttttttttt ttttgtttga gacggagtct tgctgtgtcg cccagagctg gagtgcaatg 143220
gtgcgatctc agctcactgc aacctctgcc tcctgggttc aagcaattct cctgcctcag 143280
tcttccaagt agctgggatt acaggcgcgt gccaccacat ctagctaatt tttgtatttt 143340
tagtagagac agggtttcac catgttggcc aggctggtct cggaactcct gacctcgtaa 143400
tctgcccacc tcggcctccc aaagtgctga gattacaagt gtgagccact gtgcccagcc 143460

-continued

```
atcttatttt ctttcttttt ttttgtcggg tgggaggggg acagagtcta gctctgtcgc 143520
caggcttggc tcactgcaac ctctgccccc caggttctag caattattct gcctcagcct 143580
cccaagtagc tgggattata ggcacctgcc accacgcctg gctaattttt tgttattttt 143640
agtagagatg ggttttgct atgttgacca tgctggcctc aagtgatccg cccaccttgg 143700
cctcccaaag tactgggctt acaggcgtga gcttgtattg ggtaaaagaa caatattggg 143760
ggctgcatgg tggttcatac ctgtaatctg agcactttgt gagactgaga tggaaggagt 143820
gttggagccc aggagggtga ggctgcggct gcagtgaatt gtgatcacgc cattgcactt 143880
ccacctaggt aatggagcaa gaccatgtct ctaaaaaaca aaacacaatt tttttaagga 143940
atactgggaa gaggtcagtg gtggttttag aacagaggaa gtgccagatg acctttgtga 144000
ggcattggcc aggaagaact ctacagtgtc tttaggtagc ttctgtccat aaggataatg 144060
gggtctcctc cccagtatta atagaaaatc tctgagctgt tttttttgt ttgtttgttt 144120
tgtttttttt tcctgagatg gagtctctct ctgtcggcca ggctggagtg ctgtggcgcg 144180
atcttggctc actgcaagct ctgcctccca ggttcacacc attctcctgc ctcagcctcc 144240
caagtagctg ggactacagg tgtccaccac cacgcccagc taattttttg ttatttttag 144300
tagagatggg gtttcaccat gtcagccagg atggtctcga tctcctgacc tcgtgatccg 144360
ctcgcctctg ccttgcaaag tgctggagtt acaggcgtga gccaccgtgc ctggcctggt 144420
tttttgttg ttgttattta tttatttatt tatttatttt ttgagacaga ctctcgctct 144480
gtcgcccggg ctggagtgta gtggcacgat gtcggctcac tgcaagctct gcctgccagg 144540
ttcaagccat tctcctgcct cagcctcctg agtagcaggg accacaggcg ctcgccacca 144600
cgcccggcta attttttgta tttttagaag agacggggtt tcaccgcatt agccaggatg 144660
gtctcgatct cctgatgtcg tgatccgccc acctcggcct cccaaagtgc tgggattaca 144720
ggtgtgagcc accgtgcctg gcctgatttt tttttttttt taatctggtc tcatacctct 144780
gacagctcat gaagaagtgc tcctgcttca tatgtatatg tgttagcata gtgttaacat 144840
agcataggtg ttcggtgttt gcagtttctg tttgttttat atgaattaag gtgtattatg 144900
agcagttgaa gatatatagg aaattttttc ccaaaccact atctctgctc gttctattca 144960
ttcagtctgt ttatgttatt ccttcattca ttcattttat agaacagtgg agtgcctact 145020
gtatgcatct attgttctgg gtcctgggga agaaaacaaa gttcctgctt tcatggaact 145080
tacattatat tggcggagac agtaacagac aaacaaatgt agcctgtgta catgtgttac 145140
atgaaaagca gggtaggggg ctgggagaga gtagtaggga gtgctatttt cgaggtggtt 145200
gtcaggaaag gcctcactga ggaggtggca ttttgagtag acctgagcgc agcgggggcg 145260
taagcccagg cagcatgtgg aggaagagtg ttcttggtga aaggaacaag gatagaggcc 145320
cgaagctaga gagctcagca tgatcaagga acagcaagcc ccgtgtggct ggaatggagt 145380
gagcaaagga atgagcagta gaaggtgagt gagttgggag gtcaccagag accatggcaa 145440
ggacttgaaa gtgtcaggga cacattggaa gttggagcag ggaaatgatg ggatttatgt 145500
tttgtttttg ttttatgttt agtgttttta agggattgct ctatcagcta tttggaaaat 145560
ttagtgtagg gcttcaagaa gagaagcaga gaaacaacat tcttgccata gtcatagtct 145620
aagtaaggga tgatggtggt gtggattagg ctggtagtgg aagaccagtc cagttcgggt 145680
tgtatttgaa ggtagaggca aaaagattat atttctacca gcaagcccat ctatgaagtt 145740
acttgtatta ttaatttaat tgagacatgc ccacataaac taataaatag gaatttctgc 145800
agtttggtta aacacccctg tatatcctgg ttcttctttt agttgtccag atgtctcttt 145860
```

-continued aagtcaagta tttttggtg gtgtaggagc ctagagattg aatttattca cccaaaaggc 145920
atttgagtga ttactatgtg ccaggcacta tgctgaatgc caaggatgta aataagaggg 145980
cgtagtctca gtctgtttta ctccagcttg gttccttttt aatgaccctg acttgttaag 146040
catatcagtt atcctacaga atgtttaatc ttctgtactt tcctggttgt gttatttagc 146100
ttatttctct ttccttgaca tttcttgtaa actggaagtt acacctatag tcttgatgat 146160
tcgtgttaca cattttagat tagaacacat catgtgttgt atatggtgtt tttgaaagcc 146220
tctctgtata ttggtctgta cattaaaatg ttgcctgaat ggatacacat aaaatttaac 146280
agtgattaca ttagagatga gaagaaagag gtgcctttta cttttcaata taccttttcc 146340
tctgcttttt gaactttctt gccctatgca tacgttattg cttaatcatc cacctcatct 146400
cttcccctgt ggctttctgt tgcatttgga atgaaatcta gcctctttgc tgttacctgt 146460
ggatgtccct tgctggcctc tatcacctta ctttgaacca ctcctttcat ggactgagct 146520
ctcattggac tatcttttat tcttttgctg aagtttcttc actttgagtg cctctgcagt 146580
tgctatttca tggctgtggc aagccctgcc atggctttca tgcaaggatg gttcctcctt 146640
ctcatctcaa tattatctct tcagagaggg accttcccaa ctccgatgat ctaaaatcct 146700
ttgtatatac cactcactac cacttctttc ttttctttc cttttatctt tttttttt 146760
tttttttt gagatagggt cttgctctgt tgcccaggct ggaatcacga ctcactgcag 146820
cctcatcttc ttgggctcaa atgatcctct cacctcagcc tctcgagtag ctggaactgc 146880
aggcacacac caccatactt ggcttattat tttactttt gtagagacag ggtttcacca 146940
aggctggtct caagctcctg ccgcaagcaa tccacatctc tcagcctccc aaagtattgg 147000
gattatagga gtgagccact actcctggcc tattttctta ttcactgtct aaaattatct 147060
tgttcattta tttacatact tgtttatagc ttatttctca gctggacatg gtgcctcaca 147120
cctgtaatct caatactttg ggaggctggg ttggagaatt ggttgagccc aggacttcaa 147180
gaccagcctg ggcaacaaag tgagaccctg tctataaaaa attgtttaaa aattagctgg 147240
gcatggtggc acatgcctgt ggtcccagct acttgggagg cagaggtggg agaatcgctt 147300
gggcccagga ggttgaggcg acggtgagcc atgattgtgc cactgcactc tagcctagtg 147360
acagagtgag accatgtgtc taaaaagtaa ataaaaatag tttctctttc atgactagaa 147420
tattacctct atgtgggcag ggagtttgtc tatactattt ggcactatat ttcctgattc 147480
tgaaattatg cctagcacat ggtaagtact ccttaaatat ttattgactg aattatttaa 147540
tacttaagaa tttcatttgg gattatctga gtggtaagat tacggattat atttatgtaa 147600
gaaaaaatca ttttttaaac ttggttgccc tttgccacac tgacatagac actaagtttt 147660
cttagccaga ttacttccga ggatactcac agaggccatt ctcttctcaa tccccaaata 147720
attgatattt cttagcactt tcaagctaat gcaattctta gatgatgtat ctgtgtatat 147780
catatcctca ttctacaaat gtagaaattg aagtctgggc acagtggctc tcacctgtaa 147840
tctcagcagt ttgggaggcc aaggcgagcg gatcactgag gacaagagtt aagaccagcc 147900
tggccaacat ggtaaagcct tgcctctatt aaaaatacaa caattagggc cgggcgtggt 147960
ggctcacgcc tataatccca gcacgttggg aggccaaggc aggcagatca cgaggtcagg 148020
agttcgagac catcctggct aacacagtga aaccccatct ctactaaaaa tacaaaaaat 148080
tagccaggca tggtggcacg cgcttgtagt cccagctatc gggaggctga ggcaggtgaa 148140
tcccttgaac ccgggaggcg gaggttgcaa tgagctgaga ttgcaccgct gaactccagc 148200

-continued

```
ctggtcaaca gagggagact ctgtctcaaa aaaaaaaaaa aaaaacaatt agccaggcgt 148260
ggtggcgggt acgagtacct gtaatcccag ctactaggga ggctgaggga ggagaatcac 148320
ttaaacccag gaggtggagt ttgcagcggg ctgataatgc accactacat tccagcctgg 148380
gcaacagagt gagactctgt cttaaaaaaa aaaaaaagaa agaaagaaat tgaggaatgt 148440
ggagattgtg gtctgtgatt tgttaggaat cacacagcag gttagtagca actacagggc 148500
tttggttcag aataccacct tgacaatggt ttgtttacag ttcggctccc cttcctctgc 148560
ctttctctcc ttccttattg agggcagctg gaaagaattt tcatcattta ctagcctata 148620
gctttaattt gagttttgaa accttgataa tagagcacag aggaaaagac tgagttttct 148680
tttttgaga cagtcttgct ctatggccca ggctggagtg cagtgacacc atctcagctg 148740
gttgcaacct ctgcctccca ggttcaagca attctgcctc agcctctcga gtagctgaga 148800
ttacaggcac gtgtcaccac gcccagctaa ttttctgttt ttgtttcgtt ttgttttttt 148860
ctgagatgga gtcttgctct gtcacccagg ctggagtgca gtggtgcgat gttggctcac 148920
tcaaacctct gtctcctggg ttcaagcaat tcttctgcct cagcctcccc agtagctggg 148980
actacaggta cgtgccacca tccctagttc atttttgtat gtttagtaga gatggggttt 149040
cactatgttg accaggctgg tctcgaactc ctgatctcag gtgatctact cgtctcagtt 149100
tcccaaagtg ctgggattat tggcacacgc ctatttttgt atttttagta gagacggggt 149160
ttcaccatgt tggttagact ggtctcaaac ttctgacctc aagtgatttg cccgccccag 149220
cctcccaaag tgctgggatt acaggcgtga gccaccgtgc ccagccaaga ttgagttttg 149280
aaaagagcct tctgagatta tgagaagggc aagcaagata acttaagaag ttacattaaa 149340
atcatctaag agacagtgta acaagaagga attgtaaaat gatgttatga gcacgtgccc 149400
aatgtagtgg caatcccttg tgcttcgata cattggtggg agacaaaact gtacttaaat 149460
tgataaatcc cttacatgtc attttaagga gcttagactg actcccatca tgtagacatc 149520
agagatttct tttttttttt tttttttttt tttttttttt tttgtgacag agttttgctc 149580
ttgttgccga ggctggagtg caatggcgtg atctcggctc accacaacct ccacctccca 149640
ggttcaagca attctcctgc ctcagcctcc cgagtagctg ggattacagc catgcaccac 149700
cacgcctggc taattttgta tttttagtag agacggggtt tctccatgtt gtggctggtc 149760
tcgaactcct gacctcaggt gatcctcccg cctcagccac ccaaagttct gaaattacag 149820
gcgtgagcca ccgcgcccag cccagagatt tctaaacaga gttctaacca gatgcttttc 149880
cctgtcagta gaatgagaat gaattggagg tgggagagac tggcatgagg gacaccagtc 149940
agccagtgga attagctggt aatgttgata ggagaagaaa aagattcaaa gttaggtagt 150000
ggtagcaaga attagaggga aggtcggatt tatgatatgt ccaaggttga attctaaggt 150060
gaaatttggt ggcagatttc atgtgtaaat tgggaaggta gattgagttt ttttaacatg 150120
ggttttctaa catgtcaata gagtgactct gcagggggc ctgacgagag aacagtgcat 150180
ggggtgattc aacagccagt tgagccttca tgcagagcat ttaacactgt gactctgtag 150240
actctggttg gcagtaaaat ttcattaaac caatatttaa acccttaggt aataataaaa 150300
attgagggaa aaggatccag gttttgtatt ttttatgaat tcagttattg aattaaacag 150360
gaccttgcct caagaaataa tctaccaaca attaacttgt tttaaagcaa agttaggaag 150420
tgagcatgtt caaattatta aataaaaaag taagctgtgt atttcattca tagaaataga 150480
ggctggccta cttcggatga ttctcagcat gtgattacag atgtgggctt atacatccta 150540
gggagttaag gcgtactctg gcttggatag agtagagctc tttgaaactc ttctctcacc 150600
```

-continued

```
cagctagttt atatagacta gagaactaga atgtagcagc atactctgtc ttagaagccc 150660
ttttatatag gagctggtct ggaaggtttg aaaacataac aaatgtgttg gtgtctccca 150720
atgtattgct agattcttac ccaagagcat tatcctggtt agggtttggt ttggttttgt 150780
tttgtttttt aatgtttgcc acaaactaac actagatgtt agttctttca tcaagtgagg 150840
agagtagaag aaaagtccag aactctgaaa cacctttca aaagtttttc aagccatgat 150900
gtttgcaagt taaatgctct gttatgtaag caatataatc agtttttatt aatgtaacat 150960
tccttagtgt tttggggtat cacacaaaaa agaatatcca tatctggaag caacagcttt 151020
taaataagag cattgtggtg gtggtggtga tagtggtttt tttttttttt tttgagttgg 151080
agtctcgctc tgttgcccag gttggagtgc agtggcacga tctcagctcg cttcaacctc 151140
tgctcccagg ttcaagcaat tcttctgcct cagcctcctg agtagctggg attataggca 151200
cctgctacca tgcctggctg atttttatta ttttagtaga gacaggtttc accatgttgg 151260
ccaggctggt cttgaactct taacctcagg tgaatcaccc acctcggcct cccaaagtgc 151320
tggaattaca ggcatgaacc accatggcca gccaaataag agcattttta atgtaaaatt 151380
atgcatgaaa tgtacattca attttgtctt tgtttactag gatccatgtt ctcacaagct 151440
atgaagaaat gggtgcaagg aaatactgat gaggtaaatc ctacctttag gataaaaaga 151500
tttctgttta taagtgccac cctcatgtaa gtgaggttta aaattttcct tttctttagg 151560
tcccatgttt aagcagcatg gcacatttat gttctcttac ccagaatgta ccaagaaagg 151620
gtggtccctt cttaacatct aacaattgcc tggtagtagc agtgaaggta tcttcagtca 151680
gaggctagga ccactgaagg atatacatgc attcaagttt ccatcagcca gcaggcatca 151740
gtaatcagtg tgtagatcaa aagctcaaat gtttccttcc ccactggcag ttttacttca 151800
agtagtggag gcttgctttt ttaatagtta attaagtaca ttgagagatg ggaggtgaaa 151860
aaaggaaaat gttttatttt gaccatctaa tatgaaagta gttcggtgtt aggtatccag 151920
tagttgacac tggaagacag ggaatgacat gttaatattc atagccagag ggtggcccag 151980
gttttttcgt acatgggaat gaaattctta tccaaataag tagaaattat gtgcgtaagc 152040
catttgttaa gagcactgag tatgtgcatc tcgatccatc taatgaataa ccattatcac 152100
cagtttaaat tattttcttt aggcccagga agagctagct tggaagattg ctaaaatgat 152160
agtcagtgac attatgcagc aggctcagta tgatcaaccg ttagagaaat ctacaaaggt 152220
aaggatgact tcgttttgtg taaactaaaa agtattattt tccaggtgta aaaataaaaa 152280
agaacataag ggtttctttt gcctttgaag gattaactgc tgtggggatt accttcttat 152340
cataagcaac tagaaaattg acaaactaaa tgaaacaact gtttgcatat attggacaat 152400
gggcaataca gggaaaccat ggaaaccaaa cagagcccag tagtcttgct gaacgaaaga 152460
gttaaatatc aaagttcagg ccaggtgcag tggctcacgc ctgtaatccc agcactttgg 152520
gaggccaagg cgggtgaatc acttgaggtc aggagttcaa gaccagcctg gccaacatgg 152580
tgaaaccctg tcttagccgg gtgtggtggc aggcacctgt aatcccaact atttgggagg 152640
ctgaggcagg agaatcgctt gaaccaggga ggcggaggtt gcagtgagcc gagatcacac 152700
cactgcactc cagcctgggc gacgagcgaa accccatttc aaaaaaaaaa tcaaagttca 152760
gagagctcaa tttgagtaga agttgtagga taaggtagca gaaaagagga agctgcccag 152820
aaagaaagcc gtagagatat ttagagagat tcccatggat ccttggccta ggagtgatct 152880
gtatatgtgt ggggtgaaaa cgcatgtgtc caggtagaga aaccccccaga aattagtagg 152940
```

-continued

```
ctgaatgatt gctggaacat agggctaaga aaagttcatg gccagaagga tctggccaga 153000
gtagagagac ttagtaatac acaaggcatt gggtagtgtc ttcacagagg ttatgcctta 153060
ctactgaaga taaattagtc ctagagtaca agcacctgaa ccaagtttca aagcaaattt 153120
ttaaagggtc aaattaccta acaactgcat gccaaaacaa aggcctaacc ctctttacag 153180
taacacaaca aaattcagca cttcacagtg taaagttaga atgtctgacg tccaggctgg 153240
gcgcagtggc tcatgcctgt aatcccagca ctttgggagg ccgaggcagg tagatgacct 153300
gaggtcagga gttcaagacc agcctggcta acatggtgca accccgtctc tattaaaaat 153360
acaaaaactt agccaggcat ggtggccggc acctgtgatc ccggctactt gggaggctga 153420
ggcaggagaa ttgcctgaac ccaggaggtg aaggttgcag tgagccgaga tcgcaccact 153480
gcactctggt ctgggcaaaa agagcaaaac tcaggctcaa aaaaaaaaaa gaatgtctga 153540
cgtcaatcac aaattaccaa gcatgacatg aagttgacct ataaccagga gaaaactcaa 153600
tctatagaaa cagacccaga tgtgagaaag atgatgaatt tagcagacaa agaccatcaa 153660
gtggctattt taaatattaa aaatatgttc aagtggccag gtgcagtggc tcatgcctgt 153720
aatcccagca ctttgggagg ccaaggtggg taggagttca agaccagctt ggccaatatg 153780
gtgaaacccc ttctctacta aaaatacaaa aaaattagct gggcatggtg gcaggtgcct 153840
atagtcccag ctatatggga ggctgaggca caagaatcac ttgaacccgg gaggtggagg 153900
ttgaggttgc agtaagccga gattgtgcca cttgtactcc agcctggaca acagagtgag 153960
actctgtctc aaaaaaaaaa aaaaaaaagt taaagaaaac aagagtataa tgagaaaaat 154020
gcaaaatagt tttaaaagaa ccaaatggaa tttcttaaaa taaaaaatac cagaaatggg 154080
ggccgggcgt ggtagctcac gtctataatc ccagcacttt gtgggggctg aggcaggcag 154140
atcacctgag atcggtagtt caaggccagc ctgaccaaca tggagaaacc tcatctctac 154200
taaaaataca aaattagctg ggcgtggtgg cgcattgcct gtaatcccag ctacttggga 154260
ggctgaggca ggagaattgc ttgaacccgg gaggcagagg ttgcggtgag ctgagattgc 154320
accagtgcac tccagcttgg gccacaagag tgaaactccg tctcaaaaaa aaaacaaaaa 154380
aaaacagtag actcgaagaa ctagctgagt ttttctttac tttaggcagt aagtgtgacc 154440
ttttgcaggt gactacttta gttcctcatg tcctcattag tagatcagag aaattcgaca 154500
ccaaaacccc aaaagaaaaa ccccttctaa tcctcattcc atgattttat gaatgcatga 154560
agtcctaggc ctgcgaagga atactcattc tctttatcct gtgttgatac ctctctgctt 154620
caacctccaa ctcgacattt gcctatagga tgtacttgga cattcagcat aaactacctc 154680
acaccattac tgaattgctt catgtgcaca tgtcccatgc cacaataccg gggaccttgt 154740
cttccgtgat atttgtccgc agtgctgtga ctacaggagg gagtcagtga atgtctgcat 154800
gtgtgtcttt accatccctc ttgaatatgc tctagggtta attcctagaa gtagaattac 154860
tctattgaaa attggcaata tttttcattc taatatctat tgccaacatg ggaaagcaag 154920
tctggatgcc agtccttgtt atatgcccct tgggtaagtt acgtaacctc tttaagcttc 154980
tgttcactca tattttaaca aggaaaatta caatatttta cctcacaaaa ttgtagtcag 155040
cttctggctg tcttaaactc tggtatatag taaacactaa gtgttggtgt ccatccttaa 155100
tttgtaataa taggtcactt gttagagaaa tgcaccttac cattttcttt tcttttcttt 155160
tttcagttat gactcaaaac ttgagataaa ggaaatctgc ttgtgaaaaa taagagaact 155220
tttttccctt ggttggattc ttcaacacag ccaatgaaaa cagcactata tttctgatct 155280
gtcactgttg tttccaggag agaatgggag acaatcctag acttccacca taatgcagtt 155340
```

-continued acctgtaggc ataattgatg cacatgatgt tcacacagtg agagtcttaa agatacaaaa 155400
tggtattgtt tacattacta gaaaattatt agttttccaa tggcaataac ccatttatga 155460
gagtgtttta gcctactgga atagacaggg accacatcct ctgggaagca gataagcata 155520
gaactgatac ttgatgcaca ctcgtagtgg taactcatcc ctaatcagca ttgtaaagca 155580
ggtgccagag gtggtttgct ttgtccttcc aaagcaggtg agtcagcccc accgagagcc 155640
aggcagcttt gagtggcagc gtggtgctag cagcttcagc ggaacagggt gagagttaat 155700
tatgcagtct tcttgacagc ggcattaatt tggaaggaaa ctgacaagtc atgggtcaag 155760
tttcagtgac ttcctccttc ctctgatggc agtatatagt tttcacattt taattcctcc 155820
tcctgagatg cactatactt aaaaccattc tctcccctgc taacagaagg gtgtgaatct 155880
ggtttacttt gagcattagg atttgcccct ttggaattct gcactccagt tacttaactt 155940
tcccttcaga atacatgtgg aaagaaagaa agaaatagcg atgactccac ttttgcccct 156000
gtggcacctt gaacaaagca gttcttccca aattatactt ttttttttt taaataaggt 156060
gagcaggatg actggggaga gagaaacatt tgactttgac tgcctccccc attctttgct 156120
gtgagctgga aagtgtgcag ttggtcgtct ttcttctcct ttctttagga tagtaagaga 156180
ctcactcact gcacttctgc tcagttggct tctgcatcgg gatcacacag ccatcagcag 156240
gactgcccag ttggtgagca cactccattg accacgtggc gccagcgctt cctcaatgca 156300
catgattgag aggaaagaaa gttctcttag atgttactgc ttttgctcag actttgcaaa 156360
aaaaaaaata tatatatata tgtataaata tataattatt aatcactttt gtccttgaga 156420
aagtcttgaa tgaacagaga atttattcca ttgcaatatt tgattgtata gaggcacact 156480
gtttcatcga cagaagaagc aaaaaggctt tgtgtaagtt tttggtacta tgtaccacct 156540
ctgttattct tttaaagctg aagtattcat gtacttaaac catattatat ttaattgtgt 156600
ttgattttaa aatatatata tatgaattct atttaaaatt gtgtcaactt tctgctttca 156660
gggcatttat ggctcttctg ttgaaatata ttgatctttc caaatatttt catttgcttt 156720
ctaaaaaccc agaacatgag ccactactgg actttgcctt gtgtttgaag tgtatggcat 156780
aaacccaagg tttttattag tcatctatgc tgtgattaat tcattttgtt cttttaacaa 156840
aatatttcca tccacttcac attgcttcaa tctttaacag aaaagcaata taaaggttat 156900
agaataaaat gtggttttgg gcaactcttg ctgcctctgc atgttttgga ataacaattt 156960
ctacaagact ctaggctgtt taaactagtg ctttcagtta agataaattc taatcatttc 157020
tttgtatata cattttgtgc ttctgagcta gagatgccaa gtagttgtaa actgcttata 157080
aagagaatag cagcaaattt gagactcggc tactttttc tgccccacct gctttgagac 157140
acagaagcgg agtgtggccc gaaattatta gccagattta atatttgatc taaagtaggt 157200
ccttgtactc attttaaagt tggaatttga ttcctccaac attgagcacc caccatgttc 157260
caggctctgt gcattgtgcc cacaaaataa gattccctgg tggagttttt atgggttcaa 157320
ataatcagtt gaacaccctt catctttatc atgttgttga cattgacaca aattgtttaa 157380
aaagaaaaga tattagagag aaagtggtac ctttgtaact tgatgtgtct tcatcattcg 157440
gtaagatttg atgaaagtaa aaagcaaatg tcagccaaat ccagtgaaca gcaataaaac 157500
agggagtaac tttttataac tttttctact tggatttcaa cattcagtag agcttttcga 157560
aatgtaagta gtttacagta ctggaggttt gactagttca gtaggaattt ggaggggaag 157620
gtcattctga attgtaacaa agtacaaact tctttgctgt tttatttaag tactgagagc 157680

-continued taagcacctg atgaagtgac tgacctctct ccagtgacag tgtttgggta cctgcctgac 157740
ttcaggagtg gggtttatgt ttctacacag tgaccttttc tctcgccctc tcctccctct 157800
tgcccacaca ccagttgatt ggacctgggt tgaactcctg atccagacag gcccaagaca 157860
gttcttaatg ttaagaattt tggggccggg cacggtggct catgcctgta attgcaacac 157920
tttgggaggc cgagacaggc ggatcacttg aggtcagggg ttcgaggcca gcctggccaa 157980
catggtgaaa ccctgtcttt actaaaaata caaaaattag ctgggcatgg tggcgcacgc 158040
ctgtaatccc agctacgtgg gtggctgaga caggggaatc gcttgaacct ggaggcggag 158100
gttgtgcaat gagccgagac cgtgtcactg cattccagcc tgggtgacag agggagactc 158160
tgtctccaaa aataaaaata agaaaaagaa ttttgggcta ggtgcagtgg ctcacgcctg 158220
taattacagc attttggaag gcccaagatg ggcagatcac ttgaggacag gagttcgaga 158280
ccagcctgga caacatggtg aaactccatc tctactaaaa agacaaaagt tagccagatg 158340
tggtgatggg cacctataat cctagctcct cgggaggctg gggcaggaga atcacttgaa 158400
cccaggaagc agagattgca gtgagccaag atcacatctc tgcactccag cctgggcaac 158460
agagcaagac tctgtctcaa aaaaaaaaga atttggccag gcgcagtggt tcacgcctgt 158520
aatcccagca ctttgggagg ccaaggcagg cagatcacga ggtcaggaga tcgagattgt 158580
cctggctaac atggtgaaac cctgtctcta ctaaaaatac aaaacattag ccgggtgtgg 158640
tggtgggcac ctgtagtccc agctactagg gaggctgagg cagaggaagg atgtgaaccc 158700
aggaggcgga gcttgcagta agccaagatc gtgccactgc actacagtct gggcgacaga 158760
gtgagactcc gtctcaaaaa aaaaaagaat tttggccggg tgcggtggca catgcctgta 158820
gtcccagcac tttgggagac caaagtgggc ggattacctg aggtcaggag ttcaagacca 158880
gtccggccaa tatggcgaaa ccctgtctct tactaaaaaa aatacaaaaa ttagccaggt 158940
gtggtggcgg gcacctgggg aggctgaggc agggagaaat gcttgaaccg gggaggcaga 159000
ggttgcagta agccaagatc gtgccactgc actccagagc aagactcttt ctcaaaaaaa 159060
aaaaaaaaag aattttgcat ggggaaggag agatactgtt caccatctgg aatggtgctt 159120
ggatgtggca cttacaaaat caggagccag cactgcatgg acaaacagaa gcatgtgggc 159180
ctgagatagc aggtaccttg ataaccctga agacatcctt ggtttctgca tctattcctg 159240
catccttgca ttggactaca ttaatctgtc agttatcctt ataatgattt ttgatttttt 159300
ttttttgaga tggagtttcg ctcttgttgc ccaggctgga gtgcaatggc acgatctcgg 159360
ctcaccacaa cctccacctc ccaggttcaa gtgattctgc tgcctcagcc tcctgagtaa 159420
ctgggattac aggcatgcgc caccacacct ggctaatttt gtatttttag tagagacggg 159480
gtttctccat gttggtcagg ctggtctcga actcccaacc tcaggtgatc accctgtctc 159540
ggcctcccaa agtgctggga ttacaggcgt aagccatggt acccggtctg tttttgatt 159600
ttttgaaacc agtctgaagt gagtttttt aattacgtga aaggagtttg gctaaaatac 159660
tgccatactg ccctaatgcc taatgattat gtattctcag catgtctgca aagtactgct 159720
gatttctgga gaataatttt tctttagtaa acttcactta agtcgtcatg tgtattctct 159780
caaaatggta tcctaaccta atggagctaa aagacacccc ttgtttttat aacaagcagt 159840
tactgaggcc caggaagggg agaagtccct ggcttgtgag atgatcacca ttagaactca 159900
ggcctgggcc agtgcctttt catgcttctc agatccttcc aaagaataat gaagattata 159960
accgctttta gcaattgtaa taaacccaga aatagaaagc tttttggtta gagtactggt 160020
agaagtttgg cgggagagat aatttttaca aaatttgtaa atacctgcca attctatata 160080

-continued ctaggcaagg tctctggcct tgtaaaaccc ctcaaggtta caactttggt ggcccacact 160140
aatagttacc cactgaggcc ctctccgggt gaacattgag cactagagga agcccctctg 160200
cttgggcagg actgggcgtg gtgcagagta ggagcggtga tactgtggat tctgggcagg 160260
tggagatggc cagtgatgtc caataaagga cactggaggg agcagtgtga gtaaaggccc 160320
tgagggcatt catgttcagg gagggttgct gcccactggc ttgcttggca cacaggagag 160380
tgggtattcc tgccttagta actttatgta aacaagtatt tcctcagtct gttcctctca 160440
aactgcctgc tctggcacat tcagaatgtc acagaactca cctggatgca ttcagcccct 160500
tgcctaaagg tgacagtgca tctccttccc caccccaccc ctcataccac tgaagcacct 160560
gtcagactgg cccagtctgt gggcaaggag cctagagagg gcttagtttc agcttgaaag 160620
gagctgggat ttaccaagaa gcaaatgaga gacgaggatt gcaacaactg tgccatttcc 160680
ccagcttcag ctgactcctg tatattgact gtgccttcag actcatccgt aagtgacccc 160740
aggctggcct ctcccacatc acagtaagaa ttccacacac catacaactt ggaaagaggc 160800
tccagctgaa ggaagcccca cacttctttc aagtttttct tagtcttctc ttcttggcaa 160860
agagtacctt ttgtttcttc taattatgta actattggtt tagtaaatat tcacccattc 160920
agtcaccctg taagtggcag gcactgttta cagggacaca ggaaggaata aaaacttgca 160980
ggcaccttgg agcttgcatt ctattgaaga ggtaatggaa gttgggatag cagctaaact 161040
atgctggtat tggccaggcg cagtggctca cacctgtaat cccagcactt tggaggccaa 161100
ggtgggcaga tcatgaagtc aggagatcga gaccatcctg gctaacatgg tgaaaccccg 161160
tctctactaa aagtaaaaaa aaaaattagc caggtgtggt ggcgggcgcc tgtagtccca 161220
gctacttggg aggctgaggc aggagaatgg tgtgaaccca ggaggcgaag attgcagtga 161280
gccgagatgg caccactgca ctccagcctg ggtgacagag cgagactctg tctcagaaaa 161340
aaaaaatatg ctggtagttt tgattcaaga tggcctttgg agcccatgat ttaggtctcg 161400
tacccaccaa ggtctactgg aaaacatcag gctctcctgc tatagaccca tagggagagc 161460
tgcagccgag agggggagct gaagagaagt gccccttctg tgtcctgtca gcctcatcct 161520
tccgcaagga ccagttgctg tgccactcca ttcacttgct gcaagactgg aggtttttcc 161580
tcaggtgttg agcacctggt ttacaagatg tcagcatctt gatgcctgag accatcaagg 161640
caagtctctg aacagggctt accttagagt aaggcttaga agaggccgta aagtcagtct 161700
cagctccgtg gctctgcaga gctttgggac atgtgaattc ttaaaaacaa gactattgta 161760
cagttactat atgcatgcag tataaaatta taaccttgga aaatcctagc tagctgttga 161820
gctaattcca taaagtaatc agctcctgag ttctgcagtg gtaataataa tcagcataat 161880
gagtaaacac tgtgtgtgcc aggcagcgtc tcatttgatc cttgtgataa tcttgtaagt 161940 actgatttc tcccttcttt aaacaaagtt tttttttttt ttttagagag ggtctcacta 162000
tgttgcccag gctagtcttg aattc 162025

<210> SEQ ID NO 36
<211> LENGTH: 162025
<212> TYPE: DNA
<213> ORGANISM: Homo Sapien
<220> FEATURE:
<221> NAME/KEY: mutation
<222> LOCATION: 156,277
<223> OTHER INFORMATION: Nucleotide Base Change: T to C

<400> SEQUENCE: 36

-continued

```
gaattcctat ttcaaaagaa acaaatgggc caagtatggt ggctcatacc tgtaatccca     60
gcactttggg aggccgaggt gagtgggtca cttgaggtca ggagttccag gccagtctgg    120
ccaacatggt gaaacactgt ctctactaaa aatacaaaaa ttagccgggc gtggtggcgg    180
gcacctgtaa tcccagctac tcaggaggct gaggcaggag aattgcttga acctgggaga    240
tggaggttgc agtgagccga gatcgcgcca ctgctctcca gcctgggtgg cagagtgaga    300
ctctgtctca aaaagaaaca aagaaataaa tgaaacaatt ttgttcacat atatttcaca    360
aatttgaaat gttaaaggta ttatggtcac tgatatcctg tttcattctt tatataatca    420
ttaagtttga aatgtatact tgcactacta acacagtagt taatcttagt cctacaagtt    480
actgctttta cacaatatat tttcgtaata tgtatgcact ggtgtttatg tacgtgttta    540
tgtttatatc tgttaaaatt agcagtttcc atctttttct attttgtacc atcacatcag    600
ttcagaagga ttgacagagc aaaatgattt gatgaagtat aaaagtcaca tggtgagtgg    660
cataaataca actctgaaca attaggaggc tcactattga ctggaactaa actgcaagcc    720
agaaagacac atatcctata tgtcaagaga tgtaccaccc aggcagttaa agaagggaag    780
tacacataga aagcacaatg gtgaataatt aaaaaattgg aatttatcag acactggatt    840
catttgctcc taaagtcaga gtcctctatt gtttttttgt ttttgtgggt ttctttttaa    900
atttttttat tttttgtaga gtcggagtct cactgtgtta cccgggctgg tctagaactc    960
ctggcctcaa acaaacctcc tgcctcagct tcccaaagca ttgggattac agacatgagc   1020
cactgagccc agcccagacg ctttagcatt tatgaagctt ctgaaatagt tgtagaaacc   1080
gcataagctt tccatgtcac tttcaaagtt tgatggtctc tttagtaaac caaccaagtt   1140
attcctcaag ggcaaaataa catttctcag tgcaaaactg atgcacttca ttaccaaaag   1200
gaaaagacca caactataga ggcgtcattg aaagctgcac tcttcagagg ccaaaaaaaa   1260
aggtacaaac acatactaat ggaacattct ttagaagagc cccaaagtta atgataaaca   1320
ttttcatcaa agagaaaaga gaacaaggtg ttagcaaatt cctctatcaa ataacactaa   1380
acatcaagga acatcaatgg catgccatgt ggaagaggaa gtgctagctc atgtacaaac   1440
cagtagataa tttcaacttg ctgccgaatg aaacctcttt gcaaggtatg aatcagcact   1500
tctcatgttt gttttgcttt gttttgtttt gtttttagag acaggccctt gctctgtcac   1560
acaggctgga gtgcagtggc acgatcagag ctcactgcaa cctgaaactc ctgggctcaa   1620
gggatcctcc tgccttagcc tcccaagtag ctgggactac aggcccacca tgcccagcta   1680
attttttaaa ttttctatag agatgggatc tcactagcac ctttcatgtt tgatgttcat   1740
atacaacgac caaggtacaa tgtggaaaag ggtctcaggg atctaaagtg aaggaggacc   1800
agaaagaaaa ggggttgcta catagagtag aagaagttgc acttcatgcc agtctacaac   1860
actgctgttt tcctcagagc agagttgatg atctaaatca ggggtcccca acccccagtt   1920
catagcctgt taggaaccgg gccacacagc aggaggtgag caataggcaa gcgagcatta   1980
ccacctgggc ttcacctccc gtcagatcag tgatgtcatt agattctcat aggaccatga   2040
accctattgt gaactgagca tgcaagggat gtaggttttc cgctctttat gagactctaa   2100
tgccggaaga tctgtcactg tcttccatca ccctgagatg ggaacatcta gttgcaggaa   2160
aacaacctca gggctcccat tgattctata ttacagtgag ttgtatcatt atttcattct   2220
atattacaat gtaataataa tagaaataaa ggcacaatag gccaggcgtg gtggctcaca   2280
cctgtaatcc cagcacttcg ggaggccaag gcaggcggat cacgaggtca ggagatcgag   2340
accatcctgg ctaaaacggt gaaaccccgt ctactaaaaa ttcaaaaaaa aattagccgg   2400
```

-continued

```
gtgtggtggt gggcacctgt agtcccagct actcgagagg ctgaggcagg agaatggtgt   2460
gaacctggga ggcagagctt gaggtaagcc gagatcacgc cactgcactc cagcctgggc   2520
gacagagcga tactctgtct caaaaaaaaa aaaaaaaaaa aaagaaataa agtgaacaat   2580
aaatgtaatg tggctgaatc attccaaaac aatcccccca ccccagttca cggaaaaatt   2640
ctcccacaaa accagtccct ggtgccaaaa aggttgggga ccgctaatct aaataatcta   2700
atcttcattc aatgctaaaa aatgaataaa ctttttttta aatacacggt ctcactttgt   2760
tgcccaggct ggagtacggt ggcatgatca cagctcactg tagcctcaat cacccaggcc   2820
ccagcgatcc tcccacctaa acttcctgag tagctgggac tacaggcacg caccaccatg   2880
cccagctaat ttttaaattt tttatagaga tgggggtctc accatgttgc ccagactggt   2940
ctcaaaccct gggctcaagt gatcctccct caaactcctg gactcaagtg atcctccttc   3000
cttggcctcc caaagtgctg ggattacaag catgagccac tgtacccagc tggataaaca   3060
ttttaagtcg cactacagtc atggacaatc aggcttttca acatgcagta tggacagtga   3120
gtcccagggt ctgcttttcc atactgaaat acatgtgata ctaaggagaa aggtgctcgc   3180
aaggatattt aaaatgaaga atatttaaaa tgaggaaaaa actgtttctt catgactttg   3240
ataaggctga taaagaccat ttctgtgatc tcaggtgatt cactcaagta gtatatttca   3300
gtaatcatta tctggaacag cctgaatctt aaccaaaata ccatgatttt ttaatgctgt   3360
tatgatacct tgatgatatg accaaactgc aatgtaggca gctaaatctc cacgagtttg   3420
acttccccga gagttgacag ttttcttcac aaattaaaga aatatatttt ttgatacatg   3480
attggcatat ttaaaaacta cactgaaatg ctgcaaaatg atataaagaa acattttcca   3540
gaatcaaatg caatcaaaga gtggattagg aatctactca ccattatcaa ctaaatagaa   3600
acacttggac tgggtgtggt ggctcacatc tgtaatctca gcactttggg aggccaaggc   3660
aggtggattg cttgaggcca ggagctcaag accagcctga gcaacatagc aaaactctgt   3720
ctctacaaaa aaaaaaaaaa attaaccagg catggtggca gatgcttgta atcccagcta   3780
ctctggaagc tgaagtagga ggactgcttg agcccaggag atcaagactg cagtgagccg   3840
tggtcatgct gcgccacagc ctgagtgaca gagagagacc ctgtctcaaa aacaaaaaca   3900
aacaaaaaac acttaacctt cctgtttttt gctgttgttg ttgttgtttg tttgttttga   3960
gatggagtct cactctgttg cccaggctgg agtgcagtgg cgtgatcttg gctcactgca   4020
agctctgcct cccgggttca cgccattctc ctgcctcagc ctcccgagta gctgggacta   4080
taggcgcccg ccaccacgcc cggctacttt tttgcatttt tagtagagat ggggtttcac   4140
cgtgttagcc aggatggtct tgatctcctg acctcgtgat ccacctgcct cggcctccca   4200
aagtgctggg attacaggca tgagccaccg cacccggcca acctttctgt tttttagttt   4260
gatatgcttg ttaactcagc agctgaaaga atgctgaaag tggccttcag taaaaaaatt   4320
tcactagaat ctctacatcc atatttaatc tgaatgcata tccagattga tcagttagag   4380
caaaaacact catcatcatt cctgatgacc tctaattctg gtttcggctt tctatttcaa   4440
tggaaacaga ataaggaaag aaatggaagg gctctggaaa tttgtcctgg gctatagata   4500
ctatcaaaga tcaccaacaa taagatctct cctataaata taaaacaagt ataattaatt   4560
ttttaattat ttttttctct tcagaggatt ttatttcaag ataaaacata acttctaccc   4620
atactattga ttccaaaggt tagaaaaagt gtttttcctc atcttatcct tcaaagaggt   4680
cacagcaatg caaacatcta taaaatgcct ctgcataatt gtcagaagct atagtccaga   4740
```

-continued

```
aatcattgaa aatgcttttc cattttaagc ttaggtgagg tgtcttagga aacctctatg   4800

acaacttact ctatttattg ggaggtaaac tcccagactc tcccagggtc tcctgtattg   4860

atctcatttt ttaggcttcc taatcccttg aagcacaatc gaaaaagccc tggatctctt   4920

ttctgcacat atcatcgcgg aattcattcg gcttccagca agctgacact ccatgataca   4980

agcggcctcg cccttctccg gacgccagtc cttgctgcgg ttagctagga tgaggggttt   5040

gctgggcttc agtgcaggct tctgcgggtt cccaagccgc accaggtggc ctcacaggct   5100

ggatgtcacc attgcacact gagctcctgg caggctgtac caattttta attatttaat   5160

atttatttt aaaattatgg tgaatatttt ggtattctgc tctaaaatag gcccataaat   5220

gcacagcaga tatctcttgg aacccacagc tttccactgg aagaactaag tatttttctt   5280

ttaaagatgc tactaagtct ctgaaaagtc cagatcctct acctctttcc atcccaaact   5340

aagacttgga atttatgaga gatctagcta acagaaatcc cagacacatc attggttctt   5400

cccagagtgc agtcctccta aagaggctca gccctaagca ggcccctgca ccaggagggt   5460

gggtctgaga cccacatagc acttcccaag gtgcatgctc cagagaggca ctgaaacagc   5520

tgagcacaag cctgcaagcc tggagaactc tcacagtcag aacggagggg gcccagtggg   5580

actaacataa agagaaaagg gaacacagag aaatggatgg caccaacaac cagcaaagcc   5640

ttcatggcca atgaaagcat cagtgacggg gccagaaccc tcatccccaa agactcttca   5700

ctgcctttag tgaaaaacaa tggctagaga gtgaagttat gatcatgtat agagaggtaa   5760

agttacattt ttatattctg actctgctaa tgtgaaattc cctatctgct agactaaaag   5820

tttcagacac cctgttcaaa tatcccatta gttgctagag acttaaaatg aacagaacgc   5880

acattgtcag gatgactatt accaaaaaat caaaagacag caagtattgg tgaggatgta   5940

gagaaactgg aacttttgtg cactgtttat gagaatgtaa aatggagcag ctgctgtgga   6000

aaagagtatg caggttcctc aaagagtaaa accaagatgt ggaaacaact aaatgcccat   6060

cagtggatga aggggtagac aatatgtggt atatacatac catggagtac tattcagcct   6120

ctaaaaaaaa aaaaggaaat tctataacat gcaacagcat ggatgaatct tgaggacatt   6180

ttgctaatga aataaggcag tcatagaaag acaaatactg cacgactcca cttatatgag   6240

ataccaaaaa tagacaaatt catagaatca aagagtacaa tggaggttac ctggagctgc   6300

agggcgggaa acgaggagtt actaatcaac gaacataacg ttgcagttaa gtaagatgaa   6360

taagctctca agatcagctg tacaacactg tacctagagt caacaataat gtattgtaca   6420

cttaaaaatt tgttaagggt agattaacaa atgtagtaga tccacaaatg tggttaagtg   6480

ttcttaccac agtaaaataa aaaaagaata tcaagcccag gagttcgaga ctagcctggg   6540

taacatggtg aaaccctgtc tctacagaaa atacaaaaat tagccagctg tggaggtgca   6600

ctcctaggga ggctgaggtg ggaggcttgc ttgagcccag gaggtcaagg ctgcagtgag   6660

ccatgattgc accactgtac tccagcccag atgacagagc aagacaccac cccccccaaa   6720

aaaagaaaaa gaatatcaaa cattttaaaa gatcagatac gcaagaacaa caacaaaaaa   6780

gagatgaaca gagcatcgac cctcatctag tgggattctt ggtctaactg aaaaacagac   6840

attgagagac aaacaatgac agtgatgtga tcacagcaat tacacaggta tcccctgggg   6900

actgcagaag aaaggaggaa tgcctaactt tcagaaaata gagaaagcgt caaacagttg   6960

gtgaaagcct tccaaaacta gagagaactg cacacaccaa atcacagaaa gaagaaaagc   7020

cgtgggagat tctgggaccc accggctatt tttgatggct gaacaccctg ctgcaggaga   7080

gacaggagct ggaaagcatg gtgggatgaa acctcaaaca gctttgcctg cattgcttaa   7140
```

-continued

```
gatgactggg cttgattaac tctagtcaat ggggacaatt caatcaaaga agaaagatgc   7200
tcaaattcac attttagaat gattttttat ggcagtatgg ggaatagatt aaaagagagt   7260
gaagctggag gcaagaaact tgttaagagg caactgaaac agtctagatg ataaataata   7320
aactgacaga gtgactagaa aaatcagaac aggctgaatc aacagatacc tagatgaaaa   7380
taacaggact tgatcaccag ttgtatcttg gagaggaagg agttgtttcc ttgctttccc   7440
tacgactggg aatacggaag gtttgccgtg tgtattggtt atatactggt gtgtagccaa   7500
tcactgacaa ccatttagca gcttaaaaca caaaggctta tctcccagtt tctgtgggcc   7560
aggaatctaa gataggctta gctggctggt tctggctcag agtttctcaa gaggttgcaa   7620
tcaagatgtc agctggggtt gcatcatctg aaggctcaac tggggccgga gggtccactt   7680
ccaaggagtt cactcacctg cctgacaagg cagtgctggt tgttggcagg agatctcaat   7740
tcattgccaa gtgagcctct ctatagcatt gctggaacat cctccccatc tggcagttgg   7800
cttctctcag catgagtgat ctgagagaga gagcaaggag gaagccacag tgttcttcct   7860
actcctactc ctaacactat ggacctactc ctaacactct cacttctgcc ttattccatt   7920
agttagaaag ggaactaagc tccacctctt gaaataagaa gtgtcaaaga atttgtggat   7980
atatttaaaa atcatcacac tgtggaagtg gatagggggt tcaattaatg ctgaacttga   8040
aatgcctgag acattcaaat gtccaacagg caatgaacat acccatagat ggtcatgact   8100
ttagcaagaa tagaggaaga tcacagaatt aaggaggaat tgaaaggtaa aagaagtgga   8160
gtcagattcc ccctgaaaag tgagccatga aaggaacttt aactattgag ttagaggtca   8220
gagtaggaaa tttcggtgga attctttttt aaagaaagga accatataag catgttttga   8280
ggtagaggga gaataaatca gtagacaggg agaggtaaaa aacataaatg ataggggata   8340
gttgacaaag gtcttggcag aatcccttac ccattgactt ggggccaaga gagggacact   8400
tctttgtttg agggataagg aaaataagaa agaatgggtg ctatttagtg tggtcctgtc   8460
tctagggcaa acgcataggt aacaaactgt gtgtgttagg aatatagatg tgacctcaca   8520
ttgagattct cacctcaaat ccattttgtt gttacctgta ccttcctacc ttctcttttt   8580
gctacatgca gactgctgtt ttgtcttcct ggcctgttcc aggtttcagc attctggcat   8640
atctgctacc ctgttcccaa acctctctag agtccatgct ccttccttgg atagtgtttg   8700
attgggccac gtatctaaga agtgatgcct tcagttaggc ctgagaacct cctctatgga   8760
aatctccatc agtgaccctg acagacttgg tatcttggag atgtcactgc tcccagcctg   8820
tggtctagga gaatctcagc ctgggcctct agtagtatgg ataaggcgtt aaggtatctt   8880
tgaaccagag tctgtcatat tcctcaatgt gggacagata aaacagtggt agtgctggtg   8940
tttctgagct agaactctgg tttttggtct agattctttg atgtatgacc tttcagaggt   9000
attaaaattt gttctaatac aatgttcaat acaaatgtag ttccttttct gttaggacct   9060
caacaaaaca tgaccaactg tagatgaaca ttaaactatg acaattcatg gaaatgaata   9120
cagtaatacc tgcggttccc ccattttagc agtcactatg gtgacatttg gcacaaatgg   9180
ctatttaagg gtgcttttgt taaaacctac catcttacta ggcacatgat attgaaacta   9240
atgaaataat ggagaaactt cttaaaaact tttaatgaat aaagtgatga agtgataata   9300
ttttagctgc tatttataaa gtgactatta caggtcaaac attcttctag ggttttttg   9360
ttgaagttgt cacatttaat ccttaataac ccactatgag tcaggtattc ttctctcccc   9420
tttggacagt tggggaaatg ggggtcagag aggttaggta atttgctcag ggccacacaa   9480
```

-continued

```
cctgcatgta gaaaatctga gatttgtaca ggaacgtatc aaactctgaa gtccatgctt   9540
ctattttccc atgctgcctt tctaataaaa ggtaactaat gctactggat gctgccccca   9600
aagtgagtca ctttcacccc accctacttg attttctcca taaaactaat cacatcctga   9660
caacttattt attgctgatc tcccccacta gattataaac tcaataaaag caagatcctt   9720
gtctgctgaa tatcagtacc taaaacgctg tctagcacag agcaagtaat taatatttgt   9780
tgaatgaaca aataaaggaa aaaaattcaa aggaagaaaa agccctaaaa cagatgttta   9840
cctaaacata cattttaaaa gaaagcatat aacaaattca ggacagaatt taaatttgat   9900
tttttaaaga aataaccaag tgctagctgg gcacagtggc tcacacctgt aatcctagca   9960
ctctgggagg ccgaggcagg cagatcactt gaggtcaaga gttcaagacc agcctggcca  10020
acatggtgaa acctgtctct actaaaaata cagaaattat ccaggcatgg tggcaggtcc  10080
ctgtaacccc agctactcag gaggctgagt caggagaatt gcttgaaccc aggaggcaga  10140
ggttgcagtg ggccaagatt gcaccactgc actccagcct gagtaacaaa gcaagactct  10200
gtctgaagga gaaggaaaga aagaaggaaa gaaggaaaga aggaaagaag gaaagaagga  10260
aagaaagaaa gaaagaaaga aagaaagaaa gaaagaaaga aagaaagaaa gaaagaaaga  10320
aagaaagaaa aagaaagaaa gaaagaaaga accaagtgct tatttgggac ctactatgct  10380
atgtttttcc atgcacgcta ttttcagtaa agcagttagc aaacttgcaa gatcataaca  10440
acaaatatat gcttctataa ctctaaaatt gtgctttaag aagttcctct ttaccagctc  10500
atgtatgcat tagttttcta agagttacta gtaacttttt ccctggagaa tatccacagc  10560
cagtttattt aaccaaagga ggatgcttac taacatgaag ttatcaaatg tgagcctaag  10620
ttgggccagt tcatgttaat atactccaga acaaaaacca tcctactgtc ctctgacaat  10680
tttacctgaa aattcatttt ccacattacc aaggagccag ggtaggagaa tatagaaaga  10740
ccacccaaga atccttactt ctttcagcaa aatcaattca aagtaggtaa ctaaacacat  10800
gccctaacaa tgaatagcag attgtgctca gaagaatgat ctacaacatc ttactgtgaa  10860
ggaactactg aaatattcca ataagacttc tctccaaaat gattttattg aatttgcatt  10920
ttaaaaaata ttttaagcct aaattttaaa aggtttgata ttggtacatg aatagacaaa  10980
cagacatgga ctagaccaag aattaggttc aaacatatac aggaatttaa tatacgataa  11040
atctagtatt ccaaaggaac caacaaatgg tgttcagaca gcaggatagg catcaggaaa  11100
aacacagttg ggcaccctac cttactccta acaccaggag taactgaagg agcaccaaat  11160
atttatttat tttaattata gttttaagtt ctagggtacg tgtgcacaac atgcaggttt  11220
attacatagg tatacatgtg ccatgttggt gaggagcacc aaatatttaa aagaaaaaaa  11280
ttggccaggg gcggtggctc acacctgtaa tcccagcact ttgggaggcc aaggtgggca  11340
gatcacctga ggtcgggagt tcgagaccag cctgagcaac atggagaaac cccatctcta  11400
ctaaaaatac aaaattagcc aggcatggtg gcacatgcct gtaatcccag ctacttggga  11460
ggctgaggca ggagaatagc tttaatctgg gaggcacagg ttgcggtgag ctgagatatt  11520
gcactccagc ctgggcaaca agagcaaaac ttcaactcaa aaaaattaat aaataaataa  11580
aaataaagaa agaaaagaaa aaaatgaaaa tagtataatt agcagaagaa aacaccgtag  11640
aatcctcgga ctcttaggat ggggaatgcc tataatataa aaaccctgaa gttataaaag  11700
agaaaatcac ctacatacaa accaaatctt tctacatgcc taaaacatag cacaaacaca  11760
gctaaataat catagctgaa tgaactggga aaacaaaact tgactcatat ccagacagag  11820
ttaattttcc tacacataaa gagtacctat ataaacccaa caaaaaaacc accactaacc  11880
```

-continued

```
caaaataaaa atgtgacagg taatgaacag gtagttcaca gagaatacaa atggctcttc  11940
ggcacataag atgctcagac tgacttttac ttatttattt tttgagagac agggtctcac  12000
gatgttgccc aggttaggct caaactcctg ggctcaaatg atagtaccag gactacaggt  12060
gtgccccacc gcacctggct cctcaaccac ctgtattaac aggaaatgca aaataaaact  12120
ttcaaatcta ttttacctat tagaatggca aaaatttgaa aaacttcaaa catcatcatg  12180
ttggtgagaa tgtgaggaga ctggcactct catttttttgc tgatagcata tatatactga  12240
tggcttctat ggaaagcaat ctggcagcgt ctatcaaatg tacaagtgca tatatccttt  12300
gacaaagcaa ttccactcta ggaatgtgtt ctatatggtt gtgcttcctg gggctgggaa  12360
ctgggagcta agggacaggg gcagaagata atcttctttt ccctccttcc ccgttaaaca  12420
tgttgaattt tatatactgt aatatattat ttttcacaaa agataatttt taagcgatat  12480
gtctgggaat tttttttttt cttttctgag acagggtctc actctgtcat ccaggctgga  12540
atgccatggt atgatctcag ctgactgcag cctcgacctc ctgggttcaa gcaatcctcc  12600
cacctcagcc tcctgagtag ctgggactac aggcacgtgc catcatgcta atttttgtat  12660
atacagggtc tcactatgtt gcccaggcta atgtcaaact cctaggctca agcaatccac  12720
ccacctcagg ctccaaagtg ctgggattac aggcgtgagc caccgcgcct ggccctggga  12780
attcttacaa aagaaaaaat atctactctc cccttctatt aaagtcaaaa cagagaagga  12840
aattcaacct ataatgaaag tagagaaggg cctcaaccct gagcaacaaa cacaaaggct  12900
atttctgaga caggaatttg ctgaacaaaa tcgagggaag atgacaagaa tcaagactca  12960
cttctcggct gggcgcagtg gctcacacct gtaatcccag cactttggga ggccgaggcg  13020
gacagatcac gaggtcagga gattgagacc atactggcta acacagtgaa acccagtctc  13080
tactaaaaat acaaaaaatt agccgggcgt ggtggcaggt gcctgtagtc ccagctactt  13140
gggaagctga ggcaggagaa tggcgtgaac ccaggaagcg gagcttgcag tgagccgaga  13200
tcacgccact gcactccagc ctgggtgaca gagcaagact ctgtctcaaa aaaaaaaaaa  13260
aagactcatt tctctagatc ttgagccgta ttcaaattta tctcagctta gtgagaggtt  13320
aaagcaagga atatccttcc ctgtgggccc tgctccttac tgaaggaagg taacggatga  13380
gtcaaggaca ccaatggaga aaagcactaa caccattatc tgatgaacat tacgtgaaga  13440
agggtaagaa gtgaagtgga attgctgaag aagtcagtga aagcggacat tcatttgggg  13500
aaatggaata taggaaatcc ataaaagtga ttaaaaagat gttagaggct gaggcggggg  13560
gaccacaggg tcaggagatc gagaccatcc tggctaacac ggtgaaaccc catctctact  13620
aaaaatacaa aaaattagcc aggcgtggtg gcaggcacct gtagtcccaa ctactcggga  13680
gactgaggca ggagaatggc atgaacctgg gagacggagc ttgcagtgag ccgagatcac  13740
gccactgcac tccagcctgg gtgacagagt gagactccat ctcaaaaaaa aaagttagat  13800
acgagagata aagatccaac agacacacaa ctgctaattc tgaacagaac aaaacaaatg  13860
gcacaggaaa agaaaattta agatataaca ccggaaaact ttcctgaaat tgagtaactg  13920
aatctatagc ttgaaagggt ttagcatatg ccaagaaaaa tcagtagagt ccaaccagca  13980
caagacacat ctagcaaggc tggtgattct accaacacag agaaagaagt gggtgaccca  14040
taatgcggaa aaaggcagac catctgcagt cttctccaga acactggagt ctgaagacaa  14100
aagaatgctg cctactgagc cagaagggag agaaagtgac ccaacacatc tttaccaagt  14160
tagaatgtca cgcattattt aaaggctgca aaagccatga aagacatgaa agaacacaag  14220
```

-continued

```
catttacaac atgaaagaac acaagcattc tcatactcaa gaatccttaa gaaaaatgta  14280
gtcctaatcc agcccactga aagttaaatg tacttaatgt gctcattaat gggaacttca  14340
tagcttcaaa tcagtctggt cccatctacc aacatctctc gcccggcttt cctgcaatag  14400
tcagcacctt tccctcctcc cagtcttgtc ccctggagtc tgctctcagc atagcagagt  14460
gaccacatca acacccaagt cagagccctc cagtgcgcac tggtctacaa agcccttccc  14520
accccccacc ccacgtgccc tccggatcct tgtgacgtgt ctcctgcata ccctagcagc  14580
cctggcctcc tcactgcccc tcctgtacat caggaaggcg actccttgag tcttggctct  14640
ggccgcctcc tccacctgca gtgagttaac tcccttacct actctaggtc attgctcaaa  14700
tgtcagcatc tcaatggggc cctccctgac taccctattt aaattctaca tactcccctt  14760
gaccccatgg acctcactca ccctattcca cttttattct tacaatttag cacttgttct  14820
cttctaacgt attctaagac ttactcattt attacattgt ttgccacccc ctctagtaca  14880
taaactccag aggggcaggg atttctgtct atttattcat ttctttatcc ctaggacata  14940
gaacagggca tagttcagag tattcaatgt tatcaatgaa tgaactagca gtagtaccag  15000
ttccagttag gcacagaatt aaatctaaat agaattaaat ctcatggtct gggttaacta  15060
tggatagaaa attagatata attttaagaa gcctagaaag aaaaaattaa taatgtaaaa  15120
ataatattaa tttgataata ataacaaaaa ctctgccagg cactgtggct caaatctgca  15180
atcccagcta ctcaggaggc tgaggtggaa ggatcacttg agaccagagt tcaagactca  15240
gcctaggcaa cacggcaaga aactgtctct aaaaaaatta aaacttaaat ttttaaaaaa  15300
gaattctcaa agcgtcacaa aaactggaga ttaaggtaca ggaagtgtga agtaatatta  15360
ctatgctaat ggtttttttt ttttttagaa aggtataacc aaaagatttc tttctcaagt  15420
cgataaactg agaaagataa gcatatcttc caattaacag agggggagga aaagccagat  15480
acaacaaaat aagatataaa ttagtttcca gttgaaaaca agagtaggag ttattttgca  15540
tcacctcacc tgtgacctcc cccagcccaa aaaacactac tgataaacag ggtagaaaag  15600
catcatctca gataaagcag gaaaaactgc cacagtctca aaccacaaac tataagcaca  15660
cacctggcca accctgccaa gtctgggctc agtaggagga acgtgctgag agctaggatg  15720
taccaactta gacattctgt gggatacaga tgtccctgga agggtcacac catctcaaag  15780
gcacctgtaa tgcccactga ttacagccac catatgtgag agagaaactc agggcactta  15840
gagagtataa caagaacctt atgtcatctg agatgaggaa tcctcagccc tgcaaattaa  15900
ccaactcttt agaacaactg gcaaaacata aatatccaca acttttgttt cagtaattcc  15960
actcttagat atcaatccaa agtacatgag acagcagata cacacacaaa atggtattta  16020
ctgcagcatt gtttataata gcaaaaaaca agaaataatc catatgtctc aataggatac  16080
tgggtacatg agggtatgta cccatcattc aaccatcaaa aagagtgata tggatgtcca  16140
cagatggaca taaaaagctg tgtgttacgt gaaaacaaac tcaagcagca gcaggatggg  16200
cttatgatag tcagtatgag ctaatttctg gaaaaaaaaa tctagtgtgt gcacagaaaa  16260
catctgaaag aacagaaaca aaactatcag cagaatattg agatgtttta ctaagttgta  16320
tatctatact gcttgtaatt tttaccccaa gcaagaatta ctttttggaa aaagaaaatt  16380
caggaaataa agcatttctt taaacttcat gtttaaacaa atggtgatgg aataaaagag  16440
ttcttattca tcataaacac acacagcaca catgcacgca tgtgcgtgag cacacccttt  16500
acttgataaa taccatgttg aatattttag tctttccttt taggttctat cccttcactc  16560
aaaatgcggt tataaataaa tgtacttttc atgtgccttc tgcctaaacc cactttaata  16620
```

-continued taactttaca gtcccattat cattatagtc tcaaagctag actcagcctg aaactaccct 16680
ttcatttgga acccttatta aaatgccaca tacagctcct tcaaataaaa acaaaccccta 16740 ggacctgaca ctaggcttcc tttgttgcta ctcataatgg ccaagttctg tgcttataat 16800
acatcttctt tcattttatt gctacatatc caagggtttt atatgttttt cttattatat 16860
cttaattcaa aacaccatca cgctcttttc cagatgaaaa taaggaaaag aaattgagca 16920
actgactgac ttaaaggtca taaaactata tagtagcaga gtcagcaaaa gaagaaacac 16980
acatctccca agtagaggct gaaaaccagt accattcacc tccagggtga gctatataca 17040
gattacaaag tcaccttctc taaatgttca aactgaatcc catacccata ctttaccact 17100
acctcgtaag aacagcctca gatcttgtta tagccttttt tttagcatgc tgaagccaat 17160
aaaatgcttc ccattcagca agagaaacaa gttctgaaac actgaataat ctgcccaggg 17220
cctatgaaca tttccactgt gagaaatgtt ctccactgtg tggagaagat ccttactctt 17280
ctccacacag gcagaacatt agaaaaattc ttggattcta tgatgcacag cttaggagtc 17340
tgtttagcac aatttaagtc caaatagtta ttaaatcctc ctctgttcca gaaacagtgc 17400
taaatactgt gaatataaaa attgaaaaga tactctcctg gctcccaaga aagtcagcca 17460
gatagaggag acacaggcac acaaatcact gtcacatgaa gctctacctc cctaacttca 17520
aacgagggcc taagtcacca agaatacagt agcagttgtg actacgagta actactataa 17580
ttcaatactt tatcttccct tagaaaactc ttctcccttg gaaatttatt tgcatttcta 17640
aataccattc cttactaaaa ggaagcaggg ctccttgggg aaatagctga ttctaggtgt 17700
ggactatgaa atgaaaatgg tgagtctggg acatcccatg ttgcccagaa atcaaggaac 17760
tgcccaaaga ttaacagagt catgttaaat ggacctaaga gtgaaccaga aggagctcac 17820
tttgccccgc gtggaacaat ttcaagaaaa acatgacagt aatgaattat aaaacatgaa 17880
ttaaaataca tattggtact aaaaagagaa caaaaggatg tggctttgga taaagctctt 17940
cttcatggaa gaataccagc taataaatgt aaaggaaatg agagaattag aaaaattatc 18000
attttgtaaa ccttaatata ttcacctaga catgctaaaa ccactgagta aaaggctgct 18060
tgggaagagg atgctcacat gatctcagag tttcacacca cagataattt attagataca 18120
ggaaggaaga tgtgatcaag cttcctgtga cccccagcca ggccccacaa cactatgtgc 18180
ctccttgtga tgtgggagct acacagcatc gcccacacag cttctcgcca aaactgtttg 18240
aagctaatca caagggaaga actggacagc ttctgaccat gagacgctcc accagacaac 18300
ttgcttggcc tctccaaaga aacttgcttg gcctctccaa agaaaactca gtttcattta 18360
aaaacaaaac taattattta aaaacaaacg aaaagcaagt tgtggacttg agctccaggg 18420
acagagcaga catacttttc cctgttcttc ccagtaagtg gtaataaaaa ccctcaacac 18480
tagatataaa acaaatataa gaaggttctg gaaggggaag aggaggcaga ctatccaggt 18540
gccttgaggc ccacagaaca acccagtgat gggttcactg ggtcttcttt ttgcttcatt 18600
atctcagact tggagctgaa gcagcaggca acttcaaaac accaaggggc acagattgaa 18660
aagccccaag aaaagcctgc cctctctagc caaaggacca ggaaggagac agtctaatga 18720
gatggaacac atttagacag taactgccca tttaccagca ataactgagc agggagccta 18780
gacttccagt cttgtgagga cgtaccaagg tacccaacac ccccaccaag gctgagtaag 18840
gactgcgact tttatccctg catggcagta gtaaggagcc catccctcac ccgccagcag 18900
tgtcagggga acctggactt ccactcccac ccaggagtga tgaggccctc cctgctgggg 18960

-continued

```
tcatgtcaga ggaggcctag tggagattca gtgacttaac cttttcccag agataatgag  19020
gccacctttc ctccctcttc ccccatggtg acagtgaaag cactgtggca agcagtaggc  19080
actcctaccc ctcctagcca gggaggtatc agggaggcca agtagggaac cagaataccc  19140
acaaccaccc agcagcaaca ggggtccccc accccattgg gtgtcaatgg aagcagagcg  19200
gaaagcctgg atatttaccc ccatctagaa gtaacaagct gatgtccccc ttcttctact  19260
acaatggtgt tcaaaacagg tttaaataag gtctagagtc tgataacgta atacccaaat  19320
cgttgaagtt ttcattgagg atcatttata ccaagagtca ggaagatccc aaactgaaag  19380
agagaaaaga caattgacag acactagcac taagagagca cagatattag aactacctga  19440
aaggatgtta aagcacatat cataagcctc aacaggctgg gcgcggtggc tcacgcctgt  19500
aaccccagca ctttgggagg ccgaggcagg tggatcacaa gatcaggaga tcgagaccat  19560
cctggctaac acggtgaaac cccgtctcta ctaaaaatac aaaaaaaaat agcaaggcat  19620
ggtggtgggc acctgtagtc ccagctactc gggagcctga ggcaggagaa tggcatgaac  19680
ctgggaagag gagcagtgag ccgagatcgc accaccgcac tccagcctgg gcaacagagc  19740
aagacttcgt cccaaaaaaa aaaaaaaaaa aaaaaaaagc ctcaacaaac aactacaaac  19800
gtgcttgaaa caaatgaaaa aaaaatcttg gcaaagaaat aaaagatata tattttggcc  19860
aggtgcagtg gctcacagcc tgtaatccct gcactttggg aggctgaggc aggcggatca  19920
cctgaggtca ggagtttgag accagcctga ccaacatgga gaaaccccgt ctctactaaa  19980
aatacaaaat tagccagtca tggtggcaca tgcctgtaat cctagctact caggaggccg  20040
aggcaggaga atcgcttgaa ctcaggaggt ggaggttgcg gtgagccgag atcccgccat  20100
tgcacattgc actccagcct gggcaacaag agcaaaactc catctcaaaa aaatagatac  20160
atattttaat ggaaatttta gaattgaaaa atacagtaac caaattgaat ggaaagacaa  20220
catagaatgg agggggcaga caaaataatc agtgaacttc aacagaaaat aatagaaatt  20280
acccaatatg aagaacagaa agaaaataga ctggccaaaa aataaagaag aaaaaagagg  20340
agcagcagga ggaatgatgg aaaaagagaa aggaaggaag gaagggaagg agggagggaa  20400
ggagtgaggg agaaagtctc aaagacctct gagactaaaa taaaagatct aacacttgtc  20460
atcagggtcc aggaaagaga caaagatggc acagctggaa acgtattcaa aaaataatag  20520
ctgaaaactt cccaaatttg gcaagagaca taaacctata gattcgaaat gctgaacccc  20580
aaataaaaag cccaataaaa tccacaccaa aatacatcat agtcaaactt ctgaaaagac  20640
gaaaagagaa aacgtcttga aagcagtgag tgaaacaaca cttcatgtat aagggaaaaa  20700
caattcaagt aacagatttc ttacagaaat taaggaagcc agaaggaaat gacacaatgg  20760
ttttcaagtg ctgaaagaaa agaagtgtca acacaaaatt ctagattcag taaaaatatc  20820
cttcaagaat caatgggaaa tcaagacagt ctcagataaa gcaaaataag agaatatgtt  20880
gccagcagat ctcccctaaa ggaatggcaa aaggaagatc atgcaacaga ccaaaaaatg  20940
atgaaagaag gaatccagaa acatcaagaa gaaagaaata acatagtaag caaaaataca  21000
tgtaattaca ataaaatttc tatctcctct taagacttct aaattatatt gatggttgaa  21060
gcaaaaatta taaccctgtc tgaagtgctt ctactaaatg tatgcagaga attataaatg  21120
gggaaagtat aggtttctat acctcattga agtggtaaaa tgacaacact gtgaaaagtt  21180
acatacacac acacacgtaa gtatatataa atatatgtgt gtatatgtgt gtgtatatat  21240
atatatacat ataatgtaat acagcaacca ctaacaacac tatacaaaga gataataacc  21300
aaaaacaatt tagataaatt gaaatggaat tctaaaaaat attcaaatac tctacaggaa  21360
```

```
gacaagacaa aaagagaaaa aaagaggagg acaaactaaa ttttttaaaa acataaataa  21420
aatggtagac ttaagcccta acttatcaat aattacataa atgtaaatga tctaattata  21480
tcaattaaaa gacagagata gcagagttaa tttaaaaaca tagctataag aaacctgctt  21540
tgggctgagt gcagtgactc acacttgtaa tcccagcact tcgggaggcc aaggcgggtg  21600
gatcacctga ggtcaggagt tccagaccag cctggacaac atggtaatac cccatctcta  21660
ctaaaaatac aaaaaaatta gccaggcatg gtggcacacg cctgtagtcc caactactca  21720
ggaggctgcg acacaagaac tgcttgaacc cgggcagcag aggtagcagt gggccaagat  21780
tgcgccactc cagcctgaac gacagagtga gactccacct cagttgaaaa acaaaaaaga  21840
aacctgcttt aaatatacca acatatgttg gttgaaatta aaagaataaa atatatcatg  21900
aaaacattaa tcaaaagaaa ggagtggcta tattaataac ataaaataga cttcagagaa  21960
aagaaaattt caagagacag gaataaaagg atcaagaaaa gatcctgaaa gaaaagcagg  22020
caaatcaatc attctgcttg gagattcaac accctctctt aacaactgat agaacaacta  22080
gacaaaaaaa tcagcatgga gttgagaaga acttaacacc actgaacaac aggatctaat  22140
agacatttac ggaacactct acccaacaat agcaaaataa acattctttt caagtattca  22200
ctgaacatat ccttagaccc taccctgggc cataaaacaa agctcactag tgattgccga  22260
aggcttggat ggacagtgga agagctgcat ggggagggag aaggtgacag ttaaagagtg  22320
taggatttct ttttgggata atgaaaatgt tccaaaattg attgtggtga tgttggcgca  22380
actctacaaa tataaaaaag gccattgaat tgtacgtttt aagtgggtga aacatatggt  22440
atgtggatta tatctaacgc tttttaaaaa cttaacacat ttcaaagaat agaagtcata  22500
cagagtgtgc tctactggaa tcaaactaga aagaggtaac tggaggataa cgagaaaagc  22560
ctccaaatac ttgaaaactg gacagcacat ttctaaaatc atccgtgggt caaagatatt  22620
catttctgat attcattttt attgtttaat gtatttttaa aaatttctta agggaaataa  22680
actgactaaa aatgaatatg gctgggtgcg gtggctcacg cctgtgatcc cagcactttg  22740
ggaggccgag gctggtggat cacaagatca ggagttcgag accagcctgg ccaagatggt  22800
gaaaccccgt ctcaactaaa aaactacaaa aagtagccaa gcgcagtggc gggagcctgt  22860
ggtcccagct acttgggagg ctgaggtagg agaatcgctt gaacacaggc agcagaggtt  22920
gcagtgagcc aagattgtgc cactgcacgc cagcctgggc gacagagact gcctcaaaaa  22980
aaaaaaaaaa aaaaagaata tcaaaatttg tgggacatag ttaaagcaat gctgagaggg  23040
aaatttataa cactaaatgt ttacattaga aaagagaaaa agtttcaaat caatagtctc  23100
cactcccatc tcaagaacac agaagatgaa gagcaaaata aacccaaagc aagcaaaaga  23160
aagaaaatat aaaaataaat cagtaaaatt gaaaacagaa acacaataaa gaaaatcagt  23220
gaaacaaagt actgattctt cgaaagatta ataaaattga caaacctcta gcaaggctaa  23280
caaacaaaaa agaaagaaga cacggattac cagttattag aatgaaagca taattagaaa  23340
caactctaca cattataaat ttgacaatgt agatgaaatg gactaattac tgaaaaaaca  23400
caaattacca caactcaccc aatatgaaat agataattgg gatagcctga taactactga  23460
gaaaattgaa tttgtaattt taacactctt aaaacagaaa cattaaactt aatattttat  23520
aaatattaga taaggtaatt atacccttcc ttaacaaata aaaacgacaa attattttgc  23580
agctaaagag atgtatgtac tgtgaaaaat atcttcagaa aaatagaact ttgtttgaag  23640
aataaggatt taaaaaatgt ttttaactct caagaagcaa atatctgggc ccagatggtt  23700
```

-continued

```
tcactgaaga attctaccaa atgtttaatg aagaattacc accaactcta catagcatct  23760
ttgagaaaac tgaagagaag ggaacatctc ccagttcatt ttatgaagtg ggtgttactc  23820
tgatactaga actgtataag gacagctact cttgacacac tgcctatggg tagctctgct  23880
ctgcaggaac agtcagaaaa aaaaaaaaaa gaagcactgg acaagggcag tataaaaaaa  23940
gaaaactggg ccaggtgcag tggctcacac ctgtaatctc agcactttgg gaggctgacg  24000
ctggtggatc acctgaggtc aggagtttga gactagcctg gccaacatgg taaaaccctg  24060
tctctactaa aatacaaaaa ttagccaggc agggtggtgg ggaaaataaa aaggaaaaaa  24120
aaacaaaaat aaactgcaga ccaatatcct tcatgagtat agacacaaaa ctccttaaac  24180
tccttaacaa aatattagca agtagaagca atatataaaa ataattatac accatgatca  24240
agtgggactt attccagaaa cgcaagtctg gttcaacatt tgaaaacaag gtaacccact  24300
atatgaacgt actaaagagg aaaactacat aatcacatca atcaatgcag aaaaaagcat  24360
ttgccaaaat ccaatatcca ttcatgatac tctaataaga aaaataagaa taaaggggaa  24420
attccttgac ttgataaagc ttacaaaaga ctacaaaagc ttacagctaa cctatactta  24480
atggtgaaaa actaaatgct ttcccctacg atcaggaaca aagcaaggat gttcactctc  24540
attgctctta tttaacatag ccctgaagtt ctaacttgtg caaaacgata agaaagggaa  24600
atgaaagacc tgcagattgg caaagaagaa ataaaactgt tcctgtttgc agatgacatg  24660
attgtctcat agaaaatgta aagcaactag gggtaggggg gcagtggaga cacgctggtc  24720
aaaggatacc aaatttcagt taggaggagt aagttcaaga tacctattgc acaacatggt  24780
aactatactt aatatattgt attcttgaaa atactaaaag agtgggtgtt aagcgttctc  24840
accacaaaaa tgataactat gtgaagtaat gcatacgtta attagcacaa cgtatattac  24900
tccaaaacat catgttgtac atgataaata cacacaattt tatctgtcag tttaaaaaca  24960
catgattttg gccaggcaca gtggctcata cctgtaatcc cagcatttta ggaggctgag  25020
gcgagcagaa aacttgaggt cgggagtttg agaccagaat ggtcaacata gtgaaatccc  25080
gtctccacta ataatacaaa aattagcagg atgtggtggc gtgcacctgt agacccagct  25140
acttgggagg ctgaggcacg agaattgctt gaacaaggga ggcagaggtt gcagtgagct  25200
gggtgccact gcattccagc ctggtgacag agtgagactc catctcaaaa aaaataaaat  25260
aaagcatgac ttttcttaaa tgcaaagcag ccaagcgcag tggctcatgc ctgtaatccc  25320
accactttgg gaggccgagg caggcagatc acaaggtcag gagtttgaga ccagcctgac  25380
caacatggtg aaaccccatc tctactaaaa aatatataaa ttagccaggc atgtgtagtc  25440
tcagctactc aggaggctga ggcaggagaa tcacttgaac ccggaggcag aggttgcagt  25500
gttgagccac cgcactccag cctgggtgag agaacgagac tccgtctcaa aaaaaaaaag  25560
caaaataacc taattttaaa aacactaaaa ctactaagtg aattcagtaa gtctttagga  25620
ttcaggatat atgatgaaca tacaaaaatc aattgagctg gacaaaggag gattgtttta  25680
ggtcagtagt ttgaggctgt aatgcacaat gattgtgcct gtgaatagct gctgtgctcc  25740
agcctgagca gcataatgag accacatctc tatttaaaaa aaaaaaaatt gtatctctat  25800
gtactagcaa taagcacatg ggtactaaaa ttaaaaacat aataaatact gtttttaatt  25860
gcctgaaaaa aatgaaatac ttacatataa atctaacaaa atgtgcagga cttgtgtgct  25920
gaaaactaca aaacgctgat aaaagaaatc aaagaagact taaatagcgt gaaatatacc  25980
atgcttatag gttggaaaac ttaatatagt aaagatgcca attttatcca aattattaca  26040
caggataaca ttattactac caaaatccca gaaaaatttt acatagatat agacaagatc  26100
```

-continued

```
atacaaaaat gtatacggaa atatgcaaag gaactagagt agctaaaaca aatttgaaaa  26160
agaaaaataa agtgggaaga atcagtctat ccagtttcaa gacttacata gctacagtaa  26220
tcaagactgt gatattgaca gagggacagc tatagatcaa tgcaaccaaa tagagaacta  26280
agaaagaagc acacacaaat atgcccaaat gatttctgac aaaggtgtta aaacacttca  26340
acgggggaag atatgtctct cattaaaggg tgtagagtca ttgcacatct ataggcaaaa  26400
agatgaacct gaacctcaca ccctacagaa aaattaactc aaaatgactc aaggactaaa  26460
cataagatat acatctataa aacatttaga aaaaggccac gcacggtggc tcacgctcgt  26520
aatcccagca ctttgggagg ccaaggcagg tggatcacct aaggtcagga gtttgagacc  26580
agccggatca acatggagaa gccccatctc tactaaaaat acaaaattag ctggacgtgg  26640
tggcacatgc ctgtaatccc agctacttgg gaggctgagg catgagaatc gcttgaaccc  26700
ggggggcaga ggttgcggtg agccaagatc acaccattgc actccagcct gggcaacaag  26760
agcaaaactc caactcaaaa aaaaaaaaaa aaaggaaaaa tagaaaatct ttgggatgta  26820
aggcgaggta aagaattctt acacttgatg ccaaactaag atctataagg ccagtcgtgg  26880
tggctcatgc ctgtaattcc agcactttgg tcaactagat gaaaggtata tgggaattca  26940
ctgtattatt ctttcaactt ttctgtaggt ttgacatttt tttagtaaaa aattggggga  27000
aagacctgac gcagtggctc acacctgtaa tcccagcact ttgggaggcc ggggcaggtg  27060
gatcacacgg tcaggagttc gagaccagcc tggccaacat ggtgaaaccc cgtctctacc  27120
aaaaatataa aaaattagcc gggtgtcatg gtgcatgcct gtaatcccag ctactgagga  27180
ggctgaggca ggagaatcac ttgaacctgg gaggtggaag ttgcagtgag ccgagattgt  27240
gccactgcac tccagccttg ggtgacagag cgagactccg tctcaaaaga aaaaaaaaaa  27300
aaagaatatc aaacgcttac tttagaaact atttaaagga gccagaattt aattgtatta  27360
gtatttagag caatttttat gctccatggc attgttaaat agagcaacca gctaacaatt  27420
agtggagttc aacagctgtt aaatttgcta actgtttagg aagagagccc tatcaatatc  27480
actgtcattt gaggctgaca ataagcacac ccaaagctgt acctccttga ggagcaacat  27540
aaggggttta accctgttag ggtgttaatg gtttggatat ggtttgtttg gccccaccga  27600
gtctcatgtt gaaatttgtt ccccagtact ggaggtgggg ccttattgga aggtgtctga  27660
gtcatggggg tggcatatcc ctcctgaatg gtttggtgcc attcttgcag gaatgagtga  27720
gttcttactc ttagttccca caacaactgg ttattaaaaa cagcctggca ctttccccca  27780
tctctcgctt cctctctcac catgtgatct cactggttcc ccttcccttt atgcaatgag  27840
tggaagcagc ctgaagccct cgccagaagc agatagtgat gccatgcttc ttgtacagcc  27900
tacaaaacca tgagcccaat aaaccttttt tctttataaa ttatccagcc tcaggtattc  27960
ctttatagca agacaaatga accaagacag ggggaaatca acttcattaa aataatctat  28020
gcagtcacta aacaaataag aacaagaggc tccagaagtg ggaagccaat acccagagtt  28080
cctacaatac agtatctgaa aagtccagtt tccaaccaaa aaatatatat atacaggccg  28140
gacatggtag cttatgtctg taatcccagc actttgggat gctgaggcgg gcagatcacc  28200
ctaggtcagg agttcgagac cagcctggcc aatatggcaa aaccccgtct ctactaaaaa  28260
tacaaaaatt agccaggcat ggtggtggat gcctgtaatc ccagctactc gggaggctga  28320
ggcagggaat cacttgaacc caggaggcag aggttgcagt gagccgagat cacgccactg  28380
aactccagcc tgggcaacaa agtgagactc cacctcaaaa aaaaaaaaaa tatacatata  28440
```

-continued

```
tatatgtgtg tgtgtgtgtg tgcgcgcgtg tgtgtatata cacatacaca tatatacata  28500
tatacagaca cacatatata tatgaagcat gaaaagaaac aaggaagtat gaaccatact  28560
ttctgtggtt atgataggat ggggtatcac gggggaagta gacaagggaa actgcaagtg  28620
agagcaaaca gttatcagat ttaacagaaa aagactttgg agtaaccatt ataaatatgt  28680
ccacagaatt aaagaaaagc gtgattaaaa aaggaaagga aagtatcata acaatattac  28740
tccaaataga gaatatcaat aaaggcatag aaattataaa atataataca atggaaattc  28800
cggagttgaa aggtagaata actaaaattt aaaattcact agagaaggtt caacactata  28860
tttgaactgg cagaagaaaa atttagtgag acaaatatac ttcaatagac attattcaaa  28920
tgaaaaataa aaagaaaaaa gaatgaagaa aaataaacag aatctcagca aaatgtggca  28980
caccattaat cacattaaca tatgcatact gagagtaccg gaagcagatg agaaagagga  29040
agaaaaaata ttcaaatgat ggccagtaac ttcctagatt tttgttttaa agcaataacc  29100
tatacaatca agaaactcaa tgaattccaa gtaggataaa tacaaaaaga accacaaaca  29160
gatacaccat ggtaaaaatg ctgtaagtca aaaacagaga aaatattgaa agcagctaga  29220
ggaaaactta taagagaacc tcacttacaa aagaacatca cttataaaag aaccacaata  29280
atagaaacag ttgacctctc atcagaaaca atgaatgata acatatttga agtgctcaaa  29340
gaaaaaaaat aaagattcct atatacgaca aagctgtctt tcaaaaatat acatccaaaa  29400
ggattgaaac cagggtcttg aagagttatt tgtacatcca tgttcatagc agcattattc  29460
acaatagcca aaaggtagaa gcaacccaag ggtccatcga caaataaata aaatgtggta  29520
tatgtataca caatggaatt tattcagtat taaaaaggaa tgaaattctg acacatgcta  29580
caacatggct aaaccttgag aacactatgc taagtgaaat aagccagcca caaaaggaca  29640
aataccatat tacttcactt gtatgaaata cctagggtag tcaaattcag agatagaaag  29700
taaaacagtg gttgccaagg gctgagggag ggagtaacgt ggagttattg ttgaatgggt  29760
acagaatttc agttttgcaa gataaaaaga gttctggaga cagatggtgg tgagggtggt  29820
acaacaatac aaatatactt tatactactg aacagtatac ttaaaaatga ttaacatggt  29880
gaaaccccgt ctctactaaa aatacaaaaa aattagctgg gtgtggtggc gggcacctgt  29940
aatcccagct acttgggagg ctgaggcagc agaattgctt gaaaccagaa ggcggaggtt  30000
gcagtgagct gagattgcgc caccgcactc tagcctgggc aataagagca aaactccgtc  30060
tcaaaaaata aaaaataaaa aaaatttaaa aatgattaag caggaggcca ggcacggtgg  30120
ctcacaccta taatgccagc actttgggag gccgaggcag gcgatcactt gagaccagga  30180
gtttgagacc agcctggcca acatggcaaa accctgtctc tgctaaaaat acaaaaatta  30240
gccaggcatg gtggcatata cttataatcc cagctactgg tgagactgag acacgagaat  30300
tgcttgaacc caggaggcag agattgcagt gagtcgagat cgcgccactg aattccagcc  30360
tgggcgacag agcaagattc tgtctcgaaa aaacaaaaac aaaaacaaaa agcaaaacca  30420
aaaaataatt aagcaggaaa cgagattgct gctgaggagg agaaagatgt gcaggaccaa  30480
ggctcatgag agcacaaaac ttttcaaaaa atgtttaatg attaaaatgg taaattttat  30540
atgtatctta ccacaaaaaa aagggctggg gggcaggaaa tgaaggtgaa ataaagacat  30600
cccagagaaa caaaagtaga gaatttgttg ccttagaaga aacaccacag gaagttcttc  30660
aggctgaaaa caagtgaccc cagagggtaa tctgaattct cacagaaaat tgaagcatag  30720
cagtaaaggt tattctgtaa ctatgacact aacaatgcat attttttcct ttcttctctg  30780
aaatgattta aaaagcaatt gcataaaata ttatatataa agcctattgt tgaacctata  30840
```

-continued

```
acatatatag aaatatactt gtaatatatt tgcaaataac tgcacaaaag agagttggaa  30900
caaagctgtt actaggctaa agaaattact acagatagta aagtaatata acagggaact  30960
taaaaataaa attttaaaaa atttaaaaat aataattaca acaataatat ggttgggttt  31020
gtaatattaa tagacataat acaaaaatac cacaaaaagg gaagaagaca atagaactac  31080
ataggaataa cattttggta tctaactaga attaaattat aaatatgaag tatattctgg  31140
taagttaaga cacacatgtt aaaccctaga tactaaaaag taactcacat aaatacagta  31200
aaaaaataaa taaaataatt aaaatgtttg tattagtttc ctcagggtac agtaacaaac  31260
taccacaaat tgagtggctt aacacaactt aaatgtattt tctcccagtt ctggaggcta  31320
aacacctgca atcaaggtga gtacagggcc atgctccctg tgaaggctct aggaaagaat  31380
cctcccttgt ctcttccagc ttccagtggt tctcagtaac cctaagtgct ccttggcttg  31440
tagctatatc attcctagca accagaaaga agaaaataat aaagattatg gcaaaaaata  31500
atgaaatcaa aaggagaaaa atggaaaaaa ataaataaaa ccaaaagcta gttctttgaa  31560
aagatcaacc aagttaacaa acctttttaac tagactgaca aaaaggaggt aagactcaaa  31620
ttactagaat cagaaataaa agaggggaca ttactaatga gggattagaa aagaatacta  31680
cgaacaaatg tgtgccaaca aattagaaaa cttagatgaa atggacaggt tcctaggaca  31740
acatcaacta ccaaaattta ctcaagaaga aagagacaat ttgaatgagc tataacaagg  31800
gaagagactg aattgacaac caagaaacta tccacaaaga aaatcccagg cccagaagat  31860
ttcactgtga aattctttca aacttataaa tataaattaa catcagttct tcacaaactc  31920
ctccaaaaaa aagaacagat ctctatttac aggcgatacg atctttagaa aatcctaagg  31980
gaactactaa gacactatga taactgataa acaagttcag caaggctgca ggatagaaaa  32040
ccaatataca aaaatctatt atatttctat acacttgcag tgaacaaccc aaaaatgaga  32100
ttaagaaaat aattcaattt acaataacat caaaaagaat aaaaacactc aaaaataaat  32160
ttattcaagt aagtgcaaaa cttatactct agaagctaca aaacactgtt aaaagaaatt  32220
aaaggtttac ataaatgaaa aactatccca tgttcatgga tcaaaagact tattactggc  32280
aatgctctcc aaattgatct ataaattcaa caaaatcctt atcaaaatcc cagatgaggc  32340
tgggggtggc ggttcatgcc tgtaatccca gcactttggg aggctgaggc acgcagatta  32400
cctgaggtcg ggagctcgag atcagcctga ccaacatgga gaaaccctat ctcttctaaa  32460
aatacaaaat tagtcaggcg tggtggcaca tgcctataat cccagctact cgggaagctg  32520
aggcaggaga atcgcttgaa cccaggaggc agaggttgca gtgagccaag atcgtgccat  32580
tgcactccag cctgggcaac aagagcaaaa ttccatctca aaaaaaaaaa aaaaaaaatc  32640
ccagatgact tcactgttga aattgaaaag attattctaa aattcacatg gaattgcaag  32700
accttgagaa tagccaaaac aaacttgaaa aacacgaaca aaatatagga tgactcactt  32760
gccaattgca aatgttacga cacagcaaca gtaatcaaga ctgtgtggta ctggcaaaag  32820
acacatacat acatacatat caatggaata taattgagag tacagaaaca agcctaaaca  32880
tctatggtaa gtgcttttct attttttttct tttttttttt cttttttgta gagatagaat  32940
ctcaccatgt tgcccaggct ggtcttcaac ttctgggctc aagcaatcct cccactgtgg  33000
cctcccaaag tgctgggata actggcatga gccaccacat ccagcccaga tgattttcaa  33060
aaaagtcaac aagaccattc ttttcaacaa ataggtctgg gatgatcaga tagtcacatg  33120
aaaaaaaaaa tgaagttgga ccctccatca cactaaagtg ctgcgattat aggcatcagc  33180
```

-continued

```
caccacatcc agcccaaatg attttcaaaa aggtcaacaa gaccattctt ttcaacaaat  33240
aggtctggga taatcagata gtcacatgaa aaaaaaaatg aagttggacc ctccatcaca  33300
ccatatgcaa aaattaattc aaaaatgaat tgatgactta aacgtaagag ttacgactgt  33360
aaaactctta gaaggaaaca tacgggtaaa tcttaaagac gttaggtttg acaaagaatt  33420
cttagacatg acaccaaaag catgaccaac taaggtaaaa tagggtaaat tgtacctacc  33480
aaaatgaaaa acctttgtgc tggaaaggac accatcaaga aatggaaagc caaaatagcc  33540
aaggcaatat taagcaaaaa gaacaaagct ggaggcatca tactacctga cttcaaagca  33600
acagtaacca aaacagcatg gtactagtag aaaaacagac acatagacca atggaacaga  33660
ataaagaacc caaaaataaa tccacatatt tatagtcaac tgatttttga caatgacacc  33720
ccttcaataa atgatactag gaaaactgga tatcgatatg cagaagaata aaactagacc  33780
cctatctctc accatataga aaaatcaact cagactgaat taaagacttg aatgtaagac  33840
ccaaaactat aaaactactg gtagaaaaca taaggaaaaa cgcttcagga cattggtcca  33900
ggcaaagatc ttatggctaa aacctcaaaa acacaggcaa caaaaacaaa aatggaaaaa  33960
tagcacttta ttaaactaaa aagctcctgc acagcaaagg aaacaacaga atgaaaagac  34020
aacctgtaga atgggagaaa atatttgcaa actatccatc catcaaggga ctagtatcca  34080
gaacacacaa gtgactaaaa caactcaaca gcaaaaaagc aaataatctg gtttttatat  34140
gggcaaaaga tctgaataaa cattctcaaa ggaagacata caaatgtcac tatcattctg  34200
ccagtaccac actgtcttga ttacttgtta gtgtataaat ttttaaattg ggaagtgtga  34260
gtcatcctac actttgttct tgtttttcaa gtttgttttg gctattctgg gagccttgca  34320
agtataaaat agccaacaag tatgaaaaaa tgctcaccat cactaatcat cagagaaata  34380
aaaatcaaga ccactatgag atatcctctc actccagtta gaatggctac tatcaaaaag  34440
acaaaatata atggatgctg gcaaagattt ggagaaaggg gaactcctat acactgtggg  34500
tagggatgca aattggtaat ggccattatg gaaaataata ctgaggtttt tcaaaaaact  34560
gaaaatagaa ctaccatatg atccagcaac cctactactg ggtatttatc caaaggaaag  34620
aagtcagtat actgaagaaa tatatgcact ctcatgttaa ttgcaacact gttcacaaca  34680
gccaagacag ggaataaatc taaatgtgca tcaacagatg aatggataaa gaaaatgtgg  34740
catatacact caatagaata ctattcagcc attaaagaag aatgaaatcc tgtcatccca  34800
gcaacatgga tgaacctgga ggacattata tttaatgaaa taagtaaagc acaaaaagat  34860
aaacagtaca tgttctcact cagacatggg tgctaaaaag aaaatggggt cacagaatta  34920
gaaggggagg cttgggaaaa gttaatggat aaaaatttac agctatgtaa gaagaataag  34980
ttttagtgtt ctatagaact gtagggcgag tatagttacc aataacttat tgtacatgtt  35040
caaaaagcta gaagagattt tggatgttcc cagcacaaag gaatgataaa tgtttgtgat  35100
gatggatatc ctaattaccc tgattcaatc attacacatt gcatacatgt atcaaattat  35160
cactctgtac ctcataaata tgtataatta ttacgtcaac aaaaaaagga aaaaaaagaa  35220
aattaagaca acccacataa tggaagaaat aaaatatctg caaattatat atatctgata  35280
aatatttaat atttataata tataaagaac tcctacaact caagaacaac aacaaaacaa  35340
cccaattcaa aaatgggtaa aagccttgaa tatacactta tctaaagact atatacaatt  35400
ggccaataaa gacacgaaaa gatgctcaac atcactagtc atcagggaaa tataaatcaa  35460
aaccacaatg tagaatgtag acaccacttc atatgcacta ggatggctag aataaaaagg  35520
taataacaaa tgttggtaag gatgtgaaaa aatcagaaac ctcattcgct gctgttggga  35580
```

-continued atgtaaagtg atgcagccac tttggaaaac agtctggcag ctcctcaaat tattaaatac 35640
agagttaccg tatgacccag gaatattcct cctgggtcta taaccaaaaa aatgaaaaca 35700
tatatccaca taaaaacttg tacatgggca tttatagcaa cattattcat aacagcaaag 35760
gtggtaagaa cccatatgcc catcatctga tgaacaggta aataacatgc ggtattatcc 35820
atacactaga atattatctg cccatacaag gagtgacatc cagctacatg ctacaaggat 35880
gaatctcgga aaccttatgc taagtgaaag aagccagtca caaatgacca cagattatga 35940
ttccatgcat cggaaatgac cagaataggg aaatctatag agacagaaag tagattagtg 36000
gttgggtggg gctgggagga caggtagtac actactttcc cagaactact ggaacaaagt 36060
accacaaact ggggagctta aacatagaaa ttgatttcct cacagttctg gagactagga 36120
ctctgagatc aaggtgtcag cagagctggt tctttctgag ggccctgagg caaggctctg 36180
tcccaggcct ctctccttgg ctggcaggtg gccatcttct ccctgcgtct tcacatcatc 36240
ttttctctgt gtgtgcccat gtccaaattt tgattggctc attctgggtc atggccaatt 36300
gctatgcaca aagtgaagtc tacttccaaa agaagggaag agggaacact gactaggcta 36360
aacttatagt cattttaatg tccgcttttc ctatgagatt gtgaacacac agaagtaggg 36420
tttttatcta cattgtgcaa agtttaataa gaaaaataga attcaagaga agcagttcaa 36480
tagcaggaat ttaatatggg aactaattac aaggtttagg gcaggactaa aaagccagtt 36540
gggatggtga gccaacccag agattagcaa cagtgggacc ccatctacct accacccatg 36600
aagctggaag gataaaggag gggctattat cagagtccac aagccagtgt cagagtcctt 36660
ggctggagct gggaccaccc tagagacact gtgcaaagca gaaaacaagg gggaaaaacc 36720
ctgacttctc ccttcctccc acctttcaat ctcccactag tgcttcctac tagccatact 36780
tggccagaga cagtgacaag gaacactgca aaatgaagtt tgtaggaatc atctccctct 36840
gagacagaga aatatggaag ggtagaaaat gaatcagagg ataaagagaa aaaaccctga 36900
gtactatctt atttatcttt gtatctccag tgcctaatct gtctctcaaa aaaggaaagc 36960
aattgagaga aactgaaaac tccaattgaa atgaaagaat ggagaattac tggactagaa 37020
gagaagagaa aaatttattc cgcatagagt aaacaagaat ggattcacaa aggacgtgat 37080
gaatgaaaag ctataatcag caaagatttg ccagagaaat taaaaagtgg taaactcagc 37140
cacgctgtac aacctgaagg cacaatgcat gaaaacgttt caagaaatga caagatttga 37200
agtcaaattc taagtgcttt tccagaatct ctcaagacga ttatatagct accccatttt 37260
attaaataaa atggaaactt actaaacttt ccccttgtat taaactaaca tatgtcctaa 37320
tagcaaacga ttctggaatt cctagagtaa aatatatttc gtcaaagtgt attgctcttt 37380
taatattctg ctgacctcct tttgctattt aggatatttg tatacacatc acacgtaaat 37440
ttggtctata gtttacatct acgggcttat actgttcttt ttttcatttt tttaaaattt 37500
ccaaccccca gtatccatat actgctctct atcagggtta ttttaacttt gtaaaatcag 37560
ctgagatgct ttccatgttt ttttttttta ttttctgcca catttgaata gcataggagt 37620
taccaccatc aaccttggat tatttaagca ttcacgattc cacgtgtgga ttttttattc 37680
agagtctttc ttgtcattcc tgctatcagc acagaaccca atctcagctt tccagctata 37740
ctctcacccc atggaatttg cagatgaagt tcaaaaggac ctttgcatta tcctgcctcg 37800
ccctcttccc ccttcattta gacatcacct tcttctagaa cgtcttacct gacatgccct 37860
gctcccaacc cctgctgccc aattgtgtgc tctcccgtgt cctggcctgc catcctcttt 37920

-continued

```
agtaattgcc tgctccctca tctgtctccc cacccagaca ttaagctgaa tagactggat  37980
ttgtgtcttg tccatcacta taatctcagc acctagtacc tagtaggtac ttaccatgta  38040
ttcattagca aaatgttatg tataaccttg caccttaaaa acaagagaag gaagacaaaa  38100
ttaagtctta agactatggt ttagaacatg gatcagaaac tacagtctgc agcccaaatc  38160
cagaccaaat gaagagacca tgttcattta catacaacct atagcagctt tcacactaca  38220
ggagcagagc taagtagttc caagggaaca cacggccctg caaagcctaa aatatttact  38280
ctatagctct tcacagaaaa agttttcaga tccctcgttt agaactcttg ttcatatgca  38340
atttcactaa accatagttt tttgggtttg tttggttttt tttggcaaaa aggaatgagc  38400
cgatccagaa aaggttgaaa agaatgaatc attactgctg aaagaatgtg cacacagtcc  38460
gtcagtattc tgctgccatg ctgacaccca tccaatagtg tcatgagatg cagcagctac  38520
tactgtgttc tcaatgccga gtccacccac tccataacca tgtccaagca atcttgggaa  38580
catcatcacc atgcttgttt atccttaagg tattgcctca catacagcag tggctggtca  38640
taaagtcaaa tgacactagt ggccaggagg tcaagagaat gagtgaggac aggtgggtag  38700
gcagcccagg ccctagcaac agcaggagct cacccctcag tcactctagc caggactgaa  38760
atacttttca ccctttcaag agagactagg aatctggatt tttatgtgaa atatcttgat  38820
tactaaatgt tgtcaacaga catgtcaaaa ggtaaaacta agtaagttca tggggcagat  38880
tgactattca ggttatagaa ttaaggattc ttatccaaca cagataccaa ccaaaaagct  38940
gacgtataac atattaggag aaactatgtg cactgtcgaa acatcaacaa ggggctaatg  39000
tctaaaatag tctatattgg attccagttg aaacatgggg aaaggacatg aacaggcaac  39060
ttatgtcaat ggaaactcaa aaagataaca agcatatata aaagcattct caaattcagt  39120
agtaaacaga cagatgcaaa taaaaagagg gaaactgctg ccgggcacag tggctcacac  39180
ctgtaatccc agcactttgg gaggccgagg cgggcggatc atgaagtcag gagatcgaga  39240
ccatcctggc taacatggtg aaaccccgtc tctactgaaa acacaaaaaa ttagccaggc  39300
gtagtggtgg gcaccagtag tcccagctac tcaggaggtt gaggcaggag aatggcatga  39360
acccaggagg cggagattgc agtgagccga gaccatgcca ctgcactcca gcctgggcga  39420
ctgagtgaaa ctccatctca aaaaatataa taataattat aattataata ataataaata  39480
gtaaataaat aaaaagagag agactgctaa agtctagaaa gttgaatgat gccaagcgca  39540
tgcaaagatc agggccttgg gatggccggg tgcagtggct cacgcctgta atcccaccac  39600
tttgggaggc caaggcgggc ggatcatgag gtcaagagat caagaccatc ctggccgaca  39660
cagtgaaacc cggtctctac taaaagtaca aaaaaatata tatatatata tatattatta  39720
tattatatat atatatatca gagccttggg aatccttgtg tgctgctggg gaaggtagtg  39780
gtgcagccac ccttgacagc aatctggcag tacttggtta tattaagtat aggcacacac  39840
cacgaccagg cagtcctact cctgggtcta aatcccaaag aattctcaca caagtccata  39900
aggagacatg tacgaggctc attcagcatt actgggagtg ggaatcaacc tgggtgtcca  39960
tctacaggag acgagatgga caaaatgtgg tggatattaa gaccagaatc accaagtaac  40020
agagatgggt ggtgagtgac aatcctaaga tacagaataa aggctagaac atgatgccat  40080
tcatgtaaat taaaaataga tgcacacaaa gcagtatacg cgtgaccctt gaatagcaca  40140
ggtttgaact gcctgtgtcc acttacatgt ggattttctt ccacttctgc tacccccaag  40200
acagcaagac caacccctct tcttcctcct ccccctcagc ctactcaaca tgaagatgac  40260
aaggatgaag acttttatga taatccaatt ccaaggaact aatgaaaagt atattttctc  40320
```

-continued

```
ttccttatga ttttctttat ctctagctta cattattcta agaatatggt acataataca  40380
catcacacgc aaaataaatg ttaattgact gtttatatta tgggtaaggc ttccactcaa  40440
cagtaggctg tcagtagtta agttttggga gtcaaaagtt atacacagat tttcaactgt  40500
gcaggcaatc agttcccctg accccctcat tgttcacggg tcaactgtat atacacaaaa  40560
gtattatatg aacctcatta gaatagctgt ctatagggag aagagaatga gagtgggata  40620
aaacggaatg aacaaataaa ccaacaaatg cattaacaag caaaacaaca gaggggcttg  40680
catgggccag tgatgataaa gggctaagaa tgagaatata attaattcaa ttcctcacac  40740
ctgaggtcta aaaccaagga aagggagggc caggcgtgga ggctcacgcc tgtaatccca  40800
gcactttggg aggctgaggc gggcggatca caagattagg agtttgagat cagcctggcc  40860
aacacagtga aagcccatct ctacaaaaaa tacaagaatt acccaggtgt ggtggcacat  40920
gcctgtagtt agctactctg gaggctgagg caggagaatc acttgaaccc aggaggcgga  40980
ggttgcaggg agccgagatc acaccattgc actccagcct gggtgacaga gtaagactct  41040
gtctcaaaaa aataaaaaaa ataaaaaaac agagaaaggg aggaaactag atccaggctg  41100
actagataca gcctttagag ttagaaaaga tgatttgaca atctaagccc acactcagat  41160
tgaatgaaat tgaaaagcct ttcaaactaa aacatttaat tacaccatct gctgcagaca  41220
gaactcagac aactcaaaca ggtaatgtca gcgtggtgtt ttatatcacc accctcaaca  41280
cagaataaaa atcagctgca tgtgaagcag tgactagaat gaagaaaagg ctgcttctta  41340
cttccttcta gtggttcttt ccgaaaacat taataggcac cagctctatg catgtcaccc  41400
tgcagggaga catggggtat ataactatga cttactgttc attcctcaag gaattcccaa  41460
tcttgtggaa gattatacac aatgaggcaa caaaaactat ccaataaaac cacggaaaag  41520
aagccagtga caaagaagcc agtgatgaaa ggccctgtga gcagagctga tggccatttg  41580
gggaagaaag accaacatgg atgggggtga tcagggtggc tccgtgggaa agctggaaga  41640
gaagtggcag atctctgagc tggatgatgg gccactacca tctgtatatg gctaattaaa  41700
gaccatgtgt ggattttta ttcagctctt tcgtgtcatt cctgctatca gcacagaacc  41760
caatctcaac tttccagcta tattgagcta aacttctcac ctcatggaat ttgcagataa  41820
agttcaaaag gatccttgcc ttttcaaaat aattttgaat ggttgagtag tccctctgtg  41880
ctctctcact gacaccctct caaggctgct gagcacgtgc catgctatgg ctttctccaa  41940
catcaggaaa tgttctccac tcagtttcac cttaatacaa atgtgttctc tcttcagaga  42000
aggcaaaaaa attcatgacc atctgactgg gagaagtcat ttctaggtaa agtgtccatc  42060
tttttctgag gaacacagga ggaaaatctt acagaaaaga gttaacacag caggcctaag  42120
actgcttttt aaaataaata aataaataaa taaataaata aataaataaa taaataaata  42180
aataaatgaa tgatagggtc ttctgtattg gccaggctag tctcaaattc ctggcttcaa  42240
gagatcctcc caccttggtc tcccacagtg ttgggattat agacatgagc cattgtgctt  42300
ggcccaagac tgttattctt aaaaagtctc ataaaaagca tggttaatcc ttggctggca  42360
cctgggaact tagatttcag aagggttccc accatccaac ctggaaagag ggactcactg  42420
tgcctaaatt attgtgtggt ttatgctgaa ctcctgcttt tcttcaggta gcgtggaatg  42480
tggtatgtgc tgggcaaagg gggcctgcat gaccagcccc caataaaaac cctgggtgtt  42540
gggtctctag tgagtttccc tggtagacag catttcacat gcgttgtcac agctccttcc  42600
tcggggagtt aagcacatac atcctgtgtg actgcactgg gagaggatgc ttggaagctt  42660
```

-continued

```
gtgcctggct tcctttggac ttggccccat gcacctttcc ctttgctgat tgtgctttgt  42720
atcctttcac tgtaataaat tacagccgtg agtacaccac atgctgagtc ttccaagtga  42780
accaccagat ctgagcatgg tcctgggggc ccccaacaca gaaataaatt ataaaagacc  42840
aaggactggg catggtggcc catgccggta atctcagcgc tttgggaggc cgaggcagga  42900
ggaccagtta agcccaaaag ttcaaagtta cagtgaccta tgactgcgcc aatgcactct  42960
aacctgggag acagagcaag accctgtccc caaaacaata aactaaacac atacttctgc  43020
cttccaagtg tcttaaaatt caatggaatg gtagaaacat ttttaaaaca ctaaatcaaa  43080
agaaacctgg aaaacaagag tgccgatggc caactaaaat gtctaggaaa tttctgaaaa  43140
gtaaaaagta ctcagaacca gattacctga gcaaaccata gcccaataca agcttgggag  43200
gaggctgtta tgcagaagga aatggtaaca ggtttccagg aacagacttg taacagcaga  43260
tagaacagca gaggtagaac ctgacaaggt gattacctgg ggaactgcag tctgaatgac  43320
caggactgtt ggacccttcc cctcacatgg aatacacacg ccactcagca gcacaccaca  43380
gctcttcaac aatcacagga ggcacgctac gcctagtaag acaggaaaaa aggaattctc  43440
aaacttcgaa gatgaacaca taaagaatca ccaagttttt attcagtatg atgaaacagg  43500
gacactgaat caacagaaca caaacccaag caaagataat tactagagca catagaagaa  43560
attattagat attcttggga agacctaagg ggacattata aagagcaagc agttggtatg  43620
tgacgatctt tgtgatatac caagaaataa aaacacagga tgaagaccag atagagaata  43680
atgctactat ttgtgcaaaa aaggagaaat ggagaatctg attcatattt gcttgtattt  43740
gcatgaagaa actttggaag gtacataagt aactaacaac aatggttacc tacttgtaag  43800
gcgagagaag taagaggaca ggaatggtgg gaacaccttt tgtgtccgga attggtgggt  43860
tcttggtctg acttggagaa tgaagccgtg gaccctcgcg gtgagcgtaa cagttcttaa  43920
aggcggtgtg tctggagttt gttccttctg atgtttggat gtgttcggag tttcttcctt  43980
ctggtgggtt cgtagtctcg ctgactcagg agtgaagctg cagaccttcg cggcgagtgt  44040
tacagctctt aagggggcgc atctagagtt gttcgttcct cctggtgagt tcgtggtctc  44100
gctagcttca ggagtgaagc tgcagacctt cgaggtgtgt gttgcagctc atatagacag  44160
tgcagaccca aagagtgagc agtaataaga acgcattcca aacatcaaaa ggacaaacct  44220
tcagcagcgc ggaatgcgac cgcagcacgt taccactctt ggctcgggca gcctgctttt  44280
attctcttat ctggccacac ccatatcctg ctgattggtc cattttacag agagccgact  44340
gctccatttt acagagaacc gattggtcca tttttcagag agctgattgg tccattttga  44400
cagagtgctg attggtgcgt ttacaatccc tgagctagac acagggtgct gactggtgta  44460
tttacaatcc cttagctaga cataaaggtt ctcaagtccc caccagactc aggagcccag  44520
ctggcttcac ccagtggatc cggcatcagt gccacaggtg gagctgcctg ccagtcccgc  44580
gccctgcgcc cgcactcctc agccctctgg tggtcgatgg gactgggcgc cgtggagcag  44640
ggggtggtgc tgtcagggag gctcgggccg cacaggagcc caggaggtgg gggtggctca  44700
ggcatggcgg gccgcaggtc atgagcgctg ccccgcaggg aggcagctaa ggcccagcga  44760
gaaatcgggc acagcagctg ctggcccagg tgctaagccc ctcactgcct ggggccgttg  44820
gggccggctg gccggccgct cccagtgcgg ggcccgccaa gcccacgccc accgggaact  44880
cacgctggcc cgcaagcacc gcgtacagcc ccggttcccg cccgcgcctc tccctccaca  44940
cctccctgca aagctgaggg agctggctcc agccttggcc agcccagaaa ggggctccca  45000
cagtgcagcg gtgggctgaa gggctcctca agcgcggcca gagtgggcac taaggctgag  45060
```

-continued

```
gaggcaccga gagcgagcga ggactgccag cacgctgtca cctctcactt tcatttatgc  45120
ctttttaata cagtctggtt ttgaacactg attatcttac ctattttttt tttttttttt  45180
tgagatggag tcgctctctg tcgcccagac tggagtgcag tggtgccatc ctggctcact  45240
gcaagctccg cctcccgggt tcacaccatt ctcctgcctc aacctcctga gtagctggga  45300
ctacaggcaa tcgccaccac gcccagctaa tttttttattt tatttttttt ttagtagaag  45360
cggagtttca ccatgttagc cagatggtct caatctcctg acctcgtgat ccatccgcct  45420
cggcctccca aagtgctggg attacagacg tgagccactg cgccctgcct atcttaccta  45480
tttcaaaagt taaactttaa gaagtagaaa cccgtggcca ggcgtggtgg ctcacgcctg  45540
taaccccagc actttgggag gccgaggcgg gcggatcacg aggtcaggag atcgagatca  45600
tcctggttaa cacagtgaaa ccccgtcgct actaaaaata caaaaaatta gccgggcgtg  45660
gtggtgggca ccggcagtcc tcgctactgg ggaggctgag gcaggagaat ggcgtgaacc  45720
tgggaggcag agcttgcagt gagccgagat agtgccattg ccttccagcc tgggcgacag  45780
agcgagactc cacctcaaaa aaaaaaaaaa aaaatagaga cccggaaagt taaaaatatg  45840
ataatcaata tttaaaaaca ctcaagagat gggctaaaga gttgacggaa caaatctaaa  45900
tattagattg gtgacctgca aaaccagccc aaggaacatc ccagaatgca gcccataaag  45960
ataaagagag catttccgct gggcacagtg gtatggcagg ggaattgcct gagtccaaga  46020
gttgcaggtc acattgaacc acaccattgc actccaggcc tgggcaacac agcaatactc  46080
tgtctcaaaa aaaaaaaaaa ttaaattaaa aaagacagaa tatttgagag aaaaaaatgc  46140
ttatttcaag aaacatgaaa gataaatcaa gatattctaa ttcccaagta agaataattc  46200
cagaagcaga aaatagaata gaggcaagga aacactcaaa acttctccag tgccatagaa  46260
atgtgtatta atctttagaa tgaaacggac taccaaatgc tgagcaggaa gaacaaaaga  46320
gatccactct taagccagtg tggtgcccaa gcgcagtggc tcatgcctgt aatcccagca  46380
ctttgggagg ccgaggcagg tggatcacct gaggtcagga gtttgagatc agtcaggcca  46440
acatggtgaa accctgtctg tactaaaaat acaaacatta gctgggtatg gtggtgcaca  46500
tctgtaatcc caactacttg ggaggctaag gcaggagaat cacttgaaac caggaggtgg  46560
aggttgtagt gagccgagat catgccacac tcccagcctg ggtgacagag caagattcca  46620
tctcaaaaaa aaaatccact cctagacaaa taatagttaa attttagaac accaaggaga  46680
aagaaaaaaa attgtaaagc ttcagagaaa ataaacatta actacaaaga aacgagagtc  46740
agacgcgtgc acttcttcct agataccagc agataaagca atatctccaa aattcagaag  46800
gttttaacgt agaatcctat acccagtcaa gaatattcac atggaaaagt gaaataaaaa  46860
acattgttta aacatgcaag ggttcagaaa gtttaccatt cacagaatcc ctgaaaacaa  46920
aaccaaataa tcacttaagg actcattaag aaaacaaatg aaataaaagc accaatgatg  46980
agtaaataat cagaaaaatt tacagtttac ctaaataact gtttatgcat aatgtatgaa  47040
aacccaaaaa tttaatatgg gacagaatta aaatcatgat aagattcttt tttgctttac  47100
tcatggagag ttcacataaa cagattatct tttaatagca agagaaaaaa atgtttagat  47160
atgtgtgaaa aactaagggt accaaaacag tgcaaattca tttatcatca ggaaaatcca  47220
aattaaaacc acagtatcca ccagaataac taaaaggtaa aagacagaaa ttaccaagag  47280
ttggcaagaa tgtggagcaa ccacatatac ttctggggta aataagttgg tgcaaccggt  47340
actgaaaact gtttgctagt atctactaaa accgagcaca tgcacagact acaaccaagc  47400
```

-continued

```
agttccactc ccagatacac actcaacaga aatgcacaca ctcactcaac aaaagacgtg  47460
tactagagtg ttcatgtact tactattcat aatagtccaa aaatgcaaac aaccaactgc  47520
caatcaaagt caaatgtata tctatattag ggatatatac aatggcatat acacagcaat  47580
gagaatgaaa tgaaccagct cggcacagtg gttcatgcct gtaatctcag cactttgggc  47640
gggtaaggca ggcagatcac ttgaggtcag aaatttgaga ctagcctggc caacacggtt  47700
aaaacctgtc cccactaaaa acacaaaaat tagccgggca tagtggttgc aggcctgtaa  47760
ttccagctac tcgggaggct gggttgggag aatcgtttga acccgaaagc cggaggtcgc  47820
agtgagcgga gatcgtgcca ctgcactcca gcctggacga tagagcaaga ctccgtctca  47880
aaaaaggaaa tcaaaaatat aaaataagat gacaggaata atccgcaaaa gatcagtaat  47940
caaaataaat ataaatgggc taaagctacc tattaaaaga caaagatttc acacccataa  48000
ggatagctac tatcaaaaaa agagagagaa taacagatgt tagcaaggat gtatggaaac  48060
tgaaattctc acgcattgct ggtgagaata taaaatggtt cagcctctgc ggaaaacact  48120
atgctgggtc atcaaaaaat taaaaataga agtactactt gatccaacaa ttctacttct  48180
gggtatatac ccaaataact gaaagcaggg tcttgaagag atatttgtac acccatgatc  48240
atggcagcat tattcataat agctatgatg tggaaccaac ataaatatcc tttgataaat  48300
atatggataa gcaaaatgtg gtgtatacat tcaatggaat attaattagc aataaaaatg  48360
aagaaaattc tgacacatgc tacaacatgg atgaaccttg agggcattac attaaatgaa  48420
ataagccagt tataaaaaga caaatactat atgaggtact atattagata ctcatgcaag  48480
gtacctaaaa taggcaaatt catagagaca aaaagcagaa tggtggttgc caggggctgc  48540
ggtaatggat acagagcttc aattttgtaa gatgaaaaaa ttctggagat tggttgcata  48600
acaatgtgca cacacttaac actggggaac tgtaaactta aaagtagtaa atggtaaaaa  48660
taaaaataat aaataataaa ttttatgtta ttttaccaca atatttatta aaagacaaag  48720
attaactaat taaacaaaat ccagccataa gctaatggta agagtaacaa ttaaagaaga  48780
cacagaaaat tgaaaatcag tgactagaaa aagatattcc atataaatgc taacaaaaag  48840
caagtacagc aatataaaga gaatgaacaa aaaaaaaatt aaataagatg gctcgtttat  48900
tcccaaaagg tacaattcac caagaagata caagaattgt gaacctttaa gcacataaaa  48960
cagcttcaaa aatacaacat ttaaagaaaa atatatatta aacatagaaa tagtacaaaa  49020
acccctacaa gaatcataat gggagtcttc aatacaactc tccatatcaa caggtcaaac  49080
agagaaaaaa aataagttaa ggatgcagaa aacctgaatt accatcaata aacttgagat  49140
taatatagaa ctgtataccc aatatactaa gagttcaggg aacagtcgtg actgacagtg  49200
gactgcaaat taatctgttc ttaatctttg tttttctttc agcactgtgg cagaatagag  49260
atcctaaaaa ccttccagct acaaaacatc tttttaaaaa tataaaaaaa tacaaaaata  49320
actctgaaat caatagaaga cacatggtga aaccaaaatt ctagaataca gggagaataa  49380
aggcattttc agatattaca aaaacagaaa attgatcatt gctgaagtaa tttctaaaga  49440
atgtacttga gggagaagaa aaatgttcca aagaaaagta tctgtgatac aagaaggaat  49500
ggaaagtgaa gaaatggtaa acaggtagat aaagctaata aatgttgacc tagaaaataa  49560
caaaaacaat agcaataatg tctcgttgga agggttgaag taaaaataca attaaggcca  49620
aatgtgaggt aagtggaatg aaagaattag aagtccttgc cttgttcaca ggactgatta  49680
aataaatgag ccaggttttc cattcaaaca gttaaaactt gaacaaaata aactcaaatt  49740
aagtagaaag ataaaaaaca gaaattaatg tcatagaaaa ataaaaaatc aatagaatta  49800
```

-continued

```
atcaataaat cctggttaat aaaagctggt tctttgaaag gattaataaa ataatcatta  49860
agcaagtctg atcaaaaaaa aagagaaaag gtaccaaaaa aagtactgta tcagaaagag  49920
aacatacaga tacatacaga tatgtaagag tctgttttct tacaccagaa tactatatac  49980
aacattatgc tagcatatat taaatttcaa taatgttaat gattttctag gaaaacagaa  50040
aatattaaat ttactttgaa gaaacagaaa aactgagaaa aataaatgat catgaaaaaa  50100
atgaaaaggt aattaaatac tgatattaac tgcctaaaca acaccagcag cagcccaggc  50160
agtctgcagt caagttctgc caaacttgag ggaacagata attcttctat tccagagcat  50220
agaaaatgat ggaaagtttc ccaatttaat cagagaggac agcctgatcc ttgttatgaa  50280
cacagataaa aatggggtaa actatatgcc aaactcagat accaaaaccc taaataagat  50340
gctagcttat tgatgtgaac aatccaaaag tgcattttaa attagcccag ggttttagag  50400
aaagaaaatc tagcaatgtg accaccactt atgttaacaa ttttaagacg aaaatctaca  50460
tgatcatatc aatgcatgct acacaaaagc atttgggcaa aaaacccaac acccaccctt  50520
gactttttaa actcttagta attaggcata aacagaaatg tacttaatgt gatagaatac  50580
actcggtgaa gatacagagg gaatgctccc taaaaccaag cccaagacaa agattcctat  50640
ttaacctcaa tagtcaacac tgcagcgaga gtaatctatg gaagacaagg aaaaaagtaa  50700
aaacatgaga gacatctgtt gtttaacaga caataagatc acctacttgg aagaggcaaa  50760
cgaatcaagc gaaaaactat taaaactgag acaggcttta gtatggaggc tcagcttcag  50820
ctgtagtttg ggctaccaaa ttcaactcgc ttgcttggag agttaatcct gcaaagctaa  50880
tttctgttga ggtattagga ttgacaagcc tgtgctcctc cctcctcccc catcttcaac  50940
actgaaataa cacggtgttt ggaactggat aacagaatct tccaaaaaca aaaattgtcc  51000
tgaagggctg acttgtgccc ttactcaaaa aacactttat ctgctgcctg cagctcctac  51060
agttgctggt ggataagcct gccaaccagc tcggcgtaat tcttcctgca gagggcaagg  51120
aagagcactt tcacaggaaa attttttttcc gaactgtatg ccgcttatta cataaactta  51180
cgtgctggca aatggagctc cagcaaaata agatattcag agtcaaactt ccttaggaaa  51240
aaaaaaaaaa aaaagcaagc acataacact aatttccttg catgggcact ggggaaggag  51300
gtcgttactt ccgcacgccc gcaggtccgc accaccggga aacccacggg caccgcgcgc  51360
tgcccccggg ccttccaggt gcactgcgcc gcggcgcccc agctgacccg ggatgcgcag  51420
ccctagccct tcccctgtca ccccggccag gaaggggcgg gagcgcggcg gacgccgagg  51480
gcgaagggct tctcggtcct ctgcaccacg cagcaccccc aaggcacaac agggagggtg  51540
cgggaggctc ccgagaccca ggagccgggg ccgggcgtgc ccgcgcacct gtcccactgc  51600
ggcgagggct ggggtcgcct ccagggccgc agctgtcggg agccacctgg ctctcagtcc  51660
cgggtccctg cgacaaccct cgggcccgga ggggaggagg cggccacctg ccgctgccac  51720
ctgcggcacc ggtcccaccg ctccgggccg ggcaggacag gccaggacgt ccctcctggg  51780
ctggggacag gacacgcgac gaggggaccg gggcccccgc ggcgaagacg cagcacgcct  51840
tcccagaaag gcagtcccgt gcccccacga cggactgccg gacccccgcg ctcgcccgcc  51900
catcccttca gaccacgcgg ctgaggcgca aagagccggc cggcgggcgg gctggcggcg  51960
cggctagtac tcaccggccc cgctggctca gcgccgccgc aacccccagc ggccacggct  52020
ccgggcgctc actgatgctc aggagaggga cccgcgctcc gccggcgcct ccagccatcg  52080
ccgccagggg gcgagcgcga gccgcgcggg gctcgctggg agatgtagta cccggaccgc  52140
```

-continued

```
cgcctgcgcc gtcctccttc agccggcggc cgggggcccc ctctctccca gctctcagtg  52200
tctcatctcc ctatctgctc atcctctggt cgcacataat cgatgtttgg gcgtcccaag  52260
ccagatgtgg accccatttc cgcactctac actggaggtt ttctaagggt ggtgcccgga  52320
ccagcagctt cagcctcatc tgggaacttg agaaaatgca gattctccgt cccacccagc  52380
ctattcggtt tttcctgcac taaaaccatg aaggtggggc ccagcagtcc acattctcgc  52440
aagcccgtca agtgattctg aggcgccctc cagtttgaga gctatgctca cggcctcacc  52500
tccgccccgc aaggagcccg gtcttgcctg tggcgctagc cgcacacgga cacctcatcc  52560
tgcggggccc gcccccccgc tgcaccctca ccgcccaacg cctcctccgg gatgcagcgg  52620
aggcgcctgg aagtcggcaa ggtcaacatc cccctcagca tcttccctac cctcacggct  52680
cctcctccag gggtgcctca tggccagggg ttagaaagag ccactgtgtt tcttgacatg  52740
gaagtggcct aagaccttaa tgaaaactgc aggagtggaa tgacagaacc tttggtcata  52800
cttgagggcg tgaagctcaa atgaggagga aggaaaggat ccagggagaa taaccaaccc  52860
tggcaagttg tggcgcccag gtagaggggc gagcctaggc tagcggttct cgaccagggc  52920
cggtgttgcc cctcctcgcc gccccgcgta catttgggga ggtctggaga catttttggt  52980
tgtcatgatg cgggagttgc tactgttgcc taagtgggta gacacgaggg tgctcctcaa  53040
catcctacct gaaggacagg actgccccac aaggaagaat gatccggccc caaataagaa  53100
accctgggct ggtcagcaac aaccccttg ttctgagaag agaggaggaa agaataaaag  53160
aagtggggtg aagttttggt ttggtagagg aaacttgaag acattttcac tggaaaggaa  53220
gagaggaaga ggagggagat gtctgtaagg acgagcaaac cgggtgacag ctgatttcct  53280
catattgaag taatgagtcc tagttataat aaattcctaa taaaaaccca gtttatccct  53340
gcaataaact tgtctttttt ttttaaatat actgcttgat tctgtttgct aatattttat  53400
ttacaggctt tgcattgata tgcaaaaatg agatgggcaa taattttctt tttgaatgtc  53460
taatgttgtt tggtttcaga atcaatgtta tgctcacatc ataaaaaatt tggaaccgag  53520
gcaggaggag tgcttgaggc cagaagttcg agaccagtct aggaaacaca gtgagacccc  53580
cccatctcta caaaaaaaaa aaaagaaaaa aaaatgggca tgtttgcttt ttcctttac  53640
tctgaacaat ttaaggagca ttaaaattat ctattctttg aggtttgatc atttcccagt  53700
taaaaatgtt cctcccagcc tgatgctttc tttggggagg gtaaatcttt taaggctaga  53760
aaagtttctt ctgtggcaat tttattattt acattttaaa aattattcta gagttaattt  53820
tgataaagca tgtatttctt aaaacaaatt atcctttttt tccagatgtt caagtgtatt  53880
tgcataaagt tgaggaaagt agtcttttgt gaatctttta acttctccca aatatcttat  53940
tttgtgtatt tttgcttctt tattttgtta acttttaaaa gtgtattttt ttttcaaaga  54000
atcagctctt aggtttatgt ttttggttat actggagctt ttttcttctt ctttttaaaa  54060
tatttttctt cctttatttt ttagacgtat tttgatctaa cgtaatcgga agaaggtaaa  54120
ttagaatctt ttgttactat tgtgttttta tttctcctta tttctctgaa gtcctgcttt  54180
ataaatagta ccatgttatt tgtgcataaa tattcatttg tcttatattc ttgggaattt  54240
tcccacttca tcataaaatg accttccttg tctcatttaa tgtgttcaaa ctttgccctg  54300
aatttaactt tgtctgatat tttaccatcc tgctgaattt tgtttgttac cccaaacaac  54360
ctttgctgtt ttcgtctttt ctgaaccctt tattttaggt aatcccttga attagagcac  54420
taagttttgc tttgtgatta aatctgaaaa tctttatctt gccatagatg agttgagccc  54480
tattcatgtg acagctatat tatgctgttt catagccctt ttggtccttt tttcactctt  54540
```

-continued

```
gcattgcata ttttgtgttt attgtgtttt gtgtttcttc tgataatttg gaaggtttgt  54600
atttttattc agggagttgc cttataatca tactccgcaa tacacatcgt cctcagtttc  54660
ttcagactgt ctgttaactc cctattctga ataaaaatga cattgtaatt tccctctttt  54720
ttctttaccc cttttcttct cctcacctaa tgtaaatgat tttatccttc tttagtattt  54780
gctttttaa ttaactacat ttataaatat ctttatcact tgatttttaa atcagctttg  54840
aatgagatat ttggattcct agatataaaa gatgttaatt ataccatttc cacgttagta  54900
ggtttataaa atcatacatt ctgctgtgta accataatcc cacgtttgtt ttagttccac  54960
tcctacagtt aaaagattca gaagtattat taacagttat tttgccatag ttttttcccc  55020
aacccatttt gtggtaagtt atgatcctgc tttagtttct taagaataat ttatagagca  55080
gagtgtggtg gctcacgttt gtaatcccag cactttggga gacaagaggt agaaggatcg  55140
cttgaagcca gcagttcaag accaccctga gcaacatagt gagaccttgt ctctacaaaa  55200
aattttaaaa tttagccaga cgtagtggcg tgtgcctata gtcccagcta ctcaggaggc  55260
tgaggcaaga ggattgctag agcccagaag tttgaggctg cagtgacctc tgattgtgcc  55320
actgcacccc agtctgggca agaaagtgag aacctatctc tttaaaataa caataataac  55380
ttatgaaaat tatattccct gagtttttca tgtttaaaaa tatttgttgc ctttatcctg  55440
taaaagtttg agtataaatt cttgggttat actttattta ttgaagaatg tataagtatt  55500
gtcttctaga attgagtgtt gctgtaatga aaccagaagt cagcctggtt tatttttcct  55560
cagaaatgag gtaattgccg gccggacacc gtggctcatg cctgtaatcc caacactttg  55620
ggaggccgag acaggtggat cacgaggtca ggagattgag accatcctgg ctaacatggt  55680
gaaaccccgg ctctactaaa agtacaaaaa gttagctggg catggtggtg gacgcctgta  55740
atcccagcta cccgggaggc tgaggcagga gaatggcgtg aacctgggag gaggagcttg  55800
cagagagctg agatcgcgcc actgcactcc agcctgggcg acagagtgag actccgtctc  55860
aaaaaaacaa aaaaaaaaca aagaagtgaa gtaattgcca tgatgctcca agaattatct  55920
ctttgtctat gaaatccaga aatctcactg ttatacattt tggaattatt attctgggcc  55980
aatatttcct gggacacaat agattgactc tatagattta attttttttt tttttttgag  56040
acagagtctc actgcaatct cagcttactg caacctctgc ctcacgggtt caagcaattc  56100
tcctgcctca gcctcccaag tagctgggac tacaggcgcg tggcaccatg cctggctaat  56160
ttttgtcttt ttagtagaga cagggtttca ccatgttggc caggctggtc ttgaacgcct  56220
aacctcaagt gatccacctg cctcagcctc ccaaagtgct gggattacag gcgtgagcca  56280
ccatgcccag cctcaattcc tctttctatc tggtaatttt tctgaagttg aaaacatttg  56340
ttctaatacg ttatttcagt gttcttctaa gatgtgtaaa gcaccctatt cccaggtcag  56400
cccccatctt gctagtgagc tcggctggtt cttcacaaga gctctggttt tctcctgctt  56460
aatctcaagt acctctgtca gcctccacct ggtttatgat ttggagtttt ttggtttttg  56520
tttttgtttt ttgacagagt cttactctgt cacccaggct ggagagcagt ggcataatct  56580
cagctcactg caacctctgt ctcccaggtt tgagcgattc tcctgcctca gcctactgag  56640
tagctgggat tacaggcgcg tgccaccaca cccggctaat ttttgtattt ttagtagaga  56700
tggggtttca ccatgttggc cagggtggtc ttgaactcct gacctcaggt aatccacctg  56760
cctcagcctc ccaaagtgct gagattacag gcgtgagcca ccgcgcctgg catggtttgg  56820
agttttaatc tgtagtttta ataaagatag tgcttatgtt tgtgtttctt atatttcttg  56880
```

-continued

```
gtactcttgg gtaatttgta agatccccat atctacacaa gaagtccatt ttcaattctt  56940
ttcttcagac tgtttatttt attttatttt attttatttt tatgtttgag atggagtctc  57000
gctgtgtcac ttctggaggc tggagtgcag tggcgcgatc tcaggtcact gcaacctccg  57060
tctcccgggt tcaagcaatt ctcctgcctc agcctcccga gtagctggga ttacaggcac  57120
ctgccacttt ttaatttttt tagagacaga gtctcgcttt gttgaccagg ctggagtgcg  57180
gtggtgcaat catggctgac tataacctcc aaatcctggg ctcaagtgat cctcctgcct  57240
cagcctcctg agtagctggg actacaggca catgccacca tgcccagtta attttaattt  57300
ttttgtagag acagggtctc catatgttgc ccaggctggc ctcctactcc tggcctcaag  57360
taatcctcct acctcagcct cccaaattac taggattata agcatgagcc accatgccca  57420
gccttgttct actactttaa tttcatatgt taggtgacca tgtaattgat catccaaacc  57480
aggatactgt aagaatgaaa gaggctgaca gtagtatgat gctgggacta gcattgtgca  57540
ctgagattat ttctgggaaa gcaggagata cggtcaccct acttatagtg tgcttgtctt  57600
tggattgttg aatttggagt ttctatttgc aggcttattt caactgggca gccttgatcc  57660
gccctgccca gcaatgctac cgttctctcc accgggtctc tgggacccct tcagtcacta  57720
tacttagctc agttccccac cctcccactc cctaaaagcg taaccaggaa tcctgcctca  57780
ggtctactgc cgtcttccgt gggctgtttc agttcctatt acccagagtc aaactcccag  57840
cattccctac ctgattccag acttggagtc cagagcttta acctcttcag gccaactccc  57900
cactttgcat ttctgtccct atatcttagt ccatggagat acatttcatg tctttgagtc  57960
tacttacaaa gtaaattttg ctgtttttta attttttttt tgagatggag tcttgccctg  58020
tcacccaggc tgtggtgcaa tgacgccatc tcggctcact gcaacctccg cctcctgggt  58080
tcaagcgatt catctgcctc agcctcccaa gtagctgtga ttacagacag gcaccaccac  58140
gcccagctaa ttttttttat cttttagtag agacagggtt tcaccatgtt ggccaggctg  58200
gtcttgaatt cctgacctcg tgatctgccc atctcggcct cccaaagtgc tgagattaca  58260
ggcgtgagcc actgtgccca gccaattttg cttttttttat atttcattgc tatatgttta  58320
gaggataagt ttacagtgct atatgcattc ccaaatatta gaccaaaaaa atctccaaaa  58380
aattagaaag aaaatccaaa aaatctcaaa aaataccaaa aagcaacaat ctcacagacc  58440
atactcactg acccccaata aaataaaatt agaaattaac cacaacttaa caaaataaag  58500
tactcaagtc agagaggaaa gaggaaataa acatcaaaat tacaaagtct aggcggtggc  58560
tcacgcctgt aatcccagca ctttgggagg ccaaggcggg cagatcacaa ggtcaggaat  58620
tcgagaccag cctggccaat atggtgaaac cccgtttcca ctaaaaatac aaaaattagc  58680
caggcatagt gatgtgtgcc tgtaatccag ccacttggga ggctgaggca ggagaatcac  58740
tgaacccagg gagacgaaga ttgcagtgag ccaaaatcgt gccactgcac ttcggcctgg  58800
gtgacaaagc gagactccat ctcaaaaaaa aaaaaattac aaactcttta gatagaaatt  58860
ttggtgtttt tttttgagac ggagtctcac tctgtcgcag aggctggagt gcagtgggac  58920
tatgtcagct caccgcaacc tccatctcct ggattcaagc aattctcctg tctcagcctc  58980
ccaagtagct aggattacag gcgcccacca ccagacccag ctagttttta tatttttagt  59040
agagatggtg tttcaccatg ttggccaggc tggtctcaaa ctcctgacct caagtgatcc  59100
acctgcttca gcctcccaaa gtgctcagat tacaggcgtg agccaccgca ccccacctag  59160
atagaaattt caacatgagg ccgggcacaa tggctcacgc ctgtaatctc agcacttcag  59220
gaggctgagg cgtgggagga tcacttgggc ccaggagttc aggaccagca tgggtgacag  59280
```

-continued

```
agacagaccc tgtctctatt tatttgaaaa aaaaaaaaaa aaagagagag agaaagaaat  59340
ttcaacatga aaagtatctc tcaaaccctt cgagatgttg gcaaaaagcg actcaaagga  59400
aaatgtatta ctgtgtgtga atttgcttga aaataagaaa gaggccgggt gtggtggcta  59460
acacctgtaa tcccaacact ctgggagtcc gaatcaagtg gatcatgagg tcaggagatc  59520
gagaccatcc tggctaacat ggtgaaaccc tgtctctact aaaaatacaa aaaattagct  59580
aggcgcggtg gctcatgcct gtaatcccag cactttggga ggctgaggca ggtggatcac  59640
ctgaggtcag ggtttgaga ccagcctggc ctacatggtg aaacctcgtc tcttctacaa  59700
atacaaaaat tagctgggcg tggtggtggg tgcctgtaat cccagctact cagaggctga  59760
ggcaggagaa tcgcttgaac ccgggaggcg gaggttgcgg tgagccgaga tcgcaccact  59820
acactccagc ctgggcaaca gcctgggtga cacagtgaga ctccatctca aaaaatacaa  59880
aaaattagct gggtgtggtg gcctgcgcct gtagtcccag ctacccggga ggctgaggca  59940
ggagaatgga gtgaacctgg gaggaggagc ttgcagtgag ccgagatccc accactgcac  60000
tccagcctgg gcgacagagc aagactcttg tctcaaaaaa aagaaaaaaa aaggaaaaaa  60060
gaaccctgat aataaagaaa ccaaatgttc aactctcaaa gctcggacac tttaaagaaa  60120
taattaataa aggcagaagt taaagggagg atgataaagc aatttttttt gttggttttt  60180
ttgagatgga gtcttgctct gtcacccagg ctggagtgca gtgatgcgat cttggctcac  60240
tgcaacctct gcctcccggg ttcaagcaat tctcctgcct cagcctcctg agtagctggt  60300
actacaggtg cgcgccacct ggcccagcta atttttgtat ttttattaga gacggggttt  60360
caccatattt gttaggctgg tctcaaactc ctgatctcag gtaatctgcc cacctcggcc  60420
tctcaaagtg ctgggattac aggcaggcgc caccgcgcct ggcctaaagc aaaatattgg  60480
ttctgtgcaa aaggtcaata aaaagagcaa acgtttacaa actggagcca gcacccattc  60540
agctcagtgt gtctggagaa aaaacaatct cgcttcagaa ttcatgatta cgcagccctt  60600
tttgcttcct aaaaatccta ctatgttgct gttgaccatt ctctctcttt ctctctctct  60660
tgctttctct ccagaaaagc tattcagaca ttctcctctt tcctcaaacc tccaacactt  60720
cctcctccat ccttagcctc agctgctgac ctcacttcta atcattgaga aaccaggaga  60780
agcatttaag agtgaacctc cgcctccccg cacgggcaaa accacccacc cacagaattg  60840
tgccccaatt ctgcgtcctc tcctctcacc atggatggac ggtccaggct ccgagccaaa  60900
gccaggcctc ccctggagct ctggatccac cacctgcagc ttctcaggca gggccccagc  60960
agctcccctg ctcccttgta ccatcaatcc ctcccctcac tgggtcactc ccaacaatat  61020
atatatttag tgatgtttct cccatgtggt aaaatcactt agcctctctc ctcccccagc  61080
tactatccta tttgtttctt tccattctct gcaaaacttc tcaaagcatt gtgtctatgt  61140
gctgactcca tttatcttct cccgttctct gctgagtcct tcccacagac tctcacccca  61200
gttactccat gaaatgacct ctgcactgcc acatccaatg gtgaatgttc agttcttaat  61260
tttattcagt ctttcagcag catttgacct ggccgatcac tccctcttct taaaaatact  61320
tttctcagcc aggcgtgatg gctcacacct gtaatcccaa cactttggga ggccaaggcg  61380
ggaggatcat gagagcccag gagttcaaga tcagcctggg caacatggca agaccctatc  61440
tctacaaaaa ctaaaaagta gccagtgtga tggcatgcac ctgtagtccc atctacttag  61500
gaggctgagg cagtaggatg acttgagcct gggaaatcaa ggctgcagtg agccatgatt  61560
gcaccactgc actccagcct gagtgacagc gagaccctgt ctcaaaaaga caaaatagga  61620
```

-continued aacttttctc agcatattcc tctgattctc ctgctgcttc tgtctgcaca gattcagtct 61680
cctttgccgg ttcttcctca tcctcctgat ctcttgacct tgaagtgccc cagagtacag 61740
tctttttttt tttttttgag acgcagtctc gtctgtcacc caagctggag tgcaatggcg 61800
aggtctcagc tcatgcaacc tctgcctcct gggttcaagc gattctcctg cctcagcctc 61860
ccaagtagcc aggactacag gcacatgcca ccatgcccag caaattgttg tatttttagt 61920
agagacaggg ttttactata ttggccacgc tggtctcaaa ctcctgaact cgtgaaccac 61980
ccgcctcggc ctcccaaagt gctgagatta caggcatgag ccaccacacc cggcccagag 62040
tacagtcttt agacggcctc tctacctata cttgctcccc tcataaactc ctcctgcctc 62100
atggctttaa ataccatcgg tagactgatg actcccatat ttctcttttt tttttggaga 62160
cggagtctcg ctcagtcccc caggctggag tgcagtggcg cgatctcggc tcactgcaag 62220
ctccacctgc caagttcaca ccattctcct acctcagcct ctccagtagc tgggactaca 62280
ggcacccgcc accacgcctg gctaattttt ttgtattttt agtagagatg gggtttcacc 62340
atgttagcca ggatggtctc gatctcctga cctcgtgatc cgcccatctc ggcctcccaa 62400
agtgctggga ttataggtgt gagccaccgt gcccagccga tgactcccat atttctatct 62460
cttgctgtgt gggagttctc ctcagaactc catactcata aatccaactc tcataaatag 62520
tatctcaaat gggcaatatg ctcaaaagtc aattcctact tttctcccta aacttgcttt 62580
cctgcagtct ccaccatctt aatgtccaat ctaacattag gaggcaaaaa ctttgaagtc 62640
attcttgact cttctctatt acacacccta tccaatcttt ctgcagatcc agtcgacccc 62700
caaatccagt tagctctcat catctcccct gttacccccct ggtccaggcc atcttcctct 62760
ctcacctgaa tcactgcagc attctcctca ctggtctctt tggttctgtt ttcactccac 62820
cttagcatag tctccacaga gcagtcagag ggatcctttt aaagtgtaat tcccatcctg 62880
tccctgctct gctcaaaacc ctgtcgtgat tcccgtttta atctgtcaga ttaaaagcca 62940
gagtctttcc agtgacctac atgatctgcc tattatcacc tcccacttct ttccccttgc 63000
tcactccact ccagctctgc agctgtcctt tctgtttcct gaacagccca gatttgcttt 63060
ctttagaacc tttgtatttg ctgtcccctc tgtctggaat gtttttccag gaagtcacct 63120
ggctctctcc tgcacttcct tcctgaccac catgtttaaa aatcactcaa acacacttca 63180
ggccggacat ggtggctcac gcctgtaatc ccagcacttt gggaggccaa ggtgggtgga 63240
tcacctgagg tcaggagttc gagaccagcc tggccaacat ggtgaaactt cgtctctact 63300
acaaatacaa atagtagcca ggtgtagtgg cacacacctg taatctcagc tactcaggag 63360
gctgaggcag gagaatcgct tgaacccaga aggcagagga ggtgcagtga gccaagatca 63420
cgccacaaca ccccagcctg ggtgacagag caagacccca tctcaaaaaa aaaaaaagaa 63480
aaaaaaatca cacaaacaca cttctcttca tattcctttt ccaagtttta tttttctcca 63540
gaatacttta cattgtttta atggaagttc tccgtttccc cccaactaga atggatactt 63600
cctgcaggta ggcactctag tcctcccatc caagtactaa ccaggctcaa ccctgcttag 63660
cttctgagag caggggagat caggcctgtt cagggtggta tggcccagga attttgattc 63720
tgttttattc attgctgttc tgttgattct cttttgttcc tcctcctagt gctgagaaca 63780
ctacttgtac ataataagca ttcaataaat atttgttgaa tgaatgactt gttgaatgaa 63840
ttaatctcag aaatgcagga ctggttctac attagaaaat ttttcaaggt cattctctgt 63900
tgtcgtaaca cattaagaga ggaaaatttt gtactctaaa tcatttgata aaatacatac 63960
tgatttctgt tttcaaaaac tcttagtggc tgggcgaggt ggctcacatc tataatccca 64020

-continued

```
gcattttggg aggacgaggt gggcggatca cttgaggtca ggagtttgag accagcctgg  64080
ccatcatggt gaaaccctat ctctactgaa aatagaaaaa ttagccgggt gtggtggcgc  64140
atgcctgtag tcccagctac ctgggaggct gaggcaggag aatggcttga acccgggagg  64200
cggaggttgc agtgagccaa gatcatgcca ttgcactcca gcctgggtaa cagagtgaga  64260
ctccatctca aaagaaaact cttagtgagt ttaggaatcc aaggaagacc ctcaaactaa  64320
atagataatc tagctaccag aagccttcag taaaccttaa cactccatgg tgaaacatta  64380
gaaacattcc tactaaaaga caggctaaga atgcctgcaa tcttcacggc tagtccaaga  64440
agtcaaaaag aagaaatgag cgctgattta aaaaaataaa caaacaaaaa actaccgatg  64500
cagaggctgg cagcaaggac tgaaggactg tacagtactt gcctggagca ggcggatggc  64560
cacaccccctg cgaagcctgc tcagctggct gggggacgct ccagtgtgtg agtggcagga  64620
tgcagggtac ttcctctgcc agggagttgc actggggaga tcctccccca ctcacacttt  64680
ggcagctggg gctttggaat gtgacttagc ttctgtcaaa gggtcaatcc accctttgat  64740
atatgatgca aaggcgaaca tatgatgcaa aggtgagaga acagcccaaa ttaggacttt  64800
taccacagct gtggaggtgg acagcgacag tggtgggccc tggccagact tttcatgctc  64860
aaaggtggtg gttgttcttc ctacttcttg tccctccagg gcttcctttg cctgtgtgct  64920
gaacctgctt cttttaattt tttttaactt ttttaaattt ttaattgttt taattaaaac  64980
aaattttgaa aactgtctga acctgctttt gaaccctgct atgatttgaa tgtttgtccc  65040
ctgccaaact gattttgaaa cttaatctcc aaagtggcaa tattgagatg gggctttaag  65100
cagtgactgg atcatgagag ctctgacctc atgagtggat taatggatta atgagttgtc  65160
atgggagtgg catcagtggc tttataagag gaagaattaa gacctgagct agcatggtcg  65220
ccccttcacc atttgatatc ttacactgcc taggggctct gcagagagtc cccaccaaca  65280
agaaggctct caccagatac agctcctcaa ccttgtactt ctcagcctct gtaactgtaa  65340
gaaataaatg ccttttcttt atgaattacc cagtttcaga tattctgtta taaacaatag  65400
aaaacgaact aaggcaaact ctcatgattc tactgccatg ccattccaat aaactccctt  65460
tatgcttaag agagccagag ttggccaggc gtggtgactc acgcctgtaa ttccagcact  65520
ttgggaggcc gaggcaggtg gatcacaagg tcaggagatc gagaccatcc tggctaacac  65580
ggtgaaaccc cgtctctact aaaaatacaa aaaaattagc tgggcgtggt agtgggtgcc  65640
tgtagtccca gctactcggg aggctgaagc aggaggagaa tggcgtggac ccaggaggcg  65700
gagcttgcag tgagtcgaga tcgtgccact gcactccagc ctgggtgaca gaatgagact  65760
ccgtctcaaa aaaaaagaga gccagagttt atttctgttg cttgcaacca agaaatctgg  65820
ctggtgcact gaagtttcca taaataatag caatttaaag actctttcca agccaggcaa  65880
tgcctagcct tgtgtagtcc ttgtggtaat acattcattc attcatttgt tcaaccaact  65940
gtgctccaga gactaagaat acaaaaatgg gggccgggtg tggtggctca cacctataat  66000
cctagcactt tgggaggccg aggcaggtag atcacctgag gtcaggagtt cgagaccaac  66060
ctggccaaaa tggtgaaacc cctactctac taaaaataca aaaaattagc tgggggtggt  66120
ggcggacacc tgtaatccca gctactcgtg agactgaggc aggagaatca cttgaacccg  66180
ggaggcagag gttgcagtga gccgagatcg caccactgca ctccagcctg ggcaacaaga  66240
gcgaaactcc acctcgaaaa aaaaaaaaaa aaaaaaagag ggccggggct gggcgcagtg  66300
gctcacgcct gtaatcccag cactctggga ggccaaggca ggagaattac gaggtcagca  66360
```

-continued

```
gatcgagacc agcctgacca acatggtgaa accccatctc tactaaaaat acaaaaatta  66420
tccgggcgtg gtggcgcaca cctctagtcc cagctacttg ggaggctgag gcaggagaat  66480
cgcttgaacc cgggaggcag aggttgcagt gagccgaaat catgccactg cactccagcc  66540
tgggtgacag agtgagactc cgtctcaaaa aaaaaataaa aaaaaaaaaa gaattcaaaa  66600
attgtagagt tatagtgtgc ttctagttta gttgagagga catctgtcct tcaaggaagg  66660
ctagaatcta taccctgagt ccttactgaa atcaatccag cagtcaaaac atgggaccaa  66720
cgatcacagc agtaagatag gaagagcacc tttgtacatt tagctcatgt tgagataagc  66780
cactgacaga gctgaaggaa gctcacagtt ctgggttcca tcctttggca tttaaaaaga  66840
aaagtgctaa gaaaattcgg ttggtcacgg tggctcacgc ctgtaatccc aacactttga  66900
gaggccaagg caggcagatc acgaggtcag gagttcgaaa ccagcctggc caacatggtg  66960
aaaccccgtc tctactaaaa acagaaaaat tagccgggca tggtggcgca tgcctataat  67020
cccagctact caggaggctg aggcaggaga attgcttgaa cccgggaggg ggaggttgca  67080
gcgagtgaga gcaggccact gcactccagc ctgggagaca gagcaagact ctgtctcaaa  67140
aaaaaaaaag aaaaaaagaa agaaaggaaa aaaagaaaga aaaaaaaaga aaaaagaaaa  67200
ttcaggccag gccaggcctg gtggctcaca cctgtaatcc caacactttg ggaggctgaa  67260
gcgagacggt gccttagccc aggagtttga gaccagcctg agcaacatag cgagaccctg  67320
tctctataaa aaaaaatttt tttttggcca gacgcagtgg ctcacgcctg taatcccagc  67380
actttgggag gccgaggcag gtggatcacg aggtcaggag atggagacca tcctggctaa  67440
cacggtgaaa ccccatctct actaaaaaat acaaaaaatt aaccgggcgt ggtggcgggc  67500
gcctgtagtc ccagctactc gggaggctga ggcaggagaa tggcgtgaac ccgggaggcg  67560
gagcttgcag tgagccgaga ttgcgccact gcactccaga ctgggagaga gtgagactcc  67620
gtctcaaaaa aaaaaaaaaa aaaaaaaaat taattgtcag gtgtgctggc atgcagctgt  67680
agtcctagct actcgggagg ctgaggtaag aagatcgctt gagcccagga gttcaaggct  67740
gcagtaatag tgcctctcac tctaccctgg gtgacaatga gaccctctct caaaaagaaa  67800
gaaaaaaggg aaagaagaaa agaaagaaag aaagagaaga aaggaaggaa gaaagaaaga  67860
aaaagaaaag gaaggaagga agaagaaaaa aaaagaaaga aagaaaagag agagaagttc  67920
aaagaccaaa gggtcaggat cccaaaatag tttttatgtt ttatttattt atttacttat  67980
ttatttttga gacagtatgg ctctgtcgcc caggctggag tgcagtgatg cgattgcggc  68040
tcactgcagc ctccaaactg ggctcaggtg gccctcccac ctcagcctcc cgagtagctg  68100
ggaccacagg cgcgtgccac catgcccagc taattttta attctttgta gagatgaggt  68160
ctctatatgc tgcccaggct ggtctcgagc tcctgggctt aagccatcca cccgcctggg  68220
cctcccaaag tgctgggatt acagaagtga gccaccgcgc ctaatcgggt ggtttgtttg  68280
tttattgacg gggtctcgct gctgcccagg ctggagtgcc agtggctgtt cacaggtgca  68340
gtcctggagc attgcatcag ctcttgggct ctagcgatcc tccagagtag ctgcagctgg  68400
gattccaggc gcgccaccgc gcggggctca gaatgggttt ttatattgag ggttatgctg  68460
ccacctagag gatatatgta gtaccgaact gtgtgcgcag ggaggctgag gttgcagtga  68520
gccaagatga tgccagggca ctccagcgtg ggtgacagag caagatttca tctcaaaaaa  68580
aaaaaaaaaa aaaaaaaaaa aagaattgaa agtaaggtct tgaagagata tttgtgcctg  68640
tatggtcata gcagtattaa ctttgaccca ctagctaaaa cacaaaagca acatgtgtct  68700
gtcagcaggt gaacggataa acaaaatgtg gtatatatgt acaattgaat attattcagc  68760
```

-continued

```
ctttaaaaag gaataaaagg ctggatgcgg gggctcacgc ctgtaatcct aacactttgg  68820
gagactgagg tgggtggatc acccgaggtt aggagtttga gaacagcctg gccaacatgg  68880
tgaaacttca tctctactaa aaatactaaa attagccggg catggtggca cttgtctgta  68940
atccaagcta ctggggaggc taaggcagga gaattgcttg aactcaggag ccggaggttg  69000
cagtgagcta agatggcacc actgcactcc agcctgggca acagagtgag actccatctc  69060
aaaacaaaca aacaaaaaat tattatttcc aaagaaacaa gaccctgggt ccatttccca  69120
gcccacacct gatgttgact cacaacacac agcctggttt gctatgagcc tgcttcattt  69180
aattgtcacc ttaacttcac atcaccctca agtcctggaa taactctttg ctgacctttg  69240
tgtgctgagc catctccatg tcgctcaacg tgcagtccct ctcactgcac tgagtcaata  69300
gccagacgtg gtctgactgc agggtcatcc ttggtggctt aggctgactc gggcatagca  69360
gggtgctctg agacctcacc gcatataggc tttgccccca ataaactcta tataatattc  69420
atattatgtg gtctgggtgt gtgtagcttt gcactgtctt ctcgtgacag tgccctcaac  69480
ctctttccca ggatttcctc ctctacctcc tcaagtccca ctgctctgca aagaccaaaa  69540
gctgcagagt cccagctccc tcctttacac cccacgacgc agcctcctct ctcagaaccc  69600
tttaaacaga gtcttttact gcagatccca agaacagcca cacccctctc tcccacccac  69660
tccagacaca cccaggtaat tatagcaccc agggtaacta tgtagatgga gtccctggaa  69720
catgtggata gtgccccctg ggagtatgca aaagcaacat tgctggcacc tgcagagaac  69780
agggtgacat ccaggaatca gagcatgggc ctctgggagg tagggatgtg gccaggcagg  69840
ctgccaaaaa ttggtagagc aaggccacag gatctttctg accttccttc caaacagagg  69900
ctcctgtact ggtgatccct gtgttgattg accactccct tcctgggggt cgtggtctct  69960
gtcccagttg cccggacttc tgtgagtgtc ctactgaggt ccttttcatg agaagcatgc  70020
tgtccttcca cctgctggga gcaagagtga caacttcaat actataatag cagtggcata  70080
cagagaagaa gaaagatgaa gtggcaagaa aaacaggctt ccaagcagga gtttttctat  70140
aaaaacaaaa acgtttacaa gcaaactttt tataaagggc tagatagtaa atattttagg  70200
ctttgagagc cacatagact tgtttgcagg gactcaatgt cgctattgta gtttgaaagc  70260
agccatcagg gttatgtaaa tgagtgagtc tgattttgtt tcagcaaaat tttatttacc  70320
aaaacagaca atgagtgggc tggatttggc ccatgatcct tagtttgcca actcctgctt  70380
tgggctcacc cagatctgat tttgaattct ggctctgcta ctggttagct gcaggagctt  70440
ggaaggctct ctgagcctgt ttcctcatct gtaaaattaa agcaataatt tctaacactc  70500
aagagtgtta cctcacgcct gtaatcccag cactttggag gctgaggcag gcggatcacc  70560
tgaggtcaga agttcaagac cagcgtggcc aacgtggcaa aaccctgtct ctactaaaaa  70620
atacaaaaag tagccgggca tggtggcgcg catctgtaat cccagctact tgggaggctg  70680
aggcagggat actgctagaa cctgggaggt ggagcgtgca gtgagtggag atcacacctc  70740
cacactccag cctggccgac agagcgagac tccatctcaa aaaaaaaaaa aaaaagagtg  70800
ttagaaggtt ttgagataat gaataaaaga tgccttgtgt atactaagta ttcaacaact  70860
gatagctgca ttggtctaat tataacagtt tagaagcgat tgagtcaaca aatgctggat  70920
ttgtcaggga ggacttccta tcaggaggta gatcttgggc tgagtcctga agcaaagata  70980
ggcattggat agaggagttg agagaacacc ctaggactgt tattattatt attcgacacg  71040
gagtctcttg ctctgtcacc caggctggag tgcagtggcg cgatctcggc tcactgcaac  71100
```

-continued

```
ctctgcctcc caggttcaag cgattctcct gcctcctaag tagctgagac tacaggtgtg  71160
tgccaccaca cccggctaat ttttatattt ttagtagaga cagagtttca ccatgttggc  71220
catgctggtc tcgaactcct gacttcaggt gatccacccg cctcagcctc ccaaagtgct  71280
ggaataacag atgtgagcca ccgcacccag cccagaacca tttttcaatc cttggctctg  71340
ccttttatta gctgcaagat ctcaggcaat ttatttaacc tctccaaaga ctcatttttct  71400
cattcacaaa atgaggcaaa taataatatc tactatccca ggttgtcatg agaattaaat  71460
gcaacatgac atttaatgaa atgagaagtc ccttggacat taactggcta aagtatgtgc  71520
tcgacaagga tatcatttta ggtggatact tagcatctca gaactgatgc tcacaatgga  71580
atatcattga aacgcattaa aattcatttt aaatgattgt aggtagtgag gcaattgaaa  71640
gaagaagaca agaggactga ttataatgct tcaggctcac tagtctcctt ttaggaggga  71700
aaaacaattt caagttaaat tttaggctct agatttttac ccctgctgct cattagaatc  71760
acccagattg atgaaatcag agcccatctg aggctgtgtt tttcatctcc agaatgagag  71820
ctgttgtggg gattaagttt ttgaaaaagt acatctaaca ggtgatcgaa aatgatagtg  71880
atattattgc agtgatggtc attattgttg ttattattat actgaaagag gcttcagttt  71940
tctgatccat aaagtgaggg aattgcatga gaccattgct aagattcctt ctagctctgt  72000
tttttgttt ttgtttttta gacagagtct ctgtcgccca ggctggagtg caatggcatg  72060
atcttggctc actgcaacct ccgcctcccg ggttcaaatg atcctcctgt ctcagcctcc  72120
gaagtagctg ggactacagg cacacaccac catgcccagc taacttttat atttttaata  72180
gaggtggggt ttcaccatat tggtcaggct ggtctcaaac tcctgacctc aggtgatcca  72240
cccgcctcgg cctcccaaca tgctgggatt acaggcatga gccactgtgc ccaacccctt  72300
ctagctttct tgatcactga ttctagggtt ctctgctgaa atatatttga gacatcctgg  72360
ataaaagatc atgcaagagc tcccaatatg gtattaataa ttgattctgg aggcttagct  72420
actcctgatg gattagacat gactcaactg cctctcttat gtgtacaaca caacaacaca  72480
accaagaaag gttattctgg cattccattt attcagttta tttacagccc ttacttccag  72540
cagcacgtta aagatatggc cagggccggg tgcagtggct caagtctgta atcccaggac  72600
tttgggaggc caaggtgggc ggatcacaag gtcaggagtt tgagaatctg gcaattcttc  72660
agacttagaa gcaaccagct cgataacaca gtcttgtgtg ggctctccct ctgtccctcc  72720
ctcgcttccc tcatttctca tccctgcccc tgagactgtg caccttcaca tagccctgcc  72780
atgagacctt catctcaggc tttgctttct ggggtaactg aggctaaaca ctgagtggcc  72840
ctaaaagagg attgggattt ggaagttaga ttattcacca gagaacagac tttgctgatg  72900
atcaggccca ggttgtaatt gttgaaaaaa agagaggatg catagtctta tctcatctcc  72960
tagtcaaagt caacaccatg ataaataaga gtcaaatcct gagatgtgaa ttggggacat  73020
ttgagtggtt aaccctgaga agcttgcacc ttcagacccc tcaatacccc tgctccccag  73080
agaaggctgg acattgacct cagcacaggc aggagccctg caagatgcca tttgtcctac  73140
taaagatgga cccctccact ctgtttctag gtaaataacc aaagtcaagt ctccacacag  73200
cctgagcaag aaagtcagag cctgctacag gagaaaatac cacactggcc aaaggattca  73260
ctagccctgg ccactgtgtg tgggaggaac cagggaatca tgtgtgggag tcaatgttga  73320
agctgttgga ctgggggtgg ggtggaatat aagcctggcc ctggggagtt tttcccgttt  73380
gagggccttt acccacaact caagatccag tgctatagca ggagatccca gagctagtcc  73440
taacagatgg tcaggattga acttggccta gagtaaaatg aggaggatag tgccagaact  73500
```

-continued

```
ttctcaacat actattgagg aagaggtcag aaggcttaag gaggtagtgt aactggaaag  73560
gggtcctgat ccagacccca ggagagggtt cttggacctt gcataagaaa gagttcgaga  73620
cgagtccacc cagtaaagtg aaagcaattt tattaaagaa gaaacagaaa aatggctact  73680
ccatagagca gcgacatggg ctgcttaact gagtgttctt atgattattt cttgattcta  73740
tgctaaacaa agggtggatt atttgtgagg tttccaggaa aggggcaggg atttcccaga  73800
actgatggat ccccccactt ttagaccata tagagtaact tcctgacgtt gccatggcgt  73860
ttgtaaactg tcatggccct ggagggaatg tcttttagca tgttaatgta ttataatgtg  73920
tataatgagc agtgaggacg gccagaggtc gctttcatca ccatcttggt tttggtgggt  73980
tttggccggc ttctttatca catcctgttt tatgagcagg gtctttatga cctataactt  74040
ctcctgccga cctcctatct cctcctgtga ctaagaatgc agcctagcag gtctcagcct  74100
cattttacca tggagtcgct ctgattccaa tgcctctgac agcaggaatg ttggaattga  74160
attactatgc aagacctgag aagccattgg aggacacagc cttcattagg acactggcat  74220
ctgtgacagg ctgggtggtg gtaattgtct gttggccagt gtggactgtg ggagatgcta  74280
ctactgtaag atatgacaag gtttctcttc aaacaggctg atccgcttct tattctctaa  74340
ttccaagtac caccccccgc ctttcttctc cttttccttc tttctgattt tactacatgc  74400
ccaggcatgc tacggcccca gctcacattc ctttccttat ttaaaaatgg actggggctg  74460
ggcgcggtgg ctcatgcctg taatcccagc actttgggag gccgaggcgg gcggatcatg  74520
aggtcaggag atcgagacca tcctggctaa cacggtgaaa ccccgtctct actaaaaatg  74580
caaaaacatt agccaggcgt ggttgcaggt gcctgcagtc ccagcggctc aggaggctga  74640
ggcaggagaa tggcgtgaac ctgggaggtg gaggttgcaa tgagccgaga ttgtgccact  74700
gcactccagc ctgggtgaca gagcgagact ccgtctcaaa aaaaaaaaaa aaaaaaaaaa  74760
tagctgggca tggtggcgcg tgcctgtaat accagctact ctggaggctg aggcaagaga  74820
atcgcttgaa cccagtaggc ggaagttgca gtgagccgag atcttgacac tgcactccag  74880
cctggtgaca gagtgagact ctgtctcaaa aaaaaaaaaa agaaaaaaaa agacagaaag  74940
aaagagcaca gacagagtca caggtatttg cagtaggaag ctgtcaggtt agagtgcacg  75000
gaaatagaaa gtatatttta cacttacagc acatcttcgt ttgattagcc acatttaaaa  75060
tactgaatag caacgtgtgg ctatttagta ttcactaaaa tcttggacag tgcaagtcta  75120
aagaatcctt gatccgtccg gcatggtggc tcacgccttt aatcccagca ctttgggagg  75180
ccaaggtgga aggatcactt aaggtcagga gttcgagacc agcctggcca acatggtgaa  75240
acctcgtctc tactaataat acaaaaaaaa ttagccgggc atggtggtgc atgcctgtaa  75300
tcccaggtac ttgggaggct gaggcaggag aatagcttga atccaggagg cgctgcagtg  75360
agccgagatc atgccatgcc actactgcac tccagcctgg gcaacagagt gagactgtct  75420
caaaaaaaaa aaaaaaattg ttgggcgtgg tggctcacgc ctgtaatccc agcactttgg  75480
gaggctgagg ggggtggatc acctgggttc tggagttcga gaccagcctg gccaacatgg  75540
tgaaacccca tctctactaa aaatacaaaa attagctggg cgtggtggtg ggcacctgaa  75600
atctcagcta ctcaggaggc tgaggcagga gaatttcttg aacccaggag gcagaggttg  75660
cagtgagcca agatcgcgcc tctgcactcc atcctgggtg gcagagcaag actatgtctc  75720
aaaaaaaaaa aaaaaaatac ttgattgtct ggacattctg cagaacatca tatggagaca  75780
ctatgttgac gacatcatgc tgattgtaag caagaaatgg caagtgttcc agaaacacag  75840
```

-continued

```
tcaagacaca tacatgccag aaggtgagat ataaactcta ctaagattca gtggcctgcc  75900
acactggtga catttttaaa cctgctagat gtttgtgtag aaaaggattt aaccttgccc  75960
aaagaggggt ctggcctttg tccccagcta ctggacataa tctctttaaa ctcttgaaat  76020
atcattcctg atagaagtat ttttgttttg actaggggcc ttgggccagc cagatagcaa  76080
caatgtgatc tgggttgggg gctttggatc aggtggcatc agtgtgacct cctgagtggc  76140
tagagactag aatcaaccac atgggcagac aacccagctt acatgatgga attccaataa  76200
agactttgga cacaagggct tgggtaagct ttcctggttg gcaatgctct atactgggaa  76260
acccattctg actccatagg gagaggacaa ctggatattc tcatttggta cctccctggg  76320
ctttgcccta tgcatttttc ccttgtctga ttattattat tattatgaga tggaatctcg  76380
ctctgtcacc caggctggag tgcagtggaa tgatctcaac tcactgcaac ctctgcctcc  76440
ccggttcaag cgattttcct gtctcggcct cccgagtagc tgggactaca gatgcatacc  76500
accacacccg gctaattttt ttgtattttt agtagagacg gggtttcacg ttagccagga  76560
tggtctcgat ctcctgacct catgttccgc ctgcctcggc ctctcaaagt gctaggaata  76620
catgtgtgag ccaccgcgcc cagcccccttt ggctgattat taaagtgtat ccttgagctg  76680
tagtaaatta taaccgtgaa tataacagct tttagtgagt tttgtgagca cttctagcaa  76740
attatcaaac ctaaggatag ccttggggac ccctgaactt gcagttggtg tcagaaataa  76800
gggtgctcat gtgtgtacca tgccctctaa ttttgtagtt aattaacttt cacaacttta  76860
ttattaccgc ttacactcaa tgtttattca catttatcca cataccactt attctagtgc  76920
cttgcatcaa agactttcta tctcatgtac tttattctgc ttgaagtaaa tcctttagga  76980
tattcttttt tttttttaaa ctttgcacat acatactttt attttttatt tatttttaat  77040
tttgttattt ttgtgggtac gtagtagata tatgtattta tggagtacat gagatgtttt  77100
gatacaggca tgcaatgtga aataagcaca tcatggagaa tggggtatcc atcctctcaa  77160
gcaatttatc cttcaagtta caaacaatcc aattacactc tttaagttat tttaaaatgt  77220
acatttaatt ttgtattgac tagagtcact ctgttgtgct atcaaatata attttttttt  77280
tttttgagac agagtctcac tcagtggccc agactgaaag tgcagtggca caagctcggc  77340
tcacttcaat ctctgcctcc ctggttcaag cgaatctcct gcctcagcct cccacatagc  77400
tgggattaca ggcacacacc accatgccca gctaattttt atattttttt agtagagacg  77460
ggttttcgcc atgttggcca ggctggtctt gaactcctgg cctcaaatga tctgaccacc  77520
tcagcctccc aaagtgctag gattacaggc atgagccacc acacctggcc aaaatagaat  77580
attctttagt gaggtctgct ggtgacaatt tttttctttt ttttgagact gagtctcgct  77640
gttgtcagct tgggctggag tgcaatagca cgatctcagc tcactgcaac ctccacctcc  77700
cggattccag caattctcct gcctcagcct cccaagtagc tgagagatta caggcaccca  77760
ccaccacacg cggctaattt ttgtattttt agtagaaatg gggggttcacc gtgttggcca  77820
ggctggtctc gaactcctga cctcaggtga tccacccacc ttggcctccc aaagtgctgg  77880
gattacaagc atgagccacc acgcacagcc aattttttcc gtttttgtct gaaatcttat  77940
tttgtgtcat ctttgaaata tatttttgat ggatataaaa ttgttggttg atagttatta  78000
tcattattat tattattttg agacagggtc tcactctgtt gcctatgctg gggtgtagta  78060
atgtgatctc ggttcactgc agacttgacc tcctagggct caggtgatct tcccacctca  78120
gcctccctag tagctgggac tacagatgca tgccaccata cccaactaat ttttctattt  78180
tttgtagaga tgaggctttg ccacatttcc caggctggtc tctaactcct gagctctagc  78240
```

-continued

```
aatccaccca ccttggcctt acaaagtgct gggccatgac tagccagcag ttacttttta  78300
tagcatattg aatatttaat atgaatcttc tggcatccac tgtaactgtt taaaaaatca  78360
gctgtttact tggcactctt tttttttttt tttttttga gacagagtct tgccctgtcg  78420
cccaggctgg agtgcagtgg cgtgatcttg gctcactgca agctctgcct cccgggttca  78480
cgccattctc ctgcctcagc ctccggagta gctgggacta aaggcgcccg ccaccacgcc  78540
cggctgattt ttttgtattt ttcgtagagt tggggtttca ccgtgttagc caggatggtc  78600
tcgatctcct gacctcgtga tctgtccgcc tcggcctccc aaagtgctgg gattataggc  78660
gtgagccacc gcgcccagcc tctttttttt tttttttag acggagtctt actctgtcat  78720
ctaggctggt gtacagtggc gtgatctcag ctcagtgcaa cctccacctc ctgcctcagc  78780
ctgccaaata gctgggatta caggtgcgta ccatcacgcc cggctaattt ttgtattttc  78840
agtagagatg gggtttcacc atgttagaca ggctggtctc gaactcctgg cctcaagtga  78900
tctgcctgcc ccagcctccc aaagattaca ggcatgagcc accgcacccg gccaagtagc  78960
actcctttga aggtaatctg cttcccctac ccctagcaat ttttaacaat ttttcttcat  79020
ttttatttcc tgaagttttg ttattaataa tctgtgtgca gatttctttg tatttctttt  79080
gtttgcagtt catagtgatt cttgaattag tgtgttggtt tctgttatca ccacaggaaa  79140
attgtcagcc gttagctttt caaatatttc cttgctaaat tctctcttct cccctttcgg  79200
tacaattgat ttgattaaaa ctaaaaccag ggccgggtgc agtgactcat gcctgtaatc  79260
ccaacacttt gagaggctga ggcaggtgga tcacctaagc tcaggagttc aagaccagcc  79320
tggccaatat ggtgaaaccc cgtctctact aaaaatacaa aaattaccag gcatggtggc  79380
acacatttgt agtcaggagg ctgaggcagg agaattgctt gaatccagga ggtggaggtt  79440
gcagtgagct gagatcccac cactgcagtc tggcctgggc gacagagtga gatgagaatc  79500
tgtctcgaaa aaaaaagtta tgaatgtttg ataaactata tttgttagaa tgtttgttgt  79560
agaatactat tcattgattt ttaaacaatg ttagattaaa ccattcactg gatttgtgat  79620
aattaactta ctgattttac ctcactgatt tgttgtaatt aatacaactg gtataaaaag  79680
actgtgacga ggccgggcat ggtggctccc gcctataatc ccagcacttt gggaggctga  79740
ggcaggcgga tcacctgagg tcaggagttc aagaccagcc tgaccaacat ggtgaaaccc  79800
catctttact aaaaatacaa aattagccgg tcgtggtggt gcatgcctgt aatcccagct  79860
cttcgggagg ctgtggcagg agaatcactt gaacccggga ggtggaggtt gcagtgagcc  79920
gatatcgcgc cattgcactc cagcctgggc aacaagagcg aaactccgtc taaaaaaaaa  79980
aaagaaaaaa aacacataaa acaaaacaac actgtgacgg ttcccaaaaa ttaggagcat  80040
aattaaagga actcctgata aaaattaatt ttatcttaca tgtaaactaa aatgacttta  80100
tgaagttaat tcagaaatac aatgcagggt attagtttgc cacagctgcg tattcagcct  80160
aatgtaatat tcttgttatt tttaaattct tcttttaact ttactcatat gtggatcatc  80220
aaatttcaaa agattaaatg acaatactct tagcagcaag cttccctaag catataaaca  80280
ttttaatggg tgatgattca gaaggtaccc gaagaatatg tactgccaga tatcattcac  80340
ccccatatac ctgcccgaca gacatcccat tttgggaccc tggataaatg tgtgggtgga  80400
gagaaagata ggagaaagtg gtataagcaa atggctttgg agtctgattg acagcgattg  80460
aaatcctgtc tctacctctt aacagcctca tgatcctaca taagttaccc cgatcctcag  80520
ggccacatct gtaaattggg ggttgcgatg gcagccatct cacagggtct cttttcgggg  80580
```

-continued

```
aagggcagga attatggatt aagtgagcta gtaattgtaa agcacttaat acaaggaggg  80640
cgcataataa gtacttcata aataatgacg gccattatca tgactgaggt gtatgcagct  80700
gtcggggatt acggcgactt cagaatttct ggtgggcagg gctcaaaggc agcaaatcac  80760
actggaagtc gaggtgaggc actgcttctg cacagactgc ttagctggag agaatgagga  80820
aggcttagag gagatttaga ggaacttaga gtcctccgcc tccaactctg tgggatctgc  80880
tcccgtgcca gagacattca ggggatttct cgcactctcc cctcccctac gtccctcccg  80940
ccccatccaa ctaaccacac aacacataca aaatagcccc tgcgaggttc tgcacgctgg  81000
aagggaacag gagaagggcg ctgcgctttc ttgctgatgc cctgtacttg ggcccctggt  81060
agacacagcc acttgtcccc tcagcctgca gagaaatccc acgtagaccg cgcccgggtc  81120
cttggcttca gccaatctcc ctttggtggg ggtgggatgc acgatccaag gttttattgg  81180
ctacagacag cggggtgtgg tccgccaaga acacagattg gctcccgagg gcatctcgga  81240
tccctggtgg ggcgccgctc agcctcccgg tgcaggcccg gccgaggcca ggaggaagcg  81300
gccagaccgc gtccattcgg cgccagctca ctccggacgt ccggagcctc tgccagcgct  81360
gcttccgtcc agtgcgcctg gacgcgctgt ccttaactgg agaaaggctt caccttgaaa  81420
tccaggcttc atccctagtt agcgtgtgac cttgagcagt tgactttatt tttcagtgcc  81480
tagttttcca gataccagga ctgactccaa ggactattac tcatctggag ggtttagcac  81540
agtaccgtcg catagtaaat ttccatgtca gttttggtta cctttcatgc acttgcaaac  81600
atgccatgct ctgaaacgaa ataggcacat cttttttttt ttttttttta aggagtcttc  81660
ctctcgccca ggctggagtg cagtggcgcg atcttggctc actgcaacct ccacctcccg  81720
tgttcgagat tctcctgcct cagcctcctg attagctggg actacaggca tgccacgacg  81780
cccagttaat ttttgtattt ttagtagaga cggggtttcg ccatcttggc caggctggtc  81840
taactcctga cctcaggtga tctgactgcc tcagcctctc aaagtgttgg gattacaggc  81900
ataagccact gcatctggcc agaaatgaaa taagtaaatc ttttaacctg ctctaacaat  81960
atagtgaaaa gaccatatta ttattagagc aggttaaggg atttgcctat ttcgggttct  82020
agttatagtc ttaaacttgg acattcttgt agaaagtaaa aagtttcctc ttcaaagttc  82080
cccttcttgt taaagaatac atcataagtg ttagaagtaa tagtttattt taaagactaa  82140
ctttcttcaa gcctccttgc tttgtgctaa taactctttg ttaagcccta tcctatgtaa  82200
ctgttggaca tgctcacagg cacgttccag ttcacagcct atgccccttc cttatttgga  82260
aatgttattg cttccttaaa cctttcggta agcaacttcc tctccttctt cgttcttcct  82320
tgcacttacc tatttagaaa gttttaggct attagcaaat cggctatcag tttaagagtg  82380
tgaggtcccg ctccagccaa tggatgcagg acatagcagt gaggacgacc caaatgcgta  82440
agggataaat atgtttgctt ttcctttgtt caggtgtgct ctcgacatcg ttccatctgc  82500
gattgagcac cctttctgca gaaagtaaag attgccttgc tggagatctt ttgtctccgt  82560
gctgactttt cttcgtggca ccgattatct atttctaaca attttggtat ttctaacatt  82620
ctgaacaatc ttgggctagt tgtctcttct gggcctgttt ccccatccgt cacatgataa  82680
acttcattgg tttaaaaacc ccagcgaaca tttattgagt tactattacc ttcctgccct  82740
ccccaacccc aaccccaggg agcagttaca acctcagccg ctgagcgcac tcgccgggtg  82800
ttaagaagca ccaaagacag ggaggcttga ttgattttgc tttgggagta gagggtcaga  82860
agattcacag gaaaatggca tttgagcaag gatgattcac tggagctagc ttttaaatac  82920
tggcgaggct tttatgttgc agtcccttac aaagttgagc attcgcaggg actgcactcc  82980
```

-continued

```
gaaataagcc cgcttcccct tttcattcgc taatgatcca gggagctgct ggttccgcat  83040
gcggcaggtt gtgccttttc ctaatcaggg ttctgcatcg cctcgaaccc gcaggccgtg  83100
gcgggttctc ctgaggaagc agggactggg gtgcagggtg aagctgctcg tgccggccag  83160
cgcctgtgag caaaactcaa acggaggagc aggaggggtc gagctggagc gtggcagggt  83220
tgaccctgcc ttttagaagg gcacaatttg aagggtaccc aggggccgga agccggggac  83280
ctaaggcccg ccccgttcca gctgctggga gggctcccgc cccagggagt tagttttgca  83340
gagactgggt ctgcagcgct ccaccggggg ccggcgacag acgccacaaa acagctgcag  83400
gaacggtggc tcgctccagg cacccagggc ccgggaaaga ggcgcgggta gcacgcgcgg  83460
gtcacgtggg cgatgcgggc gtgcgcccct gcacccgcgg gagggggatg gggaaaaggg  83520
gcggggccgg cgcttgacct cccgtgaagc ctagcgcggg gaaggaccgg aactccgggc  83580
gggcggcttg ttgataatat ggcggctgga gctgcctggg catcccgagg aggcggtggg  83640
gcccactccc ggaagaaggg tcccttttcg cgctagtgca gcggcccctc tggacccgga  83700
agtccgggcc ggttgctgaa tgaggggagc cgggccctcc ccgcgccagt ccccccgcac  83760
cctccgtccc gacccgggcc ccgccatgtc cttcttccgg cggaaaggta gctgaggggg  83820
cgccggcggg gagtcaggcc gggcctcagg ggcggcggtg gggcaggtgg gcctgcgagg  83880
gctttcccca aggcggcagc aaggccttca gcgagcctcg acctcggcgc agatgccccc  83940
tgagtgcctt gctctgctcc gggactcttc tgggagggag aaggtggcct tcttgcgcga  84000
ggtcagagga gtattgtcgc gctggttcag aagcgattgc taaagcccat agaagttcct  84060
gcctgtttgg ttaagaacag ttcttaggtg ggggttagtt tttttgtgtt tctttgagga  84120
ccgtggatca agatcaagga aatctcttta gaaccttatt atggaagtct gaagtttcca  84180
aatgttgagg gttttatgtc taaaagcaac acgtgaaaaa attgttttct tcacccagtg  84240
ctgtcttcca atttcctctt tggggggagg ggtagttact gctgttacta aaataaaatt  84300
acttattgct aaagttcccc aacaggaaga ccactacttt tgatgacttt ggcaagtttg  84360
ctaactactg gaaccctaac ttacaaacga actacttaca tttttgattt ccagttgtat  84420
tacctgccca atgtttacgt agaaacagct taattttgat tctgggtaac gttgttgcac  84480
ttcattaaaa atacatatcc gaagtgagca agtatgggtc tgtggacagc agtgattttt  84540
cctgtcaatt cctgttgctt cagataaaat gtaccagaca gaggccgggc gcggtggctc  84600
acgcctgtaa tcccagcact ttgggaggct tggcgggtgg atcacctgag atcgggagtt  84660
caagaccagc ctgaccaaca tggagaaacc ccgtgtctac taaaaataca aaattagcca  84720
gggtggtggc gcatgcctgt aatgccagct acttgggagg ctgaagcagg agaatcgctt  84780
gaacctggga ggcggaggtt gcggtgagcc gagatagcac cattgcactc cagcctgggc  84840
aaaaagagcg aaactccgtc tcaaaaaaaa agtaccagac agaaatgggt tttgttttct  84900
ttttttgttt tgagacggag tttcgctctt gttgcccagg ctcgagtgca atggcgcgat  84960
ctcagtctcg gctcactgca acctctgtct cccaggttta atcgattctc ctgcctcagc  85020
ctcccaagta gctgggatta cccatgcccc accatgcccg gctaattttt gtatttttag  85080
tagaaacggg gcttcaccat gttaggctgg tcttgaaccc ctgacctcaa gtgggcctcc  85140
cacctcggcc tcccaaagtg ccaggattac aggcatgagc caccgcggcc agccagaaat  85200
gggttttgga aaaagcacta aacaaaatcg aacttggttt catatgacag ctctgctgct  85260
aactgtaaca ggggcagacc agttaaccta cttttctgtc ttctgtcagc tgagaattag  85320
```

-continued atgattccca aaggcccatt gaactctgaa tgactttaaa tacttcttct taagtgggta 85380
cacggttttg gtaactgatg ccaggtgatg aatgcatgaa agtgcttaat gaatgaaacc 85440
ggtaaaatag taggaggaag ctttattggt aaggcagggg tatacctaat agctctctaa 85500
tttattggta ttgaagtggt taacttttgt ttttttaagg ggggaaaaca ttctaagaat 85560
aatgaggcaa actgcatatt gcacaagaga ctgttgtctc tattcaacaa ataccttttg 85620
agtgtccaga gtctgccagg tgctgtgcta ggccctcacg attgagtagt gaaccagaga 85680
atgtccctgc acccatggag cttattgtct actggggtag acagataata aataagcaaa 85740
caaatcttct ctcttctccc tttcgctcca tgtaagtgtg tgtgtatagg tgtatactta 85800
caagttgagt aaagtgttat gaaagattaa gaggagaaat gcattttggt tagatgttag 85860
aggactcagc aggtgacctt gaaacttaga gctgaaggat cagtaggagg taactagaga 85920
ggccagggaa tcgcatgttc aaaggccagg aggcaagaaa gagcatggtg cccttcaaga 85980
gaggaaagaa ggctactgtg actggagcat agatgtaggc aagtgttggg tgattgagag 86040
ctctacgggc catggttagg ttttattcct aatgccgaga tgccaaacat ggtggttcat 86100
atctgtaatc ccagtatttt aggaggccga ggcaggaata tagcttgaac ccaggagttc 86160
aagaccagcc tgagcaacat gagacctgta caaaacattt aaaaaattgc tgggtatgat 86220
ggtgcacacc tgtggtccca gctactcagg aggctgaggc agaaggatca cttgagccta 86280
ggaggtggag gctacaatga gccatatttg agtcactaca ctccagcctg gatgacaaag 86340
tgagaccatg tgtcaaacaa aatacagaaa gaatattaat ttaaaatttt gaaagaggag 86400
tgatctgaac ttatatctta aaaagatcat tctagggcat ggtggctcat gcctgtaatc 86460
aagggctttg ggaggctgag acaggaggat cacctgaggc cagttcgaga tcaacctgta 86520
cagcatagag agactccatc tctacaaaaa gaaaaaataa atagctgggt gttgtgagtt 86580
attcaggagg ctgaagcaga aagatcactt gagcccagga gtttgaggct gcagtaagct 86640
atgatcccac cactgcaaca cagtgagatc ttgtctcaaa aaaaaaaaaa aatcattcta 86700
ggtgcttttt ggaggctgga tgtggtaaga gtagaagctg gagatggtcc tgttagggat 86760
tcgattcaga ctttaaatac catcaatgca ttgagtccca aatttacatc actacgttgg 86820
atccttgccc ctgaatccag actggtatat ccaactttag gttcagtttg tatctctacc 86880
tgaccaatat agaggtgtcc agtcttttgg cttccctagg ccacattgga agaagaattg 86940
tcttgagcca cacatagagt acactaacgc taacaatagc agatgagcta aaaaaaaatc 87000
gcaaaactta taatgtttta agaaagttta cgaatttgtg ttgggcacat tcagagccat 87060
cctgggccgc gggatggaca agcttaatcc agtagatacc ttcaacttac aatatctaaa 87120
attttatgcc agatttagtc attttaaacc tgctcatcag tttttctcaa gaagtagtat 87180
tttggctttt tttcttttct ttttttttgag atggagtttc gctcttatcg ttcaagctgg 87240
agtgcagtgg cggatcttgg ctcactgcaa cctccgcctc ctgggttcaa gtgattctcc 87300
tgcctcagcc tcgcaagtag ctggaattac aggcatgcgc caccatgacc agctaatttt 87360
tggagacagg gtttcaccat gttggtcagg ctggttttgt actcctgacc tcaggtgatc 87420
tgcctgcctc ggcctcccaa aggctgggat tacaggcatg agccaccgct cccggctgca 87480
tttttggatt tttagttgct cagcccaaaa ctttagtaca tctttgaacc tcttctttcc 87540
tcctactcta tatctgatcc atcagcaaat ctgttaggtc tacctcacac atatcgaaat 87600
cctaccacgt ctcaccatct gtgacaatta acaccctggt ctaggcagtc atctctgtta 87660
agattgagtg gttaaggatg tcctctaagg agatgacatt caaatcttag cttaaatgtc 87720

-continued

```
aagagggagc tggttttata aagattgagg aggcagcatt attttgccat aggcttccat  87780
ttggtttcca ttccattctt gatacttatg gtatatattc aaaacaaatg cacagaaaca  87840
gacccaggta tattgggaat ttcggatata gagttcctag ttgggaaaag atagactgat  87900
ctgtaaatga tgctagttat ccatcatctg gcaaaaaata atttcctgcc tcctctcata  87960
tatctcagat caacagactt tttctgttaa gggccaaatc ataaatattt taggctttcc  88020
agaccatatg gtttctgtca cactctcctt tatccttgaa gccatagaca atatgtaaac  88080
aaatgggcat ggctgtgcta cgataaaact ttacttacaa aaactggtag tgggccagtt  88140
taggcatggc cagcactttg ggaggctaag gcagatggat cacttggggt caggagtttg  88200
agaccagcct ggccaacatg gtgaaaccct gtctctacta aaaatacaaa aaatagctgg  88260
gcatggtggt gggtgtctat aattccagct actctggagg ctaagacaca agaatcactt  88320
gaacccagga ggcagaggtt gcagtgagct gagatagcac cactgcactc cagccagggt  88380
gacggagtct taaagcaaaa caaaacaaaa ggtagtgggt tgtatttggc ccatgggctg  88440
tagtttgcca atccctgatg cagaaacaaa ttccaggtaa ataagagcct ggaatgttaa  88500
aaaaacaaaa cttgaagtca tgtagaagaa caggtagggg gaacaatcct gatctcagga  88560
taggaaggga tattgcttaa aataagacac aggaaaatat aatccatgtt gtgtaaattt  88620
gactacgtta aaacttaaaa ctttcgccaa gcgcggtggc tcacgcctgt aataccagta  88680
ctttgggagg ccgaggtgag cagatcacca ggtcaggaga ttgagaccat cctggctaac  88740
acggtgaaac cccgtctcta ctaaaaatac aaaacattag ccgggcgtgg tggcgggcgc  88800
ctgtagtccc agctacttgg gaggctgagg caggagaatg gcctgaaccc gggaggcgaa  88860
gcttgcagtg agctgagatc gcgccactgc actccagcct gggcgacaga gtgagattcc  88920
gtctcaaaaa aacaaaacaa aacaaagcaa aaaacctaaa actttcatac aataaagtat  88980
acctaagata cttctagaag agaagattta catccaggac gtgtatggaa tttctgcaag  89040
taataagtaa aagacaaggg acatgaagag gcagttcaca aaagaggaag ccaaaatgac  89100
caataaacat gaaaggatgt ttaacctcaa aggaaacaag gaaatgaatt aaaaacatca  89160
aatgccattt caaaactagt aagttggcaa aattaaaaat accaaggatg agaatatgaa  89220
gcatggctat atgagtgcat ggaatggtac agtcactttc attaaaaatg cacataattt  89280
gtttttattt tattttttg agacagtcta tgtcgcccag gctagaatgc agtggcatga  89340
tctcggctca ccacaatctc tgcctcctgg gttcaagcaa ttctcctgcc tcagcctcct  89400
gagtagctgg gattacaggc acatgccaca acgcccggtt aagttttgta tttttagtag  89460
agacagggtt ttgccatgtt ggccaggctg gtctcgaact cctgacctca ggtgagctgc  89520
ttcccaaagt gctgggatta gaggcgtgag ccaatgctcc tggctgaaaa aaatgcacat  89580
aatttgttac ctagcaattc catgtctaga ggcttatcct agagaaattc ttgcttatat  89640
gcataggaag acgtgtacta gaatgttcac tagttgaatg tttaagtgaa aattaggaaa  89700
taaagtaaat gttcattaac aggaaaatga gtaaaggtat atttataaaa caattaagta  89760
gctaaaatga ataaactaga gctgcgtgaa tgaactagaa ctggttcaat agtcatgtca  89820
gattattgaa tgaatacagg tcagatatgt atagagtgtc atttgtgtaa ttaatttttt  89880
ttttttttt gagatggagt ctcactctgt tgcccaggct ggagtgcagt ggcgtgatct  89940
cagctcactg caacctccac ctcctgggtt aaagtgattc tcctgcctca gcctcccgag  90000
tagttgggat tacaggcatg caccaccatg cccagctcat tttcctattt ttagtggcca  90060
```

-continued cagggtttca ccatgttggc caggctggtc ttgaactcct gacctcaagt gttccaccca 90120
acttggcctc ccaaagtgct aggattacag gcgtgagcca ccgtgctcag ccatttgcgt 90180
gatttttaaa gatgtgcaga ataatgccat taaaaaaaat acacatacat gtatatatat 90240
acacgtttgg ctgggtgtgg tggctcacac ctgtaatccc agcactttgg gaggctgagg 90300
caggaggatc acttgagccc aggtgtacaa gactagcctg ggcgagatag caagacccca 90360
tctcaacaac agaaaggata attaggtatg gtggcatgag aggatcactt gagcccagga 90420
gttcgagtgt tatcaggcca ctgcactcta gcctggacaa caaagcaaga ccgtgtctca 90480
aaaaaataaa aataaaaagt atttgtatgt ggtcatagtc aaaaaacgta catggaagga 90540
aaatgtcttt atttatttat ttattttttt tttttaaga cagagtcttg ctctgtcacc 90600
caggctgggg tacagtggtg taatctcagc tcaccgcaat ctcggcctcc cgggttcaag 90660
cgattcttct gcctcagcct tctaagtagc tgggactaca ggtacccgcc accacaccct 90720
gctaattctt gtgttttcag tagagacagg gtttcaccat gttggcaagg ctggtctcga 90780
actcctgacc ttaagtgagc cacccgcctt ggcctcccaa agtcctggga ttacaggtgt 90840
gagccactgc gcttggccag gaaatatcta atttagtaag tatttatatc tgggaaagga 90900
agggtcaggt ggtgattcat aggaactcta aagtctatgt ataatactta gggggacaga 90960
aggaaataaa gcaaaatgct gatatttgat tgttgagttg tgtatatgtt agaagtataa 91020
cataggagat ctgattgata gtaggagaat gtttttaggt ggtaaaagtg gaaccgtggt 91080
ggtttgtttt ggcagtagaa tcagttggtc atagtttgta tgtggaaggt aataaacaga 91140
ccatgttaag gatgacttcc ggaattttgg tctgagtagt gggtggatga cagtgtcatt 91200
catgagggaa gatgaagact gaggtaggaa caggtttggg agaagatgac atgttccctt 91260
ttagacaagt ggaattatgg aagatggcag gtaggtggtt agctatatga atttgagata 91320
aaagatttag gatggagata taaatttagg agtaacagcg tatctatggt attgtaagcc 91380
ttaagaatgg gtaggatcag ccaggaaata cagatgtata tgcagaagag aggagtcaag 91440
gaagccaaga caagttaatg tttaaagtga gtgatgtagt ccatgggcag atgctgctga 91500
gagggctgca aacaccagtg accctacaac atttttaaat gtcgtcttcc tgacagcagt 91560
gatcagtacc tgcaacgatc ttatttattt ttttcatgtt agtctccaca cacttgaatg 91620
tagacttttt gaaggcaaaa tcattgcctt ttctgagctg ggagcatgtc tggcacatac 91680
caagcactca acagttgatg tattgacttc atccagatac tctgagggcg agttatttcc 91740
tgctactagc ctttcacctt tcaatgttta agagcacaaa tacagagatg ggcacgtttt 91800
ggcatttctt attttgataa ccttttcctg gtaagatttt ttaatgttga aaaaaaaaaa 91860
caagaaaaga gggttaaaaa tagtcttatg tcagatcctg tgatagaatt cacacttggc 91920
ttaagctgct gggcaccttc ctatcttgga tgtcatatta gcttatctac agcagaattt 91980
ttactgtttt atgtagtaag gaagcaatta tatgattatt ttacagacaa attattcttt 92040
atcttttatt tttttagacg gagtctctct ttgtctccca ggctggagta cagtgtcgcg 92100
atctcggctc actgcaacct ccgcctcctg ggttcaagca attctctgcc tcagcctccc 92160
aagtagctgg gcttacaggt gtccgccacc acacccagct cattgttttg tattttttagt 92220 agagatgggg tttcaccatg ttggccaggc tggtcttgag ctactgacct caggtgatcc 92280
acccgccttg gcatcccaaa gtgctggaat tacaggcgtg agccaccgtg cctggcccag 92340
acaaattatt atactctgag tgttagaggc ttaggatgtt ttcacttgat gctatgggag 92400
gaataagtaa taagatatga tacacaacca aagacctttc ttcactatgc ttctagtagc 92460

-continued

```
tagtactatg gatgacacat ggtaataata ttggttagca tttgtcctca atttactgtg  92520
ctagttactc ttctaagccc cttacaggta tatatttttt ttcatcaata atcctctaag  92580
gtagttttta ttattgacct aattttataa atcaagaaaa ttaagaccca gagaagtaag  92640
taacttgtcc aagatcacat ggcttataag tggtagagcc agaatttgac cccagatgtt  92700
gtgactacat tgtctctcca taagcaggtt caactctttt gactggatgc tgttccaagg  92760
tcacttcctt agagaagcct ttgctgacaa ctaccctcct gtgccctcct ccaaggctgt  92820
ccattgttct agaactttga atactcatct tagaataaag ctggtctaat ttttacagtg  92880
ttatagaatg gatctctgac tgcaaaagtt ggtcataatt atctttttat gttctagtga  92940
aaggcaaaga acaagagaag acctcagatg tgaagtccat taaaggtaag ttctgccctt  93000
ggcagtccac tgcattaaaa agtgatgtgc tttgcatttg tgagttcttt aatcctgtta  93060
tactctctct tttggcatta atcatttctg ccttatttta taattactta tgattttgat  93120
ttatttccct ctttaacctg tataatgctt taacatctag catataataa gtaggctttt  93180
tttttttttt tttttttgga gacggagtct tgctctgtta cccaggctgg agtgcagtgg  93240
cgcgatcttg gctcactgca agctctgtct cccgggttca caccattctc ctgcctcagc  93300
ctccccagca gctgggacta caggtgcacg gcgccacgcc tggctaattt tttgtatttt  93360
ttagtagaga cagagtttca ccatgttagc cagtatggtc tcgatctcct gaccttgtga  93420
tccgcccgcc tcggcctccc aaagtgctgg gattacaagc gtgagccacc gcacccggcc  93480
gtaagtaggc ttttttttacc ttaattttat ttttttgaga tggagtcttg ctcttatccc  93540
caggctggag tgcagtggtg ccatctcggc tcactgcagc atccacctcc cgggttcaag  93600
cgattctcct gcctcagcct cccgagtagc tgggattaca ggtggccgcc accatgccca  93660
gctaattttt gtatttttag tagagacagg gtttcaccgt gttggccagg ccagtctcaa  93720
actcctgacc tcaagtgatc cactcgcctt ggcctcccaa agtcctggga ttacaggcgt  93780
gagccaccat gcctggccat aagtaggctt ttactgagcc ttgtgtgtat tggctatcct  93840
agtgattaca gtgaaccagt gcccttctta ttaatcacac atttaattgt tccctaaaag  93900
tgattagttc actttattta tttagtaaga caaaaaatga agaatactct taactgagca  93960
gtctgttaac tgtaggaaag cactgacact tataaggctt agttttctgt catttatcca  94020
gaagtatggt tgattacagt ttttactttt ttatttgaat gaacaacctt aatttaaaat  94080
atattttgtt tatttttttgt tgggatcgat acattgtcct tgtttataga ttagagcatg  94140
ctttttaaag atgctgtatt actcactgat tttatttgtc cagtgtacag agattgaagt  94200
gggaaaatta taatggaaat tgtttccata gtcattacat attaatttca tcaatttatt  94260
tccataaaat ctgtagattg ctacttattt agatttttcc ttcaaatgtt tttatgttgt  94320
attgcttgca ctgagtattt attctatatg ctcaatttgc tggagaagaa gactaattat  94380
aacttaggca agttgtaaaa ttagggaaaa aagtaaggta ccttacagcc tagtttactt  94440
atttcttatg taaagccagt tagattccac attagttcaa actgccttct ttgagcaaaa  94500
cttgattggc agtgataaag gcttaaagcc cttctcaagc agagacctgt aaagactaga  94560
tctgactgta gtagaaggaa ggaacttaga tgtttcaggc agtgagaaca ccagtcttcc  94620
actctaaact ttgccactaa cagtatgacc ttgggaagtt gtaactttct tcagattctt  94680
catttgttga atggggggat tggcctagct aatttctaaa tctctactgg gctaaaaaat  94740
tctgtgctta tactctgatt atgaagtaca taatctgtgc ttaacattca ctgacttatc  94800
```

-continued

```
cttaggataa tacagaagca gtacaagaaa cagcccctca agatgtttgc agtctggtta  94860
gaaagacaaa cttatacaca gaacagtagc aaatagacca aaataataat agctgccatt  94920
tatagaacac ttcttctgtt ctgggcatta gacaaaaact gactataacg gtgaacaaaa  94980
aagacttagg tcctgccctc attgaactta cagattagta ggggagagga acattaatca  95040
agtaattcca cagatggctt agcctagatt ggtagtgatg gaagtaaaga gatgtgaacg  95100
gacttgaaaa aaaattcgga ggcaaaatgg atagaagttt attattgatt aaatatgagg  95160
tgtgagagag agggatattt aagattgata cctaccttct ggcttgccta acagaaccaa  95220
aacaggaaat tatatgttca gttttgttat gttgggtggg aggtgctttt gagtcattca  95280
tttatatatg ttatatatgt tattttatat gcatagtaat tttaaggtct gagttttaaa  95340
ccaaaggtta gagagtgatt ttttagagtc tagcaaacct aagttgaaat cctgcctgtt  95400
gaaatggctg tttactagct cattaaccta gggcaaagta ttcaacttgt tttcattttt  95460
gtcttcatct ctaaaatgag gaaaatatgg tcttacaaga ttgtcctgag agatagatga  95520
aataatatcc aaaaaaaaaa aaggtacata gagaaactcg tatagtgcct ggtatatagt  95580
aggtcctcca ttggtagcta tcattatcta gttttaacat agccttcagt ttgttgaatt  95640
agtcaaactg agtgaagcac tgcaaggaat tcagaggaat ttgagatcaa caaatgattt  95700
ctgaagttta gggaagactt catggcaatg acacttacct tgtataaaag ttgaagaata  95760
agaaagattt gaatgagaga ttctttctct tctccctacc agcccagctt cttatttgag  95820
gatatattgg gcaaaggggc cttcagacaa gtagagggag atttttacag aaagattgag  95880
atgaaggtat agaaggctgt aaagaccaga aaagagaatt gagacagagg aagcaggaag  95940
ccactgtagg tttttgagca agatattgat gctgtaagta tggtgtttat gaaaggttag  96000
tctggaagag atttgcagga tggagacccc ggaagttttt ttgttataat acagaaagac  96060
ttgcactgag ggtgaggtgt taaaaataaa caggtaagta aatgtttaaa catcttgaag  96120
gaaaagtcaa caaatcttgg caagtaaaca gataacagtg aaaaagaatg ggaccaagat  96180
tttgagtttt ggagactggt ggattgaaca gacagggaaa ttgagaggag aatcagatga  96240
tgatgtttta agttgatatt tagacagatt gtgcttgaga tggtaaagtc aatgtgggtg  96300
ggaatgctta gtagcgagta atcagtgata caagaccaaa gcccaggtca aagacaagtc  96360
acagatacag atcagggctt tttcatctgc tccacagagg tgtaccctag gagctgttgc  96420
aaacagtcca tgtggagggt gtgagtaaga tgtttccctt gaatttgcca gaattacttt  96480
tttgttgttg ttgttgtttt ttctgagaca gattctcgct ctgttgccca ggctggaggg  96540
cagtggcgag atcgcgcagc tcactgcaac ctctgcctct cgggttcgag tgattctcct  96600
gcctcagcct cccaagtagc tgggattaca ggcttgtgcc accaagccca gctaatttct  96660
tttgtatttt tagtagagat ggggtttcac catgttggcc agactggtct cgaactcctg  96720
gcctcgtgat ctgcctgcct cagcctccaa aagttctggg attacaggcg tgaaccactg  96780
cacccggtcc cttgttaagt ttattttggt gggaagcaaa ggaggtttca gcttttaaaa  96840
agtttgaaaa ttattgctct ggtaataatt aaagatttga gagtaaatat gctttctagc  96900
agaaagaata aaagaagaac agatagcctc aagaagggga gccaaagaag caggctatat  96960
ctgacacact gggtgttgat aaatgggtat taaaagaatg agagcaatga gcagatagaa  97020
gaggaaatta ggagagtata ataccatgga gaccaagaaa gatagactat caggaaggag  97080
tggtaaaaat aagttactag ttctaagaga gatgttaaga gggaccgggg aaagccttgt  97140
acaaatgagt tagtagcatt ttacattata tacatctaat taagaaacaa tgcgagagtc  97200
```

-continued

```
tcaccattcc tatagactct tacttgtact tgtctgaaca cgaaaactgg cttttgttta  97260
taaataagct aaaaattatt ttgctccaat ttctcatgaa aataaaaata aaccttcttt  97320
taacattgaa aaaatagttt gaagacagtc actcttcatt ttgtaattcc cacaactatt  97380
attgaatgac tgaaattatc tttattctga agccaaaggg gtgatactga tatttcttca  97440
gactactaaa aatatatttt atgaattttt agtgtgcttt atcttttttt gttttttttt  97500
ttgagatgga gtttcactcc cgttgctcag gctggagggc agtggtgcaa tctcagctca  97560
ctgcaacctt cgcctcccag attcaagcaa ttctcctgcc tcggtctccc aagtagctgg  97620
gattacaggc acctgccccc acacccagct aatttttgt  attttagta gagacagggt  97680
ttcaccatgt tggtcaggct ggtcttgaac tcctgacctc aggtgatcca cccaccttgg  97740
cctcccaaag tactgcgatt gcaggcatga gccaccatgc ctggcctgag gaatattttt  97800
ctaggttccc cccaccccaa gcatttattc tgcaatttta gttttgttcc taaagcaagc  97860
aaggtttaag gatttaaaaa taatccgtat tttagaatgc tttctggctt tgttactttt  97920
tatccacagt agaagttctc agagaatgat ctccctcttt taatttaact ttttggcaca  97980
gtattttgag aattataaat aatattagaa tgtttttctgg ctgggtgtgg tggctcatgc  98040
ctgtaatcct ggctacttgg gaggctgagg caggagaatc acttgaacat gggaggcaga  98100
ggttgcagtg agccgaggtc atgccactgc actccagcct gggtgacaga gcaagactct  98160
gtctgggaaa aaaaaaaaaa aaaaaaagag tgttttcttt cctattttcc accacttgat  98220
taagttactt ttcctcttaa gtattttttg ctgagtatgc tgacttaaga gtaatgttac  98280
aaaatttaat ttttaaagtt ctctgaaagc ccctttatga gagttttagg ctatcaaatt  98340
gtgtttaatt cttaacaatt ttttgaaaaa ttatagcttc aatatccgta cattccccac  98400
aaaaaagcac taaaaatcat gccttgctgg aggctgcagg accaagtcat gttgcaatca  98460
atgccatttc tgccaacatg gactcctttt caagtagcag gacagccaca cttaagaagc  98520
agccaagcca catggaggcc gctcattttg gtgacctggg taagtaacta tcattttttta  98580
ttaacttgta ttagaaggat ttgagtacaa tatgtgaaac ttctgtcata ggatacagaa  98640
ctatataatt ggaaagtgct ttggaaaaaa tgtatttaaa ataacagcta caagtataat  98700
gggtagctgt gttgtgttcc tgtaaatata gaatataaag catgcccagt agaaaaacaa  98760
gcatttccag aagaaatata tctgatcact aaatataaat atatgaaaaa gatgtctcac  98820
tttattactg agggaagtgc aaattaaaat aatcagttaa tgttctccta acacattagc  98880
atatttttta aagtttgaca atttgaatgt cagtgaagat gcagggaaat accccctccta  98940
tttagtgata atataatctg gtgaagactc tttggaaagc aatttggaaa tcagtataaa  99000
atatgcatgt catttaggcc actctttcta agacctagcc ctcagatatg ctcattcata  99060
tgtgcaggtg tgtatgtgtg tgtgtgtgtg tgtgtgtgtg tgtatatgta tgtatgtatg  99120
tatgtatgta tgtatgttga aggctattca ttatagtatt gtttgtgata gcaaaaaatt  99180
atggacaaca tataaatatc tgttataggg aaataaccaa attgtggtat acgcatgctc  99240
tggagtataa tatagccatt tgtttctatt tatttatttt cttgagacag ggttttactc  99300
tgttgcccag gctggagtgc agtggtatga tcatggttca ctgcagcctt cacctcctgg  99360
gcacaagcca ttctctcgcc tcagcctcca gagttactag gactgcaggc atgtgtcacc  99420
acacccagat aattttttaa ttttttgtag agacagggtc tcactatgtt gcctaagctg  99480
gtctcaaact cctggcctca agcaattctc ccacacaggc ctcccaaagt gctgggatta  99540
```

-continued

```
ccaacgtgaa ccaccacacc tggttcagtg tagccattta gaaatctaaa aaagacgtgg  99600
gaaaatgtct aaggcatgtt taaatgtgag aaaagcaagt cacagtatgc atggtaaaat  99660
ccgttatatt aaaataagtt cttccaaaac aaaaacatat gcaggagacc tttattttgt  99720
cagtatttct tacccaaatt tctgcactta gaaaattgca tgtcatgttg tcataagttg  99780
aaaaaaagat ccatgaacca atggacttct aataaaatca gtcctgcttt tgacatctct  99840
ctctactttt gtgtatattc aaaccagagt gtcaatgtgt ttgtggggca cacttagcaa  99900
taatacatag cagacaaaat gcatatagct cagagagtaa aattgtaagt tttgctagat  99960
cactcataaa ttgctgatga gaatttaaaa tggtgcagat gctctggaaa acaggcagtt 100020
tctttctttc ttttttttt tctttttgag acagggtctc actctgttgc gcaggctgga 100080
gtacagtggc gtgattacaa ctcactgcag cctcaccctc ctcaggttca ggtgatcctc 100140
cctcagtctc ctgagtagct gggactatag gcatgcacca ccacgcctgg ctaatttttg 100200
tatttttttt ttttttttt gtagagacgg ggtttcgcca tgtttcccag gctggtctca 100260
aactcctgga atcaagcgat ccacttgcgt aggcctccca aagtgctggg attacgggcg 100320
tgagctactg tgcctggcct aggcagtttg tttgtttgtt tgtttgtttg tttatttatt 100380
tgtagacgga gtctcacagg ctggagtgca gtggcccaat ttttggctca ctgcaacctc 100440
cgcctcccag gttcaagcta ttctcctgcc tcagcctcct gagtagctgg gatgacaggt 100500
gcctgccata atgcctggct gatttttgta tatttagtag atatggggtt tcaccatgtt 100560
ggtcaggctg gttttgaact cctgacctca ggtgatcagc ccgcctcggc ctcccaaagt 100620
gctgggatta caggcatgag ccgtcatccc tggctggtgg tttcttatga cgtgaaacat 100680
gcaattacca tatgacctag cagttgcact ctgtatttat cccagataaa tgaaaactta 100740
ccttccaata aaaacctgtg cacaaatgtt catagcagct taatattgaa aaactggatg 100800
ttcttcagca ggtgaatgaa ctggttcatt cataccatgg aataccattc agcaataaaa 100860
aggaacaaac tgttgataca tttaaccacc tggatgaata tcaagggaat tatgctgtca 100920
gacaaaaacc agtccctaaa gactacatat agtatgattc cgtttggata atattcttga 100980
aatagagaaa ttaagagaaa tgaaaagatt agtgtttgcc agatgttaga gacagggagg 101040
tgagaggggt aagtgggtgt agttataaaa gtgcaacatg agggatcttt gtgatgttga 101100
agttgtatct tggcagtgga tgcagaaatc tcaatgtgat aaaattacaa agaactaaaa 101160
acaagaatga gtatagataa aactggggaa atctgaacaa gttagagtgt tgtatcactg 101220
tcagtatctt agagtgatat tgtactatag ctttgcaaga tgttaccatg ggagaaacta 101280
aagtgtacaa gggatctcta ggtattatta ttttttaga gatggggttt cactatgttc 101340
cccaggccgg tcttgaactc ctgggctcta gtgatccgcc tgccccagcc tcctaaagta 101400
ctggaattac aggcgtgagc gaccatgcct ggccctttca gtattgtatc ttagaacttc 101460
atgtgaatct agcattatct catagaattt aattaaaaga aattgtaaac ctcacagaag 101520
atcagaattt cctcaagttt gtgatgttga caaagatgaa ctagttgaca ctgacagtaa 101580
gactgaggat gaagacacga cgtgcttcaa aaaaatgatt tgaatatcaa tggattaaga 101640
agaactcttt tgacaaattg atgaaaccct cagtcagttt tataagaatg cccatcttta 101700
tgatcatgct atgaaagcca atttttaaaa aaattttttg tctttcctaa caattagctt 101760
gtggttataa tttaaattta gttaaatata agataaatga ttttttatta agtttagttt 101820
catttttcaa ggtacgatct caaagctact ctttaaccta ctatgaatga ataatgctga 101880
gttcataaca tctttgtaga tatatccaca attttccctc aggataagtg cctacaagtg 101940
```

-continued

```
gaattactgg actgaaaata atgcagtttg ctaagacttt gctatctgtt cctgaatgct 102000
cctccaaaaa ggttttgcca gtttacatcc tcatgaccag cgaatgagag tgttgcctat 102060
tttcctgtgc ccttgttact gcttaataat tttgaaaaa aatctaattt gacagacaaa 102120
aatgcatttt atgttaattt gcttttctgg gatttttaat gaggttgagt atagttttta 102180
atatttttat tggccccttt ggaactagta tcataagttt tttttcttaa gaatttatgt 102240
agtctgggct gggcgcagtg gctcacgcct gcaatcccag cactttggga ggccgaggtg 102300
ggtggattgc cgaaggtcag gagtttgaga ccatcctgac caacatggtg aaaccgaatc 102360
tctactaaaa gtacaaaaac tagctcagcg tggtggcggg tgcctgtaat cccagctact 102420
taggaggctg agtcaagaga atcgcttgaa cccgggaggt ggaggttggt tgcattgagc 102480
cgagatcgcg ccattgctct ccagcctagg caacaagagt gaaaagtctc aaaaaaaaaa 102540
aaaaaaaaaa aaaaaagaat ttacatggtc tgaattgcca ttaaaagaga tatgagaatt 102600
attgagtaac aaataacttt ttaataattt aggcaagttt tggacgattg tactttgttt 102660
agaaaccaaa agcatagtat ttgtagtttt tttatttact ttagttgcta ggaagtaaac 102720
tttattcaag gtctctggta ccagttgttg ctaaaagtga ttgactaatc tgtcaatctg 102780
aaattatttg ttgctgaact gctaattctt ttgcttctat cttttaggca gatcttgtct 102840
ggactaccag actcaagaga ccaaatcaag cctttctaag acccttgaac aagtcttgca 102900
cgacactatt gtcctccctt acttcattca attcatggaa cttcggcgaa tggagcattt 102960
ggtgaaattt tggttagagg ctgaaagttt tcattcaaca acttggtcgc gaataagagc 103020
acacagtcta aacacagtga agcagagctc actggctgag cctgtctctc catctaaaaa 103080
gcatgaaact acagcgtctt ttttaactga ttctcttgat aagagattgg aggattctgg 103140
ctcagcacag ttgtttatga ctcattcaga aggaattgac ctgaataata gaactaacag 103200
cactcagaat cacttgctgc tttcccagga atgtgacagt gcccattctc tccgtcttga 103260
aatggccaga gcaggaactc accaagtttc catggaaacc caagaatctt cctctacact 103320
tacagtagcc agtagaaata gtcccgcttc tccactaaaa gaattgtcag gaaaactaat 103380
gaaaagtgag tatgtgattt tcttgtgtgt acatatgtgt ctcactttct ttttttaatt 103440
tactaagcag aacttcagat gaggaataaa atgattggaa tattttttt ctcctctaac 103500
tacttgtaaa tttgggagaa tttggagagt gtagtagagt cagatcagtg tatggaaaag 103560
gagcaggagt gactggacct tctaagaagt gtgttatcag aattagtaaa tgaagggtca 103620
aatgtcctac ttttcccctc cactgatttt gacatcaaac cattatccac atagccttat 103680
ttcctccctc ggtcttaatt ttattaatat tttactgcac tttgcagata aaatttttaa 103740
aaaattttta aaaattgcca ataagtgaca tttattaagt tcagtgctta gtgtatattt 103800
ggattttatt tattagtcac aagacctttg tgcaggtagt aggcatgatt atcttttttt 103860
ttttgagatg gagtcttgct ctgtcgccca ggctggagtg caatggcgcg gtctcggctc 103920
actgcaacct ccgggttcat gccattctcc tgcctcagcc tcccaaatag ctgggactac 103980
aggcgcctgc caccacaccc ggctaatttt tttgtatttt tagtagagac ggggtttcac 104040
catgttcgcc aggatggtct cgatctcctg actttgtgat ccgcctgcct cggcctccca 104100
aagtgctggg attacaggca tgagccaccg cgcccggact gattatctta tttacacatg 104160
agaaaaccag ggcttagaaa ggttaggtaa cttcctctag gttgtacagt aaatgtggac 104220
ctagaagcat tttgacaaga gcacctgttt ttttttcttc tctattagtt tagaaattat 104280
```

-continued atactcttaa ttatcacctg ggattttgat tagacagcct tcatgttctt tttcatctta 104340
aatgttcttt gtgtcttaaa gggctaagtg atttcttcag atcttttagt tcactcattc 104400
tcagtgaact aaaatgaggt ctaatctgct actgaatcaa gttttcagca tgttatttcc 104460
ttcctccctc cctccctcct tccttccctc aaccaggctc ccgaggagct gggattacag 104520
gcgcccgcca ccactcctgg ctaattttta tattttagta gagacggggt ttcaccatgt 104580
tggtcaggct gatcttgaac tcctgacctc aagtgaccca cctgcctcgg cctcccaaag 104640
tgctgggatt acaggcatga atcaccacac ctgacggcat gttattttca tcgcaaagtt 104700
actgtaagct gggagaagtg gcacacactt gtactcccag ctactcagga agcttaaggt 104760
gagaagattg cttgagccca ggagttttga gaccaacctg ggcaacacag caagacccca 104820
gctcaaacaa agaaaaaaag ttattgaatt ttttatttct atggatcatt ttttgtagtt 104880
tcttattcct ttcacccttc attcccactt ttgatcccat cttttattta tttagtttta 104940
ttaaatgtat atttgtctga taattctgct atctacagtt ttttgtggac ctgactcagc 105000
atttctttgt ttcttcggat tcagactgtt ggtggcttgt gattttagtg atttttggcc 105060
gtgaacatgt ttcttggact tttgtctgtg ggaattctct gtgtactctg tataaattaa 105120
gttacttcag gtgttttgca ttttcttttg ccatgcacct ggggcctggg tcactaccct 105180
tctggtacca cttaaaactg aatttttgtc ttgggtgctc gtactgatcc tgtatgagta 105240
caggtttata cttactgtag aaatatggtg tttgattatg ggtattgtc ccagatggtg 105300
ctggagtatt aatatgctct ctgttaaact taatgtgttg tccctgtaaa actccaaaat 105360
tctgaattcc agaatactac tggccccaaa tgtttaagat aagggcactg cctgtatttg 105420
tttctgcctc ccactatttt ccttagttta acacaaactc accttttttaa aaaacatttt 105480
gagagaattc agtattggga agagtttcta acctgtttct ggaaatggaa gtccaaagtc 105540
tgtttctgta attgtttttt ttttgagatg gagtctcact ctgtcaccca ggctggagtg 105600
caatgacgta ctctcagctc actgcaacct ccacctcccg ggttcaagcg attctcttgc 105660
ctcagccccc tgagtagctg ggattacagg tgcccaccac catgcctggc tgatttttgt 105720
atttttagaa gagatggggt ttcgccatgt tggccaggct ggtcttgaac tcctgacttt 105780
gtgatctgcc cacctcagcc tcccaaagtg ctaggattat gtttctgtaa ttgtaataca 105840
tttattgttt ttagaaactg tctttgcttt agtggtaatt ttcaataaaa atagaaatag 105900
cagtggagtt attaaaagag cattagttac atttttccct ttttcattat cttcaaatat 105960
tatatatagt aagtttgacc tttttaaaat gtatacttgt atcagtttta acacatacat 106020
agattcctgt aactgtcacc actataaggg taaagaacag ttagttcctt cacctttgaa 106080
gtcaagcccc acctctatcc caacacttgg caaccgctga tctttctccg tctcaatagc 106140
tttgcctttt ctcttttttt ttcttatttt tttttttgag acagcgtctt gctctgtcgc 106200
ccgagctgga gtgcagtgag gcaatctcgg ctcactgcaa cctccgcctc ctgggttcaa 106260
gcagttctcc tgccttagcc tccctagtag ctgggattat aggcacgcac caccacaccc 106320
ggctgatttt tttgtatttt tagtagaaat ggggtttcac catgttggcc aggctggtct 106380
caaactcttg acctcaagtg atccacctgc ctcggcctcc caaagtgctg ggattacagg 106440
cgtgagccac tgtgcccaat caggactttt ttttttaaa tttacattca acttgtcatt 106500
tttttcttgt atggattgtg ccttcagagt cacacctaag agccctttgc ctaagcaaag 106560
gtcatgaaga ttttctcata tgtttccttt taaaagtatt gtggttggcc aggtgccatg 106620
gcttatgcct gtaatctcag cactttgaga agctgaggtg ggcagattac gaggtcagga 106680

-continued gatcgagacc atcctggcta atgcggtgaa accccatctc tactaaaaat acaaaaaaaa 106740
aaaaaaatta gccgggcgtg gtggcgggca cctgtagtcc cagctacttg agaggttgag 106800
gcaggagaat agtgtgaacc cgggaggtgg agcttgcagt gagccgagat cgcgccactg 106860
cactccagcc tgggcaacac agtgagactc catctcaaaa aaaaaaaaaa agtattatgg 106920
ttttacactt tacgtttaga tatatatctt ttttgagtta atgtcgtata agtatgaggg 106980
ttacgtcaga ttttttgttt tttgtttatt tttacatatg gatgtctagt tgttctaata 107040
ccatttgttg aaaagacaac ctttactcca ttgaattgcc tttgtacttt tgccatattt 107100
gtctaggcct gtttttggac tccttttttct gtttcatgat gtgtgtgtct attcctttgt 107160
taataccaca tggtcttaat tactgtatag taagtcttaa aattgggtaa tgctggcctt 107220
ataaaacgaa ttgggaagtt tttattttta ctcttatttc cattttctag aagagattgt 107280
gtagaattgg tgtcatttct tctttagata tttggttgaa ttgggaagtg atgccatctg 107340
ggcctagggt tttgtttttt gtgtgtgaga cagagtctca cttctgtcac ccaggttgga 107400
gtgcagtggt gagatcttgg cttactgcaa cctctgcctc ccaggttcaa gttatcctcc 107460
tgcctcagcc tcccaaatag ctgggattac aagcgtgtgc caccatgccc gactaatttt 107520
tgtattttta atgcagacag ggtttcacca tgttagccaa gctggtctcg aacttgtgac 107580
ctcaagtgat tagcccacct tggcctccca aagtgttagg attatagatg tgagccaccg 107640
tgcctggcag gggcctaggg ttttcttttt cagagtattt taaactatga attcagatta 107700
tttaatagat ataggactat ttaagttatc tgtttcttct tgagtgaatt tttactgtag 107760
tttatggcct ttgagtaatt aattgtattg aattgtcaaa tttatgagcg tgtaattatt 107820
tatagcattt cgggtttgta gtggtatccc tcttttattc ctggtgttgg caattgtgtc 107880
ttgtttttct ttgtcagatt gtatagggat ttattagtct tttcaaagaa ctagcttttg 107940
ttttgatttt tctgttgttt tgttttcaat tttattgatt ttctgctctt tattatttct 108000
tttctattat ttctgcttgc tttgggttta ttttactctt tttttttct ccaagttgct 108060 taaagtagaa acttagattt ctggtttgag acctttcttt tctaagataa gcatttaata 108120
ctgtaaattt ccttctaacc actgctttag ttacaccccc acaaattctg gtattttgaa 108180
ctgagcacaa atgaaatgtt ctaatttccc ttgaatctta ttcttttacc aatgaattat 108240
ttagaaatat gttatttagt ttgcaagcaa ttggagactt ttttcctgtt atttttctac 108300
catttatttc tcatttcatt atattatggt cagagaatat attttgaatg atttcattta 108360
ttaattttta aaaataacat taaaaaattt ttttaaaatgt gaatatacca catacagtat 108420
aaagattgta cattctgttt ttggacagtt ttctataaat gtcaagttga tttagttggt 108480
taatgatggt gttcagtttt tctttattct tgctgatact ttgtatgcag ttatatcact 108540
ttattactca gaagagtgtt gaactttcca actacaattt ttttttccaa ttttactttc 108600
agctctatct ggttttgctt catgtatttt gaggctctgt tgttaggtgt gtacacattc 108660
aggatgatat cttctgggtg aattgcctgt tttatcatta tgtaattccc tctttatggt 108720
aattttcctt gttctaagat cagaaatatc tgttgtccaa tttatataga cactgcagct 108780
ttcatttgat tagtgcttgc atggcatatc tttttccatt tttttacttt tgatctacct 108840
ttataattct atttaaaggg ggcttcttgt aggcagcata tagttgggta gtgttattta 108900
tttatttatt tatttattta tttatttatt tattgagaca gagttttgct cttgttgccc 108960
aagctggagt gcagtggtgc aatcctggct taccacaacc tccacctcct gggttgcagt 109020

-continued gattctcctg cctcagcctc ccaagtagct gggattacag gcacgcgcac catgcctggc 109080
tgattttttg tatttttagt agaaacggat tttcaccatg ttagccaggc tcgtcttgaa 109140
ctcctgacct caggtgatcc acctgctttg gcctcccaaa gtgctgggat tacaggcgtg 109200
agccactgca cccggctgag tcatgttatt tttaatcttt tctcacaata cagggttttt 109260
gttggtaaat ttaattattt taatataaat tttagtataa ttatttacat taaatgtaac 109320
tgttgcactg ggtatttat aatgtgtaaa tataattatt ggtattaata taattatatt 109380
actcataata atattaatat ctttggattt agattaccag tttagtatat gtttttctgt 109440
ttctccctct ttgatttccc ctttttgct ttttttttt ttttaattct tatttttttt 109500
tagtatttgt tgatcattct tgggtgtttc ttggagaggg ggatttggca gggtcatagg 109560
acaatagttg agggaaggtc agcagataaa catgtgaaca aggtctctgg ttttcctaga 109620
cagaggaccc tgcggccttc tgcagtgttt gtgtccctgg gtacttgaga ttagggagtg 109680
gtgatgactc ttaacgagca tgctgccttc aagcatctgt ttaacaaagc acatcttgca 109740
ccacccttaa tccatttaac cctgagtggt aatagcacat gtttcagaga gcagggggtt 109800
gggggtaagg ttatagatta acagcatccc aaggcagaag aatttttctt agtacagaac 109860
aaaatggagt ctcccatgtc tacttctttc tacacagaca cagtaacaat ctgatctctc 109920
tttcttttcc ccacatttcc cccttttcta ttcgacaaaa ctgccatcgt catcatggcc 109980
cgttctcaat gagctgttgg gtacacctcc cagacggggt ggcagctggg cagaggggct 110040
cctcacttcc cagatggggc agccgggcag aggcgccccc cacctcccag acggggcagt 110100
ggccgggcgg aggcgccccc cacctccctc ccggatgggg cggctggccg ggcgggggct 110160
gaccccccac ctccctcccg gacggggcgg ctggccgggc gggggctgac cccccacctc 110220
cctcccagat ggggcggctg gccgggcggg ggctgccccc cacctccctc ccggacgggg 110280
cggctgccgg gctgaggggc tcctcacttc gcagaccggg cggctgccgg gcggaggggc 110340
tcctcacttc tcagacgggg cggccgggca gagacgctcc tcacctccca gatggggtgg 110400
cggtcgggca gagacactcc tcagttccca gacggggtcg cggccgggca gaggcgctcc 110460
tcccatccca gacggggcgg cggggcagag gtggtcccca catctcagac gatgggctgc 110520
cgggcagaga cactcctcac ttcctagacg ggatggcagc cgggaagagg tgctcctcac 110580
ttcccagacg gggcggccgg tcagaggggc tcctcacatc ccagacgatg ggcggctagg 110640
cagagacgct cctcacttcc cggacggggt ggcggccggg cagaggctgc aatctcggca 110700
ctttgggagg ccaaggcagg cggctgggaa gtggaggttg tagggagctg agatcacgcc 110760
actgcactcc agcctgggca acattgagca ttgagtgagc gagactccgt ctgcaatcct 110820
ggcacctcgg gaggccgagg caggcagatc actcgcggtc aggagctgga gaccagcccg 110880
gccaacacag cgaaaccccg tctccaccaa aaaatgcaaa aaccagtcag gtgtggcggc 110940
gtgcgcctgc aatcccaggc actctgcagg ctgaggcagg agaatcaggc agggaggttg 111000
cagtgagccg agatggcggc agtacagtcc agcctcggct ttcacaactt tggtggcatc 111060
agagggagac cggggagagg gagagggaga cgagggagag cccctttttt gctttctttt 111120
ggattatttg aatttttcct taaatttatt tatcttactt atttatttat ttttttgagt 111180
gattctcctg ccacagctcc caagtagctg ggactgcagg catgtgccac tacacccagc 111240
taattttttt gtatttttag tagagacagg gtttcaccat attggccagg ctggtcttga 111300
actcttgacc tcaagtgatc cacctgcctc ggcctcccaa agtgctggga ttacaggcgt 111360
gagccaccat gccctgcctt tttctagaat ttatatattg agttcttgat tgtatctttt 111420

-continued

```
tatgtaggct ttttagtggc ttctctagga attacaatat acatactttt cacagtgtac 111480
tcacatttaa tattttgtaa cttcaagtgg aatgtagaaa acttaaccac cataaaaata 111540
gaactaggga tgaggttaaa aaagagagag aaaagaaatg taataaagat ttaataacac 111600
cgtttttttt tttttttctc tttttttttt gagacagagt ctctctttct gttaccaggc 111660
tggagtgcag tggcgtgatc ttggctcact gcaacctccg cctcctgggt tcaagtgttt 111720
ctcctgcctc agcctactga gtagctggga ttacaggtgc gcgccaccat gcccagctaa 111780
tttttgtatt tttagtagag acggtttcac tgtgttggcc aggatggtct cgatttcttg 111840
accttgtgat tcgctctcct cagcctccca aagtgctggg attacaggcg tgagccaccg 111900
cgcccggcta agtctttaaa tatttttttg acattgcact ttttctcttt tccttctagg 111960
attttagtaa cccaaatgtt agttttgtta ttgtttggca ggttcctgag gctttcctta 112020
cttctttaaa ttttttttc ctgttgttca gcttcgaaaa tttctattca tctgtcttca 112080
aattcactgg ttctttcccg ttatttccat tctgttattg agtctttgta gtgaatttta 112140
aattttgttt attatgtttt ttagttctaa aattttcttt ttttgtgtat gtcttatact 112200
ttgctcctga aactcttatt tgtttcagga gtgatcttat ttcttagagc atggttttag 112260
tagctactta aaatttgttt tatcatccca gcatatgtgt cctcttgatt gtcttttctc 112320
ttgtgagata atgggatttt ctggttcttt atatgacaat taattttgga ttgtatcttg 112380
gacagtttga cttacgttac atgattctga atcttgttta aatcctgtgg aaaatattga 112440
agtttttgct ttaacaagca gttgacctag ttaggttcag tccacaaatt ctaagcagca 112500
ttctgtcggc tctggttcca tcatcagttc agttttgtat cttatctgct tatgtgcctt 112560
tctgtgtcca gtctgggacc tggccaatgg tcaggtccca aagcctttgt acacttttag 112620
aagcagggcc atgcacaccc agctcacgag tggccccggg agtgcacata caactcgacg 112680
ttttcatggg ctccttcttt tctgtgatgt ccctgacacg ttctgccttc taagaacctc 112740
cctttatccc tttcctgttg tctggctaga aagtcagggc tttagattcc ctatacttca 112800
gcacacttcc tgtagctatg tcaacctctg tggccacgac ttcttcttct tgggactgca 112860
gtttctcttg tcagaaagta ggattcttgg agctgctgtc attgctgctg tggctgctct 112920
gatgctgcct gggagtcgaa ggagagaaag gaacaaaaca aaacaaccca ggggatttcc 112980
tccactctct ttgatccgtg agagccccct ttcctgttcc tcagaccaga aatagagggc 113040
ctgtcttgga acttcttctt tgtgcatctg gtgtgcagtt tcagcttttg agtccaggcc 113100
aggaggtgct ggacaaactt gtcaggagta cggaggtact gcaagttctg attacttttc 113160
tcagtccacc tgcttccaag tccttggatg catttgtcca ttgttttgag ttgcattcca 113220
tgggagagac agaagagtgt gcttatttca tcttgacata cttattagga tttcatatca 113280
aatcaacgga tgatattctc tatattaatt tgctgttttc cctttagcaa gcacattagg 113340
aaaataacac tttaacaccc gcctttggtg gtttctgtca taattattaa tacttgactt 113400
tttttttttt tttgagacgg agtctcactc tgtcctttga ggcattgtcc ccataaactt 113460
ttggtaaagc atcaataatt ttatctttca tccacacaag cttcaccata aatttgatgt 113520
ttattcttcc attttagcag aattcatgtt gctccaatag gggctgtctt caaactgatg 113580
ttttctcctt cttagtgcct cagagtagat cctgttcaga tacgttataa caggttaata 113640
tgagtttatt ttggtgtaaa agtactttga aattcatgca tagttttttc atcatatgca 113700
ttttccatag ctttgaacac ccccatgtaa ctctcctctt ccacaaacca aacaatgaaa 113760
```

-continued aagcaccttt gtgatggaag tttattttgc aataggaact cacagtgatc taagccctgc 113820
tattcatgaa tataattcat tactggagtc caagttgctt tttggttttt gaagttctct 113880
tcttcccttg caggtataga acaagatgca gtgaatactt ttaccaaata tatatctcca 113940
gatgctgcta aaccaatacc aattacagaa gcaatgagaa atgacatcat aggtaagcag 114000
tgcttgaaac tatggcaaaa aaaaaatgac aaaaaatgca cagaactgac aattttcgtt 114060
attgactaag ataatttttt cttaacatgg aatttagcag ttcccttcct aatttgtttt 114120
ctgagtattt tttatatcgg attatagctc actttaaaag tttctcggct gcattcggtg 114180
cgagggtctt tgcctgggcc agatgggctg cagtgtagcg ggtgctcagg cctgcccgct 114240
gctgagcagc cgggccggcg ggcggctacg ctaaccggca cagaccaccg gatggactgg 114300
ccggcagccc cgcaccagtg cacgaagtgg gcgggacaga aacttctggg gttggaagtc 114360
cagtgaggct aaaagccggt accaaagtct ctaggcatca gggctgcagc ccaagagtct 114420
cacgaccagt gggcaactgg atggccagac aggtgtctca gtggtggcct ctccgtctca 114480
gggcttcatc ccacttctca gtgggcctga cgtccctggg caccctggat gtctacctgc 114540
attagccaga gccatcacat ggcctgtgac ttgccttttt ttgccagttg attgtgccac 114600
acacagtgtc atttctgtgt catttggcac agctggaggt gcaaggagga gggcagcctc 114660
atgtccagtc ccagtttcac gtaactttat tcttctgaat aaagacaatt tgctaacctt 114720
aaaaaaaaaa aaaaaaaaaa agtttttctt atatgttgga cccaaattct taggctttaa 114780
cctgaataac aatgacagca agatcaataa atagtacaca tttattaaac actcactgtg 114840
tcccagacaa tattccaagc actttttatg gatagactca ttttaacttc taaagaactt 114900
tgtgggataa atacagttat tttatagatg aagaaactga agcacagaga agttaagtgc 114960
tttgtccagg gtaacagctc agatatggca gagtcaggat ttgaaactag accctcacat 115020
accttaactg ctgtgctgtg gcagtgtttt tcatactgta ggttgggacc agccttctct 115080
tatgccctca ccccctgcca aaaaaaaaaa aaaaaaaaaa aaatatatat atatatatat 115140
atatatatat atatatatat aatatatata tatataaaat atatatatat ataaaatata 115200
tgtattagta tatatgcata tatagtatat attatatatt agtatatata ctaatatata 115260
atatacatat tagtgtgtgt atatatatat atactagaat aaaaaaatca aagtatctca 115320
gagtagtaag gacaaacatt tcagaaaaat gttttcatta tatatacatg tatgtatgtg 115380
tatgctgatt caacaaatat atttcttata ggttatagca aaatagtttg aaagctttta 115440
ctgtgtttta tcaggaagac cttaggtgaa cgtatattca cagataaaag aggttattta 115500
ttcattcaat aaatattaca ttctcataag tcctaatatt atgtattttt attcttcaaa 115560
aaagttagta tttgtgattt atgaaataag acatgttctt gcacttttag cagatctgtc 115620
ccgatgttgg gcttctttaa tccttagtgt gggtgctttg cactcactca ctgctgggga 115680
cagcaagacc cctgttagtc tcagctgtgt ttcttaaatt ggcccactgt accttccagt 115740
tagctattct ggggtccatg tcatgttggc tccattttcc ttttctttct cccacacaga 115800
tacctataac ggctataaca taggcctggt ggctgttggt ggcttatccc tatctgcttg 115860
tatttaaggg gtactgtttc actgagtttt gctgacagat gttgtcatga gatttgaggt 115920
tttctgtgtt gttgctctat ttttatgtgg gaatttgcta ctatcatcat ccctagacca 115980
gcttttccta gtaatacaac agggatgttc tgactgatta gagtttgcct gtttgaagaa 116040
ttggttggct agtgattttt ttttgagggg agtctgtacc agttaatagc ctgactggcg 116100
tgtggataaa aaggaagcag tttcaagtca aataaaacac ttaaaatgaa accacactgc 116160

-continued aactctcttt cttttactta agcttaatca aattaatgat gatgtaatcc catgaaggaa 116220
aagtcttctg aaggatcaag ttgataacat tttgtgatca aagaatttga gaaaacctct 116280
atcccagtgt ctatcattat atattttagg atgttaatta cctgtgtggc tttaggcaag 116340
tcatttttcc tccttgagcc ccattcttaa tcctgtccaa attatttgtc tcctcttgca 116400
gttggactat tttaatatag ctgtccttca agtgagtttt gttcaaagga gccttcactt 116460
tagctcttac tgtgtaccca ctttgcatag tcttgtttta aatgtaatcc ttggattttt 116520
ggtgttgcta actaattact gtttttatgt gaggatttag agtgatccag aatctatact 116580
tgcactacct ccttcatctt ccacaaatgt ttgaagtggt agaattttta aaaactttga 116640
aggtacagct gacagaattt gctgatggtt tggaagtgag tggtatgaga gggaaaaaaa 116700
ggaataaagc atgactgcat tttttgtttg tttgtttgtt tgtttttgag acggagtctc 116760
actctcgcca ggctggagtg cagtggcgtg atcttggctc acggcaacct ccgcctcctg 116820
ggttcaagcg attcccctgc ctcagcctcc caagtagctg ggactacagg cgctcgccac 116880
cacgcctggc taattttttt ttttgtattt tagtagaaac ggggtttcac cgtgttggcc 116940
aggatggtct ccatctcctg acctcatgat ctactcacct tggcctccca aagtgctgag 117000
gttacaggca tatatataag catataaagt gtgttatagc atacaaacag gtatatatat 117060
aaacatgcag tccacacagc tgataggaat gaggcagtag tgaaggagaa gttgatgtag 117120
gagaggggac agttgttaca ggaaagaagt ctggaggcag aagggatgaa ttccagtgct 117180
cacatagaag attgcttaga tgggagcaag gacaatttat ctagagtcac aggaaagaat 117240
gcagtacacg ggtagagatg caggtgagtt gaaagatgtg agagatgatg gaaataattt 117300
tctgattgct tctatattct caaggaagca ggaagcaaag tcctcagcaa agagaataga 117360
agaggtgtta aatatttgag aaaggagatg tactgtagaa aaaaaaaaaa ctcagtttct 117420
ccttctgaac tctcacaaaa cagaaccctt ccatgactct agttgtgtgg ggtttttttcc 117480
ctgtcagcta ccaattctgc agatgattgt tcagtgaaca ccaactgggt gtcctctaag 117540
tcagttcagt tctcacactg tttacctgga gatagcatca gatcccacag attgaggact 117600
ctgtcccaca agactgcctc cacttcagat gccagtctca agtacaagtt gtggcctgtg 117660
cttctgactg accttctata aattggagtt cccacagtcc cctccttggg ttcaataaat 117720
ttgctagagc agctctcaga actcagggaa atgctttaca tatatttacc catttattat 117780
aaaggatatt acaaaggata cagattgaac aggcagatgg aagagatgca tgggcaaggt 117840
atgggagagg ggcacagagc ttccatgcac tctccaggtc atgccaccct ccaagaacct 117900
ctacagattt agctattcag aagccccccct ccccattctg tccttttggg ttttttgtgg 117960
agacttcatt atataggcat gattgatcat tggctattgg tgatcagctc aaccttcagc 118020
cccctcatcc cgggaggttg gtgggtaggg ctgaaagtcc caaacgtgta attctgcctt 118080
ggtctttctg gtgattagcc ctcatcctaa agctctttag aggccacagc cacaagtcat 118140
ctcattagcc ttcaaaagaa tccagagatt ccatgaattt taggcgctgt atgctaagaa 118200
actggctaaa ggccagttgc aatgtctcag gcctgtaatc ccagcacttt gggaggctga 118260
ggcaggagga tcgtttcagg ccatgagatc aaaaccagcc tggtcaacat agtgagaccc 118320
ccttacaaaa aatttaaaaa ttggccaggc gtaatagctc ttgtctgtag tctcagctac 118380
tcagaaggct gaggatcact gagccctgga gttgaaggca gcagtgagcc atgatcgtgc 118440
cactgactcc ggcttgggtg acaaagtgag accttgtctc agaagaaaaa ggaaaaaaaa 118500

-continued

```
aaaactgggc aaagactaaa taacatattt cacagtatca cagatttgta ttgtctagga 118560
aagtgaatgt aaacagacca ggacactagt atgatccctt ggtttcatga aggtcccact 118620
aaagtcatga acacaaagtg agactaggca tcatgttata tggtttttcc agccatgttt 118680
aacagctagc taaatagcta attgtttcgc tgcagtttat tttagcagtt ccttatttta 118740
gcacatttca tgttttaaaa tttctaccaa taacatttta ataaactttt ttacagataa 118800
cttcacaaat ccataatttt ttaagttaca atcccagaaa tagaattgct cattgaaagg 118860
gtatgttcat ttttaaagtt atgctagaaa ctgccaaatt gccttcagaa aaaggtgttt 118920
gtatccccac taacactagt gttagttttc ttgtgccctt gctcaagtat acatattatt 118980
aaaaacaatg ttgggccagt ttactagata aaaggtgtag tgcctcctta ttctaatcta 119040
tttgattact agtgagtatg tatgtctttt cacgttggtc attttatgtt tgttcctttg 119100
tggattgtca tgtcctttgc tcatttttct tttggaacat ttcttagtag tttataagag 119160
ctcttggtat tttaatgata gtaacctttt aactgtcatg catgctgcaa atcttttttc 119220
tgtttgtttg cctttgtatt ttgtttttgg agggtttcta tgtataggaa ttaaatttta 119280
tgttgttaaa tcttttgatt tctgcttttg catatgtact tcaaaagact ttctatttta 119340
agatcaagtg ttacctgtat tttcttttag ttctatttaa aacctcttaa tttatatgcc 119400
tgtgctgtta actcccaagt tgattcacaa gtgtgtatac atagtttgaa tttagtggca 119460
atttaattat ttacaacttc ttttgcagca aggatttgtg gagaagatgg acaggtggat 119520
cccaactgtt tcgttttggc acagtccata gtctttagtg caatggagca agagtaagtt 119580
agttcatatt ttcacattgt gcatcctagg gaatttgggt tcattgttag gaatgggctt 119640
cactcagcta aaaacaaagt atttttgaga atttaaatat tttggatatt tacaagatca 119700
tataaagcat actctatctt ggttaacagt ttcttttaaa tataaattat gtgaactctt 119760
aaaattttca ttttcatttt caatgttaat atttcctaag ttaaaataat ttgtttttag 119820
ttctgaaata atttggggag tgattgagtc tgtagtgatt atgactatta gaattggttt 119880
atttatttaa ataatgcatg tcttcagatg gctctcctaa tttgttagtt aggctttaag 119940
ctaaatggat gctatataac taaatccaca tagatttgtt gaaatggctc cagaggtttt 120000
ttagatttat tactgctatg tgcccttaaa aaaaatctat tcattctttc acttaacatt 120060
tatcagaaga gtgctctgtg taagacgtgg ttaggcatag tgccagtctt gaaggaagtt 120120
acagcctaat aaaagacata gggcatgttg tttggttact gtaatatgaa gtggcatgtg 120180
ttaaatgtca ggggagaact acaaagtcat aaaaaggtgg gagagattac atacaggtaa 120240
aggaatcagg aatgacacca tggggagtaa ggtagtgttg acctaggcct ttaagataca 120300
atagggacag tatggaaaga gtatattttt cccacttaaa ctctttcctt ggtcgttccc 120360
tcaaattttc ccttttgtcc atgtgcaggc actttagtga gtttctgcga agtcaccatt 120420
tctgtaaata ccagattgaa gtgctgacca gtggaactgt ttacctggct gacattctct 120480
tctgtgagtc agccctcttt tatttctctg aggtaaagtc tgcatttctt ttcacactct 120540
attcgagcat tccagcctct aactatcaat gctggggccc tgtctatagg aaataacaca 120600
gaagagccaa gtcatttcca aaaagatgta tcattgtttc aagttgtttc tgatggcaag 120660
agtaatttaa taatatatta gagagaacat gaaaattcaa tgtattaaat aactctaatt 120720
ttgagaaacc taattaaact actgcatgta agagagtgca tgtttttaat tatttggagc 120780
tattttaaaa ccacagaatt tgaaacttgc ttccagtgca taaattgcag accagacttc 120840
agaagagaaa aaaagtagta aattttttct tatgctcatc atttttactt tagtcacttg 120900
```

-continued

```
ataggattgc ccagtgaaga agcatttgca acagacaatg agtatattaa tctttttgag 120960
gcatacagtt tagtataatg ctctttgtta ggcttcaaca agtgaaatta ttttgttgga 121020
aagcaaatga ctattaagta gaaagaggat tcccagtctc acaaagcagt aatttagaca 121080
ctcgattctg cctctttaca agaatacagg tactcagttg atttgttttc tcactccctt 121140
tctttgctat aagtttaaat caacaatttg tttaggttaa tatgtcctca tggaatggtg 121200
gaaatgatca gatataaaat atttggtttg gttagtttac tctttatatg tttgctggca 121260
aggaaccaca aatccagttt agtataattt ttactctagt tcactaaaag tttgcatcca 121320
gctgtgtagg tagtgtttgt ttcttgttaa cttttttttc gtctaaaaga atactttaaa 121380
acttttcaat ctcaaatgac tgtaacttgc tgacaggtgt taacagaaga agtagatctt 121440
tttgtttttt gcttatgacc tgtattttaa tatttgagct tatagattag agattgtgag 121500
agaaatctgt ttatagtctt attttccctt gtgtattttt tcttcctagt acatggaaaa 121560
agaggatgca gtgaatatct tacaattctg gttggcagca gataacttcc agtctcagct 121620
tgctgccaaa aagggccaat atgatggaca ggaggcacag aatgatgcca tgattttata 121680
tgacaagtga gttatattga tagatggatt cagcagatac ttattgaaca tttgatatgt 121740
tttgtggaaa taaagatgaa taaactcagt ctctgttgtc aaggagctca caggaggcag 121800
cataaaagct gcttttatat ggtgtttgta aagctttggg ggttcttaga acaaaagttt 121860
ctgctgggaa aggggaggtg tatgtggggt aaacaggatg gcaatggtgg tgttcaagga 121920
gtgtttccca gaagagagat tttgtttgga tcccaaagaa agaagggaat tttgctaccc 121980
agagaaggca gaaaacaaca ttctaggcaa aggcattggc ccagaagcca tggaaacgta 122040
ggggaaagtg gcactttcaa gaaacttgag tttagataat caaaggagtg gggaataaat 122100
atgaggatgc tggtactaat tggaatagat tgtaagggac cttgaatgcc tatttatggg 122160
tatattatac tttctgtata aatctgctca ggcacgttgt taattagttt tttattagtt 122220
ttcactgaaa atgagaggat ggaaacatca tacagtaaac aaaattgaaa atatctggtc 122280
aggcagatga tgagcttgtg gccagctctg taacgtatgg tattcttttc atttaacttt 122340
tcttactctg taaaaaaagt aattcgtggt cgggcacggt ggctcactcc tgtaatcaca 122400
acactttgag aggcagaggc aggtgaatcg cttgagccca ggaatttgag accagcctgg 122460
gcaacatggc aaaacccgcc tttactaaaa atacaaaaat tagctgagcg tgatggcgtg 122520
cgcctgttgt cctagctact taggggcctg aggcagaagg atcacctgag ccttgggagg 122580
tcgaggctgc agtgagctgt gatccactgt actccaccct gggcagggca gtagagtgag 122640
accctgtctc caaaaaaaaa aaaaacaaca aaggtaattt gttatttgta tccttaagca 122700
aatgctaaag gggtaacttg gggatagaga aaagtccaca gatgttaggg tttgaagaca 122760
ctaatagtat ctaggccagt ggttcctgaa cattagtctg tgggctcttg ctgggctgtc 122820
tgcataggaa tcacctgaga gcttattaaa aataggtttt caggctggtt gcggtggctc 122880
acgcctataa tcccagcact ttgggaggct gaggcaggcg gattacttga ggtcaggcgt 122940
tcaagaccag cctggccaac atggtaaaac cccgtctcta ctaaaaatac aagaattagc 123000
caggcatgat ggcacacacc tgtaatccca gctactcagg aggctgagga aggagaattg 123060
ctcgagcccg ggaggtggag gttgcagtga gcggagatca tgccactgca ctccaggctg 123120
gctgacagag ggagactctg tctcagaaaa aaaaaaaaaa ataggttttc agtctgggta 123180
ccggtggctc acacctgtaa tcccagcact ttgggaggcc aaggcaggca gatcacttga 123240
```

-continued ggtcaggagt ttgagaactg cctggccaac atagtgaaac cttgtctcta ctagaaacta 123300
caaaaaatta actgggcatt ttgacgggtg cctataatcc cagctactag ggaggctgag 123360
gcaggagaat tgcttgaacc cgggaggcag aggactgcat ctcaaaaaaa aaaaaaaaaa 123420
aaaggtttcc agtccccctg tctcagaaat tctgattctg caggtttgag gtgtgaccag 123480
gaatctttat ttttagaaga cataccagat aattctgata aatagccagt ttagggatgt 123540
agtctaattt tcctattttg caagtaagga aaataaggcc cagagaggta atgattttct 123600
caaagtcaca gaacaagtta gtggcagaat ttggactgga atgcagttct taatgttctg 123660
tccagtgttt attctggtac agtatgtttg tagaaggtat tacgtaagaa acattgttat 123720
atagatgttg agataggaag agtttacatt tagaaatttg gtctaaaatg cctgaacatt 123780
caagtcgtgg aggagtattg accaacttac tcaatacaac ataggagatt cacattttgt 123840
tacaaaaatg ctgatttaaa aggagagttt tctttttttt cttctttttt attttttgag 123900
atggagtctt gctctgtcac ccaggctaga gtgcagtgac acgatctcag ctcactgcaa 123960
cctccacctc ctgggttcaa gcggttctcc tgcctcagcc tcctgagtag ctgggattac 124020
aggtgggggc caccacgccc agctaatttt tgtattttta gtagagacag ggtttcacca 124080
tgttggccag gccggtcttg aactcctgac ctcaagtgat ccacccacca ctgcctccca 124140
aagtgctggg attataggcg tgagccactg tgcccagcct gcttgttttt gtatcatata 124200
tatgcatcat cataatcatg cattatcaac ctttgtattt ctgtcaggac atagaaacca 124260
ttagagtgct tggaagagag cctttttttt tttctcgcat ttaatgcttt ttttggtatt 124320
catttcataa tcagcttacc aaaacattac ctgcattata ccccatcaag gtagaaatct 124380
ttgtgttatc aatattggtt actccctttc cacaccgagt catcagtaag tcctgttcta 124440
tccaaatagg tcatatgcat ctagctcacc cctcagtgct gttttgtttt gaatttgtac 124500
atgtttactc ctgatgcctt gtagttatga tgatgtgttc ttattttatt ctgtgcatac 124560
aagttctcag ctcgcttttt agggaaaatg accatgtctt cctttcctat aaattccttt 124620
ctatctatca agtcctcaac agagaatagg tacccataaa tatgtgattg ttagtttctt 124680
tgcctcagtt gtagtctgat ccttacagct tttaaacaac agtagagttc accgtcaaga 124740
actaaggatg gttggcaggc agatagaaag gtagcaagtt gacccaacta tctctgggga 124800
agtgggaaca aagaaaggtt acatcagcac tgtcatcaca tagctctata gttctaggcc 124860
tgcaggctca atcaagtagc cttgtataag attctctgga ggaggtgctg aaagttgctt 124920
atacttgcta tggaatttga ttttacttcg gatatctttt taccataggt acttctccct 124980
ccaagccaca catcctcttg gatttgatga tgttgtacga ttagaaattg aatccaatat 125040
ctgcagggaa ggtgggccac tccccaactg tttcacaact ccattacgtc aggcctggac 125100
aaccatggag aaggtaaccc agaacttcaa acgtatcaaa ctacaagaag ttttattggt 125160
agaactcata aaatataagg tgggaaaacc aagcagaata gcacagtgga aattgaagca 125220
gtccagcaaa gtgattaaga gcagaggcct tgagtctggc ctggtatgta cagtcacgtg 125280
ccacataaca ttttagtcaa cagtggactg cgtgtacgat ggtcctgtac gattataatg 125340
gatcaaagct ggtagtgcaa taataacaaa agttagaaaa aataaatttt aataagtaaa 125400
aaagaaaaaa gaaaaactaa aaagataaaa gaataaccaa gaacaaaaca aaaaaaatta 125460
taatggagct gaaaaatctc tgttgcctca tatttactgt actatacttt taatcattat 125520
tttagagtgc tccttctact tactaagaaa acagttaact gtaaaacagc ttcagacagg 125580
tccttcagga ggtttccaga aggaggcatt gttatcaaag gagatgacgg ctccatgcgt 125640

-continued gttactgccc ctgaagacct tccagtggga caagatgtgg aggtgaaaga aagtgttatt 125700
gatgatcctg accctgtgta ggcttaggct aatgtgggtg tttgtcttag tttttaacaa 125760
acaaatttaa aaagaaaaaa aaaattaaaa atagaaaaaa gcttataaaa taaggatata 125820
atgaaaatat ttttgtacag ctgtatatgt ttgtgtttta agctgttatg acaacagagt 125880
caaaaagcta aaaaaagtaa aacagttaaa aagttacagt aagctaattt attattaaag 125940
aaaaaaattt taaataaatt tagtgtagcc taagtgtaca gtgtaagtct acagtagtgt 126000
acaataatgt gctaggcctt cacattcact taccactcac tcgctgactc acccagagca 126060
acttccagtc ttgcaagctc cattcatggt aagtgcccta tacagatgta ccattttta 126120 tcttttatac tgtattttta ctgtgccttt tctgtatttg tgtttaaata cacaaattct 126180
taccattgca atagtggcct acgatattca ttatagtaac atgtgataca ggtttgtagc 126240
ccaaaagcaa taggttgtac catatagcca aggggtgtag taggccatac catctaggtt 126300
tgtataagta cactctgtga tgttagcaca atggcaagca gcctaacgga aattctgttt 126360
attgattgat tgattgattg attgattgag acagagtttc actccattgt ccaggctgga 126420
gtgcagttgc acagtcttgg cacactgcaa cttctgcctc ccaggttcaa ccaattatcc 126480
tgcctcatcc tcccaagtag ctgggattac aggcaggcac caccatacct ggctaatttt 126540
tgtattttag tagagacagg gtttcaccat tttggccagg ctgttctcga actcctgacc 126600
ttaagtgatc tgcctgcttt ggcctccgaa agtgctggga ttacaggcat gagctaccat 126660
gcctgggcag taactgaaat tctctaatgc cattttcctt atctgtaaag tgacgataat 126720
atgcacgttt acctcaaagt tactttgatg attaaagtaa ggtaatgtat ataaaataca 126780
tattaacata gtacctgaca catggtaagc atcaaaaaat gttaactact tttattacta 126840
ttattattac gtatttttaa ataattagag agcagtatca aaaattagct gggcgtagtg 126900
gcatgcacct atagttccag ctactcagga ggctgaagct ggaggattgc atgagcctgg 126960
gaattaaagg ctgcagtgag ccgtgttcat gcccctgcac tccagccttg gtgacagagc 127020
aagaccctgt cttgaacaat taaagaaggc attatgccgc aacgttagct tagaaatgat 127080
ccacatatat caccagtaac tgtcaacagg attggaaccc tagttttggg tattatgatc 127140
acaaggtatt attaatagct tattaataat aaagcgttgg ctaggcacgg cgactcacat 127200
ctgtaatccc agcactttgg gaggccgagg tgggtggatc acctgaggtc aggagtttga 127260
gaccagcctg accaacatgg agaaacccca tctctactaa aaatacaaaa ttagccgggc 127320
gtggtggtgc atgcctgtaa tcccagctac ttaggaggct gaggcaggaa aatctcttga 127380
acccgggagg cagaggttgc agtgagctga gatcgcacca ttgcactcca gcctgggcaa 127440
caagagcaaa actccgtctc aaaaatataa ttataataaa taaataaaag taaagtattg 127500
atgtttgtga atgatttatt cttctaatga actagaggag atttttccag gaatttcaga 127560
gccagtgagg ttatgttgct tgtatgtgtc atgtgtatcc aggtgaaaaa acttaattaa 127620
acgctattat ataataccat acataaaaac tgaattttag gaatactgaa gaatgacata 127680
tagaagtcaa atcattaaat agctagtagt aaacagaata gagtgtcagc tgttacccaa 127740
tgatgataat attttcacga ttaaaattaa accttttctg attttaaagg aaaagttcag 127800
atctgtatca tataaagaat gtaaattttc agggtaataa aattaaaatg cagagagaaa 127860
aatgcaaaaa tagttcttac tagatgtgtg tatgtaagga acttagacta attttaagaa 127920
cactgtcaag accctggtag ttaggtagga aaaaagacat gaatgattca ttcaacaaaa 127980

-continued

```
actttgagta tttctgtgct agatggtagt gttacagtgg taaacaaaat aaatgtgttt 128040
ctgctatcct ggagcttagt ctacaaaaaa ggtacatatt ggccgggcac ggtggctcac 128100
gcctgtaatc ctagcacttt ggaagatcga ggcgggtgga tcacctgagg tcaggagttc 128160
aagaccagct tggccaacat ggcgaaaccc cgtctctact aaaaatacaa aaattaactg 128220
ggtgtggtgg cggacacctg taatcccagc tactcgggag gctgaggcag gagaatcact 128280
tgaacctggg agacagaggt tccagtgagt cgagatcatg ccactgcatt ccagcccggg 128340
ggacaaaagc gaaaatacgt ctcaaaaaaa caaaaacaaa caacaaaggc acgtattaaa 128400
tacgaacata aatatttaca aattatactg aataagttct catgtttatt atttgcttgt 128460
ccagttacaa acttttcctt cgtagaatta gaaatataaa taataaacat gagaactcat 128520
tcagtataat taataattat taaatgtaaa taaaaacatc tatgtacaat taggcattta 128580
tttaagaatt atttgaaaaa aaaacaatgt ggaaacagat attttgatat attgctagtg 128640
attgaaattg ataatgttct tttgaagagt aaagtgacca tatatattaa agttaaaatt 128700
taactcagca atcacacgcc tggtgagtta tcttaaggaa atcagtttga aagtaaaatc 128760
aatatatgca caaagacttt aacatttatc ataaaccaga aaaatcgagt ttcaaattat 128820
atcctatgga ctattttctg ctaaaaagta ttaatatcaa ctttatgtaa tactttcgtg 128880
acaaatattt tgggggagaa aacccaacaa aattacatgc attgtaattt tttttttttt 128940
ttttttttta gacagtcttg ctccagcgtc caggctggag tgcagtggtg caatctcggc 129000
tcactgcaac ctccatctcc caggttcaag caattctcct gcctcaggcc tcccgagtag 129060
ctgggattac aggcgctcac caccatgcct agctaatttt tatagttttt agtagagatg 129120
gggtttcatc atgttggcca ggctggtctt gaactcctgg tctcaagtga tccgtctgcc 129180
tcggcctcct agagtgctga gattacaggt gtaagccact gcacccagcc ttatgcatta 129240
taattttaat ttgtaaactg tacaaaggga taatacttgt agtacaacaa gaagtaaaaa 129300
catttgttat aggtagttaa catttgtaac cagtagaatt ataggtaaaa tttatttatt 129360
taaaacagtt ttagttggat ttgatttcaa ctttaaaata atgcttttca tctctatcag 129420
gtctttttgc ctggcttttt gtccagcaat ctttattata aatatttgaa tgatctcatc 129480
cattcggttc gaggagatga atttctgggc gggaacgtgt cgctgactgc tcctggctct 129540
gttggccctc ctgatgagtc tcacccaggg agttctgaca gctctgcgtc tcaggtattg 129600
actgattgcg tctgccatta gggagaaaag catacacatc ctttccttca catcccagta 129660
acagatccta ttatttgtaa attttaagtt gtggaaaaaa aagataaaag ccaggcacag 129720
tggcctgtgc ctgtaatccc agcactttgg gaggctgcgg tgggcggatc acacgaggtc 129780
aggaattcga gaccagcctg gccgacatgg tgaaacccca tctctactaa aaatacaaaa 129840
attagccggg catggtggca ggcacctgta atcctagcta cttgggaggc tgaggcagga 129900
gaatcgcttg aacccaggag gcagaggttg caatgaacca aaatcacgcc actgcactcc 129960
agcctgggtg acaaagtgag actgtgtctc aaaaaaaaaa aaaaaagaga gaaataaaat 130020
tagcctactt actatcttct aatcaaagca tttgtggtaa cttaaaatat actgtattgt 130080
aaagtatcat gctgtttcat ttaggccatt attctatttg aatctgtggc tgtttctctt 130140
aataaatcaa gtaatatgga atatattcat agcctctgaa gagctcttta tgtaagtatt 130200
tatttaggat actttttgta aaataagtga atgaattctt aggtctcctt tttttttctt 130260
ttcttgagac agggtctcct cgctgcaacc tggaaattct gggctcaaat aatccaccca 130320
ccacagcctc ctgaatagct gggactagag gcatgcacca ccacgcctgg ctaatttgaa 130380
```

-continued atttttttt ggccaggcat gatggttcac gcctgtaatc ccagcacttt gggagaccga 130440
ggcaggcaga tcacgaggtc gggagatgga gaccagcctg gccaacgtgg tgaaaccccg 130500
tctctactaa aaatacaaaa attagctggt tatggtggct catgcctgta atcccagcta 130560
cttgggaggc tgaggcagga gaatggcttc aaccagggag tcggaggttg cagtgagccg 130620
agatcacgcc actgcactcc tgcatggtga cagagtgaga ctccatctca aaaaaaattt 130680 ttttttaaa tgatggagtc ttgctgtgtt gctcaggctg gtcttgaacc cctgacctca 130740
aatgccgcct gcttcagcct aagtttcttt tttttttgta aagagacagg gtcttgctat 130800
gttggccagg gtagtctcaa actcctggct tcaagcagtc ctcccacctt ggcctctcaa 130860
agtgctggga ttacaggcgt gaaccactac ctataatgtt gtgtttcact caaggccttt 130920
tgatttcgtt ttgcattacc gtgccacatt gtgcatttcc ttgacctttt ttgggttttt 130980
tggagtgctt tcatatgtta aaccatacct gattctcctc aaaatcacac aaagtagaat 131040
atcctaagac aagaaatcta aggaggcata aagaagttaa ctggttttat taaactcaca 131100
cagtaaatga tagagccaga aatattcccc ttctagtgtt cttcaccatc agcttaatgt 131160
agcataataa ttttctaatt actgttgaca aataaataac cctttgaatt ttcaatactg 131220
ggccttggat aaattttcct aatttgtaag agagtattat cgtattgcca tttacaaagc 131280
tctcctgagt atctttttct tctgttaagt ttacctagga gataaactgc tgagtatggt 131340
tgccattttg gtttttgat ataggttaga atgtcttggt tttttttttt tttttttttg 131400
gtttttgttg ttgtcattgt ttgagacagc atcttgctct gtcgcccagg ctggagtgca 131460
atggcacgat cgtggctcac tgcaacctcc acctcccggg ttcaagcaat tctcctgcct 131520
cagcttcctg agtagctggg attacaggca tgtgcaacca cacctggcta atttttgtgt 131580
ttttagtaga gaaggggttt caccatgttg gtcaggctgg tattgaactg ctgacctcat 131640
gatccacctg cctcggcctc ccaaagtgct gggattgcag gcatgagcca ctgcacctgg 131700
ctgaatgtct tgtttttgat taggcactta agaaaggcct aggtactaac cataaaatat 131760
atttttatac cttttgttga tactatatat atagaaaact gcacttatca taaccttaga 131820
caccttgaag aatgttcaca agcagaacta acccatgtga cccagcatcc agatcaaaaa 131880
cagcattatc agcccctcta gaagccctct tgggcccctt ccattcactg tccttcttgt 131940
caccagggta gctactatcc tgacttttga tggcatagat tagcattacc tgttcttgtc 132000
attttataaa taaaaccata ctgtgtattc ttttcttgta cagctttatt gtgctaattc 132060
acatttacat catacaattc agtggttttt atatggtcac agagttaggt aaccattacc 132120
acatcgattt tagaacattt ttttcactcc agatagaaac cccctttact taaactccaa 132180
atcccccact ccaccagccc taggcagcca ctagtctact ttttatctct atagagacaa 132240
tagatttgct tattctggac atttcataaa catggaaccg tatattatgt ggtcttttgt 132300
tgccaactgt ctttcactta gcatcatgtg ttcaaaagag catcatgtta tccatgtttg 132360
gcatgtatca gaattttatt cctcattatg gccaaatatc ccattgcaag gatttatgac 132420
attttatttg aattgtaccc tcctttctgc catttatcaa taatgctact gtgaccattt 132480
gtgtacaagt ttttgtgtgg atacaggttt tctttttgtt tttaaatttg aggtggagtc 132540
ttgctctgtc gcccaggctg gagtgcagtg gcacaatctc ggctcactgc aacctctgtc 132600
tcctgggttc aagcagttct cctgcctcag cctcccgagt atctgggact ataggcacgc 132660
accaccacgc ccagctaatt ttttagtaga gatggggttt caccatgttg gccagtctgg 132720

-continued tctcgaactc ttgacctcaa gtgatccacc catctcggcc tcccaaagtg ctgggattac 132780
aggggtgagc cactatgccc ggctgtggtt ttcatttctt ttgttgtata tacataggag 132840
tagaattgct gagtcaagag gtaactctta aacttattga aaaactgcca gattgttttc 132900
cgaaaaggct gcaccatttt gcaatcccac cagcagtgta tgagttttac agcttctcca 132960
catttcattg gaacttatta tctgtttggc tgtttttaaa aatgatagtc attccaataa 133020
gttctacttc agtgtggttt ttgcacttct ctgatgagta atgatgttga gcatcttttc 133080
atttgcttat tggcctttgt tctagctttg gaaaaatgtt tattcaaatc ctttggccat 133140
ttttattttt atttttattt atttattttt ttttgagacc aagtctcact ctgtcagcca 133200
ggctggagta caatggtgtg gtctcagctc actgcaacct ccgcctcctg tgttcaagtg 133260
attctcctgc ctcagcctcc cgagtagctg ggattacatt tcaggcacct gccagcatgc 133320
cgggctgatt tttgtatttt tactagtgac agggtttcac catgttagcc aggctggtca 133380
caaactcctg acctcaggtg atctgcctgc ctaggcttcc caaagtgctg ggattacagg 133440
cgtgagccat tgggcccagc ctagattttc ttttttcttt tttttttgga gaaggagtct 133500
tgctcttgtt gcccaggctg gagtgcaatg gcacaatctt ggctcactgc aacctctgcc 133560
tcctgggttc aagcgatttt cctgcctcag cctccccagt agctgggatt acaggtgcct 133620
accaccacac ccagctaact tttgtatttt ttttagagac agggtttcac catgttggcc 133680
aggctggtct caactcctga cctcaggtga tccacctgcc ttggcctccc gaagtgctgg 133740
gattaccggc atgagctacc aggcccagcc aattttctca ttatattgcc caggctggtc 133800
tcaaactcct gggttcaagt gatcctcctg ccttggcctc ccaaagtgtg gggagtacag 133860
gcgtgagcca ccttgctcag ccccttttgcc catttttaaa ttagattgcc tttttatatt 133920
gagtttcagg agtcctttat atattctaga taaatgtccc ttatcaaatt atattatttc 133980
caggtatttt cttcattctg tgagttgtct ttcctctacc ttttaaaaaa ggtgggtttt 134040
tgtttgtttg tttgtttgtt tttttaagat aaggtctcat tctgctgccc aggctggagt 134100
gcagtggcac aatcacagct cactgccacc tcaacttcct gggccgaagt gatcctctta 134160
cttcagcctc ctgaatagct agggccatag atacacacta tcacacccag cttttttttt 134220
ctgtttgtag agacagatct tactgtgttg cccaagttgg tctcaaactc taggctcaaa 134280
gtgattctcc cacctctgcc tcccagagtg ctgggattac aggtgtgagc cacacgcaac 134340
ctgtcttttc actattaata gtgtcttcct gcttcagcct cccgagtagc tgggattaca 134400
ggcacccacc accatgcctg gctaattttt ttgcattttt agtagagaca gtgtttcacc 134460
atgttcaccc ggctggtctt gaactcctga cctcaggtga ttcacctgcc atggcctccc 134520
aaagtgctgg gattacaggc gtgagccact gcacccggcc aaaatattgc cttcttaaca 134580
gtattgtctt ctaatttgtg aacatggatg tatcttcatg tatttatgtg ttctttcatt 134640
tcagcagaat tttgtagttt tcagagtaga agcctttcac ctccttgggt catttattcc 134700
tatgttttaa gttcttttcg attccattat aaatagaatt gttttcttaa tttcattttc 134760
agattgtttg atgagagagc atagaaatac aagtgatttt tacatgttga tcttgcaact 134820
tcaactttga taaatctgat tgttagctct aatagttttc ttgtggattc tttaggattt 134880
tcaatatata agatcatgtc atttatggat agagatagtt ttttttctgg ctagaactta 134940
cagagcaatg atgagtagaa gtggcagaag caaaaatctt tgtcttgttt cctatctgac 135000
agggaaagct ttcagtttca tcatttaata tgatgttagg tgtgggtttt caataaatgc 135060 ctttttttcag attcaggaat ttccctatca ttcctgattt tttaaggctt tttttttttt 135120

-continued ttaaatcatg aaagggtgtt gaatattgtc atgttctttc tgtatcagta taaatgatcc 135180
tatggatttt gggttttatt ctgttgatgt gaaatattaa ttgattttca gatgttaaac 135240
caaccttgca tacctgagat gaatctcact tggtcatggt gtataatctt ttcaatatgc 135300
tgctggattc catttactgg tattttgttg aagattttgt atctgaacgc ttaagataac 135360
atttacactc tatcagaaat gaattgacca taaatgtgag agtgtatttg tgggttcttg 135420
attctcttcc attccaaaga tagacataca tccgtctgta tgtctgtctt tatgccagta 135480
ccatactctc ttgattacta ttgctttgta ataagttttg aaatcagaaa gtataaatga 135540
gattttggta tctgagtaac agtcctcata gaattagttg ggaaatattc cctctttatt 135600
ctggtccctc tttcttttt gtttaactgt gtatcttgga gattgttcct tctcaacaca 135660
tgagagccgc tttccctacc ctcccacccc tgctatagag aggtctataa gtgtctgttc 135720
aattatttta tttacttaac ctattactta gtcggggaca ttaagcttgt ttatgtcttt 135780
tattttaaac aatgctgcag tgaataatct tgtatataag tcattttcca tcaatataag 135840
tctctctgta actgaatttt tagaagtgga atttctaggt caacctatgg ctctgtattt 135900
cacaaaaata ccaattctgg tttttcttgt ggaggtgggg agtaggaggt agaatgctgg 135960
aggagaactt gctgtactca gctggctagt cattttagaa aggtttcctt agcttctttt 136020
tgtcatatgg cctcaccaag aatcaaaaac attcctattt accctgtaaa catggggctt 136080
tactacccaa gatacatatt tctggatgta tgacagcttt tcatattgaa gaaataatgc 136140
tgtgagtaca gcacatttgt tggaacttag gtcgttaaga atgtcttata aattcataca 136200
ttatacattt tattttattt tattttttag tttttgatac agagtcttcc tctgtcgccc 136260
aggccagcgt gcagtggtac aatcttggct cactgcgacc tccatctcct gggctcaagt 136320
gattctcatg tctcagcctc cagagtagct atggttacag gcatgcacca ccatgcccgg 136380
ctaatttttt tatttttagt agaaactggg tttcaccata ttgaccatgc tggcctcgaa 136440
ctcttggcct caagtgatcg gcctgcctca gcctcccaaa gtgctgggat ccttgtattg 136500
ggtaaaagat gaatattgag ggctgcatgg tggctcatac ctgtaatccc agcactttct 136560
gagactgagg tgggaggagt cctggagccc aggagggtga ggctgcagtg agttgtgatc 136620
gcgccattgc acttcaacct aggaattata ggcttcagtc actgtgcccg gcatgtacat 136680
tttaatattg tgctttcctc ttttagctat agtatgaggt tacatttcag agtcattgtt 136740
gttaagcatc ttaatagtga tgaggttgag tgaaagttac ttctatttca aacactgaag 136800
aaaattttgt acaaatctgt cacattccaa gcccaggact gattgtttca tatacttcta 136860
attttacaat ttctattgta gtccagtgtg aaaaaagcca gtattaaaat actgaaaaat 136920
tttgatgaag cgataattgt ggatgcggca agtctggatc cagaatcttt atatcaacgg 136980
acatatgccg ggtaagctta gctcatgcct agaattttta caagtgtaaa taactttgca 137040
tcttttaaat tttttaatta aattttacat ttttttctaa tctattatta tatgcccaga 137100
actttcactt agagtgtgca gtataatgtg gtggttaagt ataaaggctc tggagtgact 137160
tcctgggttt taatcttggc tctgccattt attggcagcc gctaacctct tggtatctca 137220
gtttcttcat ctgtaaaatg agaataataa agtgaaaaga tgccaacatc atttactctg 137280
ggctgcataa ctgatacttg gaaaaagtat tcctttgagt ttaagaatta agttggttat 137340
tcattttagc ttgtaataaa aagatagtga ttcataggat atgccactta ctgaaattta 137400
ccacagatcc aatcataaaa tcactttctc ttccctaaag atagcttgat taacatgtaa 137460

-continued

```
aggtgtgtaa aggcttgatt acactaccct gatccgtacc ccagttccca gcagcaccat 137520
gaaaaaggga tttcaacata tttaattact ttcagtagaa agtaacagtg gtaggccagg 137580
cgcagtggct cacacctgta atcccagcac tttgggaggc cgaggtgggc ggatcacgag 137640
gtcaggagat tgagaccatc ctggctaaca cgatgaaacc ccgtctctac taaaaataca 137700
aaaaattagc cgggcatggt ggcaggcacc tgtagtccca gctacttggg aggctgagac 137760
aggagaatgg cgtgagcccg ggaggcggag cttgcagtga gcttagattg tgccactgca 137820
ctccagcctg cgcagtggag cgagactctt gtctcaaaaa aaaagaaagt aacagtggta 137880
ttgggagact gaggagccta gaaagtactt gaaggaagta aaaggtttgt ttgaccacat 137940
tgtatttgga aagccagctt tttcagctgt gtcagctttg tgtagtgatt tttagttctt 138000
cttttagaaa ataacggaca aggccgggca cggtggctca cgcctgtaat cccaccactt 138060
tgggaggccg agacgggcgg attacctgat ctcaggagtt cgagaccagc ctgggcaaca 138120
tggtgaaacc ccgtctctac taaaatacaa aaagttagcc gggcgtggtg gcgtgtgcct 138180
gtagtcccag ctactccgga ggctgaggca ggagaattgc ttgaacccgg gaggcggagg 138240
ttgcagtgag ccaagatcac accattgcac tgcagcctgc gcgacagagt aagactctgt 138300
ctcaaaaaat aataataaaa taaaaaagaa tggacagtaa acctaaatga gttcattccc 138360
aaagatgatg ttattcttaa gggatggttc atttatttaa gaccttacat aaagtctatc 138420
aattgcgtga tttttcactt ctgtaattgt gtgtatgtat aatgtaaata tatatgtttt 138480
tgttttgttt tggtttttttg agacggagtc tcgctctgtt gctcaggctg gaatgcagtg 138540
gtgcaatctc agctctctgc aacctctgtc tcccaggttc aagcgtttct tctgcctcat 138600
cctcccaagt agctgggact acaggcacgt gccaccacgc ccggctaatt ttttgtattt 138660
ttagtagaga tggggtttca ccgtgttagc caggatggtc tcaatctcct gacctcgtga 138720
tccacccgcc ttggcttccc aaagtgttgc tattacaggc atgagccacc acacccagca 138780
tgtatttttt aaatgtataa aatgaagcag aaaagagaaa tgataatttt tcttcatctt 138840
gaaagattat cttcaccagg cgcagtggct cacacttgta atcccagcac tttgggaggc 138900
ctcggcaggc ggctcacttg agttcgaaac cagcctggcc gacatggtga aactccgtct 138960
ctactaaaaa taaataaata aagatggttt taatatatgt tttagtttta tgattttagc 139020
atctttctga aatttttctc aaggcaagta aatttgtatc agttggtata ttggtaccca 139080
tctatgaaat aacttattag gaagatatct ctaaaataag atcactttgc ctaaaataaa 139140
ctgatatatt gatgttcaca gaatttttct tttaaccgac ttgataaatg cattattctt 139200
gacgtcaagt gatccacctt cctcagcctc ccaaagtgct gggattacac acatgagcca 139260
ccgcacctgg cattattctt ataaaaggtt aaatttctag ttaagtttaa tgtcctcttt 139320
gttcatgtac cattgcttat tttcttccct tcctactcac agtaatcatt cttatggtat 139380
gcacttttgt ttgcttattt ttatgtaatt gatattacgc tccattctgt acgttgtact 139440
ttcattcaca gtgagttttg gacattccta tgttcatcta tacagactta cttcatttta 139500
actacactgt agtattccgt atgtaatatt tactataact catcactgta gcagagcatc 139560
tcatagtgta tgtattactg ttttgccatt ttggtatcaa tgagtattta agtcatttgc 139620
agtttttccc tcttataccc agtattacag aggatctctt tttatatgct tctttgtacc 139680
aagaggcaga ttaaaaaatt tttttttgaa aaaattttttg aaaaaaaatg aaatgaagtc 139740
tcactatgtt gcccaggctg gtctcaaact cctaggctca agcaatcctt ccatcttggc 139800
ctcccaaagt gctggggtta caggcatgag ccaccatgcc tggcctacat tttaaatttt 139860
```

-continued

```
gatagctctt acaatttact ttgtaaagta tctgcatcat tttatgttct caccagtctt 139920
taataagaat acttcatact tttggctgga cacagtggct cacgcctgta atcccagcac 139980
tttgggaggc cgaggcgggc agatcaagag atcgagacca ccctggccaa tatggtgaaa 140040
ccctgtctct actaaaaata caaaaattag ctgggcgtgg tggcgcaccc gtagtcccag 140100
ctactcgaga ggctgagaca ggagaatcac ttgaacccgg gaggtggagg ttgcagtgaa 140160
cttagatcac accactgcac tccagcctag caacagagtg agactctgtc tcaaaaaaaa 140220
aaaagaatac ttcagactta atttttttc cagtcttaag tgtttgctaa tgagattgag 140280
tttcttttgg tatgtctctt gattgttcag gtttttttctt ttatgaattg actgttcatc 140340
tctttttcac attatttctg ttgggtgatt ttattagtga cttgttaaaa ttctgtatat 140400
tttttcagca tgacacttca ttattcaaaa aaaaaaaaag attctctatg tttctcgata 140460
ctaatcattg gttggtaata ccttaaaaat aagaccctta ctgtattttt tgcttttttt 140520
ttttttttt ttttttttt tttgagatag agtcttgctc tgttgcccag gctggagtgc 140580
aatggtatga tctcggctct cagctcactg caactgcaac ctctacctcc ctgtttcaag 140640
caattctcct gccttagcct cccaagtagc tgggattaca ggcatccacc accacaccca 140700
gctaattttt gtatttttag tagagacagg gtttcaccat gttggccagg ctggtctcaa 140760
actactggcc tcaagtgatc cgcctgcctc ggcatcccaa agtactggga ttacaggcat 140820
gagccacagt gcctagccac tttttgcttt ttaactttgt tttatagtac tatagtttta 140880
gtataaacag atgtatgtat acacacaact atggctttat aatatgtttc agtcattgtt 140940
agagcaaggc ctacctttg ggtgcttctt ttacaaaatt gtcttggcta ttcttgtgcc 141000
tttttctta tttgtgaatt ttagaattgt gaattacctg ttgactcacc atgttttgta 141060
aactgaggat tttgaatgga attgcactca attaaagatt atcttgcttt ctgtgcagca 141120
atgttttatt tcaaataatc cctactttaa attacttagg atagctataa attgtgtttc 141180
tggctttcta gatttagatg aaacgcttta aattgattgt tttctcctaa atttaaaact 141240
gattgttaga agttaaagtc ttctgttcat tcttatttag gaagatgaca tttggaagag 141300
tcagtgactt ggggcaattc atccgagaat ctgagcctga acctgatgta aggaaatcaa 141360
aaggtttgtg gtgtttttat acttcatatt aagcctttac tcacattagt gattgactgt 141420
aagtcaaaga ccacttaagg tttaaactgt ttattttgta aagtaaccac tgtatctttc 141480
accttgtgtt tatagtcaga agtaagtaca agggcttcct gtagtcacat ctttatgcaa 141540
tctcctctga atcaaaagtt agtgaacttg ctttgccact ccagaaggca catgaatatg 141600
aaaaagcatt gtctattttc ttatttaatg gcaaaatacc cgacctaagt tggacttaat 141660
gtttgagacc gtttatttta ttaaattata ttttttctct tttcttttt ttttttgaga 141720
cagttcttgc tctgtcaccc agaccggagt gcagtggtct gaccgcacct cactgcaacc 141780
tctgcttcct aggttcaagc gattttcctg cctcatcctc ctgagtagct gggactacaa 141840
gtgcgcacca ccacacctgg ctaatttttg tatttttagc agagatgagg tttcaccacg 141900
ttggctaggc tggtctcata ctcctgacct caagcaatcc atccgccttg gcttcccaaa 141960
gtgctgggat tacaagtgtg agccaccatg cctggcctta ttaaattatt tttattaaat 142020
ttcctcaaga ttgatgaaag taatgaaata taaaagtaat gaaatatatg tggaaaatag 142080
actggattaa gaaaatgtgg cacatataca ccatggatac tatgcagcca taaaaaagga 142140
tgagttcatg tcctttgtag ggacatggat gaagctggaa accatcattc tgagcaaact 142200
```

-continued

```
gtctcaagga tagaaaacca aacaccgcat gctctcactc ataggtggga attgaacaat 142260
gagaacactt ggacacaggg tggggaacat cacacgctgg ggcctgtcgt ggggtggggg 142320
gctgggggag gaatagcatt aggagatata cctaatataa atgacgagtt aatgggtgca 142380
gcacaccaac atggtacatg tatacatatg taacaaagct gcacgttgtg cacatgtacc 142440
ctagaactta aagtataata aatttaaaaa aaataaatat atgtggaaaa tattaatagg 142500
tcaaaattca aattgttcat ttaatcagaa gagtagttta gtcaaatcca agggttagac 142560
aacagaaatc tttttgtca agtgcattct ttgtgactga tttcattttc ttcctggttt 142620
acacaggaag atttcagaaa caaatgtgga tccgtgacag atggtatcta gaagttttta 142680
gtttggttga attgacagta ttttattgag taaaagatac taatttttgt aagaagaaaa 142740
attcaatttt gataagtatg tttaagatta agagctattg gccaggcgct gtggctcatg 142800
cctgtaatcc tagcactttg ggaagctgga gcaggtgggt cacgaggtca agagattgag 142860
accatcctgg ccaacatggt gaaaccctgt ctctactaaa ttagccaggc gtggtggcac 142920
atgcctgtgc acccgcctcc gggtttaagc gatcctactg cctcaggctc ctgagtagct 142980
gggattacag gcgccatggc taatttttgc atttttagta gagacagggt ttcactacat 143040
tggccaggct ggtctggtct caaactcctg acctcaggtg atctgcccgc cttagcctcc 143100
caaagtgctg ggattacagg catgattcac catgtctggc catttatctt attttctttt 143160
ttttttttt ttttgtttga gacggagtct tgctgtgtcg cccagagctg gagtgcaatg 143220
gtgcgatctc agctcactgc aacctctgcc tcctgggttc aagcaattct cctgcctcag 143280
tcttccaagt agctgggatt acaggcgcgt gccaccacat ctagctaatt tttgtatttt 143340
tagtagagac agggtttcac catgttggcc aggctggtct cggaactcct gacctcgtaa 143400
tctgcccacc tcggcctccc aaagtgctga gattacaagt gtgagccact gtgcccagcc 143460
atcttatttt ctttcttttt ttttgtcggg tgggaggggg acagagtcta gctctgtcgc 143520
caggcttggc tcactgcaac ctctgccccc caggttctag caattattct gcctcagcct 143580
cccaagtagc tgggattata ggcacctgcc accacgcctg gctaattttt tgttattttt 143640
agtagagatg ggttttgct atgttgacca tgctggcctc aagtgatccg cccaccttgg 143700
cctcccaaag tactgggctt acaggcgtga gcttgtattg ggtaaaagaa caatattggg 143760
ggctgcatgg tggttcatac ctgtaatctg agcactttgt gagactgaga tggaaggagt 143820
gttggagccc aggagggtga ggctgcggct gcagtgaatt gtgatcacgc cattgcactt 143880
ccacctaggt aatggagcaa gaccatgtct ctaaaaaaca aaacacaatt tttttaagga 143940
atactgggaa gaggtcagtg gtggttttag aacagaggaa gtgccagatg acctttgtga 144000
ggcattggcc aggaagaact ctacagtgtc tttaggtagc ttctgtccat aaggataatg 144060
gggtctcctc cccagtatta atagaaaatc tctgagctgt ttttttttgt ttgtttgttt 144120
tgttttttt tcctgagatg gagtctctct ctgtcggcca ggctggagtg ctgtggcgcg 144180
atcttggctc actgcaagct ctgcctccca ggttcacacc attctcctgc ctcagcctcc 144240
caagtagctg ggactacagg tgtccaccac cacgcccagc taattttttg ttatttttag 144300
tagagatggg gtttcaccat gtcagccagg atggtctcga tctcctgacc tcgtgatccg 144360
ctcgcctctg ccttgcaaag tgctggagtt acaggcgtga gccaccgtgc ctggcctggt 144420
tttttgttg ttgttattta tttatttatt tatttatttt ttgagacaga ctctcgctct 144480
gtcgcccggg ctggagtgta gtggcacgat gtcggctcac tgcaagctct gcctgccagg 144540
ttcaagccat tctcctgcct cagcctcctg agtagcaggg accacaggcg ctcgccacca 144600
```

-continued cgcccggcta atttttgta tttttagaag agacggggtt tcaccgcatt agccaggatg 144660
gtctcgatct cctgatgtcg tgatccgccc acctcggcct cccaaagtgc tgggattaca 144720
ggtgtgagcc accgtgcctg gcctgatttt tttttttttt taatctggtc tcatacctct 144780
gacagctcat gaagaagtgc tcctgcttca tatgtatatg tgttagcata gtgttaacat 144840
agcataggtg ttcggtgttt gcagtttctg tttgttttat atgaattaag gtgtattatg 144900
agcagttgaa gatatatagg aaatttttc ccaaaccact atctctgctc gttctattca 144960
ttcagtctgt ttatgttatt ccttcattca ttcattttat agaacagtgg agtgcctact 145020
gtatgcatct attgttctgg gtcctgggga agaaaacaaa gttcctgctt tcatggaact 145080
tacattatat tggcggagac agtaacagac aaacaaatgt agcctgtgta catgtgttac 145140
atgaaaagca gggtaggggg ctgggagaga gtagtaggga gtgctatttt cgaggtggtt 145200
gtcaggaaag gcctcactga ggaggtggca ttttgagtag acctgagcgc agcgggggcg 145260
taagcccagg cagcatgtgg aggaagagtg ttcttggtga aaggaacaag gatagaggcc 145320
cgaagctaga gagctcagca tgatcaagga acagcaagcc ccgtgtggct ggaatggagt 145380
gagcaaagga atgagcagta gaaggtgagt gagttgggag gtcaccagag accatggcaa 145440
ggacttgaaa gtgtcaggga cacattggaa gttggagcag ggaaatgatg ggatttatgt 145500
tttgtttttg ttttatgttt agtgttttta agggattgct ctatcagcta tttggaaaat 145560
ttagtgtagg gcttcaagaa gagaagcaga gaaacaacat tcttgccata gtcatagtct 145620
aagtaaggga tgatggtggt gtggattagg ctggtagtgg aagaccagtc cagttcgggt 145680
tgtatttgaa ggtagaggca aaaagattat atttctacca gcaagcccat ctatgaagtt 145740
acttgtatta ttaatttaat tgagacatgc ccacataaac taataaatag gaatttctgc 145800
agtttggtta aacacccctg tatatcctgg ttcttctttt agttgtccag atgtctcttt 145860
aagtcaagta ttttttggtg gtgtaggagc ctagagattg aatttattca cccaaaaggc 145920
atttgagtga ttactatgtg ccaggcacta tgctgaatgc caaggatgta aataagaggg 145980
cgtagtctca gtctgtttta ctccagcttg gttccttttt aatgaccctg acttgttaag 146040
catatcagtt atcctacaga atgtttaatc ttctgtactt tcctggttgt gttatttagc 146100
ttatttctct ttccttgaca tttcttgtaa actggaagtt acacctatag tcttgatgat 146160
tcgtgttaca cattttagat tagaacacat catgtgttgt atatggtgtt tttgaaagcc 146220
tctctgtata ttggtctgta cattaaaatg ttgcctgaat ggatacacat aaaatttaac 146280
agtgattaca ttagagatga gaagaaagag gtgcctttta cttttcaata taccttttcc 146340
tctgcttttt gaactttctt gccctatgca tacgttattg cttaatcatc cacctcatct 146400
cttcccctgt ggctttctgt tgcatttgga atgaaatcta gcctctttgc tgttacctgt 146460
ggatgtccct tgctggcctc tatcacctta ctttgaacca ctcctttcat ggactgagct 146520
ctcattggac tatcttttat tcttttgctg aagtttcttc actttgagtg cctctgcagt 146580
tgctatttca tggctgtggc aagccctgcc atggctttca tgcaaggatg gttcctcctt 146640
ctcatctcaa tattatctct tcagagaggg accttcccaa ctccgatgat ctaaaatcct 146700
ttgtatatac cactcactac cacttctttc ttttcttttc cttttatctt tttttttttt 146760
tttttttttt gagatagggt cttgctctgt tgcccaggct ggaatcacga ctcactgcag 146820
cctcatcttc ttgggctcaa atgatcctct cacctcagcc tctcgagtag ctggaactgc 146880
aggcacacac caccatactt ggcttattat tttactttt gtagagacag ggtttcacca 146940

-continued

```
aggctggtct caagctcctg ccgcaagcaa tccacatctc tcagcctccc aaagtattgg 147000
gattatagga gtgagccact actcctggcc tattttctta ttcactgtct aaaattatct 147060
tgttcattta tttacatact tgtttatagc ttatttctca gctggacatg gtgcctcaca 147120
cctgtaatct caatactttg ggaggctggg ttggagaatt ggttgagccc aggacttcaa 147180
gaccagcctg ggcaacaaag tgagaccctg tctataaaaa attgtttaaa aattagctgg 147240
gcatggtggc acatgcctgt ggtcccagct acttgggagg cagaggtggg agaatcgctt 147300
gggcccagga ggttgaggcg acggtgagcc atgattgtgc cactgcactc tagcctagtg 147360
acagagtgag accatgtgtc taaaaagtaa ataaaaatag tttctctttc atgactagaa 147420
tattacctct atgtgggcag ggagtttgtc tatactattt ggcactatat ttcctgattc 147480
tgaaattatg cctagcacat ggtaagtact ccttaaatat ttattgactg aattatttaa 147540
tacttaagaa tttcatttgg gattatctga gtggtaagat tacggattat atttatgtaa 147600
gaaaaaatca ttttttaaac ttggttgccc tttgccacac tgacatagac actaagtttt 147660
cttagccaga ttacttccga ggatactcac agaggccatt ctcttctcaa tccccaaata 147720
attgatattt cttagcactt tcaagctaat gcaattctta gatgatgtat ctgtgtatat 147780
catatcctca ttctacaaat gtagaaattg aagtctgggc acagtggctc tcacctgtaa 147840
tctcagcagt ttgggaggcc aaggcgagcg gatcactgag gacaagagtt aagaccagcc 147900
tggccaacat ggtaaagcct tgcctctatt aaaaatacaa caattagggc cgggcgtggt 147960
ggctcacgcc tataatccca gcacgttggg aggccaaggc aggcagatca cgaggtcagg 148020
agttcgagac catcctggct aacacagtga aaccccatct ctactaaaaa tacaaaaaat 148080
tagccaggca tggtggcacg cgcttgtagt cccagctatc gggaggctga ggcaggtgaa 148140
tcccttgaac ccgggaggcg gaggttgcaa tgagctgaga ttgcaccgct gaactccagc 148200
ctggtcaaca gagggagact ctgtctcaaa aaaaaaaaaa aaaaacaatt agccaggcgt 148260
ggtggcgggt acgagtacct gtaatcccag ctactaggga ggctgaggga ggagaatcac 148320
ttaaacccag gaggtggagt ttgcagcggg ctgataatgc accactacat tccagcctgg 148380
gcaacagagt gagactctgt cttaaaaaaa aaaaaaagaa agaaagaaat tgaggaatgt 148440
ggagattgtg gtctgtgatt tgttaggaat cacacagcag gttagtagca actacagggc 148500
tttggttcag aataccacct tgacaatggt ttgtttacag ttcggctccc cttcctctgc 148560
ctttctctcc ttccttattg agggcagctg gaaagaattt tcatcattta ctagcctata 148620
gctttaattt gagttttgaa accttgataa tagagcacag aggaaaagac tgagttttct 148680
ttttttgaga cagtcttgct ctatggccca ggctggagtg cagtgacacc atctcagctg 148740
gttgcaacct ctgcctccca ggttcaagca attctgcctc agcctctcga gtagctgaga 148800
ttacaggcac gtgtcaccac gcccagctaa ttttctgttt ttgtttcgtt ttgttttttt 148860
ctgagatgga gtcttgctct gtcacccagg ctggagtgca gtggtgcgat gttggctcac 148920
tcaaacctct gtctcctggg ttcaagcaat tcttctgcct cagcctcccc agtagctggg 148980
actacaggta cgtgccacca tccctagttc atttttgtat gtttagtaga gatggggttt 149040
cactatgttg accaggctgg tctcgaactc ctgatctcag gtgatctact cgtctcagtt 149100
tcccaaagtg ctgggattat tggcacacgc ctatttttgt atttttagta gagacggggt 149160
ttcaccatgt tggttagact ggtctcaaac ttctgacctc aagtgatttg cccgccccag 149220
cctcccaaag tgctgggatt acaggcgtga gccaccgtgc ccagccaaga ttgagttttg 149280
aaaagagcct tctgagatta tgagaagggc aagcaagata acttaagaag ttacattaaa 149340
```

-continued atcatctaag agacagtgta acaagaagga attgtaaaat gatgttatga gcacgtgccc 149400
aatgtagtgg caatcccttg tgcttcgata cattggtggg agacaaaact gtacttaaat 149460
tgataaatcc cttacatgtc attttaagga gcttagactg actcccatca tgtagacatc 149520
agagatttct tttttttttt tttttttttt tttttttttt tttgtgacag agttttgctc 149580
ttgttgccga ggctggagtg caatggcgtg atctcggctc accacaacct ccacctccca 149640
ggttcaagca attctcctgc ctcagcctcc cgagtagctg ggattacagc catgcaccac 149700
cacgcctggc taattttgta tttttagtag agacggggtt tctccatgtt gtggctggtc 149760
tcgaactcct gacctcaggt gatcctcccg cctcagccac ccaaagttct gaaattacag 149820
gcgtgagcca ccgcgcccag cccagagatt tctaaacaga gttctaacca gatgcttttc 149880
cctgtcagta gaatgagaat gaattggagg tgggagagac tggcatgagg gacaccagtc 149940
agccagtgga attagctggt aatgttgata ggagaagaaa aagattcaaa gttaggtagt 150000
ggtagcaaga attagaggga aggtcggatt tatgatatgt ccaaggttga attctaaggt 150060
gaaatttggt ggcagatttc atgtgtaaat tgggaaggta gattgagttt ttttaacatg 150120
ggttttctaa catgtcaata gagtgactct gcagggggc ctgacgagag aacagtgcat 150180
ggggtgattc aacagccagt tgagccttca tgcagagcat ttaacactgt gactctgtag 150240
actctggttg gcagtaaaat ttcattaaac caatatttaa acccttaggt aataataaaa 150300
attgagggaa aaggatccag gttttgtatt ttttatgaat tcagttattg aattaaacag 150360
gaccttgcct caagaaataa tctaccaaca attaacttgt tttaaagcaa agttaggaag 150420
tgagcatgtt caaattatta aataaaaaag taagctgtgt atttcattca tagaaataga 150480
ggctggccta cttcggatga ttctcagcat gtgattacag atgtgggctt atacatccta 150540
gggagttaag gcgtactctg gcttggatag agtagagctc tttgaaactc ttctctcacc 150600
cagctagttt atatagacta gagaactaga atgtagcagc atactctgtc ttagaagccc 150660
ttttatatag gagctggtct ggaaggtttg aaaacataac aaatgtgttg gtgtctccca 150720
atgtattgct agattcttac ccaagagcat tatcctggtt agggtttggt ttggttttgt 150780
tttgtttttt aatgtttgcc acaaactaac actagatgtt agttctttca tcaagtgagg 150840
agagtagaag aaaagtccag aactctgaaa caccttttca aaagtttttc aagccatgat 150900
gtttgcaagt taaatgctct gttatgtaag caatataatc agtttttatt aatgtaacat 150960
tccttagtgt tttggggtat cacacaaaaa agaatatcca tatctggaag caacagcttt 151020
taaataagag cattgtggtg gtggtggtga tagtggtttt tttttttttt tttgagttgg 151080
agtctcgctc tgttgcccag gttggagtgc agtggcacga tctcagctcg cttcaacctc 151140
tgctcccagg ttcaagcaat tcttctgcct cagcctcctg agtagctggg attataggca 151200
cctgctacca tgcctggctg atttttatta ttttagtaga gacaggtttc accatgttgg 151260
ccaggctggt cttgaactct taacctcagg tgaatcaccc acctcggcct cccaaagtgc 151320
tggaattaca ggcatgaacc accatggcca gccaaataag agcattttta atgtaaaatt 151380
atgcatgaaa tgtacattca attttgtctt tgtttactag gatccatgtt ctcacaagct 151440
atgaagaaat gggtgcaagg aaatactgat gaggtaaatc ctacctttag gataaaaaga 151500
tttctgttta taagtgccac cctcatgtaa gtgaggttta aaattttcct tttctttagg 151560
tcccatgttt aagcagcatg gcacatttat gttctcttac ccagaatgta ccaagaaagg 151620
gtggtccctt cttaacatct aacaattgcc tggtagtagc agtgaaggta tcttcagtca 151680

-continued

```
gaggctagga ccactgaagg atatacatgc attcaagttt ccatcagcca gcaggcatca 151740
gtaatcagtg tgtagatcaa aagctcaaat gtttccttcc ccactggcag ttttacttca 151800
agtagtggag gcttgctttt ttaatagtta attaagtaca ttgagagatg ggaggtgaaa 151860
aaaggaaaat gttttatttt gaccatctaa tatgaaagta gttcggtgtt aggtatccag 151920
tagttgacac tggaagacag ggaatgacat gttaatattc atagccagag ggtggcccag 151980
gtttttttcgt acatgggaat gaaattctta tccaaataag tagaaattat gtgcgtaagc 152040
catttgttaa gagcactgag tatgtgcatc tcgatccatc taatgaataa ccattatcac 152100
cagtttaaat tattttcttt aggcccagga agagctagct tggaagattg ctaaaatgat 152160
agtcagtgac attatgcagc aggctcagta tgatcaaccg ttagagaaat ctacaaaggt 152220
aaggatgact tcgttttgtg taaactaaaa agtattattt tccaggtgta aaaataaaaa 152280
agaacataag ggtttctttt gcctttgaag gattaactgc tgtggggatt accttcttat 152340
cataagcaac tagaaaattg acaaactaaa tgaaacaact gtttgcatat attggacaat 152400
gggcaataca gggaaaccat ggaaaccaaa cagagcccag tagtcttgct gaacgaaaga 152460
gttaaatatc aaagttcagg ccaggtgcag tggctcacgc ctgtaatccc agcactttgg 152520
gaggccaagg cgggtgaatc acttgaggtc aggagttcaa gaccagcctg gccaacatgg 152580
tgaaaccctg tcttagccgg gtgtggtggc aggcacctgt aatcccaact atttgggagg 152640
ctgaggcagg agaatcgctt gaaccaggga ggcggaggtt gcagtgagcc gagatcacac 152700
cactgcactc cagcctgggc gacgagcgaa accccatttc aaaaaaaaaa tcaaagttca 152760
gagagctcaa tttgagtaga agttgtagga taaggtagca gaaaagagga agctgcccag 152820
aaagaaagcc gtagagatat ttagagagat tcccatggat ccttggccta ggagtgatct 152880
gtatatgtgt ggggtgaaaa cgcatgtgtc caggtagaga accccccaga aattagtagg 152940
ctgaatgatt gctggaacat agggctaaga aaagttcatg gccagaagga tctggccaga 153000
gtagagagac ttagtaatac acaaggcatt gggtagtgtc ttcacagagg ttatgcctta 153060
ctactgaaga taaattagtc ctagagtaca agcacctgaa ccaagtttca aagcaaattt 153120
ttaaagggtc aaattaccta acaactgcat gccaaaacaa aggcctaacc ctctttacag 153180
taacacaaca aaattcagca cttcacagtg taaagttaga atgtctgacg tccaggctgg 153240
gcgcagtggc tcatgcctgt aatcccagca ctttgggagg ccgaggcagg tagatgacct 153300
gaggtcagga gttcaagacc agcctggcta acatggtgca accccgtctc tattaaaaat 153360
acaaaaactt agccaggcat ggtggccggc acctgtgatc ccggctactt gggaggctga 153420
ggcaggagaa ttgcctgaac ccaggaggtg aaggttgcag tgagccgaga tcgcaccact 153480
gcactctggt ctgggcaaaa agagcaaaac tcaggctcaa aaaaaaaaaa gaatgtctga 153540
cgtcaatcac aaattaccaa gcatgacatg aagttgacct ataaccagga gaaaactcaa 153600
tctatagaaa cagacccaga tgtgagaaag atgatgaatt tagcagacaa agaccatcaa 153660
gtggctattt taaatattaa aaatatgttc aagtggccag gtgcagtggc tcatgcctgt 153720
aatcccagca ctttgggagg ccaaggtggg taggagttca agaccagctt ggccaatatg 153780
gtgaaacccc ttctctacta aaaatacaaa aaaattagct gggcatggtg gcaggtgcct 153840
atagtcccag ctatatggga ggctgaggca caagaatcac ttgaacccgg gaggtggagg 153900
ttgaggttgc agtaagccga gattgtgcca cttgtactcc agcctggaca acagagtgag 153960
actctgtctc aaaaaaaaaa aaaaaaaagt taaagaaaac aagagtataa tgagaaaaat 154020
gcaaaatagt tttaaaagaa ccaaatggaa tttcttaaaa taaaaaatac cagaaatggg 154080
```

-continued

```
ggccgggcgt ggtagctcac gtctataatc ccagcacttt gtgggggctg aggcaggcag 154140
atcacctgag atcggtagtt caaggccagc ctgaccaaca tggagaaacc tcatctctac 154200
taaaaataca aaattagctg ggcgtggtgg cgcattgcct gtaatcccag ctacttggga 154260
ggctgaggca ggagaattgc ttgaacccgg gaggcagagg ttgcggtgag ctgagattgc 154320
accagtgcac tccagcttgg gccacaagag tgaaactccg tctcaaaaaa aaaacaaaaa 154380
aaaacagtag actcgaagaa ctagctgagt ttttctttac tttaggcagt aagtgtgacc 154440
ttttgcaggt gactacttta gttcctcatg tcctcattag tagatcagag aaattcgaca 154500
ccaaaacccc aaaagaaaaa ccccttctaa tcctcattcc atgattttat gaatgcatga 154560
agtcctaggc ctgcgaagga atactcattc tctttatcct gtgttgatac ctctctgctt 154620
caacctccaa ctcgacattt gcctatagga tgtacttgga cattcagcat aaactacctc 154680
acaccattac tgaattgctt catgtgcaca tgtcccatgc cacaataccg gggaccttgt 154740
cttccgtgat atttgtccgc agtgctgtga ctacaggagg gagtcagtga atgtctgcat 154800
gtgtgtcttt accatccctc ttgaatatgc tctagggtta attcctagaa gtagaattac 154860
tctattgaaa attggcaata tttttcattc taatatctat tgccaacatg ggaaagcaag 154920
tctggatgcc agtccttgtt atatgcccct tgggtaagtt acgtaacctc tttaagcttc 154980
tgttcactca tattttaaca aggaaaatta caatatttta cctcacaaaa ttgtagtcag 155040
cttctggctg tcttaaactc tggtatatag taaacactaa gtgttggtgt ccatccttaa 155100
tttgtaataa taggtcactt gttagagaaa tgcaccttac cattttcttt tcttttcttt 155160
tttcagttat gactcaaaac ttgagataaa ggaaatctgc ttgtgaaaaa taagagaact 155220
tttttccctt ggttggattc ttcaacacag ccaatgaaaa cagcactata tttctgatct 155280
gtcactgttg tttccaggag agaatgggag acaatcctag acttccacca taatgcagtt 155340
acctgtaggc ataattgatg cacatgatgt tcacacagtg agagtcttaa agatacaaaa 155400
tggtattgtt tacattacta gaaaattatt agttttccaa tggcaataac ccatttatga 155460
gagtgtttta gcctactgga atagacaggg accacatcct ctgggaagca gataagcata 155520
gaactgatac ttgatgcaca ctcgtagtgg taactcatcc ctaatcagca ttgtaaagca 155580
ggtgccagag gtggtttgct ttgtccttcc aaagcaggtg agtcagcccc accgagagcc 155640
aggcagcttt gagtggcagc gtggtgctag cagcttcagc ggaacagggt gagagttaat 155700
tatgcagtct tcttgacagc ggcattaatt tggaaggaaa ctgacaagtc atgggtcaag 155760
tttcagtgac ttcctccttc ctctgatggc agtatatagt tttcacattt taattcctcc 155820
tcctgagatg cactatactt aaaaccattc tctcccctgc taacagaagg gtgtgaatct 155880
ggtttacttt gagcattagg atttgcccct ttggaattct gcactccagt tacttaactt 155940
tcccttcaga atacatgtgg aaagaaagaa agaaatagcg atgactccac ttttgcccct 156000
gtggcacctt gaacaaagca gttcttccca aattatactt tttttttttt taaataaggt 156060
gagcaggatg actggggaga gagaaacatt tgactttgac tgcctccccc attctttgct 156120
gtgagctgga aagtgtgcag ttggtcgtct ttcttctcct ttctttagga tagtaagaga 156180
ctcactcact gcacttctgc tcagttggct tctgcatcgg gatcacacag ccatcagcag 156240
gactgcccag ttggtgagca cactccattg accacgcggc gccagcgctt cctcaatgca 156300
catgattgag aggaaagaaa gttctcttag atgttactgc ttttgctcag actttgcaaa 156360
aaaaaaaata tatatatata tgtataaata tataattatt aatcactttt gtccttgaga 156420
```

-continued

```
aagtcttgaa tgaacagaga atttattcca ttgcaatatt tgattgtata gaggcacact 156480
gtttcatcga cagaagaagc aaaaaggctt tgtgtaagtt tttggtacta tgtaccacct 156540
ctgttattct tttaaagctg aagtattcat gtacttaaac catattatat ttaattgtgt 156600
ttgattttaa aatatatata tatgaattct atttaaaatt gtgtcaactt tctgctttca 156660
gggcatttat ggctcttctg ttgaaatata ttgatctttc caaatatttt catttgcttt 156720
ctaaaaaccc agaacatgag ccactactgg actttgcctt gtgtttgaag tgtatggcat 156780
aaacccaagg tttttattag tcatctatgc tgtgattaat tcattttgtt cttttaacaa 156840
aatatttcca tccacttcac attgcttcaa tctttaacag aaaagcaata taaaggttat 156900
agaataaaat gtggttttgg gcaactcttg ctgcctctgc atgttttgga ataacaattt 156960
ctacaagact ctaggctgtt taaactagtg ctttcagtta agataaattc taatcatttc 157020
tttgtatata cattttgtgc ttctgagcta gagatgccaa gtagttgtaa actgcttata 157080
aagagaatag cagcaaattt gagactcggc tacttttttc tgccccacct gctttgagac 157140
acagaagcgg agtgtggccc gaaattatta gccagattta atatttgatc taaagtaggt 157200
ccttgtactc attttaaagt tggaatttga ttcctccaac attgagcacc caccatgttc 157260
caggctctgt gcattgtgcc cacaaaataa gattccctgg tggagttttt atgggttcaa 157320
ataatcagtt gaacaccctt catctttatc atgttgttga cattgacaca aattgtttaa 157380
aaagaaaaga tattagagag aaagtggtac ctttgtaact tgatgtgtct tcatcattcg 157440
gtaagatttg atgaaagtaa aaagcaaatg tcagccaaat ccagtgaaca gcaataaaac 157500
agggagtaac tttttataac tttttctact tggatttcaa cattcagtag agcttttcga 157560
aatgtaagta gtttacagta ctggaggttt gactagttca gtaggaattt ggaggggaag 157620
gtcattctga attgtaacaa agtacaaact tctttgctgt tttatttaag tactgagagc 157680
taagcacctg atgaagtgac tgacctctct ccagtgacag tgtttgggta cctgcctgac 157740
ttcaggagtg gggtttatgt ttctacacag tgaccttttc tctcgccctc tcctccctct 157800
tgcccacaca ccagttgatt ggacctgggt tgaactcctg atccagacag gcccaagaca 157860
gttcttaatg ttaagaattt tggggccggg cacggtggct catgcctgta attgcaacac 157920
tttgggaggc cgagacaggc ggatcacttg aggtcagggg ttcgaggcca gcctggccaa 157980
catggtgaaa ccctgtcttt actaaaaata caaaaattag ctgggcatgg tggcgcacgc 158040
ctgtaatccc agctacgtgg gtggctgaga caggggaatc gcttgaacct ggaggcggag 158100
gttgtgcaat gagccgagac cgtgtcactg cattccagcc tgggtgacag agggagactc 158160
tgtctccaaa aataaaaata agaaaaagaa ttttgggcta ggtgcagtgg ctcacgcctg 158220
taattacagc attttggaag gcccaagatg ggcagatcac ttgaggacag gagttcgaga 158280
ccagcctgga caacatggtg aaactccatc tctactaaaa agacaaaagt tagccagatg 158340
tggtgatggg cacctataat cctagctcct cgggaggctg gggcaggaga atcacttgaa 158400
cccaggaagc agagattgca gtgagccaag atcacatctc tgcactccag cctgggcaac 158460
agagcaagac tctgtctcaa aaaaaaaaga atttggccag gcgcagtggt tcacgcctgt 158520
aatcccagca ctttgggagg ccaaggcagg cagatcacga ggtcaggaga tcgagattgt 158580
cctggctaac atggtgaaac cctgtctcta ctaaaaatac aaaacattag ccgggtgtgg 158640
tggtgggcac ctgtagtccc agctactagg gaggctgagg cagaggaagg atgtgaaccc 158700
aggaggcgga gcttgcagta agccaagatc gtgccactgc actacagtct gggcgacaga 158760
gtgagactcc gtctcaaaaa aaaaaagaat tttggccggg tgcggtggca catgcctgta 158820
```

-continued

```
gtcccagcac tttgggagac caaagtgggc ggattacctg aggtcaggag ttcaagacca 158880
gtccggccaa tatggcgaaa ccctgtctct tactaaaaaa aatacaaaaa ttagccaggt 158940
gtggtggcgg gcacctgggg aggctgaggc agggagaaat gcttgaaccg gggaggcaga 159000
ggttgcagta agccaagatc gtgccactgc actccagagc aagactcttt ctcaaaaaaa 159060
aaaaaaaaag aattttgcat ggggaaggag agatactgtt caccatctgg aatggtgctt 159120
ggatgtggca cttacaaaat caggagccag cactgcatgg acaaacagaa gcatgtgggc 159180
ctgagatagc aggtaccttg ataaccctga agacatcctt ggtttctgca tctattcctg 159240
catccttgca ttggactaca ttaatctgtc agttatcctt ataatgattt ttgatttttt 159300
tttttgaga tggagtttcg ctcttgttgc ccaggctgga gtgcaatggc acgatctcgg 159360
ctcaccacaa cctccacctc ccaggttcaa gtgattctgc tgcctcagcc tcctgagtaa 159420
ctgggattac aggcatgcgc caccacacct ggctaatttt gtatttttag tagagacggg 159480
gtttctccat gttggtcagg ctggtctcga actcccaacc tcaggtgatc accctgtctc 159540
ggcctcccaa agtgctggga ttacaggcgt aagccatggt acccggtctg tttttgatt 159600
ttttgaaacc agtctgaagt gagttttttt aattacgtga aaggagtttg gctaaaatac 159660
tgccatactg ccctaatgcc taatgattat gtattctcag catgtctgca aagtactgct 159720
gatttctgga gaataatttt tctttagtaa acttcactta agtcgtcatg tgtattctct 159780
caaaatggta tcctaaccta atggagctaa aagacacccc ttgtttttat aacaagcagt 159840
tactgaggcc caggaagggg agaagtccct ggcttgtgag atgatcacca ttagaactca 159900
ggcctgggcc agtgcctttt catgcttctc agatccttcc aaagaataat gaagattata 159960
accgctttta gcaattgtaa taaacccaga aatagaaagc tttttggtta gagtactggt 160020
agaagtttgg cgggagagat aatttttaca aaatttgtaa atacctgcca attctatata 160080
ctaggcaagg tctctggcct tgtaaaaccc ctcaaggtta caactttggt ggcccacact 160140
aatagttacc cactgaggcc ctctccgggt gaacattgag cactagagga agcccctctg 160200
cttgggcagg actgggcgtg gtgcagagta ggagcggtga tactgtggat tctgggcagg 160260
tggagatggc cagtgatgtc caataaagga cactggaggg agcagtgtga gtaaaggccc 160320
tgagggcatt catgttcagg gagggttgct gcccactggc ttgcttggca cacaggagag 160380
tgggtattcc tgccttagta actttatgta aacaagtatt tcctcagtct gttcctctca 160440
aactgcctgc tctggcacat tcagaatgtc acagaactca cctggatgca ttcagcccct 160500
tgcctaaagg tgacagtgca tctccttccc caccccaccc ctcataccac tgaagcacct 160560
gtcagactgg cccagtctgt gggcaaggag cctagagagg gcttagtttc agcttgaaag 160620
gagctgggat ttaccaagaa gcaaatgaga gacgaggatt gcaacaactg tgccatttcc 160680
ccagcttcag ctgactcctg tatattgact gtgccttcag actcatccgt aagtgacccc 160740
aggctggcct ctcccacatc acagtaagaa ttccacacac catacaactt ggaaagaggc 160800
tccagctgaa ggaagcccca cacttctttc aagtttttct tagtcttctc ttcttggcaa 160860
agagtacctt ttgtttcttc taattatgta actattggtt tagtaaatat tcacccattc 160920
agtcaccctg taagtggcag gcactgttta cagggacaca ggaaggaata aaaacttgca 160980
ggcaccttgg agcttgcatt ctattgaaga ggtaatggaa gttgggatag cagctaaact 161040
atgctggtat tggccaggcg cagtggctca cacctgtaat cccagcactt tggaggccaa 161100
ggtgggcaga tcatgaagtc aggagatcga gaccatcctg gctaacatgg tgaaaccccg 161160
```

-continued

```
tctctactaa aagtaaaaaa aaaaattagc caggtgtggt ggcgggcgcc tgtagtccca 161220

gctacttggg aggctgaggc aggagaatgg tgtgaaccca ggaggcgaag attgcagtga 161280

gccgagatgg caccactgca ctccagcctg ggtgacagag cgagactctg tctcagaaaa 161340

aaaaaatatg ctggtagttt tgattcaaga tggcctttgg agcccatgat ttaggtctcg 161400

tacccaccaa ggtctactgg aaaacatcag gctctcctgc tatagaccca tagggagagc 161460

tgcagccgag agggggagct gaagagaagt gccccttctg tgtcctgtca gcctcatcct 161520

tccgcaagga ccagttgctg tgccactcca ttcacttgct gcaagactgg aggtttttcc 161580

tcaggtgttg agcacctggt ttacaagatg tcagcatctt gatgcctgag accatcaagg 161640

caagtctctg aacagggctt accttagagt aaggcttaga agaggccgta aagtcagtct 161700

cagctccgtg gctctgcaga gctttgggac atgtgaattc ttaaaaacaa gactattgta 161760

cagttactat atgcatgcag tataaaatta taaccttgga aaatcctagc tagctgttga 161820

gctaattcca taaagtaatc agctcctgag ttctgcagtg gtaataataa tcagcataat 161880

gagtaaacac tgtgtgtgcc aggcagcgtc tcatttgatc cttgtgataa tcttgtaagt 161940

actgatttttc tcccttcttt aaacaaagtt ttttttttt ttttagagag ggtctcacta 162000

tgttgcccag gctagtcttg aattc                                      162025


<210> SEQ ID NO 37
<211> LENGTH: 1350
<212> TYPE: DNA
<213> ORGANISM: Homo Sapien
<220> FEATURE:
<221> NAME/KEY: CDS
<222> LOCATION: (213)...(920)
<300> PUBLICATION INFORMATION:
<308> DATABASE ACCESSION NUMBER: GenBank AJ242973
<309> DATABASE ENTRY DATE: 1999-10-26

<400> SEQUENCE: 37

gcggccgcgt cgacgtgaca gccggtacgc ccgggtttgg gcaacctcga ttacgggcgg     60

cctccaggcc cgccagcagc gccccgcgcc gcccgcccgc gcccctgccg ccccccggtt    120

ccggccgcgg accccactct ctgccgttcc ggctgcggct ccgctgccgg tagcgccgtc    180

ccccgggacc acccttcggc tggcgccctc cc atg ctc tcg gcc acc cgg agg      233
                                    Met Leu Ser Ala Thr Arg Arg
                                     1               5

gct tgc cag ctc ctc ctc ctc cac agc ctc ttt ccc gtc ccg agg atg      281
Ala Cys Gln Leu Leu Leu Leu His Ser Leu Phe Pro Val Pro Arg Met
        10                  15                  20

ggc aac tcg gcc tcg aac atc gtc agc ccc cag gag gcc ttg ccg ggc      329
Gly Asn Ser Ala Ser Asn Ile Val Ser Pro Gln Glu Ala Leu Pro Gly
    25                  30                  35

cgg aag gaa cag acc cct gta gcg gcc aaa cat cat gtc aat ggc aac      377
Arg Lys Glu Gln Thr Pro Val Ala Ala Lys His His Val Asn Gly Asn
 40                  45                  50                  55

aga aca gtc gaa cct ttc cca gag gga aca cag atg gct gta ttt gga      425
Arg Thr Val Glu Pro Phe Pro Glu Gly Thr Gln Met Ala Val Phe Gly
                60                  65                  70

atg gga tgt ttc tgg gga gct gaa agg aaa ttc tgg gtc ttg aaa gga      473
Met Gly Cys Phe Trp Gly Ala Glu Arg Lys Phe Trp Val Leu Lys Gly
            75                  80                  85

gtg tat tca act caa gtt ggt ttt gca gga ggc tat act tca aat cct      521
Val Tyr Ser Thr Gln Val Gly Phe Ala Gly Gly Tyr Thr Ser Asn Pro
        90                  95                  100

act tat aaa gaa gtc tgc tca gaa aaa act ggc cat gca gaa gtc gtc      569
```

-continued

```
Thr Tyr Lys Glu Val Cys Ser Glu Lys Thr Gly His Ala Glu Val Val
    105                 110                 115

cga gtg gtg tac cag cca gaa cac atg agt ttt gag gaa ctg ctc aag      617
Arg Val Val Tyr Gln Pro Glu His Met Ser Phe Glu Glu Leu Leu Lys
120                 125                 130                 135

gtc ttc tgg gag aat cac gac ccg acc caa ggt atg cgc cag ggg aac      665
Val Phe Trp Glu Asn His Asp Pro Thr Gln Gly Met Arg Gln Gly Asn
                140                 145                 150

gac cat ggc act cag tac cgc tcg gcc atc tac ccg acc tct gcc aag      713
Asp His Gly Thr Gln Tyr Arg Ser Ala Ile Tyr Pro Thr Ser Ala Lys
            155                 160                 165

caa atg gag gca gcc ctg agc tcc aaa gag aac tac caa aag gtt ctt      761
Gln Met Glu Ala Ala Leu Ser Ser Lys Glu Asn Tyr Gln Lys Val Leu
        170                 175                 180

tca gag cac ggc ttc ggc ccc atc act acc gac atc cgg gag gga cag      809
Ser Glu His Gly Phe Gly Pro Ile Thr Thr Asp Ile Arg Glu Gly Gln
    185                 190                 195

act ttc tac tat gcg gaa gac tac cac cag cag tac ctg agc aag aac      857
Thr Phe Tyr Tyr Ala Glu Asp Tyr His Gln Gln Tyr Leu Ser Lys Asn
200                 205                 210                 215

ccc aat ggc tac tgc ggc ctt ggg ggc acc ggc gtg tcc tgc cca gtg      905
Pro Asn Gly Tyr Cys Gly Leu Gly Gly Thr Gly Val Ser Cys Pro Val
                220                 225                 230

ggt att aaa aaa taa ttgctcccca catggtgggc ctttgaggtt ccagtaaaaa      960
Gly Ile Lys Lys  *
            235

tgctttcaac aaattgggca atgcttgtgt gattcacaat cgtggcattt aaagtgcaca   1020

aagtacaaag gaatttatac agattgggtt taccgaagta taatctatag gaggcgcgat   1080

ggcaagttga taaaatgtga cttatctcct aataagttat ggtgggagtg gagctgtgcg   1140

gtttcctgtg tcttctgggg tctgagtgaa gatagcaggg atgctgtgtt caccccttctt  1200

ggtagaagct aaggtgtgag ctgggaggtt gctggacagg atgggggacc ccagaagtcc   1260

tttatctgtg ctctctgccc gccagtgcct tacaatttgc aaacgtgtat agcctcagtg   1320

actcattcgc tgaaatcctt cgctttacca                                    1350


<210> SEQ ID NO 38
<211> LENGTH: 235
<212> TYPE: PRT
<213> ORGANISM: Homo Sapien

<400> SEQUENCE: 38

Met Leu Ser Ala Thr Arg Arg Ala Cys Gln Leu Leu Leu Leu His Ser
 1               5                  10                  15

Leu Phe Pro Val Pro Arg Met Gly Asn Ser Ala Ser Asn Ile Val Ser
            20                  25                  30

Pro Gln Glu Ala Leu Pro Gly Arg Lys Glu Gln Thr Pro Val Ala Ala
        35                  40                  45

Lys His His Val Asn Gly Asn Arg Thr Val Glu Pro Phe Pro Glu Gly
    50                  55                  60

Thr Gln Met Ala Val Phe Gly Met Gly Cys Phe Trp Gly Ala Glu Arg
65                  70                  75                  80

Lys Phe Trp Val Leu Lys Gly Val Tyr Ser Thr Gln Val Gly Phe Ala
                85                  90                  95

Gly Gly Tyr Thr Ser Asn Pro Thr Tyr Lys Glu Val Cys Ser Glu Lys
            100                 105                 110

Thr Gly His Ala Glu Val Val Arg Val Val Tyr Gln Pro Glu His Met
```

-continued

```
        115                 120                 125

Ser Phe Glu Glu Leu Leu Lys Val Phe Trp Glu Asn His Asp Pro Thr
    130                 135                 140

Gln Gly Met Arg Gln Gly Asn Asp His Gly Thr Gln Tyr Arg Ser Ala
145                 150                 155                 160

Ile Tyr Pro Thr Ser Ala Lys Gln Met Glu Ala Ala Leu Ser Ser Lys
                165                 170                 175

Glu Asn Tyr Gln Lys Val Leu Ser Glu His Gly Phe Gly Pro Ile Thr
            180                 185                 190

Thr Asp Ile Arg Glu Gly Gln Thr Phe Tyr Tyr Ala Glu Asp Tyr His
        195                 200                 205

Gln Gln Tyr Leu Ser Lys Asn Pro Asn Gly Tyr Cys Gly Leu Gly Gly
    210                 215                 220

Thr Gly Val Ser Cys Pro Val Gly Ile Lys Lys
225                 230                 235


<210> SEQ ID NO 39
<211> LENGTH: 481
<212> TYPE: DNA
<213> ORGANISM: Homo Sapien
<300> PUBLICATION INFORMATION:
<308> DATABASE ACCESSION NUMBER: GenBank AW195104
<309> DATABASE ENTRY DATE: 1999-11-29

<400> SEQUENCE: 39

ggcattattg gactgtaggt ttttattaaa acaaacattt ctcatagctc taagcaaagc      60

attagaattc atcaagcgga ctcacatctt ttctctgcac agagaggggc tgaaaaggga     120

gagaaagtcc cttatgtatg tctagatttg gtaaagcgaa ggatttcagc gaatgagtca     180

ctgaggctat acacgtttgc aaattgtaag gcactggcgg gcagagagca cagataaagg     240

acttctgggg tcccccatcc tgtccagcaa cctcccagct cacaccttag cttctaccaa     300

gaagggtgaa cacagcatcc ctgctatctt cactcagacc ccagaaaacc cagggaaacc     360

cgacagctcc actcccacca taacttatta ggagataagt cacattttat caacttgcca     420

tcgcgcctcc tatagattat acttcggtaa acccaatctg tataaattcc tttgtacttt     480

g                                                                     481


<210> SEQ ID NO 40
<211> LENGTH: 390
<212> TYPE: DNA
<213> ORGANISM: Homo Sapien
<300> PUBLICATION INFORMATION:
<308> DATABASE ACCESSION NUMBER: GenBank AW874187
<309> DATABASE ENTRY DATE: 2000-05-22

<400> SEQUENCE: 40

tttttttat tggactgtag gtttttatta aaacaaacat ttctcatagc tctaagcaaa      60

gcattagaat tcatcaagcg gactcacatc ttttctctgc acagagaggg ctgaaaaggg     120

agagaaagcc ccttatgtat gtctagattt ggtaaagcga aggatttcag cgaatgagtc     180

actgaggcta tacacgtttg caaattgtaa ggcactggcg ggcagagagc acagataaag     240

gacttttggg ggtcccccat tcctgtccag caacctccca gctcacacct tagcttctac     300

caagaagggg tgaacacagc atccctgcta tcttcactca gacccccaga agacacagga     360

aaccgcacag ctccactccc accataactt                                      390


<210> SEQ ID NO 41
```

-continued

<211> LENGTH: 43
<212> TYPE: DNA
<213> ORGANISM: Artificial Sequence
<220> FEATURE:
<223> OTHER INFORMATION: Oligonucleotide Primer

<400> SEQUENCE: 41
agcggataac aatttcacac agggagctag cttggaagat tgc 43

<210> SEQ ID NO 42
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 42
gtccaatata tgcaaacagt tg 22

<210> SEQ ID NO 43
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 43
agcggataac aatttcacac agg 23

<210> SEQ ID NO 44
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 44
actgagcctg ctgcataa 18

<210> SEQ ID NO 45
<211> LENGTH: 21
<212> TYPE: DNA
<213> ORGANISM: Artificial Sequence
<220> FEATURE:
<223> OTHER INFORMATION: Oligonucleotide Primer

<400> SEQUENCE: 45
tctcaatcat gtgcattgag g 21

<210> SEQ ID NO 46
<211> LENGTH: 43
<212> TYPE: DNA
<213> ORGANISM: Artificial Sequence
<220> FEATURE:
<223> OTHER INFORMATION: Oligonucleotide Primer

<400> SEQUENCE: 46
agcggataac aatttcacac agggatcaca cagccatcag cag 43

<210> SEQ ID NO 47
<211> LENGTH: 23
<212> TYPE: DNA
<213> ORGANISM: oligonucleotide primer

<400> SEQUENCE: 47
agcggataac aatttcacac agg 23

-continued

<210> SEQ ID NO 48
<211> LENGTH: 18
<212> TYPE: DNA
<213> ORGANISM: Oligonucleotide primer

<400> SEQUENCE: 48
ctggcgccac gtggtcaa 18

<210> SEQ ID NO 49
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 49
tttctctgca cagagagggc 20

<210> SEQ ID NO 50
<211> LENGTH: 44
<212> TYPE: DNA
<213> ORGANISM: Artificial Sequence
<220> FEATURE:
<223> OTHER INFORMATION: Oligonucleotide Primer

<400> SEQUENCE: 50
agcggataac aatttcacac agggctgaaa tccttcgctt tacc 44

<210> SEQ ID NO 51
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 51
agcggataac aatttcacac agg 23

<210> SEQ ID NO 52
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 52
ctgaaaaggg agagaaag 18

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 53
tcccaaagtg ctggaattac 20

<210> SEQ ID NO 54
<211> LENGTH: 22
<212> TYPE: DNA
<213> ORGANISM: Artificial Sequence
<220> FEATURE:
<223> OTHER INFORMATION: Oligonucleotide Primer -continued

<400> SEQUENCE: 54
gtccaatata tgcaaacagt tg 22

<210> SEQ ID NO 55
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 55
cccacagcag ttaatccttc 20

<210> SEQ ID NO 56
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 56
gcgctcctgt cggtgcca 18

<210> SEQ ID NO 57
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 57
gcctgactgg tggggccc 18

<210> SEQ ID NO 58
<211> LENGTH: 15
<212> TYPE: DNA
<213> ORGANISM: Artificial Sequence
<220> FEATURE:
<223> OTHER INFORMATION: Oligonucleotide primer

<400> SEQUENCE: 58
catgcatgca cggtc 15

<210> SEQ ID NO 59
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 59
cagagagtac ccctcgaccg tgcatgcatg 30

<210> SEQ ID NO 60
<211> LENGTH: 15
<212> TYPE: DNA
<213> ORGANISM: Artificial Sequence
<220> FEATURE:
<223> OTHER INFORMATION: Oligonucleotide primer

<400> SEQUENCE: 60
catgcatgca cggtt 15

<210> SEQ ID NO 61
<211> LENGTH: 30

-continued

<212> TYPE: DNA
<213> ORGANISM: Artificial Sequence
<220> FEATURE:
<223> OTHER INFORMATION: Oligonucleotide primer

<400> SEQUENCE: 61
gtacgtacgt gccaactccc catgagagac 30

<210> SEQ ID NO 62
<211> LENGTH: 14
<212> TYPE: DNA
<213> ORGANISM: Artificial Sequence
<220> FEATURE:
<223> OTHER INFORMATION: Oligonucleotide primer

<400> SEQUENCE: 62
catgcatgca cggt 14

<210> SEQ ID NO 63
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 63
gcctgactgg tggggccc 18

<210> SEQ ID NO 64
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 64
gtgctgcagg tgtaaacttg taccag 26

<210> SEQ ID NO 65
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 65
cacggatccg gtagcagcgg tagagttg 28

<210> SEQ ID NO 66
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 66
actgggcatg tggagacag 19

<210> SEQ ID NO 67
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 67

-continued gcactttctt gccatgag 18

<210> SEQ ID NO 68
<211> LENGTH: 14
<212> TYPE: DNA
<213> ORGANISM: Artificial Sequence
<220> FEATURE:
<223> OTHER INFORMATION: Oligonucleotide primer

<400> SEQUENCE: 68
tcagtcacga cgtt 14

<210> SEQ ID NO 69
<211> LENGTH: 14
<212> TYPE: DNA
<213> ORGANISM: Artificial Sequence
<220> FEATURE:
<223> OTHER INFORMATION: Oligonucleotide primer

<400> SEQUENCE: 69
cggataacaa tttc 14

<210> SEQ ID NO 70
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 70
caatttcatc gctggatgca atctgggcta tgagatc 37

<210> SEQ ID NO 71
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 71
caatttcaca cagcggatgc ttcttttggc tctgact 37

<210> SEQ ID NO 72
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 72
tcagtcacga cgttggatgc caataaaagt gactctcagc 40

<210> SEQ ID NO 73
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 73
cggataacaa tttcggatgc actgggagca ttgaggc 37

<210> SEQ ID NO 74
<211> LENGTH: 38
<212> TYPE: DNA
<213> ORGANISM: Artificial Sequence -continued
<220> FEATURE:
<223> OTHER INFORMATION: Oligonucleotide primer

<400> SEQUENCE: 74
tcagtcacga cgttggatga gcagatccct ggacaggc 38

<210> SEQ ID NO 75
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 75
cggataacaa tttcggatgg acaaaatacc tgtattcc 38

<210> SEQ ID NO 76
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 76
tcagtcacga cgttggatgc agagcagctc cgagtc 36

<210> SEQ ID NO 77
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 77
cagcggtgat cattggatgc aggaagctct gg 32

<210> SEQ ID NO 78
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 78
tcagtcacga cgttggatgc ccacatgcca cccactac 38

<210> SEQ ID NO 79
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 79
cggataacaa tttcggatgc ccgtcaggta ccacg 35

<210> SEQ ID NO 80
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 80
tcagtcacga cgttggatgc ccacagtgga gcttcag 37

-continued

<210> SEQ ID NO 81
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 81
gctcatacct tgcaggatga cg 22

<210> SEQ ID NO 82
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 82
tcagtcacga cgttggatga ccagctgttc gtgttc 36

<210> SEQ ID NO 83
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 83
tacatggagt tcggggatgc acacggcgac tctc 34

<210> SEQ ID NO 84
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 84
tcagtcacga cgttggatgg ggaagagcag agatatacgt 40

<210> SEQ ID NO 85
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 85
gaggggctga tccaggatgg gtgctccac 29

<210> SEQ ID NO 86
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 86
tgaagcactt gaaggatgag ggtgtctgcg 30

<210> SEQ ID NO 87
<211> LENGTH: 38
<212> TYPE: DNA
<213> ORGANISM: Artificial Sequence
<220> FEATURE:
<223> OTHER INFORMATION: Oligonucleotide primer -continued

<400> SEQUENCE: 87
cggataacaa tttcggatgc tgcgtgatga tgaaatcg 38

<210> SEQ ID NO 88
<211> LENGTH: 26
<212> TYPE: DNA
<213> ORGANISM: Artificial Sequence
<220> FEATURE:
<223> OTHER INFORMATION: Oligonucleotide primer

<400> SEQUENCE: 88
gatgaagctc ccaggatgcc agaggc 26

<210> SEQ ID NO 89
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 89
gccgccggtg taggatgctg ctggtgc 27

<210> SEQ ID NO 90
<211> LENGTH: 31
<212> TYPE: DNA
<213> ORGANISM: Artificial Sequence
<220> FEATURE:
<223> OTHER INFORMATION: Oligonucleotide Template

<400> SEQUENCE: 90
cgcagggttt cctcgtcgca ctgggcatgt g 31

<210> SEQ ID NO 91
<211> LENGTH: 43
<212> TYPE: DNA
<213> ORGANISM: Artificial Sequence
<220> FEATURE:
<223> OTHER INFORMATION: Biotinylatd primer

<400> SEQUENCE: 91
tgcttatccc tgtagctacc ctgtcttggc cttgcagatc caa 43

<210> SEQ ID NO 92
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 92
agcggataac aatttcacac aggccatcac accgcggtac tg 42

<210> SEQ ID NO 93
<211> LENGTH: 44
<212> TYPE: DNA
<213> ORGANISM: Artificial Sequence
<220> FEATURE:
<223> OTHER INFORMATION: Oligonucleotide primer

<400> SEQUENCE: 93
cccagtcacg acgttgtaaa acgtcttggc cttgcagatc caag 44

<210> SEQ ID NO 94

-continued

<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 94
agcggataac aatttcacac aggccatcac accgcggtac tg 42

<210> SEQ ID NO 95
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 95
ctccagctgg gcaggagtgc 20

<210> SEQ ID NO 96
<211> LENGTH: 17
<212> TYPE: DNA
<213> ORGANISM: Artificial Sequence
<220> FEATURE:
<223> OTHER INFORMATION: Oligonucleotide primer

<400> SEQUENCE: 96
cacttcagtc gctccct 17

<210> SEQ ID NO 97
<211> LENGTH: 23
<212> TYPE: DNA
<213> ORGANISM: Artificial Sequence
<220> FEATURE:
<223> OTHER INFORMATION: Biotinylated primer

<400> SEQUENCE: 97
cccagtcacg acgttgtaaa acg 23

<210> SEQ ID NO 98
<211> LENGTH: 100
<212> TYPE: DNA
<213> ORGANISM: Homo sapien

<400> SEQUENCE: 98
cctttgagaa agggctctgc ttgagttgta gaaagaaccg ctgcaacaat ctgggctatg 60
agatcaataa agtcagagcc aaaagaagca gcaaaatgta 100

<210> SEQ ID NO 99
<211> LENGTH: 100
<212> TYPE: DNA
<213> ORGANISM: Homo sapien

<400> SEQUENCE: 99
cctttgagaa agggctctgc ttgagttgta gaaagaaccg ctgcaacaat ctgggctatg 60
agatcagtaa agtcagagcc aaaagaagca gcaaaatgta 100

<210> SEQ ID NO 100
<211> LENGTH: 100
<212> TYPE: DNA
<213> ORGANISM: Homo sapien

<400> SEQUENCE: 100
gaattatttt tgtgtttcta aaactatggt tcccaataaa agtgactctc agcgagcctc 60

-continued aatgctccca gtgctattca tgggcagctc tctgggctca 100

<210> SEQ ID NO 101
<211> LENGTH: 100
<212> TYPE: DNA
<213> ORGANISM: Homo sapien

<400> SEQUENCE: 101
gaattatttt tgtgtttcta aaactatggt tcccaataaa agtgactctc agcaagcctc 60
aatgctccca gtgctattca tgggcagctc tctgggctca 100

<210> SEQ ID NO 102
<211> LENGTH: 84
<212> TYPE: DNA
<213> ORGANISM: Homo sapien

<400> SEQUENCE: 102
taataggact acttctaatc tgtaagagca gatccctgga caggcgagga atacaggtat 60
tttgtccttg aagtaacctt tcag 84

<210> SEQ ID NO 103
<211> LENGTH: 84
<212> TYPE: DNA
<213> ORGANISM: Homo sapien

<400> SEQUENCE: 103
taataggact acttctaatc tgtaagagca gatccctgga caggcaagga atacaggtat 60
tttgtccttg aagtaacctt tcag 84

<210> SEQ ID NO 104
<211> LENGTH: 100
<212> TYPE: DNA
<213> ORGANISM: Homo sapien

<400> SEQUENCE: 104
ctcaccatgg gcatttgatt gcagagcagc tccgagtccg tccagagctt cctgcagtca 60
atgatcaccg ctgtgggcat ccctgaggtc atgtctcgta 100

<210> SEQ ID NO 105
<211> LENGTH: 100
<212> TYPE: DNA
<213> ORGANISM: Homo sapien

<400> SEQUENCE: 105
ctcaccatgg gcatttgatt gcagagcagc tccgagtcca tccagagctt cctgcagtca 60
atgatcaccg ctgtgggcat ccctgaggtc atgtctcgta 100

<210> SEQ ID NO 106
<211> LENGTH: 100
<212> TYPE: DNA
<213> ORGANISM: Homo sapien

<400> SEQUENCE: 106
agcaaggact cctgcaaggg ggacagtgga ggcccacatg ccacccacta ccagggcacg 60
tggtacctga cgggcatcgt cagctggggc cagggctgcg 100

<210> SEQ ID NO 107
<211> LENGTH: 100
<212> TYPE: DNA

<213> ORGANISM: Homo sapien

<400> SEQUENCE: 107

```
agcaaggact cctgcaaggg ggacagtgga ggcccacatg ccacccacta ccggggcacg    60
tggtacctga cgggcatcgt cagctggggc cagggctgcg                        100
```

<210> SEQ ID NO 108
<211> LENGTH: 100
<212> TYPE: DNA
<213> ORGANISM: Hom sapien

<400> SEQUENCE: 108

```
caataactct aatgcagcgg aagatgacct gcccacagtg gagcttcagg gcgtggtgcc    60
ccggggcgtc aacctgcaag gtatgagcat accccccttc                        100
```

<210> SEQ ID NO 109
<211> LENGTH: 100
<212> TYPE: DNA
<213> ORGANISM: Homo sapien

<400> SEQUENCE: 109

```
caataactct aatgcagcgg aagatgacct gcccacagtg gagcttcagg gcttggtgcc    60
ccggggcgtc aacctgcaag gtatgagcat accccccttc                        100
```

<210> SEQ ID NO 110
<211> LENGTH: 100
<212> TYPE: DNA
<213> ORGANISM: Homo sapien

<400> SEQUENCE: 110

```
ttgaagcttt gggctacgtg gatgaccagc tgttcgtgtt ctatgatcat gagagtcgcc    60
gtgtggagcc ccgaactcca tgggtttcca gtagaatttc                        100
```

<210> SEQ ID NO 111
<211> LENGTH: 100
<212> TYPE: DNA
<213> ORGANISM: Homo sapien

<400> SEQUENCE: 111

```
ttgaagcttt gggctacgtg gatgaccagc tgttcgtgtt ctatgatgat gagagtcgcc    60
gtgtggagcc ccgaactcca tgggtttcca gtagaatttc                        100
```

<210> SEQ ID NO 112
<211> LENGTH: 100
<212> TYPE: DNA
<213> ORGANISM: Homo sapien

<400> SEQUENCE: 112

```
ggataacctt ggctgtaccc cctggggaag agcagagata tacgtgccag gtggagcacc    60
caggcctgga tcagcccctc attgtgatct gggagccctc                        100
```

<210> SEQ ID NO 113
<211> LENGTH: 100
<212> TYPE: DNA
<213> ORGANISM: Homo sapien

<400> SEQUENCE: 113

```
ggataacctt ggctgtaccc cctggggaag agcagagata tacgtaccag gtggagcacc    60
caggcctgga tcagcccctc attgtgatct gggagccctc                        100
```

-continued

<210> SEQ ID NO 114
<211> LENGTH: 80
<212> TYPE: DNA
<213> ORGANISM: Homo sapien

<400> SEQUENCE: 114
tgaagcactt gaaggagaag gtgtctgcgg gagccgattt catcatcacg cagcttttct 60
ttgaggctga cacattcttc 80

<210> SEQ ID NO 115
<211> LENGTH: 80
<212> TYPE: DNA
<213> ORGANISM: Homo sapien

<400> SEQUENCE: 115
tgaagcactt gaaggagaag gtgtctgcgg gagtcgattt catcatcacg cagcttttct 60
ttgaggctga cacattcttc 80

<210> SEQ ID NO 116
<211> LENGTH: 80
<212> TYPE: DNA
<213> ORGANISM: Homo sapien

<400> SEQUENCE: 116
tccagatgaa gctcccagaa tgccagaggc tgctccccgc gtggcccctg caccagcagc 60
tcctacaccg gcggcccctg 80

<210> SEQ ID NO 117
<211> LENGTH: 80
<212> TYPE: DNA
<213> ORGANISM: Homo sapien

<400> SEQUENCE: 117
tccagatgaa gctcccagaa tgccagaggc tgctcccccc gtggcccctg caccagcagc 60
tcctacaccg gcggcccctg 80

<210> SEQ ID NO 118
<211> LENGTH: 48
<212> TYPE: DNA
<213> ORGANISM: Artificial Sequence
<220> FEATURE:
<223> OTHER INFORMATION: Hair pin structure

<400> SEQUENCE: 118
cagagagtac ccctcaaccg tgcatgcatg aaacatgcat gcacggtt 48